(12) United States Patent
Branstrom et al.

(10) Patent No.: US 9,409,905 B2
(45) Date of Patent: *Aug. 9, 2016

(54) ANTIBACTERIAL COMPOUNDS AND METHODS FOR USE

(75) Inventors: Arthur Branstrom, East Windsor, NJ (US); Vara Prasad Venkata Nagendra Josyula, Superior Township, MI (US); Michael Andrew Arnold, Flemington, NJ (US); Aleksey I. Gerasyuto, Flemington, NJ (US); Gary Karp, Princeton Junction, NJ (US); Jiashi Wang, Monmouth Junction, NJ (US); John David Baird, Piscataway, NJ (US); Guangming Chen, Bridgewater, NJ (US); Olya Ginzburg, Bloomfield, NJ (US); Jana Narasimhan, Scotch Plains, NJ (US); Srinivasa Peddi, Piscataway, NJ (US); Hongyan Qi, Plainsboro, NJ (US); Sean Wesley Smith, Hamiliton, NJ (US); Matthew G. Woll, Dunellen, NJ (US); Tianle Yang, Mountainside, NJ (US); Nanjing Zhang, Princeton, NJ (US); Xiaoyan Zhang, Belle Mead, NJ (US)

(73) Assignee: PTC THERAPEUTICS, INC., South Plainfield, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/241,506

(22) PCT Filed: Aug. 29, 2012

(86) PCT No.: PCT/US2012/052922
§ 371 (c)(1),
(2), (4) Date: Oct. 20, 2014

(87) PCT Pub. No.: WO2013/033258
PCT Pub. Date: Mar. 7, 2013

(65) Prior Publication Data
US 2015/0038437 A1   Feb. 5, 2015

Related U.S. Application Data

(60) Provisional application No. 61/528,599, filed on Aug. 29, 2011.

(51) Int. Cl.
| | | |
|---|---|---|
| *C07D 401/14* | (2006.01) | |
| *C07D 413/04* | (2006.01) | |
| *C07D 471/04* | (2006.01) | |
| *C07D 405/14* | (2006.01) | |
| *C07D 401/04* | (2006.01) | |
| *A61K 31/4709* | (2006.01) | |
| *A61K 31/5377* | (2006.01) | |
| *A61K 31/4439* | (2006.01) | |
| *A61K 45/06* | (2006.01) | |
| *A61K 31/437* | (2006.01) | |

(52) U.S. Cl.
CPC ............ *C07D 471/04* (2013.01); *A61K 31/437* (2013.01); *A61K 31/4439* (2013.01); *A61K 31/4709* (2013.01); *A61K 31/5377* (2013.01); *A61K 45/06* (2013.01); *C07D 401/04* (2013.01); *C07D 401/14* (2013.01); *C07D 405/14* (2013.01); *C07D 413/04* (2013.01)

(58) Field of Classification Search
CPC .. C07D 471/04; C07D 401/04; C07D 401/14; C07D 405/14; C07D 413/04; A61K 31/437; A61K 31/4439; A61K 31/4709; A61K 31/5377; A61K 45/06
USPC ................ 546/249, 276.7, 271.7, 167, 275.7, 546/277.4, 113; 514/29, 314, 230.5, 300, 514/338, 210.18, 339, 210.21; 544/105
See application file for complete search history.

(56) References Cited

U.S. PATENT DOCUMENTS

| | | |
|---|---|---|
| 3,703,582 A | 11/1972 | Shen et al. |
| 3,948,903 A | 4/1976 | Doub et al. |
| 3,954,734 A | 5/1976 | Doub et al. |
| 4,331,597 A | 5/1982 | Makabe et al. |
| 4,698,352 A | 10/1987 | Narita et al. |
| 6,469,033 B1 | 10/2002 | Bohn et al. |
| 6,670,380 B2 | 12/2003 | Sulsky et al. |
| 7,067,540 B2 | 6/2006 | Devadas et al. |
| 7,629,363 B2 | 12/2009 | Devadas et al. |
| 2008/0103139 A1 | 5/2008 | Ishizuka et al. |
| 2009/0202634 A1 | 8/2009 | Jans et al. |

(Continued)

FOREIGN PATENT DOCUMENTS

| | | |
|---|---|---|
| CN | 1231161 | 10/1999 |
| CN | 1646125 | 7/2005 |

(Continued)

OTHER PUBLICATIONS

Chemical Abstracts STN Database Record for RN 1306268-23-4, database entry date Jun. 5, 2011.*

(Continued)

*Primary Examiner* — Janet L Andres
*Assistant Examiner* — Daniel Carcanague
(74) *Attorney, Agent, or Firm* — Hoffmann & Baron, LLP

(57) ABSTRACT

The present description relates to compounds and forms and pharmaceutical compositions thereof and methods for use thereof to treat or ameliorate bacterial infections caused by wild-type and multi-drug resistant Gram-negative and Gram-positive pathogens.

21 Claims, No Drawings

(56) References Cited

U.S. PATENT DOCUMENTS

| | | | |
|---|---|---|---|
| 2009/0215764 A1 | 8/2009 | Das et al. | |
| 2010/0056582 A1 | 3/2010 | Bayne et al. | |
| 2015/0038438 A1* | 2/2015 | Branstrom | A61K 31/473 514/29 |
| 2015/0080362 A1* | 3/2015 | Branstrom | A01N 43/40 514/210.2 |

FOREIGN PATENT DOCUMENTS

| | | |
|---|---|---|
| CN | 101531631 | 9/2009 |
| EP | 0308020 | 3/1989 |
| EP | 0347027 | 12/1989 |
| GB | 2058769 | 4/1981 |
| WO | WO9117987 | 11/1991 |
| WO | 03/068230 | 8/2003 |
| WO | 2005/018557 | 3/2005 |

OTHER PUBLICATIONS

Chemical Abstracts STN Database Record for RN 1305278-11-8, database entry date Jun. 3, 2011.*
Chemical Abstracts STN Database Record for RN 1291753-42-8, database entry date May 8, 2011.*
Chemical Abstracts STN Database Record for RN 1285231-11-9, database entry date Apr. 24, 2011.*
Chemical Abstracts STN Database Record for RN 1284555-52-7, database entry date Apr. 24, 2011.*
Chemical Abstracts STN Database Record for RN 1283181-10-1, database entry date Apr. 20, 2011.*
Chemical Abstracts STN Database Record for RN 1283889-86-0, database entry date Apr. 22, 2011.*
Chemical Abstracts STN Database Record for RN 1282921-52-1, database entry date Apr. 20, 2011.*
Chemical Abstracts STN Database Record for RN 1268040-15-8, database entry date Mar. 10, 2011.*
Chemical Abstracts STN Database Record for RN 1267392-94-8, database entry date Mar. 9, 2011.*
Chemical Abstracts STN Database Record for RN 1266989-99-4, database entry date Mar. 9, 2011.*
Chemical Abstracts STN Database Record for RN 1226084-48-5, database entry date May 30, 2010.*
Chemical Abstracts STN Database Record for RN 1226083-54-0, database entry date May 30, 2010.*
Chemical Abstracts STN Database Record for RN 1225669-93-1, database entry date May 30, 2010.*
Ciufolini; Targets in Heterocyclic Systems, 2000, 4, 25-55; Abstract from CAPLUS Database.*
Abdelhamid; J. Heterocyclic Chem. 2009, 46, 680-686.*
Farghaly; Journal of Chemical Research 2008, 3, 152-156; Abstract from CAPLUS.*
Chemical Abstracts STN Database Record for RN 1284524-20-4, entered on Apr. 24, 2011.*
International Search Report of PCT/US2012/052922 mailed Nov. 2, 2012.
Ito et al., XP-002734962, "Retro-ene . . . ", J. Heterocyclic Chem., vol. 29(5):1037-1044, 1992. (abstact only).
Mabkhot et al., XP-002735064, "Comprehensive and facile . . . ", Int. J. Molecular Sciences, vol. 13, pp. 2263-2275, Feb. 20, 2012. (abstract only).
Poschenrieder et al., XP-002734961, "Pyrrolidine-2,4-diones . . . ", Archly der Pharmazie, vol. 332(9):309-316, 1999. (abstract only).
Stachel et al., XP-002734959, "Reactions of 5-brornoalkylidene-3-pyrrolin-2-ones", Liebigs Annalen der Chemie, vol. 8, 1692-6, 1985. (abstract only).
Stachel et al., XP-002734960, "Derivatives of . . . ", J. Heterocyclic Chemistry, vol. 22(5), 1413-18, 1985. (abstract only).
Zhang et al., Carbonarones A and B . . . J. Antibiotics, 2007, vol. 60(2):153-157.
International Preliminary Report on Patentability of PCT/US2012/052898 mailed on Mar. 4, 2014.
International Preliminary Report on Patentability of PCT/US2012/052922 mailed on Mar. 4, 2014.
International Search Report of PCT/US2012/052898 mailed on Dec. 21, 2012.
Written Opinion of the International Searching Authority of PCT/US2012/052898 mailed on Dec. 21, 2012.
Written Opinion of the International Searching Authority of PCT/US2012/052922 mailed on Nov. 2, 2012.
Chemical Abstracts STN Database Record for RN 1282753-08-5, dated Apr. 20, 2011.
Chemical Abstracts STN Database Record for RN 1283989-97-8, dated Apr. 22, 2011.
Al-Mousawi, Tetrahedron Letters, 2011, vol. 52, pp. 202-204.
Cottarel, Trends in Biotechnology, 2007, vol. 25, pp. 547-555.
Georgopapadakou, Antimicrobial Agents and Chemotherapy, 1987, vol. 31, pp. 614-616.
Farghaly, Thoraya A., "Synthesis and reactions of 3[3-(dimethylamino)propenoyl]-1,7-diphenyl [1,2,4]truaziki[4,3-a]pyrimidin5(1H)-one", Journal of Chemical Research Mar. 2008, 152-156.
Ciufolini, et al., "Practical Synthesis of (20S)-(+)-Camptothecin: The Progenitor of a Promising Group of Anticancer Agents", Targets in heterocyclic systems: chemistry and properties, 1997, pp. 25-55.

* cited by examiner

ANTIBACTERIAL COMPOUNDS AND METHODS FOR USE

CROSS-REFERENCES TO RELATED APPLICATIONS

This application is the National Stage of International Application No. PCT/US2012/052922, filed Aug. 29, 2012, which claims the benefit of U.S. Application No. 61/528,599, filed Aug. 29, 2011, the entire contents of which are incorporated by reference herein.

FIELD OF THE INVENTION

The present description relates to compounds and forms and pharmaceutical compositions thereof and methods of using such compounds, forms or compositions thereof for treating or ameliorating a bacterial infection. More particularly, the present description relates to compounds and forms and pharmaceutical compositions thereof and methods of using such compounds, forms or compositions thereof for treating or ameliorating a bacterial infection, or for treating or ameliorating a multi-drug resistant (MDR) bacterial infection.

BACKGROUND

Currently marketed antimicrobial agents inhibit bacterial DNA synthesis by acting on the two key enzymes of DNA gyrase and topoisomerase IV (see, Mitscher, L. A. Bacterial topoisomerase inhibitors: quinolone and pyridone antibacterial agents, *Chem. Rev.* 2005, 105, 559-592; Hooper, D. C.; Rubinstein, E. Quinolone antimicrobial agents/edited by David C. Hooper and Ethan Rubinstein; or De Souza, M. V. New fluoroquinolones: a class of potent antibiotics. *Mini. Rev. Med. Chem.* 2005, 5 (11), 1009-1017).

The DNA gyrase and topoisomerase IV enzymes are both type II topoisomerases, consisting of two protein subunits active as heterodimers ($A_2B_2$). The ATPase domain resides on one polypeptide (GyrB in DNA gyrase, ParE in topoisomerase IV), while the DNA cleavage core lies on a second polypeptide (GyrA in DNA gyrase, ParC in topoisomerase IV). Current therapies, including the aminocoumarin novobiocin, function as competitive inhibitors of energy transduction of DNA gyrase by binding to the ATPase active site in GyrB (see, Maxwell, A. The interaction between coumarin drugs and DNA gyrase. *Mol. Microbiol.* 1993, 9 (4), 681-686; Flatman, R. H.; Eustaquio, A.; Li, S. M.; Heide, L.; Maxwell, A. Structure-activity relationships of aminocoumarin-type gyrase and topoisomerase IV inhibitors obtained by combinatorial biosynthesis. *Antimicrob. Agents Chemother.* 2006, 50 (4), 1136-1142).

In contrast, the nalidixic acid, ciprofloxacin and moxifloxacin preferentially bind these enzymes at the cleavage core (GyrA and ParC) and prevent decatenation of replicating DNA (see, Hooper, D. C. Quinolone mode of action. *Drugs* 1995, 49 *Suppl* 2, 10-15). Although first site resistance mutations generally occur in gyrA, mutations in gyrB also have been shown to reduce susceptibility to quinolones (see, Yoshida, H.; Bogaki, M.; Nakamura, M.; Yamanaka, L. M.; Nakamura, S. Quinolone resistance-determining region in the DNA gyrase gyrB gene of *Escherichia coli*. *Antimicrob. Agents Chemother.* 1991, 35 (8), 1647-1650).

Bacterial DNA synthesis inhibitors (e.g. fluoroquinolones) have been used to treat primarily Gram-negative infections and have historically achieved outstanding clinical outcomes (see, Emmerson, A. M.; Jones, A. M. The quinolones: decades of development and use. *J. Antimicrobial Chemotherapy*, 2003, 51 (S1), 13-20). A wealth of knowledge exists for the quinolone class of compounds (see, Hooper, D. C.; Rubinstein, E. Quinolone antimicrobial agents/edited by David C. Hooper and Ethan Rubinstein), including bioavailability, tissue distribution, PK/PD relationships and photoxicity. Structurally, quinolone antibiotics possess a bicyclic (ciprofloxacin and moxifloxacin) or tricyclic ring structure (levofloxacin) with an aryl side chain containing an acyclic ring incorporating an amine functionality.

Other ring structures such as the 2-pyridones (monocyclic and bicyclic)(see, Chu, D. T. Recent progress in novel macrolides, quinolones, and 2-pyridones to overcome bacterial resistance. *Med. Res. Rev.* 1999, 19 (6), 497-520), quinazolinediones (see, Ellsworth, E. L.; Tran, T. P.; Showalter, H. D.; Sanchez, J. P.; Watson, B. M.; Stier, M. A.; Domagala, J. M.; Gracheck, S. J.; Joannides, E. T.; Shapiro, M. A.; Dunham, S. A.; Hanna, D. L.; Huband, M. D.; Gage, J. W.; Bronstein, J. C.; Liu, J. Y.; Nguyen, D. Q.; Singh, R. 3-aminoquinazolinediones as a new class of antibacterial agents demonstrating excellent antibacterial activity against wild-type and multidrug resistant organisms. *J. Med. Chem.* 2006, 49 (22), 6435-6438; and, Tran, T. P.; Ellsworth, E. L.; Stier, M. A.; Domagala, J. M.; Hollis Showalter, H. D.; Gracheck, S. J.; Shapiro, M. A.; Joannides, T. E.; Singh, R. Synthesis and structural-activity relationships of 3-hydroxyquinazoline-2,4-dione antibacterial agents. *Bioorg. Med. Chem. Lett.* 2004, 14 (17), 4405-4409) and tricyclic isoquinolones have been described in the literature.

Though some of these molecules, such the 2-pyridone and 4-pyridones (e.g., Ro-13-5478), isoquinolones and quinazolinediones have progressed to the late preclinical stage, none have reached the market. In the 1980s, monocyclic 2-pyridone and 4-pyridones were reported to inhibit DNA gyrase (see, Georgopapadakou, N. H.; Dix, B. A.; Angehrn, P.; Wick, A.; Olson, G. L. Monocyclic and tricyclic analogs of quinolones: mechanism of action. *Antimicrob. Agents Chemother.* 1987, 31 (4), 614-616).

The monocyclic 4-pyridone class of molecules generally exhibited poor activity against quinolone-resistant ($quin^R$) strains, possessed attendant CNS side effects, and in most cases, had only limited in vivo efficacy. Recent studies on monocyclic-4-pyridone analogs (see, Laursen, J. B.; Nielsen, J.; Haack, T.; Pusuluri, S.; David, S.; Balakrishna, R.; Zeng, Y.; Ma, Z.; Doyle, T. B.; Mitscher, L. A. Further exploration of antimicrobial ketodihydronicotinic acid derivatives by multiple parallel syntheses. *Comb. Chem. High Throughput. Screen.* 2006, 9 (9), 663-681) demonstrate that these compounds elicit cross-resistance to ciprofloxacin and possess poor antibacterial activity against *E. coli*.

More recently, antibacterial spiro-tricyclic barbituric acid derivatives (QPT-1) (see, Miller, A. A.; Bundy, G. L.; Mott, J. E.; Skepner, J. E.; Boyle, T. P.; Harris, D. W.; Hromockyj, A. E.; Marrotti, K. R.; Zurenko, G. E.; Munzner, J. B.; Sweeney, M. T.; Bammert, G. F.; Hamel, J. C.; Ford, C. W.; Zhong, W-Z.; Graber, D. R.; Martin, G. E.; Han, F.; Dolak, L. A.; Seest, E. P.; Ruble, J. C.; Kamilar, G. M.; Palmer, J. R.; Banitt, L. S.; Hurd, A. R.; Barbachyn, M. R. Discovery and characterization of QPT-1, the progenitor of a new class of bacterial topoisomerase inhibitors. *Antimicrob. Agents Chemother.* 2008, 52 (8), 2806-2812; and, Ruble, J. C.; Hurd, A. R.; Johnson, T. A.; Sherry, D. A.; Barbachyn, M. R.; Toogood, P. L.; Bundy, G. L.; Graber, D. R.; Kamilar, G. M. Synthesis of (−)-PNU-286607 by asymmetric cyclization of alkylidene barbiturates. *J. Am. Chem. Soc.* 2009, 131 (11), 3991-3997), inhibitors possessing a tetrahydroindazole and piperidine motif and a 6-methoxyquinoline moiety (e.g., NXL101 and GSK299423) (see, Black, M. T.; Stachyra, T.; Platel, D.; Girard, A. M.; Claudon, M.; Bruneau, J. M.; Miossec, C. Mechanism of action of the antibiotic NXL101, a novel non-fluoroquinolone inhibitor of bacterial type II topoisomerases. *Antimicrob. Agents Chemother.* 2008, 52 (9), 3339-3349; Bax, B. D.; Chan, P. F.; Eggleston, D. S.; Fosberry, A.; Gentry, D. R.; Gorrec, F.; Giordano, I.; Hann, M. M.; Hennessy, A.; Hibbs, M.; Huang, J.; Jones, E.; Jones, J.; Brown, K. K.; Lewis, C. J.; May, E. W.; Saunders, M. R.; Singh, O.; Spitzfaden, C. E.; Shen, C.; Shillings, A.; Theobald, A. J.; Wohlkonig, A.; Pearson, N. D.; Gwynn, M. N. Type IIA topoisomerase inhibition by a new class of antibacterial agents. *Nature* 2010, 466 (7309), 935-940; Gomez, L.; Hack, M. D.; Wu, J.; Wiener, J. J.; Venkatesan, H.; Santillan, A., Jr.; Pippel, D. J.; Mani, N.; Morrow, B. J.; Motley, S. T.; Shaw, K. J.; Wolin, R.; Grice, C. A.; Jones, T. K. Novel pyrazole derivatives as potent inhibitors of type II topoisomerases. Part 1: synthesis and preliminary SAR analysis. *Bioorg. Med. Chem. Lett.* 2007, 17 (10), 2723-2727; and, Wiener, J. J.; Gomez, L.; Venkatesan, H.; Santillan, A., Jr.; Allison, B. D.; Schwarz, K. L.; Shinde, S.; Tang, L.; Hack, M. D.; Morrow, B. J.; Motley, S. T.; Goldschmidt, R. M.; Shaw, K. J.; Jones, T. K.; Grice, C. A. Tetrahydroindazole inhibitors of bacterial type II topoisomerases. Part 2: SAR development and potency against multidrug-resistant strains. *Bioorg. Med. Chem. Lett.* 2007, 17 (10), 2718-2722) and isothiazoloquinolones (e.g., ACH-702) (see, Kim, H. Y.; Wiles, J. A.; Wang, Q.; Pais, G. C. G.; Lucien, E.; Hashimoto, A.; Nelson, D. M.; Thanassi, J. A.; Podos, S. D.; Deshpande, M.; Pucci, M. J.; Bradbury, B. J. Exploration of the activity of 7-pyrrolidino-8-methoxy-isothiazoloquinolones against methicillin-resistant *Staphylococcus aureus* (MRSA). *J. Med. Chem.*, 2010, 54(9), 3268-3282) have been described as new classes of bacterial topoisomerase inhibitors. The X-ray crystallographic structure of GSK299423 bound to DNA gyrase has also been reported (Bax, B. D., et al., 2010).

Structurally, most of the known inhibitors (with the exception of QPT-1, the tetrahydroindazoles, NXL101, GSK299423 and ACH-702) possess a keto-acid functionality, either a carboxylic acid (ciprofloxacin and moxifloxacin, levofloxacin, the monocyclic and bicyclic 2-pyridone and 4-pyridones), hydroxylamine (quinazolinediones and tricyclic isoquinolones), or a hydrazine (quinazolinediones) group, which relate to DNA gyrase and topoisomerase activity and presumably bind to a divalent cation in the activated complex (see, Laponogov, I.; Sohi, M. K.; Veselkov, D. A.; Pan, X. S.; Sawhney, R.; Thompson, A. W.; McAuley, K. E.; Fisher, L. M.; Sanderson, M. R. Structural insight into the quinolone-DNA cleavage complex of type IIA topoisomerases. *Nat. Struct. Mol. Biol.* 2009, 16 (6), 667-669).

Most inhibitors also possess an amine functional group attached to the core heterocycle, making these compounds zwitterionic in nature. Monocyclic 2-pyridone and 4-pyridone (e.g., Ro-13-5478) inhibitors possess this amine functionality attached to a phenyl group (see, Tesfaye, B.; Heck, J. V.; Thorsett, E. D. European Patent Application 0308022 A2, 1987; Narita, H.; Konishi, Y.; Nitta, J.; Misumi, S.; Nagaki, H.; Kitayama, I.; Nagai, Y.; Watanbe, Y.; Matsubare, N.; Minami, S.; Saikawa, I.; UK Patent Application GB2130580, 1983; and, Narita, H.; Konishi, Y.; Nitta, J.; Misumi, S.; Nagaki, H.; Kitayama, I.; Nagai, Y.; Watanbe, Y.; Matsubare, N.; Minami, S.; Saikawa, I. U.S. Pat. No. 4,698,352; 1987).

The zwitterionic nature of these inhibitors relate to the permeation of these compounds into the Gram-negative cell using porin channels (see, Nikaido, H.; Thanassi, D. G. Penetration of lipophilic agents with multiple protonation sites into bacterial cells: tetracyclines and fluoroquinolones as examples. *Antimicrob. Agents Chemother.* 1993, 37 (7), 1393-1399; and, Tieleman, D. P.; Berendsen, H. J. A molecular dynamics study of the pores formed by *Escherichia coli* OmpF porin in a fully hydrated palmitoyloleoylphosphatidylcholine bilayer. *Biophys. J.* 1998, 74 (6), 2786-2801).

Due to increasing resistance of multiple bacteria to marketed antibiotics in hospital as well as in community settings, the discovery of new and especially novel antibiotics is urgently needed (see, Bonhoeffer, S.; Lipsitch, M.; Levin, B. R. Evaluating treatment protocols to prevent antibiotic resistance. *Proc. Natl. Acad. Sci. U.S.A* 1997, 94 (22), 12106-12111; Wang, Y. C.; Lipsitch, M. Upgrading antibiotic use within a class: tradeoff between resistance and treatment success. *Proc. Natl. Acad. Sci. U.S.A* 2006, 103 (25), 9655-9660; and, Payne, D. J.; Gwynn, M. N.; Holmes, D. J.; Pompliano, D. L. Drugs for bad bugs: confronting the challenges of antibacterial discovery. *Nat. Rev. Drug Discov.* 2007, 6 (1), 29-40).

Approximately 70% of bacterial strains causing nosocomial infections are resistant to at least one of the drugs most commonly used to treat such infections, and 25% of bacterial pneumonia cases have been shown to be resistant to penicillin (Todar, K. Todar's Online textbook of Bacteriology, www-.textbookofbacteriology.net/). Recently, there has been a dramatic decrease in the number of new antibiotic approvals, where only two new entities have been approved in the past two years.

There are some antibiotics available that have had success against MRSA (see, Perry, C. M.; Jarvis, B. Linezolid: a review of their use in the management of serious Gram-positive infections. *Drugs* 2001, 61 (4), 525-551; Peterson, L. R. A review of tigecycline—the first glycylcycline. *Int. J. Antimicrob. Agents* 2008, 32 *Suppl* 4, S215-S222; Chu, D. T. Recent developments in macrolides and ketolides. *Curr. Opin. Microbiol.* 1999, 2 (5), 467-474; Kahne, D.; Leimkuhler, C.; Lu, W.; Walsh, C. Glycopeptide and lipoglycopeptide antibiotics. *Chem. Rev.* 2005, 105 (2), 425-448; and, Zhanel, G. G.; Lam, A.; Schweizer, F.; Thomson, K.; Walkty, A.; Rubinstein, E.; Gin, A. S.; Hoban, D. J.; Noreddin, A. M.; Karlowsky, J. A. Ceftobiprole: a review of a broad-spectrum and anti-MRSA cephalosporin. *Am. J. Clin. Dermatol.* 2008, 9 (4), 245-254), but there have been no new clinically approved agents targeting Gram-negative bacteria.

Quinolones have been shown to be highly effective in the clinic, but wide-scale deployment of these current drugs, partly due to generic usage of the effective second generation quinolones (e.g., ciprofloxacin), jeopardizes their future long-term utility. Quinolone resistance is already rising in both hospitals and the community at large. Therefore, new drugs targeting MDR Gram-negative pathogens would be expected to help address this important unmet medical need (see, Talbot, G. H.; Bradley, J.; Edwards, J. E., Jr.; Gilbert, D.; Scheld, M.; Bartlett, J. G. Bad bugs need drugs: an update on the development pipeline from the Antimicrobial Availability Task Force of the Infectious Diseases Society of America. *Clin. Infect. Dis.* 2006, 42 (5), 657-668; and, Rice, L. B. Unmet medical needs in antibacterial therapy. *Biochem. Pharmacol.* 2006, 71 (7), 991-995).

As resistance to marketed antibiotics continues to increase, and new antibacterials have not been readily forthcoming from the pharmaceutical industry, the availability of new antibiotic and antibacterials agents is essential to overcome pre-existing and burgeoning resistance. As an effective monotherapy, novel compounds active against MDR strains of *E. coli* and *A. baumannii* pathogens, as well as other bacterial strains of great interest are needed, including those potentially employable as bioterror agents. New compounds that bind differently than existing DNA synthesis inhibitors and new therapies with combinations of antibacterial and antibiotic agents having additive or synergistic activities, including combinations with current quinolone antibiotics, would enable longer clinical lifetimes for proven antibacterial agents against a mechanistically validated target. Accordingly, the availability of such compounds and therapies would provide a significant current and future human health benefit with a high probability of success on several fronts for the control of difficult bacterial infections for a number of years to come.

6-methoxyquinoline based compounds for use as antibacterial topoisomerase inhibitors possessing Gram-negative activities have been reported by Glaxo-SmithKline, Johnson & Johnson and Novexel. Achillion and Rib-x Pharmaceuticals have also reported isothiazoloquinolones and quinolone (delafloxacin), respectively, that possess activity against resistant Gram-positive strains, including MRSA. Other examples in the literature include AM-1954 (Kyorin), DC-159a and DX-619 (Diaiichi), JNJ-Q2 (Johnson & Johnson), WQ-3813 (Wakunaga). However, all these compounds are derived from a quinolone moiety. Pfizer, Astra Zeneca, Achaogen and Targanta further describe quinolone-based compounds that possess an expanded spectrum of activity, especially against Gram-positive strains. Recently, the literature from 2005 to 2010 has been surveyed for new quinolone antibiotics (see, Wiles, J. A.; Bradbury, B. J.; Pucci, M. J. New quinolone antibiotics: a survey of the literature from 2005 to 2010. *Expert Opin. Ther. Patents*, 2010, 20(10), 1295-1319), including the development of compounds by AstraZeneca, Vertex Pharmaceuticals and Pfizer that act on the gyrase B sub-unit of the enzyme.

Despite the availability of quinolone based agents, the pre-existing and burgeoning resistance to such agents requires the availability of new antibiotic and antibacterials agents. However, the high conservation of sequence identity between DNA gyrase and topoisomerase IV enzymes continues to provide an opportunity for the discovery and development of non-quinolone inhibitors possessing a broad spectrum of activity against these targets. The present description relates to compounds having activity toward wild-type and MDR bacteria. The present description also relates to compounds having activity against quinolone-resistant Gram-negative strains (including MDR strains) as well as antibacterial activity to MDR resistant Gram-positive pathogens (including MRSA strains). The present description also relates to compounds with selectivity between bacterial topoisomerase IV and DNA gyrase enzyme inhibition compared to human topoisomerase II enzyme inhibition. The present description further relates to compounds that may be combined with known antibacterial agents to provide additive or synergistic activity, thus enabling the development of a combination product for the treatment of Gram-negative (especially MDR strains) and Gram-positive infections.

All other documents referred to herein are incorporated by reference into the present application as though fully set forth herein.

SUMMARY

The present description relates to a compound of Formula (I):

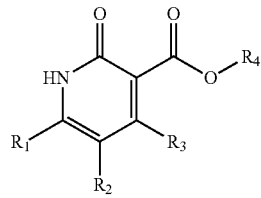

wherein $R_1$, $R_2$, $R_3$ and $R_4$ are as defined herein, and forms and compositions thereof, and also relates to uses of the compound of Formula (I) and methods of treating or ameliorating a bacterial infection, or for treating or ameliorating a multi-drug resistant (MDR) bacterial infection.

The present description further relates to a compound of Formula (I) having activity toward wild-type and MDR bacteria. The present description also relates to a compound of Formula (I) having activity against quinolone-resistant Gram-negative strains (including MDR strains) as well as antibacterial activity to MDR resistant Gram-positive pathogens (including MRSA strains). The present description also relates to a compound of Formula (I) having selectivity between bacterial topoisomerase IV and DNA gyrase enzyme inhibition compared to human topoisomerase II enzyme inhibition. The present description further relates to a compound of Formula (I) that may be combined with known antibacterial agents to provide additive or synergistic activity, thus enabling the development of a combination product for the treatment of Gram-negative (especially MDR strains) and Gram-positive infections.

DETAILED DESCRIPTION

The present description relates to a compound of Formula (I):

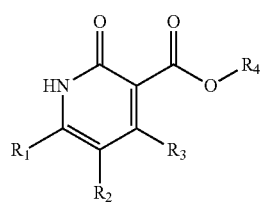

or a form thereof, wherein $R_1$ is aryl, heterocyclyl and heteroaryl each optionally substituted with one, two or three substituents each selected from $R_5$ and one additional substituent selected from $R_6$, wherein aryl, heterocyclyl and heteroaryl are selected from a bicyclic or tricyclic ring system;

$R_2$ is hydrogen, halogen, cyano, $C_{1-8}$alkyl, halo-$C_{1-8}$alkyl, hydroxyl-$C_{1-8}$alkyl, formyl-$C_{1-8}$alkyl, $C_{1-8}$alkoxy-$C_{1-8}$alkyl, $C_{1-8}$alkoxy, $C_{2-8}$alkenyl, $C_{2-8}$alkynyl, carboxy, amino, $C_{1-8}$alkyl-amino, ($C_{1-8}$alkyl)$_2$-amino, amino-$C_{1-8}$alkyl, $C_{1-8}$alkyl-amino-$C_{1-8}$alkyl, ($C_{1-8}$alkyl)$_2$-amino-$C_{1-8}$alkyl, $C_{3-14}$cycloalkyl, $C_{3-8}$cycloalkyl-oxy, aryl or aryl-$C_{1-8}$alkyl, wherein each instance of aryl is optionally substituted with one halogen substituent;

$R_3$ is hydrogen, halogen, hydroxyl, $C_{1-8}$alkyl, $C_{1-8}$alkoxy, carboxyl, amino, $C_{1-8}$alkyl-amino, ($C_{1-8}$alkyl)$_2$-amino or $C_{1-8}$alkyl-SO$_2$-amino;

$R_4$ is hydrogen or $C_{1-8}$alkyl;

$R_5$ is halogen, hydroxyl, oxo, cyano, nitro, $C_{1-8}$alkyl, hydroxyl-$C_{1-8}$alkyl, halo-$C_{1-8}$alkyl, $C_{1-8}$alkoxy, halo-$C_{1-8}$alkoxy, $C_{1-8}$alkyl-thio, carboxyl, $C_{1-8}$alkyl-carbonyl, $C_{1-8}$alkoxy-carbonyl, amino-carbonyl, amino, $C_{1-8}$alkyl-amino, ($C_{1-8}$alkyl)$_2$-amino, $C_{2-8}$alkenyl-amino, ($C_{2-8}$alkenyl)$_2$-amino, $C_{2-8}$alkynyl-amino, ($C_{2-8}$alkynyl)$_2$-amino, amino-$C_{1-8}$alkyl, $C_{1-10}$alkyl-amino-$C_{1-8}$alkyl, ($C_{1-8}$alkyl)$_2$-amino-$C_{1-8}$alkyl, $C_{2-8}$alkenyl-amino-$C_{1-8}$alkyl, ($C_{2-8}$alkenyl)$_2$-amino-$C_{1-8}$alkyl, $C_{2-8}$alkynyl-amino-$C_{1-8}$alkyl, ($C_{2-8}$alkynyl)$_2$-amino-$C_{1-8}$alkyl, halo-$C_{1-8}$alkyl-amino, (halo-$C_{1-8}$alkyl)$_2$-amino, halo-$C_{1-8}$alkyl-amino-$C_{1-8}$alkyl, (halo-$C_{1-8}$alkyl)$_2$-amino-$C_{1-8}$alkyl, $C_{1-8}$alkoxy-$C_{1-8}$alkyl-amino, ($C_{1-8}$alkoxy-$C_{1-8}$alkyl, $C_{1-8}$alkyl)-amino, ($C_{1-8}$alkoxy-$C_{1-8}$alkyl)$_2$-amino, $C_{1-8}$alkoxy-$C_{1-8}$alkyl-amino-$C_{1-8}$alkyl, ($C_{1-8}$alkoxy-$C_{1-8}$alkyl, $C_{1-8}$alkyl)-amino-$C_{1-8}$alkyl, ($C_{1-8}$alkoxy-$C_{1-8}$alkyl)$_2$-amino-$C_{1-8}$alkyl, amino-$C_{1-8}$alkyl-amino, (amino-$C_{1-8}$alkyl, $C_{1-8}$alkyl)amino, $C_{1-8}$alkyl-amino-$C_{1-8}$alkyl-amino, ($C_{1-8}$alkyl-amino-$C_{1-8}$alkyl, $C_{1-8}$alkyl)amino, ($C_{1-8}$alkyl)$_2$-amino-$C_{1-8}$alkyl-amino, [($C_{1-8}$alkyl)$_2$-amino-$C_{1-8}$alkyl, $C_{1-8}$alkyl]amino, amino-$C_{1-8}$alkyl-amino-$C_{1-8}$alkyl, (amino-$C_{1-8}$alkyl, $C_{1-8}$alkyl)amino-$C_{1-8}$alkyl, $C_{1-8}$alkyl-amino-$C_{1-8}$alkyl-amino-$C_{1-8}$alkyl, ($C_{1-8}$alkyl-amino-$C_{1-8}$alkyl, $C_{1-8}$alkyl)amino-$C_{1-8}$alkyl, ($C_{1-8}$alkyl)$_2$-amino-$C_{1-8}$alkyl-amino-$C_{1-8}$alkyl, [($C_{1-8}$alkyl)$_2$-amino-$C_{1-8}$alkyl, $C_{1-8}$alkyl]amino-$C_{1-8}$alkyl, hydroxyl-amino, hydroxyl-$C_{1-8}$alkyl-amino, (hydroxyl-$C_{1-8}$alkyl, $C_{1-8}$alkyl)amino, (hydroxyl-$C_{1-8}$alkyl)$_2$-amino, hydroxyl-$C_{1-8}$alkyl-amino-$C_{1-8}$alkyl, (hydroxyl-$C_{1-8}$alkyl, $C_{1-8}$alkyl)amino-$C_{1-8}$alkyl, hydroxyl-$C_{1-8}$alkyl-amino-$C_{1-8}$alkyl-amino, (hydroxyl-$C_{1-8}$alkyl-amino-$C_{1-8}$alkyl, $C_{1-8}$alkyl)amino, (hydroxyl-$C_{1-8}$alkyl, $C_{1-8}$alkyl)amino-$C_{1-8}$alkyl-amino, [(hydroxyl-$C_{1-8}$alkyl, $C_{1-8}$alkyl)amino-$C_{1-8}$alkyl, $C_{1-8}$alkyl]amino, ($C_{1-8}$alkyl-carbonyl, $C_{1-8}$alkyl)amino-$C_{1-8}$alkyl, $C_{1-8}$alkyl-amino-carbonyl, ($C_{1-8}$alkyl)$_2$-amino-carbonyl or ($C_{1-8}$alkyl)$_2$-amino-carbonyl-$C_{1-8}$alkyl-amino-$C_{1-8}$alkyl;

$R_6$ is $C_{3-14}$cycloalkyl, $C_{3-14}$cycloalkyl-$C_{1-8}$alkyl, $C_{3-14}$cycloalkyl-oxy, $C_{3-14}$cycloalkyl-$C_{1-8}$alkoxy, $C_{3-14}$cycloalkyl-amino, $C_{3-14}$cycloalkyl-amino-$C_{1-8}$alkyl, ($C_{3-14}$cycloalkyl, $C_{1-8}$alkyl)amino-$C_{1-8}$alkyl, ($C_{3-14}$cycloalkyl)$_2$-amino-$C_{1-8}$alkyl, $C_{3-14}$cycloalkyl-$C_{1-8}$alkyl-amino-$C_{1-8}$alkyl, ($C_{3-14}$cycloalkyl-$C_{1-8}$alkyl, $C_{1-8}$alkyl) amino-$C_{1-8}$alkyl, ($C_{3-14}$cycloalkyl-$C_{1-8}$alkyl)$_2$-amino-$C_{1-8}$alkyl, aryl-$C_{1-8}$alkyl, aryl-$C_{1-8}$alkoxy, aryl-amino, (aryl,$C_{1-8}$alkyl)amino, (aryl)$_2$-amino, aryl-amino-$C_{1-8}$alkyl, (aryl,$C_{1-8}$alkyl)amino-$C_{1-8}$alkyl, (aryl)$_2$-amino-$C_{1-8}$alkyl, aryl-$C_{1-8}$alkyl-amino, (aryl-$C_{1-8}$alkyl, $C_{1-8}$alkyl)amino, (aryl-$C_{1-8}$alkyl)$_2$-amino, aryl-$C_{1-8}$alkyl-amino-$C_{1-8}$alkyl, (aryl-$C_{1-8}$alkyl, $C_{1-8}$alkyl)amino-$C_{1-8}$alkyl, (aryl-$C_{1-8}$alkyl)$_2$-amino-$C_{1-8}$alkyl, heteroaryl, heteroaryl-$C_{1-8}$alkyl, heteroaryl-amino, heteroaryl-$C_{1-8}$alkyl-amino, (heteroaryl-$C_{1-8}$alkyl, $C_{1-8}$alkyl)amino, (heteroaryl-$C_{1-8}$alkyl)$_2$-amino, heteroaryl-$C_{1-8}$alkyl-amino-$C_{1-8}$alkyl, (heteroaryl-$C_{1-8}$alkyl, $C_{1-8}$alkyl)amino-$C_{1-8}$alkyl, heterocyclyl, heterocyclyl-$C_{1-8}$alkyl, heterocyclyl-oxy, heterocyclyl-$C_{1-8}$alkoxy, heterocyclyl-amino, (heterocyclyl, $C_{1-8}$alkyl)amino, (heterocyclyl)$_2$-amino, heterocyclyl-amino-$C_{1-8}$alkyl, (heterocyclyl, $C_{1-8}$alkyl) amino-$C_{1-8}$alkyl, (heterocyclyl)$_2$-amino-$C_{1-8}$alkyl, (heterocyclyl, $C_{3-14}$cycloalkyl)amino-$C_{1-8}$alkyl, heterocyclyl-$C_{1-8}$alkyl-amino-$C_{1-8}$alkyl, (heterocyclyl-$C_{1-8}$alkyl, $C_{1-8}$alkyl)amino-$C_{1-8}$alkyl, (heterocyclyl-$C_{1-8}$alkyl)$_2$-amino-$C_{1-8}$alkyl, heterocyclyl-oxy-amino, (heterocyclyl-oxy, $C_{1-8}$alkyl)amino, (heterocyclyl-oxy)$_2$-amino, (heterocyclyl-oxy-$C_{1-8}$alkyl, $C_{1-8}$alkyl)amino, heterocyclyl-carbonyl or heterocyclyl-carbonyl-oxy;

wherein each instance of heterocyclyl is optionally substituted with one, two or three substituents each selected from $R_7$; and, wherein each instance of $C_{3-14}$cycloalkyl, aryl and heteroaryl is optionally substituted with one, two or three substituents each selected from $R_8$;

$R_7$ is azido, halogen, hydroxyl, oxo, cyano, nitro, $C_{1-8}$alkyl, halo-$C_{1-8}$alkyl, hydroxyl-$C_{1-8}$alkyl, $C_{1-8}$alkoxy-$C_{1-8}$alkyl, $C_{1-8}$alkoxy, halo-$C_{1-8}$alkoxy, hydroxyl-$C_{1-8}$alkoxy, carboxyl, $C_{1-8}$alkyl-carbonyl, $C_{1-8}$alkoxy-carbonyl, amino, $C_{1-8}$alkyl-amino, ($C_{1-8}$alkyl)$_2$-amino, halo-$C_{1-8}$alkyl-amino, (halo-$C_{1-8}$alkyl)$_2$-amino, halo-$C_{1-8}$alkyl-amino-$C_{1-8}$alkyl, (halo-$C_{1-8}$alkyl)$_2$-amino-$C_{1-8}$alkyl, amino-$C_{1-8}$alkyl, $C_{1-8}$alkyl-amino-$C_{1-8}$alkyl, ($C_{1-8}$alkyl)$_2$-amino-$C_{1-8}$alkyl, [($C_{1-8}$alkyl)$_2$-amino-$C_{1-8}$alkyl, $C_{1-8}$alkyl] amino-$C_{1-8}$alkyl $C_{1-8}$alkyl-thio, amino-carbonyl, $C_{1-8}$alkyl-amino-carbonyl, ($C_{1-8}$alkyl)$_2$-amino-carbonyl, $C_{1-8}$alkyl-carbonyl-amino, (carboxyl-$C_{1-8}$alkyl, $C_{1-8}$alkyl)amino-carbonyl-amino, $C_{3-14}$cycloalkyl, $C_{3-14}$cycloalkyl-amino, aryl, aryl-$C_{1-8}$alkyl, aryl-amino, (aryl,$C_{1-8}$alkyl)amino, (aryl)$_2$-amino, aryl-$C_{1-8}$alkyl-amino, (aryl-$C_{1-8}$alkyl, $C_{1-8}$alkyl)amino, (aryl-$C_{1-8}$alkyl)$_2$-amino, aryl-$C_{1-8}$alkyl-amino-$C_{1-8}$alkyl, (aryl-$C_{1-8}$alkyl, $C_{1-8}$alkyl)amino-$C_{1-8}$alkyl, (aryl-$C_{1-8}$alkyl)$_2$-amino-$C_{1-8}$alkyl, aryl-amino-$C_{1-8}$alkyl, (aryl,$C_{1-8}$alkyl)amino-$C_{1-8}$alkyl, (aryl)$_2$-amino-$C_{1-8}$alkyl, aryl-amino-carbonyl, aryl-$C_{1-8}$alkoxy, aryl-$C_{1-8}$alkoxy-carbonyl-amino, heteroaryl, heteroaryl-$C_{1-8}$alkyl, heteroaryl-amino, (heteroaryl)$_2$-amino, heteroaryl-$C_{1-8}$alkyl-amino, (heteroaryl-$C_{1-8}$alkyl, $C_{1-8}$alkyl)amino, (heteroaryl-$C_{1-8}$alkyl)$_2$-amino, heteroaryl-$C_{1-8}$alkyl-amino-$C_{1-8}$alkyl, (heteroaryl-$C_{1-8}$alkyl, $C_{1-8}$alkyl)amino-$C_{1-8}$alkyl, (heteroaryl-$C_{1-8}$alkyl)$_2$-amino-$C_{1-8}$alkyl, heterocyclyl, heterocyclyl-$C_{1-8}$alkyl, heterocyclyl-amino-$C_{1-8}$alkyl or heterocyclyl-oxy;

wherein each instance of $C_{3-14}$cycloalkyl is optionally substituted with one substituent selected from $R_9$;

wherein each instance of aryl is optionally substituted with one substituent selected from $R_{10}$; and, wherein each instance of heterocyclyl and heteroaryl is optionally substituted with one substituent selected from $R_{11}$;

$R_8$ is azido, halogen, hydroxyl, cyano, nitro, $C_{1-8}$alkyl, halo-$C_{1-8}$alkyl, $C_{1-8}$alkoxy, $C_{1-8}$alkoxy-$C_{1-8}$alkyl, halo-$C_{1-8}$alkoxy, carboxyl, $C_{1-8}$alkoxy-carbonyl, amino, $C_{1-8}$alkyl-amino, ($C_{1-8}$alkyl)$_2$-amino, $C_{1-8}$alkyl-thio, aryl, aryl-$C_{1-8}$alkoxy, heteroaryl, heterocyclyl, heterocyclyl-$C_{1-8}$alkyl or heterocyclyl-oxy;

$R_9$ is amino, $C_{1-8}$alkyl-amino, ($C_{1-8}$alkyl)$_2$-amino, amino-$C_{1-8}$alkyl, $C_{1-8}$alkyl-amino-$C_{1-8}$alkyl, ($C_{1-8}$alkyl)$_2$-amino-$C_{1-8}$alkyl or aryl-$C_{1-8}$alkyl-amino;

$R_{10}$ is halogen; and, $R_{11}$ is halogen, hydroxyl, $C_{1-8}$alkyl, halo-$C_{1-8}$alkyl, $C_{1-8}$alkoxy, $C_{1-8}$alkoxy-$C_{1-8}$alkyl, halo-$C_{1-8}$alkoxy, amino, $C_{1-8}$alkyl-amino or ($C_{1-8}$alkyl)$_2$-amino.

One embodiment of the present description includes a compound of Formula (I) or a form thereof, wherein $R_1$ is aryl selected from naphthalenyl;

heterocyclyl selected from indolinyl, 1,2,3,4-tetrahydroquinolinyl, 3,4-dihydro-2H-benzo[b][1,4]oxazinyl, 2,3-dihydrobenzo[d]oxazolyl, 2,3,4,9-tetrahydro-1H-carbazolyl, 1,2,3,4-tetrahydroquinoxalinyl, 3,4-dihydro-2H-pyrido[3,2-b][1,4]oxazinyl, 6,7,8,9-tetrahydropyrido[1,2-a]indolyl, 2,3,4,9-tetrahydro-1H-pyrido[3,4-b]indolyl, 2,3,4,5-tetrahydro-1H-pyrido[4,3-b]indolyl, 1,2,3,4-tetrahydropyrazino[1,2-a]indolyl and 2,3-dihydro-1H-pyrrolo[1,2-a]indolyl; and, heteroaryl selected from 1H-indolyl, 1H-indazolyl, 2H-indazolyl, indolizinyl, benzofuranyl, benzo[b]thienyl, benzo[d]oxazolyl, quinolinyl, quinoxalinyl, 9H-carbazolyl, 1H-pyrrolo[2,3-b]pyridinyl, pyrazolo[1,5-a]pyrazinyl, [1,2,4]triazolo[1,5-a]pyridinyl, [1,2,4]triazolo[4,3-a]pyridinyl, imidazo[1,2-a]pyridinyl, 3H-imidazo[4,5-b]pyridinyl, 1H-benzo[d]imidazolyl, 1H-pyrrolo[2,3-c]pyridinyl, 6H-thieno[2,3-b]pyrrolyl and 1H-pyrrolo[3,2-b]pyridinyl.

One embodiment of the present description includes a compound of Formula (I) or a form thereof, wherein $R_1$ is aryl selected from naphthalen-2-yl;
heterocyclyl selected from indolin-5-yl, 1,2,3,4-tetrahydroquinolin-6-yl, 3,4-dihydro-2H-benzo[b][1,4]oxazin-7-yl, 2,3-dihydrobenzo[d]oxazol-6-yl, 2,3,4,9-tetrahydro-1H-carbazol-6-yl, 1,2,3,4-tetrahydroquinoxalin-6-yl, 3,4-dihydro-2H-pyrido[3,2-b][1,4]oxazin-7-yl, 6,7,8,9-tetrahydropyrido[1,2-a]indol-2-yl, 2,3,4,9-tetrahydro-1H-pyrido[3,4-b]indol-7-yl, 2,3,4,5-tetrahydro-1H-pyrido[4,3-b]indol-7-yl, 1,2,3,4-tetrahydropyrazino[1,2-a]indol-8-yl and 2,3-dihydro-1H-pyrrolo[1,2-a]indol-7-yl; and,
heteroaryl selected from 1H-indol-2-yl, 1H-indol-3-yl, 1H-indol-4-yl, 1H-indol-5-yl, 1H-indol-6-yl, 1H-indazol-4-yl, 1H-indazol-5-yl, 1H-indazol-6-yl, 2H-indazol-5-yl, 2H-indazol-6-yl, indolizin-6-yl, benzofuran-5-yl, benzo[b]thien-5-yl, benzo[d]oxazol-6-yl, quinolin-6-yl, quinoxalin-6-yl, 9H-carbazol-2-yl, 1H-pyrrolo[2,3-b]pyridin-5-yl, 1H-pyrrolo[2,3-b]pyridin-5-yl, 1H-pyrrolo[2,3-b]pyridin-6-yl, pyrazolo[1,5-a]pyrazin-2-yl, [1,2,4]triazolo[1,5-a]pyridin-6-yl, [1,2,4]triazolo[4,3-a]pyridin-6-yl, imidazo[1,2-a]pyridin-2-yl, imidazo[1,2-a]pyridin-6-yl, 3H-imidazo[4,5-b]pyridin-6-yl, 1H-benzo[d]imidazol-5-yl, 1H-pyrrolo[2,3-c]pyridin-5-yl, 6H-thieno[2,3-b]pyrrol-2-yl, 1H-pyrrolo[3,2-b]pyridin-5-yl and 1H-pyrrolo[3,2-b]pyridin-6-yl.

One embodiment of the present description includes a compound of Formula (I) or a form thereof, wherein $R_2$, $R_6$, $R_7$ and $R_8$ is
$C_{3-14}$cycloalkyl selected in each instance, when present, from cyclopropyl, cyclobutyl, cyclopentyl, cyclohexyl or cycloheptyl;
aryl selected in each instance, when present, from phenyl;
heteroaryl selected in each instance, when present, from pyrrolyl, thiazolyl, 1H-1,2,3-triazolyl, 1H-tetrazolyl, 2H-tetrazolyl, imidazolyl or pyridinyl;
heterocyclyl selected in each instance, when present, from azetidinyl, pyrrolidinyl, tetrahydrofuranyl, piperidinyl, piperazinyl, morpholinyl, 1,4-diazepanyl, 1,3-dioxolanyl, 2,5-dihydro-1H-pyrrolyl, dihydro-1H-imidazolyl, 1,4,5,6-tetrahydropyrimidinyl, 1,2,3,6-tetrahydropyridinyl, tetrahydro-2H-pyranyl, indolinyl, 2,3-dihydrobenzo[d]oxazolyl, 3,4-dihydro-2H-benzo[b][1,4]oxazinyl, 3,4-dihydroisoquinolin-(1H)-yl, 1,2,3,4-tetrahydroisoquinolinyl, 1,2,3,4-tetrahydroquinoxalinyl, hexahydropyrrolo[3,4-b][1,4]oxazin-(2H)-yl, (4aR,7aS)-hexahydropyrrolo[3,4-b][1,4]oxazin-(4aH)-yl, 3,4-dihydro-2H-pyrido[3,2-b][1,4]oxazinyl, (cis)-octahydrocyclopenta[c]pyrrolyl, hexahydropyrrolo[3,4-b]pyrrol-(1H)-yl, (3aR,6aR)-hexahydropyrrolo[3,4-b]pyrrol-(1H)-yl, (3aR,6aS)-hexahydropyrrolo[3,4-c]pyrrol-(1H)-yl, 5H-pyrrolo[3,4-b]pyridin-(7H)-yl, 5,7-dihydro-6H-pyrrolo[3,4-b]pyridinyl, tetrahydro-1H-pyrrolo[3,4-b]pyridin-(2H,7H,7aH)-yl, hexahydro-1H-pyrrolo[3,4-b]pyridin-(2H)-yl, (4aR,7aR)-hexahydro-1H-pyrrolo[3,4-b]pyridin-(2H)-yl, octahydro-6H-pyrrolo[3,4-b]pyridinyl, 2,3,4,9-tetrahydro-1H-carbazolyl, 1,2,3,4-tetrahydropyrazino[1,2-a]indolyl, 2,3-dihydro-1H-pyrrolo[1,2-a]indolyl, (3aR,6aR)-hexahydrocyclopenta[c]pyrrol-(1H)-yl, (3aR,4R,6aS)-hexahydrocyclopenta[c]pyrrol-(1H)-yl, (3aR,4S,6aS)-hexahydrocyclopenta[c]pyrrol-(1H)-yl, (3aR,5r,6aS)-hexahydrocyclopenta[c]pyrrol-(1H)-yl, 1,3-dihydro-2H-isoindolyl, octahydro-2H-isoindolyl, (3aS)-1,3,3a,4,5,6-hexahydro-2H-isoindolyl, (3aR,4R,7aS)-1H-isoindol-(3H,3aH,4H,5H,6H,7H,7aH)-yl, (3aR,7aS)-octahydro-2H-isoindolyl, (3aR,4R,7aS)-octahydro-2H-isoindolyl, (3aR,4S,7aS)-octahydro-2H-isoindolyl, 2,5-diazabicyclo[2.2.1]heptanyl, 2-azabicyclo[2.2.1]hept-5-enyl, 3-azabicyclo[3.1.0]hexanyl, (1R,5S,6s)-3-azabicyclo[3.1.0]hexanyl, (cis,cis)-3-azabicyclo[3.1.0]hexanyl, 3,6-diazabicyclo[3.1.0]hexanyl, (1S,5R,6R)-3-azabicyclo[3.2.0]heptanyl, (1S,5R,6S)-3-azabicyclo[3.2.0]heptanyl, 5-azaspiro[2.4]heptanyl, 2,6-diazaspiro[3.3]heptanyl, 2,5-diazaspiro[3.4]octanyl, 2,6-diazaspiro[3.4]octanyl, 2,7-diazaspiro[3.5]nonanyl, 2,7-diazaspiro[4.4]nonanyl, 2-azaspiro[4.5]decanyl or 2,8-diazaspiro[4.5]decanyl.

One embodiment of the present description includes a compound of Formula (I) or a form thereof, wherein $R_6$, $R_7$ and $R_8$ is
heteroaryl selected in each instance, when present, from pyrrol-1-yl, thiazol-2-yl, 1H-1,2,3-triazol-1-yl, 1H-tetrazol-5-yl, 2H-tetrazol-2-yl, imidazol-1-yl, pyridin-2-yl, pyridin-3-yl or pyridin-4-yl;
heterocyclyl selected in each instance, when present, from azetidin-1-yl, pyrrolidin-1-yl, pyrrolidin-2-yl, pyrrolidin-3-yl, tetrahydrofuran-2-yl, piperidin-1-yl, piperidin-2-yl, piperidin-3-yl, piperidin-4-yl, piperazin-1-yl, piperazin-2-yl, morpholin-4-yl, 1,4-diazepan-1-yl, 1,3-dioxolan-2-yl, 2,5-dihydro-1H-pyrrol-1-yl, dihydro-1H-imidazol-2-yl, 1,4,5,6-tetrahydropyrimidin-2-yl, 1,2,3,6-tetrahydropyridin-4-yl, tetrahydro-2H-pyran-2-yl, tetrahydro-2H-pyran-4-yl, 3,4-dihydroisoquinolin-2(1H)-yl, 1,2,3,4-tetrahydroisoquinolin-1-yl, hexahydropyrrolo[3,4-b][1,4]oxazin-6(2H)-yl, (4aR,7aS)-hexahydropyrrolo[3,4-b][1,4]oxazin-4(4aH)-yl, (cis)-octahydrocyclopenta[c]pyrrol-4-yl, hexahydropyrrolo[3,4-b]pyrrol-5(1H)-yl, (3aR,6aR)-hexahydropyrrolo[3,4-b]pyrrol-5(1H)-yl, (3aR,6aS)-hexahydropyrrolo[3,4-c]pyrrol-2(1H)-yl, 5H-pyrrolo[3,4-b]pyridin-6(7H)-yl, 5,7-dihydro-6H-pyrrolo[3,4-b]pyridin-6-yl, tetrahydro-1H-pyrrolo[3,4-b]pyridin-6(2H,7H,7aH)-yl, hexahydro-1H-pyrrolo[3,4-b]pyridin-6(2H)-yl, (4aR,7aR)-hexahydro-1H-pyrrolo[3,4-b]pyridin-6(2H)-yl, octahydro-6H-pyrrolo[3,4-b]pyridin-6-yl, (3aR,6aR)-hexahydrocyclopenta[c]pyrrol-3a(1H)-yl, (3aR,4R,6aS)-hexahydrocyclopenta[c]pyrrol-2(1H)-yl, (3aR,4S,6aS)-hexahydrocyclopenta[c]pyrrol-2(1H)-yl, (3aR,5r,6aS)-hexahydrocyclopenta[c]pyrrol-2(1H)-yl, 1,3-dihydro-2H-isoindol-2-yl, octahydro-2H-isoindol-2-yl, (3aS)-1,3,3a,4,5,6-hexahydro-2H-isoindol-2-yl, (3aR,4R,7aS)-1H-isoindol-2(3H,3aH,4H,5H,6H,7H,7aH)-yl, (3aR,7aS)-octahydro-2H-isoindol-2-yl, (3aR,4R,7aS)-octahydro-2H-isoindol-2-yl, (3aR,4S,7aS)-octahydro-2H-isoindol-2-yl, 2,5-diazabicyclo[2.2.1]heptan-2-yl, 2-azabicyclo[2.2.1]hept-5-en-2-yl, 3-azabicyclo[3.1.0]hexan-3-yl, (1R,5S,6s)-3-azabicyclo[3.1.0]hexan-3-yl, (1R,5S,6s)-3-azabicyclo[3.1.0]hexan-6-yl, (cis,cis)-3-azabicyclo[3.1.0]hexan-3-yl, 3,6-diazabicyclo[3.1.0]hexan-3-yl, (1S,5R,6R)-3-azabicyclo[3.2.0]heptan-3-yl, (1S,5R,6S)-3-azabicyclo[3.2.0]heptan-3-yl, 5-azaspiro[2.4]heptan-5-yl, 2,6-diazaspiro[3.3]heptan-2-yl, 2,5-diazaspiro[3.4]octan-2-yl, 2,6-diazaspiro[3.4]octan-6-yl, 2,7-diazaspiro[3.5]nonan-2-yl, 2,7-diazaspiro[4.4]nonan-2-yl, 2-azaspiro[4.5]decan-2-yl or 2,8-diazaspiro[4.5]decan-2-yl.

One embodiment of the present description includes a compound of Formula (I) or a form thereof, wherein $R_6$, $R_7$ and $R_8$ is heteroaryl selected in each instance, when present, from pyridinyl;

heterocyclyl selected in each instance, when present, from azetidinyl, pyrrolidinyl, tetrahydrofuranyl, piperidinyl, piperazinyl, morpholinyl, 1,4-diazepanyl, 1,3-dioxolanyl, dihydro-1H-imidazolyl, 1,4,5,6-tetrahydropyrimidinyl, 1,2,3,6-tetrahydropyridinyl, tetrahydro-2H-pyranyl, 3,4-dihydroisoquinolin-(1H)-yl, 1,2,3,4-tetrahydroisoquinolinyl, 5H-pyrrolo[3,4-b]pyridin-(7H)-yl, tetrahydro-1H-pyrrolo[3,4-b]pyridin-(2H,7H,7aH)-yl, (3aR,4R,6aS)-hexahydrocyclopenta[c]pyrrol-(1H)-yl, (3aR,4R,7aS)-1H-isoindol-(3H,3aH,4H,5H,6H,7H,7aH)-yl, 2,5-diazabicyclo[2.2.1]heptanyl or (1R,5S,6s)-3-azabicyclo[3.1.0]hexanyl.

One embodiment of the present description includes a compound of Formula (I) or a form thereof, wherein $R_6$, $R_7$ and $R_8$ is heteroaryl selected in each instance, when present, from pyridin-2-yl, pyridin-3-yl or pyridin-4-yl;

heterocyclyl selected in each instance, when present, from azetidin-1-yl, pyrrolidin-1-yl, pyrrolidin-2-yl, pyrrolidin-3-yl, tetrahydrofuran-2-yl, piperidin-1-yl, piperidin-2-yl, piperidin-3-yl, piperidin-4-yl, piperazin-1-yl, piperazin-2-yl, morpholin-4-yl, 1,4-diazepan-1-yl, 1,3-dioxolan-2-yl, dihydro-1H-imidazol-2-yl, 1,4,5,6-tetrahydropyrimidin-2-yl, 1,2,3,6-tetrahydropyridin-4-yl, tetrahydro-2H-pyran-2-yl, tetrahydro-2H-pyran-4-yl, 3,4-dihydroisoquinolin-2(1H)-yl, 1,2,3,4-tetrahydroisoquinolin-1-yl, 5H-pyrrolo[3,4-b]pyridin-6(7H)-yl, tetrahydro-1H-pyrrolo[3,4-b]pyridin-6(2H,7H,7aH)-yl, (3aR,4R,6aS)-hexahydrocyclopenta[c]pyrrol-2(1H)-yl, (3aR,4R,7aS)-1H-isoindol-2(3H,3aH,4H,5H,6H,7H,7aH)-yl, 2,5-diazabicyclo[2.2.1]heptan-2-yl, (1R,5S,6s)-3-azabicyclo[3.1.0]hexan-3-yl or (1R,5S,6s)-3-azabicyclo[3.1.0]hexan-6-yl.

One embodiment of the present description includes a compound of Formula (I) or a form thereof, wherein, $R_6$, $R_7$ and $R_8$ is heteroaryl selected in each instance, when present, from pyrrolyl, imidazolyl, 1H-tetrazolyl or 2H-tetrazolyl;

heterocyclyl selected in each instance, when present, from azetidinyl, pyrrolidinyl, tetrahydrofuranyl, piperidinyl, piperazinyl, morpholinyl, 1,4-diazepanyl, 1,3-dioxolanyl, 2,5-dihydro-1H-pyrrolyl, dihydro-1H-imidazolyl, 1,4,5,6-tetrahydropyrimidinyl, 1,2,3,6-tetrahydropyridinyl, tetrahydro-2H-pyranyl, indolinyl, 2,3-dihydrobenzo[d]oxazolyl, 3,4-dihydro-2H-benzo[b][1,4]oxazinyl, 3,4-dihydroisoquinolin-(1H)-yl, 1,2,3,4-tetrahydroisoquinolinyl, 1,2,3,4-tetrahydroquinoxalinyl, hexahydropyrrolo[3,4-b][1,4]oxazin-(2H)-yl, (4aR,7aS)-hexahydropyrrolo[3,4-b][1,4]oxazin-(4aH)-yl, 3,4-dihydro-2H-pyrido[3,2-b][1,4]oxazinyl, (cis)-octahydrocyclopenta[c]pyrrolyl, hexahydropyrrolo[3,4-b]pyrrol-(1H)-yl, (3aR,6aR)-hexahydropyrrolo[3,4-b]pyrrol-(1H)-yl, (3aR,6aS)-hexahydropyrrolo[3,4-c]pyrrol-(1H)-yl, 5H-pyrrolo[3,4-b]pyridin-(7H)-yl, 5,7-dihydro-6H-pyrrolo[3,4-b]pyridinyl, tetrahydro-1H-pyrrolo[3,4-b]pyridin-(2H,7H,7aH)-yl, hexahydro-1H-pyrrolo[3,4-b]pyridin-(2H)-yl, (4aR,7aR)-hexahydro-1H-pyrrolo[3,4-b]pyridin-(2H)-yl, octahydro-6H-pyrrolo[3,4-b]pyridinyl, 2,3,4,9-tetrahydro-1H-carbazolyl, 1,2,3,4-tetrahydropyrazino[1,2-a]indolyl, 2,3-dihydro-1H-pyrrolo[1,2-a]indolyl, (3aR,6aR)-hexahydrocyclopenta[c]pyrrol-(1H)-yl, (3aR,4R,6aS)-hexahydrocyclopenta[c]pyrrol-(1H)-yl, (3aR,4S,6aS)-hexahydrocyclopenta[c]pyrrol-(1H)-yl, (3aR,5r,6aS)-hexahydrocyclopenta[c]pyrrol-(1H)-yl, 1,3-dihydro-2H-isoindolyl, octahydro-2H-isoindolyl, (3aS)-1,3,3a,4,5,6-hexahydro-2H-isoindolyl, (3aR,4R,7aS)-1H-isoindol-(3H,3aH,4H,5H,6H,7H,7aH)-yl, (3aR,7aS)-octahydro-2H-isoindolyl, (3aR,4R,7aS)-octahydro-2H-isoindolyl, (3aR,4S,7aS)-octahydro-2H-isoindolyl, 2,5-diazabicyclo[2.2.1]heptanyl, 2-azabicyclo[2.2.1]hept-5-enyl, 3-azabicyclo[3.1.0]hexanyl, (1R,5S,6s)-3-azabicyclo[3.1.0]hexanyl, (cis,cis)-3-azabicyclo[3.1.0]hexanyl, 3,6-diazabicyclo[3.1.0]hexanyl, (1S,5R,6R)-3-azabicyclo[3.2.0]heptanyl, (1S,5R,6S)-3-azabicyclo[3.2.0]heptanyl, 5-azaspiro[2.4]heptanyl, 2,6-diazaspiro[3.3]heptanyl, 2,5-diazaspiro[3.4]octanyl, 2,6-diazaspiro[3.4]octanyl, 2,7-diazaspiro[3.5]nonanyl, 2,7-diazaspiro[4.4]nonanyl, 2-azaspiro[4.5]decanyl or 2,8-diazaspiro[4.5]decanyl.

One embodiment of the present description includes a compound of Formula (I) or a form thereof, wherein $R_2$, $R_6$, $R_7$ and $R_8$ is heteroaryl selected in each instance, when present, from 1H-tetrazol-5-yl, imidazol-1-yl, pyrrol-1-yl or 2H-tetrazol-2-yl;

heterocyclyl selected in each instance, when present, from azetidin-1-yl, pyrrolidin-1-yl, pyrrolidin-2-yl, pyrrolidin-3-yl, tetrahydrofuran-2-yl, piperidin-1-yl, piperidin-2-yl, piperidin-3-yl, piperidin-4-yl, piperazin-1-yl, piperazin-2-yl, morpholin-4-yl, 1,4-diazepan-1-yl, 1,3-dioxolan-2-yl, dihydro-1H-imidazol-2-yl, 1,4,5,6-tetrahydropyrimidin-2-yl, 1,2,3,6-tetrahydropyridin-4-yl, tetrahydro-2H-pyran-2-yl, tetrahydro-2H-pyran-4-yl, 3,4-dihydroisoquinolin-2(1H)-yl, 1,2,3,4-tetrahydroisoquinolin-1-yl, 5H-pyrrolo[3,4-b]pyridin-6(7H)-yl, tetrahydro-1H-pyrrolo[3,4-b]pyridin-6(2H,7H,7aH)-yl, (3aR,4R,6aS)-hexahydrocyclopenta[c]pyrrol-2(1H)-yl, (3aR,4R,7aS)-1H-isoindol-2(3H,3aH,4H,5H,6H,7H,7aH)-yl, 2,5-diazabicyclo[2.2.1]heptan-2-yl, (1R,5S,6s)-3-azabicyclo[3.1.0]hexan-3-yl or (1R,5S,6s)-3-azabicyclo[3.1.0]hexan-6-yl.

One embodiment of the present description includes a compound of Formula (I) or a form thereof, wherein $R_2$ is hydrogen, cyano, $C_{1-8}$alkyl, halo-$C_{1-8}$alkyl, hydroxyl-$C_{1-8}$alkyl, formyl-$C_{1-8}$alkyl, $C_{1-8}$alkoxy-$C_{1-8}$alkyl, $C_{1-8}$alkoxy, $C_{2-8}$alkenyl, $C_{2-8}$alkynl, carboxy, $C_{3-14}$cycloalkyl, aryl or aryl-$C_{1-8}$alkyl, wherein each instance of aryl is optionally substituted with one halogen substituent;

$R_3$ is hydrogen, hydroxyl, $C_{1-8}$alkoxy, carboxyl or amino;

$R_4$ is hydrogen or $C_{1-8}$alkyl;

$R_5$ is halogen, oxo, cyano, $C_{1-8}$alkyl, hydroxyl-$C_{1-8}$alkyl, $C_{1-8}$alkoxy, carboxyl, amino-carbonyl, amino, $C_{1-8}$alkyl-amino, $(C_{1-8}$alkyl$)_2$-amino, $(C_{2-8}$alkenyl$)_2$-amino, amino-$C_{1-8}$alkyl, $C_{1-8}$alkyl-amino-$C_{1-8}$alkyl, $(C_{1-8}$alkyl$)_2$-amino-$C_{1-8}$alkyl, $C_{2-8}$alkenyl-amino-$C_{1-8}$alkyl, $C_{2-8}$alkynyl-amino-$C_{1-8}$alkyl, halo-$C_{1-8}$alkyl-amino, halo-$C_{1-8}$alkyl-amino-$C_{1-8}$alkyl, (hydroxyl-$C_{1-8}$alkyl, $C_{1-8}$alkyl)amino, $(C_{1-8}$alkoxy-$C_{1-8}$alkyl, $C_{1-8}$alkyl)-amino-$C_{1-8}$alkyl, $(C_{1-8}$alkyl$)_2$-amino-$C_{1-8}$alkyl-amino, $[(C_{1-8}$alkyl$)_2$-amino-$C_{1-8}$alkyl, $C_{1-8}$alkyl]amino, amino-$C_{1-8}$alkyl-amino-$C_{1-8}$alkyl, $C_{1-8}$alkyl-amino-$C_{1-8}$alkyl-amino-$C_{1-8}$alkyl, $(C_{1-8}$alkyl$)_2$-amino-$C_{1-8}$alkyl-amino-$C_{1-8}$alkyl, $[(C_{1-8}$alkyl$)_2$-amino-$C_{1-8}$alkyl, $C_{1-8}$alkyl]amino-$C_{1-8}$alkyl or $(C_{1-8}$alkyl-carbonyl, $C_{1-8}$alkyl)amino-$C_{1-8}$alkyl;

$R_6$ is $C_{3-14}$cycloalkyl-amino-$C_{1-8}$alkyl, $(C_{3-14}$cycloalkyl, $C_{1-8}$alkyl)amino-$C_{1-8}$alkyl, $C_{3-14}$cycloalkyl-$C_{1-8}$alkyl-amino-$C_{1-8}$alkyl, aryl, aryl-amino, (aryl,$C_{1-8}$alkyl)amino, aryl-amino-$C_{1-8}$alkyl, aryl-$C_{1-8}$alkyl-amino-$C_{1-8}$alkyl, (aryl-$C_{1-8}$alkyl, $C_{1-8}$alkyl)amino-$C_{1-8}$alkyl, (aryl- $C_{1-8}$alkyl)$_2$-amino-$C_{1-8}$alkyl, heteroaryl, heteroaryl-$C_{1-8}$alkyl-amino-$C_{1-8}$alkyl, (heteroaryl-$C_{1-8}$alkyl, $C_{1-8}$alkyl)amino-$C_{1-8}$alkyl, heterocyclyl, heterocyclyl-$C_{1-8}$alkyl, heterocyclyl-amino-$C_{1-8}$alkyl, (heterocyclyl, $C_{1-8}$alkyl)amino-$C_{1-8}$alkyl, (heterocyclyl, $C_{3-14}$cycloalkyl-$C_{1-8}$alkyl)amino-$C_{1-8}$alkyl, heterocyclyl-$C_{1-8}$alkyl-amino-$C_{1-8}$alkyl or (heterocyclyl-oxy-$C_{1-8}$alkyl, $C_{1-8}$alkyl)amino;

wherein each instance of heterocyclyl is optionally substituted with one, two or three substituents each selected from $R_7$; and, wherein each instance of heteroaryl is optionally substituted with one, two or three substituents each selected from $R_8$;

$R_7$ is azido, halogen, hydroxyl, cyano, $C_{1-8}$alkyl, halo-$C_{1-8}$alkyl, hydroxyl-$C_{1-8}$alkyl, $C_{1-8}$alkoxy-$C_{1-8}$alkyl, $C_{1-8}$alkoxy, carboxyl, $C_{1-8}$alkyl-carbonyl, $C_{1-8}$alkoxy-carbonyl, amino, $C_{1-8}$alkyl-amino, ($C_{1-8}$alkyl)$_2$-amino, amino-$C_{1-8}$alkyl, $C_{1-8}$alkyl-amino-$C_{1-8}$alkyl, ($C_{1-8}$alkyl)$_2$-amino-$C_{1-8}$alkyl, [($C_{1-8}$alkyl)$_2$-amino-$C_{1-8}$alkyl, $C_{1-8}$alkyl]amino-$C_{1-8}$alkyl ($C_{1-8}$alkyl)$_2$-amino-carbonyl, $C_{1-8}$alkyl-carbonyl-amino, (carboxyl-$C_{1-8}$alkyl, $C_{1-8}$alkyl)amino-carbonyl-amino, $C_{3-14}$cycloalkyl, $C_{3-14}$cycloalkyl-amino, aryl, aryl-$C_{1-8}$alkyl, aryl-amino, (aryl,$C_{1-8}$alkyl)amino, aryl-$C_{1-8}$alkyl-amino, (aryl-$C_{1-8}$alkyl, $C_{1-8}$alkyl)amino, (aryl-$C_{1-8}$alkyl)$_2$-amino, aryl-$C_{1-8}$alkyl-amino-$C_{1-8}$alkyl, (aryl-$C_{1-8}$alkyl, $C_{1-8}$alkyl) amino-$C_{1-8}$alkyl, (aryl-$C_{1-8}$alkyl)$_2$-amino-$C_{1-8}$alkyl, aryl-amino-$C_{1-8}$alkyl, aryl-$C_{1-8}$alkoxy, aryl-$C_{1-8}$alkoxy-carbonyl-amino, heteroaryl, heteroaryl-$C_{1-8}$alkyl-amino-$C_{1-8}$alkyl, heterocyclyl, heterocyclyl-$C_{1-8}$alkyl, heterocyclyl-amino-$C_{1-8}$alkyl or heterocyclyl-oxy;

wherein each instance of $C_{3-14}$cycloalkyl is optionally substituted with one substituent selected from $R_9$; and, wherein each instance of aryl is optionally substituted with one substituent selected from $R_{10}$;

$R_8$ is $C_{1-8}$alkyl;

$R_9$ is amino, ($C_{1-8}$alkyl)$_2$-amino or aryl-$C_{1-8}$alkyl-amino; and, $R_{10}$ is halogen.

One embodiment of the present description includes a compound of Formula (I) or a form thereof, wherein $R_2$ is $C_{1-8}$alkyl selected from methyl, ethyl, propyl or isopropyl; hydroxyl-$C_{1-8}$alkyl selected from hydroxyl-methyl, hydroxyl-ethyl or hydroxyl-propyl; formyl-$C_{1-8}$alkyl selected from formylmethyl, formylethyl or formylpropyl; $C_{3-14}$cycloalkyl selected from cyclopropyl, cyclobutyl, cyclopentyl or cyclohexyl; aryl selected from phenyl; and, aryl-$C_{1-8}$alkyl selected from benzyl;

$R_3$ is $C_{1-8}$alkoxy selected from methoxy, ethoxy, propoxy or isopropoxy; or, $C_{1-8}$alkyl-SO$_2$-amino selected from methyl-SO$_2$-amino, ethyl-SO$_2$-amino, propyl-SO$_2$-amino or isopropyl-SO$_2$-amino; and, $R_4$ is $C_{1-8}$alkyl selected from methyl, ethyl, propyl or isopropyl.

One embodiment of the present description includes a compound of Formula (I) or a form thereof, wherein $R_2$ is $C_{3-14}$cycloalkyl selected from cyclopropyl or cyclobutyl and aryl selected from phenyl; and $R_3$ is $C_{1-8}$alkoxy selected from methoxy, ethoxy, propoxy or isopropoxy.

One embodiment of the present description includes a compound of Formula (I) or a form thereof, wherein $R_2$ is $C_{1-8}$alkyl selected from methyl, ethyl, propyl or isopropyl; $C_{3-14}$cycloalkyl selected from cyclopropyl, cyclopentyl or cyclohexyl; or, aryl-$C_{1-8}$alkyl selected from benzyl.

One embodiment of the present description includes a compound of Formula (I) or a form thereof, wherein $R_2$ is $C_{3-14}$cycloalkyl selected from cyclopropyl.

One embodiment of the present description includes a compound of Formula (I) or a form thereof, wherein $R_3$ is $C_{1-8}$alkoxy selected from methoxy or ethoxy.

One embodiment of the present description includes a compound of Formula (I) or a form thereof, wherein $R_4$ is $C_{1-8}$alkyl selected from methyl.

One embodiment of the present description includes a compound of Formula (I) or a form thereof, wherein $R_6$ is $C_{3-14}$cycloalkyl-amino-$C_{1-8}$alkyl, wherein $C_{3-14}$cycloalkyl is selected from cyclopropyl, cyclobutyl, cyclopentyl or cyclohexyl;

($C_{3-14}$cycloalkyl, $C_{1-8}$alkyl)amino-$C_{1-8}$alkyl, wherein $C_{3-14}$cycloalkyl is selected from cyclopropyl, cyclobutyl or cyclopentyl;

$C_{3-14}$cycloalkyl-$C_{1-8}$alkyl-amino-$C_{1-8}$alkyl, wherein $C_{3-14}$cycloalkyl is selected from cyclopropyl, cyclobutyl, cyclopentyl, cyclohexyl, cycloheptyl;

aryl, wherein aryl is selected from phenyl;

aryl-amino, wherein aryl is selected from phenyl;

(aryl,$C_{1-8}$alkyl)amino, wherein aryl is selected from phenyl;

aryl-amino-$C_{1-8}$alkyl, wherein aryl is selected from phenyl;

aryl-$C_{1-8}$alkyl-amino-$C_{1-8}$alkyl, wherein aryl is selected from phenyl;

(aryl-$C_{1-8}$alkyl, $C_{1-8}$alkyl)amino-$C_{1-8}$alkyl, wherein aryl is selected from phenyl;

(aryl-$C_{1-8}$alkyl)$_2$-amino-$C_{1-8}$alkyl, wherein aryl is selected from phenyl;

heteroaryl, wherein heteroaryl is selected from pyrrolyl, thiazolyl, 1H-1,2,3-triazolyl, 1H-tetrazolyl, 2H-tetrazolyl, imidazolyl or pyridinyl;

heteroaryl-$C_{1-8}$alkyl-amino-$C_{1-8}$alkyl, wherein heteroaryl is selected from pyridin-2-yl, pyridin-3-yl or pyridin-4-yl;

(heteroaryl-$C_{1-8}$alkyl, $C_{1-8}$alkyl)amino-$C_{1-8}$alkyl, wherein heteroaryl is selected from pyridin-3-yl or pyridin-4-yl;

heterocyclyl, wherein heterocyclyl is selected from azetidinyl, pyrrolidinyl, tetrahydrofuranyl, piperidinyl, piperazinyl, morpholinyl, 1,4-diazepanyl, 1,3-dioxolanyl, 2,5-dihydro-1H-pyrrolyl, dihydro-1H-imidazolyl, 1,4,5,6-tetrahydropyrimidinyl, 1,2,3,6-tetrahydropyridinyl, tetrahydro-2H-pyranyl, 3,4-dihydroisoquinolin-(1H)-yl, 1,2,3,4-tetrahydroisoquinolinyl, hexahydropyrrolo[3,4-b][1,4]oxazin-(2H)-yl, (4aR,7aS)-hexahydropyrrolo[3,4-b][1,4]oxazin-(4aH)-yl, (cis)-octahydrocyclopenta[c]pyrrolyl, hexahydropyrrolo[3,4-b]pyrrol-(1H)-yl, (3aR,6aR)-hexahydropyrrolo[3,4-b]pyrrol-(1H)-yl, (3aR,6aS)-hexahydropyrrolo[3,4-b]pyrrol-(1H)-yl, (3aR,6aS)-hexahydropyrrolo[3,4-c]pyrrol-(1H)-yl, 5H-pyrrolo[3,4-b]pyridin-(7H)-yl, 5,7-dihydro-6H-pyrrolo[3,4-b]pyridinyl, tetrahydro-1H-pyrrolo[3,4-b]pyridin-(2H,7H,7aH)-yl, hexahydro-1H-pyrrolo[3,4-b]pyridin-(2H)-yl, (4aR,7aR)-hexahydro-1H-pyrrolo[3,4-b]pyridin-(2H)-yl, octahydro-6H-pyrrolo[3,4-b]pyridinyl, (3aR,6aR)-hexahydrocyclopenta[c]pyrrol-(1H)-yl, (3aR,4R,6aS)-hexahydrocyclopenta[c]pyrrol-(1H)-yl, (3aR,4S,6aS)-hexahydrocyclopenta[c]pyrrol-(1H)-yl, (3aR,5r,6aS)-hexahydrocyclopenta[c]pyrrol-2(1H)-yl, 1,3-dihydro-2H-isoindolyl, octahydro-2H-isoindolyl, (3aS)-1,3,3a,4,5,6-hexahydro-2H-isoindolyl, (3aR,4R,7aS)-1H-isoindol-(3H,3aH,4H,5H,6H,7H,7aH)-yl, (3aR,7aS)-octahydro-2H-isoindolyl, (3aR,4R,7aS)-octahydro-2H-isoindolyl, (3aR,4S,7aS)-octahydro-2H-isoindolyl, 2,5-diazabicyclo[2.2.1]heptanyl, 2-azabicyclo[2.2.1]hept-5-enyl, 3-azabicyclo[3.1.0]hexanyl, (1R,5S,6s)-3-azabicyclo[3.1.0]hexanyl, (cis,cis)-3-azabicyclo[3.1.0]hexanyl, 3,6-diazabicyclo[3.1.0]hexanyl, (1S,5R,6R)-3-azabicyclo

[3.2.0]heptanyl, (1S,5R,6S)-3-azabicyclo[3.2.0]heptanyl, 5-azaspiro[2.4]heptanyl, 2,6-diazaspiro[3.3]heptanyl, 2,5-diazaspiro[3.4]octanyl, 2,6-diazaspiro[3.4]octanyl, 2,7-diazaspiro[3.5]nonanyl, 2,7-diazaspiro[4.4]nonanyl, 2-azaspiro[4.5]decanyl or 2,8-diazaspiro[4.5]decanyl;

heterocyclyl-C$_{1-8}$alkyl, wherein heterocyclyl is selected from azetidinyl, pyrrolidinyl, tetrahydrofuranyl, piperidinyl, piperazinyl, morpholinyl, 1,4-diazepanyl, 1,3-dioxolanyl, 2,5-dihydro-1H-pyrrolyl, dihydro-1H-imidazolyl, 1,4,5,6-tetrahydropyrimidinyl, 1,2,3,6-tetrahydropyridinyl, tetrahydro-2H-pyranyl, 3,4-dihydroisoquinolin-(1H)-yl, 1,2,3,4-tetrahydroisoquinolinyl, hexahydropyrrolo[3,4-b][1,4]oxazin-(2H)-yl, (4aR,7aS)-hexahydropyrrolo[3,4-b][1,4]oxazin-(4aH)-yl, (cis)-octahydrocyclopenta[c]pyrrolyl, hexahydropyrrolo[3,4-b]pyrrol-(1H)-yl, (3aR,6aR)-hexahydropyrrolo[3,4-b]pyrrol-(1H)-yl, (3aR,6aS)-hexahydropyrrolo[3,4-c]pyrrol-(1H)-yl, 5H-pyrrolo[3,4-b]pyridin-(7H)-yl, 5,7-dihydro-6H-pyrrolo[3,4-b]pyridinyl, tetrahydro-1H-pyrrolo[3,4-b]pyridin-(2H,7H,7aH)-yl, hexahydro-1H-pyrrolo[3,4-b]pyridin-(2H)-yl, (4aR,7aR)-hexahydro-1H-pyrrolo[3,4-b]pyridin-(2H)-yl, octahydro-6H-pyrrolo[3,4-b]pyridinyl, (3aR,6aR)-hexahydrocyclopenta[c]pyrrol-(1H)-yl, (3aR,4R,6aS)-hexahydrocyclopenta[c]pyrrol-(1H)-yl, (3aR,4S,6aS)-hexahydrocyclopenta[c]pyrrol-(1H)-yl, (3aR,5r,6aS)-hexahydrocyclopenta[c]pyrrol-2(1H)-yl, 1,3-dihydro-2H-isoindolyl, octahydro-2H-isoindolyl, (3aS)-1,3,3a,4,5,6-hexahydro-2H-isoindolyl, (3aR,4R,7aS)-1H-isoindol-(3H,3aH,4H,5H,6H,7H,7aH)-yl, (3aR,7aS)-octahydro-2H-isoindolyl, (3aR,4R,7aS)-octahydro-2H-isoindolyl, (3aR,4S,7aS)-octahydro-2H-isoindolyl, 2,5-diazabicyclo[2.2.1]heptanyl, 2-azabicyclo[2.2.1]hept-5-enyl, 3-azabicyclo[3.1.0]hexanyl, (1R,5S,6s)-3-azabicyclo[3.1.0]hexanyl, (cis,cis)-3-azabicyclo[3.1.0]hexanyl, 3,6-diazabicyclo[3.1.0]hexanyl, (1S,5R,6R)-3-azabicyclo[3.2.0]heptanyl, (1S,5R,6S)-3-azabicyclo[3.2.0]heptanyl, 5-azaspiro[2.4]heptanyl, 2,6-diazaspiro[3.3]heptanyl, 2,5-diazaspiro[3.4]octanyl, 2,6-diazaspiro[3.4]octanyl, 2,7-diazaspiro[3.5]nonanyl, 2,7-diazaspiro[4.4]nonanyl, 2-azaspiro[4.5]decanyl or 2,8-diazaspiro[4.5]decanyl; heterocyclyl-amino-C$_{1-8}$alkyl, wherein heterocyclyl is selected from azetidin-1-yl or piperidin-4-yl;

(heterocyclyl, C$_{1-8}$alkyl)amino-C$_{1-8}$alkyl, wherein heterocyclyl is selected from piperidin-3-yl or piperidin-4-yl;

(heterocyclyl, C$_{3-14}$cycloalkyl-C$_{1-8}$alkyl)amino-C$_{1-8}$alkyl, wherein heterocyclyl is selected from piperidin-3-yl or piperidin-4-yl; or, heterocyclyl-C$_{1-8}$alkyl-amino-C$_{1-8}$alkyl, wherein heterocyclyl is selected from pyrrolidin-2-yl, piperidin-2-yl, piperidin-3-yl, piperidin-4-yl or tetrahydro-2H-pyran-4-yl; and, (heterocyclyl-oxy-C$_{1-8}$alkyl, C$_{1-8}$alkyl)amino selected from tetrahydro-2H-pyran-2-yl-oxy-C$_{1-8}$alkyl, C$_{1-8}$alkyl) amino.

One embodiment of the present description includes a compound of Formula (I) or a form thereof, wherein R$_6$ is heteroaryl, wherein heteroaryl is selected from 1H-tetrazolyl, imidazolyl, pyrrolyl or 2H-tetrazolyl; and, heterocyclyl selected in each instance, when present, from azetidinyl, pyrrolidinyl, tetrahydrofuranyl, piperidinyl, piperazinyl, morpholinyl, 1,4-diazepanyl, 1,3-dioxolanyl, 2,5-dihydro-1H-pyrrolyl, dihydro-1H-imidazolyl, 1,4,5,6-tetrahydropyrimidinyl, 1,2,3,6-tetrahydropyridinyl, tetrahydro-2H-pyranyl, indolinyl, 2,3-dihydrobenzo[d]oxazolyl, 3,4-dihydro-2H-benzo[b][1,4]oxazinyl, 3,4-dihydroisoquinolin-(1H)-yl, 1,2,3,4-tetrahydroisoquinolinyl, 1,2,3,4-tetrahydroquinoxalinyl, hexahydropyrrolo[3,4-b][1,4]oxazin-(2H)-yl, (4aR,7aS)-hexahydropyrrolo[3,4-b][1,4]oxazin-(4aH)-yl, 3,4-dihydro-2H-pyrido[3,2-b][1,4]oxazinyl, (cis)-octahydrocyclopenta[c]pyrrolyl, hexahydropyrrolo[3,4-b]pyrrol-(1H)-yl, (3aR,6aR)-hexahydropyrrolo[3,4-b]pyrrol-(1H)-yl, (3aR,6aS)-hexahydropyrrolo[3,4-c]pyrrol-(1H)-yl, 5H-pyrrolo[3,4-b]pyridin-(7H)-yl, 5,7-dihydro-6H-pyrrolo[3,4-b]pyridinyl, tetrahydro-1H-pyrrolo[3,4-b]pyridin-(2H,7H,7aH)-yl, hexahydro-1H-pyrrolo[3,4-b]pyridin-(2H)-yl, (4aR,7aR)-hexahydro-1H-pyrrolo[3,4-b]pyridin-(2H)-yl, octahydro-6H-pyrrolo[3,4-b]pyridinyl, 2,3,4,9-tetrahydro-1H-carbazolyl, 1,2,3,4-tetrahydropyrazino[1,2-a]indolyl, 2,3-dihydro-1H-pyrrolo[1,2-a]indolyl, (3aR,6aR)-hexahydrocyclopenta[c]pyrrol-(1H)-yl, (3aR,4R,6aS)-hexahydrocyclopenta[c]pyrrol-(1H)-yl, (3aR,4S,6aS)-hexahydrocyclopenta[c]pyrrol-(1H)-yl, (3aR,5r,6aS)-hexahydrocyclopenta[c]pyrrol-(1H)-yl, 1,3-dihydro-2H-isoindolyl, octahydro-2H-isoindolyl, (3aS)-1,3,3a,4,5,6-hexahydro-2H-isoindolyl, (3aR,4R,7aS)-1H-isoindol-(3H,3aH,4H,5H,6H,7H,7aH)-yl, (3aR,7aS)-octahydro-2H-isoindolyl, (3aR,4R,7aS)-octahydro-2H-isoindolyl, (3aR,4S,7aS)-octahydro-2H-isoindolyl, 2,5-diazabicyclo[2.2.1]heptanyl, 2-azabicyclo[2.2.1]hept-5-enyl, 3-azabicyclo[3.1.0]hexanyl, (1R,5S,6s)-3-azabicyclo[3.1.0]hexanyl, (cis,cis)-3-azabicyclo[3.1.0]hexanyl, 3,6-diazabicyclo[3.1.0]hexanyl, (1S,5R,6R)-3-azabicyclo[3.2.0]heptanyl, (1S,5R,6S)-3-azabicyclo[3.2.0]heptanyl, 5-azaspiro[2.4]heptanyl, 2,6-diazaspiro[3.3]heptanyl, 2,5-diazaspiro[3.4]octanyl, 2,6-diazaspiro[3.4]octanyl, 2,7-diazaspiro[3.5]nonanyl, 2,7-diazaspiro[4.4]nonanyl, 2-azaspiro[4.5]decanyl or 2,8-diazaspiro[4.5]decanyl.

One embodiment of the present description includes a compound of Formula (I) or a form thereof, wherein R$_6$ is heteroaryl, wherein heteroaryl is selected from 1H-tetrazol-5-yl, imidazol-1-yl, pyrrol-1-yl or 2H-tetrazol-2-yl; and, heterocyclyl selected in each instance, when present, from azetidin-1-yl, pyrrolidin-1-yl, pyrrolidin-2-yl, pyrrolidin-3-yl, tetrahydrofuran-2-yl, piperidin-1-yl, piperidin-2-yl, piperidin-3-yl, piperidin-4-yl, piperazin-1-yl, piperazin-2-yl, morpholin-4-yl, 1,4-diazepan-1-yl, 1,3-dioxolan-2-yl, dihydro-1H-imidazol-2-yl, 1,4,5,6-tetrahydropyrimidin-2-yl, 1,2,3,6-tetrahydropyridin-4-yl, tetrahydro-2H-pyran-2-yl, tetrahydro-2H-pyran-4-yl, 3,4-dihydroisoquinolin-2(1H)-yl, 1,2,3,4-tetrahydroisoquinolin-1-yl, 5H-pyrrolo[3,4-b]pyridin-6(7H)-yl, tetrahydro-1H-pyrrolo[3,4-b]pyridin-6(2H,7H,7aH)-yl, (3aR,6aS)-hexahydrocyclopenta[c]pyrrol-2(1H)-yl, (3aR,4R,7aS)-1H-isoindol-2(3H,3aH,4H,5H,6H,7H,7aH)-yl, 2,5-diazabicyclo[2.2.1]heptan-2-yl, (1R,5S,6s)-3-azabicyclo[3.1.0]hexan-3-yl or (1R,5S,6s)-3-azabicyclo[3.1.0]hexan-6-yl.

One embodiment of the present description includes a compound of Formula (I) or a form thereof, wherein R$_6$ is heteroaryl, wherein heteroaryl is selected from pyridinyl; and, heterocyclyl selected in each instance, when present, from azetidinyl, pyrrolidinyl, tetrahydrofuranyl, piperidinyl, piperazinyl, morpholinyl, 1,4-diazepanyl, 1,3-dioxolanyl, 2,5-dihydro-1H-pyrrolyl, dihydro-1H-imidazolyl, 1,4,5,6-tetrahydropyrimidinyl, 1,2,3,6-tetrahydropyridinyl, tetrahydro-2H-pyranyl, indolinyl, 2,3-dihydrobenzo[d]oxazolyl, 3,4-dihydro-2H-benzo[b][1,4]oxazinyl, 3,4-dihydroisoquinolin-(1H)-yl, 1,2,3,4-tetrahydroisoquinolinyl, 1,2,3,4-tetrahydroquinoxalinyl, hexahydropyrrolo[3,4-b][1,4]oxazin-(2H)-yl, (4aR,7aS)-hexahydropyrrolo[3,4-b][1,4]oxazin-(4aH)-yl, 3,4-dihydro-2H-pyrido[3,2-b][1,4]oxazinyl, (cis)-octahydrocyclopenta[c]pyrrolyl, hexahydropyrrolo[3,4-b]pyrrol-(1H)-yl, (3aR,6aR)-hexahydropyrrolo[3,4-b]pyrrol-(1H)-yl, (3aR, 6aS)-hexahydropyrrolo[3,4-c]pyrrol-(1H)-yl, 5H-pyrrolo [3,4-b]pyridin-(7H)-yl, 5,7-dihydro-6H-pyrrolo[3,4-b]pyridinyl, tetrahydro-1H-pyrrolo[3,4-b]pyridin-(2H,7H, 7aH)-yl, hexahydro-1H-pyrrolo[3,4-b]pyridin-(2H)-yl, (4aR,7aR)-hexahydro-1H-pyrrolo[3,4-b]pyridin-(2H)-yl, octahydro-6H-pyrrolo[3,4-b]pyridinyl, 2,3,4,9-tetrahydro-1H-carbazolyl, 1,2,3,4-tetrahydropyrazino[1,2-a]indolyl, 2,3-dihydro-1H-pyrrolo[1,2-a]indolyl, (3aR,6aR)-hexahydrocyclopenta[c]pyrrol-(1H)-yl, (3aR,4R,6aS)-hexahydrocyclopenta[c]pyrrol-(1H)-yl, (3aR,4S,6aS)-hexahydrocyclopenta[c]pyrrol-(1H)-yl, (3aR,5r,6aS)-hexahydrocyclopenta[c]pyrrol-(1H)-yl, 1,3-dihydro-2H-isoindolyl, octahydro-2H-isoindolyl, (3aS)-1,3,3a,4,5,6-hexahydro-2H-isoindolyl, (3aR,4R,7aS)-1H-isoindol-(3H,3aH,4H,5H,6H,7H,7aH)-yl, (3aR,7aS)-octahydro-2H-isoindolyl, (3aR,4R,7aS)-octahydro-2H-isoindolyl, (3aR,4S,7aS)-octahydro-2H-isoindolyl, 2,5-diazabicyclo [2.2.1]heptanyl, 2-azabicyclo[2.2.1]hept-5-enyl, 3-azabicyclo[3.1.0]hexanyl, (1R,5S,6s)-3-azabicyclo[3.1.0]hexanyl, (cis,cis)-3-azabicyclo[3.1.0]hexanyl, 3,6-diazabicyclo[3.1.0]hexanyl, (1S,5R,6R)-3-azabicyclo [3.2.0]heptanyl, (1S,5R,6S)-3-azabicyclo[3.2.0]heptanyl, 5-azaspiro[2.4]heptanyl, 2,6-diazaspiro[3.3]heptanyl, 2,5-diazaspiro[3.4]octanyl, 2,6-diazaspiro[3.4]octanyl, 2,7-diazaspiro[3.5]nonanyl, 2,7-diazaspiro[4.4]nonanyl, 2-azaspiro[4.5]decanyl or 2,8-diazaspiro[4.5]decanyl.

One embodiment of the present description includes a compound of Formula (I) or a form thereof, wherein $R_6$ is heteroaryl selected in each instance, when present, from pyridin-2-yl, pyridin-3-yl or pyridin-4-yl;
heterocyclyl selected in each instance, when present, from azetidin-1-yl, pyrrolidin-1-yl, pyrrolidin-2-yl, pyrrolidin-3-yl, tetrahydrofuran-2-yl, piperidin-1-yl, piperidin-2-yl, piperidin-3-yl, piperidin-4-yl, piperazin-1-yl, piperazin-2-yl, morpholin-4-yl, 1,4-diazepan-1-yl, 1,3-dioxolan-2-yl, dihydro-1H-imidazol-2-yl, 1,4,5,6-tetrahydropyrimidin-2-yl, 1,2,3,6-tetrahydropyridin-4-yl, tetrahydro-2H-pyran-2-yl, tetrahydro-2H-pyran-4-yl, 3,4-dihydroisoquinolin-2(1H)-yl, 1,2,3,4-tetrahydroisoquinolin-1-yl, 5H-pyrrolo[3,4-b]pyridin-6(7H)-yl, tetrahydro-1H-pyrrolo[3,4-b]pyridin-6(2H,7H,7aH)-yl, (3aR,4R,6aS)-hexahydrocyclopenta[c]pyrrol-2(1H)-yl, (3aR,4R,7aS)-1H-isoindol-2(3H,3aH,4H,5H,6H,7H,7aH)-yl, 2,5-diazabicyclo[2.2.1]heptan-2-yl, (1R,5S,6s)-3-azabicyclo [3.1.0]hexan-3-yl or (1R,5S,6s)-3-azabicyclo[3.1.0] hexan-6-yl.

One embodiment of the present description includes a compound of Formula (I) or a form thereof, wherein $R_7$ is $C_{3-14}$cycloalkyl, wherein $C_{3-14}$cycloalkyl is selected from cyclopropyl or cyclobutyl;
$C_{3-14}$cycloalkyl-amino, wherein $C_{3-14}$cycloalkyl is selected from cyclopropyl;
aryl, wherein aryl is selected from phenyl;
aryl-$C_{1-8}$alkyl, wherein aryl is selected from phenyl;
aryl-amino, wherein aryl is selected from phenyl;
(aryl,$C_{1-8}$alkyl)amino, wherein aryl is selected from phenyl;
aryl-$C_{1-8}$alkyl-amino, wherein aryl is selected from phenyl;
(aryl-$C_{1-8}$alkyl, $C_{1-8}$alkyl)amino, wherein aryl is selected from phenyl;
(aryl-$C_{1-8}$alkyl)$_2$-amino, wherein aryl is selected from phenyl;
aryl-$C_{1-8}$alkyl-amino-$C_{1-8}$alkyl, wherein aryl is selected from phenyl;
(aryl-$C_{1-8}$alkyl, $C_{1-8}$alkyl)amino-$C_{1-8}$alkyl, wherein aryl is selected from phenyl;
(aryl-$C_{1-8}$alkyl)$_2$-amino-$C_{1-8}$alkyl, wherein aryl is selected from phenyl;
aryl-amino-$C_{1-8}$alkyl, wherein aryl is selected from phenyl;
aryl-$C_{1-8}$alkoxy, wherein aryl is selected from phenyl;
aryl-$C_{1-8}$alkoxy-carbonyl-amino, wherein aryl is selected from phenyl;
heteroaryl, wherein heteroaryl is selected from pyridin-2-yl, pyridin-4-yl, thiazol-2-yl or 1H-1,2,3-triazol-1-yl;
heteroaryl-$C_{1-8}$alkyl-amino-$C_{1-8}$alkyl, wherein heteroaryl is selected from pyridin-2-yl, pyridin-3-yl or pyridin-4-yl;
heterocyclyl, wherein heterocyclyl is selected from pyrrolidin-1-yl, piperidin-1-yl or morpholin-4-yl;
heterocyclyl-$C_{1-8}$alkyl, wherein heterocyclyl is selected from pyrrolidin-1-yl;
heterocyclyl-amino-$C_{1-8}$alkyl, wherein heterocyclyl is selected from (1R,5S,6s)-3-azabicyclo[3.1.0]hexan-6-yl; and,
heterocyclyl-oxy, wherein heterocyclyl is selected from tetrahydro-2H-pyran-2-yloxy.

One embodiment of the present description includes a compound of Formula (I) or a form thereof, wherein $R_7$ is $C_{3-14}$cycloalkyl, wherein $C_{3-14}$cycloalkyl is selected from cyclopropyl or cyclobutyl;
$C_{3-14}$cycloalkyl-amino, wherein $C_{3-14}$cycloalkyl is selected from cyclopropyl;
aryl, wherein aryl is selected from phenyl;
aryl-$C_{1-8}$alkyl, wherein aryl is selected from phenyl;
aryl-amino, wherein aryl is selected from phenyl;
(aryl,$C_{1-8}$alkyl)amino, wherein aryl is selected from phenyl;
aryl-$C_{1-8}$alkyl-amino, wherein aryl is selected from phenyl;
(aryl-$C_{1-8}$alkyl, $C_{1-8}$alkyl)amino, wherein aryl is selected from phenyl;
(aryl-$C_{1-8}$alkyl)$_2$-amino, wherein aryl is selected from phenyl;
aryl-$C_{1-8}$alkyl-amino-$C_{1-8}$alkyl, wherein aryl is selected from phenyl;
(aryl-$C_{1-8}$alkyl, $C_{1-8}$alkyl)amino-$C_{1-8}$alkyl, wherein aryl is selected from phenyl;
(aryl-$C_{1-8}$alkyl)$_2$-amino-$C_{1-8}$alkyl, wherein aryl is selected from phenyl;
aryl-$C_{1-8}$alkoxy, wherein aryl is selected from phenyl;
aryl-$C_{1-8}$alkoxy-carbonyl-amino, wherein aryl is selected from phenyl;
heteroaryl, wherein heteroaryl is selected from pyridin-2-yl, pyridin-4-yl, thiazol-2-yl or 1H-1,2,3-triazol-1-yl;
heteroaryl-$C_{1-8}$alkyl-amino-$C_{1-8}$alkyl, wherein heteroaryl is selected from pyridin-2-yl, pyridin-3-yl or pyridin-4-yl;
heterocyclyl, wherein heterocyclyl is selected from pyrrolidin-1-yl or morpholin-4-yl;
heterocyclyl-$C_{1-8}$alkyl, wherein heterocyclyl is selected from pyrrolidin-1-yl; and,
heterocyclyl-oxy, wherein heterocyclyl is selected from tetrahydro-2H-pyran-2-yloxy.

One embodiment of the present description includes a compound of Formula (I) or a form thereof, wherein $R_7$ is aryl, wherein aryl is selected from phenyl;
(aryl-$C_{1-8}$alkyl, $C_{1-8}$alkyl)amino, wherein aryl is selected from phenyl;
(aryl-$C_{1-8}$alkyl)$_2$-amino, wherein aryl is selected from phenyl;
aryl-amino-$C_{1-8}$alkyl, wherein aryl is selected from phenyl;
heteroaryl, wherein heteroaryl is selected from pyridin-2-yl or pyridin-4-yl;
heterocyclyl, wherein heterocyclyl is selected from piperidin-1-yl; and,
heterocyclyl-amino-$C_{1-8}$alkyl, wherein heterocyclyl is selected from (1R,5S,6s)-3-azabicyclo[3.1.0]hexan-6-yl.

In another embodiment of the present description, a compound or a form thereof is selected from:
1
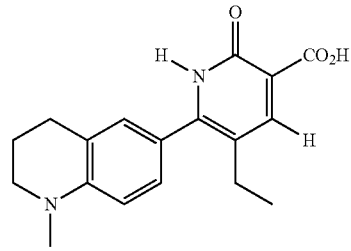
2
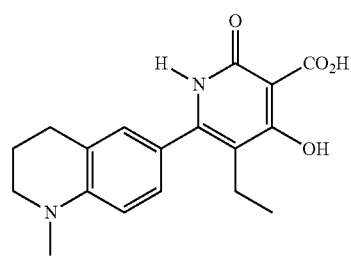
3
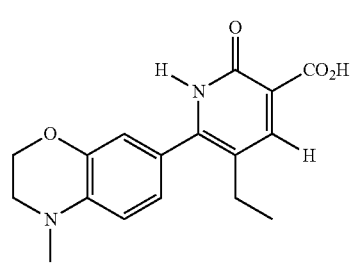
4
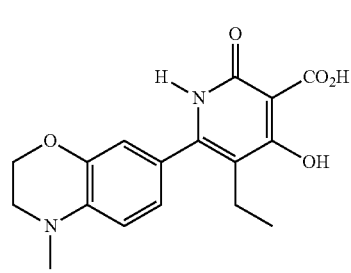
5
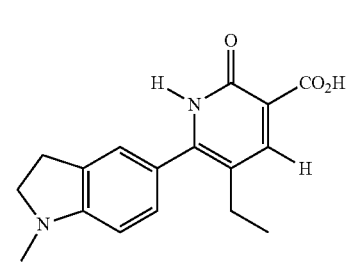
6
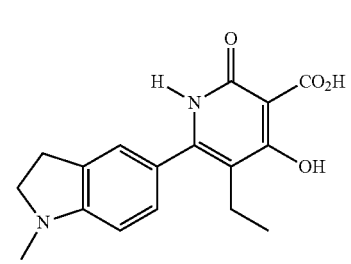
7
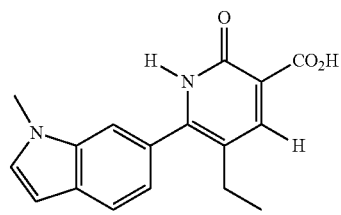
8
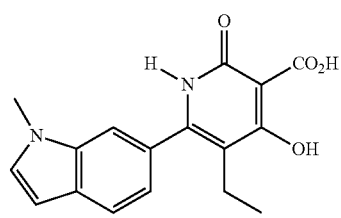
9
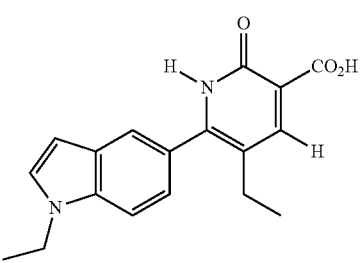
10
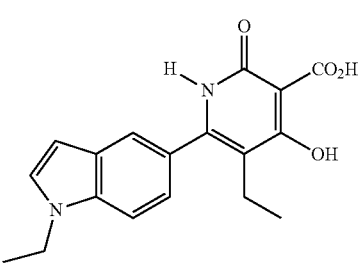
11
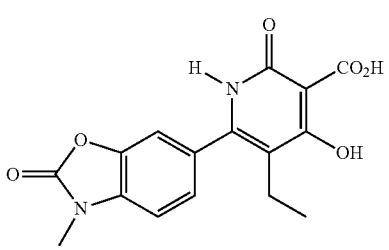
12
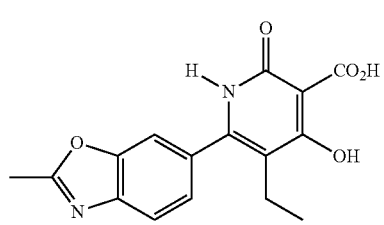

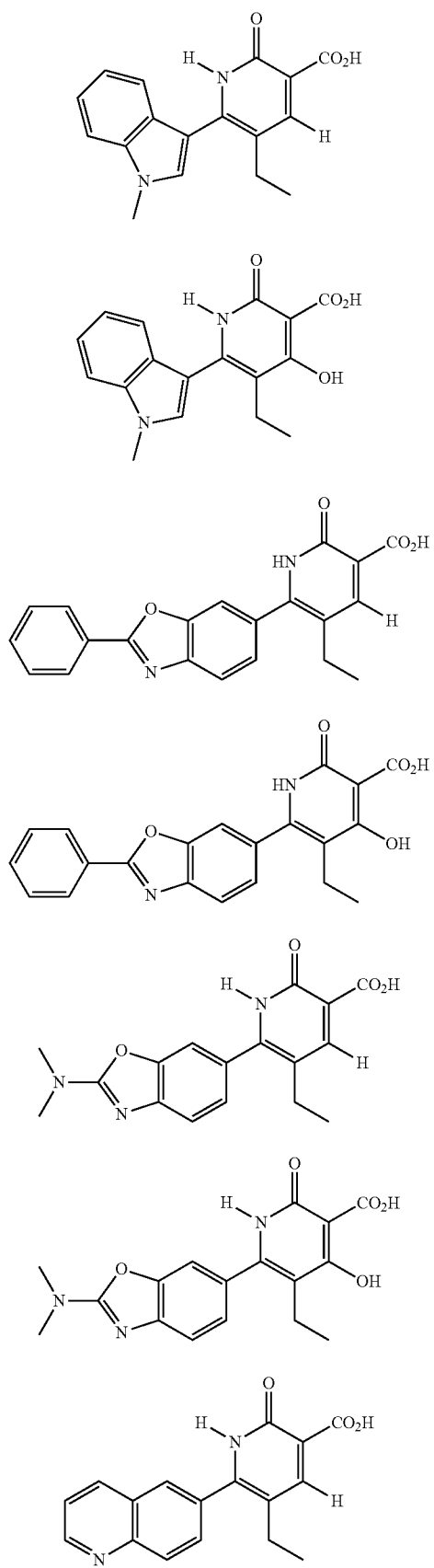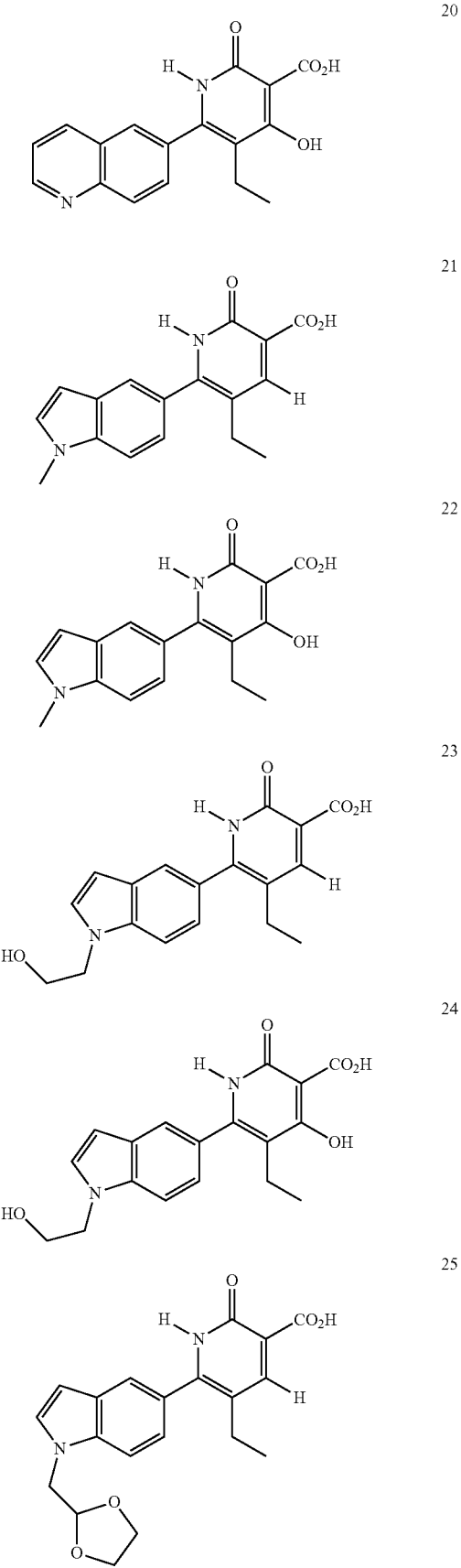

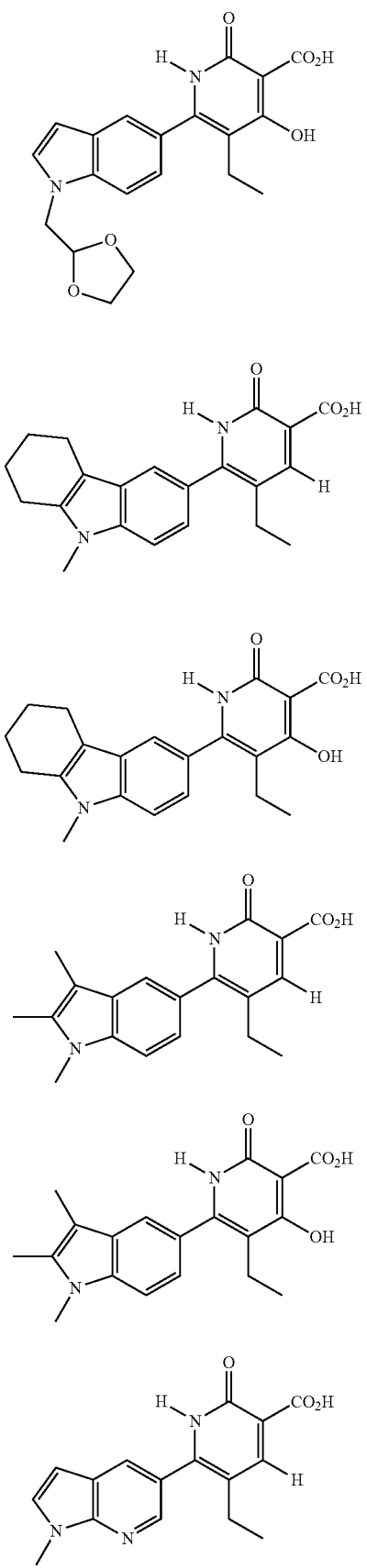
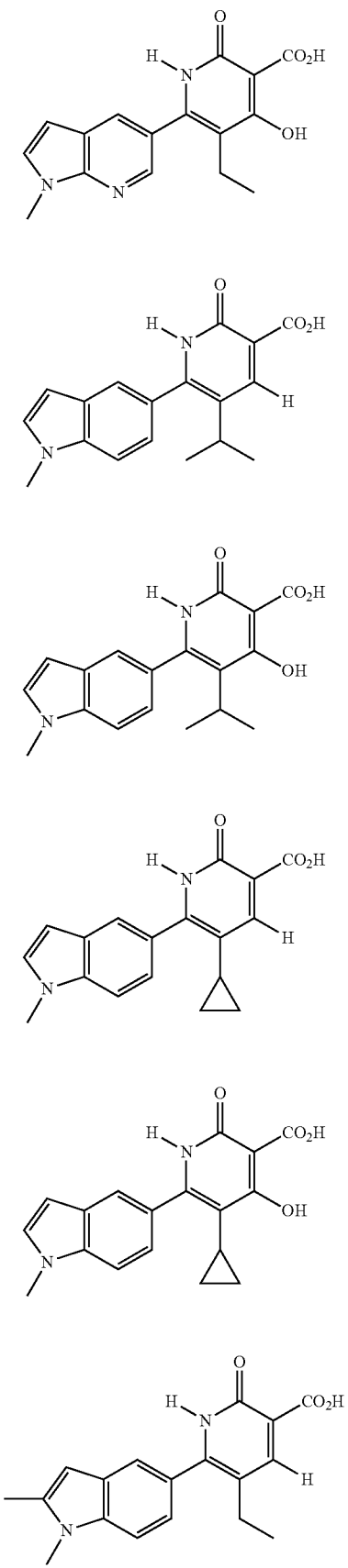

38
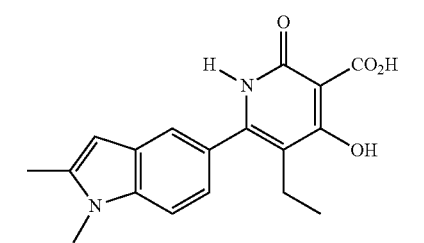
39
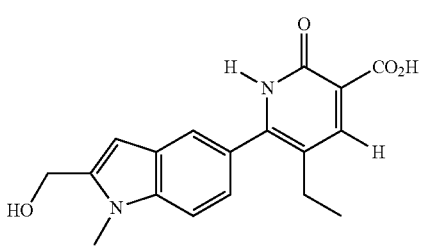
40
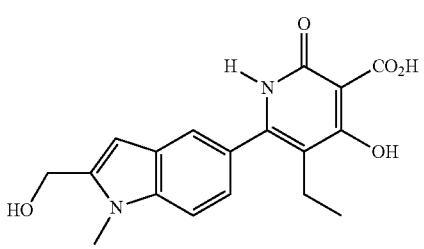
41
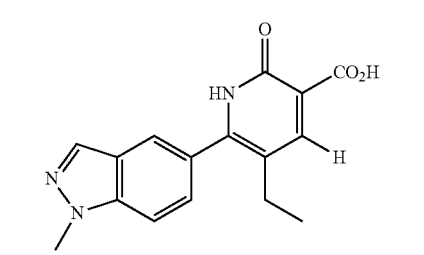
42
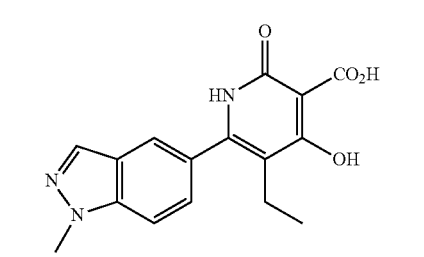
49
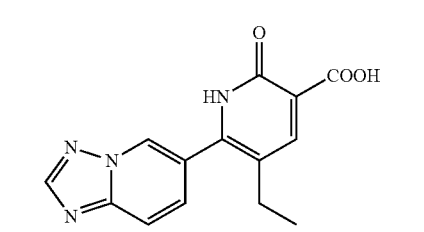
50
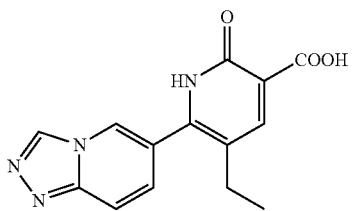
51
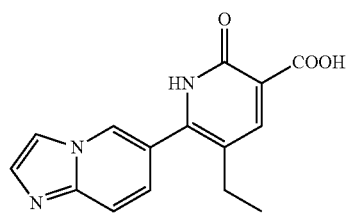
52
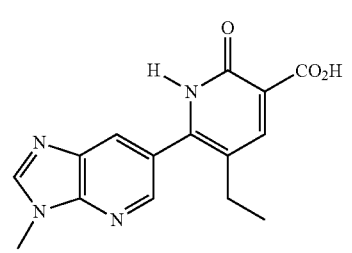
53
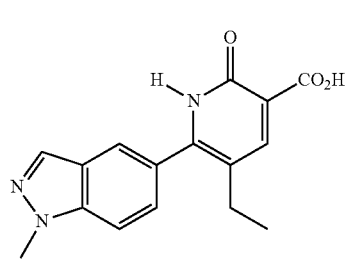
54
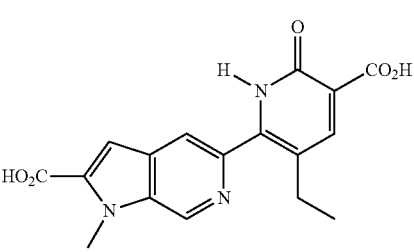
55
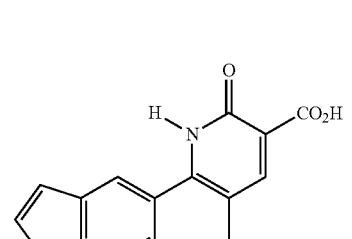

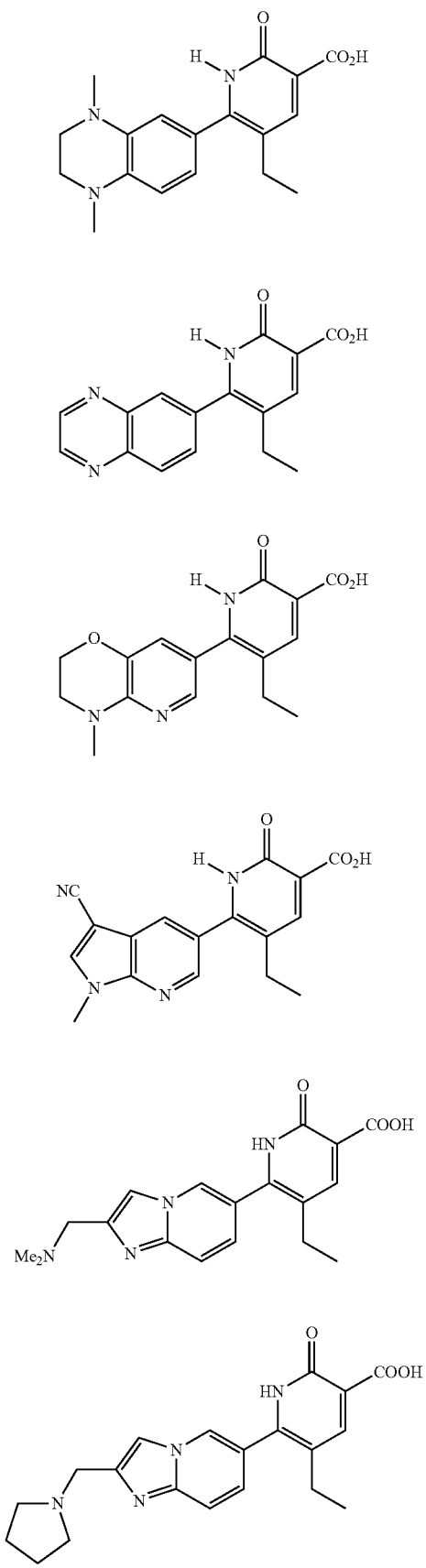
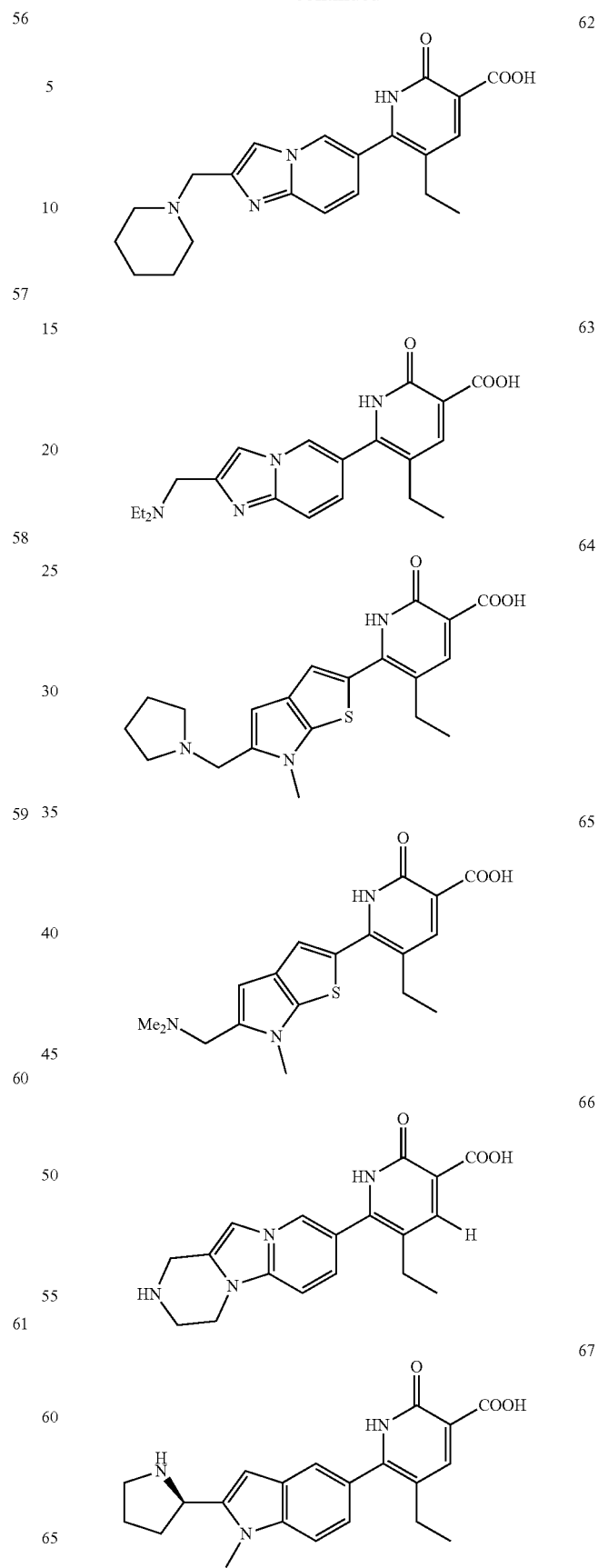

-continued

86 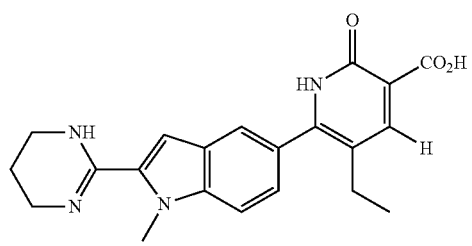
87 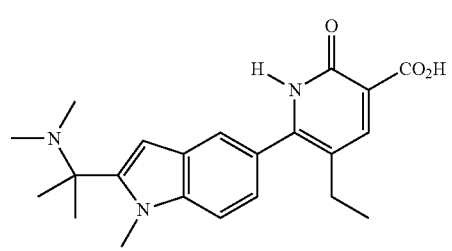
88 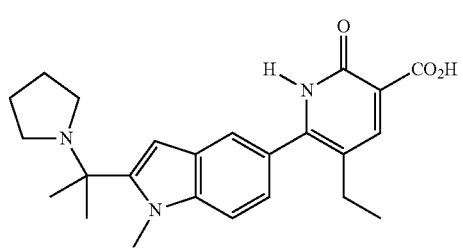
89 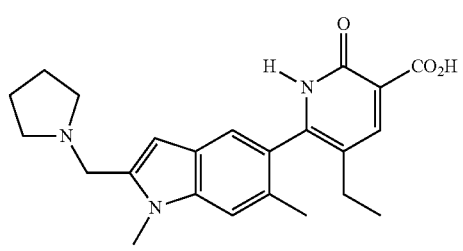
90 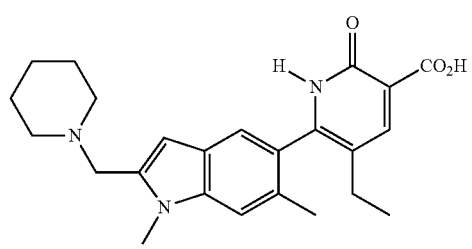
91 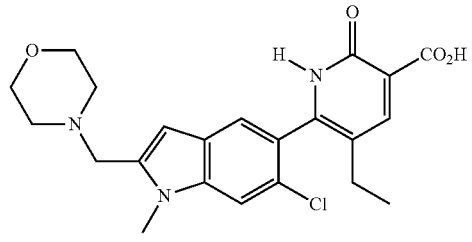
92 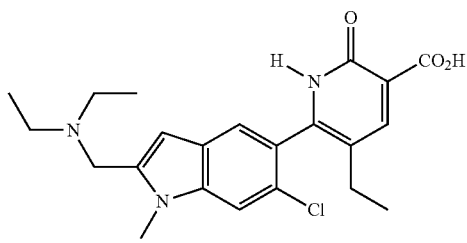
93 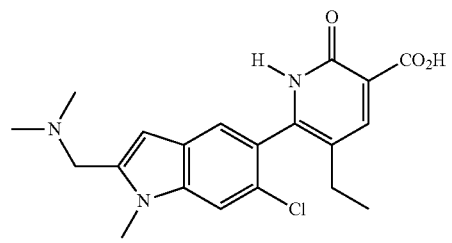
94 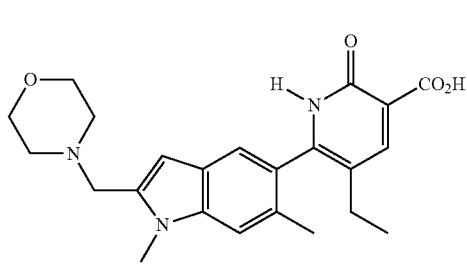
95 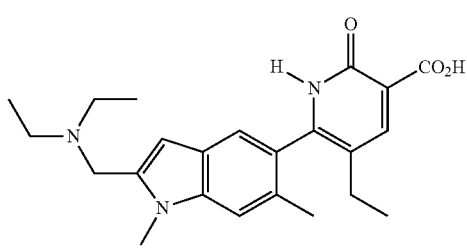
96 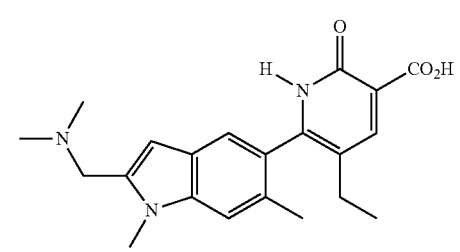
97 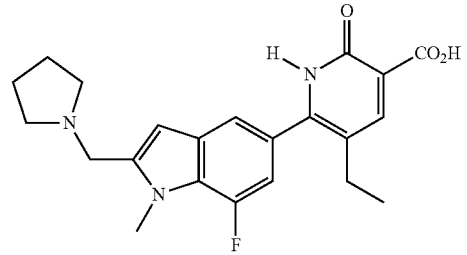

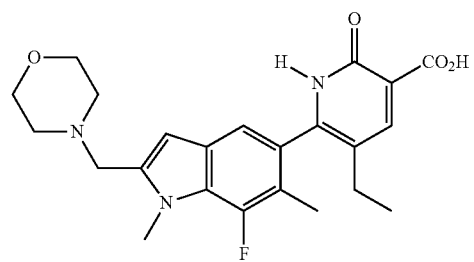
98
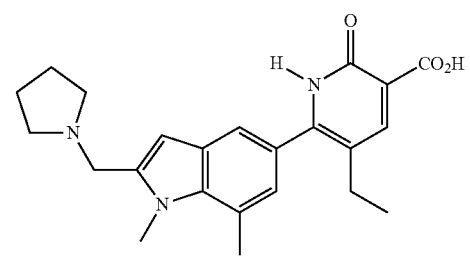
99
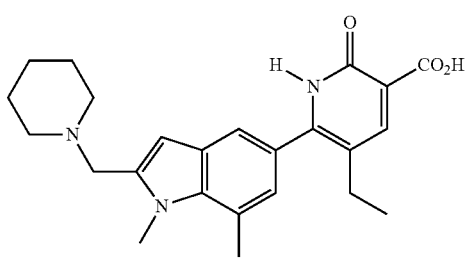
100
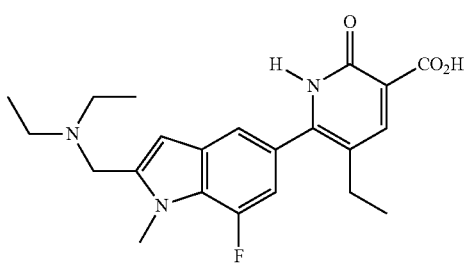
101
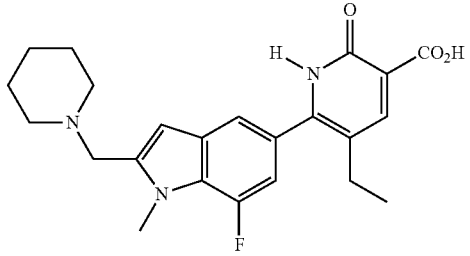
102
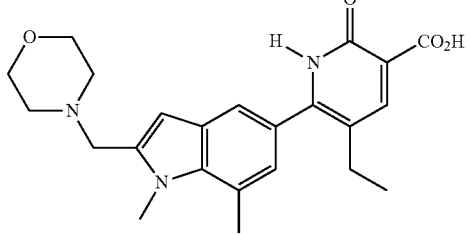
103
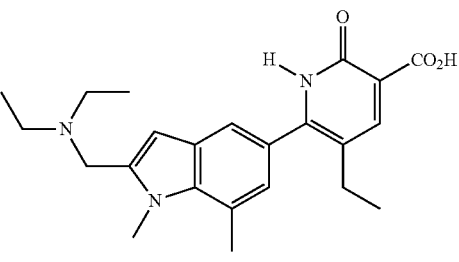
104
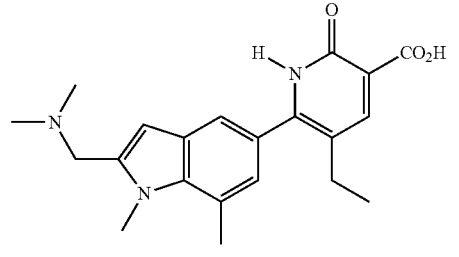
105
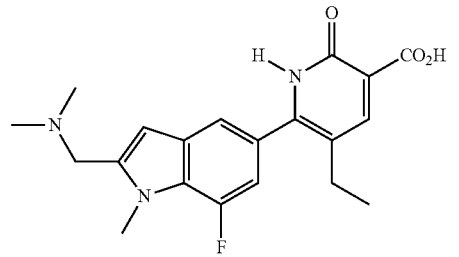
106
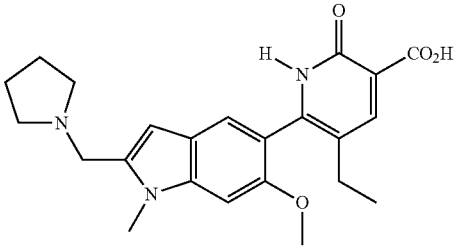
107
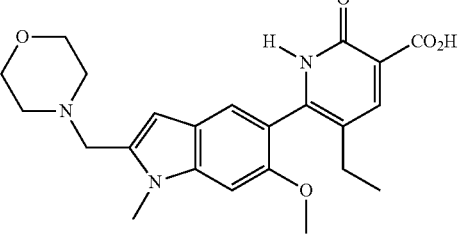
108
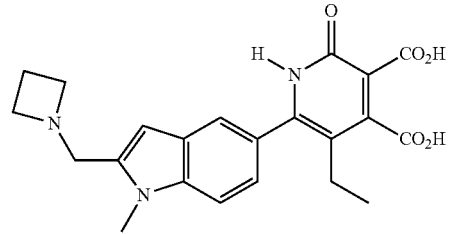
109

110
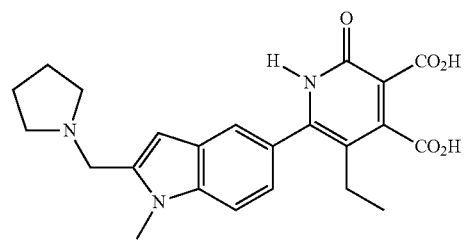
111
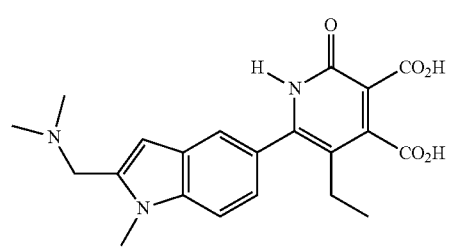
112
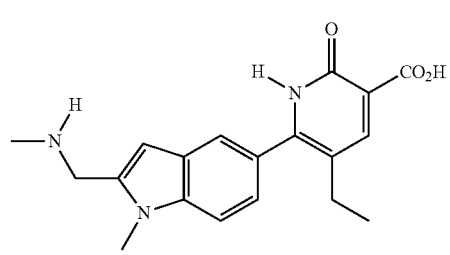
113
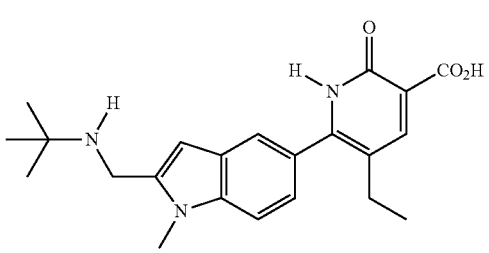
114
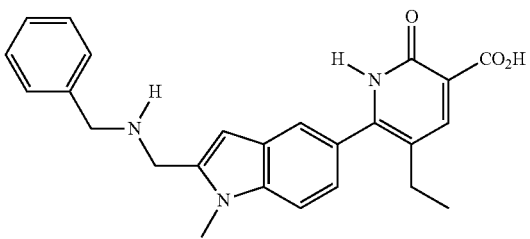
115
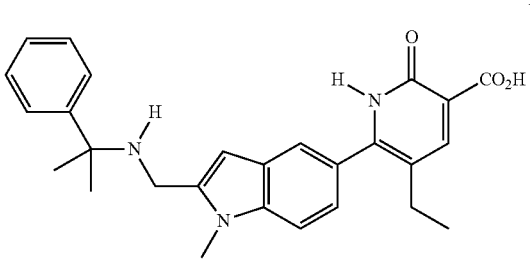
116
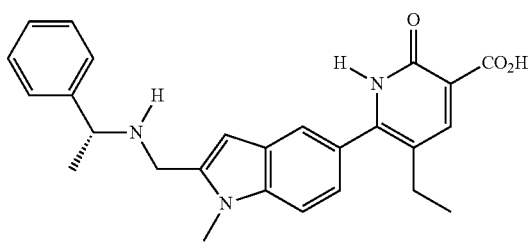
117
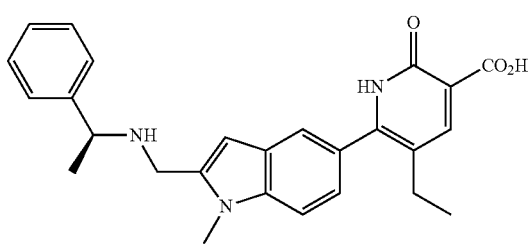
118
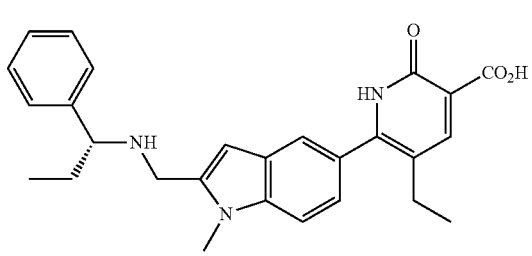
119
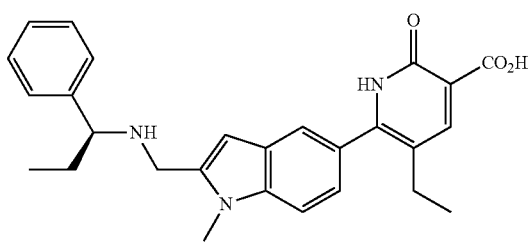
120
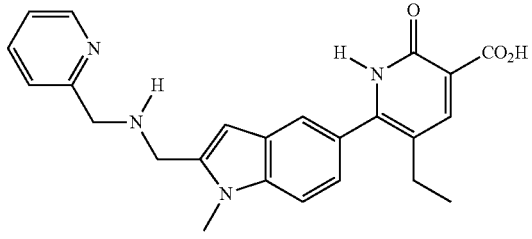
121
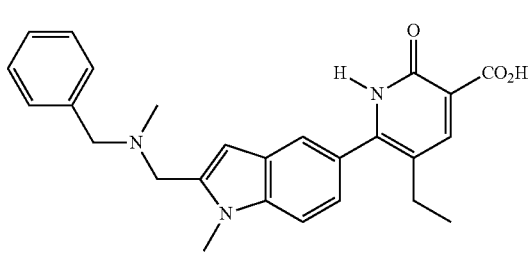

| | |
|---|---|
| 122 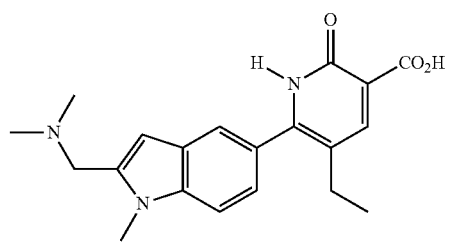 | 128 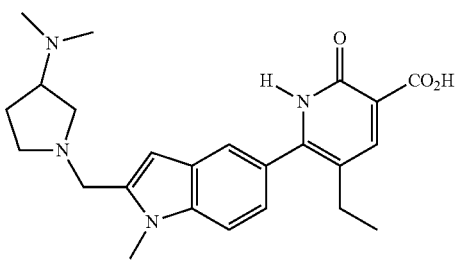 |
| 123 | 129 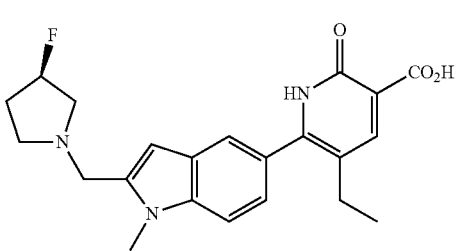 |
| 124 | 130 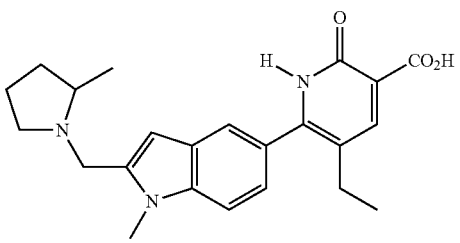 |
| 125 | 131 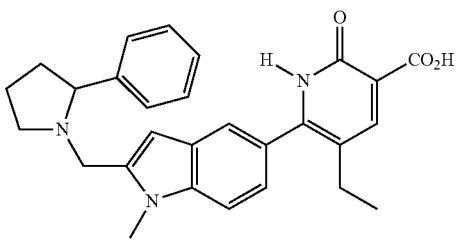 |
| 126 | 132 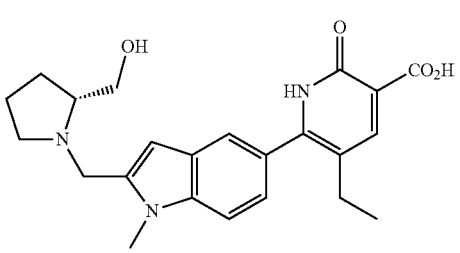 |
| 127 | 133 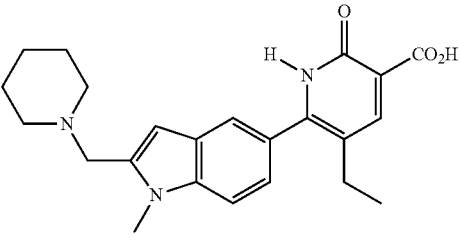 |

134 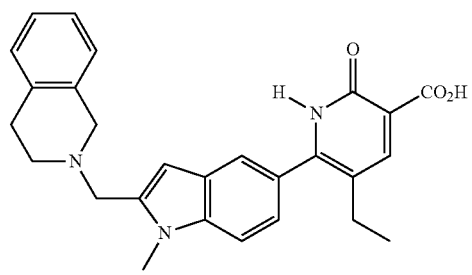
135 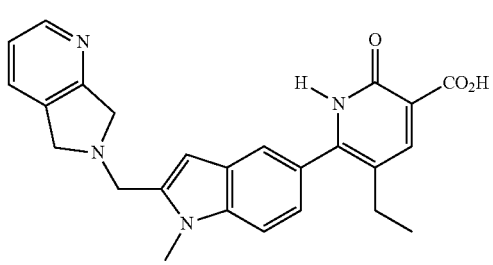
136 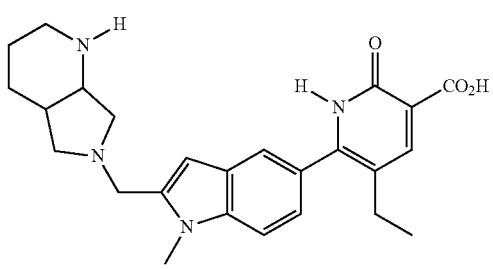
137 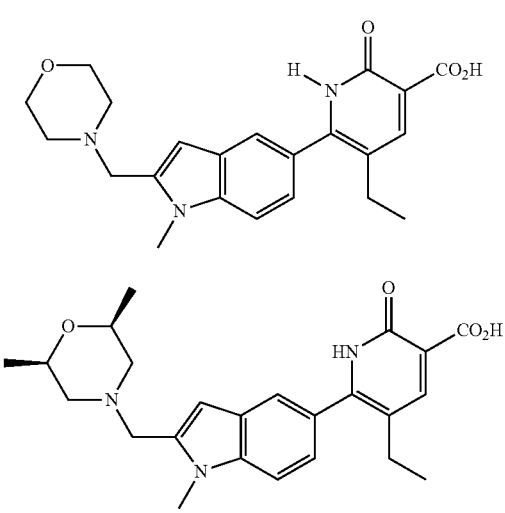
138
139 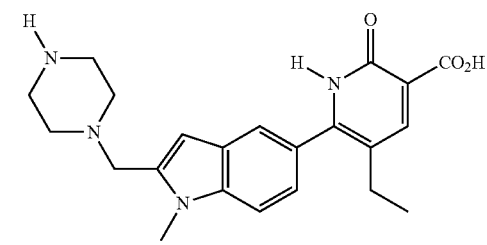
140 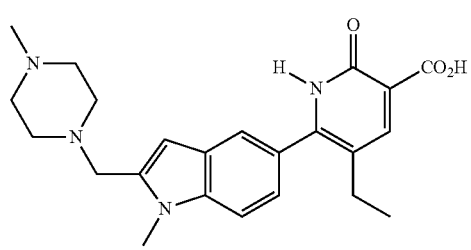
141 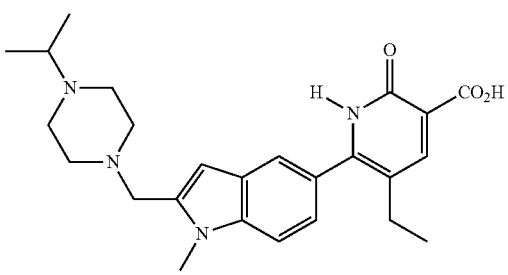
142 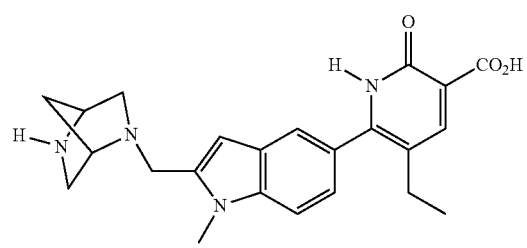
143 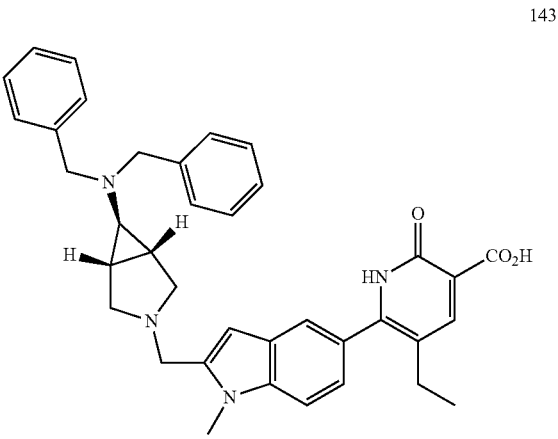
144 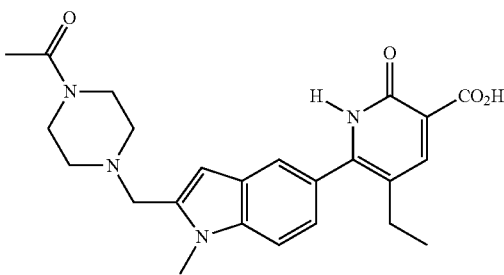

145 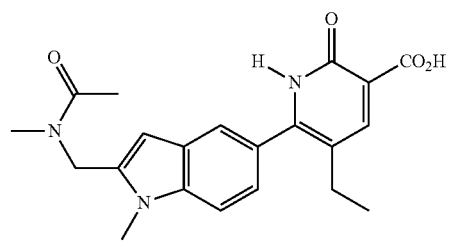
150 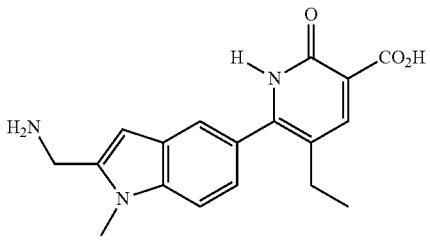
146 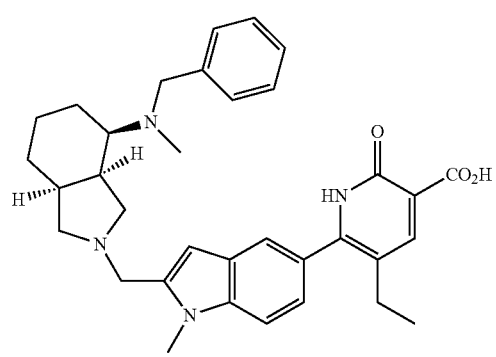
151 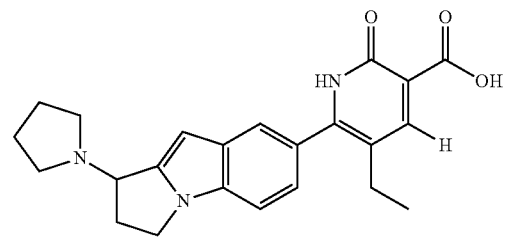 [SMILES: CCc1cc(C(=O)O)c(=O)[nH]c1-c1ccc2c(c1)cc1n2CCC1N1CCCC1]
152 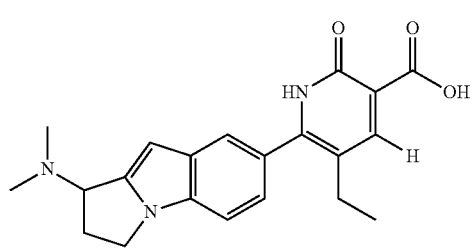
147 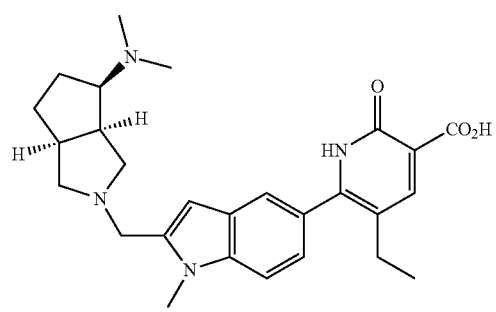
153 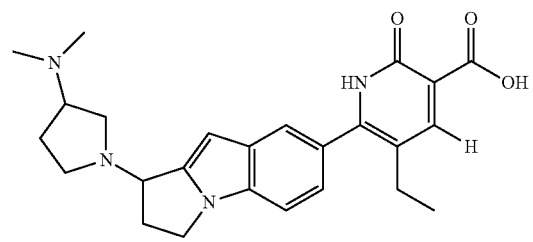
148 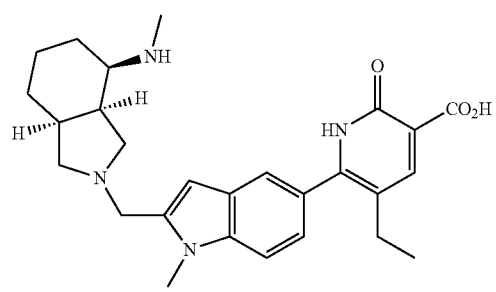
154 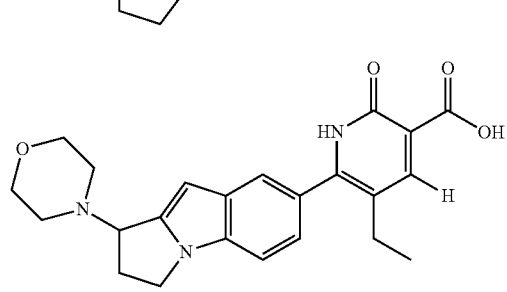
149 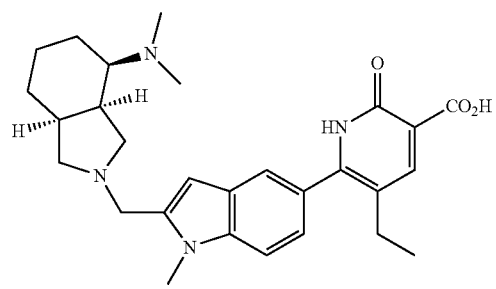
155

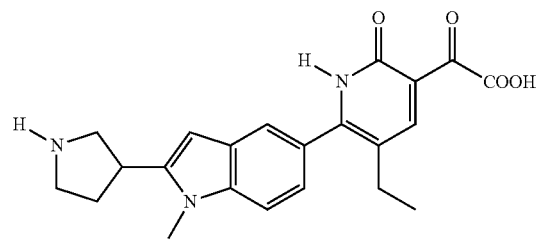
156
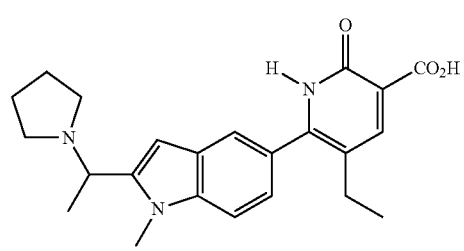
157
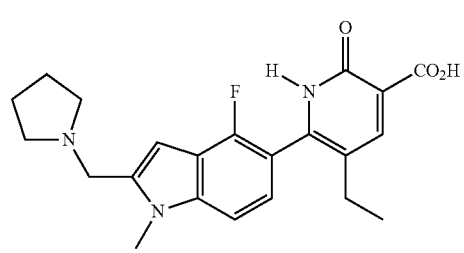
158
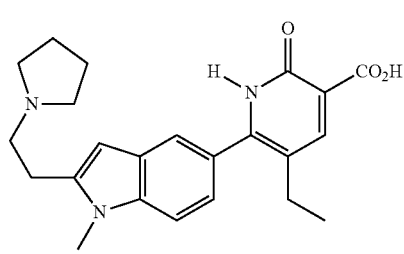
159
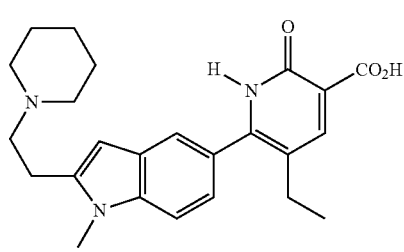
160
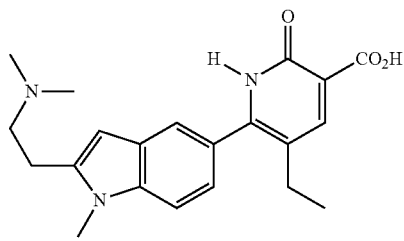
161
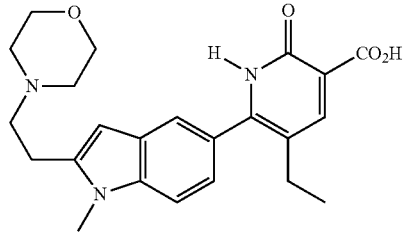
162
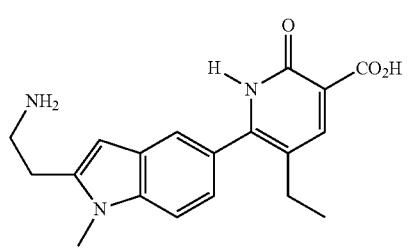
163
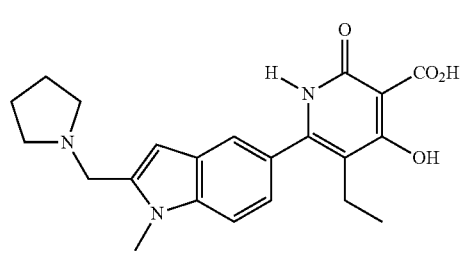
164
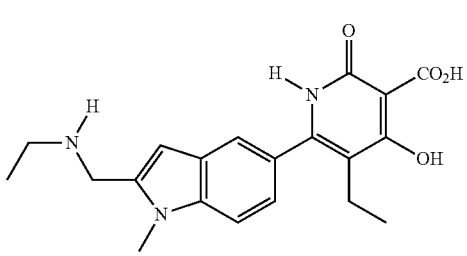
165
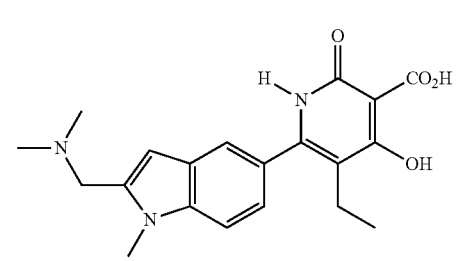
166
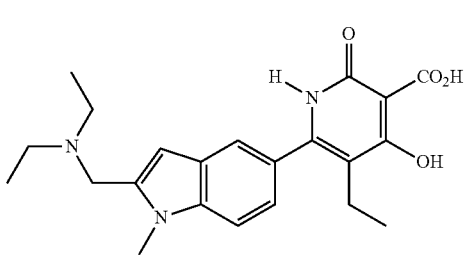
167

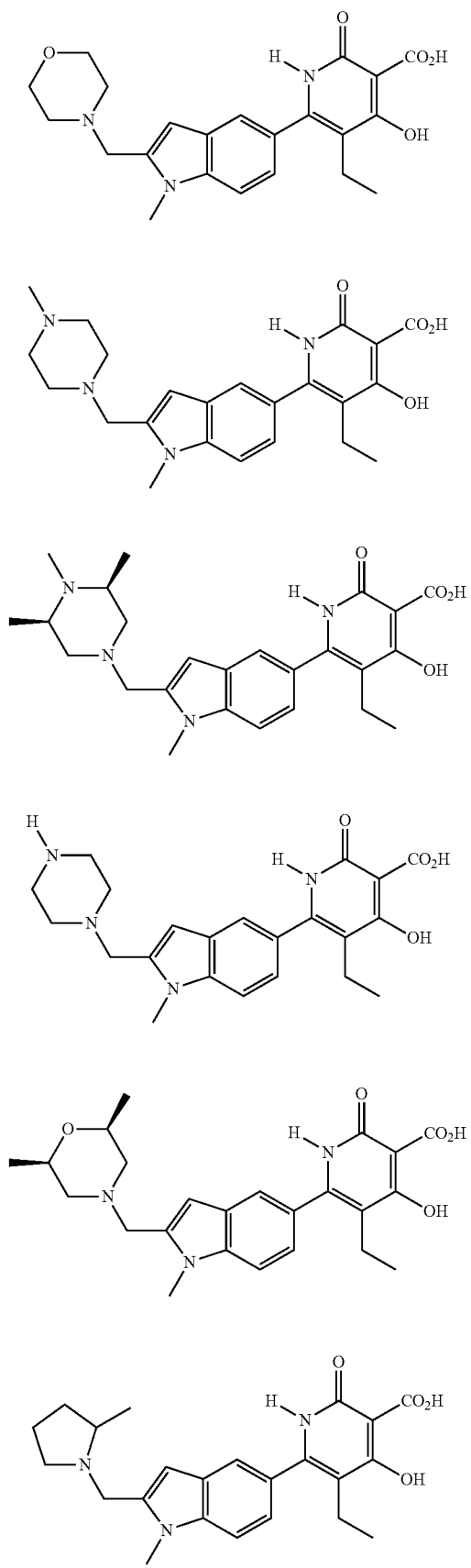
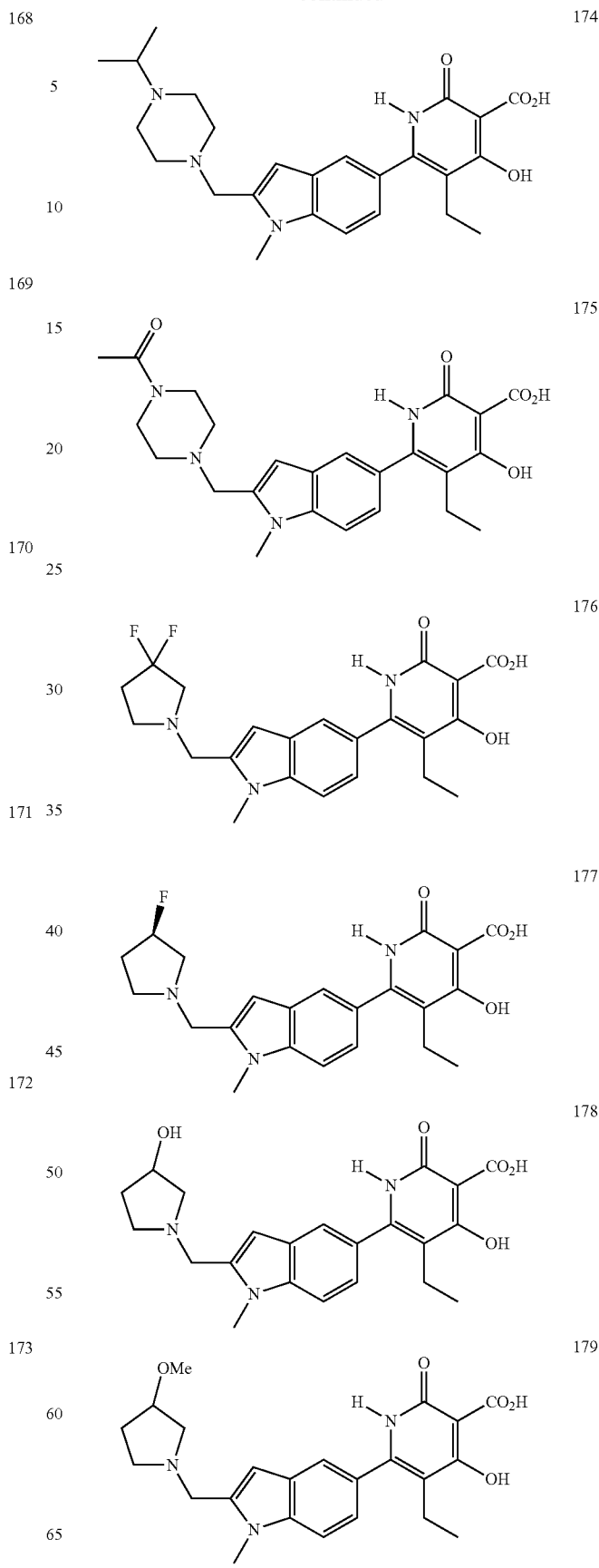

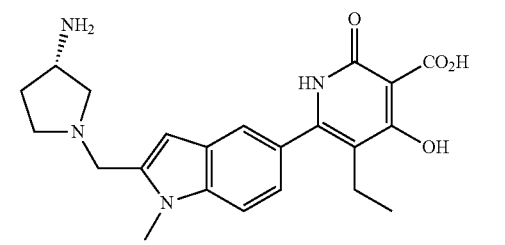
180
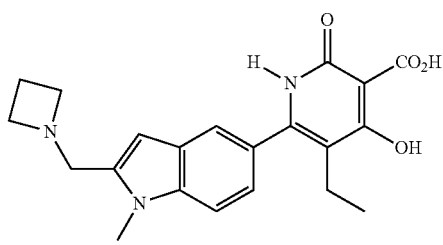
186
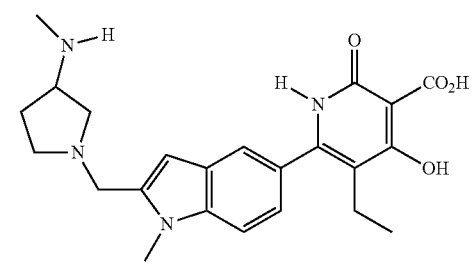
181
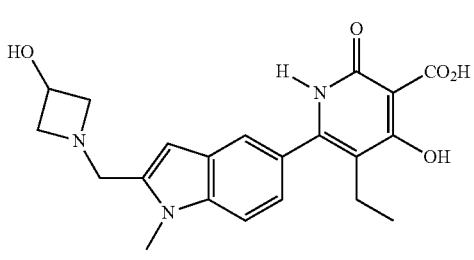
187
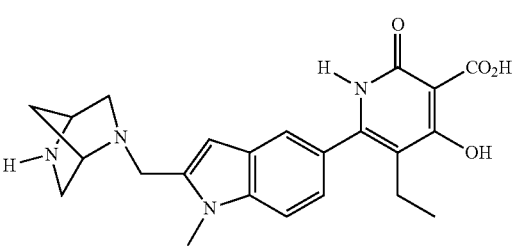
182
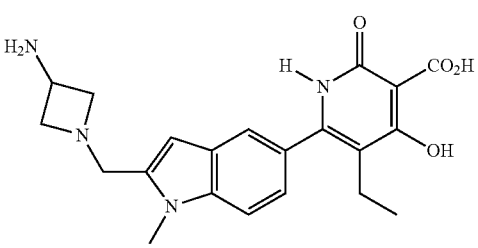
188
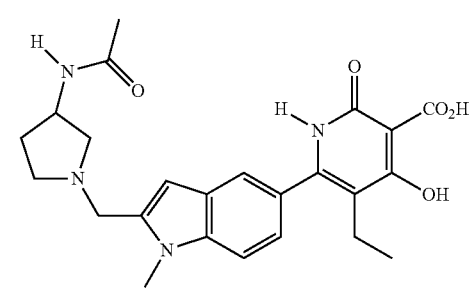
183
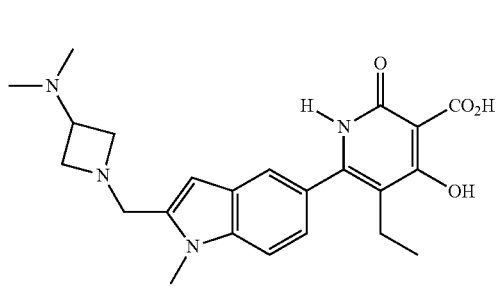
189
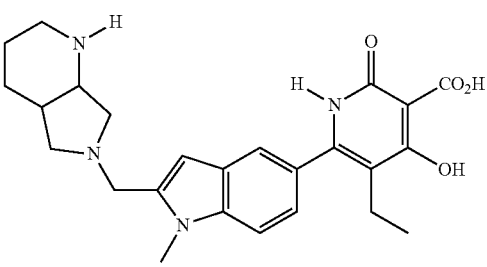
184
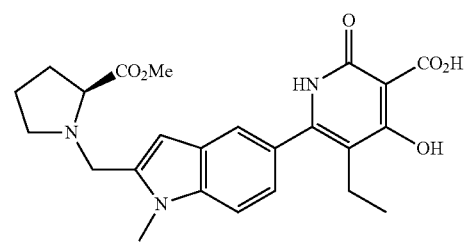
190
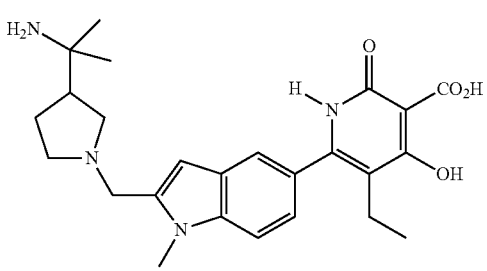
185
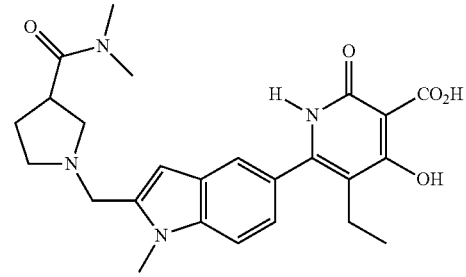
191

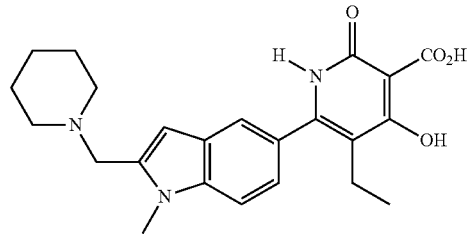
192
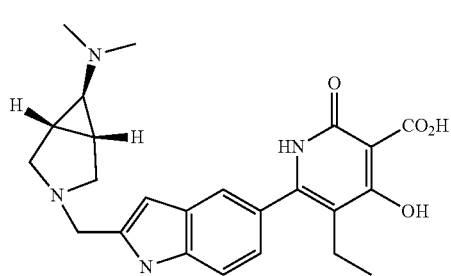
197
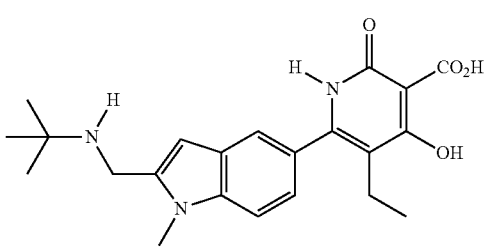
193
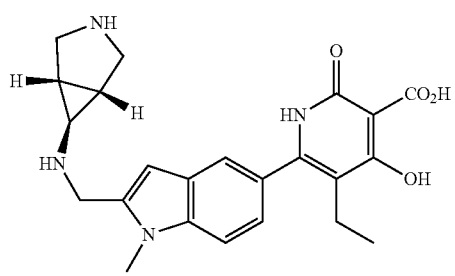
198
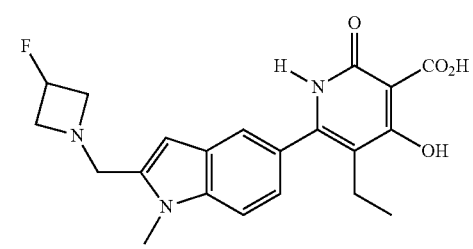
194
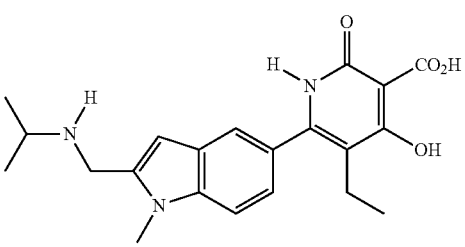
199
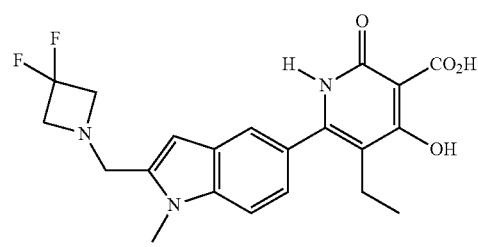
195
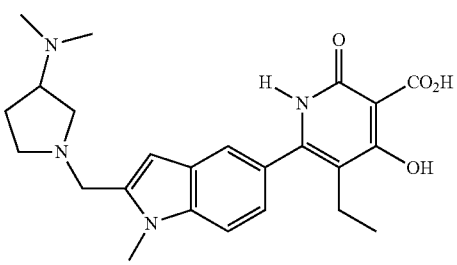
200
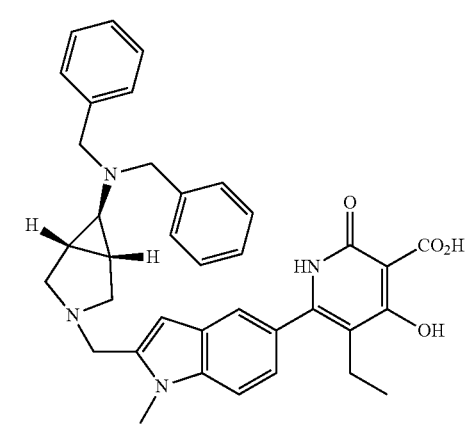
196
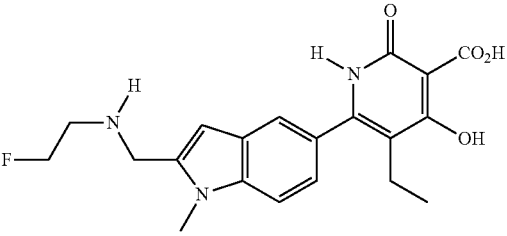
201
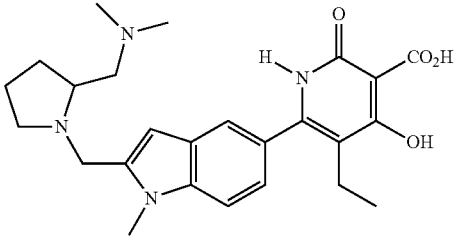
202

51
-continued
203
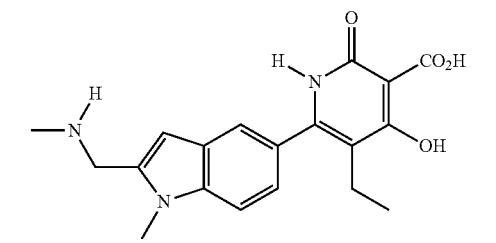
204
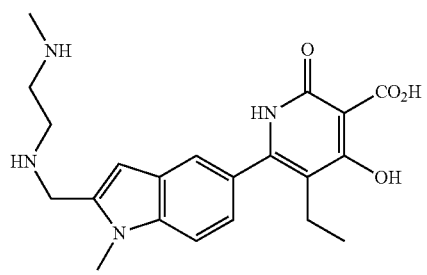
205
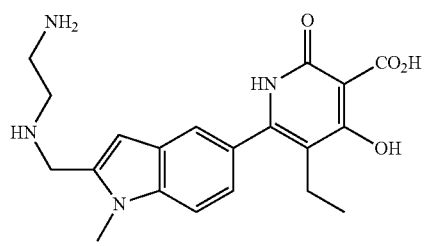
206
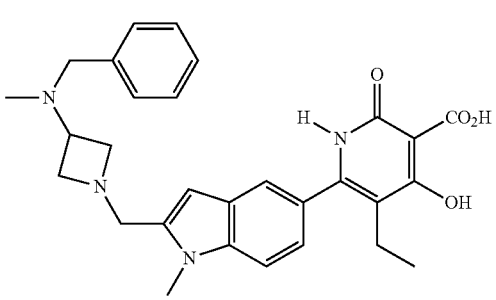
207
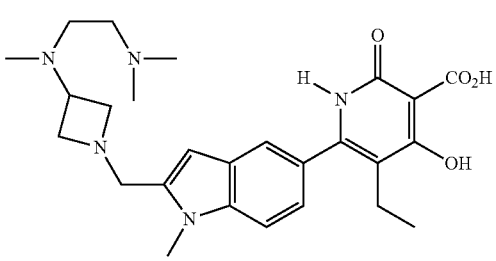
208
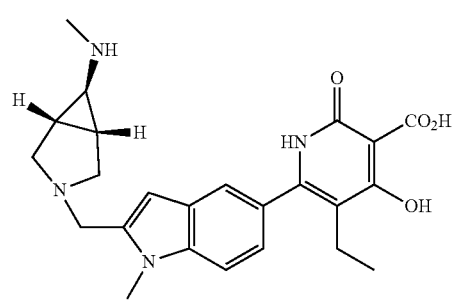
52
-continued
209
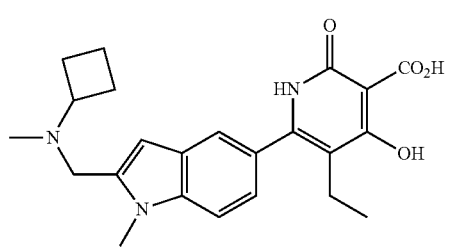
210
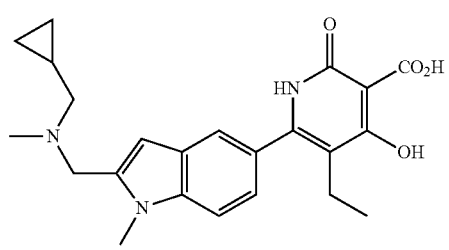
211
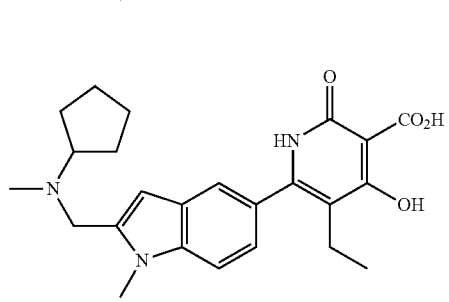
212
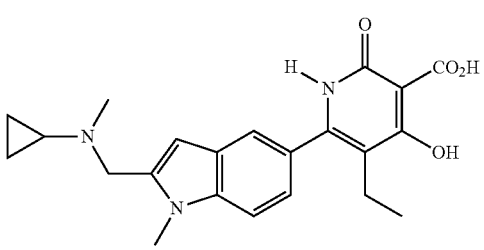
213
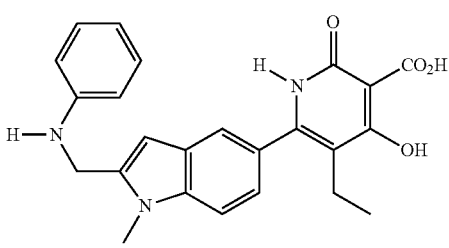
214
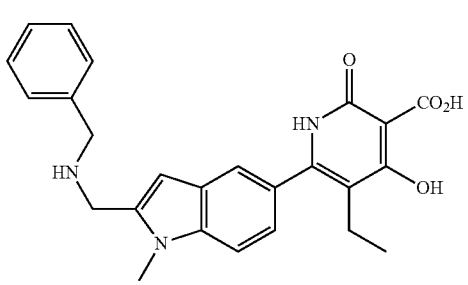

215 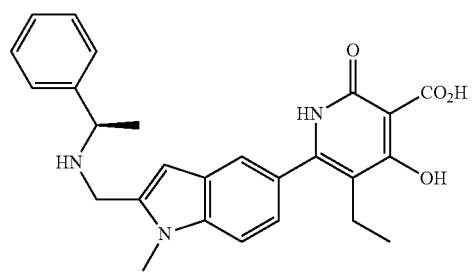
216 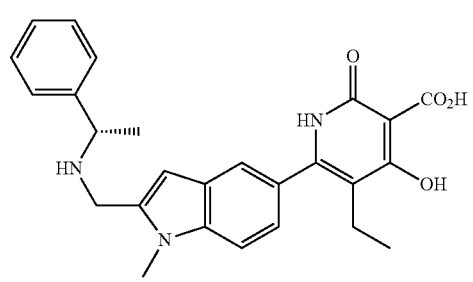
217 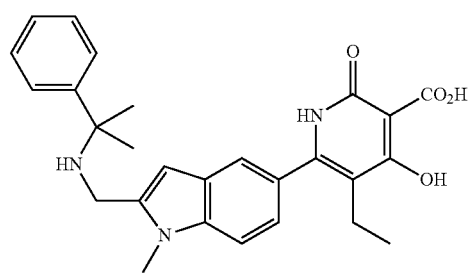
218 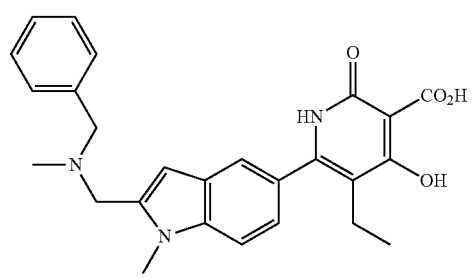
219 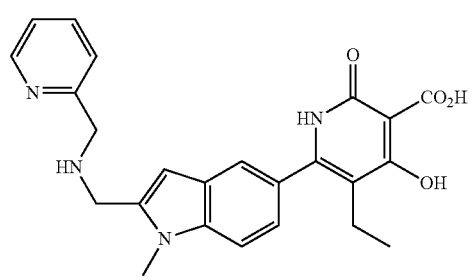
220 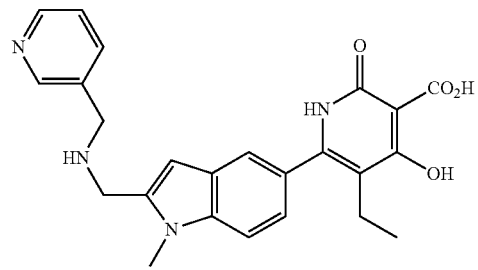
221 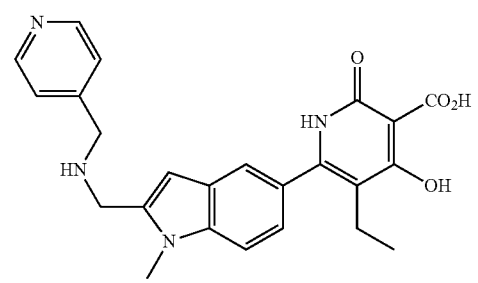
222 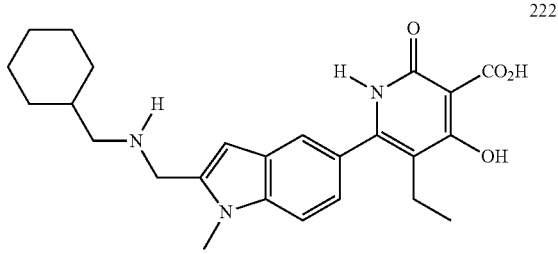
223 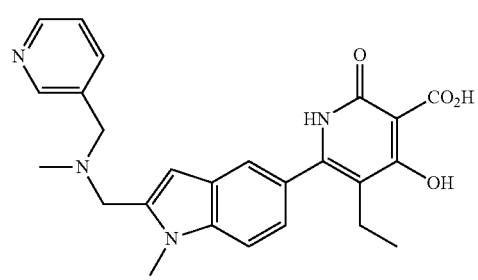
224 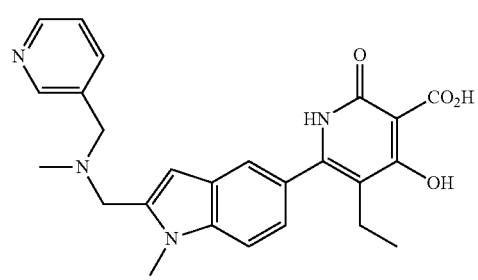
225 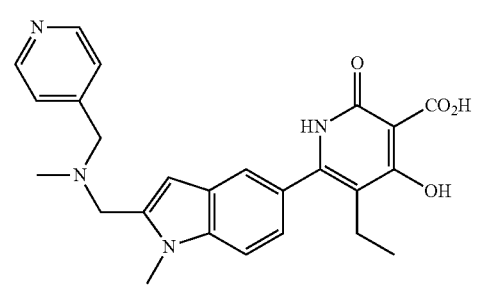

226
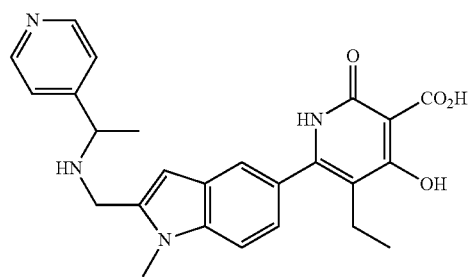
227
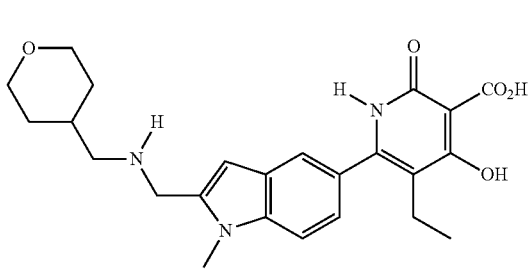
228
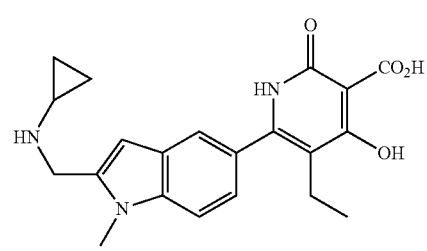
229
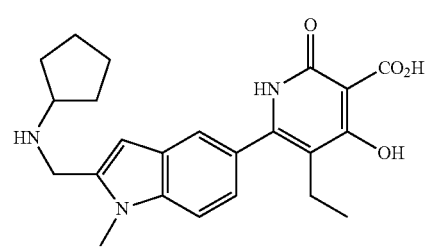
230
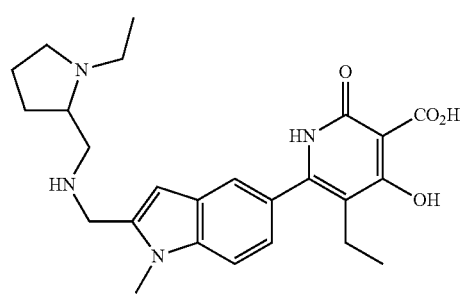
231
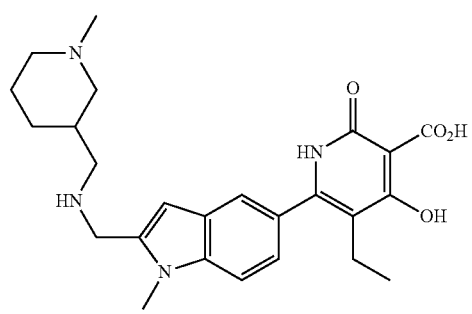
232
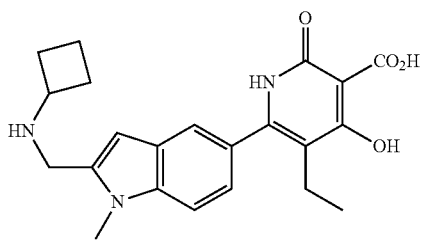
233
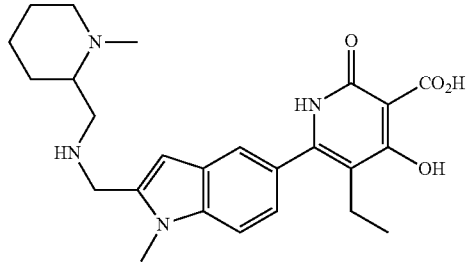
234
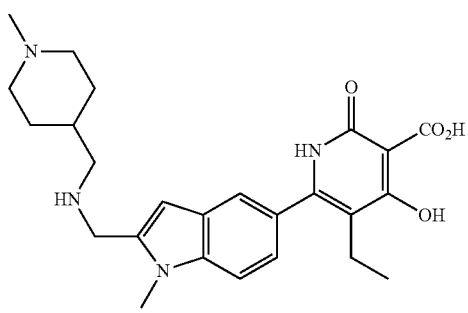
235
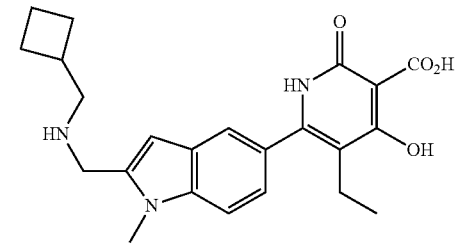
236
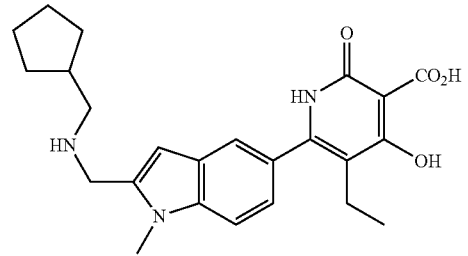
237
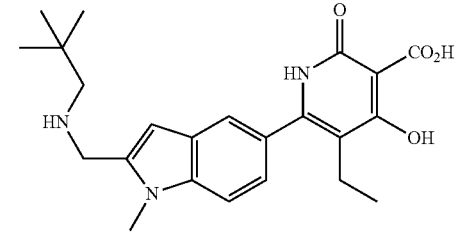

238
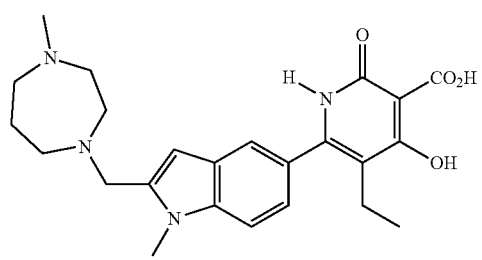
239
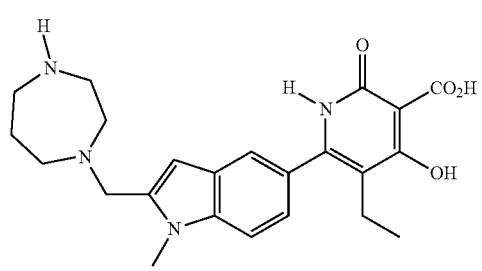
240
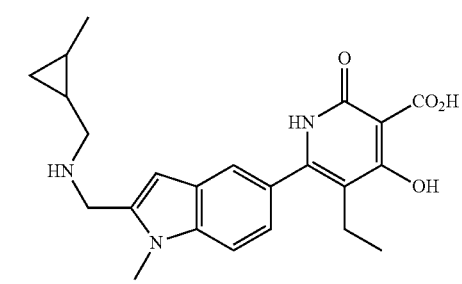
241
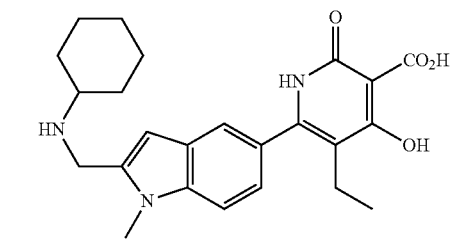
242
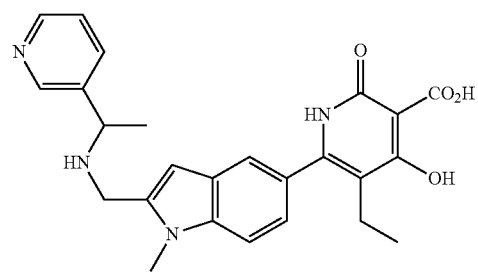
243
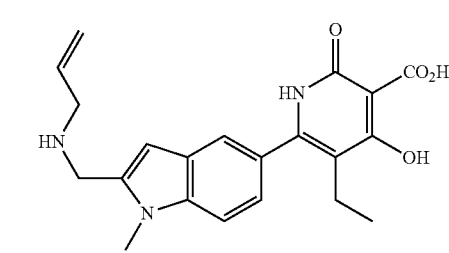
244
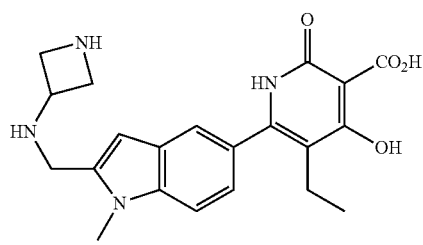
245
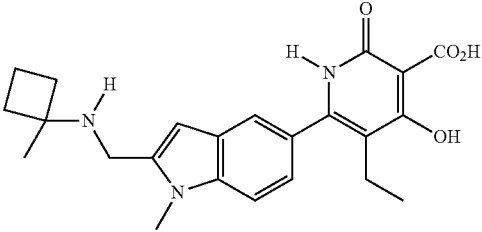
246
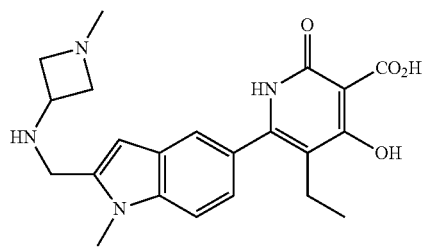
247
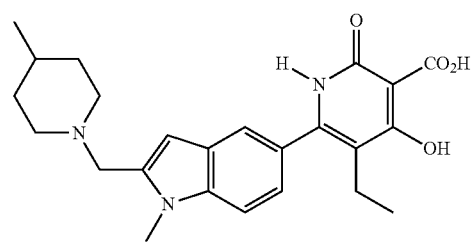
248
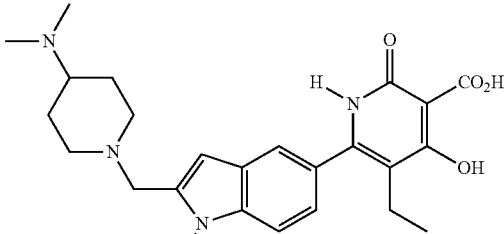
249
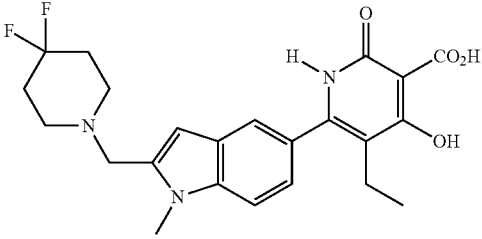

250 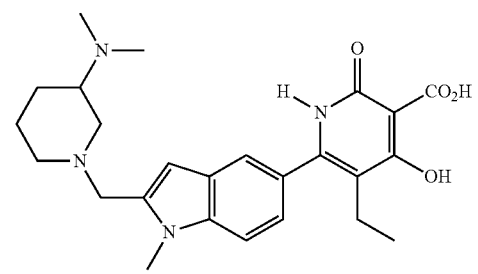
251 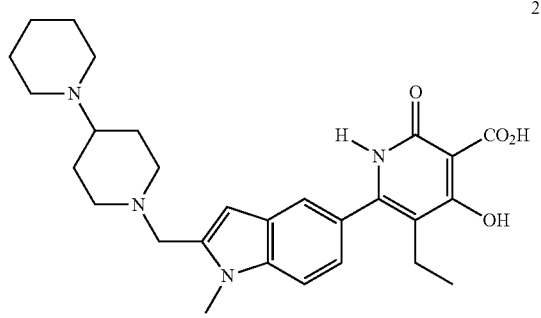
252 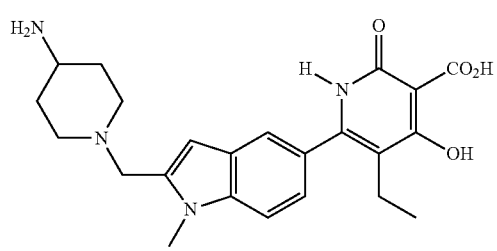
253 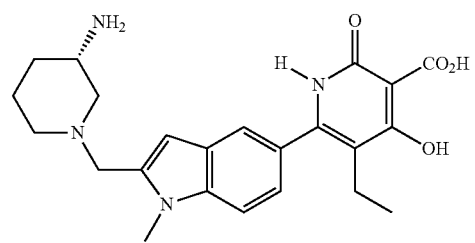
254 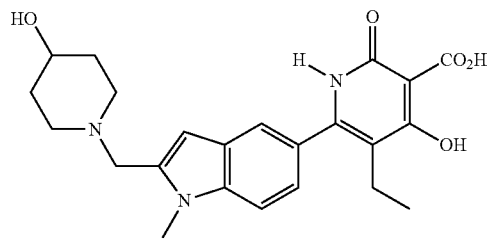
255 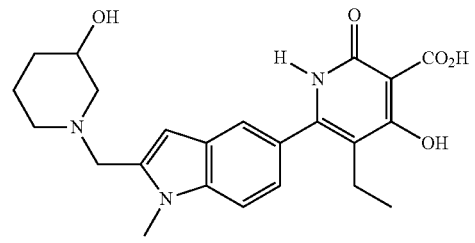
256 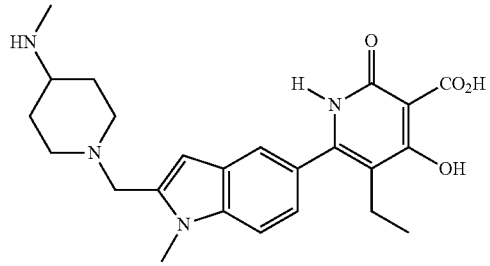
257 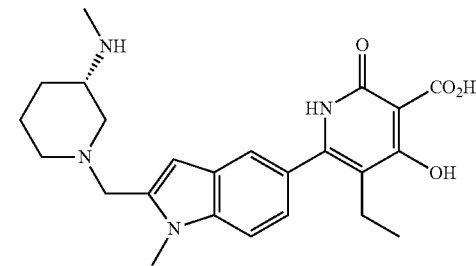
258 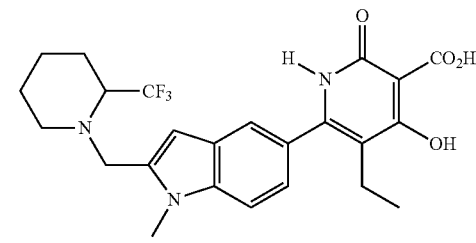
259 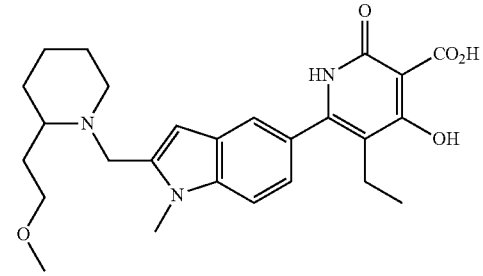
260 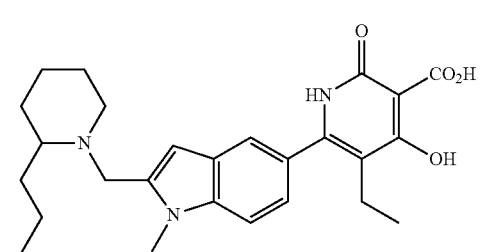
261 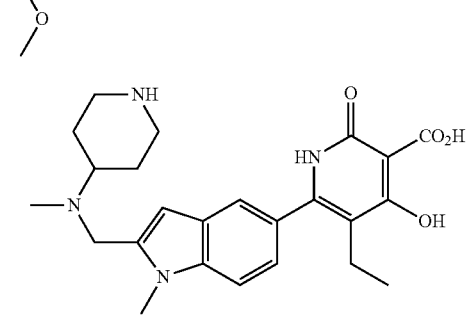

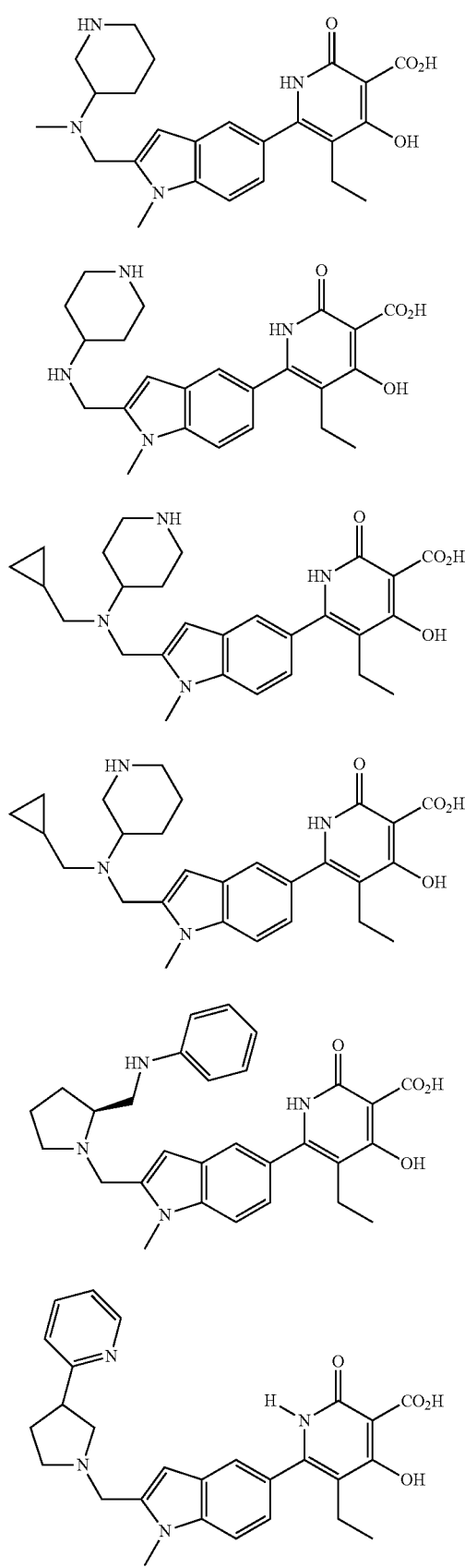

274 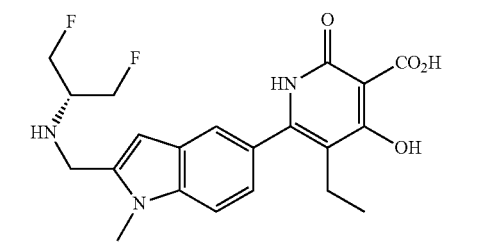
275 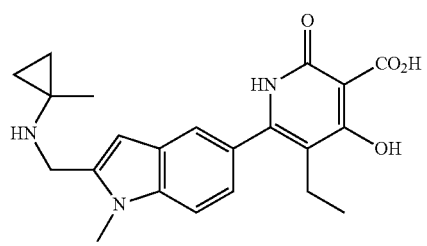
276 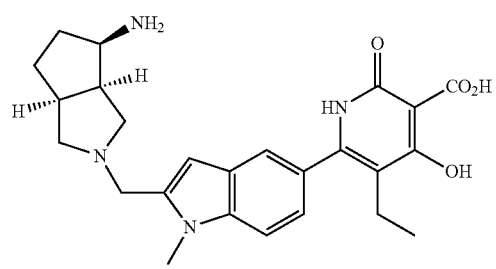
277 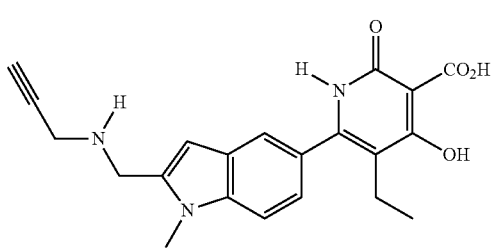
278 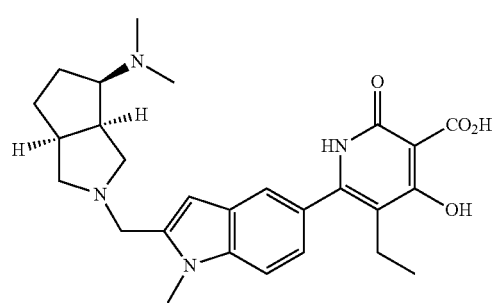
279 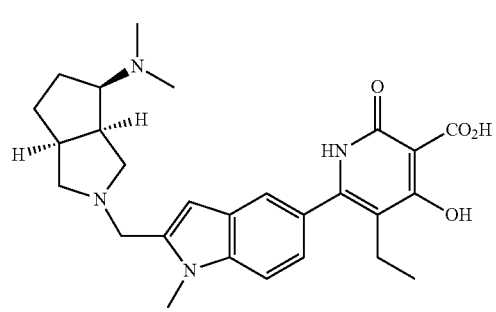
280 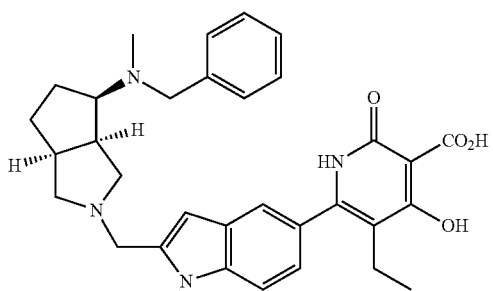
281 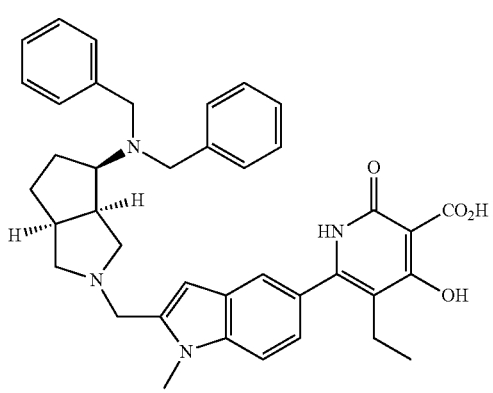
282 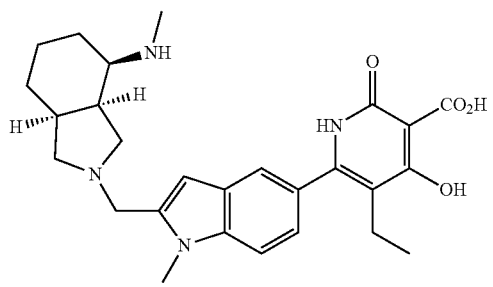
283 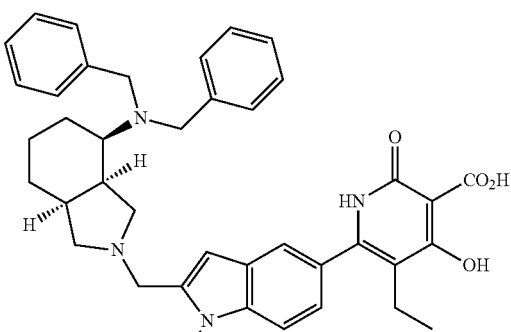
284 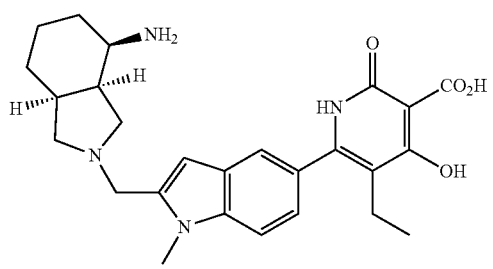

285
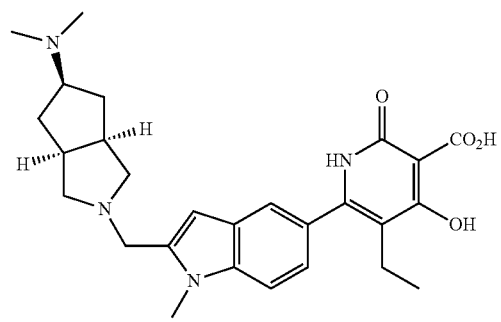
286
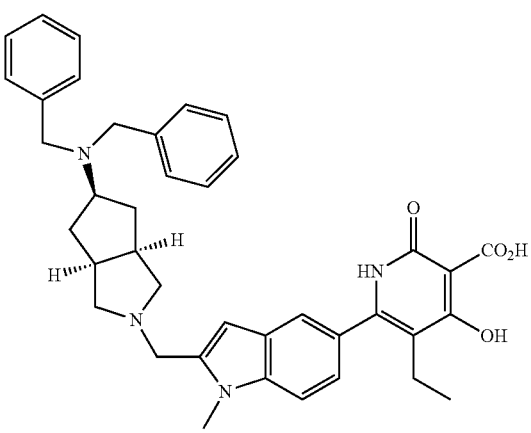
287
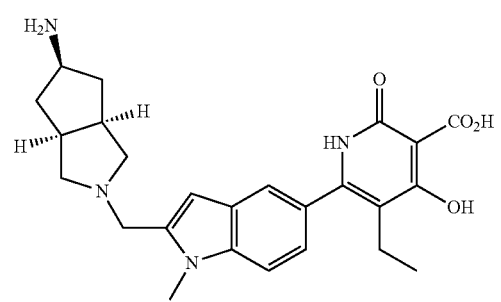
288
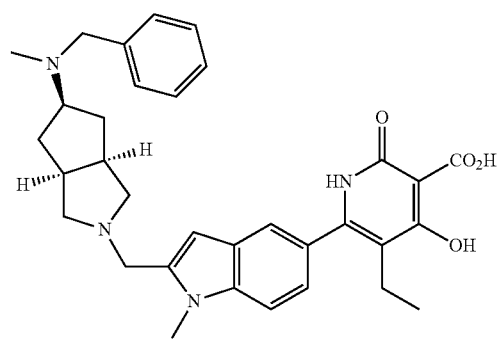
289
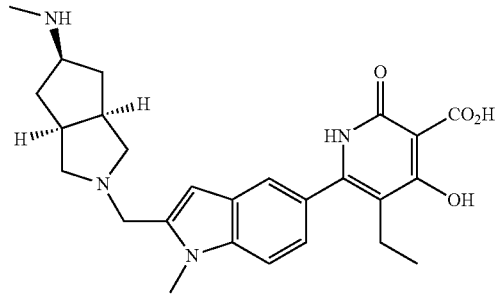
290
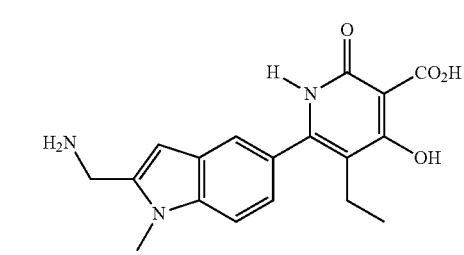
291
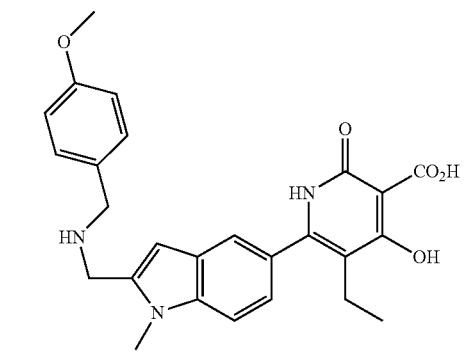
292
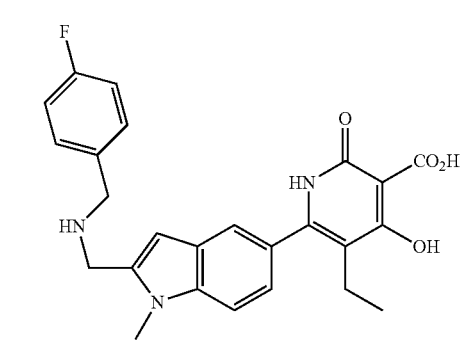
293
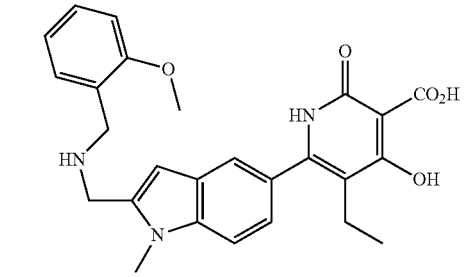

294
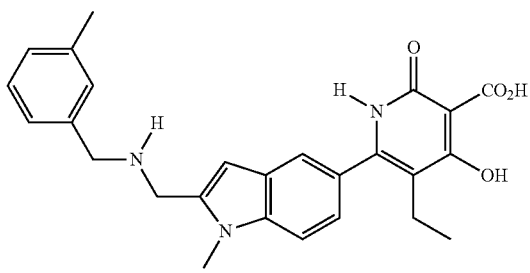
295
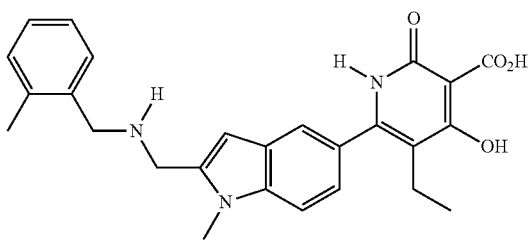
296
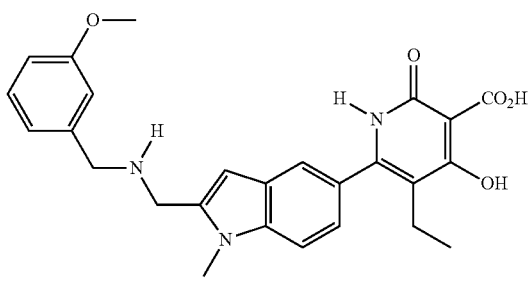
297
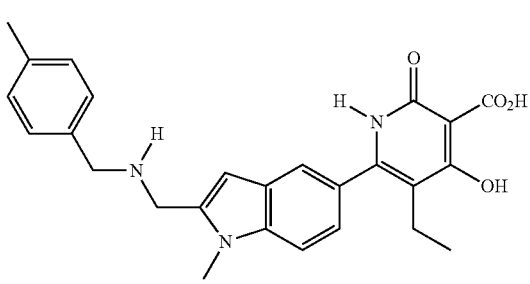
298
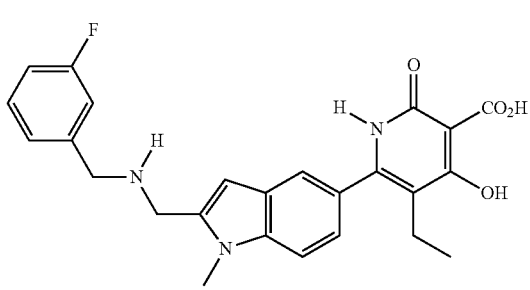
299
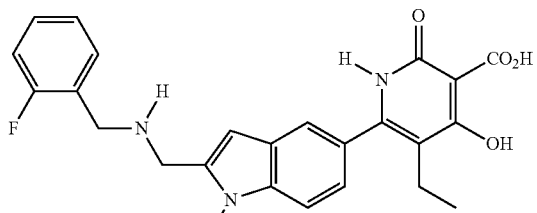
300
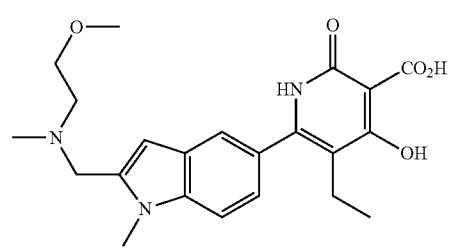
301
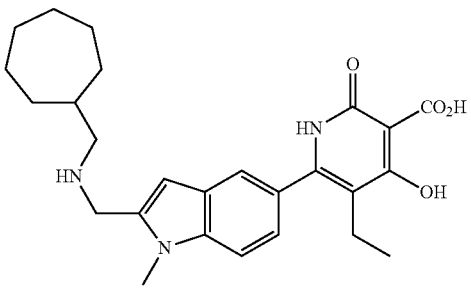
302
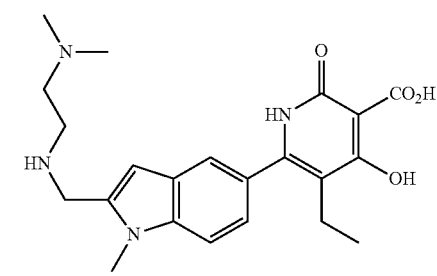
303
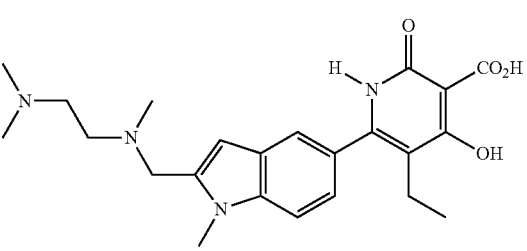
304
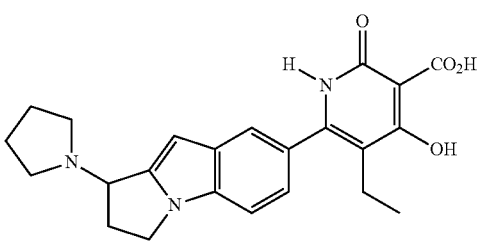

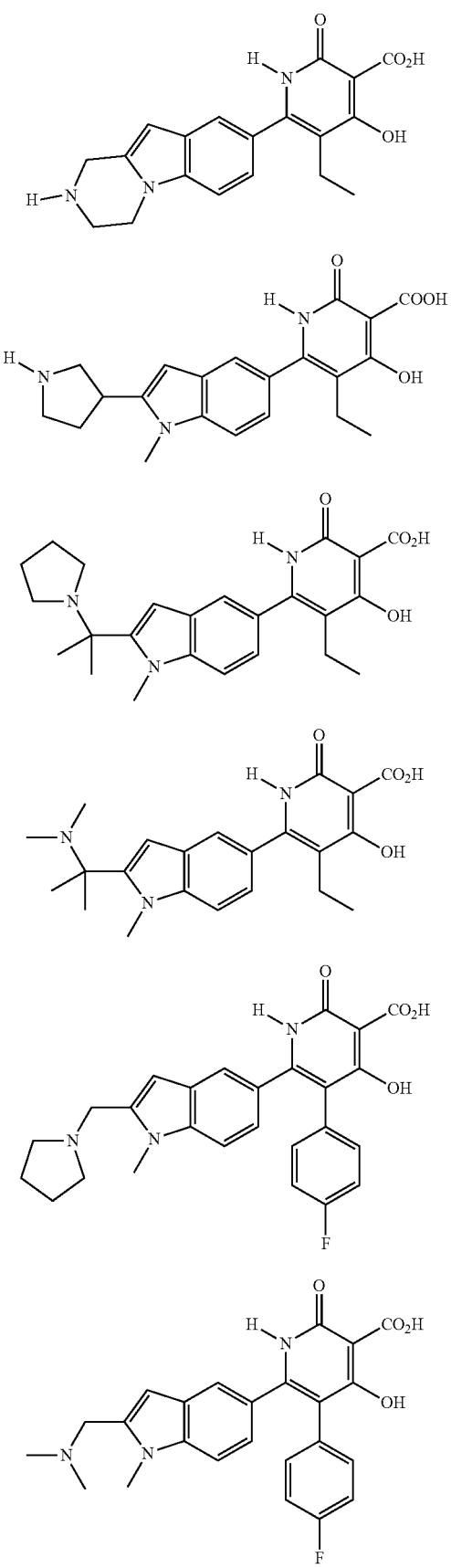
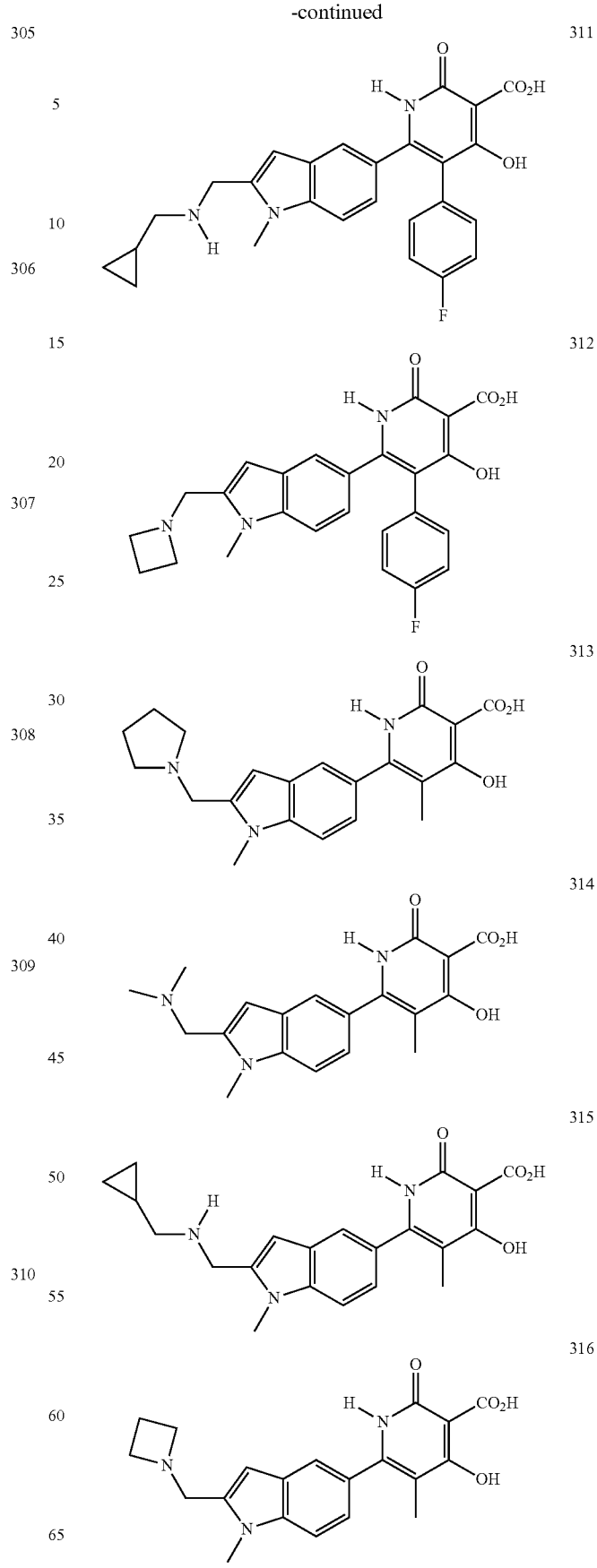

317 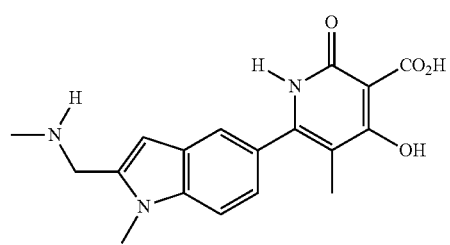
318 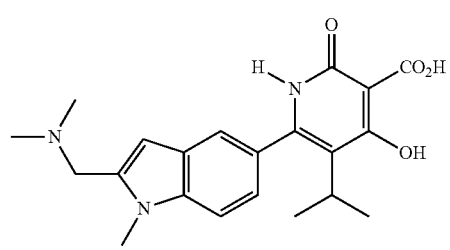
319 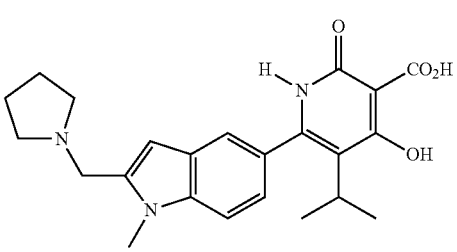
320 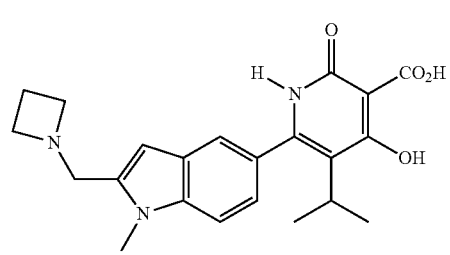
321 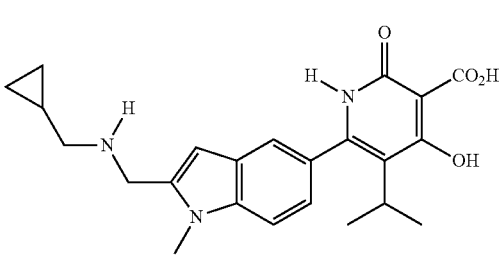
322 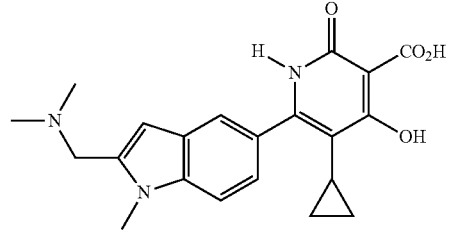
323 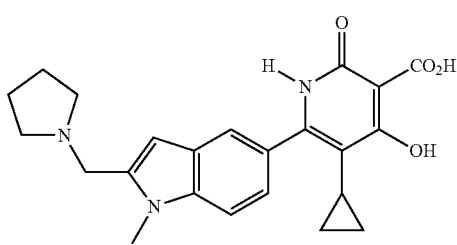
324 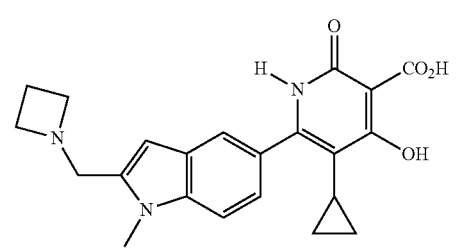
325 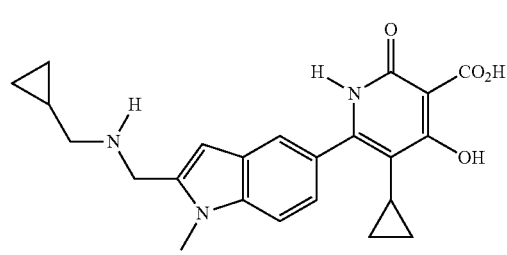
326 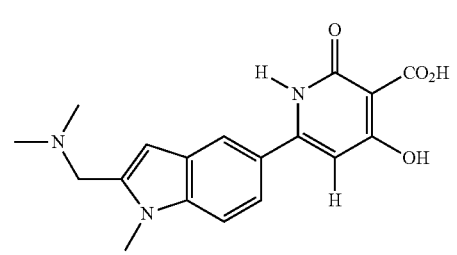
327 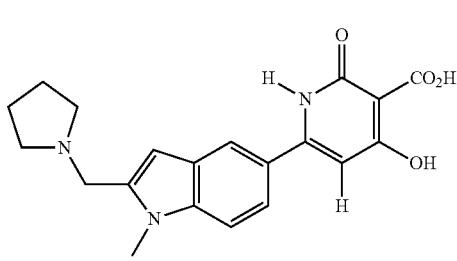
328 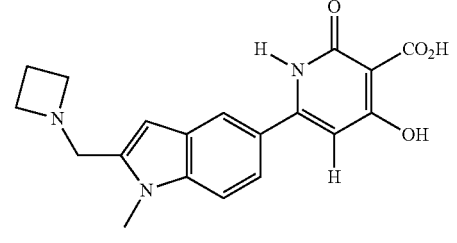

329 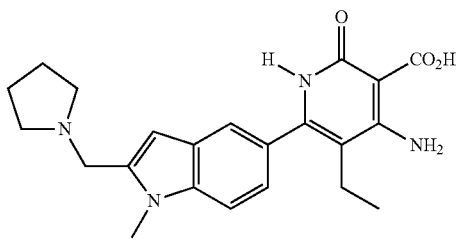
330 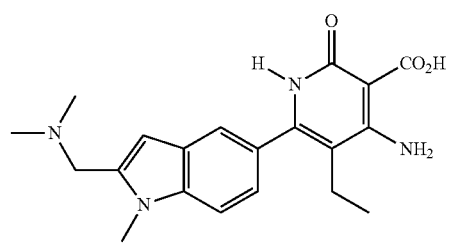
331 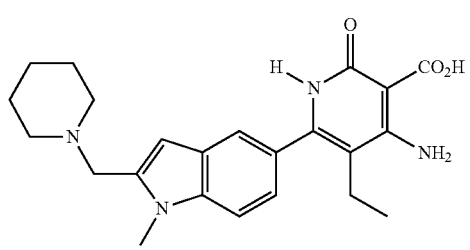
332 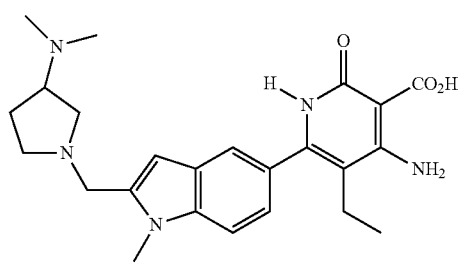
333 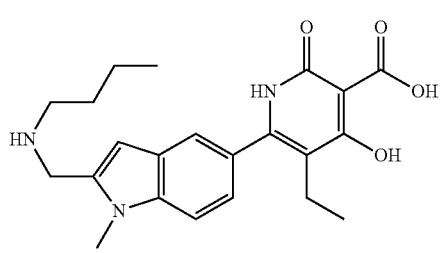
334 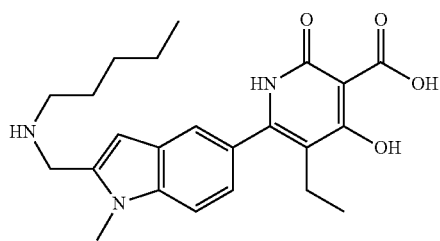
335 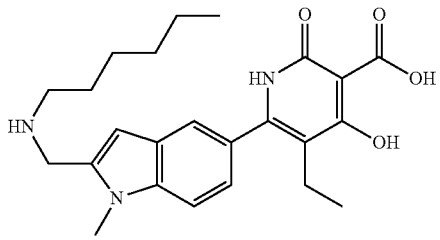
336 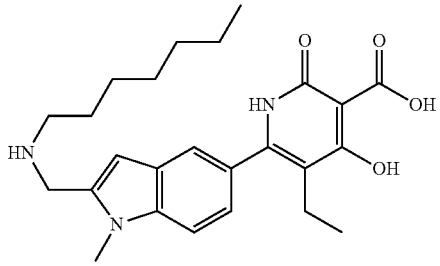
337 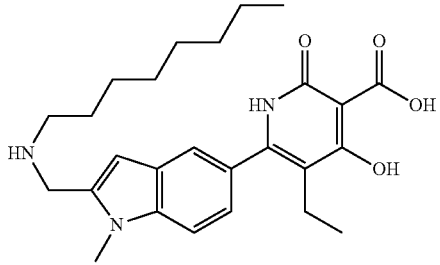
338 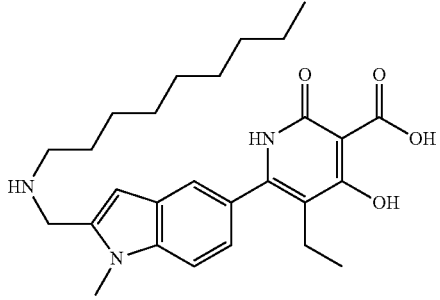
339 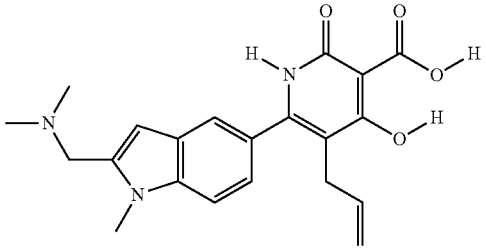
340 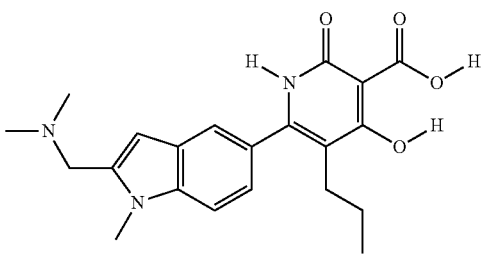

| 341 | 347 |
|---|---|
| 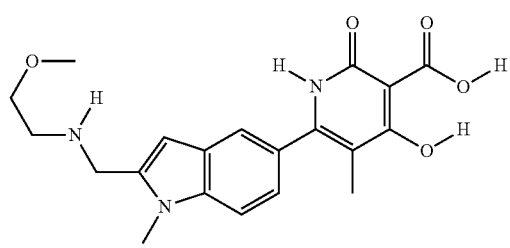 | 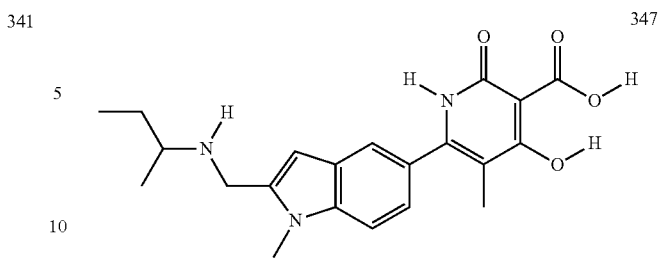 |
| 342 | 348 |
| 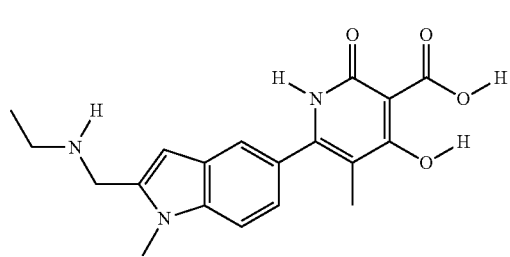 | 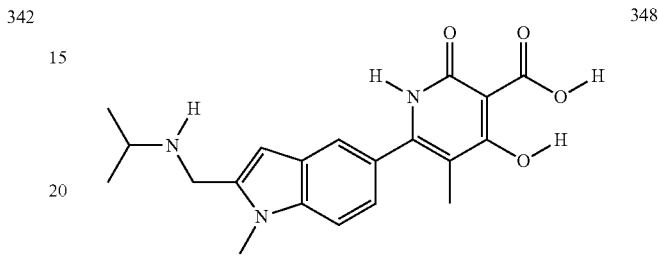 |
| 343 | 349 |
| 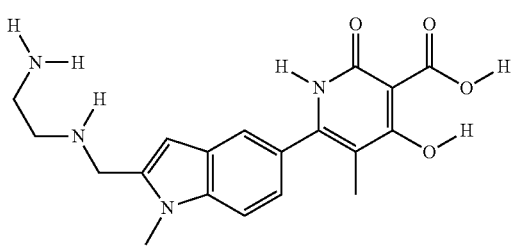 | 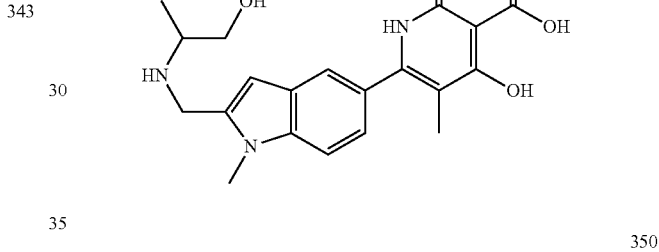 |
| 344 | 350 |
| 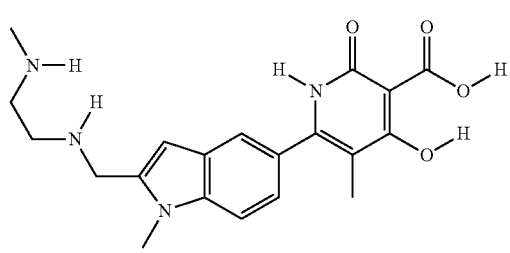 | 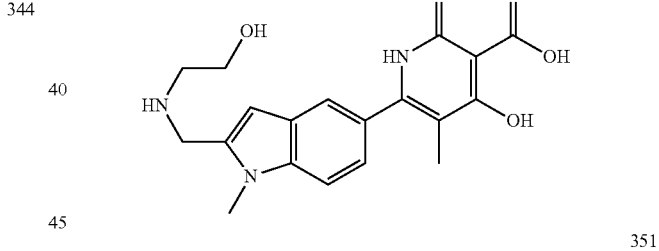 |
| 345 | 351 |
| 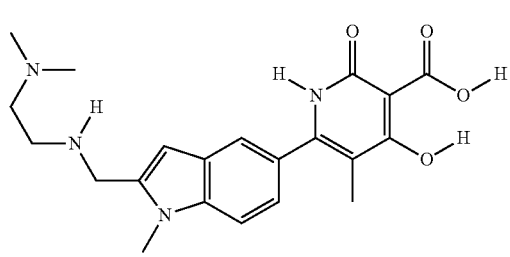 | 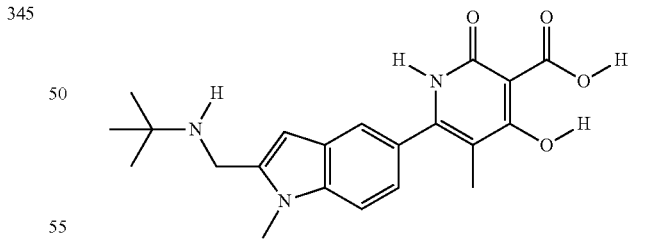 |
| 346 | 352 |
| 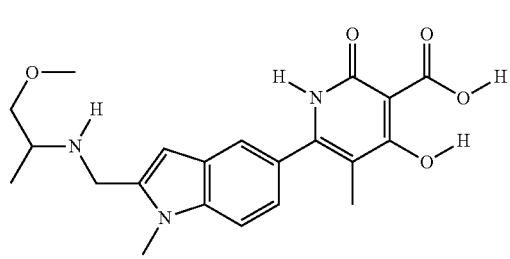 | 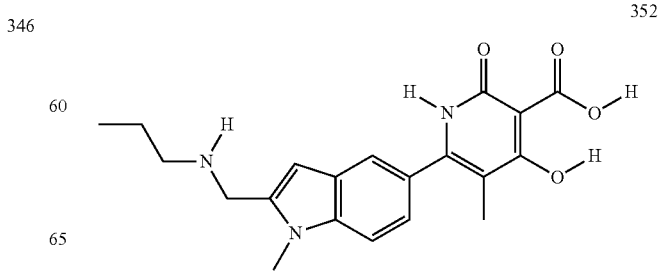 |

353
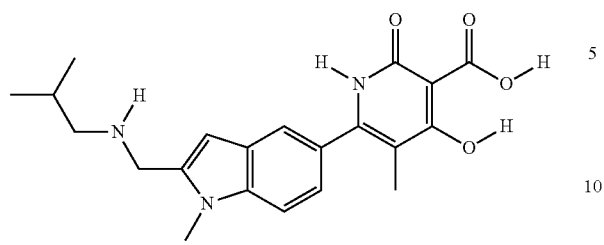
359
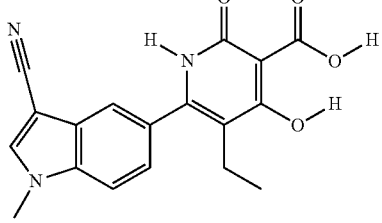
354
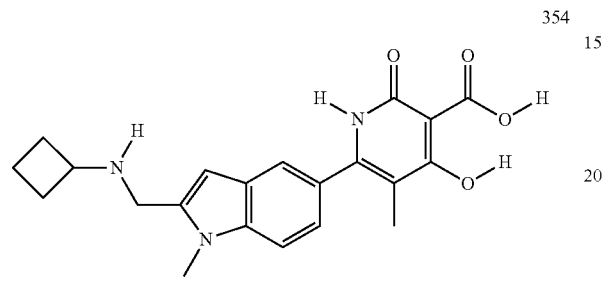
360
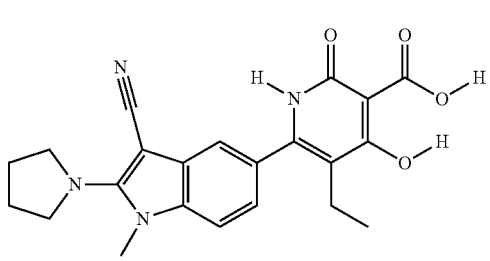
355
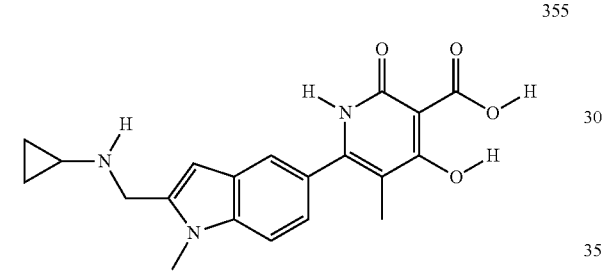
361
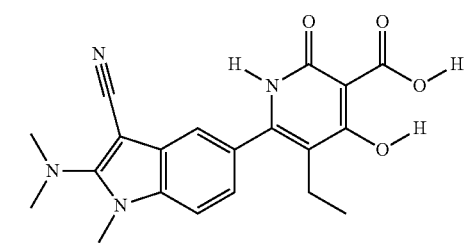
356
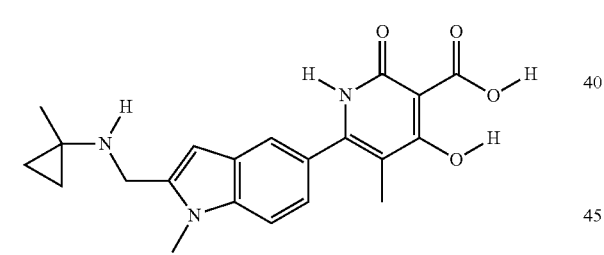
362
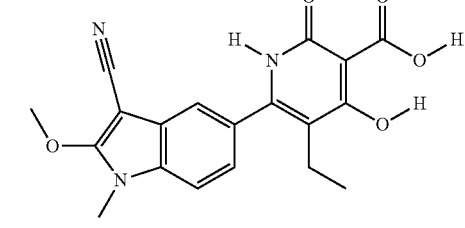
357
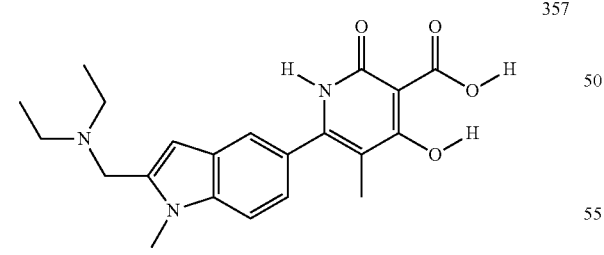
363
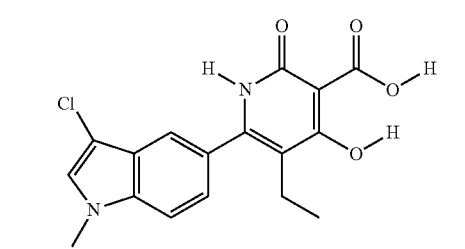
358
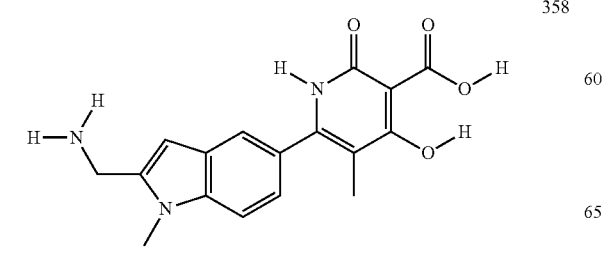
364
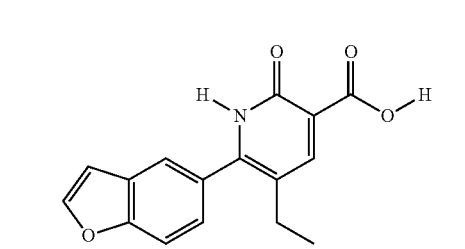

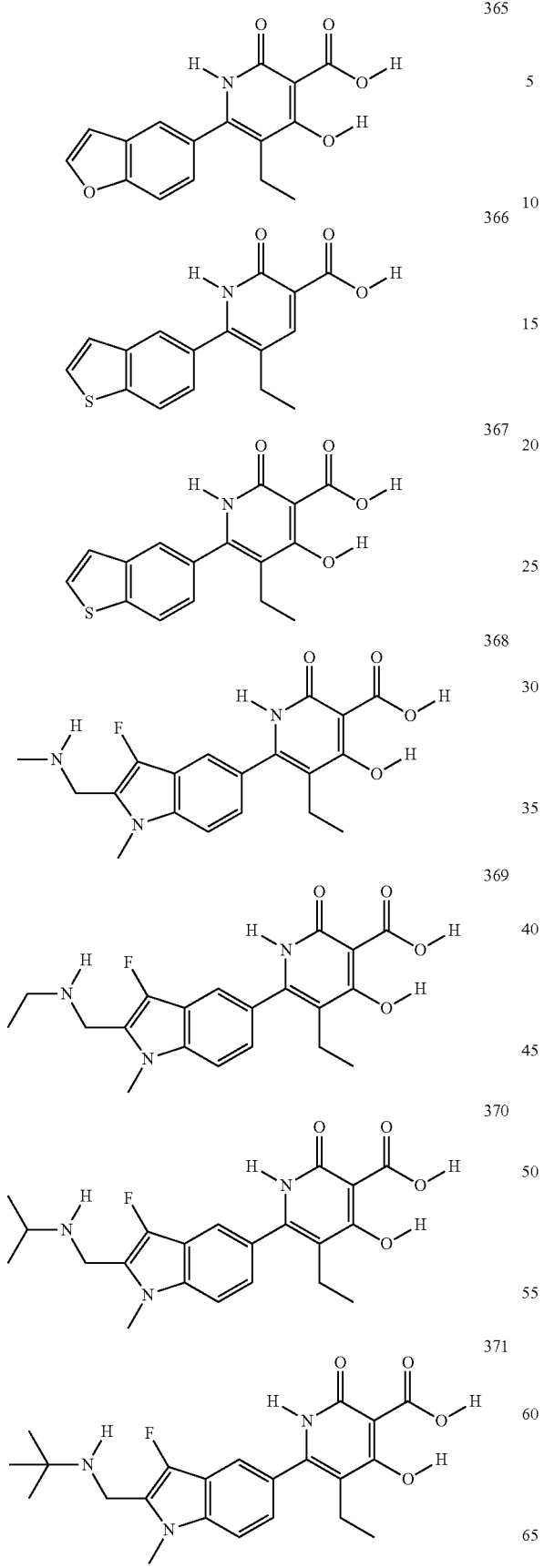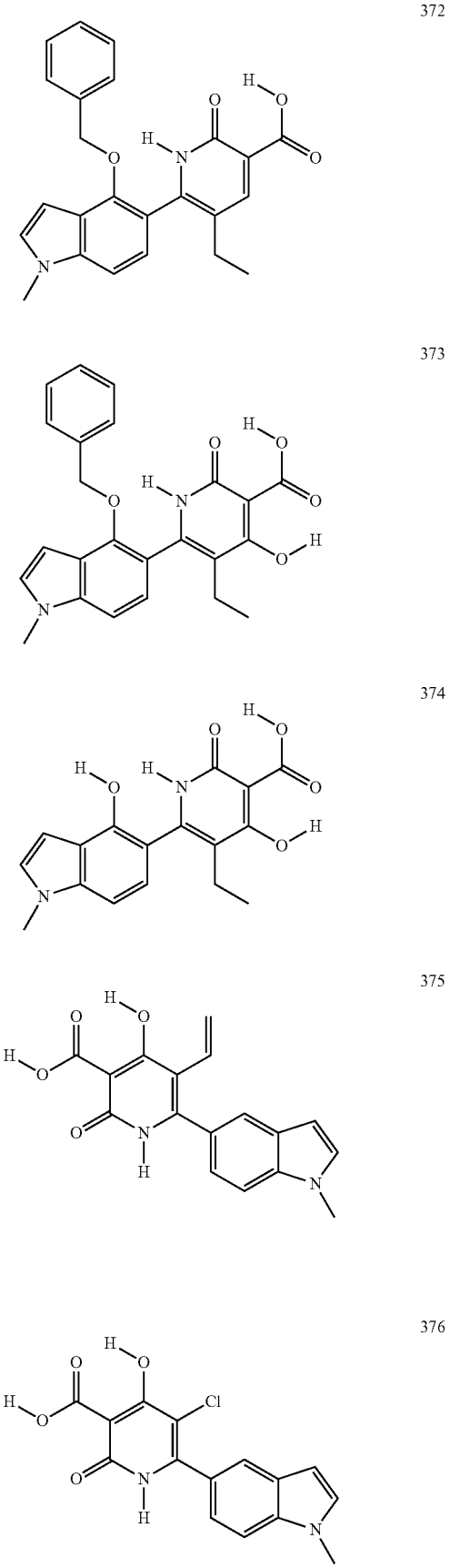

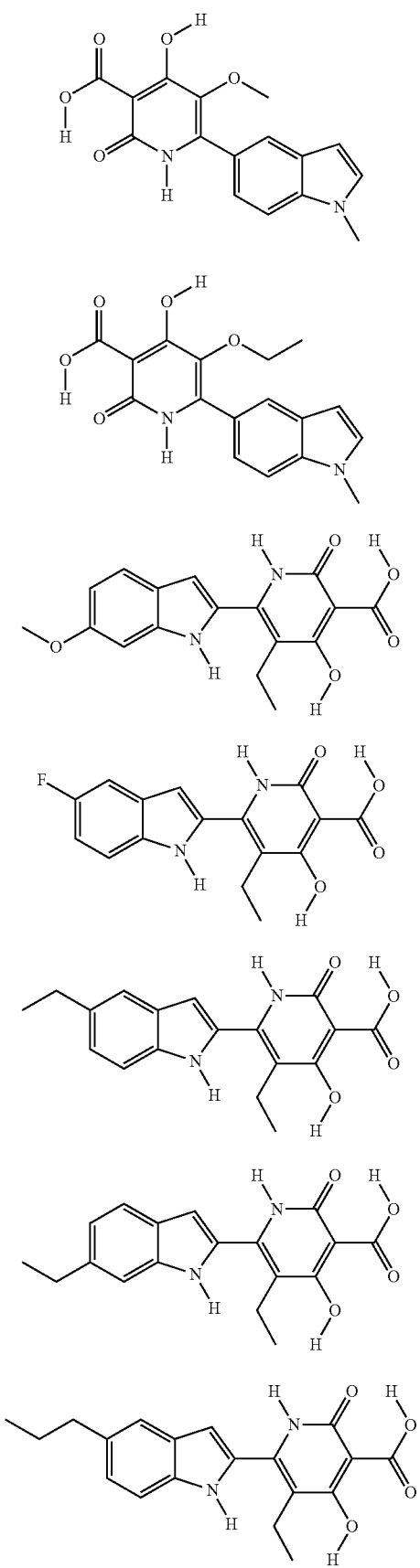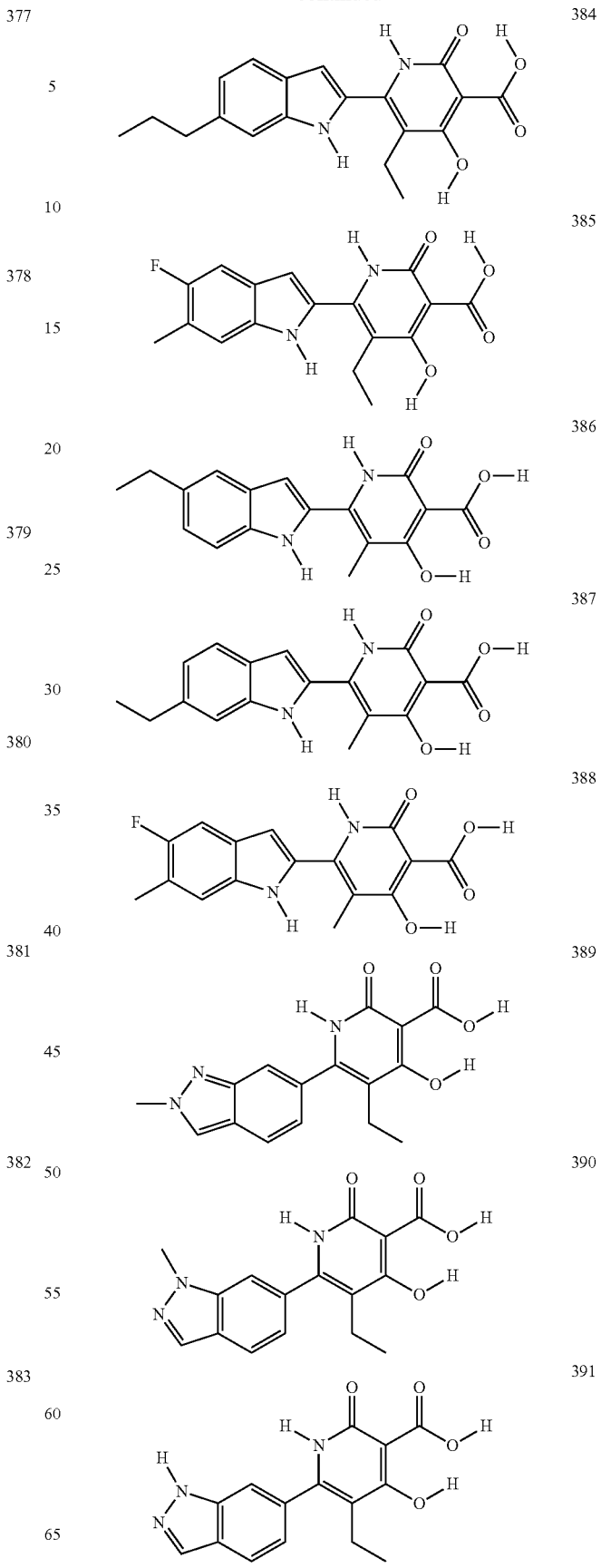

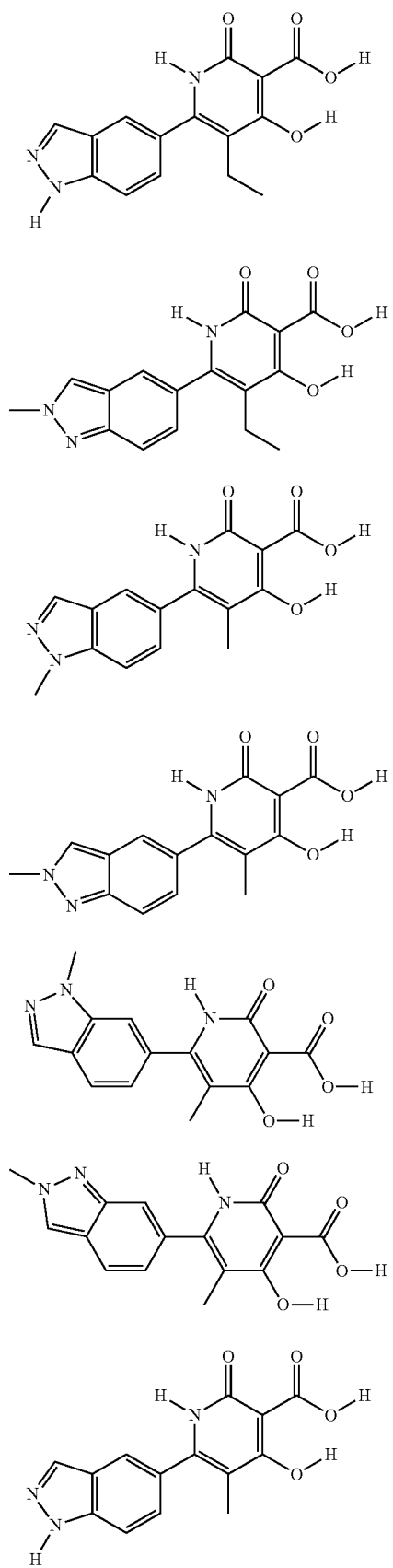
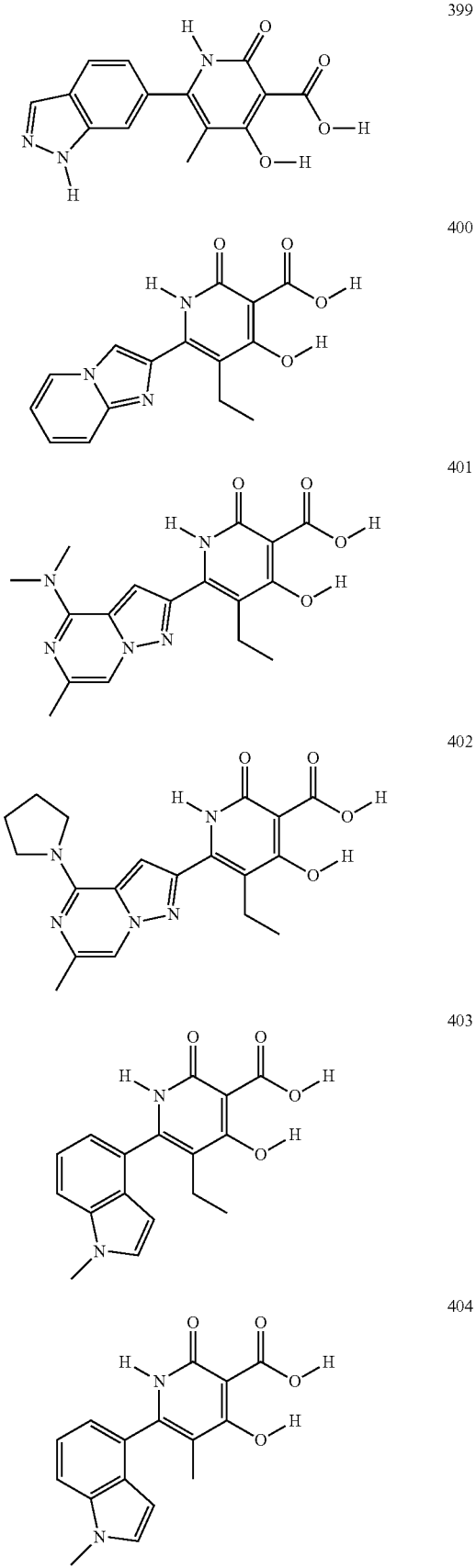

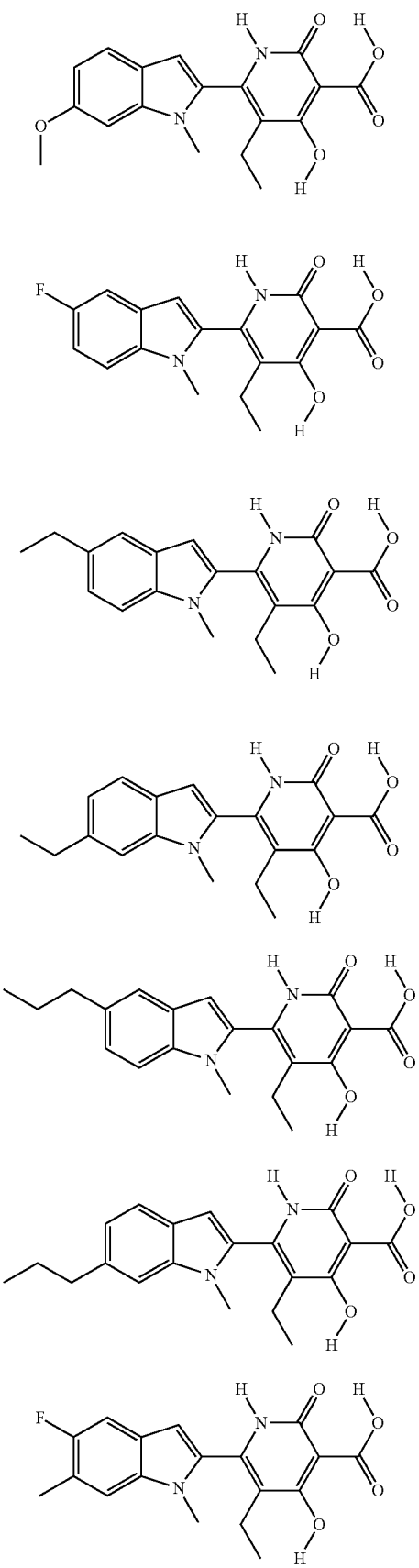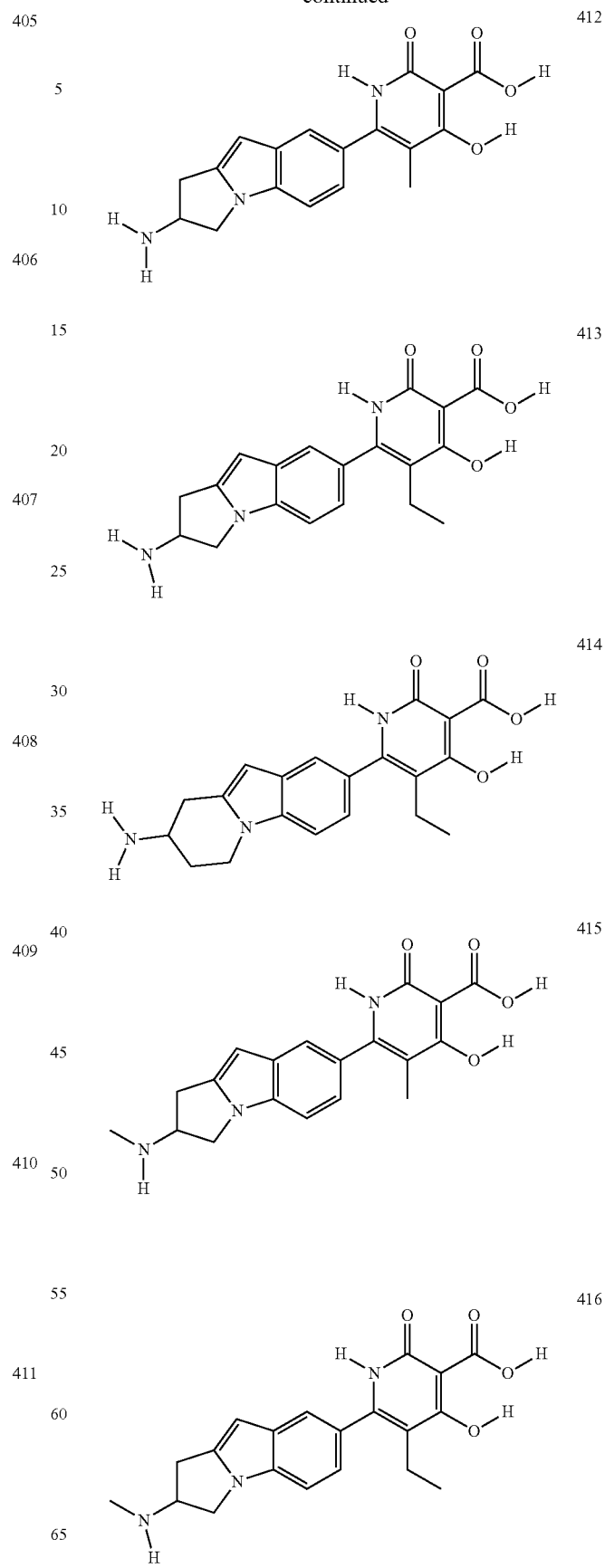

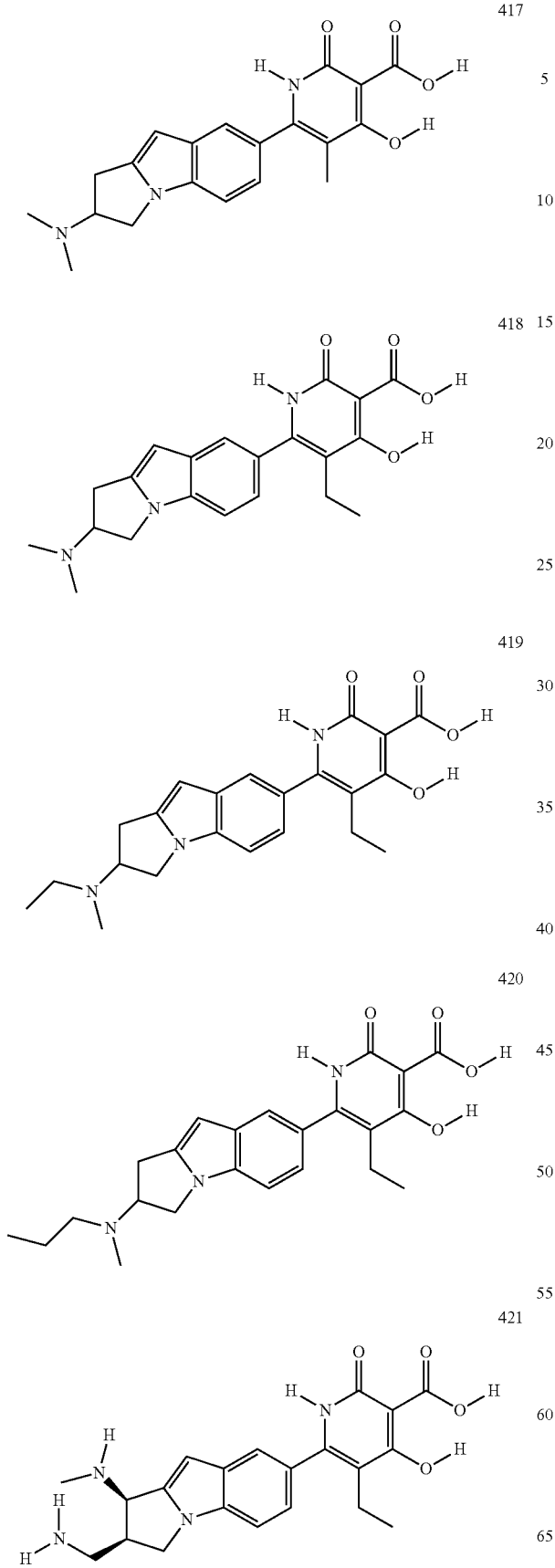
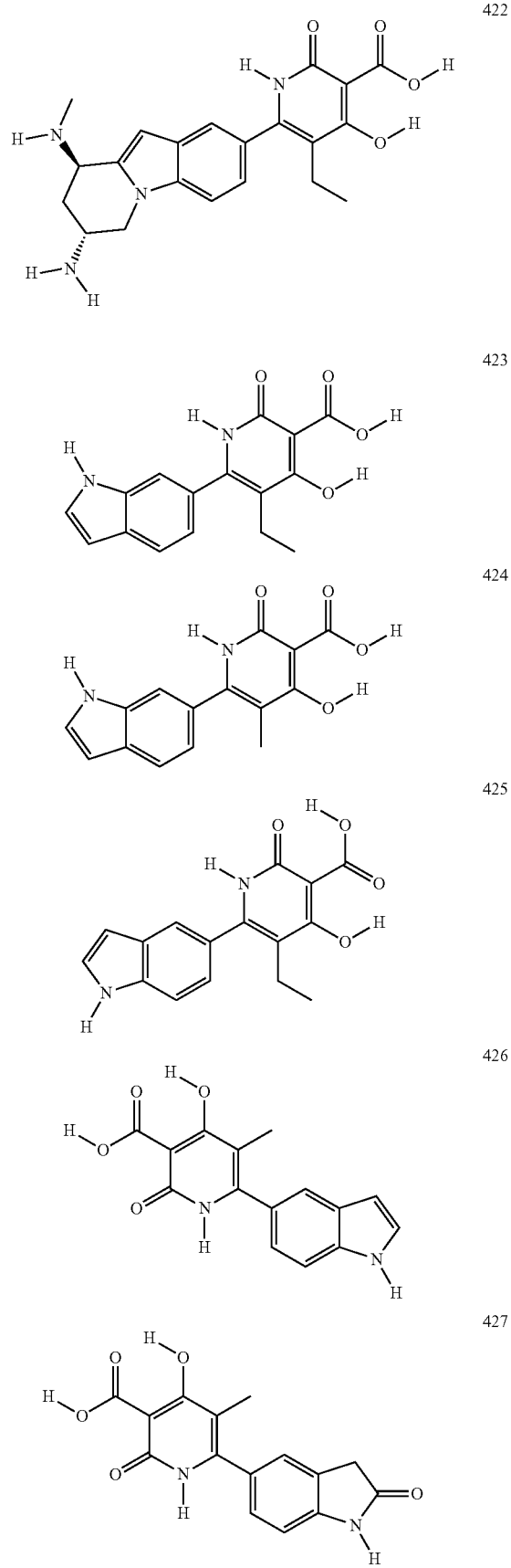

| | |
|---|---|
| 428 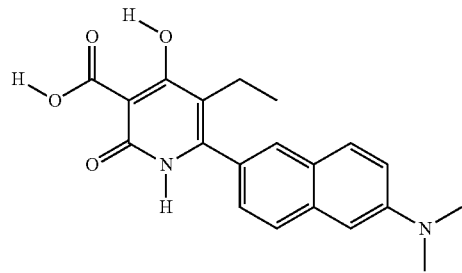 | 434 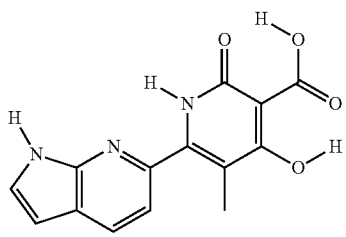 |
| 429 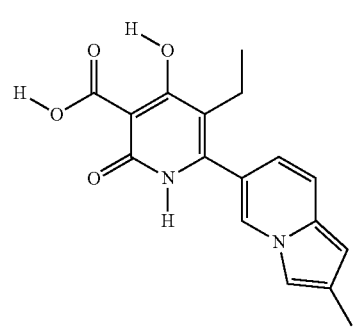 | 435 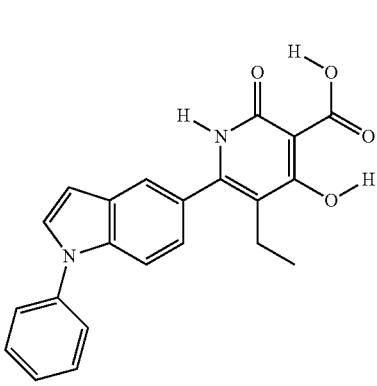 |
| 430 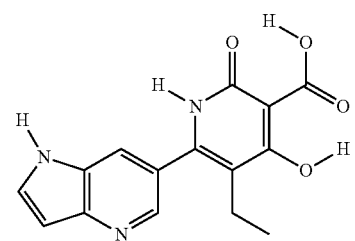 | 436 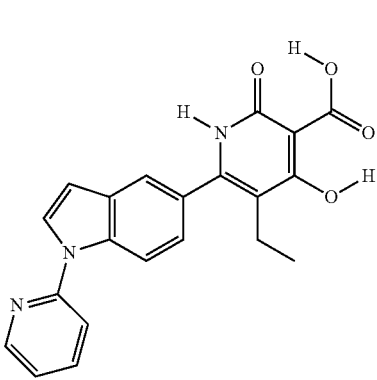 |
| 431 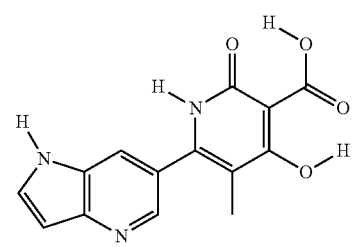 | 437 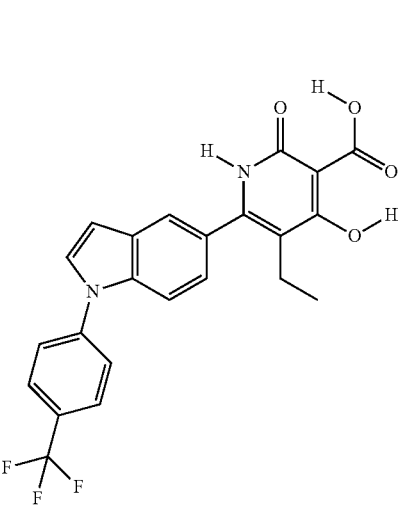 |
| 432 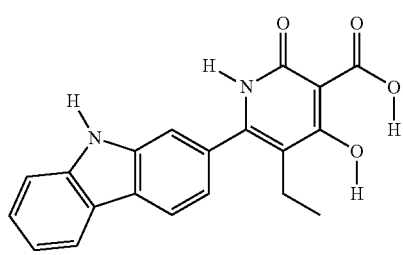 | |
| 433 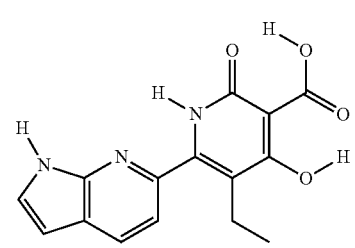 | |

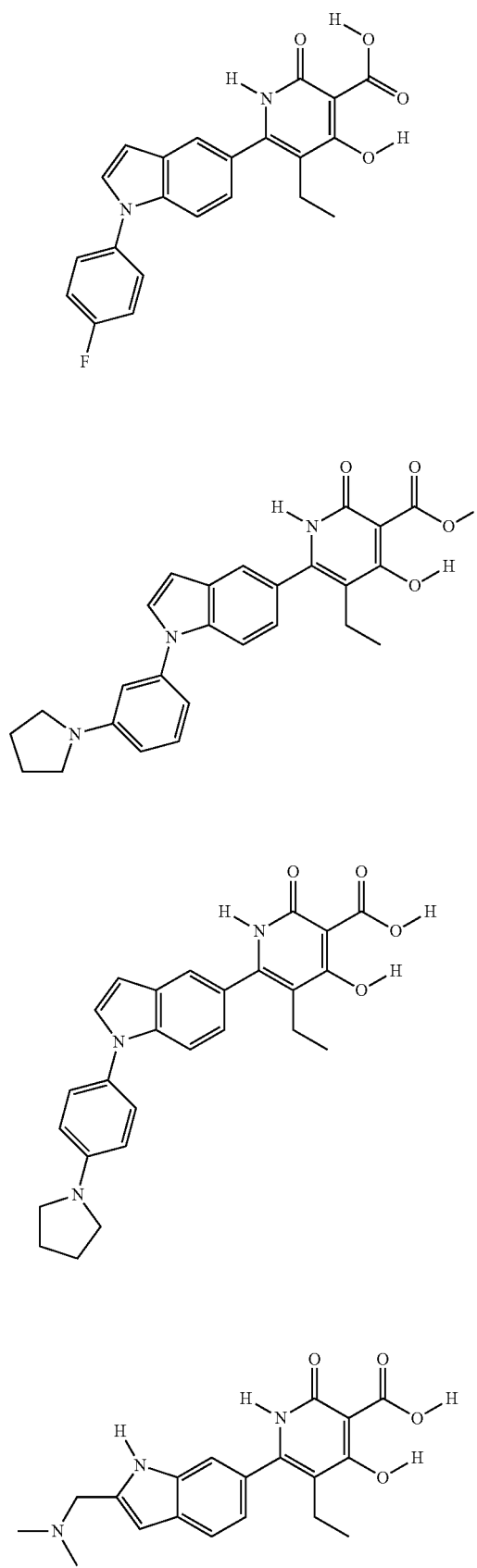
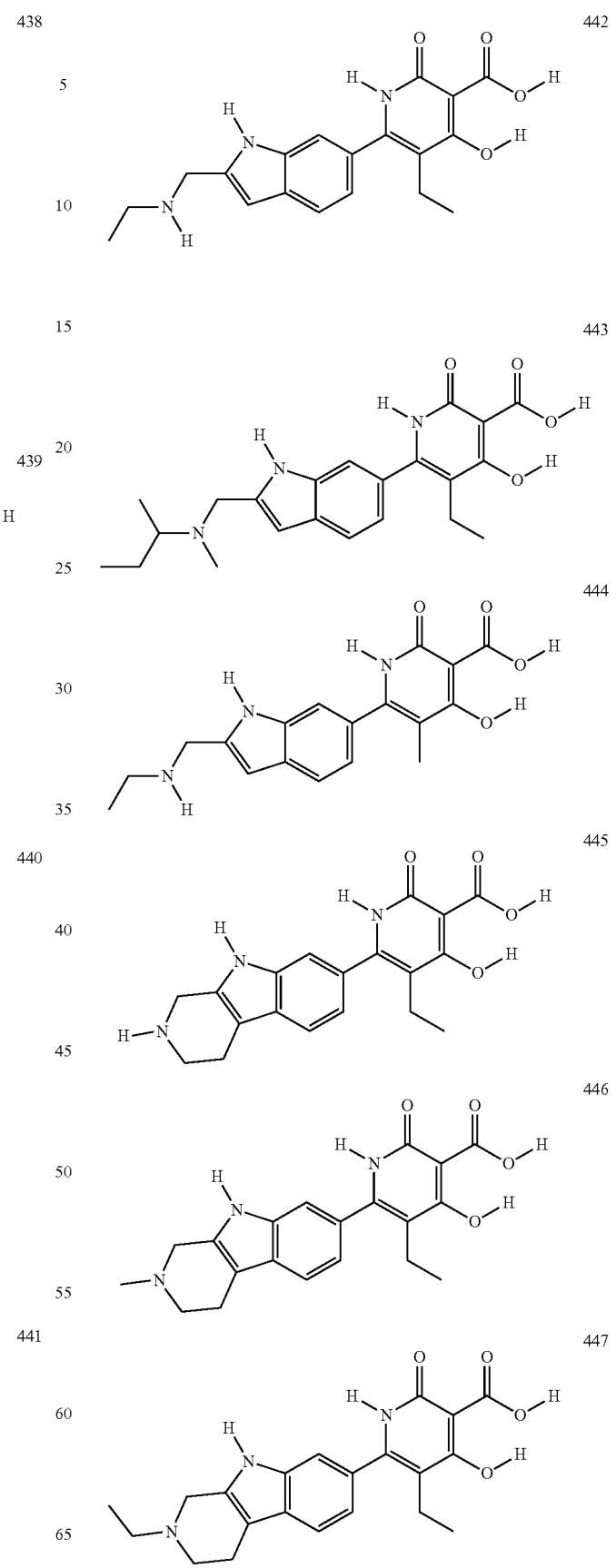

448

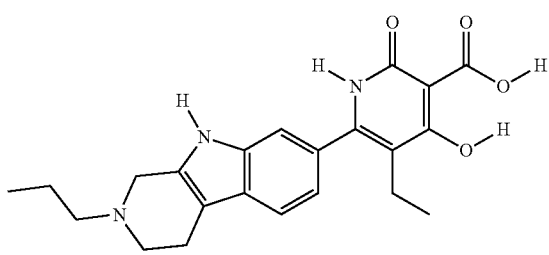

449

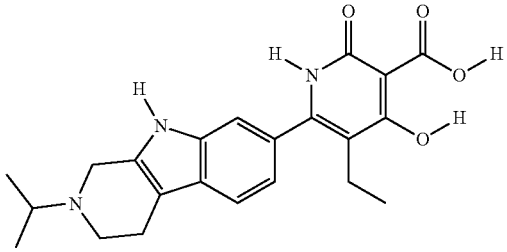

450

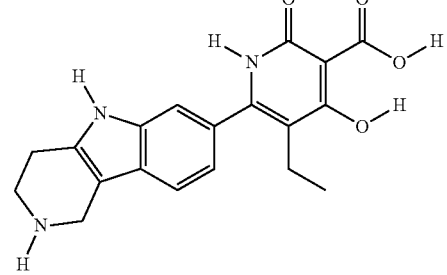

451

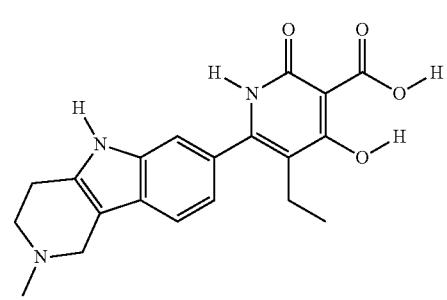

452

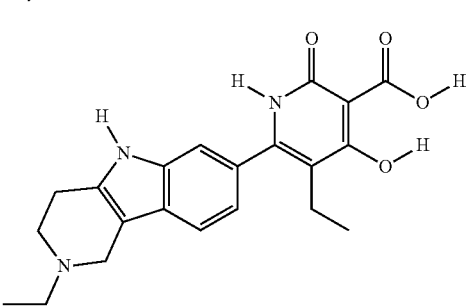

453

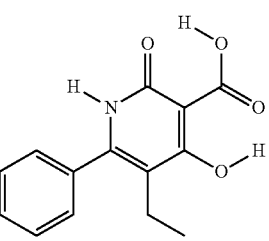

454

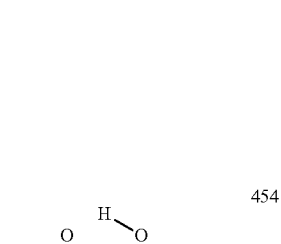

, and

455

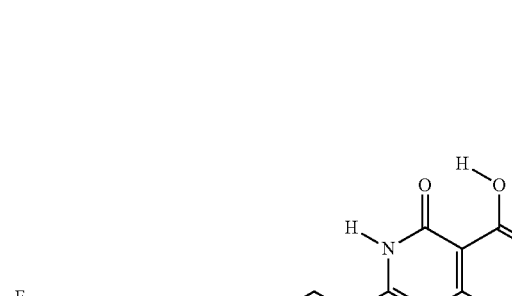

;

wherein the form of the compound is selected from a free acid, free base, salt, hydrate, solvate, clathrate, isotopologue, racemate, enantiomer, diastereomer, stereoisomer, polymorph or tautomer form thereof, and wherein the form is isolated for use.

In another embodiment of the present description, a compound or a form thereof is selected from:

| Cpd | Name |
|---|---|
| 1 | 5-ethyl-6-(1-methyl-1,2,3,4-tetrahydroquinolin-6-yl)-2-oxo-1,2-dihydropyridine-3-carboxylic acid |
| 2 | 5-ethyl-4-hydroxy-6-(1-methyl-1,2,3,4-tetrahydroquinolin-6-yl)-2-oxo-1,2-dihydropyridine-3-carboxylic acid |
| 3 | 5-ethyl-6-(4-methyl-3,4-dihydro-2H-benzo[b][1,4]oxazin-7-yl)-2-oxo-1,2-dihydropyridine-3-carboxylic acid |

-continued

| Cpd | Name |
|---|---|
| 4 | 5-ethyl-4-hydroxy-6-(4-methyl-3,4-dihydro-2H-benzo[b][1,4]oxazin-7-yl)-2-oxo-1,2-dihydropyridine-3-carboxylic acid |
| 5 | 5-ethyl-6-(1-methylindolin-5-yl)-2-oxo-1,2-dihydropyridine-3-carboxylic acid |
| 6 | 5-ethyl-4-hydroxy-6-(1-methylindolin-5-yl)-2-oxo-1,2-dihydropyridine-3-carboxylic acid |
| 7 | 5-ethyl-6-(1-methyl-1H-indol-6-yl)-2-oxo-1,2-dihydropyridine-3-carboxylic acid |
| 8 | 5-ethyl-4-hydroxy-6-(1-methyl-1H-indol-6-yl)-2-oxo-1,2-dihydropyridine-3-carboxylic acid |
| 9 | 5-ethyl-6-(1-ethyl-1H-indol-5-yl)-2-oxo-1,2-dihydropyridine-3-carboxylic acid |
| 10 | 5-ethyl-6-(1-ethyl-1H-indol-5-yl)-4-hydroxy-2-oxo-1,2-dihydropyridine-3-carboxylic acid |
| 11 | 5-ethyl-4-hydroxy-6-(3-methyl-2-oxo-2,3-dihydrobenzo[d]oxazol-6-yl)-2-oxo-1,2-dihydropyridine-3-carboxylic acid |
| 12 | 5-ethyl-4-hydroxy-6-(2-methylbenzo[d]oxazol-6-yl)-2-oxo-1,2-dihydropyridine-3-carboxylic acid |
| 13 | 5-ethyl-6-(1-methyl-1H-indol-3-yl)-2-oxo-1,2-dihydropyridine-3-carboxylic acid |
| 14 | 5-ethyl-4-hydroxy-6-(1-methyl-1H-indol-3-yl)-2-oxo-1,2-dihydropyridine-3-carboxylic acid |
| 15 | 5-ethyl-2-oxo-6-(2-phenylbenzo[d]oxazol-6-yl)-1,2-dihydropyridine-3-carboxylic acid |
| 16 | 5-ethyl-4-hydroxy-2-oxo-6-(2-phenylbenzo[d]oxazol-6-yl)-1,2-dihydropyridine-3-carboxylic acid |
| 17 | 6-(2-(dimethylamino)benzo[d]oxazol-6-yl)-5-ethyl-2-oxo-1,2-dihydropyridine-3-carboxylic acid |
| 18 | 6-(2-(dimethylamino)benzo[d]oxazol-6-yl)-5-ethyl-4-hydroxy-2-oxo-1,2-dihydropyridine-3-carboxylic acid |
| 19 | 5-ethyl-2-oxo-6-(quinolin-6-yl)-1,2-dihydropyridine-3-carboxylic acid |
| 20 | 5-ethyl-4-hydroxy-2-oxo-6-(quinolin-6-yl)-1,2-dihydropyridine-3-carboxylic acid |
| 21 | 5-ethyl-6-(1-methyl-1H-indol-5-yl)-2-oxo-1,2-dihydropyridine-3-carboxylic acid |
| 22 | 5-ethyl-4-hydroxy-6-(1-methyl-1H-indol-5-yl)-2-oxo-1,2-dihydropyridine-3-carboxylic acid |
| 23 | 5-ethyl-6-(1-(2-hydroxyethyl)-1H-indol-5-yl)-2-oxo-1,2-dihydropyridine-3-carboxylic acid |
| 24 | 5-ethyl-4-hydroxy-6-(1-(2-hydroxyethyl)-1H-indol-5-yl)-2-oxo-1,2-dihydropyridine-3-carboxylic acid |
| 25 | 6-(1-((1,3-dioxolan-2-yl)methyl)-1H-indol-5-yl)-5-ethyl-2-oxo-1,2-dihydropyridine-3-carboxylic acid |
| 26 | 6-(1-((1,3-dioxolan-2-yl)methyl)-1H-indol-5-yl)-5-ethyl-4-hydroxy-2-oxo-1,2-dihydropyridine-3-carboxylic acid |
| 27 | 5-ethyl-6-(9-methyl-2,3,4,9-tetrahydro-1H-carbazol-6-yl)-2-oxo-1,2-dihydropyridine-3-carboxylic acid |
| 28 | 5-ethyl-4-hydroxy-6-(9-methyl-2,3,4,9-tetrahydro-1H-carbazol-6-yl)-2-oxo-1,2-dihydropyridine-3-carboxylic acid |
| 29 | 5-ethyl-2-oxo-6-(1,2,3-trimethyl-1H-indol-5-yl)-1,2-dihydropyridine-3-carboxylic acid |
| 30 | 5-ethyl-4-hydroxy-2-oxo-6-(1,2,3-trimethyl-1H-indol-5-yl)-1,2-dihydropyridine-3-carboxylic acid |
| 31 | 5-ethyl-6-(1-methyl-1H-pyrrolo[2,3-b]pyridin-5-yl)-2-oxo-1,2-dihydropyridine-3-carboxylic acid |
| 32 | 5-ethyl-4-hydroxy-6-(1-methyl-1H-pyrrolo[2,3-b]pyridin-5-yl)-2-oxo-1,2-dihydropyridine-3-carboxylic acid |
| 33 | 5-isopropyl-6-(1-methyl-1H-indol-5-yl)-2-oxo-1,2-dihydropyridine-3-carboxylic acid |
| 34 | 4-hydroxy-5-isopropyl-6-(1-methyl-1H-indol-5-yl)-2-oxo-1,2-dihydropyridine-3-carboxylic acid |
| 35 | 5-cyclopropyl-6-(1-methyl-1H-indol-5-yl)-2-oxo-1,2-dihydropyridine-3-carboxylic acid |
| 36 | 5-cyclopropyl-4-hydroxy-6-(1-methyl-1H-indol-5-yl)-2-oxo-1,2-dihydropyridine-3-carboxylic acid |
| 37 | 6-(1,2-dimethyl-1H-indol-5-yl)-5-ethyl-2-oxo-1,2-dihydropyridine-3-carboxylic acid |
| 38 | 6-(1,2-dimethyl-1H-indol-5-yl)-5-ethyl-4-hydroxy-2-oxo-1,2-dihydropyridine-3-carboxylic acid |
| 39 | 5-ethyl-6-(2-(hydroxymethyl)-1-methyl-1H-indol-5-yl)-2-oxo-1,2-dihydropyridine-3-carboxylic acid |
| 40 | 5-ethyl-4-hydroxy-6-(2-(hydroxymethyl)-1-methyl-1H-indol-5-yl)-2-oxo-1,2-dihydropyridine-3-carboxylic acid |
| 41 | 5-ethyl-6-(1-methyl-1H-indazol-5-yl)-2-oxo-1,2-dihydropyridine-3-carboxylic acid |
| 42 | 5-ethyl-4-hydroxy-6-(1-methyl-1H-indazol-5-yl)-2-oxo-1,2-dihydropyridine-3-carboxylic acid |
| 52 | 5-ethyl-6-(3-methyl-3H-imidazo[4,5-b]pyridin-6-yl)-2-oxo-1,2-dihydropyridine-3-carboxylic acid |
| 53 | 5-ethyl-6-(1-methyl-1H-benzo[d]imidazol-5-yl)-2-oxo-1,2-dihydropyridine-3-carboxylic acid |
| 54 | 5-(5-carboxy-3-ethyl-6-oxo-1,6-dihydropyridin-2-yl)-1-methyl-1H-pyrrolo[2,3-c]pyridine-2-carboxylic acid |
| 55 | 5-ethyl-2-oxo-6-(1H-pyrrolo[2,3-b]pyridin-5-yl)-1,2-dihydropyridine-3-carboxylic acid |
| 56 | 6-(1,4-dimethyl-1,2,3,4-tetrahydroquinoxalin-6-yl)-5-ethyl-2-oxo-1,2-dihydropyridine-3-carboxylic acid |
| 57 | 5-ethyl-2-oxo-6-(quinoxalin-6-yl)-1,2-dihydropyridine-3-carboxylic acid |

| Cpd | Name |
|---|---|
| 58 | 5-ethyl-6-(4-methyl-3,4-dihydro-2H-pyrido[3,2-b][1,4]oxazin-7-yl)-2-oxo-1,2-dihydropyridine-3-carboxylic acid |
| 59 | 6-(3-cyano-1-methyl-1H-pyrrolo[2,3-b]pyridin-5-yl)-5-ethyl-2-oxo-1,2-dihydropyridine-3-carboxylic acid |
| 66 | 5-ethyl-2-oxo-6-(1,2,3,4-tetrahydropyrazino[1,2-a]indol-8-yl)-1,2-dihydropyridine-3-carboxylic acid |
| 68 | (R)-5-ethyl-6-(1-methyl-2-(1-methylpyrrolidin-2-yl)-1H-indol-5-yl)-2-oxo-1,2-dihydropyridine-3-carboxylic acid |
| 72 | 6-(3-cyano-1-methyl-1H-indol-5-yl)-5-ethyl-2-oxo-1,2-dihydropyridine-3-carboxylic acid |
| 73 | 6-(3-carbamoyl-1-methyl-1H-indol-5-yl)-5-ethyl-2-oxo-1,2-dihydropyridine-3-carboxylic acid |
| 74 | 6-(3-(aminomethyl)-1-methyl-1H-indol-5-yl)-5-ethyl-2-oxo-1,2-dihydropyridine-3-carboxylic acid |
| 75 | 6-(3-((dimethylamino)methyl)-1-methyl-1H-indol-5-yl)-5-ethyl-2-oxo-1,2-dihydropyridine-3-carboxylic acid |
| 76 | 6-(3-((diethylamino)methyl)-1-methyl-1H-indol-5-yl)-5-ethyl-2-oxo-1,2-dihydropyridine-3-carboxylic acid |
| 77 | 6-(3-((dibenzylamino)methyl)-1-methyl-1H-indol-5-yl)-5-ethyl-2-oxo-1,2-dihydropyridine-3-carboxylic acid |
| 84 | 5-ethyl-6-(1-methyl-2-(pyrrolidin-1-ylmethyl)-1H-pyrrolo[3,2-b]pyridin-5-yl)-2-oxo-1,2-dihydropyridine-3-carboxylic acid |
| 85 | 6-(2-(4,5-dihydro-1H-imidazol-2-yl)-1-methyl-1H-indol-5-yl)-5-ethyl-2-oxo-1,2-dihydropyridine-3-carboxylic acid |
| 86 | 5-ethyl-6-(1-methyl-2-(1,4,5,6-tetrahydropyrimidin-2-yl)-1H-indol-5-yl)-2-oxo-1,2-dihydropyridine-3-carboxylic acid |
| 87 | 6-(2-(2-(dimethylamino)propan-2-yl)-1-methyl-1H-indol-5-yl)-5-ethyl-2-oxo-1,2-dihydropyridine-3-carboxylic acid |
| 88 | 5-ethyl-6-(1-methyl-2-(2-(pyrrolidin-1-yl)propan-2-yl)-1H-indol-5-yl)-2-oxo-1,2-dihydropyridine-3-carboxylic acid |
| 89 | 6-(1,6-dimethyl-2-(pyrrolidin-1-ylmethyl)-1H-indol-5-yl)-5-ethyl-2-oxo-1,2-dihydropyridine-3-carboxylic acid |
| 90 | 6-(1,6-dimethyl-2-(piperidin-1-ylmethyl)-1H-indol-5-yl)-5-ethyl-2-oxo-1,2-dihydropyridine-3-carboxylic acid |
| 91 | 6-(6-chloro-1-methyl-2-(morpholinomethyl)-1H-indol-5-yl)-5-ethyl-2-oxo-1,2-dihydropyridine-3-carboxylic acid |
| 92 | 6-(6-chloro-2-((diethylamino)methyl)-1-methyl-1H-indol-5-yl)-5-ethyl-2-oxo-1,2-dihydropyridine-3-carboxylic acid |
| 93 | 6-(6-chloro-2-((dimethylamino)methyl)-1-methyl-1H-indol-5-yl)-5-ethyl-2-oxo-1,2-dihydropyridine-3-carboxylic acid |
| 94 | 6-(1,6-dimethyl-2-(morpholinomethyl)-1H-indol-5-yl)-5-ethyl-2-oxo-1,2-dihydropyridine-3-carboxylic acid |
| 95 | 6-(2-((diethylamino)methyl)-1,6-dimethyl-1H-indol-5-yl)-5-ethyl-2-oxo-1,2-dihydropyridine-3-carboxylic acid |
| 96 | 6-(2-((dimethylamino)methyl)-1,6-dimethyl-1H-indol-5-yl)-5-ethyl-2-oxo-1,2-dihydropyridine-3-carboxylic acid |
| 97 | 5-ethyl-6-(7-fluoro-1-methyl-2-(pyrrolidin-1-ylmethyl)-1H-indol-5-yl)-2-oxo-1,2-dihydropyridine-3-carboxylic acid |
| 98 | 5-ethyl-6-(7-fluoro-1-methyl-2-(morpholinomethyl)-1H-indol-5-yl)-2-oxo-1,2-dihydropyridine-3-carboxylic acid |
| 99 | 6-(1,7-dimethyl-2-(pyrrolidin-1-ylmethyl)-1H-indol-5-yl)-5-ethyl-2-oxo-1,2-dihydropyridine-3-carboxylic acid |
| 100 | 6-(1,7-dimethyl-2-(piperidin-1-ylmethyl)-1H-indol-5-yl)-5-ethyl-2-oxo-1,2-dihydropyridine-3-carboxylic acid |
| 101 | 6-(2-((diethylamino)methyl)-7-fluoro-1-methyl-1H-indol-5-yl)-5-ethyl-2-oxo-1,2-dihydropyridine-3-carboxylic acid |
| 102 | 5-ethyl-6-(7-fluoro-1-methyl-2-(piperidin-1-ylmethyl)-1H-indol-5-yl)-2-oxo-1,2-dihydropyridine-3-carboxylic acid |
| 103 | 6-(1,7-dimethyl-2-(morpholinomethyl)-1H-indol-5-yl)-5-ethyl-2-oxo-1,2-dihydropyridine-3-carboxylic acid |
| 104 | 6-(2-((diethylamino)methyl)-1,7-dimethyl-1H-indol-5-yl)-5-ethyl-2-oxo-1,2-dihydropyridine-3-carboxylic acid |
| 105 | 6-(2-((dimethylamino)methyl)-1,7-dimethyl-1H-indol-5-yl)-5-ethyl-2-oxo-1,2-dihydropyridine-3-carboxylic acid |
| 106 | 6-(2-((dimethylamino)methyl)-7-fluoro-1-methyl-1H-indol-5-yl)-5-ethyl-2-oxo-1,2-dihydropyridine-3-carboxylic acid |
| 107 | 5-ethyl-6-(6-methoxy-1-methyl-2-(pyrrolidin-1-ylmethyl)-1H-indol-5-yl)-2-oxo-1,2-dihydropyridine-3-carboxylic acid |
| 108 | 5-ethyl-6-(6-methoxy-1-methyl-2-(morpholinomethyl)-1H-indol-5-yl)-2-oxo-1,2-dihydropyridine-3-carboxylic acid |
| 109 | 6-(2-(azetidin-1-ylmethyl)-1-methyl-1H-indol-5-yl)-5-ethyl-2-oxo-1,2-dihydropyridine-3,4-dicarboxylic acid |
| 110 | 5-ethyl-6-(1-methyl-2-(pyrrolidin-1-ylmethyl)-1H-indol-5-yl)-2-oxo-1,2-dihydropyridine-3,4-dicarboxylic acid |
| 111 | 6-(2-((dimethylamino)methyl)-1-methyl-1H-indol-5-yl)-5-ethyl-2-oxo-1,2-dihydropyridine-3,4-dicarboxylic acid |

-continued

| Cpd | Name |
|---|---|
| 112 | 5-ethyl-6-(1-methyl-2-((methylamino)methyl)-1H-indol-5-yl)-2-oxo-1,2-dihydropyridine-3-carboxylic acid |
| 113 | 6-(2-((tert-butylamino)methyl)-1-methyl-1H-indol-5-yl)-5-ethyl-2-oxo-1,2-dihydropyridine-3-carboxylic acid |
| 114 | 6-(2-((benzylamino)methyl)-1-methyl-1H-indol-5-yl)-5-ethyl-2-oxo-1,2-dihydropyridine-3-carboxylic acid |
| 115 | 5-ethyl-6-(1-methyl-2-((2-phenylpropan-2-ylamino)methyl)-1H-indol-5-yl)-2-oxo-1,2-dihydropyridine-3-carboxylic acid |
| 116 | (R)-5-ethyl-6-(1-methyl-2-((1-phenylethylamino)methyl)-1H-indol-5-yl)-2-oxo-1,2-dihydropyridine-3-carboxylic acid |
| 117 | (S)-5-ethyl-6-(1-methyl-2-((1-phenylethylamino)methyl)-1H-indol-5-yl)-2-oxo-1,2-dihydropyridine-3-carboxylic acid |
| 118 | (R)-5-ethyl-6-(1-methyl-2-((1-phenylpropylamino)methyl)-1H-indol-5-yl)-2-oxo-1,2-dihydropyridine-3-carboxylic acid |
| 119 | (S)-5-ethyl-6-(1-methyl-2-((1-phenylpropylamino)methyl)-1H-indol-5-yl)-2-oxo-1,2-dihydropyridine-3-carboxylic acid |
| 120 | 5-ethyl-6-(1-methyl-2-((pyridin-2-ylmethylamino)methyl)-1H-indol-5-yl)-2-oxo-1,2-dihydropyridine-3-carboxylic acid |
| 121 | 6-(2-((benzyl(methyl)amino)methyl)-1-methyl-1H-indol-5-yl)-5-ethyl-2-oxo-1,2-dihydropyridine-3-carboxylic acid |
| 122 | 6-(2-((dimethylamino)methyl)-1-methyl-1H-indol-5-yl)-5-ethyl-2-oxo-1,2-dihydropyridine-3-carboxylic acid |
| 123 | 6-(2-((diethylamino)methyl)-1-methyl-1H-indol-5-yl)-5-ethyl-2-oxo-1,2-dihydropyridine-3-carboxylic acid |
| 124 | 5-ethyl-6-(1-methyl-2-(pyrrolidin-1-ylmethyl)-1H-indol-5-yl)-2-oxo-1,2-dihydropyridine-3-carboxylic acid |
| 125 | 5-ethyl-6-(2-((3-hydroxypyrrolidin-1-yl)methyl)-1-methyl-1H-indol-5-yl)-2-oxo-1,2-dihydropyridine-3-carboxylic acid |
| 126 | (S)-6-(2-((3-aminopyrrolidin-1-yl)methyl)-1-methyl-1H-indol-5-yl)-5-ethyl-2-oxo-1,2-dihydropyridine-3-carboxylic acid |
| 127 | 5-ethyl-6-(1-methyl-2-((3-(methylamino)pyrrolidin-1-yl)methyl)-1H-indol-5-yl)-2-oxo-1,2-dihydropyridine-3-carboxylic acid |
| 128 | 6-(2-((3-(dimethylamino)pyrrolidin-1-yl)methyl)-1-methyl-1H-indol-5-yl)-5-ethyl-2-oxo-1,2-dihydropyridine-3-carboxylic acid |
| 129 | (R)-5-ethyl-6-(2-((3-fluoropyrrolidin-1-yl)methyl)-1-methyl-1H-indol-5-yl)-2-oxo-1,2-dihydropyridine-3-carboxylic acid |
| 130 | 5-ethyl-6-(1-methyl-2-((2-methylpyrrolidin-1-yl)methyl)-1H-indol-5-yl)-2-oxo-1,2-dihydropyridine-3-carboxylic acid |
| 131 | 5-ethyl-6-(1-methyl-2-((2-phenylpyrrolidin-1-yl)methyl)-1H-indol-5-yl)-2-oxo-1,2-dihydropyridine-3-carboxylic acid |
| 132 | (R)-5-ethyl-6-(2-((2-(hydroxymethyl)pyrrolidin-1-yl)methyl)-1-methyl-1H-indol-5-yl)-2-oxo-1,2-dihydropyridine-3-carboxylic acid |
| 133 | 5-ethyl-6-(1-methyl-2-(piperidin-1-ylmethyl)-1H-indol-5-yl)-2-oxo-1,2-dihydropyridine-3-carboxylic acid |
| 134 | 6-(2-((3,4-dihydroisoquinolin-2(1H)-yl)methyl)-1-methyl-1H-indol-5-yl)-5-ethyl-2-oxo-1,2-dihydropyridine-3-carboxylic acid |
| 135 | 6-(2-((5H-pyrrolo[3,4-b]pyridin-6(7H)-yl)methyl)-1-methyl-1H-indol-5-yl)-5-ethyl-2-oxo-1,2-dihydropyridine-3-carboxylic acid |
| 136 | 5-ethyl-6-(1-methyl-2-((tetrahydro-1H-pyrrolo[3,4-b]pyridin-6(2H,7H,7aH)-yl)methyl)-1H-indol-5-yl)-2-oxo-1,2-dihydropyridine-3-carboxylic acid |
| 137 | 5-ethyl-6-(1-methyl-2-(morpholinomethyl)-1H-indol-5-yl)-2-oxo-1,2-dihydropyridine-3-carboxylic acid |
| 138 | 6-(2-((cis-2,6-dimethylmorpholino)methyl)-1-methyl-1H-indol-5-yl)-5-ethyl-2-oxo-1,2-dihydropyridine-3-carboxylic acid |
| 139 | 5-ethyl-6-(1-methyl-2-(piperazin-1-ylmethyl)-1H-indol-5-yl)-2-oxo-1,2-dihydropyridine-3-carboxylic acid |
| 140 | 5-ethyl-6-(1-methyl-2-((4-methylpiperazin-1-yl)methyl)-1H-indol-5-yl)-2-oxo-1,2-dihydropyridine-3-carboxylic acid |
| 141 | 5-ethyl-6-(2-((4-isopropylpiperazin-1-yl)methyl)-1-methyl-1H-indol-5-yl)-2-oxo-1,2-dihydropyridine-3-carboxylic acid |
| 142 | 6-(2-(2,5-diazabicyclo[2.2.1]heptan-2-ylmethyl)-1-methyl-1H-indol-5-yl)-5-ethyl-2-oxo-1,2-dihydropyridine-3-carboxylic acid |
| 143 | 6-(2-(((1R,5S,6s)-6-(dibenzylamino)-3-azabicyclo[3.1.0]hexan-3-yl)methyl)-1-methyl-1H-indol-5-yl)-5-ethyl-2-oxo-1,2-dihydropyridine-3-carboxylic acid |
| 144 | 6-(2-((4-acetylpiperazin-1-yl)methyl)-1-methyl-1H-indol-5-yl)-5-ethyl-2-oxo-1,2-dihydropyridine-3-carboxylic acid |
| 145 | 5-ethyl-6-(1-methyl-2-((N-methylacetamido)methyl)-1H-indol-5-yl)-2-oxo-1,2-dihydropyridine-3-carboxylic acid |
| 146 | 6-(2-((((3aR,4R,7aS)-4-(benzyl(methyl)amino)-1H-isoindol-2(3H,3aH,4H,5H,6H,7H,7aH)-yl)methyl)-1-methyl-1H-indol-5-yl)-5-ethyl-2-oxo-1,2-dihydropyridine-3-carboxylic acid |
| 147 | 6-(2-((((3aR,4R,6aS)-4-(dimethylamino)hexahydrocyclopenta[c]pyrrol-2(1H)-yl)methyl)-1-methyl-1H-indol-5-yl)-5-ethyl-2-oxo-1,2-dihydropyridine-3-carboxylic acid |
| 148 | 5-ethyl-6-(1-methyl-2-(((3aR,4R,7aS)-4-(methylamino)-1H-isoindol-2(3H,3aH,4H,5H,6H,7H,7aH)-yl)methyl)-1H-indol-5-yl)-2-oxo-1,2-dihydropyridine-3-carboxylic acid |

-continued

| Cpd | Name |
|---|---|
| 149 | 6-(2-(((3aR,4R,7aS)-4-(dimethylamino)-1H-isoindol-2(3H,3aH,4H,5H,6H,7H,7aH)-yl)methyl)-1-methyl-1H-indol-5-yl)-5-ethyl-2-oxo-1,2-dihydropyridine-3-carboxylic acid |
| 150 | 6-(2-(aminomethyl)-1-methyl-1H-indol-5-yl)-5-ethyl-2-oxo-1,2-dihydropyridine-3-carboxylic acid |
| 151 | 5-ethyl-2-oxo-6-(1-(pyrrolidin-1-yl)-2,3-dihydro-1H-pyrrolo[1,2-a]indol-7-yl)-1,2-dihydropyridine-3-carboxylic acid |
| 152 | 6-(1-(dimethylamino)-2,3-dihydro-1H-pyrrolo[1,2-a]indol-7-yl)-5-ethyl-2-oxo-1,2-dihydropyridine-3-carboxylic acid |
| 153 | 6-(1-(3-(dimethylamino)pyrrolidin-1-yl)-2,3-dihydro-1H-pyrrolo[1,2-a]indol-7-yl)-5-ethyl-2-oxo-1,2-dihydropyridine-3-carboxylic acid |
| 154 | 5-ethyl-2-oxo-6-(1-(piperidin-1-yl)-2,3-dihydro-1H-pyrrolo[1,2-a]indol-7-yl)-1,2-dihydropyridine-3-carboxylic acid |
| 155 | 5-ethyl-6-(1-morpholino-2,3-dihydro-1H-pyrrolo[1,2-a]indol-7-yl)-2-oxo-1,2-dihydropyridine-3-carboxylic acid |
| 157 | 5-ethyl-6-(1-methyl-2-(1-(pyrrolidin-1-yl)ethyl)-1H-indol-5-yl)-2-oxo-1,2-dihydropyridine-3-carboxylic acid |
| 158 | 5-ethyl-6-(4-fluoro-1-methyl-2-(pyrrolidin-1-ylmethyl)-1H-indol-5-yl)-2-oxo-1,2-dihydropyridine-3-carboxylic acid |
| 159 | 5-ethyl-6-(1-methyl-2-(2-(pyrrolidin-1-yl)ethyl)-1H-indol-5-yl)-2-oxo-1,2-dihydropyridine-3-carboxylic acid |
| 160 | 5-ethyl-6-(1-methyl-2-(2-(piperidin-1-yl)ethyl)-1H-indol-5-yl)-2-oxo-1,2-dihydropyridine-3-carboxylic acid |
| 161 | 6-(2-(2-(dimethylamino)ethyl)-1-methyl-1H-indol-5-yl)-5-ethyl-2-oxo-1,2-dihydropyridine-3-carboxylic acid |
| 162 | 5-ethyl-6-(1-methyl-2-(2-morpholinoethyl)-1H-indol-5-yl)-2-oxo-1,2-dihydropyridine-3-carboxylic acid |
| 164 | 5-ethyl-4-hydroxy-6-(1-methyl-2-(pyrrolidin-1-ylmethyl)-1H-indol-5-yl)-2-oxo-1,2-dihydropyridine-3-carboxylic acid |
| 165 | 5-ethyl-6-(2-((ethylamino)methyl)-1-methyl-1H-indol-5-yl)-4-hydroxy-2-oxo-1,2-dihydropyridine-3-carboxylic acid |
| 166 | 6-(2-((dimethylamino)methyl)-1-methyl-1H-indol-5-yl)-5-ethyl-4-hydroxy-2-oxo-1,2-dihydropyridine-3-carboxylic acid |
| 167 | 6-(2-((diethylamino)methyl)-1-methyl-1H-indol-5-yl)-5-ethyl-4-hydroxy-2-oxo-1,2-dihydropyridine-3-carboxylic acid |
| 168 | 5-ethyl-4-hydroxy-6-(1-methyl-2-(morpholinomethyl)-1H-indol-5-yl)-2-oxo-1,2-dihydropyridine-3-carboxylic acid |
| 169 | 5-ethyl-4-hydroxy-6-(1-methyl-2-((4-methylpiperazin-1-yl)methyl)-1H-indol-5-yl)-2-oxo-1,2-dihydropyridine-3-carboxylic acid |
| 170 | 5-ethyl-4-hydroxy-6-(1-methyl-2-(((3S,5R)-3,4,5-trimethylpiperazin-1-yl)methyl)-1H-indol-5-yl)-2-oxo-1,2-dihydropyridine-3-carboxylic acid |
| 171 | 5-ethyl-4-hydroxy-6-(1-methyl-2-(piperazin-1-ylmethyl)-1H-indol-5-yl)-2-oxo-1,2-dihydropyridine-3-carboxylic acid |
| 172 | 6-(2-(((2S,6R)-2,6-dimethylmorpholino)methyl)-1-methyl-1H-indol-5-yl)-5-ethyl-4-hydroxy-2-oxo-1,2-dihydropyridine-3-carboxylic acid |
| 173 | 5-ethyl-4-hydroxy-6-(1-methyl-2-((2-methylpyrrolidin-1-yl)methyl)-1H-indol-5-yl)-2-oxo-1,2-dihydropyridine-3-carboxylic acid |
| 174 | 5-ethyl-4-hydroxy-6-(2-((4-isopropylpiperazin-1-yl)methyl)-1-methyl-1H-indol-5-yl)-2-oxo-1,2-dihydropyridine-3-carboxylic acid |
| 175 | 6-(2-((4-acetylpiperazin-1-yl)methyl)-1-methyl-1H-indol-5-yl)-5-ethyl-4-hydroxy-2-oxo-1,2-dihydropyridine-3-carboxylic acid |
| 176 | 6-(2-((3,3-difluoropyrrolidin-1-yl)methyl)-1-methyl-1H-indol-5-yl)-5-ethyl-4-hydroxy-2-oxo-1,2-dihydropyridine-3-carboxylic acid |
| 177 | (R)-5-ethyl-6-(2-((3-fluoropyrrolidin-1-yl)methyl)-1-methyl-1H-indol-5-yl)-4-hydroxy-2-oxo-1,2-dihydropyridine-3-carboxylic acid |
| 178 | 5-ethyl-4-hydroxy-6-(2-((3-hydroxypyrrolidin-1-yl)methyl)-1-methyl-1H-indol-5-yl)-2-oxo-1,2-dihydropyridine-3-carboxylic acid |
| 179 | 5-ethyl-4-hydroxy-6-(2-((3-methoxypyrrolidin-1-yl)methyl)-1-methyl-1H-indol-5-yl)-2-oxo-1,2-dihydropyridine-3-carboxylic acid |
| 180 | (S)-6-(2-((3-aminopyrrolidin-1-yl)methyl)-1-methyl-1H-indol-5-yl)-5-ethyl-4-hydroxy-2-oxo-1,2-dihydropyridine-3-carboxylic acid |
| 181 | 5-ethyl-4-hydroxy-6-(1-methyl-2-((3-(methylamino)pyrrolidin-1-yl)methyl)-1H-indol-5-yl)-2-oxo-1,2-dihydropyridine-3-carboxylic acid |
| 182 | 6-(2-(2,5-diazabicyclo[2.2.1]heptan-2-ylmethyl)-1-methyl-1H-indol-5-yl)-5-ethyl-4-hydroxy-2-oxo-1,2-dihydropyridine-3-carboxylic acid |
| 183 | 6-(2-((3-acetamidopyrrolidin-1-yl)methyl)-1-methyl-1H-indol-5-yl)-5-ethyl-4-hydroxy-2-oxo-1,2-dihydropyridine-3-carboxylic acid |
| 184 | 5-ethyl-4-hydroxy-6-(1-methyl-2-((tetrahydro-1H-pyrrolo[3,4-b]pyridin-6(2H,7H,7aH)-yl)methyl)-1H-indol-5-yl)-2-oxo-1,2-dihydropyridine-3-carboxylic acid |
| 185 | 6-(2-((3-(2-aminopropan-2-yl)pyrrolidin-1-yl)methyl)-1-methyl-1H-indol-5-yl)-5-ethyl-4-hydroxy-2-oxo-1,2-dihydropyridine-3-carboxylic acid |
| 186 | 6-(2-(azetidin-1-ylmethyl)-1-methyl-1H-indol-5-yl)-5-ethyl-4-hydroxy-2-oxo-1,2-dihydropyridine-3-carboxylic acid |
| 187 | 5-ethyl-4-hydroxy-6-(2-((3-hydroxyazetidin-1-yl)methyl)-1-methyl-1H-indol-5-yl)-2-oxo-1,2-dihydropyridine-3-carboxylic acid |
| 188 | 6-(2-((3-aminoazetidin-1-yl)methyl)-1-methyl-1H-indol-5-yl)-5-ethyl-4-hydroxy-2-oxo-1,2-dihydropyridine-3-carboxylic acid |

-continued

| Cpd | Name |
|---|---|
| 189 | 6-(2-((3-(dimethylamino)azetidin-1-yl)methyl)-1-methyl-1H-indol-5-yl)-5-ethyl-4-hydroxy-2-oxo-1,2-dihydropyridine-3-carboxylic acid |
| 190 | (S)-5-ethyl-4-hydroxy-6-(2-((2-(methoxycarbonyl)pyrrolidin-1-yl)methyl)-1-methyl-1H-indol-5-yl)-2-oxo-1,2-dihydropyridine-3-carboxylic acid |
| 191 | 6-(2-((3-(dimethylcarbamoyl)pyrrolidin-1-yl)methyl)-1-methyl-1H-indol-5-yl)-5-ethyl-4-hydroxy-2-oxo-1,2-dihydropyridine-3-carboxylic acid |
| 192 | 5-ethyl-4-hydroxy-6-(1-methyl-2-(piperidin-1-ylmethyl)-1H-indol-5-yl)-2-oxo-1,2-dihydropyridine-3-carboxylic acid |
| 193 | 6-(2-((tert-butylamino)methyl)-1-methyl-1H-indol-5-yl)-5-ethyl-4-hydroxy-2-oxo-1,2-dihydropyridine-3-carboxylic acid |
| 194 | 5-ethyl-6-(2-((3-fluoroazetidin-1-yl)methyl)-1-methyl-1H-indol-5-yl)-4-hydroxy-2-oxo-1,2-dihydropyridine-3-carboxylic acid |
| 195 | 6-(2-((3,3-difluoroazetidin-1-yl)methyl)-1-methyl-1H-indol-5-yl)-5-ethyl-4-hydroxy-2-oxo-1,2-dihydropyridine-3-carboxylic acid |
| 196 | 6-(2-((((1R,5S,6s)-6-(dibenzylamino)-3-azabicyclo[3.1.0]hexan-3-yl)methyl)-1-methyl-1H-indol-5-yl)-5-ethyl-4-hydroxy-2-oxo-1,2-dihydropyridine-3-carboxylic acid |
| 197 | 6-(2-((((1R,5S,6s)-6-(dimethylamino)-3-azabicyclo[3.1.0]hexan-3-yl)methyl)-1-methyl-1H-indol-5-yl)-5-ethyl-4-hydroxy-2-oxo-1,2-dihydropyridine-3-carboxylic acid |
| 198 | 6-(2-((((1R,5S,6s)-3-azabicyclo[3.1.0]hexan-6-ylamino)methyl)-1-methyl-1H-indol-5-yl)-5-ethyl-4-hydroxy-2-oxo-1,2-dihydropyridine-3-carboxylic acid |
| 199 | 5-ethyl-4-hydroxy-6-(2-((isopropylamino)methyl)-1-methyl-1H-indol-5-yl)-2-oxo-1,2-dihydropyridine-3-carboxylic acid |
| 200 | 6-(2-((3-(dimethylamino)pyrrolidin-1-yl)methyl)-1-methyl-1H-indol-5-yl)-5-ethyl-4-hydroxy-2-oxo-1,2-dihydropyridine-3-carboxylic acid |
| 201 | 5-ethyl-6-(2-((2-fluoroethylamino)methyl)-1-methyl-1H-indol-5-yl)-4-hydroxy-2-oxo-1,2-dihydropyridine-3-carboxylic acid |
| 202 | 6-(2-((2-((dimethylamino)methyl)pyrrolidin-1-yl)methyl)-1-methyl-1H-indol-5-yl)-5-ethyl-4-hydroxy-2-oxo-1,2-dihydropyridine-3-carboxylic acid |
| 203 | 5-ethyl-4-hydroxy-6-(1-methyl-2-((methylamino)methyl)-1H-indol-5-yl)-2-oxo-1,2-dihydropyridine-3-carboxylic acid |
| 204 | 5-ethyl-4-hydroxy-6-(1-methyl-2-((2-(methylamino)ethylamino)methyl)-1H-indol-5-yl)-2-oxo-1,2-dihydropyridine-3-carboxylic acid |
| 205 | 6-(2-((2-aminoethylamino)methyl)-1-methyl-1H-indol-5-yl)-5-ethyl-4-hydroxy-2-oxo-1,2-dihydropyridine-3-carboxylic acid |
| 206 | 6-(2-((3-(benzyl(methyl)amino)azetidin-1-yl)methyl)-1-methyl-1H-indol-5-yl)-5-ethyl-4-hydroxy-2-oxo-1,2-dihydropyridine-3-carboxylic acid |
| 207 | 6-(2-((3-((2-(dimethylamino)ethyl)(methyl)amino)azetidin-1-yl)methyl)-1-methyl-1H-indol-5-yl)-5-ethyl-4-hydroxy-2-oxo-1,2-dihydropyridine-3-carboxylic acid |
| 208 | 5-ethyl-4-hydroxy-6-(1-methyl-2-((((1R,5S,6s)-6-(methylamino)-3-azabicyclo[3.1.0]hexan-3-yl)methyl)-1H-indol-5-yl)-2-oxo-1,2-dihydropyridine-3-carboxylic acid |
| 213 | 5-ethyl-4-hydroxy-6-(1-methyl-2-((phenylamino)methyl)-1H-indol-5-yl)-2-oxo-1,2-dihydropyridine-3-carboxylic acid |
| 247 | 5-ethyl-4-hydroxy-6-(1-methyl-2-((4-methylpiperidin-1-yl)methyl)-1H-indol-5-yl)-2-oxo-1,2-dihydropyridine-3-carboxylic acid |
| 248 | 6-(2-((4-(dimethylamino)piperidin-1-yl)methyl)-1-methyl-1H-indol-5-yl)-5-ethyl-4-hydroxy-2-oxo-1,2-dihydropyridine-3-carboxylic acid |
| 249 | 6-(2-((4,4-difluoropiperidin-1-yl)methyl)-1-methyl-1H-indol-5-yl)-5-ethyl-4-hydroxy-2-oxo-1,2-dihydropyridine-3-carboxylic acid |
| 250 | 6-(2-((3-(dimethylamino)piperidin-1-yl)methyl)-1-methyl-1H-indol-5-yl)-5-ethyl-4-hydroxy-2-oxo-1,2-dihydropyridine-3-carboxylic acid |
| 251 | 6-(2-(1,4'-bipiperidin-1'-ylmethyl)-1-methyl-1H-indol-5-yl)-5-ethyl-4-hydroxy-2-oxo-1,2-dihydropyridine-3-carboxylic acid |
| 252 | 6-(2-((4-aminopiperidin-1-yl)methyl)-1-methyl-1H-indol-5-yl)-5-ethyl-4-hydroxy-2-oxo-1,2-dihydropyridine-3-carboxylic acid |
| 253 | (S)-6-(2-((3-aminopiperidin-1-yl)methyl)-1-methyl-1H-indol-5-yl)-5-ethyl-4-hydroxy-2-oxo-1,2-dihydropyridine-3-carboxylic acid |
| 254 | 5-ethyl-4-hydroxy-6-(2-((4-hydroxypiperidin-1-yl)methyl)-1-methyl-1H-indol-5-yl)-2-oxo-1,2-dihydropyridine-3-carboxylic acid |
| 255 | 5-ethyl-4-hydroxy-6-(2-((3-hydroxypiperidin-1-yl)methyl)-1-methyl-1H-indol-5-yl)-2-oxo-1,2-dihydropyridine-3-carboxylic acid |
| 256 | 5-ethyl-4-hydroxy-6-(1-methyl-2-((4-(methylamino)piperidin-1-yl)methyl)-1H-indol-5-yl)-2-oxo-1,2-dihydropyridine-3-carboxylic acid |
| 257 | (S)-5-ethyl-4-hydroxy-6-(1-methyl-2-((3-(methylamino)piperidin-1-yl)methyl)-1H-indol-5-yl)-2-oxo-1,2-dihydropyridine-3-carboxylic acid |
| 258 | 5-ethyl-4-hydroxy-6-(1-methyl-2-((2-(trifluoromethyl)piperidin-1-yl)methyl)-1H-indol-5-yl)-2-oxo-1,2-dihydropyridine-3-carboxylic acid |
| 259 | 5-ethyl-4-hydroxy-6-(2-((2-(2-methoxyethyl)piperidin-1-yl)methyl)-1-methyl-1H-indol-5-yl)-2-oxo-1,2-dihydropyridine-3-carboxylic acid |
| 260 | 5-ethyl-4-hydroxy-6-(2-((2-(3-methoxypropyl)piperidin-1-yl)methyl)-1-methyl-1H-indol-5-yl)-2-oxo-1,2-dihydropyridine-3-carboxylic acid |
| 261 | 5-ethyl-4-hydroxy-6-(1-methyl-2-((methyl(piperidin-4-yl)amino)methyl)-1H-indol-5-yl)-2-oxo-1,2-dihydropyridine-3-carboxylic acid |
| 262 | 5-ethyl-4-hydroxy-6-(1-methyl-2-((methyl(piperidin-3-yl)amino)methyl)-1H-indol-5-yl)-2-oxo-1,2-dihydropyridine-3-carboxylic acid |
| 263 | 5-ethyl-4-hydroxy-6-(1-methyl-2-((piperidin-4-ylamino)methyl)-1H-indol-5-yl)-2-oxo-1,2-dihydropyridine-3-carboxylic acid |

-continued

| Cpd | Name |
|---|---|
| 264 | 6-(2-(((cyclopropylmethyl)(piperidin-4-yl)amino)methyl)-1-methyl-1H-indol-5-yl)-5-ethyl-4-hydroxy-2-oxo-1,2-dihydropyridine-3-carboxylic acid |
| 265 | 6-(2-(((cyclopropylmethyl)(piperidin-3-yl)amino)methyl)-1-methyl-1H-indol-5-yl)-5-ethyl-4-hydroxy-2-oxo-1,2-dihydropyridine-3-carboxylic acid |
| 266 | (S)-5-ethyl-4-hydroxy-6-(1-methyl-2-((2-((phenylamino)methyl)pyrrolidin-1-yl)methyl)-1H-indol-5-yl)-2-oxo-1,2-dihydropyridine-3-carboxylic acid |
| 267 | 5-ethyl-4-hydroxy-6-(1-methyl-2-((3-(pyridin-2-yl)pyrrolidin-1-yl)methyl)-1H-indol-5-yl)-2-oxo-1,2-dihydropyridine-3-carboxylic acid |
| 268 | 5-ethyl-4-hydroxy-6-(1-methyl-2-((3-(pyridin-4-yl)pyrrolidin-1-yl)methyl)-1H-indol-5-yl)-2-oxo-1,2-dihydropyridine-3-carboxylic acid |
| 269 | 6-(2-((3-carboxyazetidin-1-yl)methyl)-1-methyl-1H-indol-5-yl)-5-ethyl-4-hydroxy-2-oxo-1,2-dihydropyridine-3-carboxylic acid |
| 270 | 6-(2-((3-(dimethylcarbamoyl)azetidin-1-yl)methyl)-1-methyl-1H-indol-5-yl)-5-ethyl-4-hydroxy-2-oxo-1,2-dihydropyridine-3-carboxylic acid |
| 271 | 5-ethyl-4-hydroxy-6-(2-((3-(hydroxymethyl)azetidin-1-yl)methyl)-1-methyl-1H-indol-5-yl)-2-oxo-1,2-dihydropyridine-3-carboxylic acid |
| 272 | (R)-5-ethyl-4-hydroxy-6-(1-methyl-2-((1,1,1-trifluoropropan-2-ylamino)methyl)-1H-indol-5-yl)-2-oxo-1,2-dihydropyridine-3-carboxylic acid |
| 273 | (S)-5-ethyl-4-hydroxy-6-(1-methyl-2-((1,1,1-trifluoropropan-2-ylamino)methyl)-1H-indol-5-yl)-2-oxo-1,2-dihydropyridine-3-carboxylic acid |
| 274 | 6-(2-(((1,3-difluoropropan-2-ylamino)methyl)-1-methyl-1H-indol-5-yl)-5-ethyl-4-hydroxy-2-oxo-1,2-dihydropyridine-3-carboxylic acid |
| 275 | 5-ethyl-4-hydroxy-6-(1-methyl-2-((1-methylcyclopropylamino)methyl)-1H-indol-5-yl)-2-oxo-1,2-dihydropyridine-3-carboxylic acid |
| 276 | 6-(2-(((3aR,4R,6aS)-4-aminohexahydrocyclopenta[c]pyrrol-2(1H)-yl)methyl)-1-methyl-1H-indol-5-yl)-5-ethyl-4-hydroxy-2-oxo-1,2-dihydropyridine-3-carboxylic acid |
| 278 | 6-(2-(((3aR,4R,6aS)-4-(dimethylamino)hexahydrocyclopenta[c]pyrrol-2(1H)-yl)methyl)-1-methyl-1H-indol-5-yl)-5-ethyl-4-hydroxy-2-oxo-1,2-dihydropyridine-3-carboxylic acid |
| 279 | 6-(2-(((3aR,4R,7aS)-4-(dimethylamino)-1H-isoindol-2(3H,3aH,4H,5H,6H,7H,7aH)-yl)methyl)-1-methyl-1H-indol-5-yl)-5-ethyl-4-hydroxy-2-oxo-1,2-dihydropyridine-3-carboxylic acid checked from end to here |
| 280 | 6-(2-(((3aR,4R,7aS)-4-(benzyl(methyl)amino)-1H-isoindol-2(3H,3aH,4H,5H,6H,7H,7aH)-yl)methyl)-1-methyl-1H-indol-5-yl)-5-ethyl-4-hydroxy-2-oxo-1,2-dihydropyridine-3-carboxylic acid |
| 281 | 6-(2-(((3aR,4R,6aS)-4-(dibenzylamino)hexahydrocyclopenta[c]pyrrol-2(1H)-yl)methyl)-1-methyl-1H-indol-5-yl)-5-ethyl-4-hydroxy-2-oxo-1,2-dihydropyridine-3-carboxylic acid |
| 282 | 5-ethyl-4-hydroxy-6-(1-methyl-2-(((3aR,4R,7aS)-4-(methylamino)-1H-isoindol-2(3H,3aH,4H,5H,6H,7H,7aH)-yl)methyl)-1H-indol-5-yl)-2-oxo-1,2-dihydropyridine-3-carboxylic acid |
| 283 | 6-(2-(((3aR,4R,7aS)-4-(dibenzylamino)-1H-isoindol-2(3H,3aH,4H,5H,6H,7H,7aH)-yl)methyl)-1-methyl-1H-indol-5-yl)-5-ethyl-4-hydroxy-2-oxo-1,2-dihydropyridine-3-carboxylic acid |
| 284 | 6-(2-(((3aR,4R,7aS)-4-amino-1H-isoindol-2(3H,3aH,4H,5H,6H,7H,7aH)-yl)methyl)-1-methyl-1H-indol-5-yl)-5-ethyl-4-hydroxy-2-oxo-1,2-dihydropyridine-3-carboxylic acid |
| 285 | 6-(2-(((3aR,5r,6aS)-5-(dimethylamino)hexahydrocyclopenta[c]pyrrol-2(1H)-yl)methyl)-1-methyl-1H-indol-5-yl)-5-ethyl-4-hydroxy-2-oxo-1,2-dihydropyridine-3-carboxylic acid |
| 286 | 6-(2-(((3aR,5r,6aS)-5-(dibenzylamino)hexahydrocyclopenta[c]pyrrol-2(1H)-yl)methyl)-1-methyl-1H-indol-5-yl)-5-ethyl-4-hydroxy-2-oxo-1,2-dihydropyridine-3-carboxylic acid |
| 287 | 6-(2-(((3aR,5r,6aS)-5-aminohexahydrocyclopenta[c]pyrrol-2(1H)-yl)methyl)-1-methyl-1H-indol-5-yl)-5-ethyl-4-hydroxy-2-oxo-1,2-dihydropyridine-3-carboxylic acid |
| 288 | 6-(2-(((3aR,5r,6aS)-5-(benzyl(methyl)amino)hexahydrocyclopenta[c]pyrrol-2(1H)-yl)methyl)-1-methyl-1H-indol-5-yl)-5-ethyl-4-hydroxy-2-oxo-1,2-dihydropyridine-3-carboxylic acid |
| 289 | 5-ethyl-4-hydroxy-6-(1-methyl-2-(((3aR,5r,6aS)-5-(methylamino)hexahydrocyclopenta[c]pyrrol-2(1H)-yl)methyl)-1H-indol-5-yl)-2-oxo-1,2-dihydropyridine-3-carboxylic acid |
| 290 | 6-(2-(aminomethyl)-1-methyl-1H-indol-5-yl)-5-ethyl-4-hydroxy-2-oxo-1,2-dihydropyridine-3-carboxylic acid |
| 291 | 5-ethyl-4-hydroxy-6-(2-((4-methoxybenzylamino)methyl)-1-methyl-1H-indol-5-yl)-2-oxo-1,2-dihydropyridine-3-carboxylic acid |
| 292 | 5-ethyl-6-(2-((4-fluorobenzylamino)methyl)-1-methyl-1H-indol-5-yl)-4-hydroxy-2-oxo-1,2-dihydropyridine-3-carboxylic acid |
| 293 | 5-ethyl-4-hydroxy-6-(2-((2-methoxybenzylamino)methyl)-1-methyl-1H-indol-5-yl)-2-oxo-1,2-dihydropyridine-3-carboxylic acid |
| 294 | 5-ethyl-4-hydroxy-6-(1-methyl-2-((3-methylbenzylamino)methyl)-1H-indol-5-yl)-2-oxo-1,2-dihydropyridine-3-carboxylic acid |
| 295 | 5-ethyl-4-hydroxy-6-(1-methyl-2-((2-methylbenzylamino)methyl)-1H-indol-5-yl)-2-oxo-1,2-dihydropyridine-3-carboxylic acid |
| 296 | 5-ethyl-4-hydroxy-6-(2-((3-methoxybenzylamino)methyl)-1-methyl-1H-indol-5-yl)-2-oxo-1,2-dihydropyridine-3-carboxylic acid |
| 297 | 5-ethyl-4-hydroxy-6-(1-methyl-2-((4-methylbenzylamino)methyl)-1H-indol-5-yl)-2-oxo-1,2-dihydropyridine-3-carboxylic acid |

| Cpd | Name |
|---|---|
| 298 | 5-ethyl-6-(2-((3-fluorobenzylamino)methyl)-1-methyl-1H-indol-5-yl)-4-hydroxy-2-oxo-1,2-dihydropyridine-3-carboxylic acid |
| 299 | 5-ethyl-6-(2-((2-fluorobenzylamino)methyl)-1-methyl-1H-indol-5-yl)-4-hydroxy-2-oxo-1,2-dihydropyridine-3-carboxylic acid |
| 300 | 5-ethyl-4-hydroxy-6-(2-(((2-methoxyethyl)(methyl)amino)methyl)-1-methyl-1H-indol-5-yl)-2-oxo-1,2-dihydropyridine-3-carboxylic acid |
| 301 | 6-(2-((cycloheptylmethylamino)methyl)-1-methyl-1H-indol-5-yl)-5-ethyl-4-hydroxy-2-oxo-1,2-dihydropyridine-3-carboxylic acid |
| 302 | 6-(2-((2-(dimethylamino)ethylamino)methyl)-1-methyl-1H-indol-5-yl)-5-ethyl-4-hydroxy-2-oxo-1,2-dihydropyridine-3-carboxylic acid |
| 303 | 6-(2-(((2-(dimethylamino)ethyl)(methyl)amino)methyl)-1-methyl-1H-indol-5-yl)-5-ethyl-4-hydroxy-2-oxo-1,2-dihydropyridine-3-carboxylic acid |
| 304 | 5-ethyl-4-hydroxy-2-oxo-6-(1-(pyrrolidin-1-yl)-2,3-dihydro-1H-pyrrolo[1,2-a]indol-7-yl)-1,2-dihydropyridine-3-carboxylic acid |
| 305 | 5-ethyl-4-hydroxy-2-oxo-6-(1,2,3,4-tetrahydropyrazino[1,2-a]indol-8-yl)-1,2-dihydropyridine-3-carboxylic acid |
| 306 | 5-ethyl-4-hydroxy-6-(1-methyl-2-(pyrrolidin-3-yl)-1H-indol-5-yl)-2-oxo-1,2-dihydropyridine-3-carboxylic acid |
| 307 | 5-ethyl-4-hydroxy-6-(1-methyl-2-(2-(pyrrolidin-1-yl)propan-2-yl)-1H-indol-5-yl)-2-oxo-1,2-dihydropyridine-3-carboxylic acid |
| 308 | 6-(2-(2-(dimethylamino)propan-2-yl)-1-methyl-1H-indol-5-yl)-5-ethyl-4-hydroxy-2-oxo-1,2-dihydropyridine-3-carboxylic acid |
| 309 | 5-(4-fluorophenyl)-4-hydroxy-6-(1-methyl-2-(pyrrolidin-1-ylmethyl)-1H-indol-5-yl)-2-oxo-1,2-dihydropyridine-3-carboxylic acid |
| 310 | 6-(2-((dimethylamino)methyl)-1-methyl-1H-indol-5-yl)-5-(4-fluorophenyl)-4-hydroxy-2-oxo-1,2-dihydropyridine-3-carboxylic acid |
| 311 | 6-(2-((cyclopropylmethylamino)methyl)-1-methyl-1H-indol-5-yl)-5-(4-fluorophenyl)-4-hydroxy-2-oxo-1,2-dihydropyridine-3-carboxylic acid |
| 312 | 6-(2-(azetidin-1-ylmethyl)-1-methyl-1H-indol-5-yl)-5-(4-fluorophenyl)-4-hydroxy-2-oxo-1,2-dihydropyridine-3-carboxylic acid |
| 313 | 4-hydroxy-5-methyl-6-(1-methyl-2-(pyrrolidin-1-ylmethyl)-1H-indol-5-yl)-2-oxo-1,2-dihydropyridine-3-carboxylic acid |
| 314 | 6-(2-((dimethylamino)methyl)-1-methyl-1H-indol-5-yl)-4-hydroxy-5-methyl-2-oxo-1,2-dihydropyridine-3-carboxylic acid |
| 315 | 6-(2-((cyclopropylmethylamino)methyl)-1-methyl-1H-indol-5-yl)-4-hydroxy-5-methyl-2-oxo-1,2-dihydropyridine-3-carboxylic acid |
| 316 | 6-(2-(azetidin-1-ylmethyl)-1-methyl-1H-indol-5-yl)-4-hydroxy-5-methyl-2-oxo-1,2-dihydropyridine-3-carboxylic acid |
| 317 | 4-hydroxy-5-methyl-6-(1-methyl-2-((methylamino)methyl)-1H-indol-5-yl)-2-oxo-1,2-dihydropyridine-3-carboxylic acid |
| 318 | 6-(2-((dimethylamino)methyl)-1-methyl-1H-indol-5-yl)-4-hydroxy-5-isopropyl-2-oxo-1,2-dihydropyridine-3-carboxylic acid |
| 319 | 4-hydroxy-5-isopropyl-6-(1-methyl-2-(pyrrolidin-1-ylmethyl)-1H-indol-5-yl)-2-oxo-1,2-dihydropyridine-3-carboxylic acid |
| 320 | 6-(2-(azetidin-1-ylmethyl)-1-methyl-1H-indol-5-yl)-4-hydroxy-5-isopropyl-2-oxo-1,2-dihydropyridine-3-carboxylic acid |
| 321 | 6-(2-((cyclopropylmethylamino)methyl)-1-methyl-1H-indol-5-yl)-4-hydroxy-5-isopropyl-2-oxo-1,2-dihydropyridine-3-carboxylic acid |
| 322 | 5-cyclopropyl-6-(2-((dimethylamino)methyl)-1-methyl-1H-indol-5-yl)-4-hydroxy-2-oxo-1,2-dihydropyridine-3-carboxylic acid |
| 323 | 5-cyclopropyl-4-hydroxy-6-(1-methyl-2-(pyrrolidin-1-ylmethyl)-1H-indol-5-yl)-2-oxo-1,2-dihydropyridine-3-carboxylic acid |
| 324 | 6-(2-(azetidin-1-ylmethyl)-1-methyl-1H-indol-5-yl)-5-cyclopropyl-4-hydroxy-2-oxo-1,2-dihydropyridine-3-carboxylic acid |
| 325 | 5-cyclopropyl-6-(2-((cyclopropylmethylamino)methyl)-1-methyl-1H-indol-5-yl)-4-hydroxy-2-oxo-1,2-dihydropyridine-3-carboxylic acid |
| 326 | 6-(2-((dimethylamino)methyl)-1-methyl-1H-indol-5-yl)-4-hydroxy-2-oxo-1,2-dihydropyridine-3-carboxylic acid |
| 327 | 4-hydroxy-6-(1-methyl-2-(pyrrolidin-1-ylmethyl)-1H-indol-5-yl)-2-oxo-1,2-dihydropyridine-3-carboxylic acid |
| 328 | 6-(2-(azetidin-1-ylmethyl)-1-methyl-1H-indol-5-yl)-4-hydroxy-2-oxo-1,2-dihydropyridine-3-carboxylic acid |
| 329 | 4-amino-5-ethyl-6-(1-methyl-2-(pyrrolidin-1-ylmethyl)-1H-indol-5-yl)-2-oxo-1,2-dihydropyridine-3-carboxylic acid |
| 330 | 4-amino-6-(2-((dimethylamino)methyl)-1-methyl-1H-indol-5-yl)-5-ethyl-2-oxo-1,2-dihydropyridine-3-carboxylic acid |
| 331 | 4-amino-5-ethyl-6-(1-methyl-2-(piperidin-1-ylmethyl)-1H-indol-5-yl)-2-oxo-1,2-dihydropyridine-3-carboxylic acid |
| 332 | 4-amino-6-(2-((3-(dimethylamino)pyrrolidin-1-yl)methyl)-1-methyl-1H-indol-5-yl)-5-ethyl-2-oxo-1,2-dihydropyridine-3-carboxylic acid |
| 333 | 6-(2-((butylamino)methyl)-1-methyl-1H-indol-5-yl)-5-ethyl-4-hydroxy-2-oxo-1,2-dihydropyridine-3-carboxylic acid |
| 334 | 5-ethyl-4-hydroxy-6-(1-methyl-2-((pentylamino)methyl)-1H-indol-5-yl)-2-oxo-1,2-dihydropyridine-3-carboxylic acid |
| 335 | 5-ethyl-6-(2-((hexylamino)methyl)-1-methyl-1H-indol-5-yl)-4-hydroxy-2-oxo-1,2-dihydropyridine-3-carboxylic acid |

-continued

| Cpd | Name |
|---|---|
| 336 | 5-ethyl-6-(2-((heptylamino)methyl)-1-methyl-1H-indol-5-yl)-4-hydroxy-2-oxo-1,2-dihydropyridine-3-carboxylic acid |
| 337 | 5-ethyl-4-hydroxy-6-(1-methyl-2-((octylamino)methyl)-1H-indol-5-yl)-2-oxo-1,2-dihydropyridine-3-carboxylic acid |
| 338 | 5-ethyl-4-hydroxy-6-(1-methyl-2-((nonylamino)methyl)-1H-indol-5-yl)-2-oxo-1,2-dihydropyridine-3-carboxylic acid |
| 339 | 5-allyl-6-(2-((dimethylamino)methyl)-1-methyl-1H-indol-5-yl)-4-hydroxy-2-oxo-1,2-dihydropyridine-3-carboxylic acid |
| 340 | 6-(2-((dimethylamino)methyl)-1-methyl-1H-indol-5-yl)-4-hydroxy-2-oxo-5-propyl-1,2-dihydropyridine-3-carboxylic acid |
| 341 | 4-hydroxy-6-(2-((2-methoxyethylamino)methyl)-1-methyl-1H-indol-5-yl)-5-methyl-2-oxo-1,2-dihydropyridine-3-carboxylic acid |
| 342 | 6-(2-((ethylamino)methyl)-1-methyl-1H-indol-5-yl)-4-hydroxy-5-methyl-2-oxo-1,2-dihydropyridine-3-carboxylic acid |
| 343 | 6-(2-((2-aminoethylamino)methyl)-1-methyl-1H-indol-5-yl)-4-hydroxy-5-methyl-2-oxo-1,2-dihydropyridine-3-carboxylic acid |
| 344 | 4-hydroxy-5-methyl-6-(1-methyl-2-((2-(methylamino)ethylamino)methyl)-1H-indol-5-yl)-2-oxo-1,2-dihydropyridine-3-carboxylic acid |
| 345 | 6-(2-((2-(dimethylamino)ethylamino)methyl)-1-methyl-1H-indol-5-yl)-4-hydroxy-5-methyl-2-oxo-1,2-dihydropyridine-3-carboxylic acid |
| 346 | 4-hydroxy-6-(2-((1-methoxypropan-2-ylamino)methyl)-1-methyl-1H-indol-5-yl)-5-methyl-2-oxo-1,2-dihydropyridine-3-carboxylic acid |
| 347 | 6-(2-((sec-butylamino)methyl)-1-methyl-1H-indol-5-yl)-4-hydroxy-5-methyl-2-oxo-1,2-dihydropyridine-3-carboxylic acid |
| 348 | 4-hydroxy-6-(2-((isopropylamino)methyl)-1-methyl-1H-indol-5-yl)-5-methyl-2-oxo-1,2-dihydropyridine-3-carboxylic acid |
| 349 | 4-hydroxy-6-(2-((1-hydroxypropan-2-ylamino)methyl)-1-methyl-1H-indol-5-yl)-5-methyl-2-oxo-1,2-dihydropyridine-3-carboxylic acid |
| 350 | 4-hydroxy-6-(2-((2-hydroxyethylamino)methyl)-1-methyl-1H-indol-5-yl)-5-methyl-2-oxo-1,2-dihydropyridine-3-carboxylic acid |
| 351 | 6-(2-((tert-butylamino)methyl)-1-methyl-1H-indol-5-yl)-4-hydroxy-5-methyl-2-oxo-1,2-dihydropyridine-3-carboxylic acid |
| 352 | 4-hydroxy-5-methyl-6-(1-methyl-2-((propylamino)methyl)-1H-indol-5-yl)-2-oxo-1,2-dihydropyridine-3-carboxylic acid |
| 353 | 4-hydroxy-6-(2-((isobutylamino)methyl)-1-methyl-1H-indol-5-yl)-5-methyl-2-oxo-1,2-dihydropyridine-3-carboxylic acid |
| 354 | 6-(2-((cyclobutylamino)methyl)-1-methyl-1H-indol-5-yl)-4-hydroxy-5-methyl-2-oxo-1,2-dihydropyridine-3-carboxylic acid |
| 355 | 6-(2-((cyclopropylamino)methyl)-1-methyl-1H-indol-5-yl)-4-hydroxy-5-methyl-2-oxo-1,2-dihydropyridine-3-carboxylic acid |
| 356 | 4-hydroxy-5-methyl-6-(1-methyl-2-((1-methylcyclopropylamino)methyl)-1H-indol-5-yl)-2-oxo-1,2-dihydropyridine-3-carboxylic acid |
| 357 | 6-(2-((diethylamino)methyl)-1-methyl-1H-indol-5-yl)-4-hydroxy-5-methyl-2-oxo-1,2-dihydropyridine-3-carboxylic acid |
| 358 | 6-(2-(aminomethyl)-1-methyl-1H-indol-5-yl)-4-hydroxy-5-methyl-2-oxo-1,2-dihydropyridine-3-carboxylic acid |
| 359 | 6-(3-cyano-1-methyl-1H-indol-5-yl)-5-ethyl-4-hydroxy-2-oxo-1,2-dihydropyridine-3-carboxylic acid |
| 360 | 6-(3-cyano-1-methyl-2-(pyrrolidin-1-yl)-1H-indol-5-yl)-5-ethyl-4-hydroxy-2-oxo-1,2-dihydropyridine-3-carboxylic acid |
| 361 | 6-(3-cyano-2-(dimethylamino)-1-methyl-1H-indol-5-yl)-5-ethyl-4-hydroxy-2-oxo-1,2-dihydropyridine-3-carboxylic acid |
| 362 | 6-(3-cyano-2-methoxy-1-methyl-1H-indol-5-yl)-5-ethyl-4-hydroxy-2-oxo-1,2-dihydropyridine-3-carboxylic acid |
| 363 | 6-(3-chloro-1-methyl-1H-indol-5-yl)-5-ethyl-4-hydroxy-2-oxo-1,2-dihydropyridine-3-carboxylic acid |
| 364 | 6-(benzofuran-5-yl)-5-ethyl-2-oxo-1,2-dihydropyridine-3-carboxylic acid |
| 365 | 6-(benzofuran-5-yl)-5-ethyl-4-hydroxy-2-oxo-1,2-dihydropyridine-3-carboxylic acid |
| 366 | 6-(benzo[b]thiophen-5-yl)-5-ethyl-2-oxo-1,2-dihydropyridine-3-carboxylic acid |
| 367 | 6-(benzo[b]thiophen-5-yl)-5-ethyl-4-hydroxy-2-oxo-1,2-dihydropyridine-3-carboxylic acid |
| 368 | 5-ethyl-6-(3-fluoro-1-methyl-2-((methylamino)methyl)-1H-indol-5-yl)-4-hydroxy-2-oxo-1,2-dihydropyridine-3-carboxylic acid |
| 369 | 5-ethyl-6-(2-((ethylamino)methyl)-3-fluoro-1-methyl-1H-indol-5-yl)-4-hydroxy-2-oxo-1,2-dihydropyridine-3-carboxylic acid |
| 370 | 5-ethyl-6-(3-fluoro-2-((isopropylamino)methyl)-1-methyl-1H-indol-5-yl)-4-hydroxy-2-oxo-1,2-dihydropyridine-3-carboxylic acid |
| 371 | 6-(2-((tert-butylamino)methyl)-3-fluoro-1-methyl-1H-indol-5-yl)-5-ethyl-4-hydroxy-2-oxo-1,2-dihydropyridine-3-carboxylic acid |
| 372 | 6-(4-(benzyloxy)-1-methyl-1H-indol-5-yl)-5-ethyl-2-oxo-1,2-dihydropyridine-3-carboxylic acid |
| 373 | 6-(4-(benzyloxy)-1-methyl-1H-indol-5-yl)-5-ethyl-4-hydroxy-2-oxo-1,2-dihydropyridine-3-carboxylic acid |
| 374 | 5-ethyl-4-hydroxy-6-(4-hydroxy-1-methyl-1H-indol-5-yl)-2-oxo-1,2-dihydropyridine-3-carboxylic acid |
| 375 | 4-hydroxy-6-(1-methyl-1H-indol-5-yl)-2-oxo-5-vinyl-1,2,5,6-tetrahydropyridine-3-carboxylic acid |

| Cpd | Name |
|---|---|
| 376 | 5-chloro-4-hydroxy-6-(1-methyl-1H-indol-5-yl)-2-oxo-1,2-dihydropyridine-3-carboxylic acid |
| 377 | 4-hydroxy-5-methoxy-6-(1-methyl-1H-indol-5-yl)-2-oxo-1,2-dihydropyridine-3-carboxylic acid |
| 378 | 4-hydroxy-5-ethoxy-6-(1-methyl-1H-indol-5-yl)-2-oxo-1,2-dihydropyridine-3-carboxylic acid |
| 379 | 5-ethyl-4-hydroxy-6-(6-methoxy-1H-indol-2-yl)-2-oxo-1,2-dihydropyridine-3-carboxylic acid |
| 380 | 5-ethyl-6-(5-fluoro-1H-indol-2-yl)-4-hydroxy-2-oxo-1,2-dihydropyridine-3-carboxylic acid |
| 381 | 5-ethyl-6-(5-ethyl-1H-indol-2-yl)-4-hydroxy-2-oxo-1,2-dihydropyridine-3-carboxylic acid |
| 382 | 5-ethyl-6-(6-ethyl-1H-indol-2-yl)-4-hydroxy-2-oxo-1,2-dihydropyridine-3-carboxylic acid |
| 383 | 5-ethyl-4-hydroxy-2-oxo-6-(5-propyl-1H-indol-2-yl)-1,2-dihydropyridine-3-carboxylic acid |
| 384 | 5-ethyl-4-hydroxy-2-oxo-6-(6-propyl-1H-indol-2-yl)-1,2-dihydropyridine-3-carboxylic acid |
| 385 | 5-ethyl-6-(5-fluoro-6-methyl-1H-indol-2-yl)-4-hydroxy-2-oxo-1,2-dihydropyridine-3-carboxylic acid |
| 386 | 6-(5-ethyl-1H-indol-2-yl)-4-hydroxy-5-methyl-2-oxo-1,2-dihydropyridine-3-carboxylic acid |
| 387 | 6-(6-ethyl-1H-indol-2-yl)-4-hydroxy-5-methyl-2-oxo-1,2-dihydropyridine-3-carboxylic acid |
| 388 | 6-(5-fluoro-6-methyl-1H-indol-2-yl)-4-hydroxy-5-methyl-2-oxo-1,2-dihydropyridine-3-carboxylic acid |
| 389 | 5-ethyl-4-hydroxy-6-(2-methyl-2H-indazol-6-yl)-2-oxo-1,2-dihydropyridine-3-carboxylic acid |
| 390 | 5-ethyl-4-hydroxy-6-(1-methyl-1H-indazol-6-yl)-2-oxo-1,2-dihydropyridine-3-carboxylic acid |
| 391 | 5-ethyl-4-hydroxy-6-(1H-indazol-6-yl)-2-oxo-1,2-dihydropyridine-3-carboxylic acid |
| 392 | 5-ethyl-4-hydroxy-6-(1H-indazol-5-yl)-2-oxo-1,2-dihydropyridine-3-carboxylic acid |
| 393 | 5-ethyl-4-hydroxy-6-(2-methyl-2H-indazol-5-yl)-2-oxo-1,2-dihydropyridine-3-carboxylic acid |
| 394 | 4-hydroxy-5-methyl-6-(1-methyl-1H-indazol-5-yl)-2-oxo-1,2-dihydropyridine-3-carboxylic acid |
| 395 | 4-hydroxy-5-methyl-6-(2-methyl-2H-indazol-5-yl)-2-oxo-1,2-dihydropyridine-3-carboxylic acid |
| 396 | 4-hydroxy-5-methyl-6-(1-methyl-1H-indazol-6-yl)-2-oxo-1,2-dihydropyridine-3-carboxylic acid |
| 397 | 4-hydroxy-5-methyl-6-(2-methyl-2H-indazol-6-yl)-2-oxo-1,2-dihydropyridine-3-carboxylic acid |
| 398 | 4-hydroxy-6-(1H-indazol-5-yl)-5-methyl-2-oxo-1,2-dihydropyridine-3-carboxylic acid |
| 399 | 4-hydroxy-6-(1H-indazol-6-yl)-5-methyl-2-oxo-1,2-dihydropyridine-3-carboxylic acid |
| 400 | 5-ethyl-4-hydroxy-6-(imidazo[1,2-a]pyridin-2-yl)-2-oxo-1,2-dihydropyridine-3-carboxylic acid |
| 401 | 6-(4-(dimethylamino)-6-methylpyrazolo[1,5-a]pyrazin-2-yl)-5-ethyl-4-hydroxy-2-oxo-1,2-dihydropyridine-3-carboxylic acid |
| 402 | 5-ethyl-4-hydroxy-6-(6-methyl-4-(pyrrolidin-1-yl)pyrazolo[1,5-a]pyrazin-2-yl)-2-oxo-1,2-dihydropyridine-3-carboxylic acid |
| 403 | 5-ethyl-4-hydroxy-6-(1-methyl-1H-indol-4-yl)-2-oxo-1,2-dihydropyridine-3-carboxylic acid |
| 404 | 4-hydroxy-5-methyl-6-(1-methyl-1H-indol-4-yl)-2-oxo-1,2-dihydropyridine-3-carboxylic acid |
| 405 | 5-ethyl-4-hydroxy-6-(6-methoxy-1-methyl-1H-indol-2-yl)-2-oxo-1,2-dihydropyridine-3-carboxylic acid |
| 406 | 5-ethyl-6-(5-fluoro-1-methyl-1H-indol-2-yl)-4-hydroxy-2-oxo-1,2-dihydropyridine-3-carboxylic acid |
| 407 | 5-ethyl-6-(5-ethyl-1-methyl-1H-indol-2-yl)-4-hydroxy-2-oxo-1,2-dihydropyridine-3-carboxylic acid |
| 408 | 5-ethyl-6-(6-ethyl-1-methyl-1H-indol-2-yl)-4-hydroxy-2-oxo-1,2-dihydropyridine-3-carboxylic acid |
| 409 | 5-ethyl-4-hydroxy-6-(1-methyl-5-propyl-1H-indol-2-yl)-2-oxo-1,2-dihydropyridine-3-carboxylic acid |
| 410 | 5-ethyl-4-hydroxy-6-(1-methyl-6-propyl-1H-indol-2-yl)-2-oxo-1,2-dihydropyridine-3-carboxylic acid |
| 411 | 5-ethyl-6-(5-fluoro-1,6-dimethyl-1H-indol-2-yl)-4-hydroxy-2-oxo-1,2-dihydropyridine-3-carboxylic acid |
| 419 | 5-ethyl-6-(2-(ethyl(methyl)amino)-2,3-dihydro-1H-pyrrolo[1,2-a]indol-7-yl)-4-hydroxy-2-oxo-1,2-dihydropyridine-3-carboxylic acid |
| 420 | 5-ethyl-4-hydroxy-6-(2-(methyl(propyl)amino)-2,3-dihydro-1H-pyrrolo[1,2-a]indol-7-yl)-2-oxo-1,2-dihydropyridine-3-carboxylic acid |
| 423 | 5-ethyl-4-hydroxy-6-(1H-indol-6-yl)-2-oxo-1,2-dihydropyridine-3-carboxylic acid |
| 424 | 4-hydroxy-6-(1H-indol-6-yl)-5-methyl-2-oxo-1,2-dihydropyridine-3-carboxylic acid |
| 425 | 5-ethyl-4-hydroxy-6-(1H-indol-5-yl)-2-oxo-1,2-dihydropyridine-3-carboxylic acid |
| 426 | 4-hydroxy-6-(1H-indol-5-yl)-5-methyl-2-oxo-1,2-dihydropyridine-3-carboxylic acid |
| 427 | 4-hydroxy-5-methyl-2-oxo-6-(2-oxoindolin-5-yl)-1,2-dihydropyridine-3-carboxylic acid |

| Cpd | Name |
|---|---|
| 428 | 6-(6-(dimethylamino)naphthalen-2-yl)-5-ethyl-4-hydroxy-2-oxo-1,2-dihydropyridine-3-carboxylic acid |
| 429 | 5-ethyl-4-hydroxy-6-(2-methylindolizin-6-yl)-2-oxo-1,2-dihydropyridine-3-carboxylic acid |
| 430 | 5-ethyl-4-hydroxy-2-oxo-6-(1H-pyrrolo[3,2-b]pyridin-6-yl)-1,2-dihydropyridine-3-carboxylic acid |
| 431 | 4-hydroxy-5-methyl-2-oxo-6-(1H-pyrrolo[3,2-b]pyridin-6-yl)-1,2-dihydropyridine-3-carboxylic acid |
| 432 | 6-(9H-carbazol-2-yl)-5-ethyl-4-hydroxy-2-oxo-1,2-dihydropyridine-3-carboxylic acid |
| 433 | 5-ethyl-4-hydroxy-2-oxo-6-(1H-pyrrolo[2,3-b]pyridin-6-yl)-1,2-dihydropyridine-3-carboxylic acid |
| 434 | 4-hydroxy-5-methyl-2-oxo-6-(1H-pyrrolo[2,3-b]pyridin-6-yl)-1,2-dihydropyridine-3-carboxylic acid |
| 435 | 5-ethyl-4-hydroxy-2-oxo-6-(1-phenyl-1H-indol-5-yl)-1,2-dihydropyridine-3-carboxylic acid |
| 436 | 5-ethyl-4-hydroxy-2-oxo-6-(1-(pyridin-2-yl)-1H-indol-5-yl)-1,2-dihydropyridine-3-carboxylic acid |
| 437 | 5-ethyl-4-hydroxy-2-oxo-6-(1-(4-(trifluoromethyl)phenyl)-1H-indol-5-yl)-1,2-dihydropyridine-3-carboxylic acid |
| 438 | 5-ethyl-6-(1-(4-fluorophenyl)-1H-indol-5-yl)-4-hydroxy-2-oxo-1,2-dihydropyridine-3-carboxylic acid |
| 439 | 5-ethyl-4-hydroxy-2-oxo-6-(1-(3-(pyrrolidin-1-yl)phenyl)-1H-indol-5-yl)-1,2-dihydropyridine-3-carboxylic acid |
| 440 | 5-ethyl-4-hydroxy-2-oxo-6-(1-(4-(pyrrolidin-1-yl)phenyl)-1H-indol-5-yl)-1,2-dihydropyridine-3-carboxylic acid |
| 445 | 5-ethyl-4-hydroxy-2-oxo-6-(2,3,4,9-tetrahydro-1H-pyrido[3,4-b]indol-7-yl)-1,2-dihydropyridine-3-carboxylic acid |
| 446 | 5-ethyl-4-(hydroxy)-6-(2-methyl-2,3,4,9-tetrahydro-1H-pyrido[3,4-b]indol-7-yl)-2-oxo-1,2-dihydropyridine-3-carboxylic acid |
| 447 | 5-ethyl-6-(2-ethyl-2,3,4,9-tetrahydro-1H-pyrido[3,4-b]indol-7-yl)-4-hydroxy-2-oxo-1,2-dihydropyridine-3-carboxylic acid |
| 448 | 5-ethyl-4-hydroxy-2-oxo-6-(2-propyl-2,3,4,9-tetrahydro-1H-pyrido[3,4-b]indol-7-yl)-1,2-dihydropyridine-3-carboxylic acid |
| 449 | 5-ethyl-4-hydroxy-6-(2-isopropyl-2,3,4,9-tetrahydro-1H-pyrido[3,4-b]indol-7-yl)-2-oxo-1,2-dihydropyridine-3-carboxylic acid |
| 450 | 5-ethyl-4-hydroxy-2-oxo-6-(2,3,4,5-tetrahydro-1H-pyrido[4,3-b]indol-7-yl)-1,2-dihydropyridine-3-carboxylic acid |
| 451 | 5-ethyl-4-hydroxy-6-(2-methyl-2,3,4,5-tetrahydro-1H-pyrido[4,3-b]indol-7-yl)-2-oxo-1,2-dihydropyridine-3-carboxylic acid |
| 452 | 5-ethyl-6-(2-ethyl-2,3,4,5-tetrahydro-1H-pyrido[4,3-b]indol-7-yl)-4-hydroxy-2-oxo-1,2-dihydropyridine-3-carboxylic acid |
| 453 | 6-(2-(4-cyanophenyl)-1H-indol-5-yl)-5-ethyl-4-hydroxy-2-oxo-1,2-dihydropyridine-3-carboxylic acid |
| 454 | 5-ethyl-4-hydroxy-2-oxo-6-(2-phenyl-1H-indol-5-yl)-1,2-dihydropyridine-3-carboxylic acid, and |
| 455 | 5-ethyl-4-hydroxy-2-oxo-6-(2-(4-(trifluoromethyl)phenyl)-1H-indol-5-yl)-1,2-dihydropyridine-3-carboxylic acid; | wherein the form of the compound is selected from a free acid, free base, salt, hydrate, solvate, clathrate, isotopologue, racemate, enantiomer, diastereomer, stereoisomer, polymorph or tautomer form thereof.

In another embodiment, the compound or a form thereof is isolated for use.

In another embodiment of the present description, a compound or a form thereof is selected from:

| Cpd | Name |
|---|---|
| 49 | 6-([1,2,4]triazolo[1,5-a]pyridin-6-yl)-5-ethyl-2-oxo-1,2-dihydropyridine-3-carboxylic acid hydrochloride |
| 50 | 6-([1,2,4]triazolo[4,3-a]pyridin-6-yl)-5-ethyl-2-oxo-1,2-dihydropyridine-3-carboxylic acid hydrochloride |
| 51 | 5-ethyl-6-(imidazo[1,2-a]pyridin-6-yl)-2-oxo-1,2-dihydropyridine-3-carboxylic acid hydrochloride |
| 60 | 6-(2-((dimethylamino)methyl)imidazo[1,2-a]pyridin-6-yl)-5-ethyl-2-oxo-1,2-dihydropyridine-3-carboxylic acid dihydrochloride |
| 61 | 5-ethyl-2-oxo-6-(2-(pyrrolidin-1-ylmethyl)imidazo[1,2-a]pyridin-6-yl)-1,2-dihydropyridine-3-carboxylic acid dihydrochloride |
| 62 | 5-ethyl-2-oxo-6-(2-(piperidin-1-ylmethyl)imidazo[1,2-a]pyridin-6-yl)-1,2-dihydropyridine-3-carboxylic acid dihydrochloride |
| 63 | 6-(2-((diethylamino)methyl)imidazo[1,2-a]pyridin-6-yl)-5-ethyl-2-oxo-1,2-dihydropyridine-3-carboxylic acid dihydrochloride |
| 64 | 5-ethyl-6-(6-methyl-5-(pyrrolidin-1-ylmethyl)-6H-thieno[2,3-b]pyrrol-2-yl)-2-oxo-1,2-dihydropyridine-3-carboxylic acid hydrochloride |
| 65 | 6-(5-((dimethylamino)methyl)-6-methyl-6H-thieno[2,3-b]pyrrol-2-yl)-5-ethyl-2-oxo-1,2-dihydropyridine-3-carboxylic acid hydrochloride |

| Cpd | Name |
|---|---|
| 67 | (R)-5-ethyl-6-(1-methyl-2-(pyrrolidin-2-yl)-1H-indol-5-yl)-2-oxo-1,2-dihydropyridine-3-carboxylic acid hydrochloride |
| 69 | (S)-5-ethyl-6-(1-methyl-2-(pyrrolidin-2-yl)-1H-indol-5-yl)-2-oxo-1,2-dihydropyridine-3-carboxylic acid hydrochloride |
| 70 | 5-ethyl-6-(1-methyl-2-(piperazin-2-yl)-1H-indol-5-yl)-2-oxo-1,2-dihydropyridine-3-carboxylic acid dihydrochloride |
| 71 | 5-ethyl-6-(1-methyl-2-(1-methylpiperazin-2-yl)-1H-indol-5-yl)-2-oxo-1,2-dihydropyridine-3-carboxylic acid dihydrochloride |
| 156 | 5-ethyl-6-(1-methyl-2-(pyrrolidin-3-yl)-1H-indol-5-yl)-2-oxo-1,2-dihydropyridine-3-carboxylic acid hydrochloride |
| 163 | 6-(2-(2-aminoethyl)-1-methyl-1H-indol-5-yl)-5-ethyl-2-oxo-1,2-dihydropyridine-3-carboxylic acid hydrochloride |
| 209 | 6-(2-((cyclobutyl(methyl)amino)methyl)-1-methyl-1H-indol-5-yl)-5-ethyl-4-hydroxy-2-oxo-1,2-dihydropyridine-3-carboxylic acid hydrochloride |
| 210 | 6-(2-(((cyclopropylmethyl)(methyl)amino)methyl)-1-methyl-1H-indol-5-yl)-5-ethyl-4-hydroxy-2-oxo-1,2-dihydropyridine-3-carboxylic acid hydrochloride |
| 211 | 6-(2-((cyclopentyl(methyl)amino)methyl)-1-methyl-1H-indol-5-yl)-5-ethyl-4-hydroxy-2-oxo-1,2-dihydropyridine-3-carboxylic acid hydrochloride |
| 212 | 6-(2-((cyclopropyl(methyl)amino)methyl)-1-methyl-1H-indol-5-yl)-5-ethyl-4-hydroxy-2-oxo-1,2-dihydropyridine-3-carboxylic acid hydrochloride |
| 214 | 6-(2-((benzylamino)methyl)-1-methyl-1H-indol-5-yl)-5-ethyl-4-hydroxy-2-oxo-1,2-dihydropyridine-3-carboxylic acid hydrochloride |
| 215 | (R)-5-ethyl-4-hydroxy-6-(1-methyl-2-((1-phenylethylamino)methyl)-1H-indol-5-yl)-2-oxo-1,2-dihydropyridine-3-carboxylic acid hydrochloride |
| 216 | (S)-5-ethyl-4-hydroxy-6-(1-methyl-2-((1-phenylethylamino)methyl)-1H-indol-5-yl)-2-oxo-1,2-dihydropyridine-3-carboxylic acid hydrochloride |
| 217 | 5-ethyl-4-hydroxy-6-(1-methyl-2-((2-phenylpropan-2-ylamino)methyl)-1H-indol-5-yl)-2-oxo-1,2-dihydropyridine-3-carboxylic acid hydrochloride |
| 218 | 6-(2-((benzyl(methyl)amino)methyl)-1-methyl-1H-indol-5-yl)-5-ethyl-4-hydroxy-2-oxo-1,2-dihydropyridine-3-carboxylic acid hydrochloride |
| 219 | 5-ethyl-4-hydroxy-6-(1-methyl-2-((pyridin-2-ylmethylamino)methyl)-1H-indol-5-yl)-2-oxo-1,2-dihydropyridine-3-carboxylic acid hydrochloride |
| 220 | 5-ethyl-4-hydroxy-6-(1-methyl-2-((pyridin-3-ylmethylamino)methyl)-1H-indol-5-yl)-2-oxo-1,2-dihydropyridine-3-carboxylic acid hydrochloride |
| 221 | 5-ethyl-4-hydroxy-6-(1-methyl-2-((pyridin-4-ylmethylamino)methyl)-1H-indol-5-yl)-2-oxo-1,2-dihydropyridine-3-carboxylic acid hydrochloride |
| 222 | 6-(2-((cyclohexylmethylamino)methyl)-1-methyl-1H-indol-5-yl)-5-ethyl-4-hydroxy-2-oxo-1,2-dihydropyridine-3-carboxylic acid hydrochloride |
| 223 | 6-(2-((cyclopropylmethylamino)methyl)-1-methyl-1H-indol-5-yl)-5-ethyl-4-hydroxy-2-oxo-1,2-dihydropyridine-3-carboxylic acid hydrochloride |
| 224 | 5-ethyl-4-hydroxy-6-(1-methyl-2-((methyl(pyridin-3-ylmethyl)amino)methyl)-1H-indol-5-yl)-2-oxo-1,2-dihydropyridine-3-carboxylic acid hydrochloride |
| 225 | 5-ethyl-4-hydroxy-6-(1-methyl-2-((methyl(pyridin-4-ylmethyl)amino)methyl)-1H-indol-5-yl)-2-oxo-1,2-dihydropyridine-3-carboxylic acid hydrochloride |
| 226 | 5-ethyl-4-hydroxy-6-(1-methyl-2-((1-(pyridin-4-yl)ethylamino)methyl)-1H-indol-5-yl)-2-oxo-1,2-dihydropyridine-3-carboxylic acid hydrochloride |
| 227 | 5-ethyl-4-hydroxy-6-(1-methyl-2-(((tetrahydro-2H-pyran-4-yl)methylamino)methyl)-1H-indol-5-yl)-2-oxo-1,2-dihydropyridine-3-carboxylic acid hydrochloride |
| 228 | 6-(2-((cyclopropylamino)methyl)-1-methyl-1H-indol-5-yl)-5-ethyl-4-hydroxy-2-oxo-1,2-dihydropyridine-3-carboxylic acid hydrochloride |
| 229 | 6-(2-((cyclopentylamino)methyl)-1-methyl-1H-indol-5-yl)-5-ethyl-4-hydroxy-2-oxo-1,2-dihydropyridine-3-carboxylic acid hydrochloride |
| 230 | 5-ethyl-6-(2-(((1-ethylpyrrolidin-2-yl)methylamino)methyl)-1-methyl-1H-indol-5-yl)-4-hydroxy-2-oxo-1,2-dihydropyridine-3-carboxylic acid dihydrochloride |
| 231 | 5-ethyl-4-hydroxy-6-(1-methyl-2-(((1-methylpiperidin-3-yl)methylamino)methyl)-1H-indol-5-yl)-2-oxo-1,2-dihydropyridine-3-carboxylic acid dihydrochloride |
| 232 | 6-(2-((cyclobutylamino)methyl)-1-methyl-1H-indol-5-yl)-5-ethyl-4-hydroxy-2-oxo-1,2-dihydropyridine-3-carboxylic acid hydrochloride |
| 233 | 5-ethyl-4-hydroxy-6-(1-methyl-2-((((1-methylpiperidin-2-yl)methyl)amino)methyl)-1H-indol-5-yl)-2-oxo-1,2-dihydropyridine-3-carboxylic acid dihydrochloride |
| 234 | 5-ethyl-4-hydroxy-6-(1-methyl-2-((((1-methylpiperidin-4-yl)methyl)amino)methyl)-1H-indol-5-yl)-2-oxo-1,2-dihydropyridine-3-carboxylic acid dihydrochloride |
| 235 | 6-(2-((cyclobutylmethylamino)methyl)-1-methyl-1H-indol-5-yl)-5-ethyl-4-hydroxy-2-oxo-1,2-dihydropyridine-3-carboxylic acid hydrochloride |
| 236 | 6-(2-((cyclopentylmethylamino)methyl)-1-methyl-1H-indol-5-yl)-5-ethyl-4-hydroxy-2-oxo-1,2-dihydropyridine-3-carboxylic acid hydrochloride |
| 237 | 5-ethyl-4-hydroxy-6-(1-methyl-2-((neopentylamino)methyl)-1H-indol-5-yl)-2-oxo-1,2-dihydropyridine-3-carboxylic acid hydrochloride |
| 238 | 5-ethyl-4-hydroxy-6-(1-methyl-2-((4-methyl-1,4-diazepan-1-yl)methyl)-1H-indol-5-yl)-2-oxo-1,2-dihydropyridine-3-carboxylic acid dihydrochloride |
| 239 | 6-(2-((1,4-diazepan-1-yl)methyl)-1-methyl-1H-indol-5-yl)-5-ethyl-4-hydroxy-2-oxo-1,2-dihydropyridine-3-carboxylic acid dihydrochloride |
| 240 | 5-ethyl-4-hydroxy-6-(1-methyl-2-((2-methylcyclopropyl)methyl)-1H-indol-5-yl)-2-oxo-1,2-dihydropyridine-3-carboxylic acid hydrochloride |
| 241 | 6-(2-((cyclohexylamino)methyl)-1-methyl-1H-indol-5-yl)-5-ethyl-4-hydroxy-2-oxo-1,2-dihydropyridine-3-carboxylic acid hydrochloride |

-continued

| Cpd | Name |
|---|---|
| 242 | 5-ethyl-4-hydroxy-6-(1-methyl-2-((1-(pyridin-3-yl)ethylamino)methyl)-1H-indol-5-yl)-2-oxo-1,2-dihydropyridine-3-carboxylic acid hydrochloride |
| 243 | 6-(2-((allylamino)methyl)-1-methyl-1H-indol-5-yl)-5-ethyl-4-hydroxy-2-oxo-1,2-dihydropyridine-3-carboxylic acid hydrochloride |
| 244 | 6-(2-((azetidin-3-ylamino)methyl)-1-methyl-1H-indol-5-yl)-5-ethyl-4-hydroxy-2-oxo-1,2-dihydropyridine-3-carboxylic acid dihydrochloride |
| 245 | 5-ethyl-4-hydroxy-6-(1-methyl-2-((1-methylcyclobutylamino)methyl)-1H-indol-5-yl)-2-oxo-1,2-dihydropyridine-3-carboxylic acid hydrochloride |
| 246 | 5-ethyl-4-hydroxy-6-(1-methyl-2-((1-methylazetidin-3-ylamino)methyl)-1H-indol-5-yl)-2-oxo-1,2-dihydropyridine-3-carboxylic acid dihydrochloride |
| 277 | 5-ethyl-4-hydroxy-6-(1-methyl-2-((prop-2-ynylamino)methyl)-1H-indol-5-yl)-2-oxo-1,2-dihydropyridine-3-carboxylic acid hydrochloride |
| 412 | 6-(2-amino-2,3-dihydro-1H-pyrrolo[1,2-a]indol-7-yl)-4-hydroxy-5-methyl-2-oxo-1,2-dihydropyridine-3-carboxylic acid hydrochloride |
| 413 | 6-(2-amino-2,3-dihydro-1H-pyrrolo[1,2-a]indol-7-yl)-5-ethyl-4-hydroxy-2-oxo-1,2-dihydropyridine-3-carboxylic acid hydrochloride |
| 414 | 5-ethyl-4-hydroxy-6-(7-(methylamino)-6,7,8,9-tetrahydropyrido[1,2-a]indol-2-yl)-2-oxo-1,2-dihydropyridine-3-carboxylic acid hydrochloride |
| 415 | 4-hydroxy-5-methyl-6-(2-(methylamino)-2,3-dihydro-1H-pyrrolo[1,2-a]indol-7-yl)-2-oxo-1,2-dihydropyridine-3-carboxylic acid hydrochloride |
| 416 | 5-ethyl-4-hydroxy-6-(2-(methylamino)-2,3-dihydro-1H-pyrrolo[1,2-a]indol-7-yl)-2-oxo-1,2-dihydropyridine-3-carboxylic acid hydrochloride |
| 417 | 6-(2-(dimethylamino)-2,3-dihydro-1H-pyrrolo[1,2-a]indol-7-yl)-4-hydroxy-5-methyl-2-oxo-1,2-dihydropyridine-3-carboxylic acid hydrochloride |
| 418 | 6-(2-(dimethylamino)-2,3-dihydro-1H-pyrrolo[1,2-a]indol-7-yl)-5-ethyl-4-hydroxy-2-oxo-1,2-dihydropyridine-3-carboxylic acid hydrochloride |
| 421 | 6-(cis-2-(aminomethyl)-1-(methylamino)-2,3-dihydro-1H-pyrrolo[1,2-a]indol-7-yl)-5-ethyl-4-hydroxy-2-oxo-1,2-dihydropyridine-3-carboxylic acid bis-hydrochloride |
| 422 | 6-(trans-7-amino-9-(methylamino)-6,7,8,9-tetrahydropyrido[1,2-a]indol-2-yl)-5-ethyl-4-hydroxy-2-oxo-1,2-dihydropyridine-3-carboxylic acid bis-hydrochloride |
| 441 | 6-(2-((dimethylamino)methyl)-1H-indol-6-yl)-5-ethyl-4-hydroxy-2-oxo-1,2-dihydropyridine-3-carboxylic acid hydrochloride |
| 442 | 5-ethyl-6-(2-((ethylamino)methyl)-1H-indol-6-yl)-4-hydroxy-2-oxo-1,2-dihydropyridine-3-carboxylic acid hydrochloride |
| 443 | 6-(2-((sec-butylamino)methyl)-1H-indol-6-yl)-5-ethyl-4-hydroxy-2-oxo-1,2-dihydropyridine-3-carboxylic acid hydrochloride, and |
| 444 | 6-(2-((ethylamino)methyl)-1H-indol-6-yl)-4-hydroxy-5-methyl-2-oxo-1,2-dihydropyridine-3-carboxylic acid hydrochloride; | wherein the form of the compound is selected from a free acid, free base, hydrate, solvate, clathrate, isotopologue, racemate, enantiomer, diastereomer, stereoisomer, polymorph or tautomer form thereof.

In another embodiment, the compound or a form thereof is isolated for use.

CHEMICAL DEFINITIONS

The chemical terms used above and throughout the description herein, unless specifically defined otherwise, shall be understood by one of ordinary skill in the art to have the following indicated meanings.

As used herein, the term "$C_{1-10}$alkyl" generally refers to saturated hydrocarbon radicals having from one to ten carbon atoms in a straight or branched chain configuration, including, without limitation, methyl, ethyl, n-propyl, isopropyl, n-butyl, isobutyl, sec-butyl, tert-butyl, n-pentyl, n-hexyl, n-heptyl, n-octyl, n-nonyl, n-decyl and the like. In some embodiments, $C_{1-10}$alkyl includes $C_{1-8}$alkyl, $C_{1-6}$alkyl, $C_{1-4}$alkyl and the like. A $C_{1-10}$alkyl radical may be optionally substituted where allowed by available valences.

As used herein, the term "$C_{2-8}$alkenyl" generally refers to partially unsaturated hydrocarbon radicals having from two to eight carbon atoms in a straight or branched chain configuration and one or more carbon-carbon double bonds therein, including, without limitation, ethenyl, allyl, propenyl and the like. In some embodiments, $C_{2-8}$alkenyl includes $C_{2-6}$alkenyl, $C_{2-4}$alkenyl and the like. A $C_{2-8}$alkenyl radical may be optionally substituted where allowed by available valences.

As used herein, the term "$C_{2-8}$alkynyl" generally refers to partially unsaturated hydrocarbon radicals having from two to eight carbon atoms in a straight or branched chain configuration and one or more carbon-carbon triple bonds therein, including, without limitation, ethynyl, propynyl and the like. In some embodiments, $C_{2-8}$alkynyl includes $C_{2-6}$alkynyl, $C_{2-4}$alkynyl and the like. A $C_{2-8}$alkynyl radical may be optionally substituted where allowed by available valences.

As used herein, the term "$C_{1-8}$alkoxy" generally refers to saturated hydrocarbon radicals having from one to eight carbon atoms in a straight or branched chain configuration of the formula: —O—$C_{1-8}$alkyl, including, without limitation, methoxy, ethoxy, n-propoxy, isopropoxy, n-butoxy, isobutoxy, sec-butoxy, tert-butoxy, n-pentoxy, n-hexoxy and the like. In some embodiments, $C_{1-8}$alkoxy includes $C_{1-6}$alkoxy, $C_{1-4}$alkoxy and the like. A $C_{1-8}$alkoxy radical may be optionally substituted where allowed by available valences.

As used herein, the term "$C_{3-14}$cycloalkyl" generally refers to a saturated monocyclic, bicyclic or polycyclic hydrocarbon radical, including, without limitation, cyclopropyl, cyclobutyl, cyclopentyl, cyclohexyl, cycloheptyl, cyclooctyl, 1H-indanyl, indenyl, tetrahydro-naphthalenyl and the like. In some embodiments, $C_{3-14}$cycloalkyl includes $C_{3-8}$cycloalkyl, $C_{5-8}$cycloalkyl, $C_{3-10}$cycloalkyl and the like. A $C_{3-14}$cycloalkyl radical may be optionally substituted where allowed by available valences.

As used herein, the term "$C_{3-14}$cycloalkenyl" generally refers to a partially unsaturated monocyclic, bicyclic or polycyclic hydrocarbon radical having one or more chemically stable carbon-carbon double bonds therein, including, without limitation, cyclopropenyl, cyclobutenyl, cyclopentenyl, cyclohexenyl, cycloheptenyl, cyclooctenyl and the like. In some embodiments, $C_{3-14}$cycloalkenyl includes $C_{3-8}$cycloalkenyl, $C_{5-8}$cycloalkenyl, $C_{3-10}$cycloalkenyl and the like. A $C_{3-14}$cycloalkenyl radical may be optionally substituted where allowed by available valences.

As used herein, the term "aryl" generally refers to a monocyclic, bicyclic or polycyclic aromatic carbon atom ring structure radical, including, without limitation, phenyl, naphthyl, anthracenyl, fluorenyl, azulenyl, phenanthrenyl and the like. An aryl radical may be optionally substituted where allowed by available valences.

As used herein, the term "heteroaryl" generally refers to a monocyclic, bicyclic or polycyclic aromatic carbon atom ring structure radical in which one or more carbon atom ring members have been replaced, where allowed by structural stability, with one or more heteroatoms, such as an O, S or N atom, including, without limitation, furanyl, thienyl (also referred to as thiophenyl), pyrrolyl, pyrazolyl, imidazolyl, isoxazolyl, isothiazolyl, oxazolyl, thiazolyl, triazolyl, oxadiazolyl, thiadiazolyl, tetrazolyl, pyranyl, thiopyranyl, pyridinyl, pyrimidinyl, pyrazinyl, pyridazinyl, triazinyl, indolyl, indazolyl, indolizinyl, benzofuranyl, benzothienyl, benzimidazolyl, benzothiazolyl, benzooxazolyl, 9H-purinyl, quinoxalinyl, isoindolyl, quinolinyl, isoquinolinyl, quinazolinyl, acridinyl and the like. A heteroaryl radical may be optionally substituted on a carbon or nitrogen atom ring member where allowed by available valences.

As used herein, the term "heterocyclyl" generally refers to a saturated or partially unsaturated monocyclic, bicyclic or polycyclic carbon atom ring structure radical in which one or more carbon atom ring members have been replaced, where allowed by structural stability, with a heteroatom, such as an O, S or N atom, including, without limitation, oxiranyl, oxetanyl, azetidinyl, dihydrofuranyl, tetrahydrofuranyl, dihydrothienyl, tetrahydrothienyl, pyrrolinyl, pyrrolidinyl, dihydropyrazolyl, pyrazolinyl, pyrazolidinyl, dihydroimidazolyl, imidazolinyl, imidazolidinyl, isoxazolinyl, isoxazolidinyl, isothiazolinyl, isothiazolidinyl, oxazolinyl, oxazolidinyl, thiazolinyl, thiazolidinyl, triazolinyl, triazolidinyl, oxadiazolinyl, oxadiazolidinyl, thiadiazolinyl, thiadiazolidinyl, tetrazolinyl, tetrazolidinyl, dihydro-2H-pyranyl, dihydro-pyridinyl, tetrahydro-pyridinyl, 1,2,3,6-tetrahydropyridinyl, hexahydro-pyridinyl, dihydro-pyrimidinyl, tetrahydro-pyrimidinyl, 1,4,5,6-tetrahydropyrimidinyl, dihydro-pyrazinyl, tetrahydro-pyrazinyl, dihydro-pyridazinyl, tetrahydro-pyridazinyl, piperazinyl, piperidinyl, morpholinyl, thiomorpholinyl, dihydro-triazinyl, tetrahydro-triazinyl, hexahydro-triazinyl, 1,4-diazepanyl, dihydro-indolyl, indolinyl, tetrahydro-indolyl, dihydro-indazolyl, tetrahydro-indazolyl, dihydro-isoindolyl, dihydro-benzofuranyl, tetrahydro-benzofuranyl, dihydro-benzothienyl, tetrahydro-benzothienyl, dihydro-benzimidazolyl, tetrahydro-benzimidazolyl, dihydro-benzooxazolyl, 2,3-dihydrobenzo[d]oxazolyl, tetrahydro-benzooxazolyl, dihydro-benzooxazinyl, 3,4-dihydro-2H-benzo[b][1,4]oxazinyl, tetrahydro-benzooxazinyl, benzo[1,3]dioxolyl, benzo[1,4]dioxanyl, dihydro-purinyl, tetrahydro-purinyl, dihydro-quinolinyl, tetrahydro-quinolinyl, 1,2,3,4-tetrahydroquinolinyl, dihydro-isoquinolinyl, 3,4-dihydroisoquinolin-(1H)-yl, tetrahydro-isoquinolinyl, 1,2,3,4-tetrahydroisoquinolinyl, dihydro-quinazolinyl, tetrahydro-quinazolinyl, dihydro-quinoxalinyl, tetrahydro-quinoxalinyl, 1,2,3,4-tetrahydroquinoxalinyl, 1,3-dioxolanyl, 2,5-dihydro-1H-pyrrolyl, dihydro-1H-imidazolyl, tetrahydro-2H-pyranyl, hexahydropyrrolo[3,4-b][1,4]oxazin-(2H)-yl, (4aR,7aS)-hexahydropyrrolo[3,4-b][1,4]oxazin-(4aH)-yl, 3,4-dihydro-2H-pyrido[3,2-b][1,4]oxazinyl, (cis)-octahydrocyclopenta[c]pyrrolyl, hexahydropyrrolo[3,4-b]pyrrol-(1H)-yl, (3aR,6aR)-hexahydropyrrolo[3,4-b]pyrrol-(1H)-yl, (3aR,6aS)-hexahydropyrrolo[3,4-c]pyrrol-(1H)-yl, 5H-pyrrolo[3,4-b]pyridin-(7H)-yl, 5,7-dihydro-6H-pyrrolo[3,4-b]pyridinyl, tetrahydro-1H-pyrrolo[3,4-b]pyridin-(2H,7H,7aH)-yl, hexahydro-1H-pyrrolo[3,4-b]pyridin-(2H)-yl, (4aR,7aR)-hexahydro-1H-pyrrolo[3,4-b]pyridin-(2H)-yl, octahydro-6H-pyrrolo[3,4-b]pyridinyl, 2,3,4,9-tetrahydro-1H-carbazolyl, 1,2,3,4-tetrahydropyrazino[1,2-a]indolyl, 2,3-dihydro-1H-pyrrolo[1,2-a]indolyl, (3aR,6aR)-hexahydrocyclopenta[c]pyrrol-(1H)-yl, (3aR,4R,6aS)-hexahydrocyclopenta[c]pyrrol-(1H)-yl, (3aR,4S,6aS)-hexahydrocyclopenta[c]pyrrol-(1H)-yl, (3aR,5r,6aS)-hexahydrocyclopenta[c]pyrrol-(1H)-yl, 1,3-dihydro-2H-isoindolyl, octahydro-2H-isoindolyl, (3aS)-1,3,3a,4,5,6-hexahydro-2H-isoindolyl, (3aR,4R,7aS)-1H-isoindol-(3H,3aH,4H,5H,6H,7H,7aH)-yl, (3aR,7aS)-octahydro-2H-isoindolyl, (3aR,4R,7aS)-octahydro-2H-isoindolyl, (3aR,4S,7aS)-octahydro-2H-isoindolyl, 2,5-diazabicyclo[2.2.1]heptanyl, 2-azabicyclo[2.2.1]hept-5-enyl, 3-azabicyclo[3.1.0]hexanyl, 3,6-diazabicyclo[3.1.0]hexanyl, (1R,5S,6s)-3-azabicyclo[3.1.0]hexanyl, (1S,5R,6R)-3-azabicyclo[3.2.0]heptanyl, (1S,5R,6S)-3-azabicyclo[3.2.0]heptanyl, 5-azaspiro[2.4]heptanyl, 2,6-diazaspiro[3.3]heptanyl, 2,5-diazaspiro[3.4]octanyl, 2,6-diazaspiro[3.4]octanyl, 2,7-diazaspiro[3.5]nonanyl, 2,7-diazaspiro[4.4]nonanyl, 2-azaspiro[4.5]decanyl, 2,8-diazaspiro[4.5]decanyl and the like. A heterocyclyl radical may be optionally substituted on a carbon or nitrogen atom ring member where allowed by available valences.

As used herein, the term "$C_{2-8}$alkenyl-amino" refers to a radical of the formula: —NH—$C_{2-8}$alkenyl.

As used herein, the term "($C_{2-8}$alkenyl)$_2$-amino" refers to a radical of the formula: —N($C_{2-8}$alkenyl)$_2$.

As used herein, the term "$C_{2-8}$alkenyl-amino-$C_{1-8}$alkyl" refers to a radical of the formula: —$C_{1-8}$alkyl-NH—$C_{2-8}$alkenyl.

As used herein, the term "($C_{2-8}$alkenyl)$_2$-amino-$C_{1-8}$alkyl" refers to a radical of the formula: —$C_{1-8}$alkyl-N($C_{2-8}$alkenyl)$_2$.

As used herein, the term "$C_{1-8}$alkoxy-$C_{1-8}$alkyl" refers to a radical of the formula: —$C_{1-8}$alkyl-O—$C_{1-8}$alkyl.

As used herein, the term "$C_{1-8}$alkoxy-$C_{1-8}$alkyl-amino" refers to a radical of the formula: —O—$C_{1-8}$alkyl-NH—$C_{1-8}$alkyl-O—$C_{1-8}$alkyl.

As used herein, the term "($C_{1-8}$alkoxy-$C_{1-8}$alkyl)$_2$-amino" refers to a radical of the formula: —N($C_{1-8}$alkyl-O—$C_{1-8}$alkyl)$_2$.

As used herein, the term "$C_{1-8}$alkoxy-$C_{1-8}$alkyl-amino-$C_{1-8}$alkyl" refers to a radical of the formula: —$C_{1-8}$alkyl-NH—$C_{1-8}$alkyl-O—$C_{1-8}$alkyl.

As used herein, the term "($C_{1-8}$alkoxy-$C_{1-8}$alkyl)$_2$-amino-$C_{1-8}$alkyl" refers to a radical of the formula: —$C_{1-8}$alkyl-N($C_{1-8}$alkyl-O—$C_{1-8}$alkyl)$_2$.

As used herein, the term "($C_{1-8}$alkoxy-$C_{1-8}$alkyl, $C_{1-8}$alkyl)-amino" refers to a radical of the formula: —N[($C_{1-8}$alkyl)(—$C_{1-8}$alkyl-O—$C_{1-8}$alkyl)].

As used herein, the term "($C_{1-8}$alkoxy-$C_{1-8}$alkyl, $C_{1-8}$alkyl)-amino-$C_{1-8}$alkyl" refers to a radical of the formula: —$C_{1-8}$alkyl-N[($C_{1-8}$alkyl)(—$C_{1-8}$alkyl-O—$C_{1-8}$alkyl)].

As used herein, the term "$C_{1-8}$alkoxy-carbonyl" refers to a radical of the formula: —C(O)—O—$C_{1-8}$alkyl.

As used herein, the term "$C_{1-8}$alkyl-amino" refers to a radical of the formula: —NH—$C_{1-8}$alkyl.

As used herein, the term "($C_{1-8}$alkyl)$_2$-amino" refers to a radical of the formula: —N($C_{1-8}$alkyl)$_2$.

As used herein, the term "$C_{1-8}$alkyl-amino-$C_{1-8}$alkyl" refers to a radical of the formula: —$C_{1-8}$alkyl-NH—$C_{1-8}$alkyl.

As used herein, the term "($C_{1-8}$alkyl)$_2$-amino-$C_{1-8}$alkyl" refers to a radical of the formula: —$C_{1-8}$alkyl-N($C_{1-8}$alkyl)$_2$.

As used herein, the term "$C_{1-8}$alkyl-amino-$C_{1-8}$alkyl-amino" refers to a radical of the formula: —NH—$C_{1-8}$alkyl-NH—$C_{1-8}$alkyl.

As used herein, the term "($C_{1-8}$alkyl)$_2$-amino-$C_{1-8}$alkyl-amino" refers to a radical of the formula: —NH—$C_{1-8}$alkyl-N($C_{1-8}$alkyl)$_2$.

As used herein, the term "$C_{1-8}$alkyl-amino-$C_{1-8}$alkyl-amino-$C_{1-8}$alkyl" refers to a radical of the formula: —$C_{1-8}$alkyl-NH—$C_{1-8}$alkyl-NH—$C_{1-8}$alkyl.

As used herein, the term "($C_{1-8}$alkyl)$_2$-amino-$C_{1-8}$alkyl-amino-$C_{1-8}$alkyl" refers to a radical of the formula: —$C_{1-8}$alkyl-NH—$C_{1-8}$alkyl-N($C_{1-8}$alkyl)$_2$.

As used herein, the term "($C_{1-8}$alkyl-amino-$C_{1-8}$alkyl, $C_{1-8}$alkyl)amino" refers to a radical of the formula: —N[($C_{1-8}$alkyl)(—$C_{1-8}$alkyl-NH—$C_{1-8}$alkyl)].

As used herein, the term "[($C_{1-8}$alkyl)$_2$-amino-$C_{1-8}$alkyl, $C_{1-8}$alkyl]amino" refers to a radical of the formula: —N[($C_{1-8}$alkyl)(—$C_{1-8}$alkyl-N($C_{1-8}$alkyl)$_2$)].

As used herein, the term "($C_{1-8}$alkyl-amino-$C_{1-8}$alkyl, $C_{1-8}$alkyl)amino-$C_{1-8}$alkyl, As used herein, the term "[($C_{1-8}$alkyl)$_2$-amino-$C_{1-8}$alkyl, $C_{1-8}$alkyl]amino-$C_{1-8}$alkyl" refers to a radical of the formula: —$C_{1-8}$alkyl-N[($C_{1-8}$alkyl)(—$C_{1-8}$alkyl-N($C_{1-8}$alkyl)$_2$)].

As used herein, the term "$C_{1-8}$alkyl-amino-carbonyl" refers to a radical of the formula: —C(O)—NH—$C_{1-8}$alkyl.

As used herein, the term "($C_{1-8}$alkyl)$_2$-amino-carbonyl" refers to a radical of the formula: —C(O)—N($C_{1-8}$alkyl)$_2$.

As used herein, the term "$C_{1-8}$alkyl-carbonyl" refers to a radical of the formula: —C(O)—$C_{1-8}$alkyl.

As used herein, the term "$C_{1-8}$alkyl-carbonyl-amino" refers to a radical of the formula: —NH—C(O)—$C_{1-8}$alkyl.

As used herein, the term "($C_{1-8}$alkyl-carbonyl, $C_{1-8}$alkyl) amino-$C_{1-8}$alkyl" refers to a radical of the formula: —$C_{1-8}$alkyl-N[($C_{1-8}$alkyl)(—C(O)—$C_{1-8}$alkyl)].

As used herein, the term "$C_{1-8}$alkyl-thio" refers to a radical of the formula: —S—$C_{1-8}$alkyl.

As used herein, the term "$C_{2-8}$alkynyl-$C_{1-8}$alkyl" refers to a radical of the formula: —$C_{1-8}$alkyl-$C_{2-8}$alkynyl.

As used herein, the term "$C_{2-8}$alkynyl-amino" refers to a radical of the formula: —NH—$C_{2-8}$alkynyl.

As used herein, the term "($C_{2-8}$alkynyl)$_2$-amino" refers to a radical of the formula: —N($C_{2-8}$alkynyl)$_2$.

As used herein, the term "$C_{2-8}$alkynyl-amino-$C_{1-8}$alkyl" refers to a radical of the formula: —$C_{1-8}$alkyl-NH—$C_{2-8}$alkynyl.

As used herein, the term "($C_{2-8}$alkynyl)$_2$-amino-$C_{1-8}$alkyl" refers to a radical of the formula: —$C_{1-8}$alkyl-N($C_{2-8}$alkynyl)$_2$.

As used herein, the term "amino" refers to a radical of the formula: —NH$_2$.

As used herein, the term "amino-$C_{1-8}$alkyl" refers to a radical of the formula: —$C_{1-8}$alkyl-NH$_2$.

As used herein, the term "amino-$C_{1-8}$alkyl-amino" refers to a radical of the formula: —NH—$C_{1-8}$alkyl-NH$_2$.

As used herein, the term "(amino-$C_{1-8}$alkyl)$_2$-amino" refers to a radical of the formula: —N($C_{1-8}$alkyl-NH$_2$)$_2$.

As used herein, the term "amino-$C_{1-8}$alkyl-amino-$C_{1-8}$alkyl" refers to a radical of the formula: —$C_{1-8}$alkyl-NH—$C_{1-8}$alkyl-NH$_2$.

As used herein, the term "(amino-$C_{1-8}$alkyl, $C_{1-8}$alkyl) amino" refers to a radical of the formula: —N[($C_{1-8}$alkyl)(—$C_{1-8}$alkyl-NH$_2$)].

As used herein, the term "(amino-$C_{1-8}$alkyl, $C_{1-8}$alkyl) amino-$C_{1-8}$alkyl" refers to a radical of the formula: —$C_{1-8}$alkyl-N[($C_{1-8}$alkyl)(—$C_{1-8}$alkyl-NH$_2$)].

As used herein, the term "amino-carbonyl" refers to a radical of the formula: —C(O)—NH$_2$.

As used herein, the term "aryl-$C_{1-8}$alkoxy" refers to a radical of the formula: —O—$C_{1-8}$alkyl-aryl.

As used herein, the term "aryl-$C_{1-8}$alkoxy-carbonyl-amino" refers to a radical of the formula: —NH—C(O)—O—$C_{1-8}$alkyl-aryl.

As used herein, the term "aryl-$C_{1-8}$alkyl" refers to a radical of the formula: —$C_{1-8}$alkyl-aryl.

As used herein, the term "aryl-$C_{1-8}$alkyl-amino" refers to a radical of the formula: —NH—$C_{1-8}$alkyl-aryl.

As used herein, the term "(aryl-$C_{1-8}$alkyl)$_2$-amino" refers to a radical of the formula: —N[(—$C_{1-8}$alkyl-aryl)$_2$].

As used herein, the term "aryl-$C_{1-8}$alkyl-amino-$C_{1-8}$alkyl" refers to a radical of the formula: —$C_{1-8}$alkyl-NH—$C_{1-8}$alkyl-aryl.

As used herein, the term "(aryl-$C_{1-8}$alkyl)$_2$-amino-$C_{1-8}$alkyl" refers to a radical of the formula: —$C_{1-8}$alkyl-N[(—$C_{1-8}$alkyl-aryl)$_2$].

As used herein, the term "(aryl,$C_{1-8}$alkyl)amino" refers to a radical of the formula: —N[($C_{1-8}$alkyl)(aryl)].

As used herein, the term "(aryl,$C_{1-8}$alkyl)amino-$C_{1-8}$alkyl" refers to a radical of the formula: —$C_{1-8}$alkyl-N[($C_{1-8}$alkyl)(aryl)].

As used herein, the term "(aryl-$C_{1-8}$alkyl, $C_{1-8}$alkyl) amino" refers to a radical of the formula: —N[($C_{1-8}$alkyl)(—$C_{1-8}$alkyl-aryl)].

As used herein, the term "(aryl-$C_{1-8}$alkyl, $C_{1-8}$alkyl) amino-$C_{1-8}$alkyl" refers to a radical of the formula: —$C_{1-8}$alkyl-N[($C_{1-8}$alkyl)(—$C_{1-8}$alkyl-aryl)].

As used herein, the term "aryl-amino" refers to a radical of the formula: —NH-aryl.

As used herein, the term "(aryl)$_2$-amino" refers to a radical of the formula: —N[(aryl)$_2$].

As used herein, the term "aryl-amino-$C_{1-8}$alkyl" refers to a radical of the formula: —$C_{1-8}$alkyl-NH-aryl.

As used herein, the term "(aryl)$_2$-amino-$C_{1-8}$alkyl" refers to a radical of the formula: —$C_{1-8}$alkyl-N[(aryl)$_2$].

As used herein, the term "aryl-amino-carbonyl" refers to a radical of the formula: —C(O)—NH-aryl.

As used herein, the term "azido" refers to a radical of the formula: —N=N$^+$=N$^-$.

As used herein, the term "carboxyl" refers to a radical of the formula: —COOH, —C(O)OH or —CO$_2$H.

As used herein, the term "(carboxyl-$C_{1-8}$alkyl, $C_{1-8}$alkyl) amino-carbonyl-amino" refers to a radical of the formula: —NH—C(O)—N[($C_{1-8}$alkyl)(—$C_{1-8}$alkyl-CO$_2$H)].

As used herein, the term "$C_{3-14}$cycloalkyl-$C_{1-8}$alkoxy" refers to a radical of the formula: —O—$C_{1-8}$alkyl-$C_{3-14}$cycloalkyl.

As used herein, the term "$C_{3-14}$cycloalkyl-$C_{1-8}$alkyl" refers to a radical of the formula: —$C_{1-8}$alkyl-$C_{3-14}$cycloalkyl.

As used herein, the term "$C_{3-14}$cycloalkyl-amino" refers to a radical of the formula: —NH—$C_{3-14}$cycloalkyl.

As used herein, the term "$C_{3-14}$cycloalkyl-amino-$C_{1-8}$alkyl" refers to a radical of the formula: —$C_{1-8}$alkyl-NH—$C_{3-14}$cycloalkyl.

As used herein, the term "($C_{3-14}$cycloalkyl)$_2$-amino-$C_{1-8}$alkyl" refers to a radical of the formula: —$C_{1-8}$alkyl-N[($C_{3-14}$cycloalkyl)$_2$].

As used herein, the term "$C_{3-14}$cycloalkyl-$C_{1-8}$alkyl-amino-$C_{1-8}$alkyl" refers to a radical of the formula: —$C_{1-8}$alkyl-NH—$C_{1-8}$alkyl-$C_{3-14}$cycloalkyl.

As used herein, the term "($C_{3-14}$cycloalkyl-$C_{1-8}$alkyl)$_2$-amino-$C_{1-8}$alkyl" refers to a radical of the formula: —$C_{1-8}$alkyl-N[(—$C_{1-8}$alkyl-$C_{3-14}$cycloalkyl)$_2$].

As used herein, the term "($C_{3-14}$cycloalkyl, $C_{1-8}$alkyl) amino-$C_{1-8}$alkyl" refers to a radical of the formula: —$C_{1-8}$alkyl-N[($C_{1-8}$alkyl)($C_{3-14}$cycloalkyl)].

As used herein, the term "($C_{3-14}$cycloalkyl-$C_{1-8}$alkyl, $C_{1-8}$alkyl)amino-$C_{1-8}$alkyl" refers to a radical of the formula: —$C_{1-8}$alkyl-N[($C_{1-8}$alkyl)(—$C_{1-8}$alkyl-$C_{3-14}$cycloalkyl)].

As used herein, the term "$C_{3-14}$cycloalkyl-oxy" refers to a radical of the formula: —O—$C_{3-14}$cycloalkyl.

As used herein, the term "formyl" refers to a radical of the formula: —C(O)—H.

As used herein, the term "formyl-$C_{1-8}$alkyl" refers to a radical of the formula: —$C_{1-8}$alkyl-C(O)—H, including, without limitation, formylmethyl (also referred to as 2-oxoethyl or formylmethyl), 2-formyl-ethyl (also referred to as 3-oxopropyl or formylethyl), 3-formyl-propyl (also referred to as 4-oxobutyl or formylpropyl), 4-formyl-butyl (also referred to as 5-oxopentyl or formylpropyl) and the like.

As used herein, the term "halo" or "halogen" generally refers to a halogen atom radical, including fluoro, chloro, bromo and iodo.

As used herein, the term "halo-$C_{1-8}$alkoxy" refers to a radical of the formula: —O—$C_{1-8}$alkyl-halo, wherein $C_{1-8}$alkyl may be partially or completely substituted where allowed by available valences with one or more halogen atoms, including, without limitation, fluoromethoxy, difluoromethoxy, trifluoromethoxy, fluoroethoxy, difluoroethoxy or trifluoroethoxy and the like. In some embodiments, difluoroethoxy includes 2,2-difluoroethoxy, 1,2-difluoroethoxy or 1,1-difluoroethoxy and the like. In some embodiments, halo-$C_{1-8}$alkoxy includes halo-$C_{1-6}$alkoxy, halo-$C_{1-4}$alkoxy and the like.

As used herein, the term "halo-$C_{1-8}$alkyl" refers to a radical of the formula: —$C_{1-8}$alkyl-halo, wherein $C_{1-8}$alkyl may be partially or completely substituted where allowed by available valences with one or more halogen atoms, including, without limitation, fluoromethyl, difluoromethyl, trifluoromethyl, fluoroethyl, difluoroethyl, trifluoroethyl, fluoroisopropyl, difluoroisopropyl, trifluoroisopropyl, fluoro-tert-butyl, difluoro-tert-butyl, trifluoro-tert-butyl and the like. In some embodiments, difluoroethyl includes 2,2-difluoroethyl, 1,2-difluoroethyl or 1,1-difluoroethyl and the like; difluoroisopropyl includes 1,3-difluoropropan-2-yl and the like; trifluoroisopropyl includes 1,1,1-trifluoropropan-2-yl and the like; trifluoro-tert-butyl includes 1,1,1-trifluoro-2-methylpropan-2-yl and the like. In some embodiments, halo-$C_{1-8}$alkyl includes halo-$C_{1-6}$alkyl, halo-$C_{1-4}$alkyl and the like.

As used herein, the term "halo-$C_{1-8}$alkyl-amino" refers to a radical of the formula: —NH—$C_{1-8}$alkyl-halo.

As used herein, the term "(halo-$C_{1-8}$alkyl)$_2$-amino" refers to a radical of the formula: —N($C_{1-8}$alkyl-halo)$_2$.

As used herein, the term "halo-$C_{1-8}$alkyl-amino-$C_{1-8}$alkyl" refers to a radical of the formula: —NH—$C_{1-8}$alkyl-halo.

As used herein, the term "(halo-$C_{1-8}$alkyl)$_2$-amino-$C_{1-8}$alkyl" refers to a radical of the formula: —$C_{1-8}$alkyl-N ($C_{1-8}$alkyl-halo)$_2$.

As used herein, the term "heteroaryl-$C_{1-8}$alkyl" refers to a radical of the formula: —$C_{1-8}$alkyl-heteroaryl.

As used herein, the term "heteroaryl-amino" refers to a radical of the formula: —NH-heteroaryl.

As used herein, the term "(heteroaryl)$_2$-amino" refers to a radical of the formula: —N[(heteroaryl)$_2$].

As used herein, the term "heteroaryl-$C_{1-8}$alkyl-amino" refers to a radical of the formula: —NH—$C_{1-8}$alkyl-heteroaryl.

As used herein, the term "(heteroaryl-$C_{1-8}$alkyl)$_2$-amino" refers to a radical of the formula: —N[(—$C_{1-8}$alkyl-heteroaryl)$_2$].

As used herein, the term "heteroaryl-$C_{1-8}$alkyl-amino-$C_{1-8}$alkyl" refers to a radical of the formula: —$C_{1-8}$alkyl-NH—$C_{1-8}$alkyl-heteroaryl.

As used herein, the term "(heteroaryl-$C_{1-8}$alkyl)$_2$-amino-$C_{1-8}$alkyl" refers to a radical of the formula: —$C_{1-8}$alkyl-N [(—$C_{1-8}$alkyl-heteroaryl)$_2$].

As used herein, the term "(heteroaryl-$C_{1-8}$alkyl, $C_{1-8}$alkyl) amino" refers to a radical of the formula: —N[($C_{1-8}$alkyl) (—$C_{1-8}$alkyl-heteroaryl)].

As used herein, the term "(heteroaryl-$C_{1-8}$alkyl, $C_{1-8}$alkyl) amino-$C_{1-8}$alkyl" refers to a radical of the formula: —$C_{1-8}$alkyl-N[($C_{1-8}$alkyl)(—$C_{1-8}$alkyl-heteroaryl)].

As used herein, the term "heterocyclyl-$C_{1-8}$alkoxy" refers to a radical of the formula: —O—$C_{1-8}$alkyl-heterocyclyl.

As used herein, the term "heterocyclyl-$C_{1-8}$alkyl" refers to a radical of the formula: —$C_{1-8}$alkyl-heterocyclyl.

As used herein, the term "heterocyclyl-amino" refers to a radical of the formula: —NH-heterocyclyl.

As used herein, the term "(heterocyclyl)$_2$-amino" refers to a radical of the formula: —N[(heterocyclyl)$_2$].

As used herein, the term "heterocyclyl-amino-$C_{1-8}$alkyl" refers to a radical of the formula: —$C_{1-8}$alkyl-NH-heterocyclyl.

As used herein, the term "(heterocyclyl)$_2$-amino-$C_{1-8}$alkyl" refers to a radical of the formula: —$C_{1-8}$alkyl-N [(heterocyclyl)$_2$].

As used herein, the term "heterocyclyl-$C_{1-8}$alkyl-amino-$C_{1-8}$alkyl" refers to a radical of the formula: —$C_{1-8}$alkyl-NH—$C_{1-8}$alkyl-heterocyclyl.

As used herein, the term "(heterocyclyl-$C_{1-8}$alkyl)$_2$-amino-$C_{1-8}$alkyl" refers to a radical of the formula: —$C_{1-8}$alkyl-N[(—$C_{1-8}$alkyl-heterocyclyl)$_2$].

As used herein, the term "(heterocyclyl, $C_{1-8}$alkyl)amino" refers to a radical of the formula: —N[($C_{1-8}$alkyl)(heterocyclyl)].

As used herein, the term "(heterocyclyl, $C_{1-8}$alkyl)amino-$C_{1-8}$alkyl" refers to a radical of the formula: —$C_{1-8}$alkyl-N [($C_{1-8}$alkyl)(heterocyclyl)].

As used herein, the term "(heterocyclyl-$C_{1-8}$alkyl, $C_{1-8}$alkyl)amino-$C_{1-8}$alkyl" refers to a radical of the formula: —$C_{1-8}$alkyl-N[($C_{1-8}$alkyl)(—$C_{1-8}$alkyl-heterocyclyl)].

As used herein, the term "(heterocyclyl, $C_{3-14}$cycloalkyl-$C_{1-8}$alkyl)amino-$C_{1-8}$alkyl" refers to a radical of the formula: —$C_{1-8}$alkyl-N[(heterocyclyl)(—$C_{1-8}$alkyl-$C_{3-14}$cycloalkyl)].

As used herein, the term "heterocyclyl-carbonyl" refers to a radical of the formula: —C(O)-heterocyclyl.

As used herein, the term "heterocyclyl-carbonyl-oxy" refers to a radical of the formula: —O—C(O)-heterocyclyl.

As used herein, the term "heterocyclyl-oxy" refers to a radical of the formula: —O-heterocyclyl.

As used herein, the term "heterocyclyl-oxy-amino" refers to a radical of the formula: —NH—O-heterocyclyl.

As used herein, the term "(heterocyclyl-oxy)$_2$-amino" refers to a radical of the formula: —N[(—O-heterocyclyl)$_2$].

As used herein, the term "(heterocyclyl-oxy, $C_{1-8}$alkyl) amino" refers to a radical of the formula: —N[($C_{1-8}$alkyl) (—O-heterocyclyl)].

As used herein, the term "(heterocyclyl-oxy-$C_{1-8}$alkyl, $C_{1-8}$alkyl)amino" refers to a radical of the formula: —N[($C_{1-8}$alkyl)(—$C_{1-8}$alkyl-O-heterocyclyl)].

As used herein, the term "hydroxyl-$C_{1-8}$alkoxy" refers to a radical of the formula: —O—$C_{1-8}$alkyl-OH, wherein $C_{1-8}$alkyl may be partially or completely substituted where allowed by available valences with one or more hydroxyl radicals.

As used herein, the term "hydroxyl-$C_{1-8}$alkyl" refers to a radical of the formula: —$C_{1-8}$alkyl-OH, wherein $C_{1-8}$alkyl may be partially or completely substituted where allowed by available valences with one or more hydroxyl radicals.

As used herein, the term "hydroxyl-amino" refers to a radical of the formula: —NH—OH.

As used herein, the term "hydroxyl-$C_{1-8}$alkyl-amino" refers to a radical of the formula: —NH—$C_{1-8}$alkyl-OH, wherein $C_{1-8}$alkyl may be partially or completely substituted where allowed by available valences with one or more hydroxyl radicals.

As used herein, the term "(hydroxyl-$C_{1-8}$alkyl)$_2$-amino" refers to a radical of the formula: —N($C_{1-8}$alkyl-OH)$_2$, wherein $C_{1-8}$alkyl may be partially or completely substituted where allowed by available valences with one or more hydroxyl radicals.

As used herein, the term "hydroxyl-$C_{1-8}$alkyl-amino-$C_{1-8}$alkyl" refers to a radical of the formula: —$C_{1-8}$alkyl-NH—$C_{1-8}$alkyl-OH, wherein $C_{1-8}$alkyl may be partially or completely substituted where allowed by available valences with one or more hydroxyl radicals.

As used herein, the term "hydroxyl-$C_{1-8}$alkyl-amino-$C_{1-8}$alkyl-amino" refers to a radical of the formula: —NH—$C_{1-8}$alkyl-NH—$C_{1-8}$alkyl-OH, wherein $C_{1-8}$alkyl may be partially or completely substituted where allowed by available valences with one or more hydroxyl radicals.

As used herein, the term "(hydroxyl-$C_{1-8}$alkyl, $C_{1-8}$alkyl) amino" refers to a radical of the formula: —N[($C_{1-8}$alkyl) ($C_{1-8}$alkyl-OH)], wherein $C_{1-8}$alkyl may be partially or completely substituted where allowed by available valences with one or more hydroxyl radicals.

As used herein, the term "(hydroxyl-$C_{1-8}$alkyl, $C_{1-8}$alkyl) amino-$C_{1-8}$alkyl" refers to a radical of the formula: —$C_{1-8}$alkyl-N[($C_{1-8}$alkyl)($C_{1-8}$alkyl-OH)], wherein $C_{1-8}$alkyl may be partially or completely substituted where allowed by available valences with one or more hydroxyl radicals.

As used herein, the term "(hydroxyl-$C_{1-8}$alkyl, $C_{1-8}$alkyl) amino-$C_{1-8}$alkyl-amino" refers to a radical of the formula: —NH—$C_{1-8}$alkyl-N[($C_{1-8}$alkyl)($C_{1-8}$alkyl-OH)], wherein $C_{1-8}$alkyl may be partially or completely substituted where allowed by available valences with one or more hydroxyl radicals.

As used herein, the term "[(hydroxyl-$C_{1-8}$alkyl, $C_{1-8}$alkyl) amino-$C_{1-8}$alkyl, $C_{1-8}$alkyl)amino" refers to a radical of the formula: —N[($C_{1-8}$alkyl)(—$C_{1-8}$alkyl-N[($C_{1-8}$alkyl) ($C_{1-8}$alkyl-OH)])], wherein $C_{1-8}$alkyl may be partially or completely substituted where allowed by available valences with one or more hydroxyl radicals.

As used herein, the term "(hydroxyl-$C_{1-8}$alkyl-amino-$C_{1-8}$alkyl, $C_{1-8}$alkyl)amino" refers to a radical of the formula: —N[($C_{1-8}$alkyl)(—$C_{1-8}$alkyl-NH—$C_{1-8}$alkyl-OH)], wherein $C_{1-8}$alkyl may be partially or completely substituted where allowed by available valences with one or more hydroxyl radicals.

As used herein, the term "substituent" means positional variables on the atoms of a core molecule that are substituted at a designated atom position, replacing one or more hydrogens on the designated atom, provided that the designated atom's normal valency is not exceeded, and that the substitution results in a stable compound. Combinations of substituents and/or variables are permissible only if such combinations result in stable compounds. A person of ordinary skill in the art should note that any carbon as well as heteroatom with valences that appear to be unsatisfied as described or shown herein is assumed to have a sufficient number of hydrogen atom(s) to satisfy the valences described or shown.

As used herein, the term "and the like," with reference to the definitions of chemical terms provided herein, means that variations in chemical structures that could be expected by one skilled in the art include, without limitation, isomers (including chain, branching or positional structural isomers), hydration of ring systems (including saturation or partial unsaturation of monocyclic, bicyclic or polycyclic ring structures) and all other variations where allowed by available valences which result in a stable compound.

For the purposes of this description, where one or more substituent variables for a compound of Formula (I) encompass functionalities incorporated into a compound of Formula (I), each functionality appearing at any location within the disclosed compound may be independently selected, and as appropriate, independently and/or optionally substituted.

As used herein, the terms "independently selected," or "each selected" refer to functional variables in a substituent list that may occur more than once on the structure of Formula (I), the pattern of substitution at each occurrence is independent of the pattern at any other occurrence. Further, the use of a generic substituent variable on any formula or structure for a compound described herein is understood to include the replacement of the generic substituent with species substituents that are included within the particular genus, e.g., aryl may be replaced with phenyl or naphthalenyl and the like, and that the resulting compound is to be included within the scope of the compounds described herein.

As used herein, the term "each instance of" when used in a phrase such as " . . . aryl, aryl-$C_{1-8}$alkyl, heterocyclyl and heterocyclyl-$C_{1-8}$alkyl, wherein each instance of aryl and heterocyclyl is optionally substituted with one or two substituents . . . " (emphasis added) is intended to optionally include substitution on each appearance of aryl and heterocyclyl, whether the ring is a primary or secondary substituent, that is, where the aryl and heterocyclyl rings are the primary (first) substituent or where the primary substituent is $C_{1-8}$alkyl and the aryl and heterocyclyl rings are the secondary (second) substituent, as in, for example, aryl-$C_{1-8}$alkyl and heterocyclyl-$C_{1-8}$alkyl.

As used herein, the term "optionally substituted" means optional substitution with the specified substituent variables, groups, radicals or moieties.

As used herein, the terms "stable compound" or "stable structure" mean a compound that is sufficiently robust to survive isolation to a useful degree of purity from a reaction mixture and formulations thereof into an efficacious therapeutic agent.

Compound names used herein were obtained using the ACD Labs Index Name software provided by ACD Labs; and/or, were provided using the Autonom function of Chem-Draw Ultra provided by CambridgeSoft. When the compound name disclosed herein conflicts with the structure depicted, the structure shown will supercede the use of the name to define the compound intended.

Compound Forms

As used herein, the term "a compound of Formula (Ia)," as defined previously, refer to a sub-genus of the compound of Formula (I) or a form thereof. Rather than repeat embodiments for a compound of Formula (Ia), in certain embodiments, the term "a compound of Formula (I) or a form thereof" is used to refer to a compound of Formula (Ia) or a form thereof. Thus, embodiments and references to "a compound of Formula (I)" are intended to include compounds of Formula (Ia).

As used herein, the term "form" means a compound of Formula (I) isolated for use selected from a free acid, free base, salt, hydrate, solvate, clathrate, isotopologue, racemate, enantiomer, diastereomer, stereoisomer, polymorph or tautomer form thereof.

In certain embodiments described herein, the form of the compound of Formula (I) is a free acid, free base or salt thereof.

In certain embodiments described herein, the form of the compound of Formula (I) is an isotopologue thereof.

In certain embodiments described herein, the form of the compound of Formula (I) is a stereoisomer, racemate, enantiomer or diastereomer thereof.

In certain embodiments described herein, the form of the compound of Formula (I) is a tautomer thereof.

In certain embodiments described herein, the form of the compound of Formula (I) is a pharmaceutically acceptable form.

In certain embodiments described herein, the compound of Formula (I) or a form thereof is isolated for use.

As used herein, the term "isolated" means the physical state of a compound of Formula (I) after being isolated and/or purified from a synthetic process (e.g., from a reaction mixture) or natural source or combination thereof according to an isolation or purification process or processes described herein or which are well known to the skilled artisan (e.g., chromatography, recrystallization and the like) in sufficient purity to be characterizable by standard analytical techniques described herein or well known to the skilled artisan.

As used herein, the term "protected" means that a functional group in a compound of Formula (I) is in a form modified to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

Prodrugs and solvates of the compounds described herein are also contemplated.

As used herein, the term "prodrug" means a form of an instant compound (e.g., a drug precursor) that is transformed in vivo to yield an active compound of Formula (I) or a form thereof. The transformation may occur by various mechanisms (e.g., by metabolic and/or non-metabolic chemical processes), such as, for example, by hydrolysis and/or metabolism in blood, liver and/or other organs and tissues. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

In one example, when a compound of Formula (I) or a form thereof contains a carboxylic acid functional group, a prodrug can comprise an ester formed by the replacement of the hydrogen atom of the acid group with a functional group such as alkyl and the like. In another example, when a compound of Formula (I) or a form thereof contains an alcohol functional group, a prodrug can be formed by the replacement of the hydrogen atom of the alcohol group with a functional group such as alkyl or carbonyloxy and the like. In another example, when a compound of Formula (I) or a form thereof contains an amine functional group, a prodrug can be formed by the replacement of one or more amine hydrogen atoms with a functional group such as alkyl or substituted carbonyl.

One or more compounds described herein may exist in unsolvated as well as solvated forms with pharmaceutically acceptable solvents such as water, ethanol, and the like, and the description herein is intended to embrace both solvated and unsolvated forms.

As used herein, the term "solvate" means a physical association of a compound described herein with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. As used herein, "solvate" encompasses both solution-phase and isolatable solvates. Non-limiting examples of suitable solvates include ethanolates, methanolates, and the like.

One or more compounds described herein may optionally be converted to a solvate. Preparation of solvates is generally known. The preparation of solvates of the antifungal fluconazole in ethyl acetate as well as from water has been described (see, M. Caira et al, *J. Pharmaceutical Sci.*, 93(3), 601-611 (2004)). Similar preparations of solvates, hemisolvate, hydrates and the like have also been described (see, E. C. van Tonder et al, *AAPS PharmSciTech.*, 5(1), article 12 (2004); and A. L. Bingham et al, *Chem. Commun.*, 603-604 (2001)). A typical, non-limiting process involves dissolving a compound in a desired amount of the desired solvent (organic or water or mixtures thereof) at a higher than ambient temperature, and cooling the solution at a rate sufficient to form crystals which are then isolated by standard methods. Analytical techniques such as, for example infrared spectroscopy, show the presence of the solvent (or water) in the crystals as a solvate (or hydrate).

As used herein, the term "hydrate" means a solvate wherein the solvent molecule is water.

The compounds of Formula (I) can form salts, which are intended to be included within the scope of this description. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein.

The term "pharmaceutically acceptable salt(s)", as used herein, means those salts of compounds described herein that are safe and effective (i.e., non-toxic, physiologically acceptable) for use in mammals and that possess biological activity, although other salts are also useful. Salts of the compounds of the Formula (I) may be formed, for example, by reacting a compound of Formula (I) with an amount of acid or base, such as an equivalent amount, in a medium such as one in which the salt precipitates or in an aqueous medium followed by lyophilization.

Pharmaceutically acceptable salts include one or more salts of acidic or basic groups present in compounds described herein. Embodiments of acid addition salts include, and are not limited to, acetate, acid phosphate, ascorbate, benzoate, benzenesulfonate, bisulfate, bitartrate, borate, butyrate, chloride, citrate, camphorate, camphorsulfonate, ethanesulfonate, formate, fumarate, gentisinate, gluconate, glucaronate, glutamate, hydrobromide, hydrochloride, dihydrochloride, hydroiodide, isonicotinate, lactate, maleate, methanesulfonate, naphthalenesulfonate, nitrate, oxalate, pamoate, pantothenate, phosphate, propionate, saccharate, salicylate, succinate, sulfate, tartrate, thiocyanate, toluenesulfonate (also known as tosylate), trifluoroacetate salts and the like. Certain embodiments of acid addition salts include chloride, hydrobromide, hydrochloride, dihydrochloride, acetate or trifluoroacetic acid salts.

Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33, 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Suitable basic salts include, but are not limited to, aluminum, ammonium, calcium, lithium, magnesium, potassium, sodium, zinc, and diethanolamine salts. Certain compounds of described herein can also form pharmaceutically acceptable salts with organic bases (for example, organic amines) such as, but not limited to, dicyclohexylamines, t-butyl amines and the like, and with various amino acids such as, but not limited to, arginine, lysine and the like. Basic nitrogen-containing groups may be quaternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be included within the scope of pharmaceutically acceptable salts as described herein. In addition, all such acid and base salts are considered equivalent to the free forms of the corresponding compounds for purposes of this description.

Pharmaceutically acceptable prodrugs of compounds of Formula (I) or a form thereof include those compounds substituted with one or more of the following groups: carboxylic acid esters, sulfonate esters, amino acid esters phosphonate esters and mono-, di- or triphosphate esters or alkyl substituents, where appropriate. As described herein, it is understood by a person of ordinary skill in the art that one or more of such substituents may be used to provide a compound of Formula (I) or a form thereof as a prodrug.

Compounds of Formula (I), and forms thereof, may further exist in a tautomeric form (for example, as an amide or imino ether). All such tautomeric forms are contemplated and intended to be included within the scope of the compounds of Formula (I) or a form thereof as described herein.

The compounds of Formula (I) may contain asymmetric or chiral centers, and, therefore, exist in different stereoisomeric forms. The present description is intended to include all stereoisomeric forms of the compounds of Formula (I) as well as mixtures thereof, including racemic mixtures.

The compounds described herein may include one or more chiral centers, and as such may exist as racemic mixtures (R/S) or as substantially pure enantiomers and diastereomers. The compounds may also exist as substantially pure (R) or (S) enantiomers (when one chiral center is present). In one embodiment, the compounds described herein are (S) isomers and may exist as enantiomerically pure compositions substantially comprising only the (S) isomer. In another embodiment, the compounds described herein are (R) isomers and may exist as enantiomerically pure compositions substantially comprising only the (R) isomer. As one of skill in the art will recognize, when more than one chiral center is present, the compounds described herein may also exist as a (R,R), (R,S), (S,R) or (S,S) isomer, as defined by IUPAC Nomenclature Recommendations.

As used herein, the term "substantially pure" refers to compounds consisting substantially of a single isomer in an amount greater than or equal to 90%, in an amount greater than or equal to 92%, in an amount greater than or equal to 95%, in an amount greater than or equal to 98%, in an amount greater than or equal to 99%, or in an amount equal to 100% of the single isomer.

In one aspect of the description, a compound of Formula (I) is a substantially pure (S) enantiomer present in an amount greater than or equal to 90%, in an amount greater than or equal to 92%, in an amount greater than or equal to 95%, in an amount greater than or equal to 98%, in an amount greater than or equal to 99%, or in an amount equal to 100%.

In one aspect of the description, a compound of Formula (I) is a substantially pure (R) enantiomer present in an amount greater than or equal to 90%, in an amount greater than or equal to 92%, in an amount greater than or equal to 95%, in an amount greater than or equal to 98%, in an amount greater than or equal to 99%, or in an amount equal to 100%.

As used herein, a "racemate" is any mixture of isometric forms that are not "enantiomerically pure", including mixtures such as, without limitation, in a ratio of about 50/50, about 60/40, about 70/30, or about 80/20.

In addition, the present description embraces all geometric and positional isomers. For example, if a compound of Formula (I) incorporates a double bond or a fused ring, both the cis- and trans-forms, as well as mixtures, are embraced within the scope of the description. Diastereomeric mixtures can be separated into their individual diastereomers on the basis of their physical chemical differences by methods well known to those skilled in the art, such as, for example, by chromatography and/or fractional crystallization. Enantiomers can be separated by use of chiral HPLC column or other chromatographic methods known to those skilled in the art. Enantiomers can also be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this description.

It is also possible that the compounds of Formula (I) may exist in different tautomeric forms, and all such forms are embraced within the scope of the description. Also, for example, all keto-enol and imine-enamine forms of the compounds are included in the scope of this description.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this description, as are positional isomers (such as, for example, 4-pyridyl and 3-pyridyl). For example, if a compound of Formula (I) incorporates a double bond or a fused ring, both the cis- and trans-forms, as well as mixtures thereof, are embraced herein. Also, for example, all keto-enol and imine-enamine forms of the compounds are included herein. Individual stereoisomers of the compounds described herein may, for example, be substantially free of other isomers, or may be present in a racemic mixture, as described supra.

The use of the terms "salt", "solvate", "ester", "prodrug" and the like, is intended to equally apply to the salt, solvate, ester and prodrug of enantiomers, stereoisomers, rotamers, tautomers, positional isomers, racemates, isotopologues or prodrugs of the instant compounds.

The term "isotopologue" refers to isotopically-enriched compounds described herein which are identical to those recited herein, but for the fact that one or more atoms are replaced by an atom having an atomic mass or mass number different from the atomic mass or mass number usually found in nature. Examples of isotopes that can be incorporated into compounds described herein include isotopes of hydrogen, carbon, nitrogen, oxygen, phosphorus, fluorine and chlorine, such as $H^2$, $H^3$, $C^{13}$, $C^{14}$, $N^{15}$, $O^{18}$, $O^{17}$, $P^{31}$, $P^{32}$, $S^{35}$, $F^{18}$, $Cl^{35}$ and $Cl^{36}$, respectively, each of which are also within the scope of this description.

Certain isotopically-enriched compounds described herein (e.g., those labeled with $H^3$ and $C^{14}$) are useful in compound and/or substrate tissue distribution assays. Tritiated (i.e., $H^3$) and carbon-14 (i.e., $C^{14}$) isotopes are particularly preferred for their ease of preparation and detectability. Further, substitution with heavier isotopes such as deuterium (i.e., $H^2$) may afford certain therapeutic advantages resulting from greater metabolic stability (e.g., increased in vivo half-life or reduced dosage requirements) and hence may be preferred in some circumstances.

Polymorphic crystalline and amorphous forms of the compounds of Formula (I), and of the salts, solvates, hydrates, esters and prodrugs of the compounds of Formula (I), are further intended to be included in the present description.

Use of Compounds

The present description further relates to uses of the compound of Formula (I) and methods of treating or ameliorating a bacterial infection, or of treating or ameliorating a multidrug resistant (MDR) bacterial infection.

The present description further relates to uses of the compound of Formula (I) having activity toward wild-type and MDR bacteria. The present description also relates to uses of the compound of Formula (I) having activity against quinolone-resistant Gram-negative strains (including MDR strains) as well as antibacterial activity to MDR resistant Gram-positive pathogens (including MRSA strains). The present description also relates to uses of the compound of Formula (I) having selectivity between bacterial topoisomerase IV and DNA gyrase enzyme inhibition compared to human topoisomerase II enzyme inhibition. The present description further relates to uses of the compound of Formula (I) that may be combined with known antibacterial agents to provide additive or synergistic activity, thus enabling the development of a combination product for the treatment of Gram-negative (especially MDR strains) and Gram-positive infections.

The compounds of the present description inhibit the clinically validated bacterial targets DNA gyrase and topoisomerase IV, and, thus, may be used for the treatment of infections caused by Gram-negative and Gram-positive pathogens. The instant compounds possess in vitro antibacterial activity against a wide spectrum of bacteria which have developed resistance to almost all known treatments, including MDR Gram-negative and MDR Gram-positive pathogens and successfully effect the treatment of bacterial infections compared to current antibacterial agents that target the same enzymes. The compounds are also effective in vivo and lack cellular toxicity. In addition to monotherapeutic use, the instant compounds are amenable to combination therapy with current standards of care, having demonstrated additive and synergistic activity with one or more fluoroquinolone based antibacterial agents. The demonstrated additive and synergistic activity of the compounds indicates a mechanistically alternate binding in conjunction with the DNA gyrase and topoisomerase IV targets.

Accordingly, the present description relates to methods of using a compound of Formula (I) for treating or ameliorating a bacterial infection, or for using a compound of Formula (I) for treating or ameliorating a multidrug resistant bacterial infection. In accordance with the present description, compounds that selectively treat or ameliorate a bacterial infection have been identified and methods of using these compounds for treating or ameliorating a bacterial infection or disorders or symptoms associated therewith are provided.

One embodiment of the present description relates to a method of treating or ameliorating a bacterial infection in a subject in need thereof comprising administering an effective amount of a compound of Formula (I) or a form thereof to the subject.

An embodiment of the present description relates to a method of treating or ameliorating a bacterial infection resulting from a bacteria that is a Gram-negative or Gram-positive type in a subject in need thereof comprising administering an effective amount of the compound of Formula (I) or a form thereof to the subject.

An embodiment of the present description relates to a method of treating or ameliorating a bacterial infection resulting from a bacteria that is a resistant Gram-negative or Gram-positive type in a subject in need thereof comprising administering an effective amount of the compound of Formula (I) or a form thereof to the subject.

One embodiment of the present description relates to a use of a compound of Formula (I) or a form thereof for treating or ameliorating a bacterial infection in a subject in need thereof comprising administering an effective amount of the compound to the subject.

An embodiment of the present description relates to a use of a compound of Formula (I) or a form thereof for treating or ameliorating a bacterial infection resulting from a bacteria that is a Gram-negative or Gram-positive type in a subject in need thereof comprising administering an effective amount of the compound to the subject.

An embodiment of the present description relates to a use of a compound of Formula (I) or a form thereof for treating or ameliorating a bacterial infection resulting from a bacteria that is a resistant Gram-negative or Gram-positive type in a subject in need thereof comprising administering an effective amount of the compound to the subject.

An embodiment of the present description relates to a use of a compound of Formula (I) or a form thereof in the manufacture of a medicament for treating or ameliorating a bacterial infection in a subject in need thereof comprising administering an effective amount of the medicament to the subject.

An embodiment of the present description relates to a use of a compound of Formula (I) or a form thereof in the manufacture of a medicament for treating or ameliorating a bacterial infection resulting from a bacteria that is a Gram-negative or Gram-positive type in a subject in need thereof administering an effective amount of the compound to the subject.

An embodiment of the present description relates to a use of a compound of Formula (I) or a form thereof in the manufacture of a medicament for treating or ameliorating a bacterial infection resulting from a bacteria that is a resistant Gram-negative or Gram-positive type in a subject in need thereof comprising administering an effective amount of the compound to the subject.

An embodiment of the present description relates to a use of a compound of Formula (I) or a form thereof in the preparation of a pharmaceutical kit comprising the compound of Formula (I) or a form thereof and instructions for administering the compound for treating or ameliorating a bacterial infection in a subject in need thereof.

Another embodiment of the present description relates to the use of a compound of Formula (I) or a form thereof for treating or ameliorating a bacterial infection by selectively inhibiting DNA gyrase and topoisomerase IV compared to human topoisomerase II.

An embodiment of the present description relates to a method of treating or ameliorating a bacterial infection or disorders or symptoms associated therewith in a subject in need thereof comprising administering an effective amount of a compound of Formula (I) or a form thereof to the subject.

An embodiment of the present description relates to the use of a compound of Formula (I) or a form thereof in the manufacture of a medicament for treating or ameliorating bacterial infection or disorders or symptoms associated therewith in a subject in need thereof comprising administering an effective amount of the medicament to the subject.

An embodiment of the present description relates to the use of a compound of Formula (I) or a form thereof in the preparation of a pharmaceutical kit comprising the compound of Formula (I) or a form thereof and instructions for administering the compound for treating or ameliorating a bacterial infection or disorders or symptoms associated therewith in a subject in need thereof.

In one respect, for each of such embodiments, the subject is treatment naive. In another respect, for each of such embodiments, the subject is not treatment naive.

As used herein, the term "treating" refers to: (i) preventing a disease, disorder or condition from occurring in a subject that may be predisposed to the disease, disorder and/or condition but has not yet been diagnosed as having the disease, disorder and/or condition; (ii) inhibiting a disease, disorder or condition, i.e., arresting the development thereof; and/or (iii) relieving a disease, disorder or condition, i.e., causing regression of the disease, disorder and/or condition.

As used herein, the term "subject" refers to an animal or any living organism having sensation and the power of voluntary movement, and which requires oxygen and organic food. Nonlimiting examples include members of the human, equine, porcine, bovine, murine, canine and feline specie. In some embodiments, the subject is a mammal or a warm-blooded vertebrate animal. In other embodiments, the subject is a human. As used herein, the term "patient" may be used interchangeably with "subject" and "human".

Another aspect of the description relates to a method of treating or ameliorating a bacterial infection resulting from a bacteria that is a Gram-negative or Gram-positive type.

Another aspect of the description relates to a method of treating or ameliorating a bacterial infection resulting from bacteria that is a resistant Gram-negative or Gram-positive type.

Another aspect of the description particularly relates to a method of treating or ameliorating a bacterial infection by a wild type bacteria that is resistant to a currently available antibacterial agent, in a subject in need thereof, comprising administering to the subject an effective amount of a compound of Formula (I) or a form thereof.

Examples of bacterial infections intended to be included within the scope of the description include bacterial infections resulting from a bacteria of the phyla including, but not limited to, Acidobacteria; Actinobacteria; Aquificae; Bacteroidetes; Caldiserica; Chlamydiae; Chlorobi; Chloroflexi; Chrysiogenetes; Cyanobacteria; Deferribacteres; Deinococcus-Thermus; Dictyoglomi; Elusimicrobia; Fibrobacteres; Firmicutes; Fusobacteria; Gemmatimonadetes; Lentisphaerae; Nitrospira; Planctomycetes; Proteobacteria; Spirochaetes; Synergistetes; Tenericutes; Firmicutes; Thermodesulfobacteria; Thermomicrobia; Thermotogae; or Verrucomicrobia. The listing of phyla is obtained from the *List of Prokaryotic Names with Standing in Nomenclature (LPSN)* (see, www.bacterio.cict.fr/index.html)

Another aspect of the description relates to a method of treating or ameliorating a bacterial infection by a bacteria from a phyla that is a Gram-negative or Gram-positive type.

Another aspect of the description relates to a method of treating or ameliorating a bacterial infection by a bacteria from a phyla that is a drug resistant Gram-negative or Gram-positive type.

Another aspect of the description relates to a method of treating or ameliorating a bacterial infection by a bacteria from a phyla that is a multi-drug resistant Gram-negative or Gram-positive type.

Examples of such bacterial infections intended to be included within the scope of the description particularly include bacterial infections that result from a bacteria of the phyla selected from Proteobacteria, Spirochaetes, Bacteriodetes, Chlamydiae, Firmicutes or Actinobacteria.

In a particular example, the bacterial infections include those resulting from a bacterial species selected from *Acinetobacter baumannii, Bacillus anthracis, Bacillus subtilis, Enterobacter* spp., *Enterococcus faecalis, Enterococcus faecalis, Enterococcus faecium, Escherichia coli, Francisella tularensis, Haemophilus influenzae, Klebsiella pneumoniae, Moraxella catarrhalis, Mycobacterium tuberculosis, Neisseria* spp., *Pseudomonas aeruginosa, Shigella* spp., *Staphylococcus aureus, Streptococcus pyogenes, Streptococcus pneumoniae* and *Yersinia pestis*.

In another particular example, the bacteria are selected from *Acinetobacter baumannii* BAA747, *Acinetobacter baumannii* MMX2240 (MDR), *Bacillus anthracis* (wild-type), *Bacillus anthracis* T105-R (Cipro$^R$), *Bacillus subtilis* 23857, *Enterococcus faecalis* 29212, *Enterococcus faecalis* 44841 (quin$^R$), *Enterococcus faecium* 49624, *Escherichia coli* BAS849, *Escherichia coli* 25922, *Escherichia coli* LZ3111, *Escherichia coli* LZ3110, *Escherichia coli* ELZ4251 (MDR), *Escherichia coli* NDM-1, *Francisella* tularensis (wild-type), *Haemophilus influenzae* 49247, *Klebsiella pneumoniae* 35657, *Klebsiella pneumoniae* MMX1232 (MDR), *Moraxella catarrhalis* 25238, *Pseudomonas aeruginosa* 27853, *Staphylococcus aureus* 29213, *Staphylococcus aureus* 43300 (MDR), *Staphylococcus aureus* 700789 (MDR), *Streptococcus pneumoniae* 49150 or *Yersinia pestis* (wild-type).

Another aspect of the description relates to a method of treating or ameliorating treating a bacterial infection by a Gram-negative or Gram-positive bacteria.

Another aspect of the description relates to a method of treating or ameliorating treating a bacterial infection by a resistant Gram-negative or Gram-positive bacteria.

Another aspect of the description relates to a method of treating or ameliorating treating a bacterial infection by a drug resistant Gram-negative or Gram-positive bacteria.

Another aspect of the description relates to a method of treating or ameliorating treating a bacterial infection by a multi-drug resistant Gram-negative or Gram-positive bacteria.

As used herein, the terms "effective amount" or "therapeutically effective amount" mean an amount of compound of Formula (I) or a form, composition or medicament thereof effective in inhibiting the above-noted diseases and thus producing the desired therapeutic, ameliorative, inhibitory or preventative effect in a subject in need thereof.

In general, the effective amount will be in a range of from about 0.001 mg/Kg/day to about 500 mg/Kg/day, or about 0.01 mg/Kg/day to about 500 mg/Kg/day, or about 0.1 mg to about 500 mg/Kg/day, or about 1.0 mg/day to about 500 mg/Kg/day, in single, divided, or a continuous dose for a patient or subject having a weight in a range of between about 40 to about 200 Kg (which dose may be adjusted for patients or subjects above or below this range, particularly children under 40 Kg). The typical adult subject is expected to have a median weight in a range of between about 60 to about 100 Kg.

The dose administered to achieve an effective target plasma concentration may also be administered based upon the weight of the subject or patient. Doses administered on a weight basis may be in the range of about 0.01 mg/kg/day to about 50 mg/kg/day, or about 0.015 mg/kg/day to about 20 mg/kg/day, or about 0.02 mg/kg/day to about 10 mg/kg/day, or about 0.025 mg/kg/day to about 10 mg/kg/day, or about 0.03 mg/kg/day to about 10 mg/kg/day, wherein said amount is orally administered once (once in approximately a 24 hour period), twice (once in approximately a 12 hour period) or thrice (once in approximately an 8 hour period) daily according to subject weight.

In another embodiment, where daily doses are adjusted based upon the weight of the subject or patient, compounds described herein may be formulated for delivery at about 0.02, 0.025, 0.03, 0.05, 0.06, 0.075, 0.08, 0.09, 0.10, 0.20, 0.25, 0.30, 0.50, 0.60, 0.75, 0.80, 0.90, 1.0, 1.10, 1.20, 1.25, 1.50, 1.75, 2.0, 5.0, 10, 20 or 50 mg/kg/day. Daily doses adjusted based upon the weight of the subject or patient may be administered as a single, divided, or continuous dose. In embodiments where a dose of compound is given more than once per day, the dose may be administered twice, thrice, or more per day.

Within the scope of the present description, the "effective amount" of a compound of Formula (I) or a form thereof for use and for use in the manufacture of a medicament, the preparation of a pharmaceutical kit or in a method of treating or ameliorating bacterial infection or disorders or symptoms associated therewith in a subject in need thereof, is intended to include an amount in a range of from about 1.0 mg to about 3500 mg administered once daily; 10.0 mg to about 600 mg administered once daily; 0.5 mg to about 2000 mg administered twice daily; or, an amount in a range of from about 5.0 mg to about 300 mg administered twice daily.

For example, the effective amount may be the amount required to treat a bacterial infection, or the amount required to inhibit bacterial replication in a subject or, more specifically, in a human. In some instances, the desired effect can be determined by analyzing the presence of bacterial DNA. The effective amount for a subject will depend upon various factors, including the subject's body weight, size and health. Effective amounts for a given patient can be determined by routine experimentation that is within the skill and judgment of the clinician.

For any compound, the effective amount can be estimated initially either in cell culture assays or in relevant animal models, such as a mouse, chimpanzee, marmoset or tamarin animal model. Relevant animal models may also be used to determine the appropriate concentration range and route of administration. Such information can then be used to determine useful doses and routes for administration in humans. Therapeutic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is referred to as the therapeutic index, and can be expressed as the ratio, $LD_{50}/ED_{50}$. In some embodiments, the effective amount is such that a large therapeutic index is achieved. In further embodiments, the dosage is within a range of circulating concentrations that include an $ED_{50}$ with little or no toxicity. The dosage may vary within this range depending upon the dosage form employed, sensitivity of the patient, and the route of administration.

More specifically, the concentration-biological effect relationships observed with regard to a compound of Formula (I) or a form thereof indicate a target plasma concentration ranging from approximately 0.001 µg/mL to approximately 50 µg/mL, from approximately 0.01 µg/mL to approximately 20 µg/mL, from approximately 0.05 µg/mL to approximately 10 µg/mL, or from approximately 0.1 µg/mL to approximately 5 µg/mL. To achieve such plasma concentrations, the compounds described herein may be administered at doses that vary from 0.1 µg to 100,000 mg, depending upon the route of administration in single, divided, or continuous doses for a patient weighing between about 40 to about 100 kg (which dose may be adjusted for patients above or below this weight range, particularly children under 40 kg).

The exact dosage will be determined by the practitioner, in light of factors related to the subject. Dosage and administration may be adjusted to provide sufficient levels of the active agent(s) or to maintain the desired effect. Factors which may be taken into account include the severity of the disease state, general health of the subject, ethnicity, age, weight, and gender of the subject, diet, time and frequency of administration, drug combination(s), reaction sensitivities, experience with other antibacterial therapies, and tolerance/response to therapy. Long-acting pharmaceutical compositions may be administered every 2, 3 or 4 days, once every week, or once every two weeks depending on half-life and clearance rate of the particular formulation.

The compounds and compositions described herein may be administered to the subject via any drug delivery route known in the art. Nonlimiting examples include oral, ocular, rectal, buccal, topical, nasal, ophthalmic, subcutaneous, intramuscular, intraveneous (bolus and infusion), intracerebral, transdermal, and pulmonary routes of administration.

Metabolites of the Compounds

Also falling within the scope of the present description are the in vivo metabolic products of the compounds described herein. Such products may result, for example, from the oxidation, reduction, hydrolysis, amidation, esterification and the like of the administered compound, primarily due to enzymatic processes. Accordingly, the description includes compounds produced by a process comprising contacting a compound described herein with a mammalian tissue or a mammal for a period of time sufficient to yield a metabolic product thereof.

Such products typically are identified by preparing a radio-labeled isotopologue (e.g., $C^{14}$ or $H^3$) of a compound described herein, administering the radio-labeled compound in a detectable dose (e.g., greater than about 0.5 mg/kg) to a mammal such as a rat, mouse, guinea pig, dog, monkey or human, allowing sufficient time for metabolism to occur (typically about 30 seconds to about 30 hours), and identifying the metabolic conversion products from urine, bile, blood or other biological samples. These products are easily isolated since they are "radiolabeled" by virtue of being isotopically-enriched (others are isolated by the use of antibodies capable of binding epitopes surviving in the metabolite). The metabolite structures are determined in conventional fashion, e.g., by MS or NMR analysis. In general, analysis of metabolites may be done in the same way as conventional drug metabolism studies well-known to those skilled in the art. The conversion products, so long as they are not otherwise found in vivo, are useful in diagnostic assays for therapeutic dosing of the compounds described herein even if they possess no biological activity of their own.

Pharmaceutical Compositions

Embodiments of the present description include the use of a compound of Formula (I) or a form thereof in a pharmaceutical composition for the prevention or treatment of a bacterial infection comprising an effective amount of a compound of Formula (I) or a form thereof in admixture with a pharmaceutically acceptable excipient.

As used herein, the term "composition" means a product comprising the specified ingredients in the specified amounts, as well as any product which results, directly or indirectly, from combination of the specified ingredients in the specified amounts.

The pharmaceutical composition may be formulated to achieve a physiologically compatible pH, ranging from about pH 3 to about pH 11. In some embodiments, the pharmaceutical composition is formulated to achieve a pH of from about pH 3 to about pH 7. In other embodiments, the pharmaceutical composition is formulated to achieve a pH of from about pH 5 to about pH 8.

The term "pharmaceutically acceptable excipient" refers to an excipient for administration of a pharmaceutical agent, such as the compounds described herein. The term refers to any pharmaceutical excipient that may be administered without undue toxicity. Pharmaceutically acceptable excipients may be determined in part by the particular composition being administered, as well as by the particular mode of administration and/or dosage form. Nonlimiting examples of pharmaceutically acceptable excipients include carriers, solvents, stabilizers, adjuvants, diluents, etc. Accordingly, there exists a wide variety of suitable formulations of pharmaceutical compositions for the instant compounds described herein (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive antibodies. Other exemplary excipients include antioxidants such as ascorbic acid; chelating agents such as EDTA; carbohydrates such as dextrin, hydroxyalkylcellulose, hydroxyalkylmethylcellulose, stearic acid; liquids such as oils, water, saline, glycerol and ethanol; wetting or emulsifying agents; pH buffering substances; and the like. Liposomes are also included within the definition of pharmaceutically acceptable excipients.

The pharmaceutical compositions described herein may be formulated in any form suitable for the intended method of administration. Suitable formulations for oral administration include solids, liquid solutions, emulsions and suspensions, while suitable inhaleable formulations for pulmonary administration include liquids and powders. Alternative formulations include syrups, creams, ointments, tablets, and lyophilized solids which can be reconstituted with a physiologically compatible solvent prior to administration.

When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients suitable for use in conjunction with tablets include, for example, inert diluents, such as celluloses, calcium or sodium carbonate, lactose, calcium or sodium phosphate; disintegrating agents, such as croscarmellose sodium, cross-linked povidone, maize starch, or alginic acid; binding agents, such as povidone, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In other embodiments, pharmaceutical compositions described herein may be formulated as suspensions comprising a compound of Formula (I) or a form thereof in admixture with at least one pharmaceutically acceptable excipient suitable for the manufacture of a suspension. In yet other embodiments, pharmaceutical compositions described herein may be formulated as dispersible powders and granules suitable for preparation of a suspension by the addition of one or more excipient(s).

Excipients suitable for use in connection with suspensions include suspending agents, such as sodium carboxymethylcellulose, methylcellulose, hydroxypropyl methylcelluose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); and thickening agents, such as carbomer, beeswax, hard paraffin or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical compositions described herein may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions described herein may be in the form of a sterile injectable preparation, such as a sterile injectable aqueous emulsion or oleaginous suspension. Such emulsion or suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent. The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or di-glycerides. In addition, fatty acids such as oleic acid may likewise be used in the preparation of injectables.

The compounds described herein may be substantially insoluble in water and sparingly soluble in most pharmaceutically acceptable protic solvents and vegetable oils, but generally soluble in medium-chain fatty acids (e.g., caprylic and capric acids) or triglycerides and in propylene glycol esters of medium-chain fatty acids. Thus, contemplated in the description are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In some embodiments, the compound described herein is formulated for oral administration in a lipid-based composition suitable for low solubility compounds. Lipid-based formulations can generally enhance the oral bioavailability of such compounds. As such, pharmaceutical compositions described herein may comprise a effective amount of a compound of Formula (I) or a form thereof, together with at least one pharmaceutically acceptable excipient selected from medium chain fatty acids or propylene glycol esters thereof (e.g., propylene glycol esters of edible fatty acids such as caprylic and capric fatty acids) and pharmaceutically acceptable surfactants, such as polyoxyl 40 hydrogenated castor oil.

In other embodiments, the bioavailability of low solubility compounds may be enhanced using particle size optimization techniques including the preparation of nanoparticles or nanosuspensions using techniques known to those skilled in art. The compound forms present in such preparations include amorphous, partially amorphous, partially crystalline or crystalline forms.

In alternative embodiments, the pharmaceutical composition may further comprise one or more aqueous solubility enhancer(s), such as a cyclodextrin. Nonlimiting examples of cyclodextrin include hydroxypropyl, hydroxyethyl, glucosyl, maltosyl and maltotriosyl derivatives of α-, β-, and γ-cyclodextrin, and hydroxypropyl-β-cyclodextrin (HPBC). In some embodiments, the pharmaceutical composition further comprises HPBC in a range of from about 0.1% to about 20%, from about 1% to about 15%, or from about 2.5% to about 10%. The amount of solubility enhancer employed may depend on the amount of the compound in the composition.

Preparation of Compounds

General Synthetic Examples

Methods for preparing certain compounds useful for treating or ameliorating bacterial infections or disorders or symptoms associated therewith are available via standard, well-known synthetic methodologies.

As disclosed herein, methods for preparing the compounds described herein are also available via standard, well-known synthetic methodology. Many of the starting materials used herein are commercially available or can be prepared using the routes described below using techniques known to those skilled in the art.

General Schemes

Compounds of Formula (I) can be prepared as described in the Schemes below.

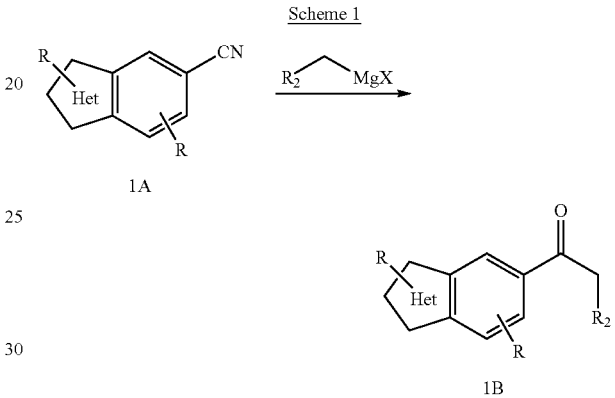

General Procedures for Scheme 1

Ketones of type 1B can be prepared from nitriles of type 1A (wherein R represents one or more optionally present substituents or protecting groups) through reaction with Grignard reagents in a suitable organic solvent such as THF and the like followed by treatment with aqueous acid.

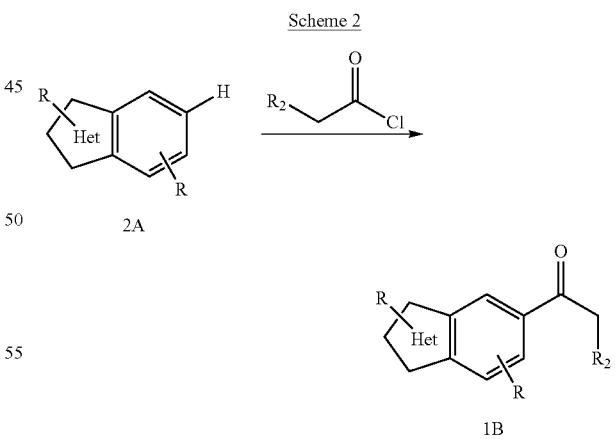

General Procedure for Scheme 2

An alternative procedure to ketones of type 1B is through the Friedel-Crafts reaction of aromatic compounds of type 2A (wherein R represents one or more optionally present substituents or protecting groups) with acid chlorides catalyzed by a suitable Lewis acid, such as aluminum trichloride and the like, in a suitable organic solvent such as DMF and the like.

Scheme 3

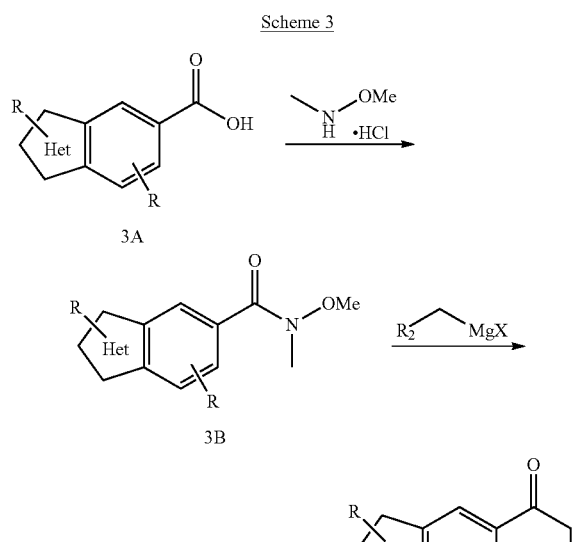

General Procedures for Scheme 3

Ketones of type 1B can be prepared from carboxylic acids of type 3A through a two step sequence beginning with treatment of 3A (wherein R represents one or more optionally present substituents or protecting groups) with an appropriate activating agent followed by reaction with O,N-dimethylhydroxylamine hydrochloride in an organic solvent such as DCM and the like. Amides of type 3B can be converted to ketones of type 1B through reaction with Grignard reagents in a suitable organic solvent such as THF and the like.

Scheme 4

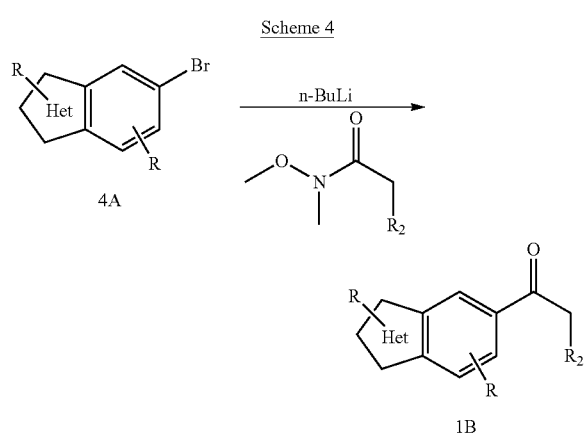

General Procedures for Scheme 4

Ketones of type 1B can be prepared from aryl bromides of type 4A through a two step procedure beginning with treatment of 4A (wherein R represents one or more optionally present substituents or protecting groups) with a suitable organometallic species such as n-BuLi and the like at temperatures ranging from −78° C. to −40° C. followed by reaction with appropriate amides in an organic solvent such as THF and the like.

Scheme 5

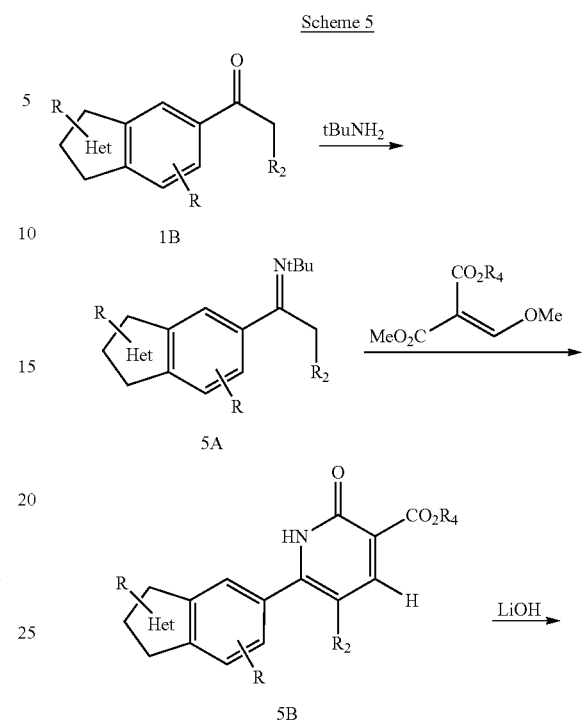

$R_4 = Me$ $R_4 = H$

General Procedures for Scheme 5

A ketone of type 1B (wherein R represents one or more optionally present substituents or protecting groups) may be converted into an imine of type 5A through reaction with an excess of tert-butyl amine in the presence of a dehydrating agent such as titanium tetrachloride in an organic solvent such as DCM and the like. Imines of type 5A may be converted into 2-pyridones of type 5B through reaction with dimethyl 2-(methoxymethylene)malonate in an organic solvent such as diphenyl ether and the like at temperatures ranging from 160° C. to 230° C. Acids of type 5C can be prepared from 2-pyridones of type 5B through hydrolysis reaction with aqueous lithium hydroxide in an organic solvent such as THF and the like at 50° C.

Scheme 6

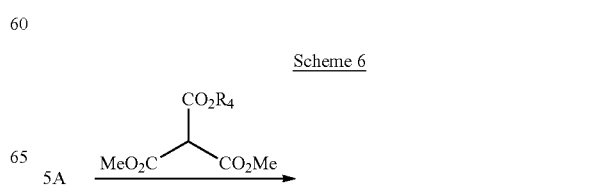

-continued

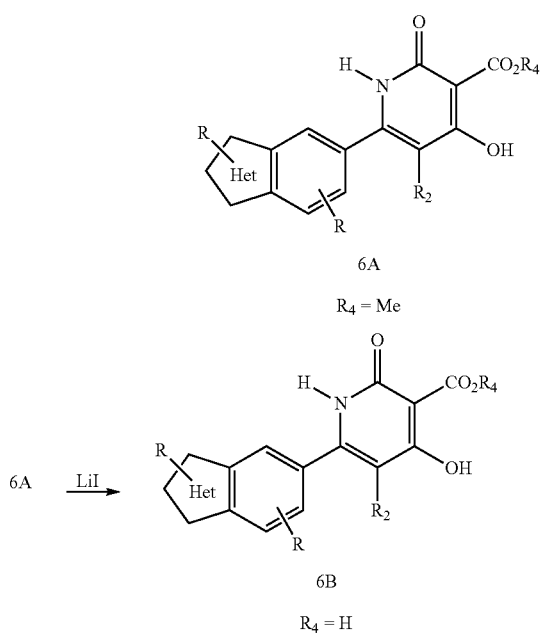

General Procedure for Scheme 6

Imines of type 5A may also be converted to 4-hydroxyl 2-pyridones of type 6A through reaction with trimethyl tricarboxylate in an organic solvent such as diphenyl ether and the like at temperatures ranging from 160° C. to 230° C. Hydrolysis of the ester moiety with 4-hydroxy 2-pyridones of type 6A can be accomplished using lithium iodide in an organic solvent such as EtOAc and the like at temperatures ranging from 50° C. to 80° C. to provide acids of type 6B.

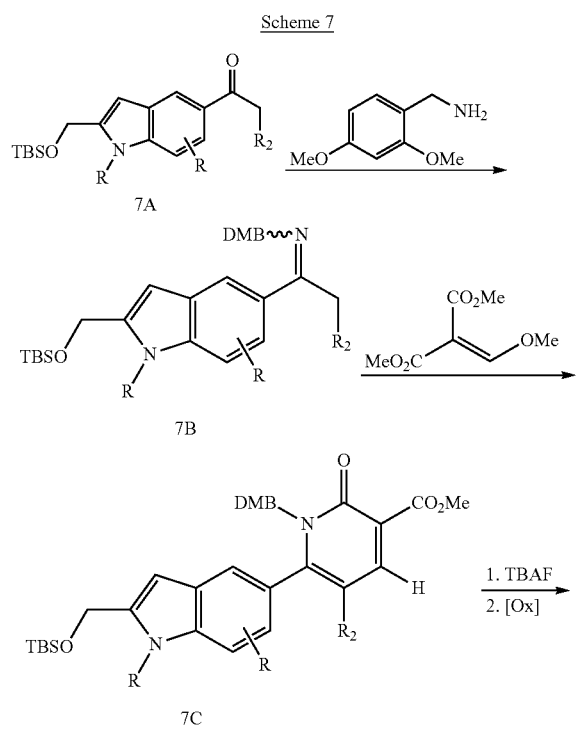

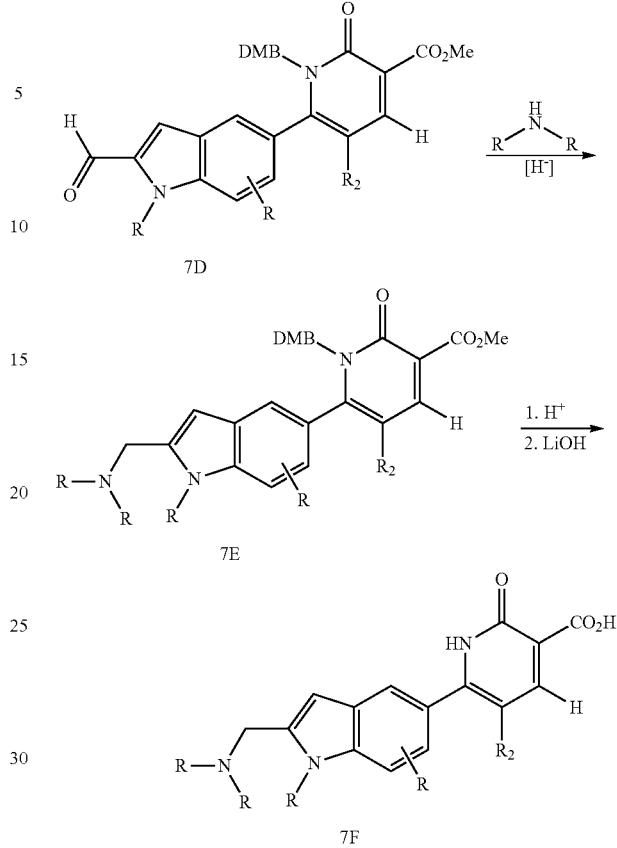

General Procedures for Scheme 7

A ketone of type 7A (wherein R represents one or more optionally present substituents or protecting groups) may be converted into an imine of type 7B through reaction with an appropriate amine such as 2,4-dimethoxybenzylamine in the presence of a dehydrating agent such as titanium tetrachloride in an organic solvent such as DCM and the like. DMB (2,4-dimethoxybenzyl) imines of type 7B may be converted into 2-pyridones of type 7C through reaction with dimethyl 2-(methoxymethylene)malonate in an organic solvent such as diphenyl ether and the like at temperatures ranging from 160° C. to 230° C. Aldehydes of type 7D can be prepared from 2-pyridones of type 7C through a two step sequence beginning with treatment of 7C with an appropriate fluoride agent such as TBAF (Tetra-n-butylammonium fluoride) and the like followed by reaction with a suitable oxidant such as $MnO_2$ and the like in an organic solvent such as DCM and the like.

Aldehydes of type 7D may be converted into amines of type 7E through reaction with an appropriate amine (wherein R represents one or more optionally present substituents or protecting groups and, wherein the amine R groups can be taken together with the nitrogen of attachment to form a heterocyclyl ring), a suitable acid such as acetic acid, and a suitable reducing agent such as $NaBH(OAc)_3$ and the like in an organic solvent such as DCE and the like. Acids of type 7F can be prepared from amines of type 7E through a two step sequence beginning with treatment of 7E with an appropriate acid such as TFA and the like followed by reaction with aqueous lithium hydroxide in an organic solvent such as THF and the like at 50° C.

Scheme 8

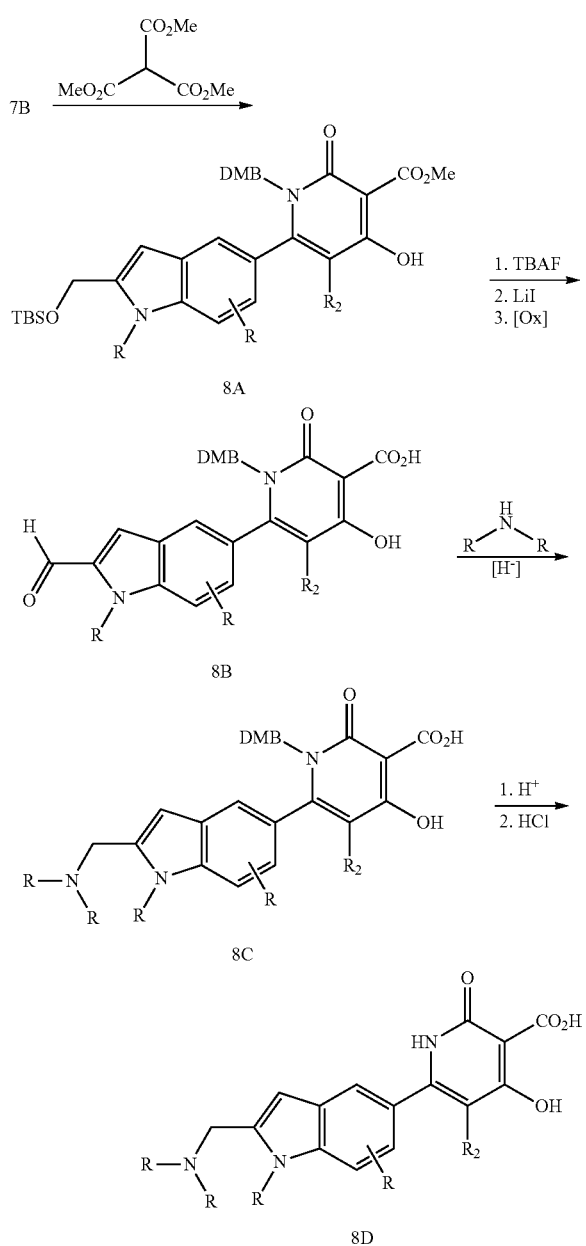

General Procedure for Scheme 8

DMB (2,4-dimethoxybenzyl) imines of type 7B may also be converted to 4-hydroxyl 2-pyridones of type 8A (wherein R represents one or more optionally present substituents or protecting groups) through reaction with trimethyl tricarboxylate in an organic solvent such as diphenyl ether and the like at temperatures ranging from 160° C. to 230° C. 4-hydroxyl 2-pyridones of type 8A can be converted to aldehydes of type 8B via a three step process including: 1. TBS-group deprotection with a suitable fluoride agent, such as TBAF (Tetra-n-butylammonium fluoride) and the like; 2. Methyl ester cleavage with a suitable nucleophilic agent, such as LiI and the like; 3. Conversion of the benzylic hydroxyl to an aldehyde with a suitable oxidant, such as $MnO_2$ and the like.

Aldehydes of type 8B may be converted into amines of type 8C through reaction with an appropriate amine (wherein R represents one or more optionally present substituents or protecting groups and, wherein the amine R groups can be taken together with the nitrogen of attachment to form a heterocyclyl ring), a suitable acid such as acetic acid, and a suitable reducing agent such as $NaBH(OAc)_3$ and the like in an organic solvent such as DCE and the like. Acids of type 8D can be prepared from amines of type 8C through a two step sequence beginning with treatment of 8C with an appropriate acid such as TFA in the presence of a suitable carbocation scavenger such as $i-Pr_3SiH$ and the like, followed by salt exchange with a suitable mineral acid, such as HCl and the like.

Scheme 9

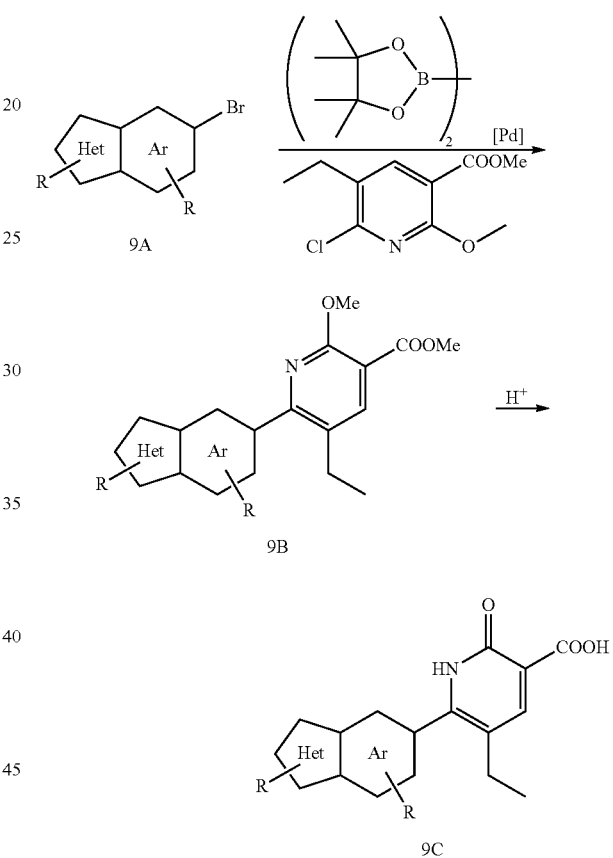

General Procedure for Scheme 9

Heteroaryl bromides of type 9A (wherein R represents one or more optionally present substituents or protecting groups) may be converted into 2-methoxy pyridines of type 9B through a two step sequence beginning with treatment of 9A with an excess of bis(pinacolato)diboron, a suitable base such as potassium acetate, and a suitable palladium catalyst such as $PdCl_2(dppf)$ and the like in an organic solvent such as 1,4-dioxane at temperatures ranging from 80° C. to 110° C. followed by reaction with methyl 6-chloro-5-ethyl-2-methoxynicotinate in the presence of a suitable base such as potassium carbonate at temperatures ranging from 80° C. to 110° C. 2-Pyridones of type 9C can be prepared through hydrolysis of 2-methoxy pyridines of type 9B with a suitable acid, such as hydrochloric acid and the like at temperatures ranging from 75° C. to 85° C.

147

Scheme 10

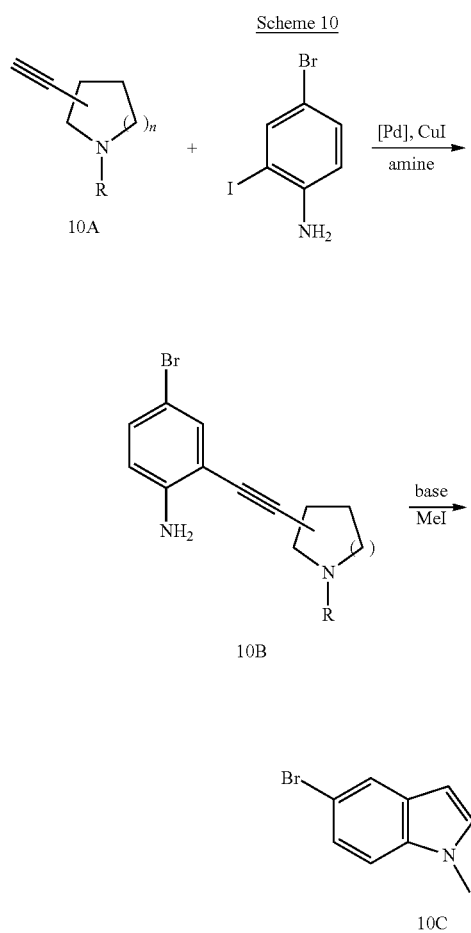

10A

10B

10C

148

-continued

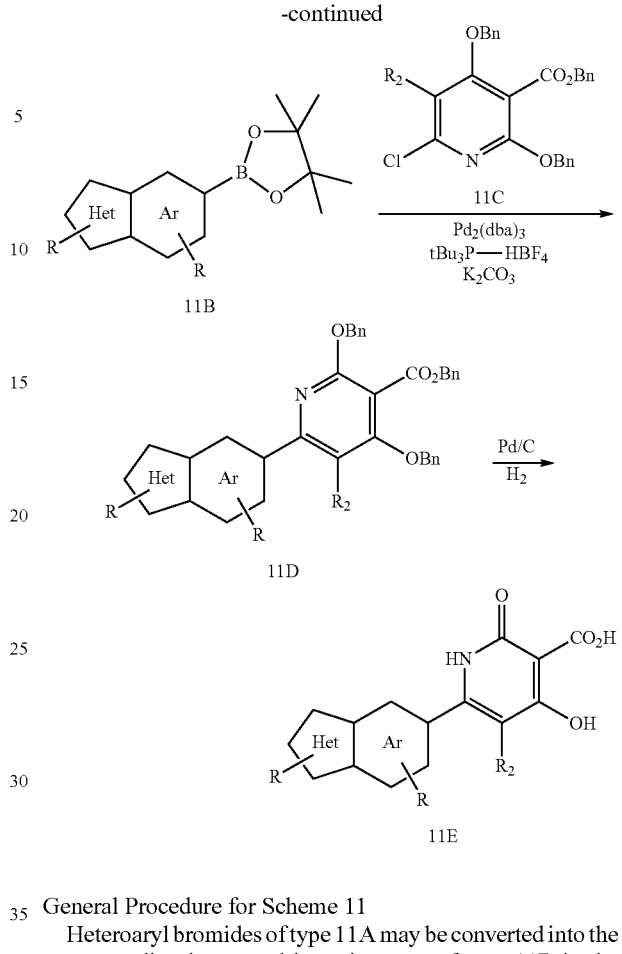

11B

11C

11D

11E

General Procedure for Scheme 10

Alkynes of type 10A (wherein R represents one or more optionally present substituents or protecting groups) may be converted to anilines of type 10B through reaction with 4-bromo-2-iodoaniline in the presence of a suitable palladium catalyst, a suitable copper agent such as CuI, and a suitable tertiary amine such as triethylamine in an organic solvent such as MeCN and the like at 50° C.

Indoles of type 10C can be prepared from anilines of type 10B through a two step sequence beginning with treatment of 10B with an appropriate base such as potassium tert-butoxide in an organic solvent such as NMP and the like, followed by reaction with an electrophilic agent such as iodomethane and the like.

Scheme 11

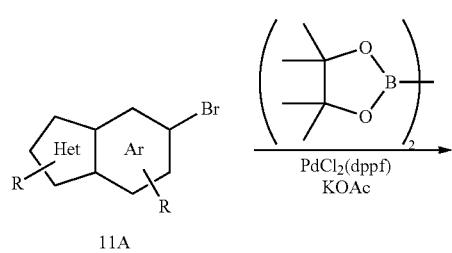

11A

General Procedure for Scheme 11

Heteroaryl bromides of type 11A may be converted into the corresponding heteroaryl boronic esters of type 11B in the presence of an excess of bis(pinacolato)diboron, a suitable base such as potassium acetate, and a suitable palladium catalyst such as $PdCl_2(dppf)$ and the like in an organic solvent such as 1,4-dioxane at temperatures ranging from 80° C. to 110° C. 2,4-Bisbenzyloxypyridines of type 11D can be prepared through Suzuki-coupling between heteroaryl boronic esters of type 11B and 6-chloro-2,4-bisbenzyloxypyridines of type 11C in the presence of a suitable base such as potassium carbonate, a suitable ligand such as tri-tert-butylphosphonium tetrafluoroborate, and a suitable palladium catalyst such as $Pd_2(dba)_3$ and the like in an organic solvent such as DMSO at temperatures ranging from 90° C. to 120° C. 4-Hydroxy-2-pyridones of type 11E can be prepared through hydrogenolysis of 2,4-bisbenzyloxypyridines of type 11D with a suitable catalyst, such as palladium on carbon under hydrogen atmosphere at room temperature.

Specific Examples

To assist in understanding the present description, the following Examples are included. The experiments relating to this description should not, of course, be construed as specifically limiting the description and such variations of the description, now known or later developed, which would be within the purview of one skilled in the art are considered to fall within the scope of the description as described herein and hereinafter claimed.

Other than in the working examples, unless indicated to the contrary, all numbers expressing quantities of ingredients, reaction conditions, experimental data, and so forth used in the specification and claims are to be understood as being modified by the term "about". Accordingly, all such numbers represent approximations that may vary depending upon the desired properties sought to be obtained by a reaction or as a result of variable experimental conditions. Therefore, within an expected range of experimental reproducibility, the term "about" in the context of the resulting data, refers to a range for data provided that may vary according to a standard deviation from the mean. As well, for experimental results provided, the resulting data may be rounded up or down to present data consistently, without loss of significant figures. At the very least, and not as an attempt to limit the application of the doctrine of equivalents to the scope of the claims, each numerical parameter should be construed in light of the number of significant digits and ordinary rounding techniques.

While the numerical ranges and parameters setting forth the broad scope of the description are approximations, the numerical values set forth in the working examples are reported as precisely as possible. Any numerical value, however, inherently contains certain errors necessarily resulting from the standard deviation found in their respective testing measurements.

Synthetic Examples

The present description is described in more detail with reference to the following non-limiting examples, which are offered to more fully illustrate the description, but are not to be construed as limiting the scope thereof. The examples illustrate the preparation of certain compounds described herein, and the testing of these compounds in vitro and/or in vivo. Those of skill in the art will understand that the techniques described in these examples represent techniques described by persons of ordinary skill in the art to function well in the practice of the description, and as such constitute preferred modes for the practice thereof. However, those of skill in the art should appreciate in light of the present disclosure that many changes can be made to the specific methods that are disclosed and still obtain a like or similar result without departing from the spirit and scope of the description. For example, various conditions were used to obtain LC-MS characterization for the compounds described herein.

As indicated for certain compounds, the 2 Minute Method uses the following column and mobile phase ratios:
Column: Acquity UPLC HSS C18 Column 2.1×50 mm, 1.8 µm
Mobile Phase A: $H_2O$/0.1% $HCO_2H$
Mobile Phase B: Acetonitrile/0.1% $HCO_2H$

|   | Time (min) | Flow (mL/min) | % A | % B |
|---|---|---|---|---|
| 1 | 0 | 0.8 | 100 | 0 |
| 2 | 0.2 | 0.8 | 100 | 0 |
| 3 | 1.5 | 0.8 | 0 | 100 |
| 4 | 2.0 | 0.8 | 100 | 0 |

As indicated for certain compounds, the 1 Minute Method uses the following column and mobile phase ratios:
Column: Acquity UPLC HSS C18 Column 2.1×50 mm, 1.8 µm
Mobile Phase A: $H_2O$/0.1% $HCO_2H$
Mobile Phase B: Acetonitrile/0.1% $HCO_2H$

|   | Time (min) | Flow (mL/min) | % A | % B |
|---|---|---|---|---|
| 1 | 0 | 0.8 | 90 | 10 |
| 2 | 0.1 | 0.8 | 90 | 10 |
| 3 | 0.8 | 0.8 | 5 | 95 |
| 4 | 1.0 | 0.8 | 90 | 10 |

As indicated for certain compounds, the Polar Method uses the following column and mobile phase ratios:
Column: Acquity UPLC HSS C18 Column 2.1×50 mm, 1.8 µm
Mobile Phase A: $H_2O$/0.1% $HCO_2H$
Mobile Phase B: Acetonitrile/0.1% $HCO_2H$

|   | Time (min) | Flow (mL/min) | % A | % B |
|---|---|---|---|---|
| 1 | 0 | 0.8 | 100 | 0 |
| 2 | 0.2 | 0.8 | 100 | 0 |
| 3 | 1.5 | 0.8 | 50 | 50 |
| 4 | 2.0 | 0.8 | 100 | 0 |

As indicated for certain compounds, Method A uses the following column and mobile phase ratios:
Column: HSS T3 Column 2.1×50 mm, 1.8 µm
Mobile Phase A: $H_2O$/0.1% $HCO_2H$
Mobile Phase B: Acetonitrile/0.1% $HCO_2H$

|   | Time (min) | Flow (ml/min) | % A | % B |
|---|---|---|---|---|
| 1 | 0 | 0.8 | 80 | 20 |
| 2 | 0.2 | 0.8 | 80 | 20 |
| 3 | 1.25 | 0.8 | 5 | 95 |
| 4 | 2.0 | 0.8 | 80 | 20 |

As indicated for certain compounds, Method B uses the following column and mobile phase ratios:
Column: HSS T3 Column 2.1×50 mm, 1.8 µm
Mobile Phase A: $H_2O$/0.1% $HCO_2H$
Mobile Phase B: Acetonitrile/0.1% $HCO_2H$
Flow

|   | Time (min) | Flow (ml/min) | % A | % B |
|---|---|---|---|---|
| 1 | 0 | 0.8 | 95 | 5 |
| 2 | 0.2 | 0.8 | 95 | 5 |
| 3 | 1.5 | 0.8 | 10 | 90 |
| 4 | 2.0 | 0.8 | 95 | 5 |

As indicated for certain compounds, Method C uses the following column and mobile phase ratios:
Column: BEH C18 Column 2.1×50 mm, 1.7 µm
Mobile Phase A: $NH_4OAc_{aq}$ 10 mM
Mobile Phase B: Acetonitrile

|   | Time (min) | Flow (ml/min) | % A | % B |
|---|---|---|---|---|
| 1 | 0 | 0.8 | 95 | 5 |
| 2 | 0.2 | 0.8 | 95 | 5 |
| 3 | 1.5 | 0.8 | 10 | 90 |
| 4 | 2.0 | 0.8 | 95 | 5 |

As used above, and throughout the description of the description, the following abbreviations, unless otherwise indicated, shall be understood to have the following meanings:

| Abbreviation | Meaning |
| --- | --- |
| AcOH or HOAc | acetic acid |
| ACN or MeCN | acetonitrile |
| BINAP | 2,2'-bis(diphenylphosphino)-1,1'-binaphthyl |
| Bn | benzyl |
| BnBr | benzyl-bromide |
| BnO or OBn | benzyloxy |
| BnOH | benzyl alcohol |
| Boc | tert-butoxycarbonyl |
| $Boc_2O$ or $(Boc)_2O$ | di-tert-butyl dicarbonate |
| $B(OiPr)_3$ or $B(Oi-Pr)_3$ | triisopropyl borate |
| $B_2Pin_2$ or $(BPin)_2$ | bis(pinacolato)diboron |
| nBu or n-Bu | n-butyl |
| tBu or t-Bu | t-butyl |
| n-BuLi | n-butyllithium |
| t-BuOK or KO$^t$Bu | potassium tert-butoxide |
| t-Bu$_3$PHBF$_4$ or BF$_4$t-Bu$_3$PH | tri-tert-butylphosphonium tetrafluoroborate |
| Cbz | benzyloxycarbonyl |
| CDI | 1,1'-carbonyldiimidazole |
| CSI | chlorosulfonyl isocyanate |
| DCE | 1,2-dichloroethane |
| DCM | dichloromethane ($CH_2Cl_2$) |
| DIAD | diisopropyl azodicarboxylate |
| DIBAL-H | diisobutylaluminium hydride |
| DME | 1,2-dimethoxyethane |
| DMF | dimethyl formamide |
| DMA | dimethylacetamide |
| DMAP | 4-dimethylaminopyridine |
| DMB | 2,4-dimethoxybenzyl |
| DMSO | dimethylsulfoxide |
| EtOAc | ethyl acetate |
| EtOH | ethanol |
| $Et_2O$ | ethyl ether |
| HPLC | high performance liquid chromatography |
| h/hr/min/s | hour(s)/minute(s)/second(s) |
| KOAc | potassium acetate |
| LAH | lithium aluminium hydride |
| LC/MS, LCMS or LC-MS | liquid chromatographic mass spectroscopy |
| LDA | lithium diisopropylamide |
| LiOH | lithium hydroxide |
| MeOH | methanol |
| $MnO_2$ | manganese dioxide |
| MS | mass spectroscopy |
| Ms | methanesulfonyl |
| MsCl | methanesulfonyl chloride |
| NaOAc | sodium acetate |
| NBS | N-bromosuccinimide |
| NCS | N-chlorosuccinimide |
| NMO | N-methylmorpholine-N-oxide |
| NMP | N-methyl-2-pyrrolidone |
| NMR | nuclear magnetic resonance |
| nPr or n-Pr | n-propyl |
| Pd° | palladium |
| $Pd_2(dba)_3$ | tris(dibenzylideneacetone)dipalladium(0) |
| $PdCl_2$dppf or Pd(dppf)$Cl_2$ | [1,1'-bis(diphenylphosphino)ferrocene]dichloropalladium(II) |
| Pd(OAc)$_2$ | palladium(II) acetate |
| Pd(PPh$_3$)$_4$ | tetrakis(triphenylphosphine)palladium (0) |
| Ph$_2$O or PhOPh | phenyl ether |
| PPh$_3$ | triphenylphosphine |
| n-PrMgCl or PrMgCl | n-propylmagnesium chloride |
| psi | pounds per square inch pressure |
| PTFE | polytetrafluoroethylene |
| p-TsOH | p-toluenesulfonic acid |
| rt | room temperature |
| RT | retention time |
| $SO_3$-Py | sulfur trioxide pyridine complex |
| S-Phos or SPhos | 2-dicyclohexylphosphino-2',6'-dimethoxybiphenyl |
| TBAF | tetra-n-butylammonium fluoride |
| TBS-Cl or TBSCl | tert-butyldimethylsilyl chloride |
| TEA or NEt$_3$ | triethylamine |
| TFA | trifluoroacetic acid |
| THF | tetrahydrofuran |
| THP | tetrahydro-2H-pyranyl |
| THPO or OTHP | tetrahydro-2H-pyran-2-yloxy |
| TiCl$_4$ | titanium tetrachloride |
| TIPS-H or TIPSH | triisopropylsilane |
| TMPMgCl—LiCl | 2,2,6,6-tetramethylpiperidinylmagnesium chloride, lithium chloride complex |
| TMSI | trimethylsilyl iodide |
| TMSOK | potassium trimethylsilanolate |
| TPAP | tetrapropylammonium perruthenate |
| TsCl | 4-toluenesulfonyl chloride |

Example 1

5-ethyl-6-(1-methyl-1,2,3,4-tetrahydroquinolin-6-yl)-2-oxo-1,2-dihydropyridine-3-carboxylic acid (Cpd 1)

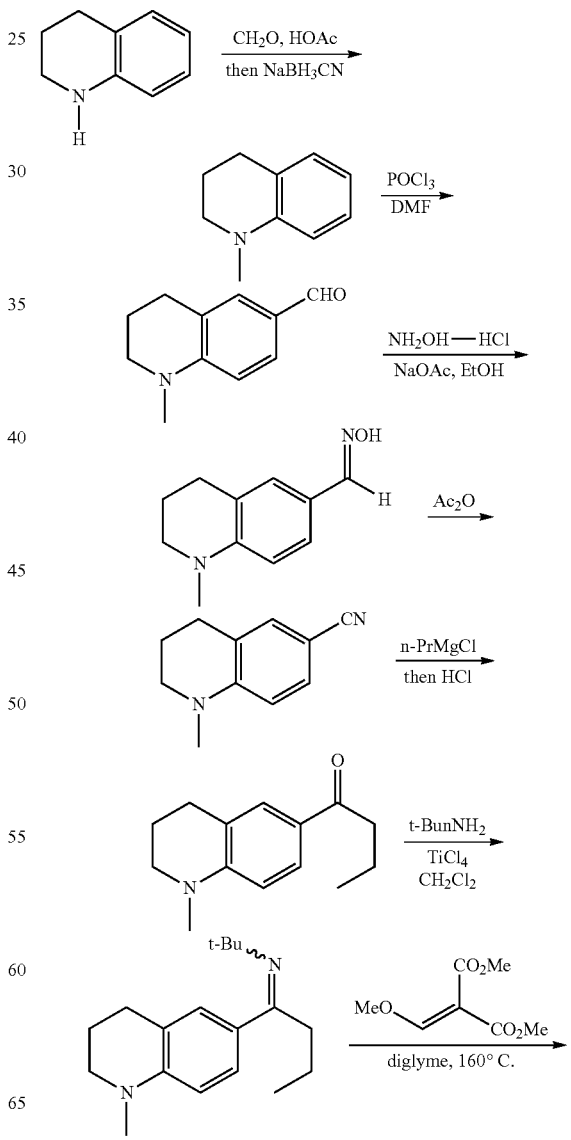

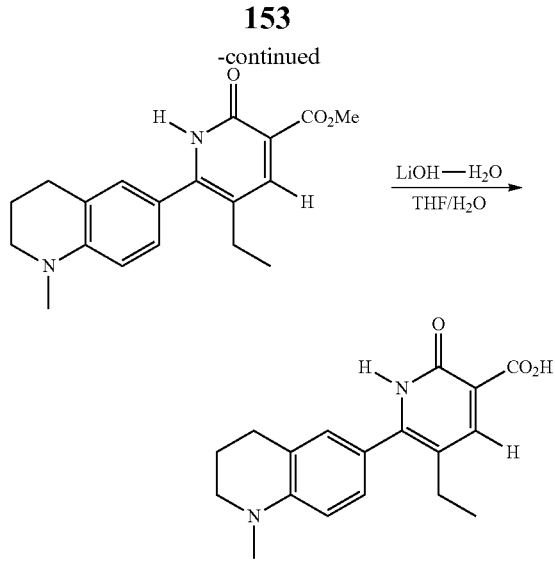

Step 1: Preparation of 1-methyl-1,2,3,4-tetrahydroquinoline

To a solution of tetrahydroquinoline (4.0 g, 30.0 mmol) in MeOH (60 mL) was added $CH_2O$ (37% aqueous solution, 2.7 mL, 36.3 mmol, 1.2 eq) and HOAc (1.73 mL, 30.0 mmol, 1.0 eq). The mixture was stirred at room temperature for 10 min then was cooled to 0° C. before $NaBH_3CN$ (1.98 g, 31.5 mmol, 1.05 eq) was added. After 1 h, the solvent was removed under reduced pressure. The reaction was quenched with saturated aqueous $NaHCO_3$ then extracted with $CH_2Cl_2$ (5×30 mL). The combined organic layers were dried over $Na_2SO_4$ then concentrated to give a crude product which was used in the next step without further purification.

$^1H$ NMR (500 MHz, $CHCl_3$-d) δ ppm 1.94-2.04 (m, 2H) 2.78 (t, J=6.46 Hz, 2H) 2.90 (s, 3H) 3.19-3.27 (m, 2H) 6.57-6.65 (m, 2H) 6.93-6.99 (m, 1H) 7.04-7.13 (m, 1H). LC-MS 147.9 $[M+H]^+$, RT 0.55 min. (1 min Method).

Step 2: Preparation of 1-methyl-1,2,3,4-tetrahydroquinoline-6-carbaldehyde

To a solution of 1-methyl-1,2,3,4-tetrahydroquinoline (4.4 g, ca. 30.0 mmol) in DMF (30 mL) was added $POCl_3$ (2.8 mL, 30.0 mmol, 1.0 eq) at 0° C. The mixture was allowed to warm to room temperature and stirred overnight. The reaction mixture was poured onto ice then extracted with $Et_2O$ (3×50 mL). The combined organic layers were dried over $Na_2SO_4$ then concentrated to give a crude product which was purified by flash column chromatography (0-20% EtOAc in hexanes) to afford the title compound (2.17 g, 12.4 mmol, 41% over two steps).

$^1H$ NMR (500 MHz, $CHCl_3$-d) δ ppm 1.92-2.03 (m, 2H) 2.79 (t, J=6.31 Hz, 2H) 3.02 (s, 3H) 3.34-3.43 (m, 2H) 6.57 (d, J=8.59 Hz, 1H) 7.42-7.51 (m, 1H) 7.57 (dd, J=8.59, 2.05 Hz, 1H) 9.68 (s, 1H). LC-MS 176.0 $[M+H]^+$, RT 0.71 min. (1 min Method).

Step 3: Preparation of 1-methyl-1,2,3,4-tetrahydroquinoline-6-carbaldehyde oxime To a solution of 1-methyl-1,2,3,4-tetrahydroquinoline-6-carbaldehyde (7.4 g, 42.2 mmol) in EtOH (100 mL) was added $NH_2OH$—HCl (3.5 g, 50.4 mmol, 1.2 eq) followed by NaOAc (4.5 g, 54.8 mmol, 1.3 eq) at room temperature. After 1 h, solvent was removed under reduced pressure then to the residue was added $CH_2Cl_2$ (100 mL). The solid was removed by filtration then the filtrate was concentrated to give a crude oxime which was carried over to next step without further purification. LC-MS 190.6 $[M+H]^+$, RT 0.69 min. (1 min Method).

Step 4: Preparation of 1-methyl-1,2,3,4-tetrahydroquinoline-6-carbonitrile

1-Methyl-1,2,3,4-tetrahydroquinoline-6-carbaldehyde oxime (8.0 g, ca. 42.0 mmol) and $Ac_2O$ (40 mL, 423.9 mmol, 10.1 eq) was mixed at room temperature then the mixture was heated to 110° C. and stirred for 4 h. The solvent was removed under reduced pressure then the residue was placed on ice (500 g). The resulting mixture was quenched with saturated aqueous $NaHCO_3$ then extracted by $CH_2Cl_2$ (4×50 mL). The combined organic layers were dried over $Na_2SO_4$ then concentrated to give a crude product which was purified by flash column chromatography (0-25% EtOAc in hexanes) to afford the title compound (4.53 g, 26.3 mmol, 63% over two steps).

$^1H$ NMR (500 MHz, $CHCl_3$-d) δ ppm 1.92-2.01 (m, 2H) 2.73 (t, J=6.34 Hz, 2H) 2.96 (s, 3H) 3.32-3.39 (m, 2H) 6.49 (d, J=8.59 Hz, 1H) 7.17 (dt, J=2.01, 0.97 Hz, 1H) 7.33 (dd, J=8.59, 2.13 Hz, 1H). LC-MS 173.1 $[M+H]^+$, RT 0.79 min. (1 min Method).

Step 5: Preparation of 1-(1-methyl-1,2,3,4-tetrahydroquinolin-6-yl)butan-1-one To a solution of 1-methyl-1,2,3,4-tetrahydroquinoline-6-carbonitrile (4.53 g, 26.3 mmol) in THF (30 mL) was added n-PrMgCl (2.0M in ether, 26.3 mL, 52.6 mmol, 2.0 eq) at room temperature. Then the mixture was heated to 50° C. and stirred overnight. The reaction was quenched with ice cold 1N HCl and stirred overnight. The biphasic mixture was extracted by $CH_2Cl_2$ (3×40 mL). The combined organic layers were dried over $Na_2SO_4$ then concentrated to give a crude product which was purified by flash column chromatography (0-25% EtOAc in hexanes) to afford the title compound (2.94 g, 13.5 mmol, 51%).

$^1H$ NMR (500 MHz, $CHCl_3$-d) δ ppm 0.99 (t, J=7.41 Hz, 3H) 1.75 (sxt, J=7.41 Hz, 2H) 1.94-2.02 (m, 2H) 2.79 (t, J=6.34 Hz, 2H) 2.81-2.86 (m, 2H) 2.99 (s, 3H) 3.32-3.38 (m, 2H) 6.52 (d, J=8.67 Hz, 1H) 7.61 (dt, J=2.15, 1.01 Hz, 1H) 7.73 (dd, J=8.67, 2.29 Hz, 1H).
LC-MS 218.1 $[M+H]^+$, RT 0.87 min. (1 min Method).

Step 6: Preparation of 2-methyl-N-(1-(1-methyl-1,2,3,4-tetrahydroquinolin-6-yl)butylidene)propan-2-amine To a solution of 1-(1-methyl-1,2,3,4-tetrahydroquinolin-6-yl)butan-1-one (2.94 g, 13.5 mmol) in $CH_2Cl_2$ (14 mL) was added 2-methylpropan-2-amine (5.7 mL, 54.2 mmol, 4.0 eq). The mixture was cooled to 0° C. before $TiCl_4$ (1.0M in $CH_2Cl_2$, 8.8 mL, 8.8 mmol, 0.65 eq) was added via syringe pump over 30 min. The reaction was allowed to warm to room temperature and stirred overnight. The reaction mixture was quenched with saturated aqueous $NaHCO_3$ (15 mL) then extracted by $CH_2Cl_2$ (5×25 mL). The combined organic layers were dried over $Na_2SO_4$ then concentrated to give a crude product which was carried over to next step without further purification. LC-MS 273.1 $[M+H]^+$, RT 0.65 min. (1 min Method).

Step 7: Preparation of methyl 5-ethyl-6-(1-methyl-1,2,3,4-tetrahydroquinolin-6-yl)-2-oxo-1,2-dihydropyridine-3-carboxylate To a suspension of 2-methyl-N-(1-(1-methyl-1,2,3,4-tetrahydroquinolin-6-yl)butylidene)propan-2-amine (1.96 g, ca. 7.2 mmol) in diglyme (7 mL) was added dimethyl 2-(methoxymethylene)malonate (2.12 g, 12.2 mmol, 1.7 eq). The reaction was stirred at 160° C. for 3 h then was cooled to room temperature. The precipitate was collected by filtration then washed with Et$_2$O to afford the title compound (402 mg, ca. 1.23 mmol) which was carried over to next step without further purification.

Step 8: Preparation of 5-ethyl-6-(1-methyl-1,2,3,4-tetrahydroquinolin-6-yl)-2-oxo-1,2-dihydropyridine-3-carboxylic acid To a suspension of methyl 5-ethyl-6-(1-methyl-1,2,3,4-tetrahydroquinolin-6-yl)-2-oxo-1,2-dihydropyridine-3-carboxylate (200 mg, 0.61 mmol) in THF (1 mL) and H$_2$O (1 mL) was added LiOH—H$_2$O (85 mg, 2.03 mmol, 3.3 eq) at room temperature. The reaction mixture was heated to 65° C. and stirred for 1 h. The reaction was monitored by LC-MS. Upon complete consumption of starting material, the reaction was quenched with 1N HCl (2 mL). The precipitate was collected by filtration then washed with Et$_2$O to afford the title compound as a yellow solid (121 mg, 0.39 mmol, 14% over three steps).

$^1$H NMR (500 MHz, CHCl$_3$-d) δ ppm 1.21 (t, J=7.54 Hz, 3H) 2.04 (dt, J=12.24, 6.14 Hz, 2H) 2.62 (q, J=7.54 Hz, 2H) 2.82 (t, J=6.38 Hz, 2H) 3.01 (s, 3H) 3.33-3.42 (m, 2H) 6.66 (d, J=8.59 Hz, 1H) 7.06 (s, 1H) 7.19 (dd, J=8.47, 2.25 Hz, 1H) 8.49 (s, 1H) 13.94 (s, 1H).

LC-MS 311.1 [M−H]$^−$, 313.1 [M+H]$^+$, RT 0.77 min. (1 min Method).

Example 2

5-ethyl-4-hydroxy-6-(1-methyl-1,2,3,4-tetrahydroquinolin-6-yl)-2-oxo-1,2-dihydropyridine-3-carboxylic acid (Cpd 2)

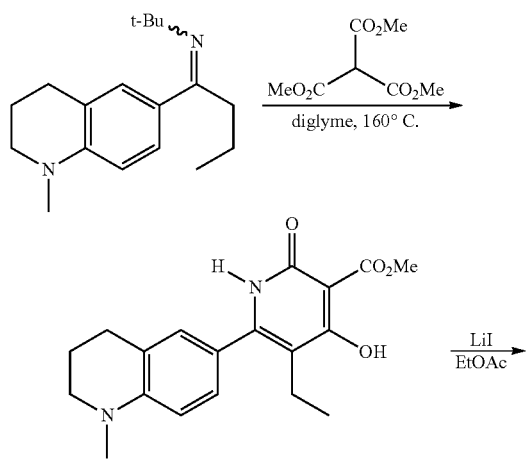

Step 1: Preparation of methyl 5-ethyl-4-hydroxy-6-(1-methyl-1,2,3,4-tetrahydroquinolin-6-yl)-2-oxo-1,2-dihydropyridine-3-carboxylate

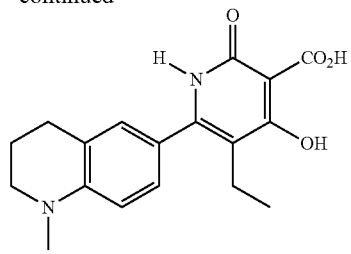

To a suspension of 2-methyl-N-(1-(1-methyl-1,2,3,4-tetrahydroquinolin-6-yl)butylidene)propan-2-amine (1.96 g, ca. 7.2 mmol), prepared according to procedure described in Example 1 Step 6, in diglyme (7 mL) was added trimethyl methanetricarboxylate (2.33 g, 12.2 mmol, 1.7 eq). The reaction was stirred at 160° C. for 4 h then cooled to room temperature. The precipitate was collected by filtration then washed with Et$_2$O to afford the title compound as a yellow solid (150 mg, 0.44 mmol, 6.5% over two steps).

$^1$H NMR (500 MHz, CHCl$_3$-d) δ ppm 1.17 (t, J=7.37 Hz, 3H) 1.95-2.08 (m, 2H) 2.51 (q, J=7.38 Hz, 2H) 2.79 (t, J=6.31 Hz, 2H) 2.97 (s, 3H) 3.29-3.37 (m, 2H) 4.01 (s, 3H) 6.61 (d, J=8.83 Hz, 1H) 7.00 (d, J=1.66 Hz, 1H) 7.14 (dd, J=8.55, 2.32 Hz, 1H) 13.81 (s, 1H).

LC-MS 342.9 [M+H]$^+$, RT 0.86 min. (1 min Method).

Step 2: Preparation of 5-ethyl-4-hydroxy-6-(1-methyl-1,2,3,4-tetrahydroquinolin-6-yl)-2-oxo-1,2-dihydropyridine-3-carboxylic acid To a suspension of methyl 5-ethyl-4-hydroxy-6-(1-methyl-1,2,3,4-tetrahydroquinolin-6-yl)-2-oxo-1,2-dihydropyridine-3-carboxylate (34 mg, 0.1 mmol) in EtOAc (1 mL) was added lithium iodide (40 mg, ca. 0.3 mmol, 3.0 eq) at room temperature. The mixture was heated to 65° C. and stirred for 1 h. The reaction mixture was diluted by EtOAc (2 mL) then quenched with 1N HCl (0.5 mL). The precipitate was collected by filtration then washed with Et$_2$O to afford the title compound as a yellow solid (20 mg, 0.061 mmol, 61%).

$^1$H NMR (500 MHz, CHCl$_3$-d) δ ppm 1.16 (t, J=7.37 Hz, 3H) 2.12-2.23 (m, 2H) 2.53 (q, J=7.41 Hz, 2H) 2.90 (t, J=6.42 Hz, 2H) 3.10 (s, 3H) 3.40-3.52 (m, 2H) 7.06-7.12 (m, 1H) 7.14 (s, 1H) 7.21-7.27 (m, 1H) 13.73 (s, 1H) 14.60 (s, 1H).

LC-MS 326.7 [M−H]$^−$, 329.0 [M+H]$^+$, RT 0.89 min. (1 min Method).

Example 3

5-ethyl-6-(4-methyl-3,4-dihydro-2H-benzo[b][1,4]oxazin-7-yl)-2-oxo-1,2-dihydropyridine-3-carboxylic acid (Cpd 3)

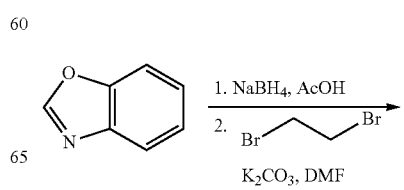

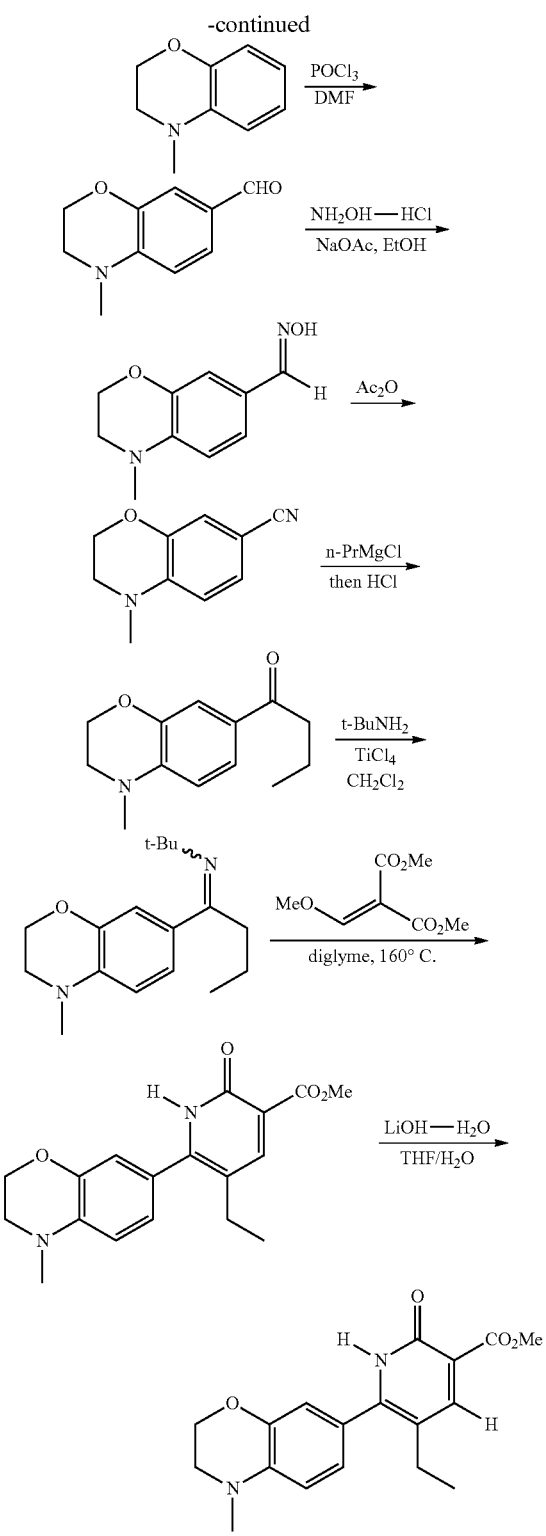

Step 1: Preparation of
4-methyl-3,4-dihydro-2H-benzo[b][1,4]oxazine

The title compound was prepared according to the literature procedure. (*J. Chem. Soc., Chem. Commun.*, 1992, 5, 404-6.)

$^1$H NMR (500 MHz, CHCl$_3$-d) δ ppm 2.90 (s, 3H) 3.25-3.30 (m, 2H) 4.29-4.34 (m, 2H) 6.63-6.72 (m, 2H) 6.78 (dd, J=7.88, 1.50 Hz, 1H) 6.82-6.89 (m, 1H). LC-MS 150.0 [M+H]$^+$, RT 1.13 min.

Step 2: Preparation of 4-methyl-3,4-dihydro-2H-benzo[b][1,4]oxazine-7-carbaldehyde The title compound was prepared according to the procedure described in Example 1, Step 2.

$^1$H NMR (500 MHz, CHCl$_3$-d) δ ppm 3.03 (s, 3H) 3.40-3.49 (m, 2H) 4.23-4.31 (m, 2H) 6.68 (d, J=8.35 Hz, 1H) 7.29 (d, J=1.89 Hz, 1H) 7.40 (dd, J=8.32, 1.93 Hz, 1H) 9.71 (s, 1H). LC-MS 178.1 [M+H]$^+$, RT 0.94 min.

Step 3: Preparation of 4-methyl-3,4-dihydro-2H-benzo[b][1,4]oxazine-7-carbaldehyde oxime The title compound was prepared according to procedure described in Example 1, Step 3.

LC-MS 193.1 [M+H]$^+$, RT 0.63 min. (1 min Method).

Step 4: Preparation of 4-methyl-3,4-dihydro-2H-benzo[b][1,4]oxazine-7-carbonitrile The title compound was prepared according to procedure described in Example 1, Step 4.

$^1$H NMR (500 MHz, CHCl$_3$-d) δ ppm 2.97 (s, 3H) 3.35-3.43 (m, 2H) 4.23-4.29 (m, 2H) 6.59 (d, J=8.43 Hz, 1H) 6.99 (d, J=1.97 Hz, 1H) 7.14 (dd, J=8.39, 1.93 Hz, 1H). LC-MS 175.2 [M+H]$^+$, RT 0.69 min. (1 min Method).

Step 5: Preparation of 1-(4-methyl-3,4-dihydro-2H-benzo[b][1,4]oxazin-7-yl)butan-1-one The title compound was prepared according to procedure described in Example 1, Step 5.

$^1$H NMR (500 MHz, CHCl$_3$-d) δ ppm 0.99 (t, J=7.41 Hz, 3H) 1.68-1.80 (m, 2H) 2.78-2.87 (m, 2H) 3.00 (s, 3H) 3.37-3.43 (m, 2H) 4.25-4.30 (m, 2H) 6.63 (d, J=8.51 Hz, 1H) 7.41 (d, J=2.05 Hz, 1H) 7.54 (dd, J=8.51, 2.05 Hz, 1H). LC-MS 220.2 [M+H]$^+$, RT 0.79 min. (1 min Method).

Step 6: Preparation of 2-methyl-N-(1-(4-methyl-3,4-dihydro-2H-benzo[b][1,4]oxazin-7-yl)butylidene) propan-2-amine The title compound was prepared according to procedure described in Example 1, Step 6.

LC-MS 275.4 [M+H]$^+$, RT 0.67 min. (1 min Method).

Step 7-8: 5-ethyl-6-(4-methyl-3,4-dihydro-2H-benzo[b][1,4]oxazin-7-yl)-2-oxo-1,2-dihydropyridine-3-carboxylic acid The title compound was prepared according to procedure described in Example 1, Step 7-8.

$^1$H NMR (500 MHz, CHCl$_3$-d) δ ppm 1.20 (t, J=7.53 Hz, 3H) 2.62 (q, J=7.57 Hz, 2H) 3.02 (s, 3H) 3.38-3.47 (m, 2H) 4.29-4.44 (m, 2H) 6.79 (d, J=8.43 Hz, 1H) 6.91 (d, J=2.13 Hz, 1H) 6.99 (dd, J=8.32, 2.17 Hz, 1H) 8.50 (s, 1H) 11.89 (br. s., 1H) 13.76 (br. s., 1H). LC-MS 313.0 [M−H]$^-$, 315.3 [M+H]$^+$, RT 0.71 min. (1 min Method).

Example 4

5-ethyl-4-hydroxy-6-(4-methyl-3,4-dihydro-2H-benzo[b][1,4]oxazin-7-yl)-2-oxo-1,2-dihydropyridine-3-carboxylic acid (Cpd 4)

Step 1: Preparation of methyl 5-ethyl-4-hydroxy-6-(4-methyl-3,4-dihydro-2H-benzo[b][1,4]oxazin-7-yl)-2-oxo-1,2-dihydropyridine-3-carboxylate The title compound was prepared according to procedure described in Example 2, Step 1.

LC-MS 343.0 [M−H]⁻, 345.4 [M+H]⁺, RT 0.77 min. (1 min Method).

Step 2: Preparation of 5-ethyl-4-hydroxy-6-(4-methyl-3,4-dihydro-2H-benzo[b][1,4]oxazin-7-yl)-2-oxo-1,2-dihydropyridine-3-carboxylic acid The title compound was prepared according to procedure described in Example 2, Step 2.

$^1$H NMR (500 MHz, DMSO-$d_6$) δ ppm 1.03 (t, J=7.37 Hz, 3H) 2.31-2.42 (m, 2H) 2.92 (s, 3H) 3.29-3.36 (m, 2H) 4.21-4.32 (m, 2H) 6.74-6.84 (m, 2H) 6.90 (dd, J=8.35, 2.13 Hz, 1H) 12.53 (br. s., 1H) 13.87 (s, 1H). LC-MS 329.0 [M−H]⁻, 331.1 [M+H]⁺, RT 1.27 min.

Example 5

5-ethyl-6-(1-methylindolin-5-yl)-2-oxo-1,2-dihydropyridine-3-carboxylic acid (Cpd 5)

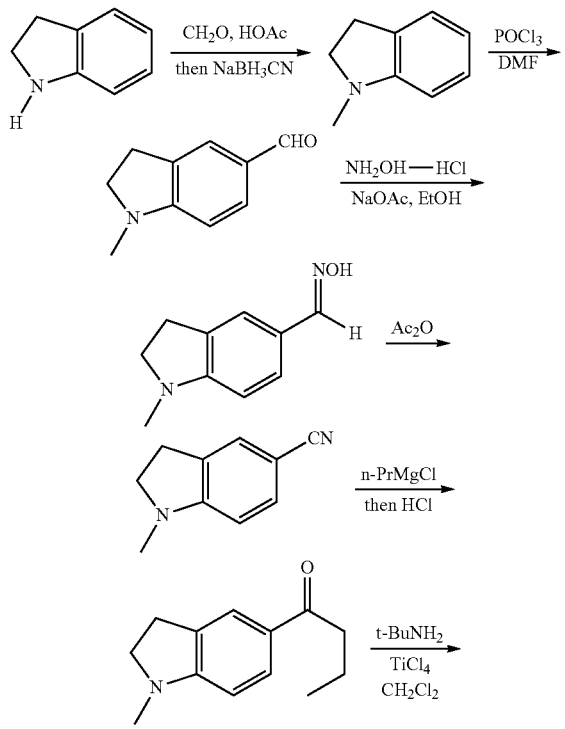

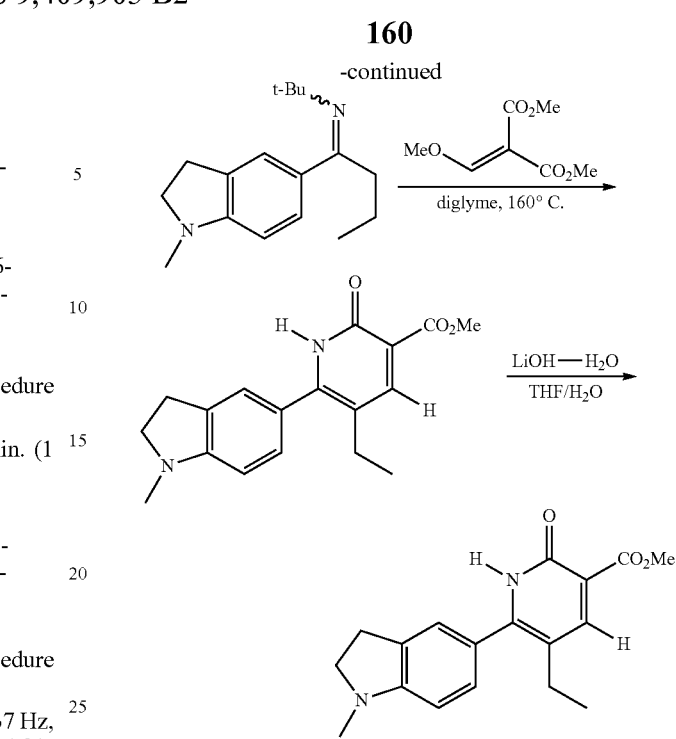

Step 1: Preparation of 1-methylindoline

The title compound was prepared according to procedure described in Example 1, Step 1.

$^1$H NMR (500 MHz, CHCl$_3$-d) δ ppm 2.78 (s, 3H) 2.89-2.99 (m, 2H) 3.25-3.35 (m, 2H) 6.46-6.56 (m, 1H) 6.67-6.75 (m, 1H) 7.08-7.14 (m, 2H).

Step 2: Preparation of 1-methylindoline-5-carbaldehyde

The title compound was prepared according to procedure described in Example 1, Step 2.

$^1$H NMR (500 MHz, CHCl$_3$-d) δ ppm 2.89 (s, 3H) 3.01-3.08 (m, 2H) 3.53-3.60 (m, 2H) 6.40 (d, J=8.12 Hz, 1H) 7.53-7.62 (m, 2H) 9.68 (s, 1H). LC-MS 161.9 [M+H]⁺, RT 0.67 min. (1 min Method).

Step 3: Preparation of 1-methylindoline-5-carbaldehyde oxime

The title compound was prepared according to procedure described in Example 1, Step 3.

LC-MS 177.0 [M+H]⁺, RT 0.61 min. (1 min Method).

Step 4: Preparation of 1-methylindoline-5-carbonitrile

The title compound was prepared according to procedure described in Example 1, Step 4.

$^1$H NMR (500 MHz, CHCl$_3$-d) δ ppm 2.84 (s, 3H) 3.00 (t, J=8.47 Hz, 2H) 3.44-3.54 (m, 2H) 6.35 (d, J=8.20 Hz, 1H) 7.19-7.25 (m, 1H) 7.34-7.40 (m, 1H). LC-MS 159.1 [M+H]⁺, RT 0.74 min. (1 min Method).

Step 5: Preparation of 1-(1-methylindolin-5-yl)butan-1-one

The title compound was prepared according to procedure described in Example 1, Step 5.

¹H NMR (500 MHz, CHCl₃-d) δ ppm 1.00 (t, J=7.41 Hz, 3H) 1.69-1.80 (m, 2H) 2.78-2.87 (m, 2H) 2.86 (s, 3H) 3.02 (t, J=8.39 Hz, 2H) 3.45-3.53 (m, 2H) 6.37 (d, J=8.35 Hz, 1H) 7.68-7.72 (m, 1H) 7.78 (dd, J=8.35, 1.81 Hz, 1H). LC-MS 204.0 [M+H]⁺, RT 0.83 min. (1 min Method).

Step 6: Preparation of 2-methyl-N-(1-(1-methylindolin-5-yl)butylidene)propan-2-amine The title compound was prepared according to procedure described in Example 1, Step 6.
LC-MS 259.0 [M+H]⁺, RT 0.62 min. (1 min Method).

Step 7-8: Preparation of 5-ethyl-6-(1-methylindolin-5-yl)-2-oxo-1,2-dihydropyridine-3-carboxylic acid The title compound was prepared according to procedure described in Example 1, Step 7-8.
¹H NMR (500 MHz, DMSO-d₆) δ ppm 1.05 (t, J=7.53 Hz, 3H) 2.46 (q, J=7.53 Hz, 2H) 2.79 (s, 3H) 2.96 (t, J=8.35 Hz, 2H) 3.40 (t, J=8.35 Hz, 2H) 6.59 (d, J=8.67 Hz, 1H) 7.07-7.19 (m, 2H) 8.30 (s, 1H) 12.96 (br. s., 1H) 15.01 (s, 1H). LC-MS 297.1 [M−H]⁻, 299.3 [M+H]⁺, RT 1.10 min.

Example 6

5-ethyl-4-hydroxy-6-(1-methylindolin-5-yl)-2-oxo-1,2-dihydropyridine-3-carboxylic acid Step 1: Preparation of methyl 5-ethyl-4-hydroxy-6-(1-methylindolin-5-yl)-2-oxo-1,2-dihydropyridine-3-carboxylate The title compound was prepared according to procedure described in Example 2, Step 1.
¹H NMR (500 MHz, CHCl₃-d) δ ppm 1.14 (t, J=7.37 Hz, 3H) 2.48 (q, J=7.36 Hz, 2H) 2.84 (s, 3H) 3.03 (t, J=8.35 Hz, 2H) 3.47 (t, J=8.35 Hz, 2H) 4.00 (s, 3H) 6.47 (d, J=8.12 Hz, 1H) 7.08 (d, J=1.34 Hz, 1H) 7.13 (dd, J=8.12, 1.89 Hz, 1H) 13.82 (s, 1H). LC-MS 328.8 [M+H]⁺, RT 0.79 min. (1 min Method).

Step 2: Preparation of 5-ethyl-4-hydroxy-6-(1-methylindolin-5-yl)-2-oxo-1,2-dihydropyridine-3-carboxylic acid The title compound was prepared according to procedure described in Example 2, Step 2.
¹H NMR (500 MHz, DMSO-d₆) δ ppm 1.03 (t, J=7.37 Hz, 3H) 2.37 (q, J=7.36 Hz, 2H) 2.79 (s, 3H) 2.96 (t, J=8.35 Hz, 2H) 3.40 (t, J=8.35 Hz, 2H) 6.55-6.68 (m, 1H) 7.05-7.17 (m, 2H) 12.51 (br. s., 1H) 13.85 (br. s., 1H). LC-MS 312.6 [M−H]⁻, 314.8 [M+H]⁺, RT 0.84 min. (1 min Method).

Example 7

5-ethyl-6-(1-methyl-1H-indol-6-yl)-2-oxo-1,2-dihydropyridine-3-carboxylic acid

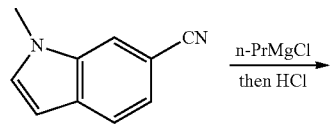

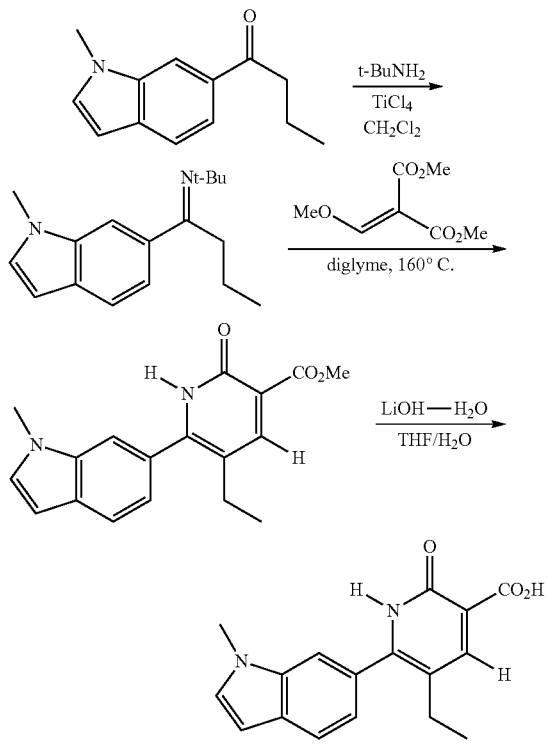

Step 1: Preparation of 1-(1-methyl-1H-indol-6-yl)butan-1-one

The title compound was prepared according to procedure described in Example 1, Step 5.
¹H NMR (500 MHz, CHCl₃-d) δ ppm 1.05 (t, J=7.41 Hz, 3H) 1.77-1.89 (m, 2H) 3.01-3.09 (m, 2H) 3.88 (s, 3H) 6.53 (dd, J=3.07, 0.87 Hz, 1H) 7.22-7.25 (m, 1H) 7.65 (dd, J=8.35, 0.63 Hz, 1H) 7.75 (dd, J=8.35, 1.50 Hz, 1H) 8.04-8.08 (m, 1H). LC-MS 202.2 [M+H]⁺, RT 1.29 min.

Step 2: Preparation of 2-methyl-N-(1-(1-methyl-1H-indol-6-yl)butylidene)propan-2-amine The title compound was prepared according to procedure described in Example 1, Step 6.
LC-MS 257.2 [M+H]⁺, RT 0.93 min.

Step 3-4: Preparation of 5-ethyl-6-(1-methyl-1H-indol-6-yl)-2-oxo-1,2-dihydropyridine-3-carboxylic acid The title compound was prepared according to procedure described in Example 1, Step 7-8.
¹H NMR (500 MHz, DMSO-d₆) δ ppm 1.05 (t, J=7.49 Hz, 3H) 2.48 (q, J=7.49 Hz, 2H) 3.31 (s, 3H) 6.53 (dd, J=2.99, 0.71 Hz, 1H) 7.13 (dd, J=8.12, 1.50 Hz, 1H) 7.51 (d, J=3.07 Hz, 1H) 7.61-7.73 (m, 2H) 8.39 (s, 1H) 13.18 (br. s., 1H) 15.04 (br. s., 1H). LC-MS 295.0 [M−H]⁻, 297.1 [M+H]⁺, RT 1.12 min.

Example 8

5-ethyl-4-hydroxy-6-(1-methyl-1H-indol-6-yl)-2-oxo-1,2-dihydropyridine-3-carboxylic acid

Step 1: Preparation of methyl 5-ethyl-4-hydroxy-6-(1-methyl-1H-indol-6-yl)-2-oxo-1,2-dihydropyridine-3-carboxylate The title compound was prepared according to procedure described in Example 2, Step 1.

$^1$H NMR (500 MHz, CHCl$_3$-d) δ ppm 1.17 (t, J=7.41 Hz, 3H) 2.54 (dt, J=7.37, 0.77 Hz, 2H) 3.87 (s, 3H) 4.02 (s, 3H) 6.57 (dd, J=3.15, 0.87 Hz, 1H) 7.15 (d, J=6.54 Hz, 1H) 7.21 (d, J=3.15 Hz, 1H) 7.41-7.44 (m, 1H) 7.70-7.74 (m, 1H) 12.29 (s, 1H) 13.89 (s, 1H). LC-MS 325.0 [M−H]$^-$, 327.1 [M+H]$^+$, RT 1.24 min.

Step 2: Preparation of 5-ethyl-4-hydroxy-6-(1-methyl-1H-indol-6-yl)-2-oxo-1,2-dihydropyridine-3-carboxylic acid The title compound was prepared according to procedure described in Example 2, Step 2.

$^1$H NMR (500 MHz, CHCl$_3$-d) δ ppm 1.16 (t, J=7.41 Hz, 3H) 2.55 (q, J=7.36 Hz, 2H) 3.87 (s, 3H) 6.60 (dd, J=3.07, 0.87 Hz, 1H) 7.14 (dd, J=8.12, 1.58 Hz, 1H) 7.23-7.26 (m, 1H) 7.37-7.40 (m, 1H) 7.76 (dd, J=8.12, 0.63 Hz, 1H) 13.92 (s, 1H) 14.92 (s, 1H). LC-MS 311.0 [M−H]$^-$, 313.1 [M+H]$^+$, RT 1.30 min.

Example 9

5-ethyl-6-(1-ethyl-1H-indol-5-yl)-2-oxo-1,2-dihydropyridine-3-carboxylic acid

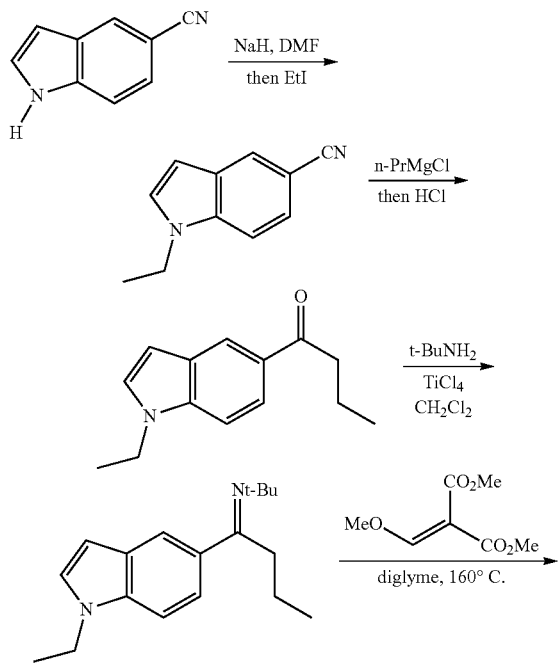

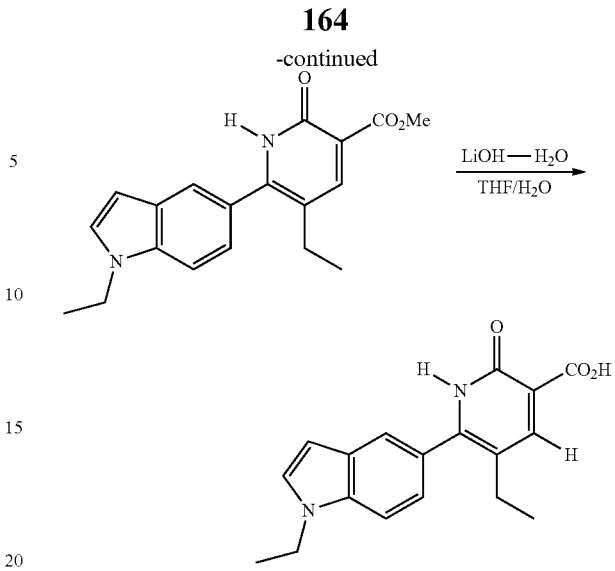

Step 1: Preparation of 1-ethyl-1H-indole-5-carbonitrile

To a solution of 1H-indole-5-carbonitrile (2.0 g, 14.1 mmol) in DMF (30 mL) was added NaH (60% suspension in mineral oil, 0.81 g, 20.3 mmol, 1.4 eq) at 0° C. The mixture was stirred at 0° C. for 30 min before EtI (1.35 mL, 16.9 mmol, 1.2 eq) was added. The reaction was allowed to warm to room temperature and stirred overnight. The reaction was quenched with H$_2$O then extracted by Et$_2$O (3×40 mL). The combined organic layers were washed with H$_2$O (50 mL) then dried over Na$_2$SO$_4$. The solvent was removed to afford crude product (2.57 g, ca. 14.1 mmol) which was used in the next step without further purification.

$^1$H NMR (500 MHz, CHCl$_3$-d) δ ppm 1.50 (t, J=7.33 Hz, 3H) 4.22 (q, J=7.30 Hz, 2H) 6.59 (dd, J=3.23, 0.79 Hz, 1H) 7.25 (d, J=3.23 Hz, 1H) 7.40 (d, J=8.59 Hz, 1H) 7.45 (dd, J=8.51, 1.42 Hz, 1H) 7.99 (dd, J=1.50, 0.71 Hz, 1H). LC-MS 171.1 [M+H]$^+$, RT 1.19 min.

Step 2: Preparation of 1-(1-ethyl-1H-indol-5-yl)butan-1-one

The title compound was prepared according to procedure described in Example 1, Step 5.

$^1$H NMR (500 MHz, CHCl$_3$-d) δ ppm 1.04 (t, J=7.35 Hz, 3H) 1.49 (t, J=7.29 Hz, 3H) 1.76-1.87 (m, 2H) 2.96-3.07 (m, 2H) 4.22 (q, J=7.30 Hz, 2H) 6.62 (dd, J=3.19, 0.83 Hz, 1H) 7.19 (d, J=3.23 Hz, 1H) 7.37 (d, J=8.75 Hz, 1H) 7.91 (dd, J=8.67, 1.66 Hz, 1H) 8.32 (dd, J=1.69, 0.51 Hz, 1H). LC-MS 216.4 [M+H]$^+$, RT 0.87 min. (1 min Method).

Step 3: Preparation of N-(1-(1-ethyl-1H-indol-5-yl)butylidene)-2-methylpropan-2-amine The title compound was prepared according to procedure described in Example 1, Step 6.

LC-MS 269.0 [M−H]$^-$, 271.4 [M+H]$^+$, RT 0.68 min. (1 min Method).

Step 4-5: Preparation of 5-ethyl-6-(1-ethyl-1H-indol-5-yl)-2-oxo-1,2-dihydropyridine-3-carboxylic acid The title compound was prepared according to procedure described in Example 1, Step 7-8.

¹H NMR (500 MHz, CHCl₃-d) δ ppm 1.19 (t, J=7.53 Hz, 3H) 1.54 (t, J=7.28 Hz, 3H) 2.63 (q, J=7.57 Hz, 2H) 4.27 (q, J=7.28 Hz, 2H) 6.63 (dd, J=3.15, 0.79 Hz, 1H) 7.26-7.31 (m, 2H) 7.52 (d, J=8.59 Hz, 1H) 7.69-7.77 (m, 1H) 8.56 (s, 1H) 13.84 (s, 1H). LC-MS 309.0 [M−H]⁻, 311.1 [M+H]⁺, RT 1.15 min.

Example 10

5-ethyl-6-(1-ethyl-1H-indol-5-yl)-4-hydroxy-2-oxo-1,2-dihydropyridine-3-carboxylic acid Step 1: Preparation of methyl 5-ethyl-6-(1-ethyl-1H-indol-5-yl)-4-hydroxy-2-oxo-1,2-dihydropyridine-3-carboxylate The title compound was prepared according to procedure described in Example 2, Step 1.
¹H NMR (500 MHz, CHCl₃-d) δ ppm 1.13 (t, J=7.30 Hz, 3H) 1.52 (t, J=7.33 Hz, 3H) 2.49 (q, J=7.36 Hz, 2H) 3.99 (s, 3H) 4.24 (q, J=7.30 Hz, 2H) 6.58 (dd, J=3.15, 0.79 Hz, 1H) 7.18-7.27 (m, 2H) 7.45 (d, J=8.51 Hz, 1H) 7.68 (dd, J=1.69, 0.59 Hz, 1H) 13.85 (s, 1H).
LC-MS 339.1 [M−H]⁻, 341.1 [M+H]⁺, RT 1.28 min.

Step 2: Preparation of 5-ethyl-6-(1-ethyl-1H-indol-5-yl)-4-hydroxy-2-oxo-1,2-dihydropyridine-3-carboxylic acid The title compound was prepared according to procedure described in Example 2, Step 2.
¹H NMR (500 MHz, CHCl₃-d) δ ppm 1.15 (t, J=7.41 Hz, 3H) 1.54 (t, J=7.33 Hz, 3H) 2.56 (q, J=7.38 Hz, 2H) 4.26 (q, J=7.33 Hz, 2H) 6.61 (dd, J=3.15, 0.79 Hz, 1H) 7.23 (dd, J=8.47, 1.77 Hz, 1H) 7.26-7.28 (m, 1H) 7.47-7.53 (m, 1H) 7.70 (d, J=1.18 Hz, 1H) 13.84 (s, 1H) 14.80 (s, 1H). LC-MS 325.1 [M−H]⁻, 327.1 [M+H]⁺, RT 1.35 min.

Example 11

5-ethyl-4-hydroxy-6-(3-methyl-2-oxo-2,3-dihydrobenzo[d]oxazol-6-yl)-2-oxo-1,2-dihydropyridine-3-carboxylic acid

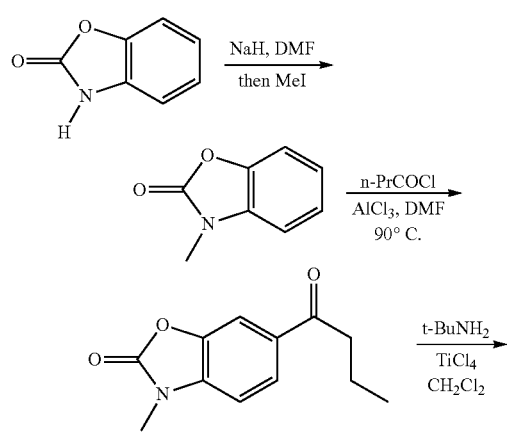

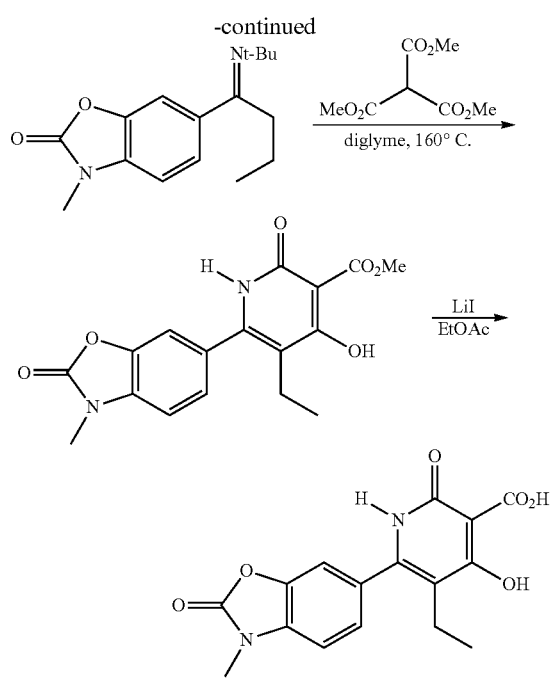

Step 1: Preparation of 3-methylbenzo[d]oxazol-2(3H)-one

The title compound was prepared according to procedure described in Example 9, Step 1.
¹H NMR (500 MHz, CHCl₃-d) δ ppm 3.42 (s, 3H) 6.94-7.00 (m, 1H) 7.10-7.16 (m, 1H) 7.17-7.24 (m, 2H). LC-MS 150.2 [M+H]⁺, RT 0.62 min. (1 min Method).

Step 2: 6-butyryl-3-methylbenzo[d]oxazol-2(3H)-one

The title compound was prepared according to a modified literature procedure (*J. Heterocyclic Chem.*, 1992, 29, 171-175). The product (5.9 g, 39.6 mmol) from Step 1 was employed in the Friedel-Crafts reaction to give a solid upon workup. The crude product (6.0 g) was suspended in CH₂Cl₂ (20 mL) then heated to reflux. Hexane (20 mL) was added slowly to the hot homogeneous solution then heat was removed and the mixture was cooled to room temperature The precipitate was collected by filtration then washed with hexanes to afford 6-butyryl-3-methylbenzo[d]oxazol-2(3H)-one (1.1 g, 5.0 mmol, 13% yield over two steps).
¹H NMR (500 MHz, CHCl₃-d) δ ppm 1.03 (t, J=7.41 Hz, 3H) 1.73-1.86 (m, 2H) 2.94 (t, J=7.29 Hz, 2H) 3.46 (s, 3H) 7.02 (d, J=8.20 Hz, 1H) 7.83 (dd, J=1.50, 0.39 Hz, 1H) 7.91 (dd, J=8.20, 1.58 Hz, 1H). LC-MS 220.4 [M+H]⁺, RT 0.73 min. (1 min Method).

Step 3: 6-(1-(tert-butylimino)butyl)-3-methylbenzo[d]oxazol-2(3H)-one

The title compound was prepared according to procedure described in Example 1, Step 6.
LC-MS 275.4 [M+H]⁺, RT 0.54 min. (1 min Method).

Step 4: Preparation of methyl 5-ethyl-4-hydroxy-6-(3-methyl-2-oxo-2,3-dihydrobenzo[d]oxazol-6-yl)-2-oxo-1,2-dihydropyridine-3-carboxylate The title compound was prepared according to procedure described in Example 2, Step 1.

¹H NMR (500 MHz, CHCl₃-d) δ ppm 1.11 (t, J=7.37 Hz, 3H) 2.42 (q, J=7.40 Hz, 2H) 3.48 (s, 3H) 3.98 (s, 3H) 7.09 (d, J=8.04 Hz, 1H) 7.28 (dd, J=8.04, 1.58 Hz, 1H) 7.31-7.36 (m, 1H) 13.90 (s, 1H). LC-MS 343.2 [M−H]⁻, 345.5 [M+H]⁺, RT 0.69 min. (1 min Method).

Step 5: Preparation of 5-ethyl-4-hydroxy-6-(3-methyl-2-oxo-2,3-dihydrobenzo[d]oxazol-6-yl)-2-oxo-1,2-dihydropyridine-3-carboxylic acid The title compound was prepared according to procedure described in Example 2, Step 2.

¹H NMR (500 MHz, CHCl₃-d) δ ppm 1.13 (t, J=7.41 Hz, 3H) 2.48 (q, J=7.46 Hz, 2H) 3.50 (s, 3H) 7.14 (d, J=8.43 Hz, 1H) 7.26-7.33 (m, 2H) 13.92 (s, 1H) 14.50 (s, 1H). LC-MS 329.0 [M−H]⁻, 331.0 [M+H]⁺, RT 1.08 min.

Example 12

5-ethyl-4-hydroxy-6-(2-methylbenzo[d]oxazol-6-yl)-2-oxo-1,2-dihydropyridine-3-carboxylic acid

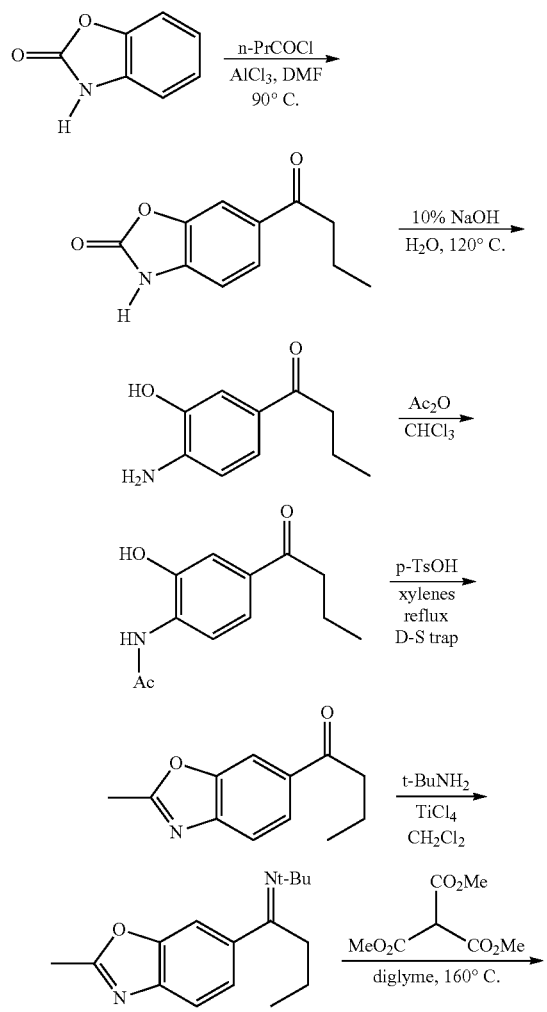

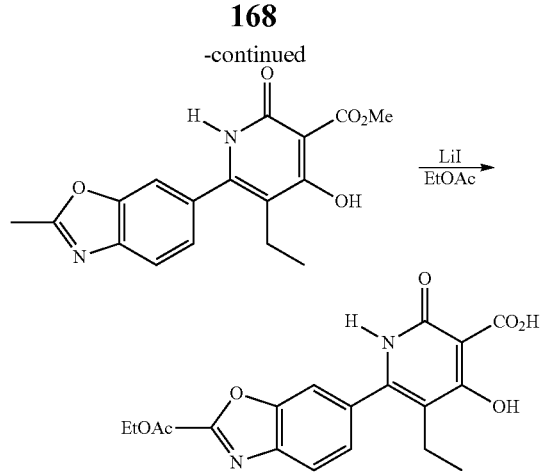

Step 1: Preparation of 6-butyrylbenzo[d]oxazol-2(3H)-one

The title compound was prepared according to procedure described in Example 11 Step 2.

¹H NMR (500 MHz, CHCl₃-d) δ ppm 1.03 (t, J=7.41 Hz, 3H) 1.74-1.85 (m, 2H) 2.90-2.98 (m, 2H) 7.14 (d, J=8.20 Hz, 1H) 7.85 (s, 1H) 7.88 (dd, J=8.16, 1.54 Hz, 1H) 8.45 (br. s., 1H). LC-MS 204.0 [M−H]⁻, 206.1 [M+H]⁺, RT 0.99 min.

Step 2: Preparation of 1-(4-amino-3-hydroxyphenyl)butan-1-one

The title compound was prepared according to literature procedure (*Synthesis*, 1990, 679-680).

¹H NMR (500 MHz, CHCl₃-d) δ ppm 1.00 (t, J=7.41 Hz, 3H) 1.69-1.82 (m, 2H) 2.81-2.90 (m, 2H) 6.68 (d, J=8.20 Hz, 1H) 7.45 (dd, J=8.12, 1.89 Hz, 1H) 7.57 (d, J=1.81 Hz, 1H). LC-MS 178.1 [M−H]⁻, 180.1 [M+H]⁺, RT 0.59 min. (1 min Method).

Step 3: Preparation of N-(4-butyryl-2-hydroxyphenyl)acetamide

To a solution of 1-(4-amino-3-hydroxyphenyl)butan-1-one (0.71 g, 4.0 mmol) in CHCl₃ (8 mL) was added Ac₂O (0.4 mL, 4.2 mmol, 1.06 eq) at 0° C. After 5 min, reaction was quenched with H₂O then extracted with CH₂Cl₂ (3×30 mL). Solvent was removed under reduced pressure to afford N-(4-butyryl-2-hydroxyphenyl)acetamide (0.81 g, 3.7 mmol, 93%) with ca. 80% purity which was used in the next step without further purification.

¹H NMR (500 MHz, CHCl₃-d) δ ppm 1.01 (t, J=7.41 Hz, 3H) 1.70-1.82 (m, 2H) 2.31 (s, 3H) 2.87-2.95 (m, 2H) 7.31 (d, J=8.28 Hz, 1H) 7.51 (dd, J=8.32, 1.93 Hz, 1H) 7.58 (br. s., 1H) 7.61 (d, J=1.97 Hz, 1H). LC-MS 219.9 [M−H]⁻, 222.3 [M+H]⁺, RT 0.92 min.

Step 4: Preparation of 1-(2-methylbenzo[d]oxazol-6-yl)butan-1-one

To a suspension of N-(4-butyryl-2-hydroxyphenyl)acetamide (0.81 g, 3.7 mmol) in xylenes (3 mL) was added p-TsOH (0.7 g, 3.7 mmol, 1.0 eq) at room temperature then the mixture was heated to 160° C. and stirred overnight. The solvent was removed under reduced pressure then saturated aqueous NaHCO₃ was added and the biphasic mixture was extracted by CH₂Cl₂ (4×20 mL). The solvent was concentrated to give a crude product which was purified by flash column chromatography (0-25% EtOAc in hexanes) to afford the title compound as a light yellow solid (262 mg, 1.3 mmol, 35%).

$^1$H NMR (500 MHz, CHCl$_3$-d) δ ppm 1.04 (t, J=7.41 Hz, 3H) 1.82 (sxt, J=7.36 Hz, 2H) 2.70 (s, 3H) 2.97-3.04 (m, 2H) 7.70 (dd, J=8.31, 0.51 Hz, 1H) 7.98 (dd, J=8.35, 1.58 Hz, 1H) 8.11 (dd, J=1.54, 0.59 Hz, 1H). LC-MS 204.5 [M+H]$^+$, RT 1.12 min.

Step 5-6: Preparation of methyl 5-ethyl-4-hydroxy-6-(2-methylbenzo[d]oxazol-6-yl)-2-oxo-1,2-dihydropyridine-3-carboxylate The title compound was prepared according to procedures described in Example 1, Step 6 and Example 2, Step 1.

LC-MS 327.1 [M−H]$^-$, 329.5 [M+H]$^+$, RT 1.05 min.

Step 7: Preparation of 5-ethyl-4-hydroxy-6-(2-methylbenzo[d]oxazol-6-yl)-2-oxo-1,2-dihydropyridine-3-carboxylic acid The title compound was prepared according to procedure described in Example 2, Step 2.

$^1$H NMR (500 MHz, CHCl$_3$-d) δ ppm 1.13 (t, J=7.41 Hz, 3H) 2.49 (q, J=7.43 Hz, 2H) 2.73 (s, 3H) 7.37 (dd, J=8.20, 1.66 Hz, 1H) 7.57 (d, J=1.18 Hz, 1H) 7.82 (d, J=8.20 Hz, 1H) 9.90 (br. s., 1H) 13.95 (s, 1H) 14.52 (s, 1H). LC-MS 313.1 [M−H]$^-$, 315.5 [M+H]$^+$, RT 0.71 min. (1 min Method).

Example 13

5-ethyl-6-(1-methyl-1H-indol-3-yl)-2-oxo-1,2-dihydropyridine-3-carboxylic acid

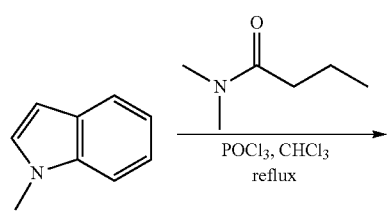

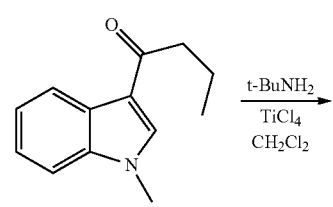

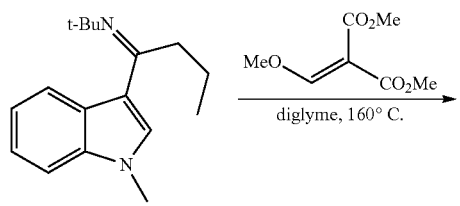

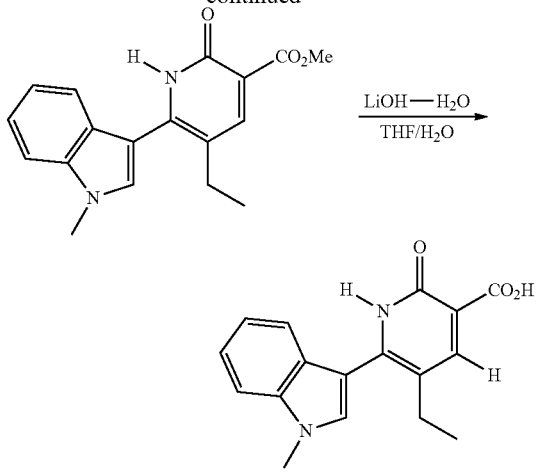

Step 1: Preparation of 1-(1-methyl-1H-indol-3-yl)butan-1-one

To a solution of 1-methyl-1H-indole (5.9 g, 45.0 mmol) in CHCl$_3$ (150 mL) was added N,N-dimethylbutyramide (5.8 g, 50.4 mmol, 1.1 eq) followed by POCl$_3$ (5.0 mL, 53.5 mmol, 1.2 eq) at 0° C. Then mixture was heated to reflux and stirred for 2 h. The reaction was quenched with saturated aqueous NaHCO$_3$ then stirred for 30 min at room temperature. The mixture was extracted by CH$_2$Cl$_2$ (3×40 mL) and combined organic layers were dried over Na$_2$SO$_4$. The crude product was purified by flash column chromatography (0-50% EtOAc in hexanes) to afford 1-(1-methyl-1H-indol-3-yl)butan-1-one (6.53 g, 32.4 mmol, 72%).

$^1$H NMR (500 MHz, CHCl$_3$-d) δ ppm 1.03 (t, J=7.41 Hz, 3H) 1.76-1.88 (m, 2H) 2.80-2.87 (m, 2H) 3.87 (s, 3H) 7.29-7.40 (m, 3H) 7.74 (s, 1H) 8.36-8.45 (m, 1H). LC-MS 202.4 [M+H]$^+$, RT 1.21 min.

Step 2: Preparation of 2-methyl-N-(1-(1-methyl-1H-indol-3-yl)butylidene)propan-2-amine The title compound was prepared according to procedure described in Example 1, Step 6.

LC-MS 257.6 [M+H]$^+$, RT 0.81 min.

Step 3-4: Preparation of 5-ethyl-6-(1-methyl-1H-indol-3-yl)-2-oxo-1,2-dihydropyridine-3-carboxylic acid The title compound was prepared according to procedure described in Example 1, Step 7-8.

$^1$H NMR (500 MHz, CHCl$_3$-d) δ ppm 1.18 (t, J=7.51 Hz, 3H) 2.68 (q, J=7.51 Hz, 2H) 3.96 (s, 3H) 7.26-7.32 (m, 1H) 7.36-7.53 (m, 3H) 7.57 (d, J=8.04 Hz, 1H) 8.57 (s, 1H) 11.56 (br. s., 1H) 13.80 (s, 1H). LC-MS 295.1 [M−H]$^-$, 297.5 [M+H]$^+$, RT 0.70 min. (1 min Method).

Example 14

5-ethyl-4-hydroxy-6-(1-methyl-1H-indol-3-yl)-2-oxo-1,2-dihydropyridine-3-carboxylic acid

Step 1: Preparation of methyl 5-ethyl-4-hydroxy-6-(1-methyl-1H-indol-3-yl)-2-oxo-1,2-dihydropyridine-3-carboxylate The title compound was prepared according to procedure described in Example 2, Step 1.

¹H NMR (500 MHz, CHCl₃-d) δ ppm 1.15 (t, J=7.37 Hz, 3H) 2.60 (q, J=7.38 Hz, 2H) 3.91 (s, 3H) 4.02 (s, 3H) 7.26 (ddd, J=8.08, 7.01, 1.06 Hz, 1H) 7.33-7.40 (m, 2H) 7.40-7.47 (m, 1H) 7.64 (dt, J=8.06, 0.94 Hz, 1H) 13.87 (s, 1H). LC-MS 325.2 [M−H]⁻, 327.5 [M+H]⁺, RT 1.19 min.

Step 2: 5-ethyl-4-hydroxy-6-(1-methyl-1H-indol-3-yl)-2-oxo-1,2-dihydropyridine-3-carboxylic acid The title compound was prepared according to procedure described in Example 2, Step 2.

¹H NMR (500 MHz, CHCl₃-d) δ ppm 1.12 (t, J=7.17 Hz, 3H) 2.66 (q, J=6.80 Hz, 2H) 3.95 (s, 3H) 7.20-7.30 (m, 1H) 7.34-7.42 (m, 2H) 7.44-7.49 (m, 1H) 7.53-7.61 (m, 1H) 13.74 (s, 1H). LC-MS 311.1 [M−H]⁻, 313.2 [M+H]⁺, RT 1.28 min.

Example 15

5-ethyl-2-oxo-6-(2-phenylbenzo[d]oxazol-6-yl)-1,2-dihydropyridine-3-carboxylic acid

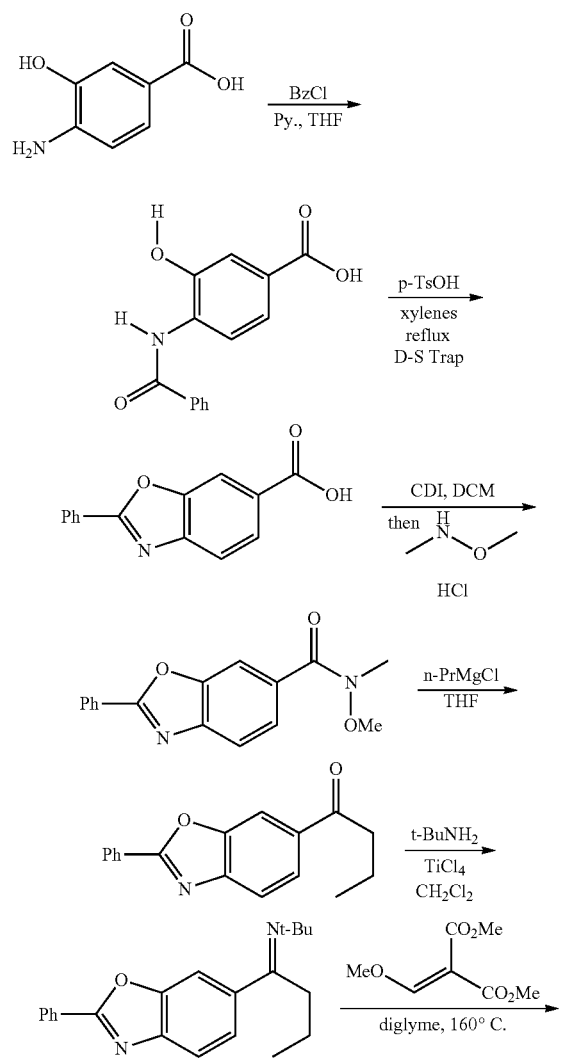

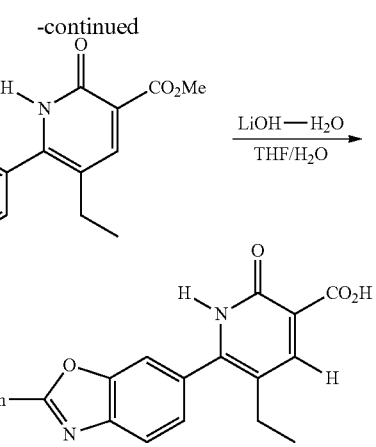

Step 1: 4-benzamido-3-hydroxybenzoic acid

To a suspension of 4-amino-3-hydroxybenzoic acid (7.66 g, 50.0 mmol) in THF (100 mL) was added pyridine (4.3 mL, 53.2 mmol, 1.06 eq) followed by benzoyl chloride (6.1 mL, 52.6 mmol, 1.05 eq) at 0° C. After 5 min, the reaction was quenched with H₂O then extracted with CH₂Cl₂ (4×80 mL). Crude product precipitated out of organic layer then was collected by filtration to afford 4-benzamido-3-hydroxybenzoic acid (10.1 g, 39.3 mmol, 79%). The product was carried over to next step without further purification.

¹H NMR (500 MHz, DMSO-d₆) δ ppm 7.46 (dd, J=8.28, 1.89 Hz, 1H) 7.49-7.58 (m, 3H) 7.58-7.65 (m, 1H) 7.92-8.05 (m, 3H) 9.47 (s, 1H) 10.34 (s, 1H) 12.72 (br. s., 1H). LC-MS 255.8 [M−H]⁻, 258.3 [M+H]⁺, RT 0.94 min.

Step 2: 2-phenylbenzo[d]oxazole-6-carboxylic acid

To a suspension of 4-benzamido-3-hydroxybenzoic acid (2.15 g, 8.4 mmol) in xylenes (12 mL) was added p-TsOH (1.6 g, 8.4 mmol, 1.0 eq) at room temperature then the mixture was heated to 160° C. and stirred overnight. The solvent was removed under reduced pressure then the reaction was quenched with saturated aqueous NaHCO₃ and biphasic mixture was extracted by CH₂Cl₂ (4×80 mL). The solvent was concentrated to give the title compound (2.0 g) which was used in the next step without further purification. LC-MS 237.9 [M−H]⁻, 240.3 [M+H]⁺, RT 1.12 min.

Step 3: N-methoxy-N-methyl-2-phenylbenzo[d]oxazole-6-carboxamide

To a suspension of 2-phenylbenzo[d]oxazole-6-carboxylic acid (2.0 g, ca. 8.4 mmol) in CH₂Cl₂ was added CDI (1.6 g, 9.9 mmol, 1.2 eq) at 0° C. The reaction was warmed to room temperature then stirred for 1 h to give a homogeneous solution. The mixture was cooled to 0° C. before MeNHOMe-HCl (0.98 g, 10.0 mmol, 1.2 eq) was added. After 12 h, the reaction was quenched with H₂O and extracted with CH₂Cl₂ (3×50 mL). Solvent was removed then crude product was purified by flash column chromatography (0-25% EtOAc in hexanes) to afford N-methoxy-N-methyl-2-phenylbenzo[d]oxazole-6-carboxamide (1.57 g, 5.6 mmol, 67% over two steps).

¹H NMR (500 MHz, CHCl₃-d) δ ppm 3.43 (s, 3H) 3.59 (s, 3H) 7.52-7.63 (m, 3H) 7.74-7.84 (m, 2H) 8.00 (dd, J=1.34, 0.63 Hz, 1H) 8.25-8.33 (m, 2H). LC-MS 283.4 [M+H]⁺, RT 1.15 min.

Step 4: 1-(2-phenylbenzo[d]oxazol-6-yl)butan-1-one

To a solution of N-methoxy-N-methyl-2-phenylbenzo[d]oxazole-6-carboxamide (1.57 g, 5.6 mmol) in THF (20 mL) was added n-PrMgCl (2.0M in ether, 4.2 mL, 8.4 mmol, 1.5 eq) at 0° C. The mixture was warmed up to room temperature then stirred for 1 h. The reaction was quenched with saturated aqueous NH$_4$Cl then extracted with EtOAc (3×40 mL). Solvent was removed then crude product was purified by flash column chromatography (0-20% EtOAc in hexanes) to afford the title compound (1.07 g, 4.0 mmol, 72%).

$^1$H NMR (500 MHz, CHCl$_3$-d) δ ppm 1.06 (t, J=7.41 Hz, 3H) 1.84 (sxt, J=7.36 Hz, 2H) 3.01-3.08 (m, 2H) 7.52-7.64 (m, 3H) 7.82 (dd, J=8.35, 0.63 Hz, 1H) 8.04 (dd, J=8.35, 1.58 Hz, 1H) 8.23 (dd, J=1.58, 0.55 Hz, 1H) 8.26-8.34 (m, 2H). LC-MS 266.4 [M+H]$^+$, RT 1.48 min.

Step 5: 2-methyl-N-(1-(2-phenylbenzo[d]oxazol-6-yl)butylidene)propan-2-amine The title compound was prepared according to procedure described in Example 1, Step 6.

LC-MS 321.5 [M+H]$^+$, RT 1.08 min.

Step 6&7: 5-ethyl-2-oxo-6-(2-phenylbenzo[d]oxazol-6-yl)-1,2-dihydropyridine-3-carboxylic acid The title compound was prepared according to procedure described in Example 1, Step 7-8.

$^1$H NMR (500 MHz, CHCl$_3$-d) δ ppm 1.22 (t, J=7.51 Hz, 3H) 2.60 (q, J=7.51 Hz, 2H) 7.46 (dd, J=8.04, 1.58 Hz, 1H) 7.54-7.66 (m, 3H) 7.72 (d, J=1.26 Hz, 1H) 7.96 (d, J=7.96 Hz, 1H) 8.26-8.38 (m, 2H) 8.59 (s, 1H) 11.68 (br. s., 1H) 13.55 (s, 1H). LC-MS 359.1 [M−H]$^-$, 361.5 [M+H]$^+$, RT 1.20 min.

Example 16

5-ethyl-4-hydroxy-2-oxo-6-(2-phenylbenzo[d]oxazol-6-yl)-1,2-dihydropyridine-3-carboxylic acid

Step 1: methyl 5-ethyl-4-hydroxy-2-oxo-6-(2-phenylbenzo[d]oxazol-6-yl)-1,2-dihydropyridine-3-carboxylate The title compound was prepared according to procedure described in Example 2, Step 1.

$^1$H NMR (500 MHz, CHCl$_3$-d) δ ppm 1.15 (t, J=7.37 Hz, 3H) 2.48 (q, J=7.33 Hz, 2H) 3.90 (s, 3H) 7.44 (dd, J=8.20, 1.66 Hz, 1H) 7.54-7.66 (m, 3H) 7.70 (dd, J=1.58, 0.55 Hz, 1H) 7.90 (dd, J=8.20, 0.55 Hz, 1H) 8.26-8.35 (m, 2H) 13.88 (br. s., 1H). LC-MS 389.1 [M−H]$^-$, 391.5 [M+H]$^+$, RT 1.31 min.

Step 2: 5-ethyl-4-hydroxy-2-oxo-6-(2-phenylbenzo[d]oxazol-6-yl)-1,2-dihydropyridine-3-carboxylic acid The title compound was prepared according to procedure described in Example 2, Step 2.

$^1$H NMR (500 MHz, CHCl$_3$-d) δ ppm 1.17 (t, J=7.41 Hz, 3H) 2.53 (q, J=7.30 Hz, 2H) 7.42 (dd, J=8.20, 1.58 Hz, 1H) 7.54-7.65 (m, 3H) 7.68 (d, J=1.10 Hz, 1H) 7.94 (d, J=8.20 Hz, 1H) 8.28-8.35 (m, 2H) 14.00 (s, 1H) 14.67 (s, 1H). LC-MS 375.1 [M−H]$^-$, 377.1 [M+H]$^+$, RT 1.40 min.

Example 17

6-(2-(dimethylamino)benzo[d]oxazol-6-yl)-5-ethyl-2-oxo-1,2-dihydropyridine-3-carboxylic acid

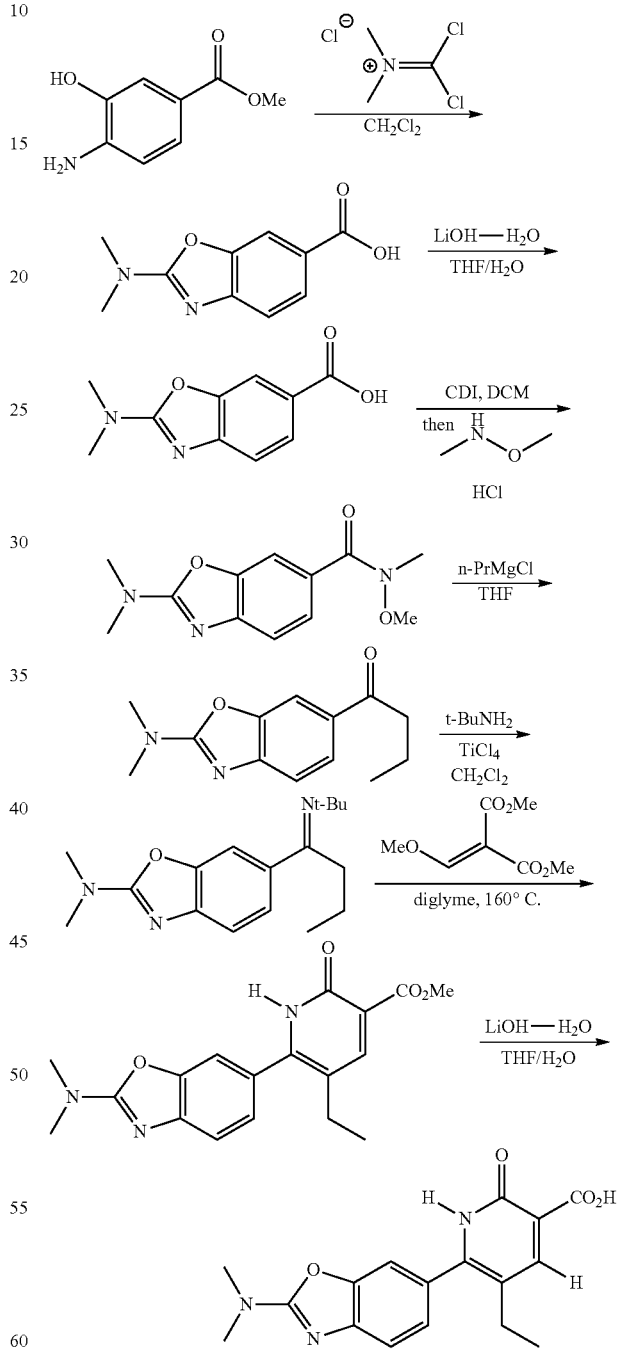

Step 1: methyl 2-(dimethylamino)benzo[d]oxazole-6-carboxylate

To a solution of methyl 4-amino-3-hydroxybenzoate (1.63 g, 9.8 mmol) in CH$_2$Cl$_2$ (30 mL) was added N-(dichloromethylene)-N-methylmethanaminium chloride (1.63 g, 10.0 mmol, 1.0 eq). The mixture was heated to reflux for 3 h. The reaction was quenched with H₂O then extracted with CH₂Cl₂ (3×30 mL). Solvent was removed under reduced pressure to afford the title compound (2.2 g, ca. 10.0 mmol) which was used in next step without further purification.

$^1$H NMR (500 MHz, CHCl$_3$-d) δ ppm 3.59 (br. s., 6H) 3.96 (s, 3H) 7.69-7.77 (m, 1H) 8.05-8.11 (m, 2H). LC-MS 221.2 [M+H]$^+$, RT 1.16 min.

Step 2:
2-(dimethylamino)benzo[d]oxazole-6-carboxylic acid

To a solution of methyl 2-(dimethylamino)benzo[d]oxazole-6-carboxylate (2.2 g, ca. 10.0 mmol) in THF (10 mL) and H₂O (10 mL) was added LiOH—H₂O (1.26 g, 30.0 mmol, 3.0 eq) at room temperature. The mixture stirred at room temperature overnight. The solvent was removed under reduced pressure then the reaction was quenched with 1N aqueous HCl (20 mL). The resulting mixture was extracted by CH₂Cl₂ (3×30 mL). The solvent was removed to give 2-(dimethylamino)benzo[d]oxazole-6-carboxylic acid (1.32 g, 6.4 mmol, 65%) over two steps. The crude product was used in the next step without further purification.

$^1$H NMR (500 MHz, DMSO-d$_6$) δ ppm 3.16 (s, 6H) 7.29 (d, J=8.20 Hz, 1H) 7.80 (dd, J=8.12, 1.58 Hz, 1H) 7.84 (d, J=1.18 Hz, 1H). LC-MS 205.1 [M-H]$^-$, 207.2 [M+H]$^+$, RT 0.89 min.

Step 3: 2-(dimethylamino)-N-methoxy-N-methyl-benzo[d]oxazole-6-carboxamide

The title compound was prepared according to procedure described in Example 15, Step 3.
$^1$H NMR (500 MHz, CHCl$_3$-d) δ ppm 3.25 (s, 6H) 3.38 (s, 3H) 3.58 (s, 3H) 7.34 (d, J=8.20 Hz, 1H) 7.64 (dd, J=8.20, 1.58 Hz, 1H) 7.70 (dd, J=1.58, 0.39 Hz, 1H). LC-MS 250.3 [M+H]$^+$, RT 0.99 min.

Step 4: 1-(2-(dimethylamino)benzo[d]oxazol-6-yl)butan-1-one

The title compound was prepared according to procedure described in Example 15, Step 4.
$^1$H NMR (500 MHz, CHCl$_3$-d) δ ppm 1.02 (t, J=7.41 Hz, 3H) 1.73-1.86 (m, 2H) 2.91-2.99 (m, 2H) 3.26 (s, 6H) 7.33 (dd, J=8.28, 0.47 Hz, 1H) 7.86 (dd, J=8.20, 1.65 Hz, 1H) 7.90 (dd, J=1.66, 0.47 Hz, 1H). LC-MS 233.1 [M+H]$^+$, RT 1.11 min.

Step 5: 6-(1-(tert-butylimino)butyl)-N,N-dimethyl-benzo[d]oxazol-2-amine

The title compound was prepared according to procedure described in Example 1, Step 6.
LC-MS 288.2 [M+H]$^+$, RT 0.79 min.

Step 6-7: 6-(2-(dimethylamino)benzo[d]oxazol-6-yl)-5-ethyl-2-oxo-1,2-dihydropyridine-3-carboxylic acid The title compound was prepared according to procedure described in Example 1, Step 7-8.
$^1$H NMR (500 MHz, DMSO-d$_6$) δ ppm 1.02 (t, J=7.53 Hz, 3H) 2.43 (q, J=7.49 Hz, 2H) 3.17 (s, 6H) 7.26 (dd, J=8.08, 1.62 Hz, 1H) 7.38 (d, J=8.04 Hz, 1H) 7.59 (d, J=1.42 Hz, 1H) 8.36 (s, 1H) 13.21 (br. s., 1H). LC-MS 326.1 [M-H]$^-$, 328.2 [M+H]$^+$, RT 1.13 min.

Example 18

6-(2-(dimethylamino)benzo[d]oxazol-6-yl)-5-ethyl-4-hydroxy-2-oxo-1,2-dihydropyridine-3-carboxylic acid Step 1: methyl 6-(2-(dimethylamino)benzo[d]oxazol-6-yl)-5-ethyl-4-hydroxy-2-oxo-1,2-dihydropyridine-3-carboxylate The title compound was prepared according to procedure described in Example 2, Step 1.
LC-MS 356.1 [M-H]$^-$, 357.8 [M+H]$^+$, RT 1.07 min.

Step 2: 6-(2-(dimethylamino)benzo[d]oxazol-6-yl)-5-ethyl-4-hydroxy-2-oxo-1,2-dihydropyridine-3-carboxylic acid The title compound was prepared according to procedure described in Example 2, Step 2.
$^1$H NMR (500 MHz, DMSO-d$_6$) δ ppm 0.99 (t, J=7.41 Hz, 3H) 2.33 (q, J=7.38 Hz, 2H) 3.17 (s, 6H) 7.24 (dd, J=8.04, 1.66 Hz, 1H) 7.38 (d, J=8.04 Hz, 1H) 7.56 (d, J=1.34 Hz, 1H) 12.74 (br. s., 1H) 13.91 (s, 1H). LC-MS 342.1 [M-H]$^-$, 344.2 [M+H]$^+$, RT 1.14 min.

Example 19

5-ethyl-2-oxo-6-(quinolin-6-yl)-1,2-dihydropyridine-3-carboxylic acid

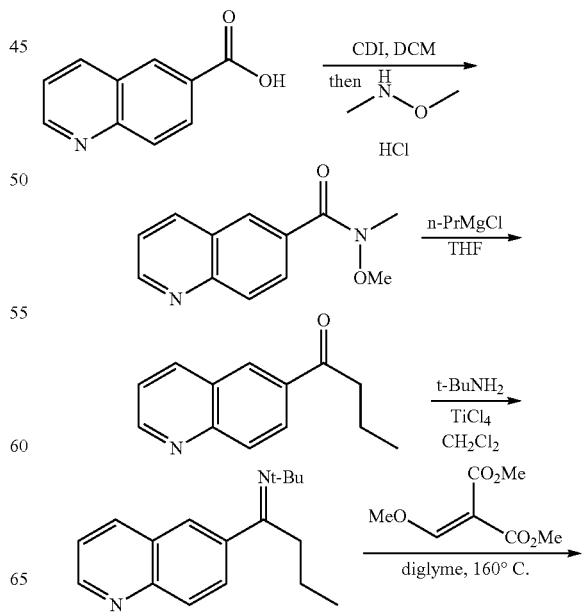

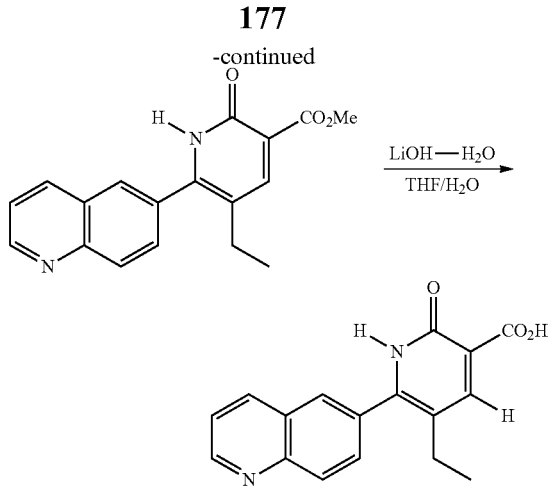

Step 1: N-methoxy-N-methylquinoline-6-carboxamide

The title compound was prepared according to procedure described in Example 15, Step 3.

$^1$H NMR (500 MHz, CHCl$_3$-d) δ ppm 3.44 (s, 3H) 3.57 (s, 3H) 7.46 (dd, J=8.28, 4.26 Hz, 1H) 8.01 (dd, J=8.75, 1.89 Hz, 1H) 8.13 (d, J=8.75 Hz, 1H) 8.20-8.26 (m, 2H) 8.99 (dd, J=4.26, 1.73 Hz, 1H). LC-MS 216.7 [M+H]$^+$, RT 0.50 min.

Step 2: 1-(quinolin-6-yl)butan-1-one

The title compound was prepared according to procedure described in Example 15, Step 4.

$^1$H NMR (500 MHz, CHCl$_3$-d) δ ppm 1.06 (t, J=7.41 Hz, 3H) 1.79-1.91 (m, 2H) 3.04-3.15 (m, 2H) 7.49 (dd, J=8.28, 4.26 Hz, 1H) 8.17 (d, J=8.83 Hz, 1H) 8.29 (ddd, J=8.37, 6.40, 1.54 Hz, 2H) 8.47 (d, J=1.89 Hz, 1H) 9.02 (dd, J=4.26, 1.73 Hz, 1H). LC-MS 200.1 [M+H]$^+$, RT 0.96 min.

Step 3: 2-methyl-N-(1-(quinolin-6-yl)butylidene)propan-2-amine

The title compound was prepared according to procedure described in Example 1, Step 6.
LC-MS 255.2 [M+H]$^+$, RT 0.57 min.

Step 4-5: 5-ethyl-2-oxo-6-(quinolin-6-yl)-1,2-dihydropyridine-3-carboxylic acid The title compound was prepared according to procedure described in Example 1, Step 7-8.

$^1$H NMR (500 MHz, DMSO-d$_6$) δ ppm 1.04 (t, J=7.49 Hz, 3H) 2.42 (q, J=7.49 Hz, 2H) 7.91 (dd, J=8.31, 4.69 Hz, 1H) 8.05 (dd, J=8.75, 1.81 Hz, 1H) 8.29-8.42 (m, 2H) 8.45 (s, 1H) 8.87 (d, J=8.28 Hz, 1H) 9.22 (dd, J=4.65, 1.34 Hz, 1H) 13.51 (br. s., 1H). LC-MS 293.2 [M–H]$^-$, 295.1 [M+H]$^+$, RT 0.80 min.

Example 20

5-ethyl-4-hydroxy-2-oxo-6-(quinolin-6-yl)-1,2-dihydropyridine-3-carboxylic acid

Step 1: methyl 5-ethyl-4-hydroxy-2-oxo-6-(quinolin-6-yl)-1,2-dihydropyridine-3-carboxylate The title compound was prepared according to procedure described in Example 2, Step 1.
LC-MS 323.2 [M–H]$^-$, 325.2 [M+H]$^+$, RT 0.95 min.

Step 2: 5-ethyl-4-hydroxy-2-oxo-6-(quinolin-6-yl)-1,2-dihydropyridine-3-carboxylic acid The title compound was prepared according to procedure described in Example 2, Step 2.

$^1$H NMR (500 MHz, DMSO-d$_6$) δ ppm 1.00 (t, J=7.41 Hz, 3H) 2.32 (q, J=7.33 Hz, 2H) 7.82-7.96 (m, 1H) 8.00 (d, J=8.43 Hz, 1H) 8.26-8.40 (m, 2H) 8.83 (d, J=7.49 Hz, 1H) 9.12-9.25 (m, 1H) 13.96 (br. s., 1H). LC-MS 309.1 [M–H]$^-$, 311.1 [M+H]$^+$, RT 0.90 min.

Example 21

5-ethyl-6-(1-methyl-1H-indol-5-yl)-2-oxo-1,2-dihydropyridine-3-carboxylic acid

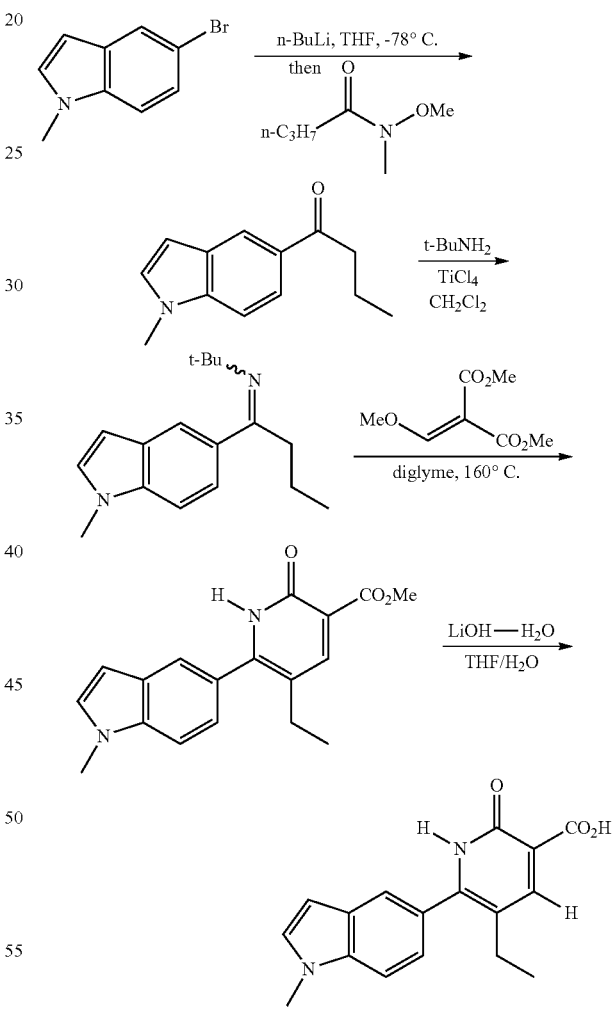

Step 1: 1-(1-methyl-1H-indol-5-yl)butan-1-one

To a solution of 5-bromo-1-methyl-1H-indole (9.8 g, 46.7 mmol) in THF (40 mL) was added n-BuLi (2.5M in hexanes, 22.3 mL, 55.8 mmol, 1.2 eq) at –78° C. dropwise over 15 min. The mixture was stirred for 30 min at –78° C. before a solution of N-methoxy-N-methylbutyramide (7.35 g, 56.0 mmol, 1.2 eq) in THF (10 mL) was added. After stirred at −78° C. for 10 min, the reaction was quenched with saturated aqueous NH₄Cl. The resulting mixture was extracted by ether (3×30 mL) and combined organic layers were dried over Na₂SO₄. The crude product was purified by flash chromatography (0-10% EtOAc in hexanes) to give the title compound (5.40 g, 26.8 mmol, 57%) as a white solid.

¹H NMR (500 MHz, CHCl₃-d) δ ppm 1.04 (t, J=7.45 Hz, 3H) 1.82 (sxt, J=7.39 Hz, 2H) 3.04 (t, J=7.39 Hz, 2H) 3.84 (s, 3H) 6.62 (dd, J=3.15, 0.87 Hz, 1H) 7.09-7.16 (m, 1H) 7.35 (d, J=8.67 Hz, 1H) 7.92 (dd, J=8.71, 1.69 Hz, 1H) 8.32 (dd, J=1.69, 0.51 Hz, 1H). LC-MS 202.2 [M+H]⁺, RT 1.26 min.

Step 2: 2-methyl-N-(1-(1-methyl-1H-indol-5-yl)butylidene)propan-2-amine

The title compound was prepared according to procedure described in Example 1, Step 6.
LC-MS 257.3 [M+H]⁺, RT 0.75 min.

Step 3-4: 5-ethyl-6-(1-methyl-1H-indol-5-yl)-2-oxo-1,2-dihydropyridine-3-carboxylic acid The title compound was prepared according to procedure described in Example 1, Step 7-8.
¹H NMR (500 MHz, CHCl₃-d) δ ppm 1.18 (t, J=7.57 Hz, 3H) 2.63 (q, J=7.57 Hz, 2H) 3.89 (s, 3H) 6.62 (dd, J=3.11, 0.59 Hz, 1H) 7.21 (d, J=3.07 Hz, 1H) 7.30 (dd, J=8.47, 1.69 Hz, 1H) 7.50 (d, J=8.51 Hz, 1H) 7.75 (d, J=1.34 Hz, 1H) 8.55 (s, 1H) 11.73 (br. s., 1H) 13.78 (s, 1H). LC-MS 294.8 [M−H]⁻, 297.0 [M+H]⁺, RT 0.67 min. (1 min Method).

Example 22

5-ethyl-4-hydroxy-6-(1-methyl-1H-indol-5-yl)-2-oxo-1,2-dihydropyridine-3-carboxylic acid Step 1: methyl 5-ethyl-4-hydroxy-6-(1-methyl-1H-indol-5-yl)-2-oxo-1,2-dihydropyridine-3-carboxylate To a suspension of 2-methyl-N-(1-(1-methyl-1H-indol-5-yl)butylidene)propan-2-amine (6.70 g, ca. 26.1 mmol), prepared according to procedure described in Example 21 Step 2, in Ph₂O (40 mL) was added trimethyl methanetricarboxylate (8.44 g, 44.4 mmol, 1.7 eq). Distillation apparatus was set up then attached to the flask. The reaction was stirred at 230° C. for 10 min then heating was removed. The mixture was cooled to room temperature. The precipitate was collected by filtration then washed with diethyl ether to afford the title compound as a yellow solid (4.85 g, 14.9 mmol, 55%).

¹H NMR (500 MHz, CHCl₃-d) δ ppm 1.14 (t, J=7.33 Hz, 3H) 2.49 (q, J=7.33 Hz, 2H) 3.87 (s, 3H) 4.02 (s, 3H) 6.58 (dd, J=3.11, 0.83 Hz, 1H) 7.18 (d, J=3.07 Hz, 1H) 7.24 (dd, J=8.47, 1.69 Hz, 1H) 7.44 (d, J=8.51 Hz, 1H) 7.68 (dd, J=1.69, 0.59 Hz, 1H) 13.88 (s, 1H). LC-MS 325.3 [M−H]⁻, 327.2 [M+H]⁺, RT 1.20 min.

Step 2: 5-ethyl-4-hydroxy-6-(1-methyl-1H-indol-5-yl)-2-oxo-1,2-dihydropyridine-3-carboxylic acid The title compound was prepared according to procedure described in Example 2, Step 2.
¹H NMR (500 MHz, DMSO-d₆) δ ppm 1.00 (t, J=7.41 Hz, 3H) 2.34 (q, J=7.41 Hz, 2H) 3.85 (s, 3H) 6.55 (dd, J=3.15, 0.79 Hz, 1H) 7.22 (dd, J=8.47, 1.69 Hz, 1H) 7.47 (d, J=3.07 Hz, 1H) 7.59 (d, J=8.51 Hz, 1H) 7.67 (dd, J=1.18 Hz, 1H) 12.73 (br. s., 1H) 13.92 (br. s., 1H).
LC-MS 311.2 [M−H]⁻, 313.2 [M+H]⁺, RT 1.26 min.

Example 23

5-ethyl-6-(1-(2-hydroxyethyl)-1H-indol-5-yl)-2-oxo-1,2-dihydropyridine-3-carboxylic acid

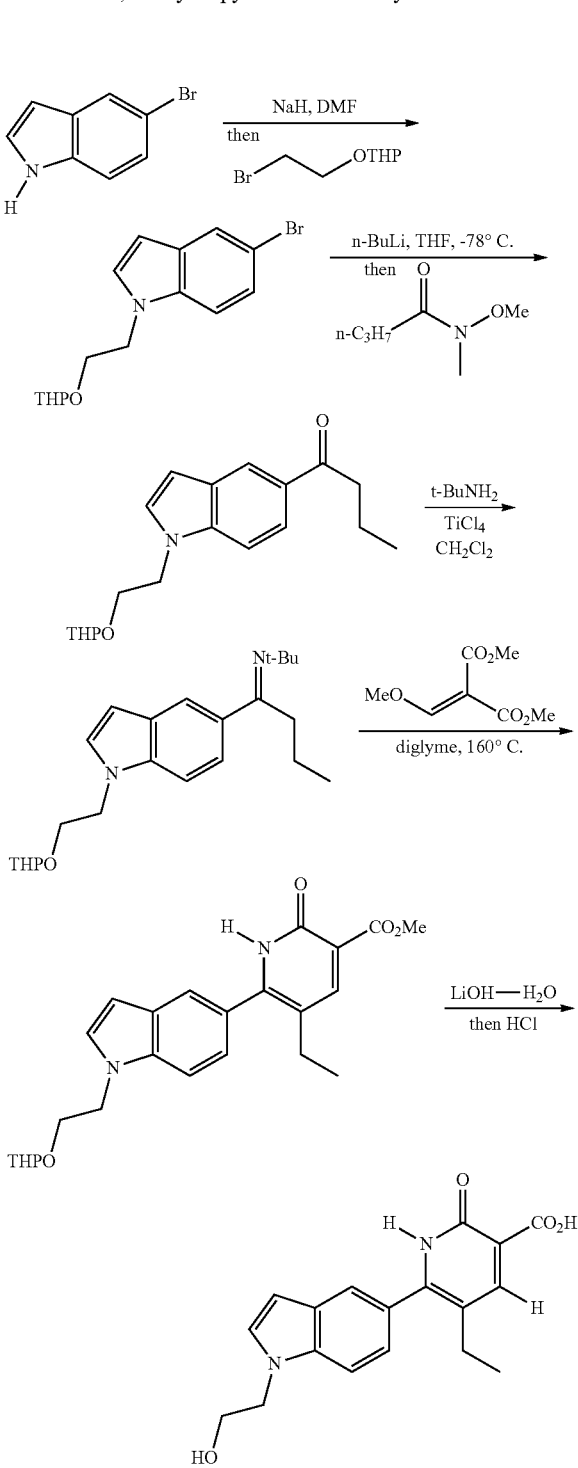

Step 1: 5-bromo-1-(2-(tetrahydro-2H-pyran-2-yloxy)ethyl)-1H-indole

The title compound was prepared according to procedure described in Example 9, Step 1.

¹H NMR (500 MHz, CHCl₃-d) δ ppm 1.42-1.58 (m, 4H) 1.59-1.66 (m, 1H) 1.67-1.82 (m, 1H) 3.33-3.42 (m, 1H) 3.48-3.57 (m, 1H) 3.67-3.75 (m, 1H) 3.98-4.08 (m, 1H) 4.31 (t, J=5.48 Hz, 2H) 4.48 (t, J=3.43 Hz, 1H) 6.40-6.46 (m, 1H) 7.18 (d, J=3.15 Hz, 1H) 7.24-7.31 (m, 2H) 7.74 (dd, J=1.50, 0.95 Hz, 1H). LC-MS 324.2/326.2 [M+H]⁺, RT 1.54 min.

Step 2: 1-(1-(2-(tetrahydro-2H-pyran-2-yloxy)ethyl)-1H-indol-5-yl)butan-1-one

The title compound was prepared according to procedure described in example 21 step 1.
¹H NMR (500 MHz, CHCl₃-d) δ ppm 1.04 (t, J=7.41 Hz, 3H) 1.37-1.58 (m, 4H) 1.58-1.77 (m, 2H) 1.77-1.87 (m, 2H) 2.96-3.07 (m, 2H) 3.33-3.41 (m, 1H) 3.53 (ddd, J=11.47, 8.79, 3.07 Hz, 1H) 3.69-3.77 (m, 1H) 4.03-4.10 (m, 1H) 4.36 (t, J=5.56 Hz, 2H) 4.50 (t, J=3.43 Hz, 1H) 6.62 (dd, J=3.23, 0.79 Hz, 1H) 7.25 (d, J=3.23 Hz, 1H) 7.42 (d, J=8.75 Hz, 1H) 7.90 (dd, J=8.67, 1.66 Hz, 1H) 8.31 (d, J=1.26 Hz, 1H). LC-MS 316.6 [M+H]⁺, RT 1.40 min.

Step 3: 2-methyl-N-(1-(1-(2-(tetrahydro-2H-pyran-2-yloxy)ethyl)-1H-indol-5-yl)butylidene)propan-2-amine The title compound was prepared according to procedure described in Example 1, Step 6.
LC-MS 371.8 [M+H]⁺, RT 1.03 min.

Step 4-5: 5-ethyl-6-(1-(2-hydroxyethyl)-1H-indol-5-yl)-2-oxo-1,2-dihydropyridine-3-carboxylic acid The title compound was prepared according to procedure described in Example 1, Step 7-8.
¹H NMR (500 MHz, DMSO-d₆) δ ppm 1.03 (t, J=7.53 Hz, 3H) 2.46 (q, J=7.53 Hz, 2H) 3.75 (q, J=5.36 Hz, 2H) 4.28 (t, J=5.56 Hz, 2H) 4.91 (t, J=5.12 Hz, 1H) 6.54 (dd, J=3.15, 0.63 Hz, 1H) 7.22 (dd, J=8.51, 1.73 Hz, 1H) 7.49 (d, J=3.07 Hz, 1H) 7.62 (d, J=8.51 Hz, 1H) 7.68 (d, J=1.26 Hz, 1H) 8.33 (s, 1H). LC-MS 325.1 [M-H]⁻, 327.1 [M+H]⁺, RT 0.92 min.

Example 24

5-ethyl-4-hydroxy-6-(1-(2-hydroxyethyl)-1H-indol-5-yl)-2-oxo-1,2-dihydropyridine-3-carboxylic acid Step 1: methyl 5-ethyl-4-hydroxy-2-oxo-6-(1-(2-(tetrahydro-2H-pyran-2-yloxy)ethyl)-1H-indol-5-yl)-1,2-dihydropyridine-3-carboxylate The title compound was prepared according to procedure described in Example 2, Step 1.
¹H NMR (500 MHz, CHCl₃-d) δ ppm 1.13 (t, J=7.37 Hz, 3H) 1.42-1.69 (m, 5H) 1.69-1.77 (m, 1H) 2.48 (q, J=7.36 Hz, 2H) 3.44-3.53 (m, 2H) 3.70-3.78 (m, 1H) 4.02 (s, 3H) 4.04-4.12 (m, 1H) 4.33-4.43 (m, 2H) 4.52 (t, J=3.47 Hz, 1H) 6.58 (dd, J=3.15, 0.79 Hz, 1H) 7.18-7.24 (m, 1H) 7.30 (d, J=3.23 Hz, 1H) 7.44-7.54 (m, 1H) 7.59-7.70 (m, 1H) 13.87 (s, 1H). LC-MS 439.1 [M-H]⁻, 441.2 [M+H]⁺, RT 1.31 min.

Step 2: 5-ethyl-4-hydroxy-6-(1-(2-hydroxyethyl)-1H-indol-5-yl)-2-oxo-1,2-dihydropyridine-3-carboxylic acid The title compound was prepared according to procedure described in Example 2, Step 2.

¹H NMR (500 MHz, DMSO-d₆) δ ppm 1.01 (t, J=7.37 Hz, 3H) 2.36 (q, J=7.30 Hz, 2H) 3.75 (q, J=5.36 Hz, 2H) 4.28 (t, J=5.52 Hz, 2H) 4.90 (t, J=5.16 Hz, 1H) 6.54 (d, J=2.76 Hz, 1H) 7.19 (dd, J=8.51, 1.58 Hz, 1H) 7.49 (d, J=3.07 Hz, 1H) 7.62 (d, J=8.51 Hz, 1H) 7.64-7.67 (m, 1H). LC-MS 341.1 [M-H]⁻, 343.2 [M+H]⁺, RT 1.18 min.

Example 25

6-(1-((1,3-dioxolan-2-yl)methyl)-1H-indol-5-yl)-5-ethyl-2-oxo-1,2-dihydropyridine-3-carboxylic acid

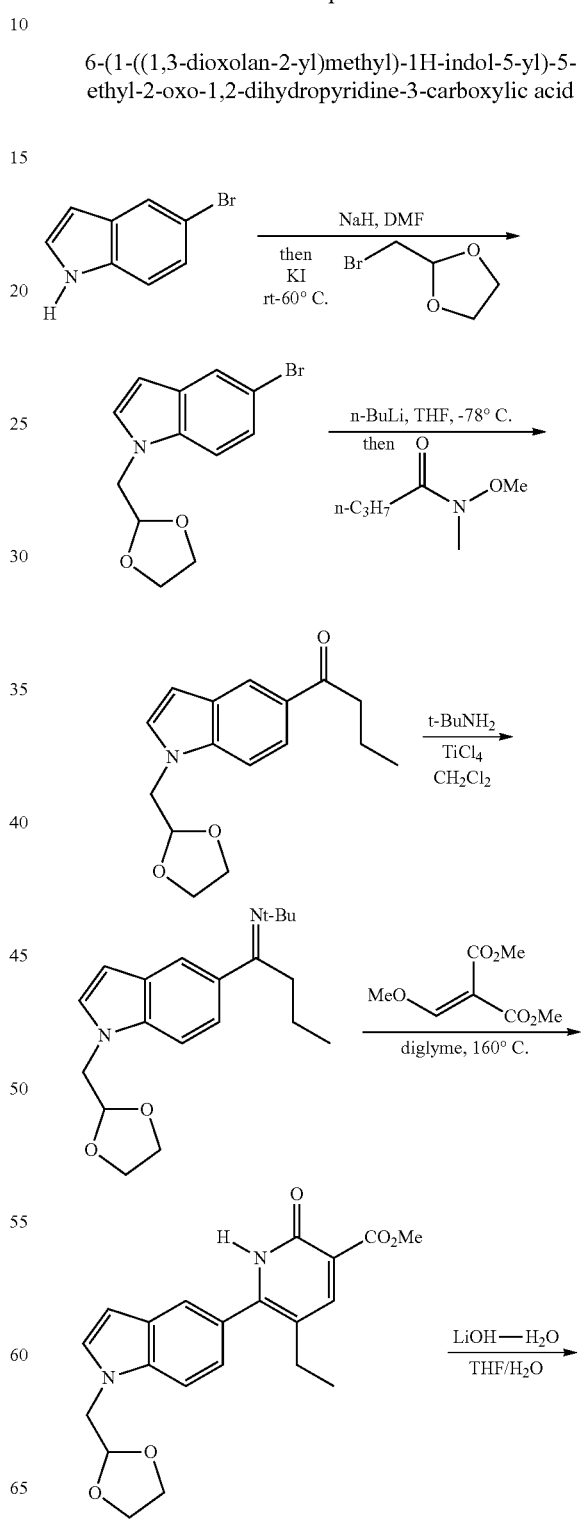

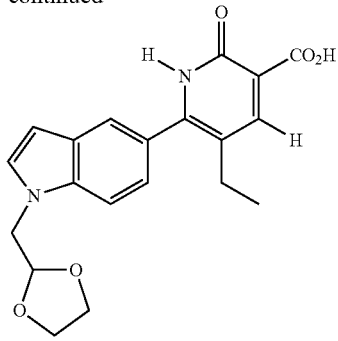

Step 1: 1-((1,3-dioxolan-2-yl)methyl)-5-bromo-1H-indole

The title compound was prepared according to procedure described in Example 9, Step 1.
$^1$H NMR (500 MHz, CHCl$_3$-d) δ ppm 3.65-3.71 (m, 2H) 3.78-3.83 (m, 2H) 4.27 (d, J=3.15 Hz, 2H) 5.21 (t, J=3.15 Hz, 1H) 6.45 (dd, J=3.15, 0.71 Hz, 1H) 7.16 (d, J=3.15 Hz, 1H) 7.25-7.34 (m, 2H) 7.73 (dd, J=1.73, 0.63 Hz, 1H). LC-MS 282.3/284.3 [M+H]$^+$, RT 1.33 min.

Step 2: 1-(1-((1,3-dioxolan-2-yl)methyl)-1H-indol-5-yl)butan-1-one

The title compound was prepared according to procedure described in example 21 step 1.
$^1$H NMR (500 MHz, CHCl$_3$-d) δ ppm 1.04 (t, J=7.41 Hz, 3H) 1.76-1.88 (m, 2H) 2.98-3.06 (m, 2H) 3.65-3.74 (m, 2H) 3.76-3.85 (m, 2H) 4.32 (d, J=3.15 Hz, 2H) 5.24 (t, J=3.15 Hz, 1H) 6.63 (dd, J=3.23, 0.79 Hz, 1H) 7.23 (d, J=3.23 Hz, 1H) 7.45 (d, J=8.75 Hz, 1H) 7.90 (dd, J=8.67, 1.66 Hz, 1H) 8.30 (d, J=1.26 Hz, 1H). LC-MS 274.1 [M+H]$^+$, RT 1.22 min.

Step 3: N-(1-(1-((1,3-dioxolan-2-yl)methyl)-1H-indol-5-yl)butylidene)-2-methylpropan-2-amine The title compound was prepared according to procedure described in Example 1, Step 6.
LC-MS 329.7 [M+H]$^+$, RT 0.89 min.

Step 4-5: 6-(1-((1,3-dioxolan-2-yl)methyl)-1H-indol-5-yl)-5-ethyl-2-oxo-1,2-dihydropyridine-3-carboxylic acid The title compound was prepared according to procedure described in Example 1, Step 7-8.
$^1$H NMR (500 MHz, CHCl$_3$-d) δ ppm 1.18 (t, J=7.51 Hz, 3H) 2.62 (q, J=7.51 Hz, 2H) 3.69-3.77 (m, 2H) 3.82-3.89 (m, 2H) 4.37 (d, J=3.15 Hz, 2H) 5.24-5.32 (m, 1H) 6.64 (d, J=3.15 Hz, 1H) 7.23-7.29 (m, 1H) 7.31 (d, J=3.15 Hz, 1H) 7.60 (d, J=8.51 Hz, 1H) 7.72 (d, J=1.42 Hz, 1H) 8.55 (s, 1H) 11.39 (br. s., 1H) 13.77 (s, 1H). LC-MS 367.1 [M–H]$^-$, 369.1 [M+H]$^+$, RT 1.07 min.

Example 26

6-(1-((1,3-dioxolan-2-yl)methyl)-1H-indol-5-yl)-5-ethyl-4-hydroxy-2-oxo-1,2-dihydropyridine-3-carboxylic acid Step 1: methyl 6-(1-((1,3-dioxolan-2-yl)methyl)-1H-indol-5-yl)-5-ethyl-4-hydroxy-2-oxo-1,2-dihydropyridine-3-carboxylate The title compound was prepared according to procedure described in Example 2, Step 1.

$^1$H NMR (500 MHz, CHCl$_3$-d) δ ppm 1.13 (t, J=7.37 Hz, 3H) 2.48 (q, J=7.36 Hz, 2H) 3.70-3.78 (m, 2H) 3.79-3.88 (m, 2H) 4.01 (s, 3H) 4.34 (d, J=3.23 Hz, 2H) 5.25 (t, J=3.19 Hz, 1H) 6.59 (dd, J=3.19, 0.75 Hz, 1H) 7.21 (dd, J=8.51, 1.73 Hz, 1H) 7.28 (d, J=3.23 Hz, 3H) 7.53 (d, J=8.51 Hz, 1H) 7.64-7.68 (m, 1H) 8.40 (br. s., 1H) 13.86 (s, 1H). LC-MS 397.2 [M–H]$^-$, 399.2 [M+H]$^+$, RT 1.20 min.

Step 2: 6-(1-((1,3-dioxolan-2-yl)methyl)-1H-indol-5-yl)-5-ethyl-4-hydroxy-2-oxo-1,2-dihydropyridine-3-carboxylic acid The title compound was prepared according to procedure described in Example 2, Step 2.
$^1$H NMR (500 MHz, CHCl$_3$-d) δ ppm 1.15 (t, J=7.41 Hz, 3H) 2.54 (q, J=7.38 Hz, 2H) 3.75 (t, J=6.86 Hz, 2H) 3.86 (t, J=6.94 Hz, 2H) 4.36 (d, J=3.07 Hz, 2H) 5.26 (t, J=2.99 Hz, 1H) 6.62 (d, J=3.31 Hz, 1H) 7.20-7.24 (m, 1H) 7.30-7.37 (m, 1H) 7.57 (d, J=8.20 Hz, 1H) 7.67 (s, 1H) 13.89 (s, 1H) 14.94 (s, 1H). LC-MS 383.1 [M–H]$^-$, 385.2 [M+H]$^+$, RT 1.27 min.

Example 27

5-ethyl-6-(9-methyl-2,3,4,9-tetrahydro-1H-carbazol-6-yl)-2-oxo-1,2-dihydropyridine-3-carboxylic acid

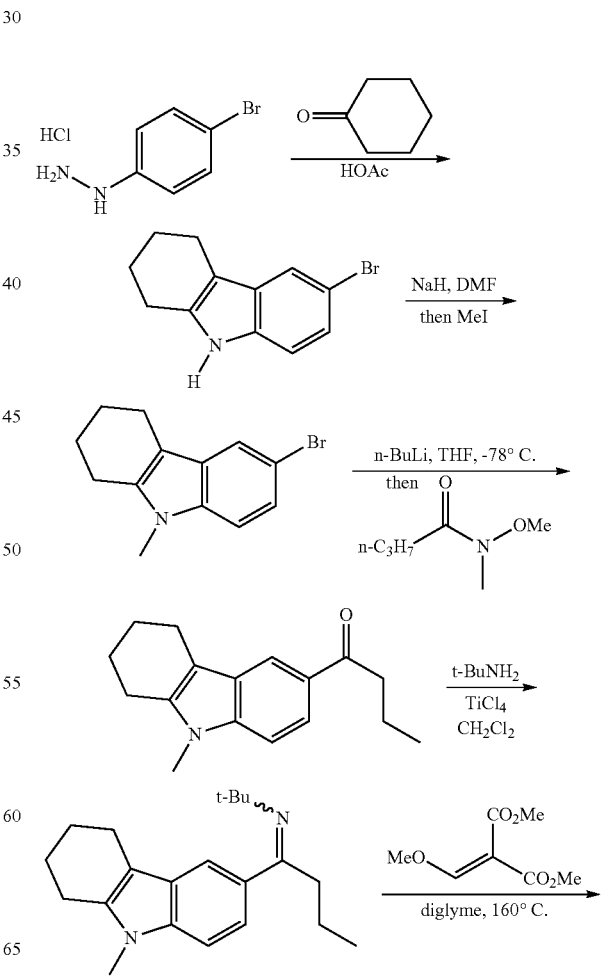

-continued

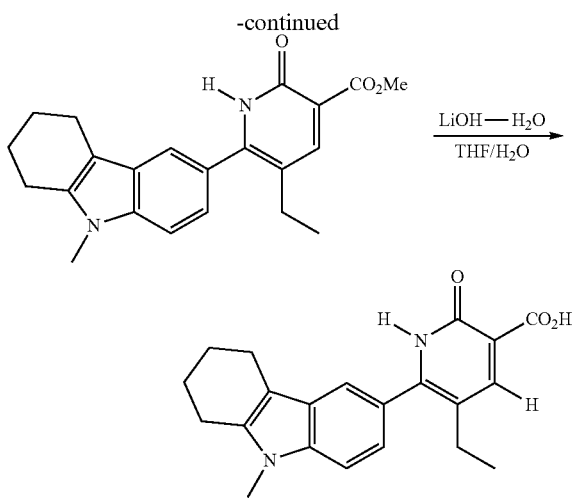

Step 1: 6-bromo-2,3,4,9-tetrahydro-1H-carbazole

To a solution of phenyl hydrazine (4.0 g, 17.9 mmol) in HOAc (25 mL) was added cyclohexanone (1.77 g, 18.0 mmol, 1.0 eq) at room temperature. The mixture was heated to reflux and stirred for 4 h. The reaction was cooled to room temperature then the precipitate was collected by filtration and washed with diethyl ether to afford the title compound (3.1 g, 12.4 mmol, 69%) which was used in the next step without any further purification.

$^1$H NMR (500 MHz, DMSO-$d_6$) δ ppm 1.72-1.87 (m, 4H) 2.58 (t, J=5.95 Hz, 2H) 2.69 (t, J=5.95 Hz, 2H) 7.07 (dd, J=8.47, 2.01 Hz, 1H) 7.19 (dd, J=8.51, 0.39 Hz, 1H) 7.47 (d, J=1.97 Hz, 1H) 10.85 (s, 1H). LC-MS 248.1/250.1 [M−H]$^-$, 250.4/252.4 [M+H]$^+$, RT 1.49 min.

Step 2: 6-bromo-9-methyl-2,3,4,9-tetrahydro-1H-carbazole

The title compound was prepared according to procedure described in Example 9, Step 1.

$^1$H NMR (500 MHz, CHCl$_3$-d) δ ppm 1.81-1.90 (m, 2H) 1.90-1.99 (m, 2H) 2.64-2.75 (m, 4H) 3.60 (s, 3H) 7.11 (d, J=8.59 Hz, 1H) 7.22 (dd, J=8.59, 1.97 Hz, 1H) 7.58 (d, J=1.89 Hz, 1H). LC-MS 264.1/266.1 [M+H]$^+$, RT 1.69 min.

Step 3: 1-(9-methyl-2,3,4,9-tetrahydro-1H-carbazol-6-yl)butan-1-one

The title compound was prepared according to procedure described in Example 21 Step 1.

$^1$H NMR (500 MHz, CHCl$_3$-d) δ ppm 1.04 (t, J=7.41 Hz, 3H) 1.76-1.85 (m, 2H) 1.85-1.92 (m, 2H) 1.93-2.01 (m, 2H) 2.69-2.81 (m, 4H) 2.99-3.07 (m, 2H) 3.65 (s, 3H) 7.25-7.27 (m, 1H) 7.84 (dd, J=8.59, 1.73 Hz, 1H) 8.16 (d, J=1.50 Hz, 1H). LC-MS 256.3 [M+H]$^+$, RT 1.56 min.

Step 4: 2-methyl-N-(1-(9-methyl-2,3,4,9-tetrahydro-1H-carbazol-6-yl)butylidene)propan-2-amine The title compound was prepared according to procedure described in Example 1, Step 6.

LC-MS 311.3 [M+H]$^+$, RT 1.05 min.

Step 5-6: 5-ethyl-6-(9-methyl-2,3,4,9-tetrahydro-1H-carbazol-6-yl)-2-oxo-1,2-dihydropyridine-3-carboxylic acid The title compound was prepared according to procedure described in Example 1, Step 7-8.

$^1$H NMR (500 MHz, CHCl$_3$-d) δ ppm 1.17 (t, J=7.53 Hz, 3H) 1.82-1.94 (m, 2H) 1.94-2.05 (m, 2H) 2.63 (q, J=7.57 Hz, 2H) 2.69-2.82 (m, 4H) 3.70 (s, 3H) 7.22 (dd, J=8.35, 1.66 Hz, 1H) 7.40 (d, J=8.35 Hz, 1H) 7.55 (d, J=1.42 Hz, 1H) 8.54 (s, 1H) 11.49 (br. s., 1H) 13.82 (s, 1H). LC-MS 349.1 [M−H]$^-$, 351.2 [M+H]$^+$, RT 1.39 min.

Example 28

5-ethyl-4-hydroxy-6-(9-methyl-2,3,4,9-tetrahydro-1H-carbazol-6-yl)-2-oxo-1,2-dihydropyridine-3-carboxylic acid

Step 1: methyl 5-ethyl-4-hydroxy-6-(9-methyl-2,3,4,9-tetrahydro-1H-carbazol-6-yl)-2-oxo-1,2-dihydropyridine-3-carboxylate The title compound was prepared according to procedure described in Example 2, Step 1.

$^1$H NMR (500 MHz, CHCl$_3$-d) δ ppm 1.13 (t, J=7.41 Hz, 3H) 1.84-1.93 (m, 2H) 1.93-2.04 (m, 2H) 2.49 (q, J=7.36 Hz, 2H) 2.67-2.79 (m, 4H) 3.68 (s, 3H) 4.01 (s, 3H) 7.16 (dd, J=8.39, 1.77 Hz, 1H) 7.30-7.39 (m, 1H) 7.51 (d, J=1.34 Hz, 1H) 8.40 (br. s., 1H) 13.85 (s, 1H). LC-MS 379.2 [M−H]$^-$, 381.2 [M+H]$^+$, RT 1.50 min.

Step 2: 5-ethyl-4-hydroxy-6-(9-methyl-2,3,4,9-tetrahydro-1H-carbazol-6-yl)-2-oxo-1,2-dihydropyridine-3-carboxylic acid The title compound was prepared according to procedure described in Example 2, Step 2.

$^1$H NMR (500 MHz, CHCl$_3$-d) δ ppm 1.14 (t, J=7.33 Hz, 3H) 1.84-1.94 (m, 2H) 1.94-2.03 (m, 2H) 2.56 (q, J=7.28 Hz, 2H) 2.75 (dt, J=16.33, 5.90 Hz, 4H) 3.70 (s, 3H) 7.18 (d, J=8.20 Hz, 1H) 7.38 (d, J=8.28 Hz, 1H) 7.53 (s, 1H) 10.20 (br. s., 1H) 13.79 (s, 1H) 14.76 (br. s., 1H). LC-MS 365.1 [M−H]$^-$, 367.1 [M+H]$^+$, RT 1.50 min.

Example 29

5-ethyl-2-oxo-6-(1,2,3-trimethyl-1H-indol-5-yl)-1,2-dihydropyridine-3-carboxylic acid

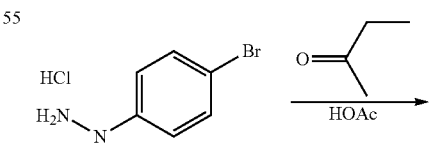

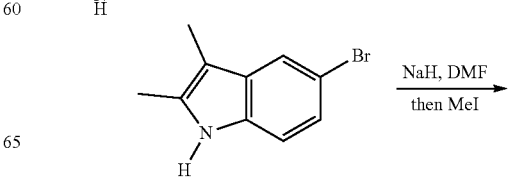

-continued

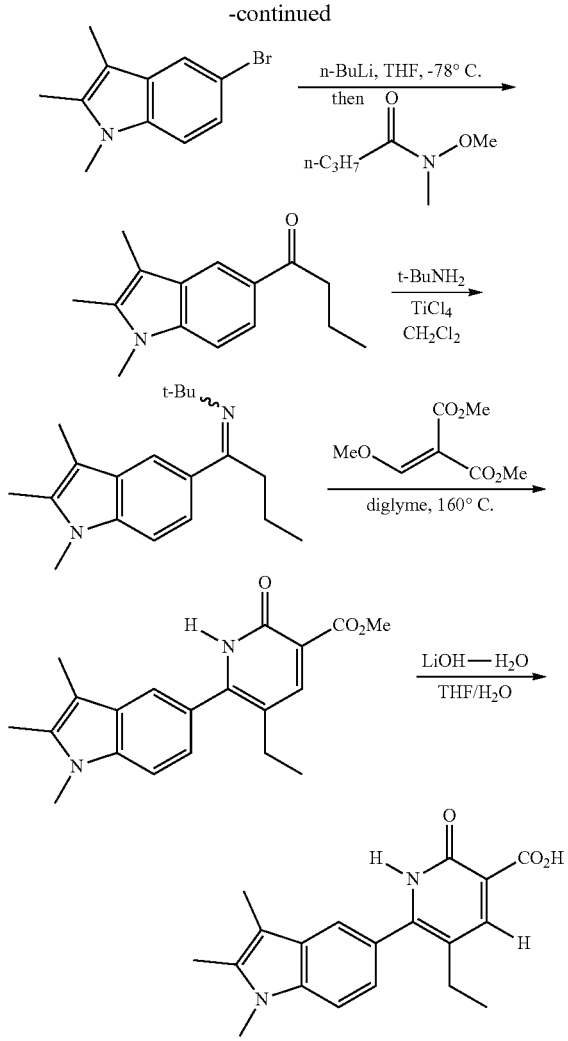

Step 1: 5-bromo-2,3-dimethyl-1H-indole

The title compound was prepared according to procedure described in Example 27 Step 1.
$^1$H NMR (500 MHz, DMSO-d$_6$) δ ppm 2.12 (s, 3H) 2.30 (s, 3H) 7.06 (dd, J=8.47, 1.93 Hz, 1H) 7.17 (d, J=8.51 Hz, 1H) 7.50 (d, J=1.81 Hz, 1H) 10.86 (br. s., 1H). LC-MS 224.2/226.2 [M+H]$^+$, RT 1.42 min.

Step 2: 5-bromo-1,2,3-trimethyl-1H-indole

The title compound was prepared according to procedure described in Example 9, Step 1.
$^1$H NMR (500 MHz, CHCl$_3$-d) δ ppm 2.21 (s, 3H) 2.35 (s, 3H) 3.63 (s, 3H) 7.10 (d, J=8.51 Hz, 1H) 7.21 (dd, J=8.59, 1.89 Hz, 1H) 7.59 (d, J=1.81 Hz, 1H). LC-MS 238.2/240.2 [M+H]$^+$, RT 1.58 min.

Step 3: 1-(1,2,3-trimethyl-1H-indol-5-yl)butan-1-one

The title compound was prepared according to procedure described in Example 21 Step 1.
$^1$H NMR (500 MHz, CHCl$_3$-d) δ ppm 1.04 (t, J=7.41 Hz, 3H) 1.82 (sxt, J=7.39 Hz, 2H) 2.28-2.32 (m, 3H) 2.35-2.39 (m, 3H) 3.01-3.08 (m, 2H) 3.68 (s, 3H) 7.21-7.26 (m, 1H) 7.84 (dd, J=8.59, 1.73 Hz, 1H) 8.18 (d, J=1.50 Hz, 1H). LC-MS 230.3 [M+H]$^+$, RT 1.47 min.

Step 4: 2-methyl-N-(1-(1,2,3-trimethyl-1H-indol-5-yl)butylidene)propan-2-amine The title compound was prepared according to procedure described in Example 1, Step 6.
LC-MS 284.8 [M+H]$^+$, RT 0.98 min.

Step 5-6: 5-ethyl-2-oxo-6-(1,2,3-trimethyl-1H-indol-5-yl)-1,2-dihydropyridine-3-carboxylic acid The title compound was prepared according to procedure described in Example 1, Step 7-8.
$^1$H NMR (500 MHz, DMSO-d$_6$) δ ppm 1.03 (t, J=7.49 Hz, 3H) 2.22 (s, 3H) 2.37 (s, 3H) 2.46 (q, J=7.51 Hz, 2H) 3.70 (s, 3H) 7.16 (dd, J=8.43, 1.73 Hz, 1H) 7.49 (d, J=8.35 Hz, 1H) 7.56 (d, J=1.50 Hz, 1H) 8.36 (s, 1H) 13.16 (br. s., 1H) 15.07 (s, 1H). LC-MS 323.1 [M−H]$^-$, 325.1 [M+H]$^+$, RT 1.22 min.

Example 30

5-ethyl-4-hydroxy-2-oxo-6-(1,2,3-trimethyl-1H-indol-5-yl)-1,2-dihydropyridine-3-carboxylic acid

Step 1: methyl 5-ethyl-4-hydroxy-2-oxo-6-(1,2,3-trimethyl-1H-indol-5-yl)-1,2-dihydropyridine-3-carboxylate The title compound was prepared according to procedure described in Example 2, Step 1.
$^1$H NMR (500 MHz, CHCl$_3$-d) δ ppm 1.15 (t, J=7.41 Hz, 3H) 2.28 (s, 3H) 2.39 (s, 3H) 2.53 (q, J=7.36 Hz, 2H) 3.71 (s, 3H) 4.02 (s, 3H) 7.18 (dd, J=8.43, 1.73 Hz, 1H) 7.33 (d, J=8.04 Hz, 1H) 7.54 (d, J=1.50 Hz, 1H) 13.85 (s, 1H). LC-MS 353.1 [M−H]$^-$, 355.2 [M+H]$^+$, RT 1.43 min.

Step 2: 5-ethyl-4-hydroxy-2-oxo-6-(1,2,3-trimethyl-1H-indol-5-yl)-1,2-dihydropyridine-3-carboxylic acid The title compound was prepared according to procedure described in Example 2, Step 2.
$^1$H NMR (500 MHz, DMSO-d$_6$) δ ppm 1.01 (t, J=7.37 Hz, 3H) 2.21 (s, 3H) 2.36 (q, J=7.36 Hz, 2H) 2.37 (s, 3H) 3.70 (s, 3H) 7.14 (dd, J=8.39, 1.69 Hz, 1H) 7.43-7.57 (m, 2H) 12.69 (br. s., 1H) 13.90 (s, 1H). LC-MS 339.1 [M−H]$^-$, 341.2 [M+H]$^+$, RT 1.39 min.

Example 31

5-ethyl-6-(1-methyl-1H-pyrrolo[2,3-b]pyridin-5-yl)-2-oxo-1,2-dihydropyridine-3-carboxylic acid

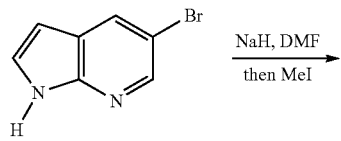

189
-continued

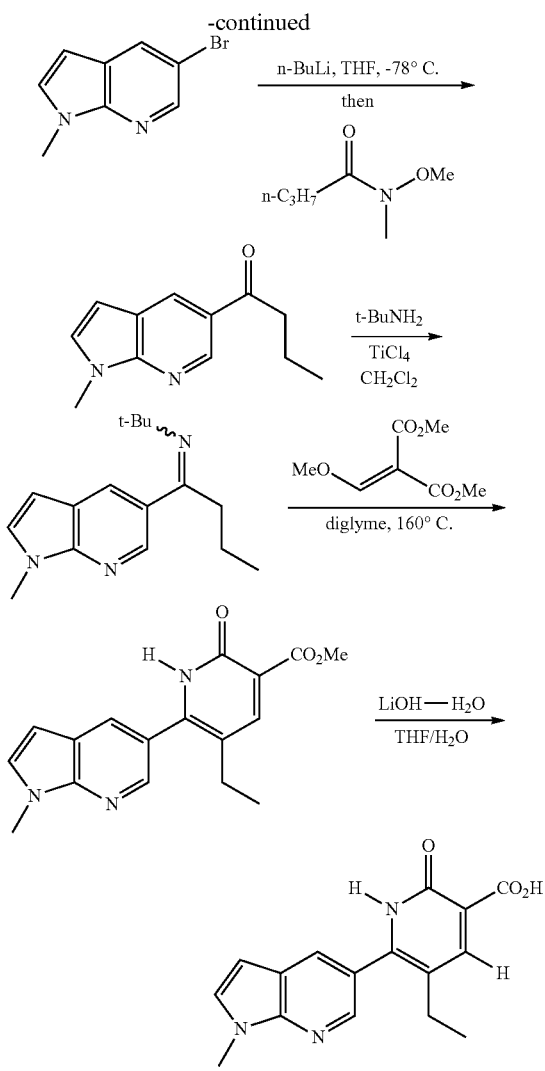

Step 1: 5-bromo-1-methyl-1H-pyrrolo[2,3-b]pyridine

The title compound was prepared according to procedure described in Example 9, Step 1.
$^1$H NMR (500 MHz, CHCl$_3$-d) δ ppm 3.88 (s, 3H) 6.41 (d, J=3.47 Hz, 1H) 7.20 (d, J=3.47 Hz, 1H) 8.03 (d, J=2.13 Hz, 1H) 8.36 (d, J=1.97 Hz, 1H). LC-MS 211.4/213.4 [M+H]$^+$, RT 1.20 min.

Step 2: 1-(1-methyl-1H-pyrrolo[2,3-b]pyridin-5-yl)butan-1-one

The title compound was prepared according to procedure described in Example 21 Step 1.
$^1$H NMR (500 MHz, CHCl$_3$-d) δ ppm 1.04 (t, J=7.45 Hz, 3H) 1.83 (sxt, J=7.38 Hz, 2H) 2.98-3.06 (m, 2H) 3.93 (s, 3H) 6.58 (d, J=3.55 Hz, 1H) 7.25 (d, J=3.55 Hz, 1H) 8.52 (d, J=2.05 Hz, 1H) 8.99 (d, J=2.05 Hz, 1H). LC-MS 203.5 [M+H]$^+$, RT 1.11 min.

Step 3: 2-methyl-N-(1-(1-methyl-1H-pyrrolo[2,3-b]pyridin-5-yl)butylidene)propan-2-amine The title compound was prepared according to procedure described in Example 1, Step 6.
LC-MS 258.5 [M+H]$^+$, RT 0.78 min.

190
Step 4-5: 5-ethyl-6-(1-methyl-1H-pyrrolo[2,3-b]pyridin-5-yl)-2-oxo-1,2-dihydropyridine-3-carboxylic acid The title compound was prepared according to procedure described in Example 1, Step 7-8.
$^1$H NMR (500 MHz, DMSO-d$_6$) δ ppm 1.03 (t, J=7.49 Hz, 3H) 2.42 (q, J=7.51 Hz, 2H) 3.88 (s, 3H) 6.60 (d, J=3.47 Hz, 1H) 7.67 (d, J=3.39 Hz, 1H) 8.15 (d, J=2.13 Hz, 1H) 8.36 (d, J=2.05 Hz, 1H) 8.40 (s, 1H) 13.32 (s, 1H). LC-MS 296.0 [M−H]$^−$, 298.4 [M+H]$^+$, RT 0.94 min.

Example 32

5-ethyl-4-hydroxy-6-(1-methyl-1H-pyrrolo[2,3-b]pyridin-5-yl)-2-oxo-1,2-dihydropyridine-3-carboxylic acid Step 1: methyl 5-ethyl-4-hydroxy-6-(1-methyl-1H-pyrrolo[2,3-b]pyridin-5-yl)-2-oxo-1,2-dihydropyridine-3-carboxylate The title compound was prepared according to procedure described in Example 2, Step 1.
$^1$H NMR (500 MHz, CHCl$_3$-d) δ ppm 1.13 (t, J=7.37 Hz, 3H) 2.45 (q, J=7.41 Hz, 2H) 3.97 (s, 3H) 3.98 (s, 3H) 6.57 (d, J=3.47 Hz, 1H) 7.33 (d, J=3.47 Hz, 1H) 7.97 (d, J=2.05 Hz, 1H) 8.39 (d, J=2.05 Hz, 1H) 13.90 (s, 1H). LC-MS 326.1 [M−H]$^−$, 328.5 [M+H]$^+$, RT 1.06 min.

Step 2: 5-ethyl-4-hydroxy-6-(1-methyl-1H-pyrrolo[2,3-b]pyridin-5-yl)-2-oxo-1,2-dihydropyridine-3-carboxylic acid The title compound was prepared according to procedure described in Example 2, Step 2.
$^1$H NMR (500 MHz, CHCl$_3$-d) δ ppm 1.15 (t, J=7.41 Hz, 3H) 2.52 (q, J=7.38 Hz, 2H) 4.06 (s, 3H) 6.68 (d, J=3.47 Hz, 1H) 7.40 (d, J=3.47 Hz, 1H) 8.11 (s, 1H) 8.45 (s, 1H) 11.18 (br. s., 1H) 13.88 (s, 1H) 14.27 (br. s., 1H). LC-MS 312.1 [M−H]$^−$, 314.4 [M+H]$^+$, RT 1.12 min.

Example 33

5-isopropyl-6-(1-methyl-1H-indol-5-yl)-2-oxo-1,2-dihydropyridine-3-carboxylic acid

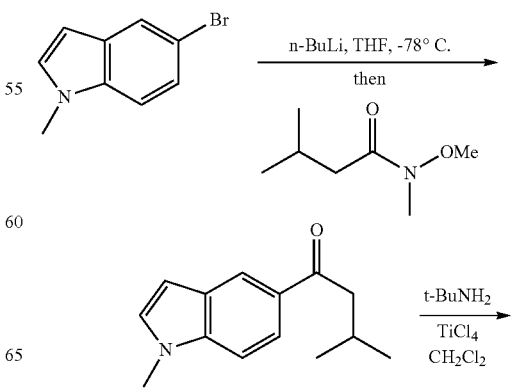

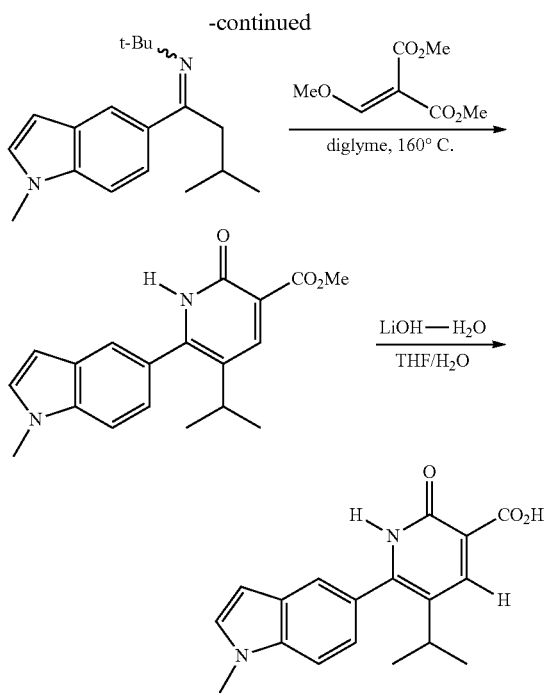

Step 1: 3-methyl-1-(1-methyl-1H-indol-5-yl)butan-1-one

The title compound was prepared according to procedure described in Example 21 Step 1.

$^1$H NMR (500 MHz, CHCl$_3$-d) δ ppm 1.00-1.06 (m, 6H) 2.29-2.41 (m, 1H) 2.92 (d, J=7.01 Hz, 2H) 3.84 (s, 3H) 6.62 (dd, J=3.19, 0.83 Hz, 1H) 7.12 (d, J=3.15 Hz, 1H) 7.35 (dt, J=8.67, 0.71 Hz, 1H) 7.92 (dd, J=8.67, 1.58 Hz, 1H) 8.31 (dd, J=1.66, 0.55 Hz, 1H). LC-MS 216.3 [M+H]$^+$, RT 1.36 min.

Step 2: 2-methyl-N-(3-methyl-1-(1-methyl-1H-indol-5-yl)butylidene)propan-2-amine The title compound was prepared according to procedure described in Example 1, Step 6.
LC-MS 271.3 [M+H]$^+$, RT 0.98 min.

Step 3-4: 5-isopropyl-6-(1-methyl-1H-indol-5-yl)-2-oxo-1,2-dihydropyridine-3-carboxylic acid The title compound was prepared according to procedure described in Example 1, Step 7-8.
$^1$H NMR (500 MHz, DMSO-d$_6$) δ ppm 1.09 (d, J=6.86 Hz, 6H) 2.75-2.90 (m, 1H) 3.85 (s, 3H) 6.55 (d, J=2.84 Hz, 1H) 7.21 (d, J=7.72 Hz, 1H) 7.47 (d, J=2.92 Hz, 1H) 7.59 (d, J=8.43 Hz, 1H) 7.67 (s, 1H) 8.40 (s, 1H) 13.18 (br. s., 1H) 15.06 (br. s., 1H). LC-MS 309.1 [M-H]$^-$, 311.2 [M+H]$^+$, RT 1.21 min.

Example 34

4-hydroxy-5-isopropyl-6-(1-methyl-1H-indol-5-yl)-2-oxo-1,2-dihydropyridine-3-carboxylic acid Step 1: methyl 4-hydroxy-5-isopropyl-6-(1-methyl-1H-indol-5-yl)-2-oxo-1,2-dihydropyridine-3-carboxylate The title compound was prepared according to procedure described in Example 2, Step 1.

$^1$H NMR (500 MHz, CHCl$_3$-d) δ ppm 1.28-1.34 (m, 6H) 3.02-3.14 (m, 1H) 3.87 (s, 3H) 4.03 (s, 3H) 6.59 (dd, J=3.11, 0.83 Hz, 1H) 7.16-7.20 (m, 1H) 7.21-7.27 (m, 1H) 7.41-7.49 (m, 1H) 7.67 (dd, J=1.69, 0.59 Hz, 1H) 14.02 (s, 1H). LC-MS 339.1 [M-H]$^-$, 341.1 [M+H]$^+$, RT 1.26 min.

Step 2: 4-hydroxy-5-isopropyl-6-(1-methyl-1H-indol-5-yl)-2-oxo-1,2-dihydropyridine-3-carboxylic acid The title compound was prepared according to procedure described in Example 2, Step 2.

$^1$H NMR (500 MHz, DMSO-d$_6$) δ ppm 1.16-1.24 (m, 6H) 2.73-2.87 (m, 1H) 3.85 (s, 3H) 6.55 (dd, J=3.07, 0.79 Hz, 1H) 7.17 (dd, J=8.43, 1.66 Hz, 1H) 7.47 (d, J=3.07 Hz, 1H) 7.59 (d, J=8.43 Hz, 1H) 7.63 (d, J=1.18 Hz, 1H) 12.69 (br. s., 1H) 14.22 (s, 1H). LC-MS 325.1 [M-H]$^-$, 327.1 [M+H]$^+$, RT 1.28 min.

Example 35

5-cyclopropyl-6-(1-methyl-1H-indol-5-yl)-2-oxo-1,2-dihydropyridine-3-carboxylic acid

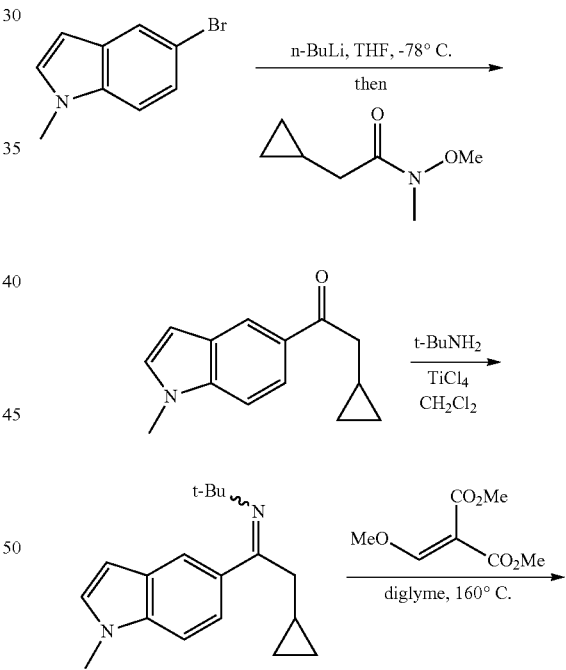

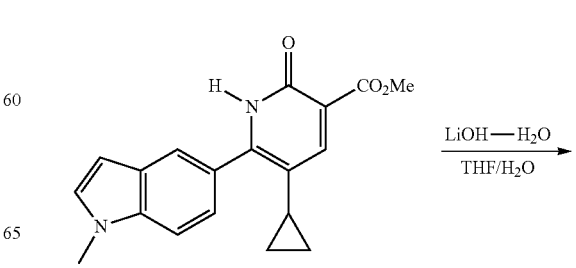

-continued

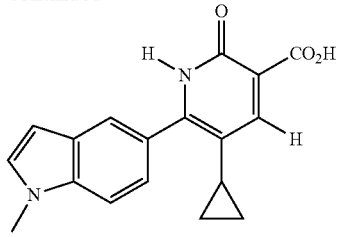

Step 1:
2-cyclopropyl-1-(1-methyl-1H-indol-5-yl)ethanone

The title compound was prepared according to procedure described in Example 21 Step 1.
$^1$H NMR (500 MHz, CHCl$_3$-d) δ ppm 0.20-0.26 (m, 2H) 0.58-0.63 (m, 2H) 1.17-1.29 (m, 1H) 2.97 (d, J=6.78 Hz, 2H) 3.84 (s, 3H) 6.61 (dd, J=3.15, 0.79 Hz, 1H) 7.12 (d, J=3.15 Hz, 1H) 7.35 (d, J=8.67 Hz, 1H) 7.92 (dd, J=8.67, 1.66 Hz, 1H) 8.29 (d, J=1.18 Hz, 1H).

Step 2: N-(2-cyclopropyl-1-(1-methyl-1H-indol-5-yl)ethylidene)-2-methylpropan-2-amine The title compound was prepared according to procedure described in Example 1, Step 6.
LC-MS 269.3 [M+H]$^+$, RT 0.83 min.

Step 3-4: 5-cyclopropyl-6-(1-methyl-1H-indol-5-yl)-2-oxo-1,2-dihydropyridine-3-carboxylic acid The title compound was prepared according to procedure described in Example 1, Step 7-8.
$^1$H NMR (500 MHz, DMSO-d$_6$) δ ppm 0.49-0.60 (m, 2H) 0.71-0.79 (m, 2H) 1.71-1.85 (m, 1H) 3.86 (s, 3H) 6.57 (dd, J=3.07, 0.63 Hz, 1H) 7.39 (dd, J=8.51, 1.66 Hz, 1H) 7.46 (d, J=3.15 Hz, 1H) 7.60 (d, J=8.51 Hz, 1H) 7.83 (d, J=1.10 Hz, 1H) 7.99 (s, 1H) 13.24 (br. s., 1H) 15.02 (br. s., 1H). LC-MS 307.1 [M−H]$^−$, 309.1 [M+H]$^+$, RT 1.09 min.

Example 36

5-cyclopropyl-4-hydroxy-6-(1-methyl-1H-indol-5-yl)-2-oxo-1,2-dihydropyridine-3-carboxylic acid Step 1: methyl 5-cyclopropyl-4-hydroxy-6-(1-methyl-1H-indol-5-yl)-2-oxo-1,2-dihydropyridine-3-carboxylate The title compound was prepared according to procedure described in Example 2, Step 1.
$^1$H NMR (500 MHz, DMSO-d$_6$) δ ppm −0.15−−0.05 (m, 2H) 0.45-0.55 (m, 2H) 1.53-1.66 (m, 1H) 3.84 (s, 3H) 3.85 (s, 3H) 6.51 (d, J=2.99 Hz, 1H) 7.31 (dd, J=8.55, 1.62 Hz, 1H) 7.41 (d, J=3.07 Hz, 1H) 7.51 (d, J=8.51 Hz, 1H) 7.72 (d, J=1.18 Hz, 1H) 11.24 (s, 1H) 13.46 (s, 1H). LC-MS 337.1 [M−H]$^−$, 339.2 [M+H]$^+$, RT 1.22 min.

Step 2: 5-cyclopropyl-4-hydroxy-6-(1-methyl-1H-indol-5-yl)-2-oxo-1,2-dihydropyridine-3-carboxylic acid The title compound was prepared according to procedure described in Example 2, Step 2.
$^1$H NMR (500 MHz, DMSO-d$_6$) δ ppm −0.01-0.10 (m, 2H) 0.49-0.61 (m, 2H) 1.62-1.73 (m, 1H) 3.86 (s, 3H) 6.55 (d, J=2.92 Hz, 1H) 7.36 (dd, J=8.47, 1.62 Hz, 1H) 7.45 (d, J=3.15 Hz, 1H) 7.56 (d, J=8.59 Hz, 1H) 7.75-7.83 (m, 1H) 12.62 (br. s., 1H) 13.88 (s, 1H). LC-MS 323.1 [M−H]$^−$, 325.0 [M+H]$^+$, RT 1.22 min.

Example 37

6-(1,2-dimethyl-1H-indol-5-yl)-5-ethyl-2-oxo-1,2-dihydropyridine-3-carboxylic acid

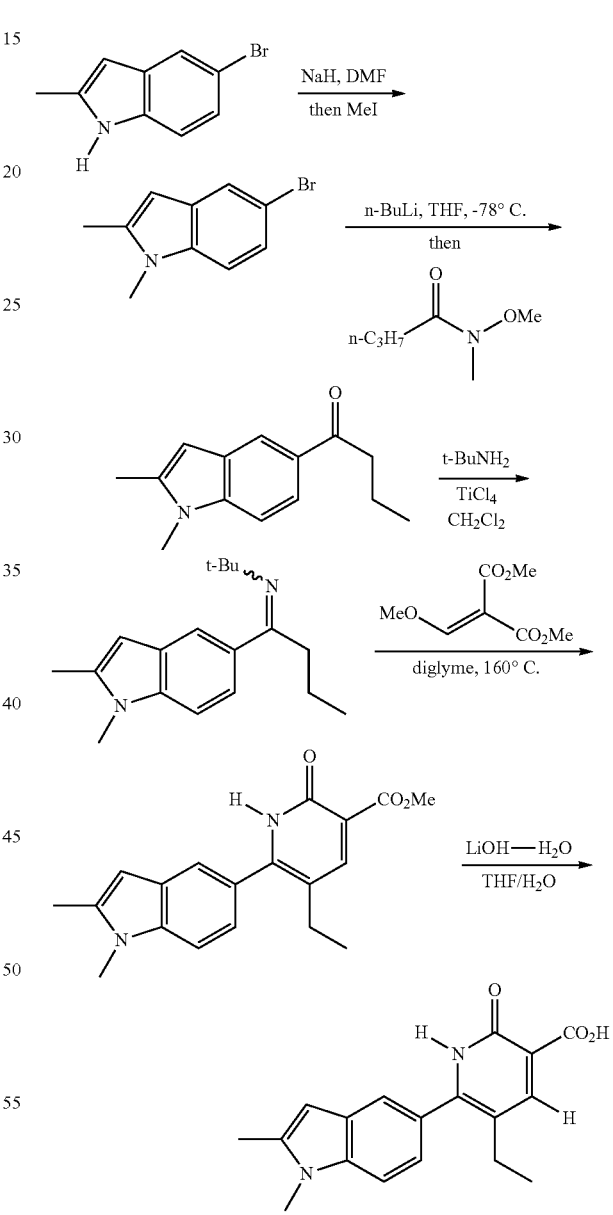

Step 1: 5-bromo-1,2-dimethyl-1H-indole

The title compound was prepared according to procedure described in Example 9, Step 1.
LC-MS 223.9/225.9 [M+H]$^+$, RT 1.35 min.

195

Step 2: 1-(1,2-dimethyl-1H-indol-5-yl)butan-1-one

The title compound was prepared according to procedure described in Example 21 Step 1.
$^1$H NMR (500 MHz, CHCl$_3$-d) δ ppm 1.03 (t, J=7.41 Hz, 3H) 1.81 (sxt, J=7.39 Hz, 2H) 2.45 (d, J=0.95 Hz, 3H) 2.98-3.05 (m, 2H) 3.70 (s, 3H) 6.34-6.39 (m, 1H) 7.27 (d, J=8.59 Hz, 1H) 7.85 (dd, J=8.67, 1.73 Hz, 1H) 8.20 (d, J=1.58 Hz, 1H). LC-MS 216.1 [M+H]$^+$, RT 1.24 min.

Step 3: N-(1-(1,2-dimethyl-1H-indol-5-yl)butylidene)-2-methylpropan-2-amine

The title compound was prepared according to procedure described in Example 1, Step 6.
LC-MS 271.2 [M+H]$^+$, RT 0.91 min.

Step 4-5: 6-(1,2-dimethyl-1H-indol-5-yl)-5-ethyl-2-oxo-1,2-dihydropyridine-3-carboxylic acid The title compound was prepared according to procedure described in Example 1, Step 7-8.
$^1$H NMR (500 MHz, DMSO-d$_6$) δ ppm 1.01 (t, J=7.53 Hz, 3H) 2.44 (q, J=7.53 Hz, 2H) 2.44 (s, 3H) 3.72 (s, 3H) 6.33 (s, 1H) 7.16 (dd, J=8.43, 1.66 Hz, 1H) 7.53 (d, J=8.51 Hz, 1H) 7.56 (d, J=1.26 Hz, 1H) 8.36 (s, 1H) 13.18 (br. s., 1H). LC-MS 309.1 [M−H]$^-$, 311.1 [M+H]$^+$, RT 1.15 min.

Example 38

6-(1,2-dimethyl-1H-indol-5-yl)-5-ethyl-4-hydroxy-2-oxo-1,2-dihydropyridine-3-carboxylic acid

Step 1: methyl 6-(1,2-dimethyl-1H-indol-5-yl)-5-ethyl-4-hydroxy-2-oxo-1,2-dihydropyridine-3-carboxylate The title compound was prepared according to procedure described in Example 2, Step 1.
LC-MS 339.2 [M−H]$^-$, 341.1 [M+H]$^+$, RT 1.26 min.

Step 2: 6-(1,2-Dimethyl-1H-indol-5-yl)-5-ethyl-4-hydroxy-2-oxo-1,2-dihydropyridine-3-carboxylic acid)

The title compound was prepared according to procedure described in Example 2, Step 2.
$^1$H NMR (500 MHz, DMSO-d$_6$) δ ppm 0.99 (t, J=7.05 Hz, 3H) 2.34 (d, J=7.25 Hz, 2H) 2.44 (s, 3H) 3.72 (s, 3H) 6.33 (s, 1H) 7.13 (d, J=7.80 Hz, 1H) 7.49-7.59 (m, 2H) 12.70 (br. s., 1H) 13.90 (br. s., 1H). LC-MS 325.1 [M−H]$^-$, 327.2 [M+H]$^+$, RT 1.34 min.

Example 39

5-ethyl-6-(2-(hydroxymethyl)-1-methyl-1H-indol-5-yl)-2-oxo-1,2-dihydropyridine-3-carboxylic acid

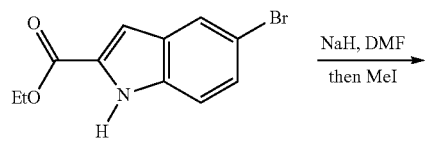

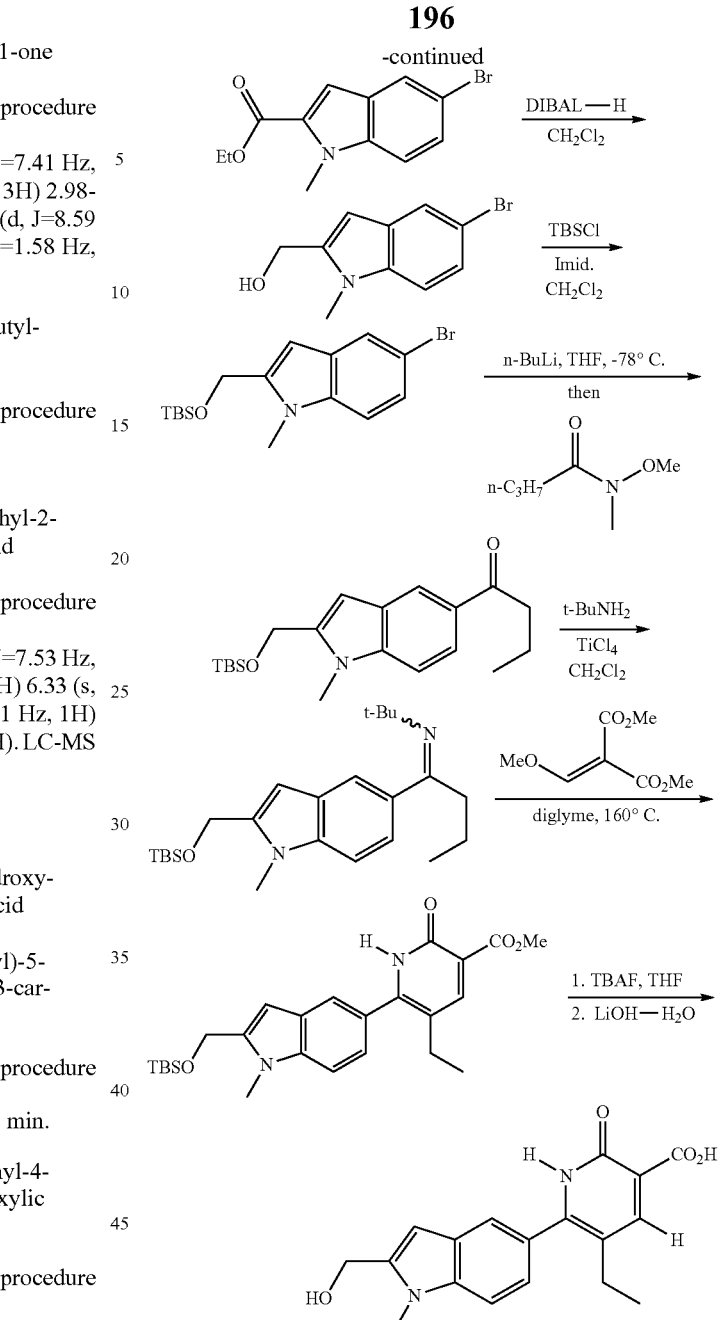

Step 1: ethyl 5-bromo-1-methyl-1H-indole-2-carboxylate

The title compound was prepared according to procedure described in Example 9, Step 1.
$^1$H NMR (500 MHz, CHCl$_3$-d) δ ppm 1.42 (t, J=7.13 Hz, 3H) 4.04-4.09 (m, 3H) 4.39 (q, J=7.17 Hz, 2H) 7.22 (d, J=0.87 Hz, 1H) 7.24-7.31 (m, 1H) 7.43 (dd, J=8.87, 1.93 Hz, 1H) 7.81 (dd, J=1.93, 0.51 Hz, 1H).

Step 2: (5-bromo-1-methyl-1H-indol-2-yl)methanol

To a solution of ethyl 5-bromo-1-methyl-1H-indole-2-carboxylate (ca. 9.0 g) in CH$_2$Cl$_2$ (80 mL) was added DIBAL-H (1.0M in hexanes, 70.0 mL, 2.2 eq) at −78° C. over 15 min. The reaction was monitored by LC-MS. After stirring for 1 h at −78° C., the reaction was quenched with 1N HCl (20 mL) at −78° C. then allowed to warm to room temperature and stirred for additional 30 min to break aluminum emulsion. The biphasic mixture was extracted by ether/EtOAc (1:1, 3×50 mL). The combined organic layers were dried over $Na_2SO_4$ then concentrated to give (5-bromo-1-methyl-1H-indol-2-yl)methanol (ca. 7.8 g, quant.) which was used in the next step without further purification.

$^1$H NMR (500 MHz, $CHCl_3$-d) δ ppm 3.80 (s, 3H) 4.81 (s, 2H) 6.41 (s, 1H) 7.20 (d, J=8.67 Hz, 1H) 7.31 (dd, J=8.71, 1.93 Hz, 1H) 7.71 (dd, J=1.89, 0.39 Hz, 1H). LC-MS 240.1/242.1 [M+H]$^+$, RT 1.12 min.

Step 3: 5-bromo-2-((tert-butyldimethylsilyloxy)methyl)-1-methyl-1H-indole

To a solution of (5-bromo-1-methyl-1H-indol-2-yl)methanol (7.8 g, ca. 31.3 mmol) in $CH_2Cl_2$ (80 mL) was added imidazole (2.6 g, 38.2 mmol, 1.2 eq) followed by TBS-Cl (5.2 g, 34.5 mmol, 1.1 eq) at 0° C. The reaction was monitored by LC-MS. After 1 h, the reaction was quenched with water then extracted by $CH_2Cl_2$ (3×50 mL). The solvent was concentrated to give a crude product which was purified by flash column chromatography (50% $CH_2Cl_2$ in hexanes) to afford the title compound (10.7 g, 30.2 mmol, 96%) over three steps as an off-white solid.

$^1$H NMR (500 MHz, $CHCl_3$-d) δ ppm 0.07 (s, 6H) 0.90 (s, 9H) 3.77 (s, 3H) 4.79-4.85 (m, 2H) 6.30-6.35 (m, 1H) 7.17 (d, J=8.67 Hz, 1H) 7.27-7.31 (m, 1H) 7.69 (dd, J=1.89, 0.47 Hz, 1H). LC-MS 354.0/356.0 [M+H]$^+$, RT 1.80 min.

Step 4: 1-(2-((tert-butyldimethylsilyloxy)methyl)-1-methyl-1H-indol-5-yl)butan-1-one The title compound was prepared according to procedure described in Example 21 Step 1.

$^1$H NMR (500 MHz, $CHCl_3$-d) δ ppm 0.08 (s, 6H) 0.91 (s, 9H) 1.03 (t, J=7.41 Hz, 3H) 1.74-1.88 (m, 2H) 2.97-3.07 (m, 2H) 3.82 (s, 3H) 4.85 (s, 2H) 6.46-6.52 (m, 1H) 7.32 (d, J=8.67 Hz, 1H) 7.90 (dd, J=8.67, 1.73 Hz, 1H) 8.26 (d, J=1.18 Hz, 1H). LC-MS 346.2 [M+H]$^+$, RT 1.71 min.

Step 5: N-(1-(2-((tert-butyldimethylsilyloxy)methyl)-1-methyl-1H-indol-5-yl)butylidene)-2-methylpropan-2-amine The title compound was prepared according to procedure described in Example 1, Step 6.
LC-MS 401.5 [M+H]$^+$, RT 1.21 min.

Step 6: methyl 6-(2-((tert-butyldimethylsilyloxy)methyl)-1-methyl-1H-indol-5-yl)-5-ethyl-2-oxo-1,2-dihydropyridine-3-carboxylate The title compound was prepared according to procedure described in Example 1, Step 7.

$^1$H NMR (500 MHz, $CHCl_3$-d) δ ppm 0.10 (s, 6H) 0.92 (s, 9H) 1.15 (t, J=7.53 Hz, 3H) 2.54 (q, J=7.53 Hz, 2H) 3.84 (s, 3H) 3.96 (s, 3H) 4.86 (s, 2H) 6.46 (s, 1H) 7.24 (d, J=8.67 Hz, 1H) 7.40 (d, J=8.43 Hz, 1H) 7.63 (s, 1H) 8.27 (s, 1H). LC-MS 453.0 [M−H]$^-$, 455.2 [M+H]$^+$, RT 1.59 min.

Step 7-8: 5-ethyl-6-(2-(hydroxymethyl)-1-methyl-1H-indol-5-yl)-2-oxo-1,2-dihydropyridine-3-carboxylic acid To a solution of methyl 6-(2-((tert-butyldimethylsilyloxy)methyl)-1-methyl-1H-indol-5-yl)-5-ethyl-2-oxo-1,2-dihydropyridine-3-carboxylate (102 mg, 0.22 mmol) in THF (2 mL) was added TBAF (1.0M in THF, 0.3 mL, 0.3 mmol, 1.4 eq) at 0° C. The mixture was allowed to warm to room temperature then stirred for 30 min. The solvent was removed under reduced pressure then crude product was purified by flash column chromatography (0-5% MeOH in $CH_2Cl_2$) to afford the ester (62 mg, 0.18 mmol, 83%) as a white solid.

According to procedure described in Example 1, Step 8, the ester obtained above (62 mg, 0.18 mmol) was used to give 5-ethyl-6-(2-(hydroxymethyl)-1-methyl-1H-indol-5-yl)-2-oxo-1,2-dihydropyridine-3-carboxylic acid (29 mg, 0.089 mmol, 49%) as a light yellow solid.

$^1$H NMR (500 MHz, DMSO-$d_6$) δ ppm 1.01 (t, J=7.53 Hz, 3H) 2.44 (q, J=7.46 Hz, 2H) 3.80 (s, 3H) 4.67 (d, J=5.44 Hz, 2H) 5.29 (t, J=5.44 Hz, 1H) 6.45-6.53 (m, 1H) 7.22 (dd, J=8.43, 1.73 Hz, 1H) 7.57 (d, J=8.59 Hz, 1H) 7.65 (d, J=1.18 Hz, 1H) 8.36 (s, 1H) 13.21 (br. s., 1H) 15.06 (s, 1H). LC-MS 325.1 [M−H]$^-$, 327.2 [M+H]$^+$, RT 1.01 min.

Example 40

5-ethyl-4-hydroxy-6-(2-(hydroxymethyl)-1-methyl-1H-indol-5-yl)-2-oxo-1,2-dihydropyridine-3-carboxylic acid Step 1: methyl 6-(2-((tert-butyldimethylsilyloxy)methyl)-1-methyl-1H-indol-5-yl)-5-ethyl-4-hydroxy-2-oxo-1,2-dihydropyridine-3-carboxylate To a solution of N-(1-(2-((tert-butyldimethylsilyloxy)methyl)-1-methyl-1H-indol-5-yl)butylidene)-2-methylpropan-2-amine (2.10 g, ca. 5.2 mmol), prepared according to procedure described in Example 39 Step 5, in $Ph_2O$ (5 mL) was added trimethyl methanetricarboxylate (1.68 g, 8.8 mmol, 1.7 eq). The mixture was heated to 230° C. for 2 h. The mixture was cooled to room temperature then purified by flash column chromatography (0-50% EtOAc in $CH_2Cl_2$) to afford the title compound (0.51 g, 1.1 mmol, 21%) as a light yellow solid. LC-MS 469.2 [M−H]$^-$, 471.2 [M+H]$^+$, RT 1.67 min.

Step 2: methyl 5-ethyl-4-hydroxy-6-(2-(hydroxymethyl)-1-methyl-1H-indol-5-yl)-2-oxo-1,2-dihydropyridine-3-carboxylate The title compound was prepared according to procedure described in Example 39 Step 7.

$^1$H NMR (500 MHz, $CHCl_3$-d) δ ppm 1.12 (t, J=7.37 Hz, 3H) 2.47 (q, J=7.33 Hz, 2H) 3.88 (s, 3H) 4.02 (s, 3H) 4.87 (s, 2H) 6.54 (s, 1H) 7.23 (dd, J=8.51, 1.73 Hz, 1H) 7.42 (d, J=8.51 Hz, 1H) 7.62 (d, J=1.26 Hz, 1H) 13.87 (s, 1H). LC-MS 355.2 [M−H]$^-$, 357.3 [M+H]$^+$, RT 1.05 min.

Step 3: 5-ethyl-4-hydroxy-6-(2-(hydroxymethyl)-1-methyl-1H-indol-5-yl)-2-oxo-1,2-dihydropyridine-3-carboxylic acid The title compound was prepared according to procedure described in Example 2, Step 2.

$^1$H NMR (500 MHz, $CHCl_3$-d) δ ppm 1.14 (t, J=7.37 Hz, 3H) 2.53 (q, J=7.36 Hz, 2H) 3.90 (s, 3H) 4.88 (d, J=5.67 Hz, 2H) 6.57 (s, 1H) 7.18-7.26 (m, 1H) 7.41-7.51 (m, 1H) 7.65 (s, 1H) 13.89 (s, 1H) 14.90 (s, 1H). LC-MS 341.1 [M−H]$^-$, 343.1 [M+H]$^+$, RT 1.02 min.

Using the procedures described above, additional compounds described herein may be prepared by substituting the appropriate starting materials, reagents and reaction conditions and include compounds selected from:

| Cpd | Name |
|---|---|
| 41 | 5-ethyl-6-(1-methyl-1H-indazol-5-yl)-2-oxo-1,2-dihydropyridine-3-carboxylic acid<br>$^1$H NMR (500 MHz, DMSO-$d_6$) δ ppm 1.02 (t, J = 7.53 Hz, 3 H) 2.42 (q, J = 7.49 Hz, 2 H) 4.12 (s, 3 H) 7.50 (dd, J = 8.67, 1.66 Hz, 1 H) 7.81 (dt, J = 8.71, 0.85 Hz, 1 H) 7.95 (dd, J = 1.62, 0.83 Hz, 1 H) 8.20 (d, J = 0.95 Hz, 1 H) 8.40 (s, 1H) 13.31 (br. s., 1 H) 15.02 (br. s., 1H). LC-MS 298.1 [M + H]$^+$, RT 1.08 min. |
| 42 | 5-ethyl-4-hydroxy-6-(1-methyl-1H-indazol-5-yl)-2-oxo-1,2-dihydropyridine-3-carboxylic acid<br>$^1$H NMR (500 MHz, DMSO-$d_6$) δ ppm 0.99 (t, J = 7.41 Hz, 3 H) 2.31 (q, J = 7.36 Hz, 2 H) 4.12 (s, 3 H) 7.47 (dd, J = 8.67, 1.66 Hz, 1 H) 7.81 (dt, J = 8.73, 0.84 Hz, 1 H) 7.93 (dd, J = 1.58, 0.87 Hz, 1H) 8.20 (d, J = 0.95 Hz, 1H) 12.82 (br. s., 1H) 13.88-14.01 (m, 1H). LC-MS 314.1 [M + H]$^+$, RT 1.24 min |

Example 49

6-([1,2,4]triazolo[1,5-a]pyridin-6-yl)-5-ethyl-2-oxo-1,2-dihydropyridine-3-carboxylic acid hydrochloride (Cpd 49)

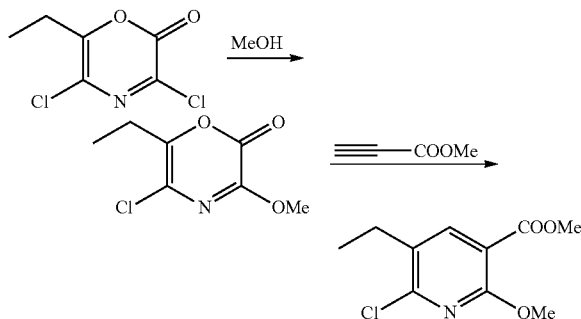

Step 1-2: methyl 6-chloro-5-ethyl-2-methoxynicotinate

To solution of 3,5-dichloro-6-ethyl-2H-1,4-oxazin-2-one (10.0 g, 52.0 mmol) in DCM (10 mL) was added dry MeOH (10.4 mL, 257 mmol). The reaction was stirred overnight at room temperature. The mixture was purified via column chromatography using EtOAc/hexanes (gradient 0-10%) to afford 5-chloro-6-ethyl-3-methoxy-2H-1,4-oxazin-2-one (4.54 g, 55%) as an oil.

The product 5-Chloro-6-ethyl-3-methoxy-2H-1,4-oxazin-2-one (4.54 g, 28.10 mmol) obtained above was mixed with methyl propiolate (6.0 mL, 71.80 mmol)) and BF$_3$-etherate (0.26 mL, 2.81 mmol). The mixture was heated at 40° C. over 72 h. Upon cooling to room temperature, the mixture was purified via column chromatography using EtOAc/hexanes (gradient 0-15%) to afford methyl 6-chloro-5-ethyl-2-methoxynicotinate (4.84 g, 75%) as off-white solid.

$^1$H NMR (500 MHz, CHCl$_3$-d) δ ppm 1.24 (t, J=7.6 Hz, 3H) 2.70 (q, J=7.6 Hz, 2H) 3.91 (s, 3H) 4.04 (s, 3H) 8.05 (s, 1H).

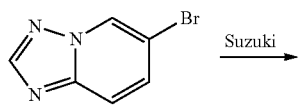

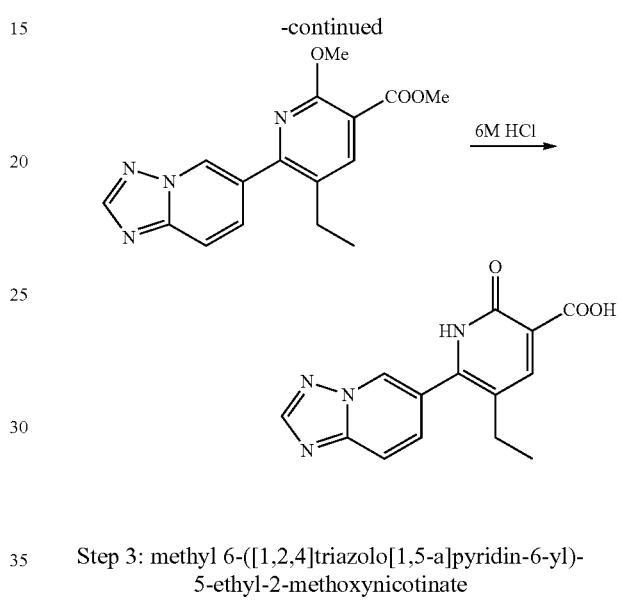

Step 3: methyl 6-([1,2,4]triazolo[1,5-a]pyridin-6-yl)-5-ethyl-2-methoxynicotinate 6-bromo-[1,2,4]triazolo[1,5-a]pyridine (0.107 g, 0.54 mmol), bis(pinacolato)diborate (0.170 g, 0.67 mmol), Pd(dppf)Cl$_2$ (15.8 mg, 0.02 mmol, 4 mol %), and KOAc (0.160 g, 1.63 mmol) were mixed together in a heat-gun dried vial. The vial was vacuumed and backfilled with argon before dioxane (1.6 mL) was added. The mixture was heated at 130° C. for ~1 h until complete consumption of the starting bromide was observed. The reaction mixture was cooled to room temperature before H$_2$O (0.20 mL), K$_2$CO$_3$ (0.220 g, 1.59 mmol) and 6-chloro-5-ethyl-2-methoxynicotinate (0.150 g, 0.65 mmol) were added. The reaction vial was resealed under argon and the mixture was heated at 120° C. for 3 h and then cooled to room temperature. Water (5 mL) was added to the reaction mixture and the product was extracted with DCM (3×5 mL). The combined organics were washed with NaCl (aqueous saturated, 5 mL) and dried over Na$_2$SO$_4$. After concentration of the solvent the residue was purified by column chromatography (EtOAc/hexanes, 0-100% gradient). Upon concentration of the desired fractions, the residue was treated with H$_2$O (5 mL) and stirred vigorously for 30 min, the solid was then filtered and washed with H$_2$O. Upon drying methyl 6-([1,2,4]triazolo[1,5-a]pyridin-6-yl)-5-ethyl-2-methoxynicotinate (0.115 g, 69%) was obtained as pale yellow solid.

$^1$H NMR (500 MHz, CHCl$_3$-d) δ ppm 1.26 (t, J=7.6 Hz, 3H) 2.76 (q, J=7.6 Hz, 2H) 3.95 (s, 3H) 4.06 (s, 3H) 7.80 (dd, J=9.0, 1.6 Hz, 1H) 7.86 (dd, J=9.0, 0.9 Hz, 1H) 8.19 (s, 1H) 8.43 (s, 1H) 8.85 (s, 1H). LC-MS 313.2 [M+H]$^+$, RT 1.06 min.

Step 4: 6-([1,2,4]triazolo[1,5-a]pyridin-6-yl)-5-ethyl-2-oxo-1,2-dihydropyridine-3-carboxylic acid hydrochloride Methyl 6-([1,2,4]triazolo[1,5-a]pyridin-6-yl)-5-ethyl-2-methoxynicotinate (90 mg, 0.29 mmol) obtained above was heated with 6 M HCl (2.0 mL) at 80° C. for 2 h. HCl was removed under reduced pressure affording 6-([1,2,4]triazolo[1,5-a]pyridin-6-yl)-5-ethyl-2-oxo-1,2-dihydropyridine-3-carboxylic acid (85.9 mg) as hydrochloride salt in 93% overall yield.

$^1$H NMR (500 MHz, MeOH-d$_4$) δ ppm 1.16 (t, J=7.6 Hz, 3H) 2.52 (d, J=7.6 Hz, 2H) 8.09 (dd, J=8.8, 1.6 Hz, 1H) 8.13 (d, J=8.8 Hz, 1H) 8.55 (s, 1H) 8.96 (s, 1H) 9.37 (s, 1H). LC-MS 283.1 [M−H]$^−$, 285.2 [M+H]$^+$, RT 0.72 min.

Using the procedures described above, additional compounds described herein may be prepared by substituting the appropriate starting materials, reagents and reaction conditions and include compounds selected from:

Example 60

6-(2-((dimethylamino)methyl)imidazo[1,2-a]pyridin-6-yl)-5-ethyl-2-oxo-1,2-dihydropyridine-3-carboxylic acid dihydrochloride

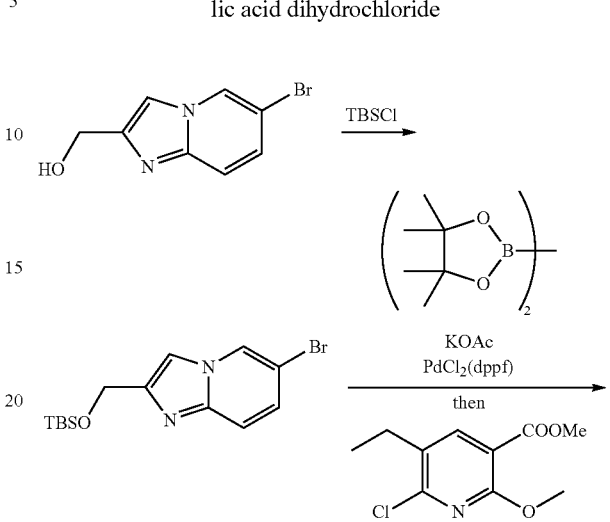

| Cpd | Name |
|---|---|
| 50 | 6-([1,2,4]triazolo[4,3-a]pyridin-6-yl)-5-ethyl-2-oxo-1,2-dihydropyridine-3-carboxylic acid hydrochloride<br>$^1$H NMR (500 MHz, MeOH-d$_4$) δ ppm 1.18 (t, J = 7.4 Hz, 3 H) 2.53 (q, J = 7.4 Hz, 2 H) 8.25 (d, J = 9.5 Hz, 1 H) 8.30 (d, J = 9.5 Hz, 1 H) 8.55 (s, 1 H) 9.21 (s, 1 H) 9.68 (s, 1 H). LC-MS 283.1 [M − H]$^−$, 285.2 [M + H]$^+$, RT 1.01 min. (Polar Method). |
| 51 | 5-ethyl-6-(imidazo[1,2-a]pyridin-6-yl)-2-oxo-1,2-dihydropyridine-3-carboxylic acid hydrochloride<br>$^1$H NMR (500 MHz, MeOH-d$_4$) δ ppm 1.17 (t, J = 7.4 Hz, 3 H) 2.52 (q, J = 7.4 Hz, 2 H) 8.09 (d, J = 8.8 Hz, 1 H) 8.14 (d, J = 8.8 Hz, 1 H) 8.20 (d, J = 1.9 Hz, 1 H) 8.39 (d, J = 1.9 Hz, 1 H) 8.56 (s, 1 H) 9.16 (s, 1 H). LC-MS 282.2 [M − H]$^−$, 284.2 [M + H]$^+$, RT 0.84 min. (Polar Method). |
| 52 | 5-ethyl-6-(3-methyl-3H-imidazo[4,5-b]pyridin-6-yl)-2-oxo-1,2-dihydropyridine-3-carboxylic acid<br>$^1$H NMR (500 MHz, MeOH-d$_4$) δ ppm 1.14 (br. s., 3 H) 2.47 (br. s., 2 H) 4.21 (br. s., 3 H) 8.55 (s, 1 H) 8.52 (s, 1 H) 8.86 (br. s., 1 H) 9.65 (br. s., 1 H). LC-MS 299.3 [M + H]$^+$, RT 0.74 min. |
| 53 | 5-ethyl-6-(1-methyl-1H-benzo[d]imidazol-5-yl)-2-oxo-1,2-dihydropyridine-3-carboxylic acid<br>$^1$H NMR (500 MHz, DMSO-d$_6$) δ ppm 1.01 (t, J = 7.41 Hz, 3 H) 2.39 (q, J = 7.46 Hz, 2 H) 4.03 (s, 3 H) 7.59 (d, J = 8.51 Hz, 1 H) 7.89-8.01 (m, 2 H) 8.42 (s, 1 H) 9.08 (s, 1 H). LC-MS 296.2 [M − H]$^−$, 298.2 [M + H]$^+$, RT 0.50 min. (1 min Method). |
| 54 | 5-(5-carboxy-3-ethyl-6-oxo-1,6-dihydropyridin-2-yl)-1-methyl-1H-pyrrolo[2,3-c]pyridine-2-carboxylic acid<br>LC-MS 342.3 [M + H]$^+$, RT 0.78 min. |
| 55 | 5-ethyl-2-oxo-6-(1H-pyrrolo[2,3-b]pyridin-5-yl)-1,2-dihydropyridine-3-carboxylic acid<br>LC-MS 284.2 [M + H]$^+$, RT 0.85 min. |
| 56 | 6-(1,4-dimethyl-1,2,3,4-tetrahydroquinoxalin-6-yl)-5-ethyl-2-oxo-1,2-dihydropyridine-3-carboxylic acid<br>$^1$H NMR (500 MHz, DMSO-d$_6$) δ ppm 8.30 (s, 1 H) 6.83 (br. s., 1 H) 6.71 (br. s., 1 H) 6.65 (d, J = 8.12 Hz, 1 H) 3.30-3.50 (m, 4 H) 2.91 (d, J = 13.64 Hz, 6 H) 2.44-2.55 (m, 2 H) 1.03-1.13 (m, 3 H). LC-MS 328.2 [M + H]$^+$, RT 1.11 min. |
| 57 | 5-ethyl-2-oxo-6-(quinoxalin-6-yl)-1,2-dihydropyridine-3-carboxylic acid<br>$^1$H NMR (500 MHz, CHCl$_3$-d) δ ppm 8.99 (d, J = 7.01 Hz, 2 H) 8.60 (s, 1 H) 8.25-8.39 (m, 2 H) 7.80-7.89 (m, 1 H) 2.60-2.61 (m, 2 H) 2.55-2.65 (m, 2 H) 1.21 (t, J = 7.49 Hz, 3 H). LC-MS 296.1 [M + H]$^+$, RT 0.83 min. |
| 58 | 5-ethyl-6-(4-methyl-3,4-dihydro-2H-pyrido[3,2-b][1,4]oxazin-7-yl)-2-oxo-1,2-dihydropyridine-3-carboxylic acid<br>$^1$H NMR (500 MHz, DMSO-d$_6$) δ ppm 8.14-8.39 (m, 1 H) 7.72-7.83 (m, 1 H) 7.23-7.52 (m, 1 H) 4.24-4.39 (m, 2 H) 3.58-3.75 (m, 2 H) 3.16-3.33 (m, 3 H) 2.39-2.71 (m, 2 H) 1.00-1.20 (m, 3 H). LC-MS 316.8 [M + H]$^+$, RT 0.81 min. |
| 59 | 6-(3-cyano-1-methyl-1H-pyrrolo[2,3-b]pyridin-5-yl)-5-ethyl-2-oxo-1,2-dihydropyridine-3-carboxylic acid<br>LC-MS 323.1 [M + H]$^+$, RT 0.92 min. |

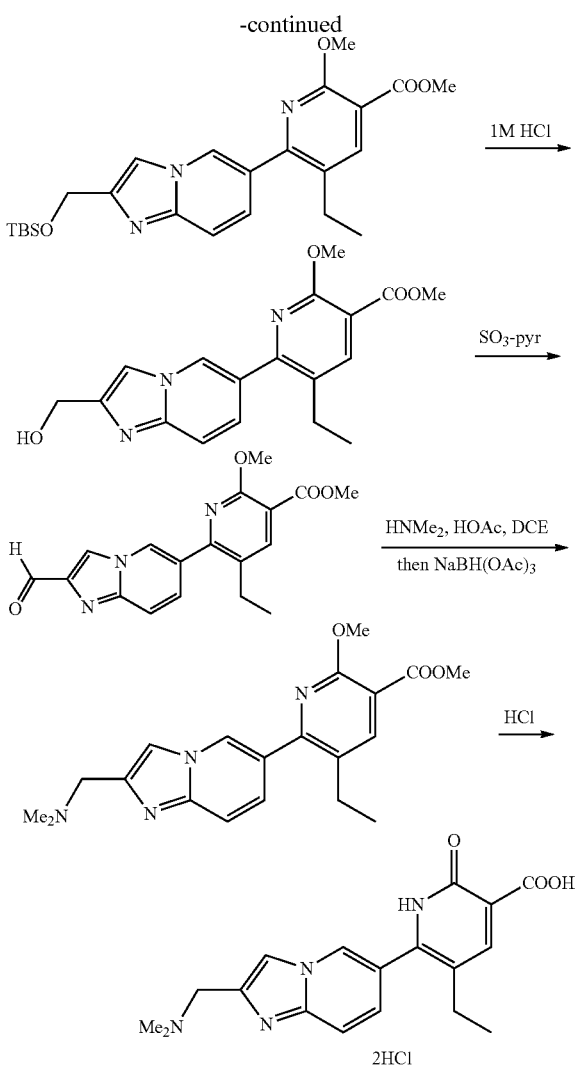

(0.892 g, 3.51 mmol), Pd(dppf)Cl$_2$ (86 mg, 0.12 mmol, 4 mol %), and KOAc (0.860 g, 8.76 mmol) were mixed together in a heat-gun dried flask. The flask was vacuumed and backfilled with argon before dioxane (9 mL) was added. Mixture was heated at 130° C. for ~3 h until complete consumption of the starting bromide was observed. Reaction mixture was cooled to room temperature before H$_2$O (0.90 mL), K$_2$CO$_3$ (1.20 g, 8.68 mmol), 6-chloro-5-ethyl-2-methoxynicotinate (0.673 g, 2.93 mmol) and fresh Pd(dppf)Cl$_2$ (60 mg, 0.08 mmol, 3 mol %) were added. Reaction flask was resealed under argon and mixture was heated at 120° C. overnight and then cooled to room temperature. Water (10 mL) was added to the reaction mixture and product was extracted with DCM (3×20 mL). Combined organics were washed with NaCl (aqueous saturated, 20 mL) and dried over Na$_2$SO$_4$. Upon concentration of the solvent residue was purified by column chromatography (EtOAc/hexanes, 0-60% gradient). After concentration of the desired fractions, residue was treated with H$_2$O (10-15 mL) and stirred vigorously for 30 min, solid was then filtered and washed with H$_2$O. Upon drying methyl 6-(2-((tert-butyldimethylsilyloxy)methyl)imidazo[1,2-a]pyridin-6-yl)-5-ethyl-2-methoxynicotinate (1.00 g, 75%) was obtained as solid.

$^1$H NMR (500 MHz, CHCl$_3$-d) δ ppm 0.16 (s, 6H) 0.98 (s, 9H) 1.23 (t, J=7.4 Hz, 3H) 2.74 (d, J=7.4 Hz, 2H) 3.95 (s, 3H) 4.06 (s, 3H) 4.97 (d, J=0.6 Hz, 2H) 7.38 (dd, J=9.3, 1.7 Hz, 1H) 7.59 (d, J=9.3 Hz, 1H) 7.61 (s, 1H) 8.16 (s, 1H) 8.34 (s, 1H).

Step 3: methyl 5-ethyl-6-(2-(hydroxymethyl)imidazo[1,2-a]pyridin-6-yl)-2-methoxynicotinate To solution of methyl 6-(2-((tert-butyldimethylsilyloxy)methyl)imidazo[1,2-a]pyridin-6-yl)-5-ethyl-2-methoxynicotinate (0.911 g, 2.00 mmol) in MeOH (8 mL) was added 1M HCl (aqueous, 3.0 mL, 3.0 mmol). Reaction mixture was stirred at room temperature until starting material was completely consumed according to LC/MS. After ~2 h MeOH was concentrated and residue was treated with NaHCO$_3$ solution (aqueous saturated, 10 mL). Product was extracted with DCM (3×20 mL). Organic phase was washed with NaCl (aqueous saturated, 20 mL) and dried over Na$_2$SO$_4$. Removal of the solvent afforded methyl 5-ethyl-6-(2-(hydroxymethyl)imidazo[1,2-a]pyridin-6-yl)-2-methoxynicotinate (0.650 g) in 95% yield.

$^1$H NMR (500 MHz, CHCl$_3$-d) δ ppm 1.22 (t, J=7.6 Hz, 3H) 2.72 (q, J=7.6 Hz, 2H) 3.95 (s, 3H) 4.06 (s, 3H) 4.89 (s, 2H) 7.42 (dd, J=9.5, 1.6 Hz, 1H) 7.61-7.65 (m, 2H) 8.16 (s, 1H) 8.33 (s, 1H). LC-MS 342.0 [M+H]$^+$, RT 0.75 min.

Step 4: methyl 5-ethyl-6-(2-formylimidazo[1,2-a]pyridin-6-yl)-2-methoxynicotinate To SO$_3$-pyr complex (0.320 g, 2.01 mmol) was added pyridine (0.16 mL, 2.02 mmol) and DMSO (0.36 mL, 5.07 mmol). Slurry was stirred at room temperature 10 min before DCM (2.0 mL) was added and mixture was cooled to 0° C. Then solution of methyl 5-ethyl-6-(2-(hydroxymethyl)imidazo[1,2-a]pyridin-6-yl)-2-methoxynicotinate (0.346 g, 1.01 mmol), Hunig's base (0.60 mL, 3.44 mmol) and DMSO (0.36 mL, 5.07 mmol) in DCM (4.0 mL) was added dropwise. Reaction mixture was stirred at 0° C. 30 min and LC/MS showed complete consumption of starting material. DCM was removed under reduced pressure and residue was treated with H$_2$O (10 mL). Solid which was formed was collected by filtration affording methyl 5-ethyl-6-(2-formylimidazo[1,2-a]pyridin-6-yl)-2-methoxynicotinate (0.270 g) in 79% yield.

Step 1: 6-bromo-2-((tert-butyldimethylsilyloxy)methyl)imidazo[1,2-a]pyridine

To solution of (6-bromoimidazo[1,2-a]pyridin-2-yl)methanol (3.21 g, 14.13 mmol) in DCM (50 mL) was added imidazole (1.30 g, 19.09 mmol) followed by TBSCl (2.60 g, 17.25 mmol). Reaction mixture was stirred at room temperature for 30 min then was diluted with DCM (50 mL) and washed with H$_2$O (50 mL). Organic phase was washed with NaCl (aqueous saturated, 50 mL) and dried over Na$_2$SO$_4$. Solvent was concentrated and residue purified by column chromatography using EtOAc/hexanes (gradient 0-50%) to afford 6-bromo-2-((tert-butyldimethylsilyloxy)methyl)imidazo[1,2-a]pyridine (3.32 g) in 69% yield as pale yellow solid.

$^1$H NMR (500 MHz, CHCl$_3$-d) δ ppm 0.14 (s, 6H) 0.96 (s, 9H) 4.93 (s, 2H) 7.23 (dd, J=9.5, 1.3 Hz, 1H) 7.46 (d, J=9.5 Hz, 1H) 7.51 (s, 1H) 8.26 (s, 1H).

Step 2: Methyl 6-(2-((tert-butyldimethylsilyloxy)methyl)imidazo[1,2-a]pyridin-6-yl)-5-ethyl-2-methoxynicotinate 6-bromo-2-((tert-butyldimethylsilyloxy)methyl)imidazo[1,2-a]pyridine (1.00 g, 2.93 mmol), bis(pinacolato) diborate $^1$H NMR (500 MHz, DMSO-d$_6$) δ ppm 1.14 (t, J=7.6 Hz, 3H) 2.73 (q, J=7.6 Hz, 2H) 3.85 (s, 3H) 3.95 (s, 3H) 7.63 (dd, J=9.5, 1.6 Hz, 2H) 7.78 (d, J=9.5 Hz, 2H) 8.16 (s, 1H) 8.71 (s, 1H) 8.92 (s, 1H) 10.07 (s, 1H). LC-MS 340.2 [M+H]$^+$, RT 1.03 min.

Step 5-6: 6-(2-((dimethylamino)methyl)imidazo[1,2-a]pyridin-6-yl)-5-ethyl-2-oxo-1,2-dihydropyridine-3-carboxylic acid dihydrochloride To a solution of methyl 5-ethyl-6-(2-formylimidazo[1,2-a]pyridin-6-yl)-2-methoxynicotinate (90 mg, 0.27 mmol) in dichloroethane (1.5 mL) was added solution of dimethylamine (2M THF, 0.20 mL, 0.40 mmol) followed by AcOH (25 µL, 0.42 mmol). After stirring at room temperature for 5 min NaBH(OAc)$_3$ (90 mg, 0.42 mmol) was added. Reaction was stirred at room temperature ~1.5 h and monitored by LC/MS until starting aldehyde was completely consumed. Reaction was diluted with DCM (5 mL) and then quenched with NaHCO$_3$ (aqueous saturated, 5 mL). Product was extracted with DCM (3×5 mL). Organic phase was washed with NaCl (aqueous saturated, 10 mL) and dried over Na$_2$SO$_4$. Removal of the solvent afforded methyl 6-(2-((dimethylamino)methyl)imidazo[1,2-a]pyridin-6-yl)-5-ethyl-2-methoxynicotinate (100.6 mg) which was used directly in the next step. LC-MS 369.3 [M+H]$^+$, RT 0.83 min.

Methyl 6-(2-((dimethylamino)methyl)imidazo[1,2-a]pyridin-6-yl)-5-ethyl-2-methoxynicotinate (100.6 mg, 0.27 mmol) was heated with 6 M HCl (1.50 mL) at 80° C. for 3 h. HCl was removed under reduced pressure affording 6-(2-((dimethylamino)methyl)imidazo[1,2-a]pyridin-6-yl)-5-ethyl-2-oxo-1,2-dihydropyridine-3-carboxylic acid (113.3 mg) as dihydrochloride salt in 99% overall yield.

$^1$H NMR (500 MHz, MeOH-d$_4$) δ ppm 1.17 (t, J=7.6 Hz, 3H) 2.53 (q, J=7.6 Hz, 2H) 3.05 (s, 6H) 4.78 (s, 2H) 8.10 (dd, J=9.1, 1.3 Hz, 1H) 8.15 (d, J=9.1 Hz, 1H) 8.55 (s, 1H) 8.63 (s, 1H) 9.15 (s, 1H). LC-MS 339.2 [M−H]$^-$, 341.2 [M+H]$^+$, RT 0.93 min. (Polar Method).

Using the procedures described above, additional compounds described herein may be prepared by substituting the appropriate starting materials, reagents and reaction conditions and include compounds selected from:

Example 64

5-ethyl-6-(6-methyl-5-(pyrrolidin-1-ylmethyl)-6H-thieno[2,3-b]pyrrol-2-yl)-2-oxo-1,2-dihydropyridine-3-carboxylic acid hydrochloride

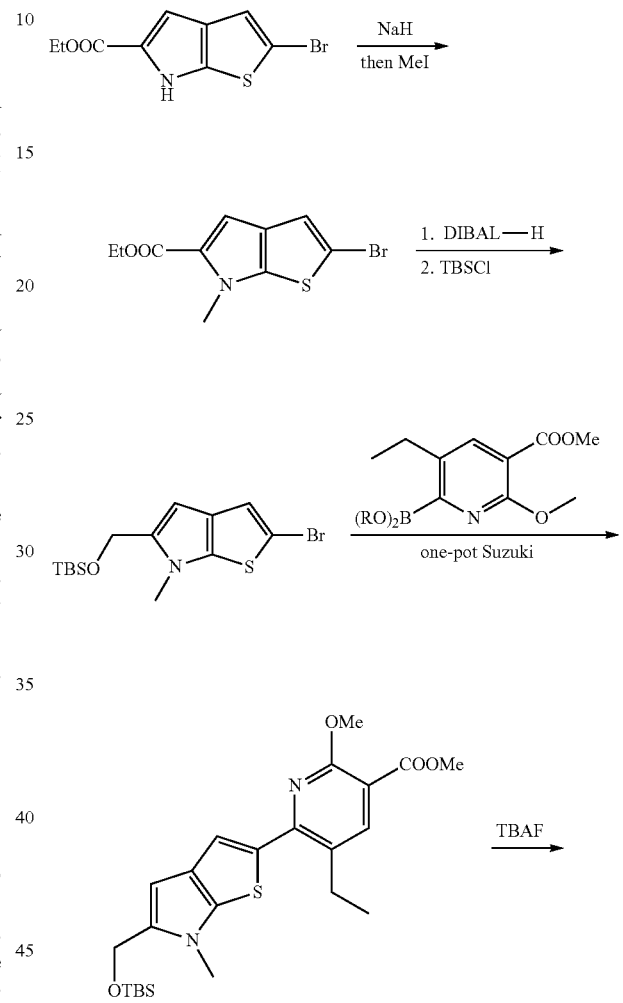

| Cpd | Name |
|---|---|
| 61 | 5-ethyl-2-oxo-6-(2-(pyrrolidin-1-ylmethyl)imidazo[1,2-a]pyridin-6-yl)-1,2-dihydropyridine-3-carboxylic acid dihydrochloride<br>$^1$H NMR (500 MHz, MeOH-d$_4$) δ ppm 1.17 (t, J = 7.6 Hz, 3 H) 2.53 (q, J = 7.6 Hz, 2 H) 3.05 (s, 6 H) 4.78 (s, 2 H) 8.10 (dd, J = 9.1, 1.3 Hz, 1 H) 8.15 (d, J = 9.1 Hz, 1 H) 8.55 (s, 1 H) 8.63 (s, 1 H) 9.15 (s, 1 H). LC-MS 365.2 [M − H]$^-$, 367.2 [M + H]$^+$, RT 0.98 min. (Polar Method). |
| 62 | 5-ethyl-2-oxo-6-(2-(piperidin-1-ylmethyl)imidazo[1,2-a]pyridin-6-yl)-1,2-dihydropyridine-3-carboxylic acid dihydrochloride<br>$^1$H NMR (500 MHz, MeOH-d$_4$) δ ppm 1.17 (t, J = 7.6 Hz, 3 H) 1.45-1.67 (m, 1 H) 1.74-2.08 (m, 5 H) 2.53 (q, J = 7.6 Hz, 2 H) 3.07-3.23 (m, 2 H) 3.56-3.74 (m, 2 H) 4.71 (s, 2 H) 8.07 (dd, J = 9.5, 1.6 Hz, 1 H) 8.13 (d, J = 9.5 Hz, 1 H) 8.55 (s, 1 H) 8.60 (s, 1 H) 9.13 (s, 1 H). LC-MS 379.2 [M − H]$^-$, 381.3 [M + H]$^+$, RT 1.00 min. (Polar Method). |
| 63 | 6-(2-((diethylamino)methyl)imidazo[1,2-a]pyridin-6-yl)-5-ethyl-2-oxo-1,2-dihydropyridine-3-carboxylic acid dihydrochloride<br>$^1$H NMR (500 MHz, MeOH-d$_4$) δ ppm 1.17 (t, J = 7.6 Hz, 3 H) 1.47 (t, J = 7.4 Hz, 6 H) 2.53 (d, J = 7.6 Hz, 2 H) 3.39 (q, J = 7.4 Hz, 4 H) 4.77 (s, 2 H) 8.04 (dd, J = 9.5, 1.6 Hz, 1 H) 8.10 (d, J = 9.5 Hz, 1 H) 8.55 (s, 1 H) 8.61 (s, 1 H) 9.10 (s, 1 H). LC-MS 367.2 [M − H]$^-$, 369.2 [M + H]$^+$, RT 0.99 min. (Polar Method). |

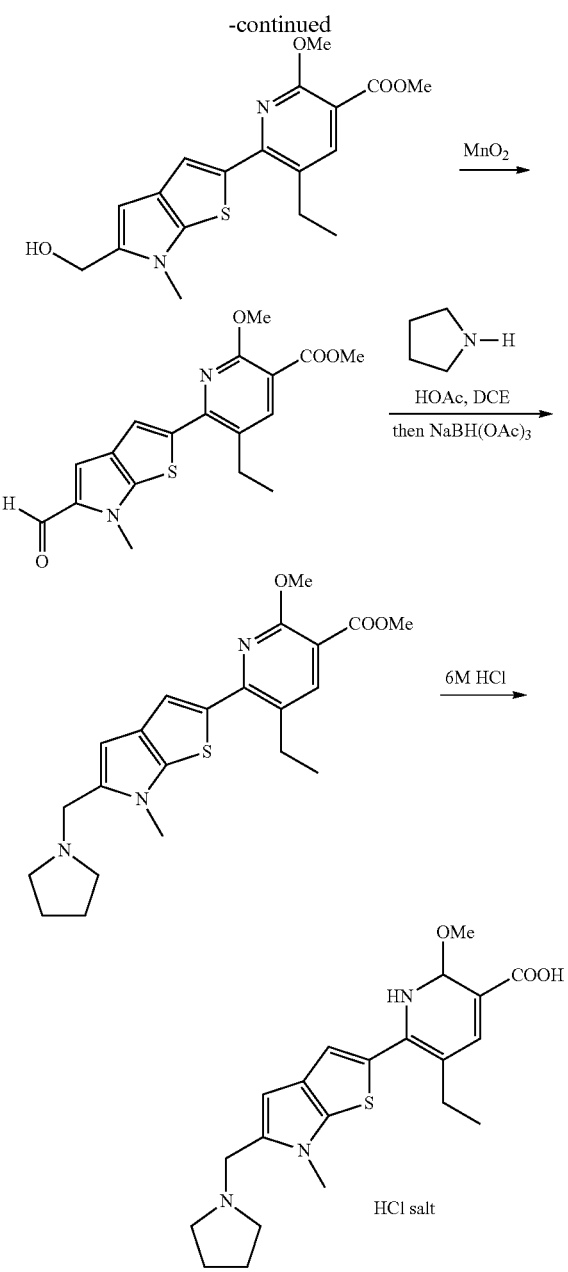

Step 1: ethyl 2-bromo-6-methyl-6H-thieno[2,3-b]pyrrole-5-carboxylate

To solution of ethyl 2-bromo-6H-thieno[2,3-b]pyrrole-5-carboxylate (6.35 g, 23.16 mmol) in DMF (80 mL) at 0° C. was added NaH (60%, 1.54 g, 38.50 mmol) in portions. Reaction mixture was stirred at 0° C. for 15 min before MeI (2.90 mL, 46.58 mmol) was added. It was then allowed to warm to room temperature and was stirred 1.5 h. Reaction mixture was cooled to 0° C. and was quenched with solution of NH$_4$Cl (aqueous saturated, 50 mL). It was then diluted with H$_2$O (~200 mL) and product was extracted with EtOAc (3×100 mL). Combined organics were washed with NaCl (aqueous saturated, 80 mL) and dried over Na$_2$SO$_4$. After concentration of the solvent residue was purified by column chromatography (EtOAc/hexanes, 0-10% gradient) to yield ethyl 2-bromo-6-methyl-6H-thieno[2,3-b]pyrrole-5-carboxylate (5.47 g) in 82% yield.

$^1$H NMR (500 MHz, CHCl$_3$-d) δ ppm 1.38 (t, J=7.1 Hz, 3H) 3.98 (s, 3H) 4.32 (q, J=7.1 Hz, 2H) 7.03 (s, 1H) 7.07 (s, 1H). LC-MS 288.0/290.0 [M+H]$^+$, RT 1.55 min.

Step 2-3: 2-bromo-5-((tert-butyldimethylsilyloxy)methyl)-6-methyl-6H-thieno[2,3-b]pyrrole To solution of ethyl 2-bromo-6-methyl-6H-thieno[2,3-b]pyrrole-5-carboxylate (5.47 g, 18.28 mmol) in DCM (55 mL) at −78° C. was added solution of DIBAL-H (1M hexanes, 42.00 mL, 42.00 mmol). Reaction mixture was stirred 30 min at −78° C. before it was quenched with Na—K-tartrate (aqueous saturated, 50 mL). Mixture was allowed to warm to room temperature and was stirred 1 h. Product was extracted with DCM (3×100 mL). Organic phase was washed with NaCl (aqueous saturated, 50 mL) and dried over Na$_2$SO$_4$. Solvent was concentrated to yield (2-bromo-6-methyl-6H-thieno[2,3-b]pyrrol-5-yl)methanol (4.55 g, 97%) as solid which was used in the next step without purification.

LC-MS 228.0/229.9 [M+H]$^+$, RT 1.11 min.

To solution of (2-bromo-6-methyl-6H-thieno[2,3-b]pyrrol-5-yl)methanol (4.55 g, 18.48 mmol) obtained above in DCM (50 mL) was added imidazole (1.60 g, 23.50 mmol). Reaction mixture was cooled to 0° C. and solution of TBSCl (3.34 g, 22.16 mmol) in DCM (25 mL) was added dropwise. Mixture was stirred at 0° C. for 30 min, then was diluted with DCM (50 mL) and washed with H$_2$O (50 mL). Organic phase washed with NaCl (aqueous saturated, 50 mL) and dried over Na$_2$SO$_4$. Solvent was concentrated and residue purified by column chromatography using EtOAc/hexanes (gradient 0-10%) to afford 2-bromo-5-((tert-butyldimethylsilyloxy)methyl)-6-methyl-6H-thieno[2,3-b]pyrrole (4.40 g) in 64% yield over 2 steps.

$^1$H NMR (500 MHz, DMSO-d$_6$) δ ppm 0.03 (s, 6H) 0.85 (s, 9H) 3.65 (s, 3H) 4.70 (s, 2H) 6.25 (s, 1H) 7.16 (s, 1H).

Step 4: methyl 6-(5-((tert-butyldimethylsilyloxy)methyl)-6-methyl-6H-thieno[2,3-b]pyrrol-2-yl)-5-ethyl-2-methoxynicotinate 6-Chloro-5-ethyl-2-methoxynicotinate (0.575 g, 2.50 mmol), bis(pinacolato)diborate (0.800 g, 3.15 mmol), Pd(dppf)Cl$_2$ (73.0 mg, 0.1 mmol, 4 mol %), and KOAc (0.750 g, 7.64 mmol) were mixed together in a heat-gun dried vial. The vial was vacuumed and backfilled with argon before dioxane (10 mL) was added. Mixture was heated at 100° C. overnight then was cooled to room temperature. 2-Bromo-5-((tert-butyldimethylsilyloxy)methyl)-6-methyl-6H-thieno[2,3-b]pyrrole (0.900 g, 2.50 mmol), fresh Pd(dppf)Cl$_2$ (73.0 mg, 0.1 mmol, 4 mol %), K$_2$CO$_3$ (1.05 g, 7.60 mmol) and H$_2$O (2.50 mL) were added and reaction vial was resealed under argon and mixture was heated at 100° C. for 2 h. Mixture was then cooled to room temperature, diluted with H$_2$O (15 mL) and product was extracted with DCM (3×20 mL). Combined organics were washed with NaCl (aqueous saturated, 15 mL) and dried over Na$_2$SO$_4$. After concentration of the solvent the residue was purified by column chromatography (EtOAc/hexanes, 0-15% gradient). Methyl 6-(5-((tert-butyldimethylsilyloxy)methyl)-6-methyl-6H-thieno[2,3-b]pyrrol-2-yl)-5-ethyl-2-methoxynicotinate (0.594 g) was obtained as oil and was taken directly into the next step.

$^1$H NMR (500 MHz, DMSO-d$_6$) δ ppm 0.05 (s, 6H) 0.87 (s, 9H) 1.27 (t, J=7.6 Hz, 3H) 2.91 (d, J=7.6 Hz, 2H) 3.71 (s, 3H) 3.89 (s, 3H) 3.96 (s, 3H) 4.74 (s, 2H) 6.36 (s, 1H) 7.60 (s, 1H) 8.03 (s, 1H). LC-MS 475.2 [M+H]$^+$, RT 1.88 min.

Step 5: methyl 5-ethyl-6-(5-(hydroxymethyl)-6-methyl-6H-thieno[2,3-b]pyrrol-2-yl)-2-methoxynicotinate To solution of methyl 6-(5-((tert-butyldimethylsilyloxy) methyl)-6-methyl-6H-thieno[2,3-b]pyrrol-2-yl)-5-ethyl-2-methoxynicotinate (0.594 g, 1.25 mmol) in THF (8 mL) was added solution of TBAF (1M THF, 1.50 mL, 1.50 mmol). Reaction mixture was stirred at room temperature for 30 min and THF was then concentrated. Residue was loaded directly on the column and product was isolated eluting with EtOAc/hexanes gradient (0-50%). Methyl 5-ethyl-6-(5-(hydroxymethyl)-6-methyl-6H-thieno[2,3-b]pyrrol-2-yl)-2-methoxynicotinate (0.233 g, 26% 2 steps) was obtained as solid.

$^1$H NMR (500 MHz, DMSO-$d_6$) δ ppm 1.27 (t, J=7.4 Hz, 3H) 2.91 (q, J=7.4 Hz, 2H) 3.72 (s, 3H) 3.80 (s, 3H) 3.96 (s, 3H) 4.52 (d, J=5.4 Hz, 2H) 5.13 (t, J=5.4 Hz, 1H) 6.31 (s, 1H) 7.60 (s, 1H) 8.03 (s, 1H). LC-MS 361.1 [M+H]$^+$, RT 1.24 min.

Step 6: methyl 5-ethyl-6-(5-formyl-6-methyl-6H-thieno[2,3-b]pyrrol-2-yl)-2-methoxynicotinate To solution of methyl 5-ethyl-6-(5-(hydroxymethyl)-6-methyl-6H-thieno[2,3-b]pyrrol-2-yl)-2-methoxynicotinate (0.233 g, 0.75 mmol) in DCM (8 mL) was added activated MnO$_2$ (0.60 g+0.60 g+0.30 g, 6.20+6.20+3.10 mmol) in 3 portions with 30 min intervals. Reaction was monitored by LC/MS. Upon complete consumption of starting material MnO$_2$ was filtered and washed with DCM. Mother liquor was concentrated affording methyl 5-ethyl-6-(5-formyl-6-methyl-6H-thieno[2,3-b]pyrrol-2-yl)-2-methoxynicotinate (0.192 g, 82%) as solid.

$^1$H NMR (500 MHz, DMSO-$d_6$) δ ppm 1.28 (t, J=7.4 Hz, 3H) 2.93 (q, J=7.5 Hz, 2H) 3.81 (s, 3H) 3.98 (s, 3H) 4.02 (s, 3H) 7.33 (s, 1H) 7.74 (s, 1H) 8.08 (s, 1H) 9.61 (s, 1H). LC-MS 359.2 [M+H]$^+$, RT 1.43 min.

Step 7-8: 5-ethyl-6-(6-methyl-5-(pyrrolidin-1-ylmethyl)-6H-thieno[2,3-b]pyrrol-2-yl)-2-oxo-1,2-dihydropyridine-3-carboxylic acid hydrochloride To solution of methyl 5-ethyl-6-(5-formyl-6-methyl-6H-thieno[2,3-b]pyrrol-2-yl)-2-methoxynicotinate (49.4 mg, 0.14 mmol) in dichloroethane (1.5 mL) was added pyrrolidine (20 μL, 0.24 mmol) followed by AcOH (15 μL, 0.25 mmol). After stirring at room temperature for 10 min NaBH(OAc)$_3$ (60 mg, 0.28 mmol) was added. Reaction was stirred at room temperature overnight and then quenched with NaHCO$_3$ solution (aqueous saturated, 5 mL). Product was extracted with DCM (3×7 mL). Organic phase was dried over Na$_2$SO$_4$ and solvent was concentrated. Product was purified by column chromatography (MeOH/DCM, 0-5% gradient). Methyl 5-ethyl-2-methoxy-6-(6-methyl-5-(pyrrolidin-1-ylmethyl)-6H-thieno[2,3-b]pyrrol-2-yl)nicotinate (49.7 mg) was obtained in 86% yield. LC-MS 343.1 [M-71+H]$^+$, RT 1.00 min.

Methyl 5-ethyl-2-methoxy-6-(6-methyl-5-(pyrrolidin-1-ylmethyl)-6H-thieno[2,3-b]pyrrol-2-yl)nicotinate (49.7 mg, 0.12 mmol) obtained above was heated with 6M HCl at 80° C. for 4 h and monitored by LC/MS. Upon complete conversion to the product HCl was removed under reduced pressure. Residue was triturated with Et$_2$O (5 mL), solid filtered and washed with Et$_2$O. Upon drying in dessicator 5-ethyl-6-(6-methyl-5-(pyrrolidin-1-ylmethyl)-6H-thieno[2,3-b]pyrrol-2-yl)-2-oxo-1,2-dihydropyridine-3-carboxylic acid (25.0 mg, 50%) was obtained as a hydrochloride salt.

$^1$H NMR (500 MHz, DMSO-$d_6$) δ ppm 1.15 (t, J=7.4 Hz, 3H) 1.86-1.97 (m, 2H) 2.03 (br. s., 2H) 3.04-3.21 (m, 2H) 3.30-3.39 (m, 2H) 3.87 (s, 3H) 4.52 (d, J=3.2 Hz, 2H) 6.79 (s, 1H) 7.54 (s, 1H) 8.30 (br. s., 1H) 10.93 (br. s., 1H). LC-MS 384.2 [M−H]$^−$, RT 0.73 min.

Example 65

6-(5-((dimethylamino)methyl)-6-methyl-6H-thieno[2,3-b]pyrrol-2-yl)-5-ethyl-2-oxo-1,2-dihydropyridine-3-carboxylic acid hydrochloride 6-(5-((Dimethylamino)methyl)-6-methyl-6H-thieno[2,3-b]pyrrol-2-yl)-5-ethyl-2-oxo-1,2-dihydropyridine-3-carboxylic acid hydrochloride (60.0 mg) was prepared according to procedure described in Example 64 Step 7-8 starting from 5-ethyl-6-(5-formyl-6-methyl-6H-thieno[2,3-b]pyrrol-2-yl)-2-methoxynicotinate (63.0 mg, 0.18 mmol) as an hydrochloride salt in 84% overall yield.

$^1$H NMR (500 MHz, DMSO-$d_6$) δ ppm 1.15 (t, J=7.6 Hz, 3H) 2.70 (q, J=7.4 Hz, 2H) 2.76 (d, J=4.4 Hz, 6H) 3.85 (s, 3H) 4.46 (d, J=4.7 Hz, 2H) 6.77 (s, 1H) 7.56 (s, 1H) 8.30 (br. s., 1H) 10.53 (br. s., 1H). LC-MS 358.3 [M−H]$^−$, RT 0.68 min.

Example 66

5-ethyl-2-oxo-6-(1,2,3,4-tetrahydropyrazino[1,2-a]indol-8-yl)-1,2-dihydropyridine-3-carboxylic acid

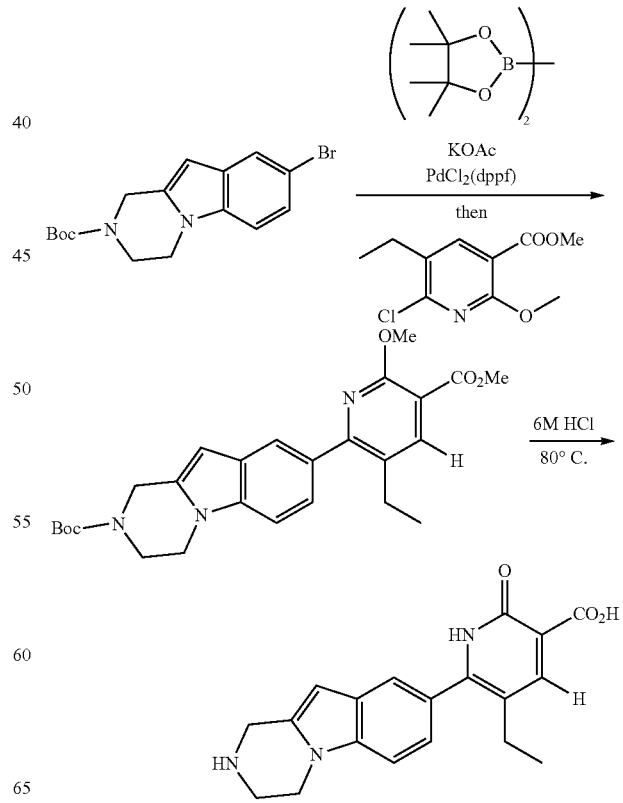

Step 1: tert-butyl-8-(3-ethyl-6-methoxy-5-(methoxy-carbonyl)pyridin-2-yl)-3,4-dihydropyrazino[1,2-a]indole-2(1H)-carboxylate To a vial was added tert-butyl 8-bromo-3,4-dihydropyrazino[1,2-a]indole-2(1H)-carboxylate (0.318 g, 0.9 mmol), bis(pinacolato)diboron (0.3 g, 1.2 mmol), potassium acetate (0.27 g, 2.7 mmol), and Pd(dppf)Cl$_2$ (26 mg, 4 mol %). The vial was evacuated and back filled with argon. Dioxane (3 mL) was added, the vial was sealed under argon and heated to 120° C. for 18 h. The reaction mixture was then cooled to room temperature and methyl 6-chloro-5-ethyl-2-methoxynicotinate (0.23 g, 1.0 mmol) was added along with K$_2$CO$_3$ (0.38 g, 2.7 mmol) and H$_2$O (300 μL). The vial was sealed again under argon and heated to 120° C. for a further 12 h. The reaction mixture was then cooled to room temperature and diluted with H$_2$O (20 mL). The aqueous layer was extracted with CH$_2$Cl$_2$ (3×50 mL). The combined organics were dried over Na$_2$SO$_4$, filtered, and concentrated. The crude residue was purified on silica gel (1:1 hexanes/EtOAc) to afford the title compound as a clear oil (0.12 g, 30%).

$^1$H NMR (500 MHz, CHCl$_3$-d) δ ppm 1.19 (t, J=7.53 Hz, 3H) 1.54 (s, 9H) 2.75 (q, J=7.51 Hz, 2H) 3.92-4.01 (m, 5H) 4.09 (s, 3H) 4.13-4.20 (m, 2H) 4.87 (s, 2H) 6.38 (br. s., 1H) 7.35-7.46 (m, 2H) 7.78 (d, J=1.18 Hz, 1H) 8.16 (s, 1H).

Step 2: 5-ethyl-2-oxo-6-(1,2,3,4-tetrahydropyrazino[1,2-a]indol-8-yl)-1,2-dihydropyridine-3-carboxylic acid To tert-butyl-8-(3-ethyl-6-methoxy-5-(methoxycarbonyl)pyridin-2-yl)-3,4-dihydropyrazino[1,2-a]indole-2(1H)-carboxylate (50 mg, 0.11 mmol) was added 6M HCl (1 mL) and the reaction mixture was heated to 80° C. for 1 h. The reaction mixture was then cooled to room temperature and concentrated to afford a crude residue that was triturated with Et$_2$O. The precipitate was filtered and rinsed with Et$_2$O to afford the title compound as a brown solid (22 mg, 50%).

$^1$H NMR (500 MHz, MeOH-d$_4$) δ ppm 1.12 (t, J=7.53 Hz, 3H) 2.51-2.59 (m, 2H) 3.90 (t, J=5.95 Hz, 2H) 4.45-4.53 (m, 2H) 4.72 (s, 2H) 6.67 (d, J=0.79 Hz, 1H) 7.36 (dd, J=8.47, 1.69 Hz, 1H) 7.66 (d, J=8.43 Hz, 1H) 7.76 (d, J=1.34 Hz, 1H) 8.52 (s, 1H). LC-MS 338.2 [M+H]$^+$, RT 0.46 min.

Example 67

(R)-5-ethyl-6-(1-methyl-2-(pyrrolidin-2-yl)-1H-indol-5-yl)-2-oxo-1,2-dihydropyridine-3-carboxylic acid hydrochloride

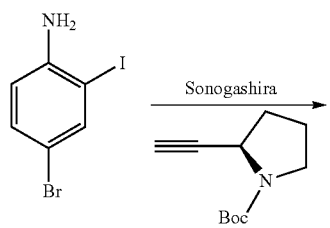

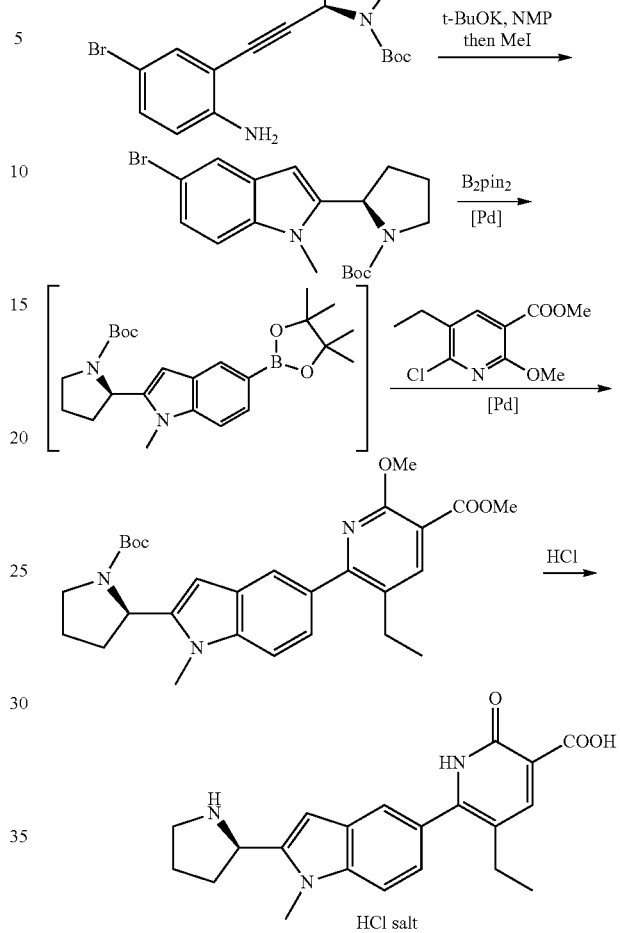

Step 1: (R)-tert-butyl 2-((2-amino-5-bromophenyl)ethynyl)pyrrolidine-1-carboxylate (R)-tert-butyl 2-((2-amino-5-bromophenyl)ethynyl)pyrrolidine-1-carboxylate (4.32 g) was prepared via Sonogashira coupling according to the general procedure described in Example 156, Step 1, from 4-bromo-2-iodoaniline (3.96 g, 13.29 mmol) and (R)-tert-butyl 2-ethynylpyrrolidine-1-carboxylate (3.25 g, 16.64 mmol) in 89% yield.

$^1$H NMR (500 MHz, CHCl$_3$-d, mixture of rotamers) δ ppm 1.49 (br. s., 9H) 1.85-1.99 (m, 1H) 2.06-2.25 (m, 3H) 3.28-3.58 (m, 2H) 4.16-4.27 (m, 1H) 4.52 (br. s., 1H) 4.71 (br. s., 1H) 6.43-6.61 (m, 1H) 7.09-7.24 (m, 1H) 7.31 (br. s., 1H).

Step 2: (R)-tert-butyl 2-(5-bromo-1-methyl-1H-indol-2-yl)pyrrolidine-1-carboxylate (R)-tert-Butyl 2-(5-bromo-1-methyl-1H-indol-2-yl)pyrrolidine-1-carboxylate (3.245 g) was prepared via t-BuOK cyclization/MeI alkylation sequence described in Example 156, Step 2, from (R)-tert-butyl 2-((2-amino-5-bromophenyl)ethynyl)pyrrolidine-1-carboxylate (3.989 g, 10.92 mmol) in 78% yield.

$^1$H NMR (500 MHz, CHCl$_3$-d mixture of rotamers) δ ppm 1.27 and 1.48 (br. s., 9H) 1.83-1.98 (m, 2H) 1.98-2.10 (m, 1H) 2.17-2.35 (m, 2H) 3.42-3.62 (m, 1H) 3.62-3.70 (m, 1H) 3.67

(br. s., 3H) 4.96-5.28 (m, 1H) 6.16 (s, 1H) 7.08-7.26 (m, 2H) 7.64 (br. s., 1H). LC-MS 379.2/381.2 [M+H]+, RT 1.59 min.

Step 3: (R)-Methyl 6-(2-(1-(tert-butoxycarbonyl) pyrrolidin-2-yl)-1-methyl-1H-indol-5-yl)-5-ethyl-2-methoxynicotinate (One-pot Suzuki coupling)

(R)-tert-Butyl 2-(5-bromo-1-methyl-1H-indol-2-yl)pyrrolidine-1-carboxylate (0.300 g, 0.79 mmol), bis(pinacolato) diborate (0.240 g, 0.95 mmol), Pd(OAc)$_2$ (6.0 mg, 0.03 mmol, 3.5 mol %), Ru-Phos ligand (26.0 mg, 0.06 mmol, 7 mol %) and KOAc (0.240 g, 2.44 mmol) were mixed together in a vial. The vial was vacuumed and backfilled with argon before dioxane (2 mL) was added. Mixture was heated at 100° C. for ~3 h until complete consumption of the starting bromide was observed. Reaction mixture was cooled to room temperature before H$_2$O (0.90 mL), K$_2$CO$_3$ (0.330 g, 2.39 mmol) and 6-chloro-5-ethyl-2-methoxynicotinate (0.182 g, 0.79 mmol) were added. Reaction vial was resealed under argon and mixture was heated at 100° C. overnight and then cooled to room temperature. Water (7 mL) was added to the reaction mixture and product was extracted with DCM (2×10 mL). Combined organics were washed with NaCl (aqueous saturated, 10 mL) and dried over Na$_2$SO$_4$. Upon concentration of the solvent residue was purified by column chromatography (EtOAc/hexanes, 0-50% gradient) to afford product as solid (0.192 g) in 49% overall yield.

$^1$H NMR (500 MHz, CHCl$_3$-d, mixture of rotamers) δ ppm 1.11-1.23 (m, 3H) 1.24-1.62 (m, 9H) 1.82-1.99 (m, 2H) 2.00-2.13 (m, 1H) 2.28 (br. s., 1H) 2.75 (br. s., 2H) 3.44-3.62 (m, 1H) 3.62-3.74 (m, 1H) 3.72 (s, 3H) 3.94 (s, 3H) 4.06 (br. s, 3H) 5.03-5.28 (m, 1H) 6.30 (s, 1H) 7.30-7.48 (m, 2H) 7.67-7.79 (m, 1H) 8.13 (br. s., 1H). LC-MS 494.4 [M+H]+, RT 1.62 min.

Step 4: (R)-5-ethyl-6-(1-methyl-2-(pyrrolidin-2-yl)-1H-indol-5-yl)-2-oxo-1,2-dihydropyridine-3-carboxylic acid hydrochloride (R)-Methyl 6-(2-(1-(tert-butoxycarbonyl)pyrrolidin-2-yl)-1-methyl-1H-indol-5-yl)-5-ethyl-2-methoxynicotinate (0.190 g, 0.38 mmol) was heated with 6M HCl (2.0 mL) at 80° C. for 2.5 h until complete conversion to the product was observed by LC/MS. HCl was removed under reduced pressure, residue triturated with Et$_2$O and solid was collected by filtration. (R)-5-ethyl-6-(1-methyl-2-(pyrrolidin-2-yl)-1H-indol-5-yl)-2-oxo-1,2-dihydropyridine-3-carboxylic acid (0.149 g, 96%) was obtained as yellow solid.

$^1$H NMR (500 MHz, DMSO-d$_6$) δ ppm 1.00 (t, J=7.6 Hz, 3H) 1.97-2.10 (m, 1H) 2.12-2.22 (m, 1H) 2.24-2.35 (m, 1H) 2.42 (q, J=7.6 Hz, 2H) 2.41-2.49 (m, 1H) 3.25-3.40 (m, 2H) 3.90 (s, 3H) 4.93-5.03 (m, 1H) 6.89 (s, 1H) 7.30 (dd, J=8.5, 1.6 Hz, 1H) 7.67 (d, J=8.5 Hz, 1H) 7.73 (d, J=1.6 Hz, 1H) 8.37 (s, 1H) 9.18 (br. s., 1H) 10.51 (br. s., 1H) 13.29 (br. s., 1H). LC-MS 364.3 [M−H]−, 366.3 [M+H]+, RT 0.75 min.

Example 68

(R)-5-ethyl-6-(1-methyl-2-(1-methylpyrrolidin-2-yl)-1H-indol-5-yl)-2-oxo-1,2-dihydropyridine-3-carboxylic acid To a suspension of (R)-5-ethyl-6-(1-methyl-2-(pyrrolidin-2-yl)-1H-indol-5-yl)-2-oxo-1,2-dihydropyridine-3-carboxylic acid hydrochloride (59.1 mg, 0.15 mmol) in dichloroethane (2.0 mL) was added aqueous NaHCO$_3$ (0.20 mL). Reaction mixture was stirred at room temperature for 10 min before solution of HCHO (37% aqueous, 50 µL, 0.67 mmol) was added followed by AcOH (~0.20 mL) to pH~3-4. Upon addition of NaBH(OAc)$_3$ (150 mg, 0.70 mmol) reaction was stirred at room temperature for 1 h. Complete consumption of starting material was observed. Mixture was quenched with addition of solution of NaHCO$_3$ (aqueous saturated, 2 mL) and product was extracted with DCM (3×5 mL). Organic phase was dried over Na$_2$SO$_4$ and solvent was concentrated. Residue was triturated with Et$_2$O and solid was collected by filtration to afford (R)-5-ethyl-6-(1-methyl-2-(1-methylpyrrolidin-2-yl)-1H-indol-5-yl)-2-oxo-1,2-dihydropyridine-3-carboxylic acid (40.0 mg, 72%) as yellow solid.

$^1$H NMR (500 MHz, DMSO-d$_6$) δ ppm 1.02 (t, J=7.4 Hz, 3H) 1.74-1.96 (m, 3H) 2.25 (s, 3H) 2.26-2.32 (m, 2H) 2.46 (q, J=7.4 Hz, 2H) 3.17 (t, J=7.7 Hz, 1H) 3.51 (t, J=7.7 Hz, 1H) 3.84 (s, 3H) 6.45 (s, 1H) 7.19 (dd, J=8.4, 1.7 Hz, 1H) 7.54 (d, J=8.4 Hz, 1H) 7.60 (d, J=1.7 Hz, 1H) 8.30 (s, 1H) 13.10 (br. s., 1H) 15.37 (br. s., 1H). LC-MS 378.2 [M−H]−, 380.3 [M+H]+, RT 0.78 min.

Example 69

(S)-5-ethyl-6-(1-methyl-2-(pyrrolidin-2-yl)-1H-indol-5-yl)-2-oxo-1,2-dihydropyridine-3-carboxylic acid hydrochloride Step 1: (S)-tert-butyl 2-((2-amino-5-bromophenyl) ethynyl)pyrrolidine-1-carboxylate The title compound was prepared according to procedure described in Example 156, Step 1.

$^1$H NMR (500 MHz, CHCl$_3$-d, mixture of rotamers) δ ppm 1.49 (br. s., 9H) 1.85-1.99 (m, 1H) 2.06-2.25 (m, 3H) 3.28-3.58 (m, 2H) 4.16-4.27 (m, 1H) 4.52 (br. s., 1H) 4.71 (br. s., 1H) 6.43-6.61 (m, 1H) 7.09-7.24 (m, 1H) 7.31 (br. s., 1H).

Step 2: (S)-tert-butyl 2-(5-bromo-1-methyl-1H-indol-2-yl)pyrrolidine-1-carboxylate The title compound was prepared according to procedure described in Example 156, Step 2.

$^1$H NMR (500 MHz, CHCl$_3$-d mixture of rotamers) δ ppm 1.27 and 1.48 (br. s., 9H) 1.83-1.98 (m, 2H) 1.98-2.10 (m, 1H) 2.17-2.35 (m, 2H) 3.42-3.62 (m, 1H) 3.62-3.70 (m, 1H) 3.67 (br. s., 3H) 4.96-5.28 (m, 1H) 6.16 (s, 1H) 7.08-7.26 (m, 2H) 7.64 (br. s., 1H). LC-MS 379.2/381.2 [M+H]+, RT 1.59 min.

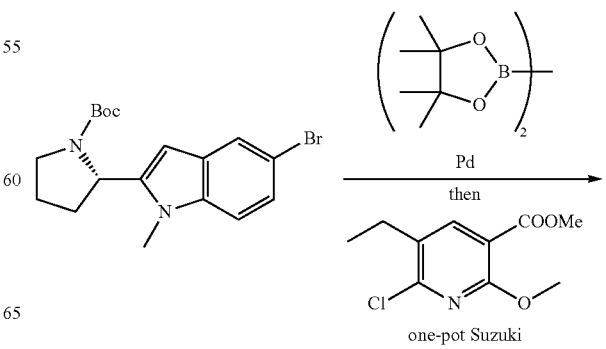

one-pot Suzuki

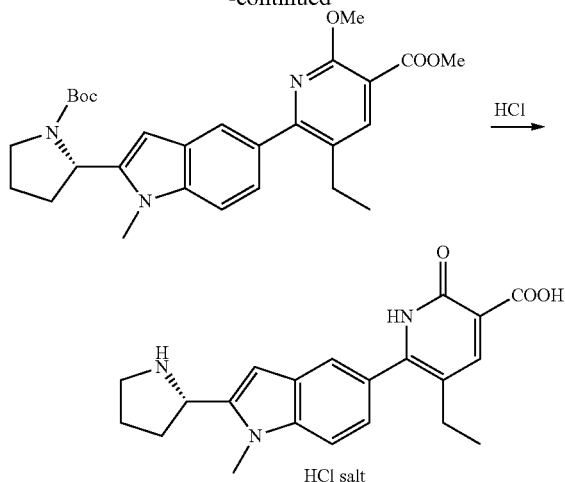

Step 3: (S)-methyl 6-(2-(1-(tert-butoxycarbonyl) pyrrolidin-2-yl)-1-methyl-1H-indol-5-yl)-5-ethyl-2-methoxynicotinate The title compound was prepared according to procedure described in Example 67 Step 3.

$^1$H NMR (500 MHz, CHCl$_3$-d, mixture of rotamers) δ ppm 1.11-1.23 (m, 3H) 1.24-1.62 (m, 9H) 1.82-1.99 (m, 2H) 2.00-2.13 (m, 1H) 2.28 (br. s., 1H) 2.75 (br. s., 2H) 3.44-3.62 (m, 1H) 3.62-3.74 (m, 1H) 3.72 (s, 3H) 3.94 (s, 3H) 4.06 (br. s, 3H) 5.03-5.28 (m, 1H) 6.30 (s, 1H) 7.30-7.48 (m, 2H) 7.67-7.79 (m, 1H) 8.13 (br. s., 1H). LC-MS 494.7 [M+H]$^+$, RT 1.62 min.

Step 4: (S)-5-ethyl-6-(1-methyl-2-(pyrrolidin-2-yl)-1H-indol-5-yl)-2-oxo-1,2-dihydropyridine-3-carboxylic acid hydrochloride The title compound was prepared according to procedure described in Example 67 Step 4.

$^1$H NMR (500 MHz, DMSO-d$_6$) δ ppm 1.00 (t, J=7.6 Hz, 3H) 1.97-2.10 (m, 1H) 2.12-2.22 (m, 1H) 2.24-2.35 (m, 1H) 2.42 (q, J=7.6 Hz, 2H) 2.41-2.49 (m, 1H) 3.25-3.40 (m, 2H) 3.90 (s, 3H) 4.93-5.03 (m, 1H) 6.89 (s, 1H) 7.30 (dd, J=8.5, 1.6 Hz, 1H) 7.67 (d, J=8.5 Hz, 1H) 7.73 (d, J=1.6 Hz, 1H) 8.37 (s, 1H) 9.18 (br. s., 1H) 10.51 (br. s., 1H) 13.29 (br. s., 1H). LC-MS 364.2 [M–H]$^-$, 366.3 [M+H]$^+$, RT 0.75 min.

Example 70

5-ethyl-6-(1-methyl-2-(piperazin-2-yl)-1H-indol-5-yl)-2-oxo-1,2-dihydropyridine-3-carboxylic acid dihydrochloride

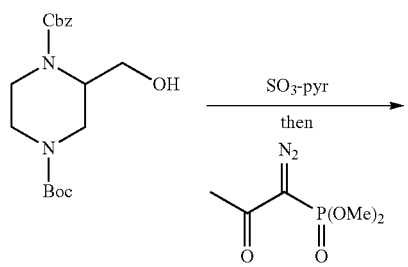

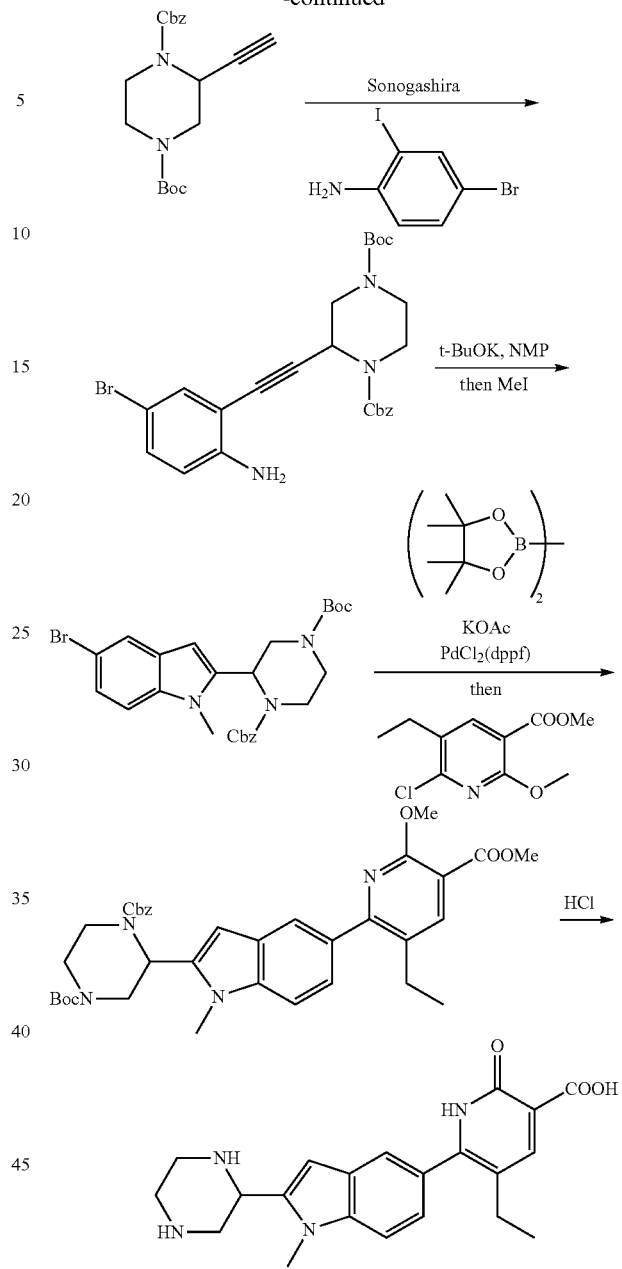

Step 1-2: 1-benzyl 4-tert-butyl 2-ethynylpiperazine-1,4-dicarboxylate

To SO$_3$-pyr complex (5.84 g, 36.69 mmol) was added pyridine (2.90 mL, 36.66 mmol) and DMSO (7.20 mL, 101.37 mmol). Slurry was stirred at room temperature 10 min before DCM (30 mL) was added and mixture was cooled to 0° C. Then solution of 1-benzyl 4-tert-butyl 2-(hydroxymethyl)piperazine-1,4-dicarboxylate (6.44 g, 18.37 mmol), Hunig's base (11.0 mL, 63.15 mmol) and DMSO (7.20 mL, 101.37 mmol) in DCM (70 mL) was added over 10 min. Reaction mixture was stirred at 0° C. 30 min and TLC showed complete consumption of starting material. Reaction was washed subsequently with H$_2$O (50 mL), cold aqueous 1N HCl (until aqueous phase stayed acidic), then NaHCO$_3$ (aqueous saturated, 50 mL) and finally NaCl (aqueous saturated, 50 mL).

Organic phase was dried over Na$_2$SO$_4$ and solvent concentrated. Crude 1-benzyl 4-tert-butyl 2-formylpiperazine-1,4-dicarboxylate (~6.40 g, quant) was obtained as colorless oil and was taken directly into the next step.

Crude 1-benzyl 4-tert-butyl 2-formylpiperazine-1,4-dicarboxylate (~6.4 g, 18.4 mmol) obtained above was dissolved in MeOH (70 mL) and dimethyl 1-diazo-2-oxopropylphosphonate (Ohira-Bestmann reagent, 4.50 g, 23.42 mmol) was added. Reaction mixture was cooled to 0° C. before powdered K$_2$CO$_3$ (5.10 g, 36.90 mmol) was added. Reaction was stirred at 0° C. 30 min and slowly allowed to warm to room temperature. After 2 h EtOAc (100 mL) was added to the mixture and solids were filtered off. Mother liquor was concentrated and residue was purified by column chromatography using EtOAc/hexanes (gradient 0-50%) to afford 1-benzyl 4-tert-butyl 2-ethynylpiperazine-1,4-dicarboxylate (3.85 g) in 61% overall yield.

$^1$H NMR (500 MHz, CHCl$_3$-d, mixture of rotamers) δ ppm 1.49 (s, 9H) 2.63-3.12 (m, 2H) 3.20-3.37 (m, 1H) 3.83-4.43 (m, 3H) 4.71 (d, J=4.1 Hz, 1H) 4.90-5.11 (m, 1H) 5.18 (s, 2H) 7.29-7.42 (m, 5H).

Step 3: 1-benzyl 4-tert-butyl 2-((2-amino-5-bromophenyl)ethynyl)piperazine-1,4-dicarboxylate The title compound was prepared according to procedure described in Example 156 Step 1.

$^1$H NMR (500 MHz, CHCl$_3$-d, mixture of rotamers) δ ppm 1.45 (s, 9H) 2.72-3.42 (m, 3H) 3.89-4.01 (m, 1H) 4.04-4.54 (m, 3H) 5.12-5.29 (m, 2H) 6.53 (d, J=8.8 Hz, 1H) 7.17 (d, J=8.8 Hz, 1H) 7.31 (br. s., 1H) 7.34-7.43 (m, 5H). LC-MS 514.1/516.1 [M+H]$^+$, RT 1.58 min.

Step 4: 1-benzyl 4-tert-butyl 2-(5-bromo-1-methyl-1H-indol-2-yl)piperazine-1,4-dicarboxylate The title compound was prepared according to procedure described in Example 156 Step 2.

$^1$H NMR (500 MHz, CHCl$_3$-d, broad peaks, mixture of rotamers) δ ppm 1.47 (br. s., 9H) 2.80-3.14 (m, 2H) 3.30 (br. s., 1H) 3.95 (br. s., 2H) 4.38-4.74 (m, 1H) 5.13-5.29 (m, 2H) 5.44-5.62 (m, 1H) 6.56 (br. s., 1H) 7.14 (d, J=8.8 Hz, 1H) 7.28 (d, J=8.8 Hz, 1H) 7.32-7.40 (m, 5H) 7.65 (d, J=1.6 Hz, 1H). LC-MS 528.1/530.2 [M+H]$^+$, RT 1.67 min.

Step 5: 1-benzyl 4-tert-butyl 2-(5-(3-ethyl-6-methoxy-5-(methoxycarbonyl)pyridin-2-yl)-1-methyl-1H-indol-2-yl)piperazine-1,4-dicarboxylate The title compound was prepared according to procedure described in Example 67 Step 3.

$^1$H NMR (500 MHz, CHCl$_3$-d, broad peaks, mixture of rotamers) δ ppm 1.18 (t, J=7.6 Hz, 3H) 1.47-1.60 (m, 9H) 2.73 (q, J=7.6 Hz, 2H) 2.81-3.20 (m, 2H) 3.34 (br. s., 1H) 3.68 (br. s, 2H) 3.94 (s, 3H) 4.06 (s, 3H) 4.35-4.82 (m, 1H) 5.23 (s, 2H) 5.47-5.71 (m, 1H) 6.69 (br. s., 1H) 7.32-7.40 (m, 6H) 7.45 (d, J=8.5 Hz, 1H) 7.72 (s, 1H) 8.13 (s, 1H). LC-MS 643.4 [M+H]$^+$, RT 1.68 min.

Step 6: 5-ethyl-6-(1-methyl-2-(piperazin-2-yl)-1H-indol-5-yl)-2-oxo-1,2-dihydropyridine-3-carboxylic acid dihydrochloride The title compound was prepared according to procedure described in Example 67 Step 4.

$^1$H NMR (500 MHz, DEUTERIUM OXIDE) δ ppm 1.09 (t, J=7.7 Hz, 3H) 2.53 (q, J=7.7 Hz, 2H) 3.54 (td, J=13.9, 4.1 Hz, 1H) 3.66-3.80 (m, 2H) 3.82-3.87 (m, 2H) 3.88 (s, 3H) 4.04 (d, J=13.9 Hz, 1H) 5.05 (br. d, J=12.3 Hz, 1H) 6.91 (s, 1H) 7.42 (dd, J=8.5, 1.3 Hz, 1H) 7.64 (d, J=8.5 Hz, 1H) 7.83 (d, J=1.3 Hz, 1H) 8.44 (s, 1H). LC-MS 379.1 [M–H]$^-$, 381.2 [M+H]$^+$, RT 0.46 min Example 71

5-ethyl-6-(1-methyl-2-(1-methylpiperazin-2-yl)-1H-indol-5-yl)-2-oxo-1,2-dihydropyridine-3-carboxylic acid dihydrochloride Step 1: Solution of 1-benzyl 4-tert-butyl 2-(5-(3-ethyl-6-methoxy-5-(methoxycarbonyl)pyridin-2-yl)-1-methyl-1H-indol-2-yl)piperazine-1,4-dicarboxylate (71.4 mg, 0.11 mmol), prepared according to procedure described in Example 67, Step 3, in MeOH (1 mL) was hydrogenated over Pd/C (10% Degussa type, 10 mg) with H$_2$-balloon. After 1 h complete consumption of starting material was observed. Catalyst was filtered and washed with MeOH (5 mL). Concentration of mother liquor afforded tert-butyl 3-(5-(3-ethyl-6-methoxy-5-(methoxycarbonyl)pyridin-2-yl)-1-methyl-1H-indol-2-yl)piperazine-1-carboxylate which was used directly in the next step. LC-MS 509.3 [M+H]$^+$, RT 1.28 min.

Step 2: To solution of tert-butyl 3-(5-(3-ethyl-6-methoxy-5-(methoxycarbonyl)pyridin-2-yl)-1-methyl-1H-indol-2-yl)piperazine-1-carboxylate (0.11 mmol) obtained above in dichloroethane (1.0 mL) was added solution of HCHO (aqueous 37%, 30 µL) followed by AcOH (50 µL) and NaBH(OAc)$_3$ (100 mg, 0.45 mmol). Reaction mixture was stirred at room temperature. After 1 h LC/MS indicated complete consumption of starting material. Reaction was quenched with NaHCO$_3$ (aqueous saturated, 1.0 mL). Product was extracted with DCM. Organic phase was dried over Na$_2$SO$_4$ and solvent was concentrated to yield tert-butyl 3-(5-(3-ethyl-6-methoxy-5-(methoxycarbonyl)pyridin-2-yl)-1-methyl-1H-indol-2-yl)-4-methylpiperazine-1-carboxylate (57.8 mg) which was used directly in the next step. LC-MS 523.3 [M+H]$^+$, RT 1.33 min.

Step 3: tert-Butyl 3-(5-(3-ethyl-6-methoxy-5-(methoxycarbonyl)pyridin-2-yl)-1-methyl-1H-indol-2-yl)-4-methylpiperazine-1-carboxylate (57.8 mg) was converted to 5-ethyl-6-(1-methyl-2-(1-methylpiperazin-2-yl)-1H-indol-5-yl)-2-oxo-1,2-dihydropyridine-3-carboxylic acid dihydrochloride (49.2 mg) according to procedure described in Example 67 Step 4 in 95% overall yield.

$^1$H NMR (500 MHz, DEUTERIUM OXIDE) δ ppm 1.08 (t, J=7.6 Hz, 3H) 2.51 (q, J=7.6 Hz, 2H) 2.75 (s, 3H) 3.61-3.72 (m, 2H) 3.80-3.96 (m, 3H) 3.90 (s, 3H) 4.06 (br. d, J=13.9 Hz, 1H) 4.91 (dd, J=11.7, 2.5 Hz, 1H) 6.98 (s, 1H) 7.39 (d, J=8.5 Hz, 1H) 7.64 (d, J=8.5 Hz, 1H) 7.82 (s, 1H) 8.37 (s, 1H). LC-MS 393.2 [M–H]$^-$, 395.2 [M+H]$^+$, RT 0.50 min.

Using the procedures described above, additional compounds described herein may be prepared by substituting the appropriate starting materials, reagents and reaction conditions and include compounds selected from:

| Cpd | Name |
|---|---|
| 72 | 6-(3-cyano-1-methyl-1H-indol-5-yl)-5-ethyl-2-oxo-1,2-dihydropyridine-3-carboxylic acid<br>$^1$H NMR (500 MHz, DMSO-d$_6$) δ ppm 8.38 (s, 1 H) 8.28-8.34 (m, 1 H) 7.75-7.82 (m, 2 H) 7.41-7.49 (m, 1 H) 3.93 (s, 3 H) 2.43 (d, J = 7.49 Hz, 2 H) 1.02 (t, J = 7.49 Hz, 3 H). LC-MS 322.3 [M + H]$^+$, RT 0.98 min. |
| 73 | 6-(3-carbamoyl-1-methyl-1H-indol-5-yl)-5-ethyl-2-oxo-1,2-dihydropyridine-3-carboxylic acid<br>LC-MS 340.3 [M + H]$^+$, RT 0.81 min. |
| 74 | 6-(3-(aminomethyl)-1-methyl-1H-indol-5-yl)-5-ethyl-2-oxo-1,2-dihydropyridine-3-carboxylic acid<br>$^1$H NMR (500 MHz, DMSO-d$_6$) δ ppm 15.02 (br. s., 1 H) 13.10-13.24 (m, 1 H) 8.40 (s, 1 H) 8.27 (br. s., 2 H) 7.98 (d, J = 1.34 Hz, 1 H) 7.58-7.67 (m, 2 H) 7.33 (dd, J = 8.51, 1.66 Hz, 1 H) 4.20 (br. s., 2 H) 3.82-3.90 (m, 3 H) 2.43-2.57 (m, 2 H) 1.04 (t, J = 7.53 Hz, 3 H). LC-MS 324.0 [M − H]$^−$, RT 0.73 min. |

Example 75

6-(3-((dimethylamino)methyl)-1-methyl-1H-indol-5-yl)-5-ethyl-2-oxo-1,2-dihydropyridine-3-carboxylic acid To a screw-cap reaction vial were added 6-(3-(aminomethyl)-1-methyl-1H-indol-5-yl)-5-ethyl-2-oxo-1,2-dihydropyridine-3-carboxylic acid (20 mg, 0.06 mmol, 1.0 eq) and DCE (1 mL). After stirring briefly, formaldehyde-37% weight solution in H$_2$O (25.0 mg, 0.3 mmol, 5.0 eq), NaBH(OAc)$_3$ (65.0 mg, 0.3 mmol, 5.0 eq), and glacial acetic acid (17.6 µL, 0.3 mmol, 5.0 eq) were added and the reaction was stirred for 16 h. The reaction was concentrated under reduced pressure and the residue was purified by HPLC to afford 2.0 mg (10%) of the title compound. LC-MS 352.2 [M−H]$^−$, RT 0.71 min.

Using the procedures described above, additional compounds described herein may be prepared by substituting the appropriate starting materials, reagents and reaction conditions and include compounds selected from:

| Cpd | Name |
|---|---|
| 76 | 6-(3-((diethylamino)methyl)-1-methyl-1H-indol-5-yl)-5-ethyl-2-oxo-1,2-dihydropyridine-3-carboxylic acid<br>LC-MS 380.2 [M − H]$^−$, RT 0.76 min. |
| 77 | 6-(3-((dibenzylamino)methyl)-1-methyl-1H-indol-5-yl)-5-ethyl-2-oxo-1,2-dihydropyridine-3-carboxylic acid<br>LC-MS 506.3 [M + H]$^+$, RT 0.99 min. |
| 84 | 5-ethyl-6-(1-methyl-2-(pyrrolidin-1-ylmethyl)-1H-pyrrolo[3,2-b]pyridin-5-yl)-2-oxo-1,2-dihydropyridine-3-carboxylic acid<br>$^1$H NMR (500 MHz, MeOH-d$_4$) δ ppm 1.20 (t, J = 7.01 Hz, 3 H) 1.98-2.25 (m, 4 H) 2.64 (m, 2 H) 3.69-3.89 (m, 4 H) 4.19 (s, 3 H) 5.01 (br. s., 2 H) 7.39 (br. s., 1 H) 7.99 (d, J = 7.65 Hz, 1 H) 8.58 (br. s., 1 H) 8.85 (d, J = 7.64 Hz, 1 H). LC-MS 381.2 [M + H]$^+$, RT 0.65 min. |
| 85 | 6-(2-(4,5-dihydro-1H-imidazol-2-yl)-1-methyl-1H-indol-5-yl)-5-ethyl-2-oxo-1,2-dihydropyridine-3-carboxylic acid<br>$^1$H NMR (500 MHz, MeOH-d$_4$) δ ppm 1.13 (t, J = 7.53 Hz, 3 H) 2.53 (q, J = 7.57 Hz, 2 H) 4.04-4.08 (m, 3 H) 4.20 (s, 4 H) 7.47 (d, J = 0.71 Hz, 1 H) 7.57 (dd, J = 8.75, 1.73 Hz, 1 H) 7.82 (d, J = 8.75 Hz, 1 H) 7.94 (dd, J = 1.66, 0.63 Hz, 1 H) 8.53 (s, 1 H). LC-MS: 365.2 [M + H]$^+$, RT 0.65 min. |
| 86 | 5-ethyl-6-(1-methyl-2-(1,4,5,6-tetrahydropyrimidin-2-yl)-1H-indol-5-yl)-2-oxo-1,2-dihydropyridine-3-carboxylic acid<br>$^1$H NMR (500 MHz, MeOH-d$_4$) δ ppm 1.12 (t, J = 7.57 Hz, 3 H) 2.18-2.26 (m, 2 H) 2.53 (d, J = 7.57 Hz, 2 H) 3.70 (t, J = 5.79 Hz, 4 H) 3.98 (s, 3 H) 7.23 (d, J = 0.63 Hz, 1 H) 7.50-7.56 (m, 1 H) 7.76-7.82 (m, 1 H) 7.87-7.94 (m, 1 H) 8.52 (s, 1 H). LC-MS: 379.2 [M + H]$^+$, RT 0.66 min. |
| 87 | 6-(2-(2-(dimethylamino)propan-2-yl)-1-methyl-1H-indol-5-yl)-5-ethyl-2-oxo-1,2-dihydropyridine-3-carboxylic acid<br>LC-MS 380.3 [M − H]$^−$, 382.4 [M + H]$^+$, RT 0.67 min. (Method A) |
| 88 | 5-ethyl-6-(1-methyl-2-(2-(pyrrolidin-1-yl)propan-2-yl)-1H-indol-5-yl)-2-oxo-1,2-dihydropyridine-3-carboxylic acid<br>LC-MS 406.4 [M − H]$^−$, 408.4 [M + H]$^+$, RT 0.95 min. (Method A) |
| 89 | 6-(1,6-dimethyl-2-(pyrrolidin-1-ylmethyl)-1H-indol-5-yl)-5-ethyl-2-oxo-1,2-dihydropyridine-3-carboxylic acid<br>LC-MS 392.4 [M − H]$^−$, 394.5 [M + H]$^+$, RT 0.69 min. (Method A) |
| 90 | 6-(1,6-dimethyl-2-(piperidin-1-ylmethyl)-1H-indol-5-yl)-5-ethyl-2-oxo-1,2-dihydropyridine-3-carboxylic acid<br>LC-MS 406.4 [M − H]$^−$, 408.5 [M + H]$^+$, RT 1.10 min. (Method B) |
| 91 | 6-(6-chloro-1-methyl-2-(morpholinomethyl)-1H-indol-5-yl)-5-ethyl-2-oxo-1,2-dihydropyridine-3-carboxylic acid<br>LC-MS 428.2 [M − H]$^−$, 430.4 [M + H]$^+$, RT 1.10 min. (Method B) |
| 92 | 6-(6-chloro-2-((diethylamino)methyl)-1-methyl-1H-indol-5-yl)-5-ethyl-2-oxo-1,2-dihydropyridine-3-carboxylic acid<br>LC-MS 414.3/416.3 [M − H]$^−$, 416.4/418.4 [M + H]$^+$, RT 1.09 min. (Method B) |

-continued

| Cpd | Name |
|---|---|
| 93 | 6-(6-chloro-2-((dimethylamino)methyl)-1-methyl-1H-indol-5-yl)-5-ethyl-2-oxo-1,2-dihydropyridine-3-carboxylic acid<br>LC-MS 386.3/388.2 [M − H]⁻, 388.3/390.3 [M + H]⁺, RT 0.68 min. (Method A) |
| 94 | 6-(1,6-dimethyl-2-(morpholinomethyl)-1H-indol-5-yl)-5-ethyl-2-oxo-1,2-dihydropyridine-3-carboxylic acid<br>LC-MS 408.3 [M − H]⁻, 410.4 [M + H]⁺, RT 0.66 min. (Method A) |
| 95 | 6-(2-((diethylamino)methyl)-1,6-dimethyl-1H-indol-5-yl)-5-ethyl-2-oxo-1,2-dihydropyridine-3-carboxylic acid<br>LC-MS 394.3 [M − H]⁻, 396.4 [M + H]⁺, RT 1.05 min. (Method B) |
| 96 | 6-(2-((dimethylamino)methyl)-1,6-dimethyl-1H-indol-5-yl)-5-ethyl-2-oxo-1,2-dihydropyridine-3-carboxylic acid<br>LC-MS 366.3 [M − H]⁻, 368.4 [M + H]⁺, RT 0.93 min. (Method B) |
| 97 | 5-ethyl-6-(7-fluoro-1-methyl-2-(pyrrolidin-1-ylmethyl)-1H-indol-5-yl)-2-oxo-1,2-dihydropyridine-3-carboxylic acid<br>LC-MS 396.3 [M − H]⁻, 398.4 [M + H]⁺, RT 0.68 min. (Method A) |
| 98 | 5-ethyl-6-(7-fluoro-1-methyl-2-(morpholinomethyl)-1H-indol-5-yl)-2-oxo-1,2-dihydropyridine-3-carboxylic acid<br>LC-MS 412.3 [M − H]⁻, 414.4 [M + H]⁺, RT 0.66 min. (Method A) |
| 99 | 6-(1,7-dimethyl-2-(pyrrolidin-1-ylmethyl)-1H-indol-5-yl)-5-ethyl-2-oxo-1,2-dihydropyridine-3-carboxylic acid<br>LC-MS 392.3 [M − H]⁻, 394.5 [M + H]⁺, RT 0.67 min. (Method A) |
| 100 | 6-(1,7-dimethyl-2-(piperidin-1-ylmethyl)-1H-indol-5-yl)-5-ethyl-2-oxo-1,2-dihydropyridine-3-carboxylic acid<br>LC-MS 406.3 [M − H]⁻, 408.5 [M + H]⁺, RT 0.71 min. (Method A) |
| 101 | 6-(2-((diethylamino)methyl)-7-fluoro-1-methyl-1H-indol-5-yl)-5-ethyl-2-oxo-1,2-dihydropyridine-3-carboxylic acid<br>LC-MS 398.3 [M − H]⁻, 400.4 [M + H]⁺, RT 0.66 min. (Method A) |
| 102 | 5-ethyl-6-(7-fluoro-1-methyl-2-(piperidin-1-ylmethyl)-1H-indol-5-yl)-2-oxo-1,2-dihydropyridine-3-carboxylic acid<br>LC-MS 410.3 [M − H]⁻, 412.4 [M + H]⁺, RT 0.70 min. (Method A) |
| 103 | 6-(1,7-dimethyl-2-(morpholinomethyl)-1H-indol-5-yl)-5-ethyl-2-oxo-1,2-dihydropyridine-3-carboxylic acid<br>LC-MS 408.4 [M − H]⁻, 410.4 [M + H]⁺, RT 0.68 min. (Method A) |
| 104 | 6-(2-((diethylamino)methyl)-1,7-dimethyl-1H-indol-5-yl)-5-ethyl-2-oxo-1,2-dihydropyridine-3-carboxylic acid<br>LC-MS 394.3 [M − H]⁻, 396.4 [M + H]⁺, RT 0.70 min. (Method A) |
| 105 | 6-(2-((dimethylamino)methyl)-1,7-dimethyl-1H-indol-5-yl)-5-ethyl-2-oxo-1,2-dihydropyridine-3-carboxylic acid<br>LC-MS 366.3 [M − H]⁻, 368.4 [M + H]⁺, RT 0.98 min. (Method B) |
| 106 | 6-(2-((dimethylamino)methyl)-7-fluoro-1-methyl-1H-indol-5-yl)-5-ethyl-2-oxo-1,2-dihydropyridine-3-carboxylic acid<br>LC-MS 370.3 [M − H]⁻, 372.4 [M + H]⁺, RT 0.63 min. (Method A) |
| 107 | 5-ethyl-6-(6-methoxy-1-methyl-2-(pyrrolidin-1-ylmethyl)-1H-indol-5-yl)-2-oxo-1,2-dihydropyridine-3-carboxylic acid<br>LC-MS 408.3 [M − H]⁻, 410.5 [M + H]⁺, RT 0.67 min. (Method A) |
| 108 | 5-ethyl-6-(6-methoxy-1-methyl-2-(morpholinomethyl)-1H-indol-5-yl)-2-oxo-1,2-dihydropyridine-3-carboxylic acid<br>LC-MS 424.3 [M − H]⁻, 426.4 [M + H]⁺, RT 1.12 min. (Method B) |
| 109 | 6-(2-(azetidin-1-ylmethyl)-1-methyl-1H-indol-5-yl)-5-ethyl-2-oxo-1,2-dihydropyridine-3,4-dicarboxylic acid<br>LC-MS 410.2 [M + H]⁺, RT 0.77 min. |
| 110 | 5-ethyl-6-(1-methyl-2-(pyrrolidin-1-ylmethyl)-1H-indol-5-yl)-2-oxo-1,2-dihydropyridine-3,4-dicarboxylic acid<br>$^1$H NMR (500 MHz, CHCl$_3$-d) δ ppm 7.74-7.79 (m, 1 H) 7.54-7.60 (m, 1 H) 7.37-7.42 (m, 1 H) 6.83-6.87 (m, 1 H) 4.65 (s, 2 H) 3.89 (s, 3 H) 2.61-2.69 (m, 2 H) 2.15-2.21 (m, 2 H) 2.07 (s, 2 H) 1.26 (s, 4 H) 1.01-1.09 (m, 3 H). LC-MS 424.3 [M + H]⁺, RT 0.81 min. |
| 111 | 6-(2-((dimethylamino)methyl)-1-methyl-1H-indol-5-yl)-5-ethyl-2-oxo-1,2-dihydropyridine-3,4-dicarboxylic acid<br>LC-MS 398.2 [M + H]⁺, RT 0.76 min. |

Example 112

5-ethyl-6-(1-methyl-2-((methylamino)methyl)-1H-indol-5-yl)-2-oxo-1,2-dihydropyridine-3-carboxylic acid

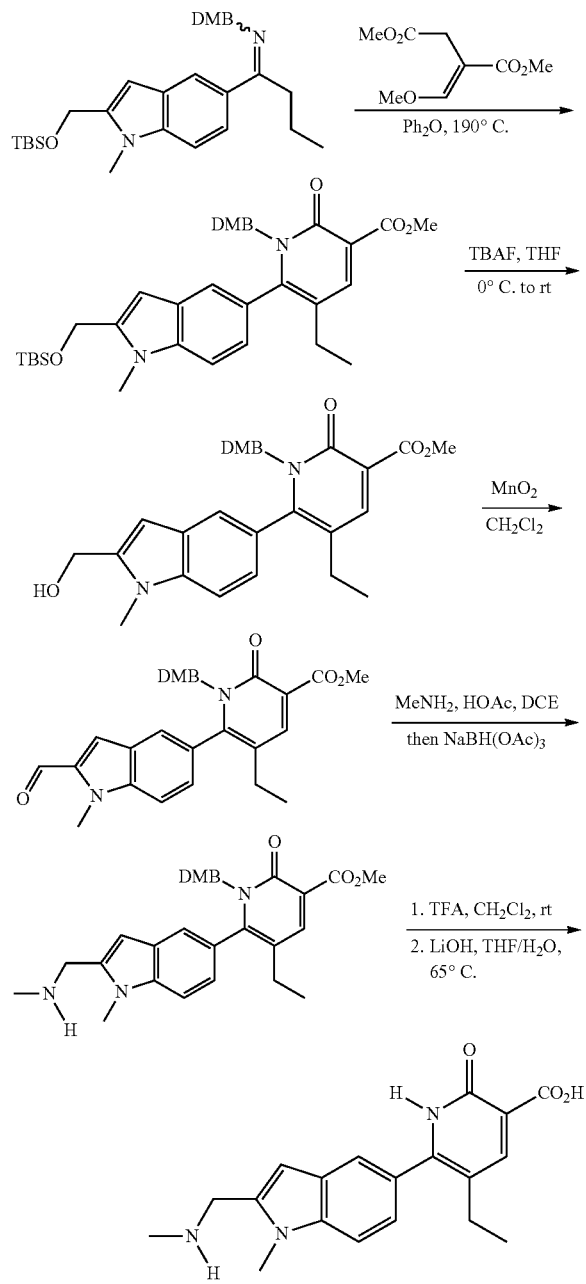

Step 1: methyl 6-(2-((tert-butyldimethylsilyloxy)methyl)-1-methyl-1H-indol-5-yl)-1-(2,4-dimethoxybenzyl)-5-ethyl-2-oxo-1,2-dihydropyridine-3-carboxylate N-(1-(2-((tert-butyldimethylsilyloxy)methyl)-1-methyl-1H-indol-5-yl)butylidene)-1-(2,4-dimethoxyphenyl)methanamine (5.94 g, 12.0 mmol), prepared according to procedure described in Example 164 Step 1, was suspended in Ph$_2$O (20 mL) then dimethyl 2-(methoxymethylene)malonate (3.55 g, 20.4 mmol, 1.7 eq) was added. The reaction mixture was heated to 190° C. for 1 h before mixture was cooled to room temperature then purified by flash column chromatography (0-50% EtOAc in CH$_2$Cl$_2$) to give the title compound. LC-MS 605.5 [M+H]$^+$, RT 1.75 min.

Step 2: methyl 1-(2,4-dimethoxybenzyl)-5-ethyl-6-(2-(hydroxymethyl)-1-methyl-1H-indol-5-yl)-2-oxo-1,2-dihydropyridine-3-carboxylate To a solution of cycloadduct obtained above (6.57 g, ca. 10.9 mmol) in THF (10 mL) was added TBAF (11.4 mL, 1.0 M in THF, 11.4 mmol, 1.05 eq) at 0° C. The mixture was allowed to warm to room temperature then stirred for 1 h. Solvent was removed under reduced pressure then crude product was purified by flash column chromatography (0-50% EtOAc in CH$_2$Cl$_2$) to give the title compound (3.08 g, 6.3 mmol) in 52% yield over two steps.
$^1$H NMR (500 MHz, CHCl$_3$-d) δ ppm 0.92-1.00 (m, 3H) 2.04-2.13 (m, 2H) 3.21 (s, 3H) 3.76 (s, 3H) 3.84 (s, 3H) 3.95 (s, 3H) 4.83 (s, 2H) 4.97 (d, J=15.29 Hz, 1H) 5.08 (d, J=15.45 Hz, 1H) 6.16 (d, J=2.36 Hz, 1H) 6.35-6.42 (m, 2H) 6.77-6.84 (m, 2H) 7.11 (s, 1H) 7.25 (s, 1H) 8.22 (s, 1H). LC-MS 491.6 [M+H]$^+$, RT 1.18 min.

Step 3: methyl 1-(2,4-dimethoxybenzyl)-5-ethyl-6-(2-formyl-1-methyl-1H-indol-5-yl)-2-oxo-1,2-dihydropyridine-3-carboxylate To a solution of above alcohol (490 mg, ca. 1.0 mmol) in CH$_2$Cl$_2$ (3 mL) was added MnO$_2$ (1.3 g, 15.0 mmol, 15.0 eq) at room temperature. The mixture was stirred for 2 h and reaction was complete. The mixture was filtered through celite then solid was washed with CH$_2$Cl$_2$ (5×25 mL). Solvent was removed under reduced pressure then crude product was purified by flash column chromatography (0-30% EtOAc in CH$_2$Cl$_2$) to give the title compound (389 mg, 80%).
$^1$H NMR (500 MHz, CHCl$_3$-d) δ ppm 0.97 (t, J=7.53 Hz, 3H) 2.05-2.13 (m, 2H) 3.11 (s, 3H) 3.77 (s, 3H) 3.97 (s, 3H) 4.13 (s, 3H) 4.94 (d, J=15.37 Hz, 1H) 5.13 (d, J=15.29 Hz, 1H) 6.12 (d, J=2.36 Hz, 1H) 6.39 (dd, J=8.43, 2.36 Hz, 1H) 6.86 (d, J=8.43 Hz, 1H) 7.00 (dd, J=8.63, 1.54 Hz, 1H) 7.16-7.20 (m, 1H) 7.22 (s, 1H) 7.36 (d, J=8.67 Hz, 1H) 8.22 (s, 1H) 9.92 (s, 1H). LC-MS 489.6 [M+H]$^+$, RT 1.32 min.

Step 4-6: 5-ethyl-6-(1-methyl-2-((methylamino)methyl)-1H-indol-5-yl)-2-oxo-1,2-dihydropyridine-3-carboxylic acid To a solution of aldehyde (200 mg, 0.41 mmol) in DCE (2.0 mL) was added methyl amine (2.0 M in THF, 0.40 mL, 0.80 mmol, 2.0 eq) and HOAc (0.05 mL, 0.82 mmol, 2.0 eq) at room temperature. The reaction was stirred for 1 h before NaBH(OAc)$_3$ (174 mg, 0.82 mmol, 2.0 eq) was added. Upon completion, reaction was quenched with H$_2$O then extracted by CH$_2$Cl$_2$ (4×20 mL). The combined organic layers were dried over Na$_2$SO$_4$ then concentrated to give a crude product which was carried over to next step without further purification. To a solution of reductive amination product (ca. 0.4 mmol) in CH$_2$Cl$_2$ (2 mL) was added TFA (0.3 mL, 4.0 mmol, 10 eq) at 0° C. The mixture was allowed to warm to room temperature then stirred for 1 h. Reaction was monitored by LC-MS. The solvent was removed under reduced pressure then crude product was used in next step without further purification.

To a suspension of above crude product (ca. 0.4 mmol) in THF (1 mL) and H$_2$O (1 mL) was added LiOH—H$_2$O (168 mg, 4.0 mmol, 10 eq) then mixture was heated to 65° C. and stirred for 1 h. Upon completion, the reaction was quenched with 4N HCl (1 mL) then mixture was filtered to remove solid waste. The filtrate was neutralized with saturated aqueous NaHCO$_3$ to pH~7 then extracted by CH$_2$Cl$_2$ (5×20 mL). The combined organic layers were dried over Na$_2$SO$_4$ then concentrated to give a crude product which was purified by flash column chromatography (0-10% MeOH in CH$_2$Cl$_2$) to give the title product.

$^1$H NMR (500 MHz, DMSO-d$_6$) δ ppm 1.01 (t, J=7.49 Hz, 3H) 2.43 (q, J=7.49 Hz, 2H) 2.65 (s, 3H) 3.86 (s, 3H) 4.44 (s, 2H) 6.80 (s, 1H) 7.31 (dd, J=8.55, 1.69 Hz, 1H) 7.66 (d, J=8.59 Hz, 1H) 7.76 (d, J=1.34 Hz, 1H) 8.38 (s, 1H). LC-MS 338.1 [M−H]$^-$, 340.3 [M+H]$^+$, RT 0.70 min.

Using the procedures described above, additional compounds described herein may be prepared by substituting the appropriate starting materials, reagents and reaction conditions and include compounds selected from:

| Cpd | Name |
|---|---|
| 113 | 6-(2-((tert-butylamino)methyl)-1-methyl-1H-indol-5-yl)-5-ethyl-2-oxo-1,2-dihydropyridine-3-carboxylic acid<br>$^1$H NMR (500 MHz, DMSO-d$_6$) δ ppm 1.02 (t, J = 7.49 Hz, 3 H) 1.19 (s, 9 H) 2.48-2.55 (m, 2 H) 3.79 (s, 3 H) 3.95 (br. s., 2 H) 6.45 (s, 1 H) 7.20 (d, J = 8.51 Hz, 1 H) 7.46 (d, J = 8.43 Hz, 1 H) 7.55 (s, 1 H) 7.98 (br. s., 1 H). LC-MS 380.1 [M − H]$^-$, 382.1 [M + H]$^+$, RT 0.77 min. |
| 114 | 6-(2-((benzylamino)methyl)-1-methyl-1H-indol-5-yl)-5-ethyl-2-oxo-1,2-dihydropyridine-3-carboxylic acid<br>$^1$H NMR (500 MHz, MeOH-d$_4$) δ ppm 1.10 (t, J = 7.53 Hz, 3 H) 2.56 (q, J = 7.49 Hz, 2 H) 3.79 (s, 3 H) 3.94 (s, 2 H) 4.05 (s, 2 H) 6.58 (s, 1 H) 7.25 (dd, J = 8.47, 1.69 Hz, 1 H) 7.27-7.33 (m, 1 H) 7.35-7.40 (m, 2 H) 7.40-7.45 (m, 2 H) 7.51 (d, J = 8.51 Hz, 1 H) 7.64 (d, J = 1.26 Hz, 1 H) 8.38 (s, 1 H). LC-MS 414.5 [M − H]$^-$, 416.8 [M + H]$^+$, RT 0.89 min. |
| 115 | 5-ethyl-6-(1-methyl-2-((2-phenylpropan-2-ylamino)methyl)-1H-indol-5-yl)-2-oxo-1,2-dihydropyridine-3-carboxylic acid<br>$^1$H NMR (500 MHz, MeOH-d$_4$) δ ppm 1.09 (t, J = 7.59 Hz, 3 H) 1.65 (s, 6 H) 2.54 (q, J = 7.59 Hz, 2 H) 3.66 (s, 3 H) 3.73 (s, 2 H) 6.51 (s, 1 H) 7.23 (d, J = 7.96 Hz, 1 H) 7.28-7.35 (m, 1 H) 7.38-7.46 (m, 2 H) 7.48 (d, J = 8.51 Hz, 1 H) 7.58-7.64 (m, 3 H) 8.39 (s, 1 H). LC-MS 442.2 [M − H]$^-$, 444.2 [M + H]$^+$, RT 0.92 min. |
| 116 | (R)-5-ethyl-6-(1-methyl-2-((1-phenylethylamino)methyl)-1H-indol-5-yl)-2-oxo-1,2-dihydropyridine-3-carboxylic acid<br>$^1$H NMR (500 MHz, DMSO-d$_6$) δ ppm 1.01 (t, J = 7.45 Hz, 3 H) 1.31 (d, J = 6.62 Hz, 3 H) 2.38-2.48 (m, 2 H) 3.71 (s, 2 H) 3.73 (s, 3 H) 3.77-3.83 (m, 1 H) 6.42 (s, 1 H) 7.14-7.22 (m, 1 H) 7.22-7.30 (m, 1 H) 7.32-7.38 (m, 2 H) 7.38-7.43 (m, 2 H) 7.54 (d, J = 8.51 Hz, 1 H) 7.61 (s, 1 H) 8.32 (s, 1 H). LC-MS 428.3 [M − H]$^-$, 430.3 [M + H]$^+$, RT 0.67 min (1 min Method). |
| 117 | (S)-5-ethyl-6-(1-methyl-2-((1-phenylethylamino)methyl)-1H-indol-5-yl)-2-oxo-1,2-dihydropyridine-3-carboxylic acid<br>$^1$H NMR (500 MHz, DMSO-d$_6$) δ ppm 1.01 (t, J = 7.33 Hz, 3 H) 1.31 (d, J = 6.31 Hz, 3 H) 2.38-2.48 (m, 2 H) 3.70 (br. s., 2 H) 3.73 (s, 3 H) 3.77-3.83 (m, 1 H) 6.41 (s, 1 H) 7.19 (d, J = 8.51 Hz, 1 H) 7.22-7.30 (m, 1 H) 7.36 (t, J = 7.29 Hz, 2 H) 7.38-7.45 (m, 2 H) 7.53 (d, J = 8.59 Hz, 1 H) 7.61 (s, 1 H) 8.30 (br. s., 1 H). LC-MS 428.9 [M − H]$^-$, 431.0 [M + H]$^+$, RT 0.92 min. |
| 118 | (R)-5-ethyl-6-(1-methyl-2-((1-phenylpropylamino)methyl)-1H-indol-5-yl)-2-oxo-1,2-dihydropyridine-3-carboxylic acid<br>$^1$H NMR (500 MHz, MeOH-d$_4$) δ ppm 0.80 (t, J = 7.41 Hz, 3 H) 1.06-1.14 (m, 3 H) 1.65-1.79 (m, 1 H) 1.83-1.94 (m, 1 H) 2.56 (q, J = 7.54 Hz, 2 H) 3.65 (dd, J = 8.87, 5.56 Hz, 1 H) 3.70 (s, 3 H) 3.74-3.85 (m, 2 H) 6.46 (s, 1 H) 7.23 (dd, J = 8.47, 1.69 Hz, 1 H) 7.26-7.33 (m, 1 H) 7.35-7.40 (m, 4 H) 7.47 (d, J = 8.59 Hz, 1 H) 7.61 (d, J = 1.34 Hz, 1 H) 8.37 (s, 1 H). LC-MS 442.0 [M − H]$^-$, 444.0 [M + H]$^+$, RT 0.64 min (1 min Method). |
| 119 | (S)-5-ethyl-6-(1-methyl-2-((1-phenylpropylamino)methyl)-1H-indol-5-yl)-2-oxo-1,2-dihydropyridine-3-carboxylic acid<br>$^1$H NMR (500 MHz, MeOH-d$_4$) δ ppm 0.80 (t, J = 7.45 Hz, 3 H) 1.10 (t, J = 7.53 Hz, 3 H) 1.65-1.78 (m, 1 H) 1.88 (ddd, J = 13.22, 7.43, 5.75 Hz, 1 H) 2.57 (q, J = 7.57 Hz, 2 H) 3.63 (dd, J = 8.75, 5.36 Hz, 1 H) 3.69 (s, 3 H) 3.78 (s, 2 H) 6.45 (s, 1 H) 7.22 (dd, J = 8.47, 1.62 Hz, 1 H) 7.29 (td, J = 5.54, 3.19 Hz, 1 H) 7.34-7.42 (m, 4 H) 7.45 (d, J = 8.43 Hz, 1 H) 7.60 (d, J = 1.26 Hz, 1 H) 8.33 (s, 1 H). LC-MS 442.2 [M − H]$^-$, 444.3 [M + H]$^+$, RT 0.62 min. (1 min Method). |
| 120 | 5-ethyl-6-(1-methyl-2-((pyridin-2-ylmethylamino)methyl)-1H-indol-5-yl)-2-oxo-1,2-dihydropyridine-3-carboxylic acid<br>$^1$H NMR (500 MHz, MeOH-d$_4$) δ ppm 1.10 (t, J = 7.53 Hz, 3 H) 2.54 (q, J = 7.54 Hz, 2 H) 3.84 (s, 3 H) 4.07 (s, 2 H) 4.13 (s, 2 H) 6.58 (s, 1 H) 7.25 (dd, J = 8.43, 1.34 Hz, 1 H) 7.31 (dd, J = 6.98, 5.24 Hz, 1 H) 7.52 (d, J = 8.51 Hz, 1 H) 7.49 (d, J = 7.80 Hz, 1 H) 7.63 (s, 1 H) 7.80 (td, J = 7.68, 1.50 Hz, 1 H) 8.42 (s, 1 H) 8.53 (d, J = 4.41 Hz, 1 H). LC-MS 415.2 [M − H]$^-$, 417.3 [M + H]$^+$, RT 0.79 min. |
| 121 | 6-(2-((benzyl(methyl)amino)methyl)-1-methyl-1H-indol-5-yl)-5-ethyl-2-oxo-1,2-dihydropyridine-3-carboxylic acid<br>$^1$H NMR (500 MHz, MeOH-d$_4$) δ ppm 1.10 (t, J = 7.57 Hz, 3 H) 2.53 (q, J = 7.57 Hz, 2 H) 2.66 (br. s., 3 H) 3.77 (s, 3 H) 4.10-4.40 (m, 4 H) 6.83 (br. s., 1 H) 7.34 (d, J = 7.88 Hz, 1 H) 7.38-7.56 (m, 5 H) 7.62 (d, J = 8.51 Hz, 1 H) 7.74 (s, 1 H) 8.48 (s, 1 H). LC-MS 428.7 [M − H]$^-$, 431.1 [M + H]$^+$, RT 0.91 min. |

| Cpd | Name |
|---|---|
| 122 | 6-(2-((dimethylamino)methyl)-1-methyl-1H-indol-5-yl)-5-ethyl-2-oxo-1,2-dihydropyridine-3-carboxylic acid<br>$^1$H NMR (500 MHz, DMSO-$d_6$) δ ppm 1.03 (t, J = 7.49 Hz, 3 H) 2.21 (s, 6 H) 2.47 (q, J = 7.49 Hz, 2 H) 3.58 (s, 2 H) 3.80 (s, 3 H) 6.45 (s, 1 H) 7.21 (dd, J = 8.47, 1.69 Hz, 1 H) 7.53 (d, J = 8.51 Hz, 1 H) 7.61 (s, 1 H) 8.25 (br. s., 1 H). LC-MS 352.3 [M − H]$^-$, 354.2 [M + H]$^+$, RT 0.75 min. |
| 123 | 6-(2-((diethylamino)methyl)-1-methyl-1H-indol-5-yl)-5-ethyl-2-oxo-1,2-dihydropyridine-3-carboxylic acid<br>$^1$H NMR (500 MHz, MeOH-$d_4$) δ ppm 1.11 (t, J = 7.57 Hz, 3 H) 1.15 (t, J = 7.04 Hz, 6 H) 2.56 (q, J = 7.57 Hz, 2 H) 2.77 (q, J = 7.04 Hz, 4 H) 3.88 (s, 3 H) 3.97 (s, 2 H) 6.58 (s, 1 H) 7.26 (dd, J = 8.51, 1.73 Hz, 1 H) 7.53 (d, J = 8.51 Hz, 1 H) 7.65 (d, J = 1.26 Hz, 1 H) 8.40 (s, 1 H). LC-MS 380.6 [M − H]$^-$, 383.0 [M + H]$^+$, RT 0.75 min. |
| 124 | 5-ethyl-6-(1-methyl-2-(pyrrolidin-1-ylmethyl)-1H-indol-5-yl)-2-oxo-1,2-dihydropyridine-3-carboxylic acid<br>$^1$H NMR (500 MHz, MeOH-$d_4$) δ ppm 1.10 (t, J = 7.53 Hz, 3 H) 1.93 (dt, J = 6.76, 3.36 Hz, 4 H) 2.56 (q, J = 7.57 Hz, 2 H) 2.91 (br. s., 4 H) 3.87 (s, 3 H) 4.14 (s, 2 H) 6.62 (s, 1 H) 7.28 (dd, J = 8.51, 1.73 Hz, 1 H) 7.54 (d, J = 8.51 Hz, 1 H) 7.63-7.67 (m, 1 H) 8.38 (s, 1 H). LC-MS 378.3 [M − H]$^-$, 380.3 [M + H]$^+$, RT 0.81 min. |
| 125 | 5-ethyl-6-(2-((3-hydroxypyrrolidin-1-yl)methyl)-1-methyl-1H-indol-5-yl)-2-oxo-1,2-dihydropyridine-3-carboxylic acid<br>$^1$H NMR (500 MHz, MeOH-$d_4$) δ ppm 1.11 (t, J = 7.57 Hz, 3 H) 1.70-1.81 (m, 1 H) 2.17 (dt, J = 14.19, 6.78 Hz, 1 H) 2.57 (q, J = 7.57 Hz, 2 H) 2.61-2.71 (m, 2 H) 2.83-2.93 (m, 2 H) 3.84-3.98 (m, 2 H) 3.87 (s, 3 H) 4.34-4.41 (m, 1 H) 6.53 (s, 1 H) 7.25 (dd, J = 8.51, 1.89 Hz, 1 H) 7.51 (d, J = 8.51 Hz, 1 H) 7.61-7.65 (m, 1 H) 8.38 (s, 1 H). LC-MS 394.2 [M − H]$^-$, 396.6 [M + H]$^+$, RT 0.73 min. |
| 126 | (S)-6-(2-((3-aminopyrrolidin-1-yl)methyl)-1-methyl-1H-indol-5-yl)-5-ethyl-2-oxo-1,2-dihydropyridine-3-carboxylic acid<br>$^1$H NMR (500 MHz, MeOH-$d_4$) δ ppm 1.10 (t, J = 7.57 Hz, 3 H) 2.31 (br. s., 1 H) 2.52 (q, J = 7.67 Hz, 2 H) 2.70 (br. s., 1 H) 3.65-4.07 (m, 5 H) 3.99 (br. s., 3 H) 4.24 (br. s., 2 H) 7.00 (br. s., 1 H) 7.39 (d, J = 8.20 Hz, 1 H) 7.68 (d, J = 8.51 Hz, 1 H) 7.78 (br. s., 1 H) 8.49 (s, 1 H). LC-MS 393.0 [M − H]$^-$, 395.0 [M + H]$^+$, RT 0.44 min (1 min Method). |
| 127 | 5-ethyl-6-(1-methyl-2-((3-(methylamino)pyrrolidin-1-yl)methyl)-1H-indol-5-yl)-2-oxo-1,2-dihydropyridine-3-carboxylic acid<br>$^1$H NMR (500 MHz, MeOH-$d_4$) δ ppm 1.10 (t, J = 7.57 Hz, 3 H) 2.27-2.36 (m, 1 H) 2.52 (q, J = 7.57 Hz, 2 H) 2.61-2.72 (m, 1 H) 2.77 (s, 3 H) 3.65-3.87 (m, 4 H) 3.98 (s, 3 H) 4.03-4.15 (m, 1 H) 4.75 (br. s., 2 H) 6.95 (br. s., 1 H) 7.37 (dd, J = 8.83, 1.58 Hz, 1 H) 7.66 (d, J = 8.51 Hz, 1 H) 7.77 (s, 1 H) 8.49 (s, 1 H). LC-MS 407.2 [M − H]$^-$, 409.2 [M + H]$^+$, RT 0.70 min. |
| 128 | 6-(2-((dimethylamino)pyrrolidin-1-yl)methyl)-1-methyl-1H-indol-5-yl)-5-ethyl-2-oxo-1,2-dihydropyridine-3-carboxylic acid<br>$^1$H NMR (500 MHz, MeOH-$d_4$) δ ppm 1.10 (t, J = 7.53 Hz, 3 H) 1.84-1.93 (m, 1 H) 2.11-2.20 (m, 1 H) 2.50 (s, 6 H) 2.57 (q, J = 7.57 Hz, 2 H) 2.60-2.74 (m, 2 H) 2.75-2.85 (m, 2 H) 3.31-3.36 (m, 1 H) 3.82 (d, J = 15.00 Hz, 1 H) 3.85 (s, 3 H) 3.87 (d, J = 15.00 Hz, 1 H) 6.49 (s, 1 H) 7.24 (dd, J = 8.47, 1.62 Hz, 1 H) 7.49 (d, J = 8.51 Hz, 1 H) 7.58-7.64 (m, 1 H) 8.35 (s, 1 H). LC-MS 421.4 [M − H]$^-$, 423.4 [M + H]$^+$, RT 0.76 min. |
| 129 | (R)-5-ethyl-6-(2-((3-fluoropyrrolidin-1-yl)methyl)-1-methyl-1H-indol-5-yl)-2-oxo-1,2-dihydropyridine-3-carboxylic acid<br>$^1$H NMR (500 MHz, MeOH-$d_4$) δ ppm 1.11 (t, J = 7.53 Hz, 3 H) 1.92-2.09 (m, 1 H) 2.12-2.28 (m, 1 H) 2.46-2.53 (m, 1 H) 2.56 (q, J = 7.53 Hz, 2 H) 2.69-2.83 (m, 1 H) 2.86-2.99 (m, 2 H) 3.87 (s, 3 H) 3.87-3.91 (m, 2 H) 5.07-5.17 (m, 1 H) 5.17-5.26 (m, 1 H) 6.51 (s, 1 H) 7.24 (dd, J = 8.43, 1.42 Hz, 1 H) 7.51 (d, J = 8.43 Hz, 1 H) 7.63 (s, 1 H) 8.41 (s, 1 H). LC-MS 396.4 [M − H]$^-$, 398.5 [M + H]$^+$, RT 0.75 min. |
| 130 | 5-ethyl-6-(1-methyl-2-((2-methylpyrrolidin-1-yl)methyl)-1H-indol-5-yl)-2-oxo-1,2-dihydropyridine-3-carboxylic acid<br>$^1$H NMR (500 MHz, DMSO-$d_6$) δ ppm 1.02 (t, J = 7.49 Hz, 3 H) 1.14 (d, J = 5.99 Hz, 3 H) 1.36 (dq, J = 12.15, 8.22 Hz, 1 H) 1.56-1.66 (m, 2 H) 1.88-2.02 (m, 1 H) 2.18 (q, J = 8.56 Hz, 1 H) 2.46 (q, J = 7.51 Hz, 2 H) 2.75-2.85 (m, 1 H) 3.27-3.32 (m, 1 H) 3.37-3.41 (m, 1 H) 3.82 (s, 3 H) 4.05 (s, 1 H) 4.15 (d, J = 13.56 Hz, 1 H) 6.46 (s, 1 H) 7.20 (dd, J = 8.47, 1.69 Hz, 1 H) 7.53 (d, J = 8.51 Hz, 1 H) 7.61 (d, J = 1.26 Hz, 1 H) 8.27 (br. s., 1 H). LC-MS 392.0 [M − H]$^-$, 394.5 [M + H]$^+$, RT 0.80 min. |
| 131 | 5-ethyl-6-(1-methyl-2-((2-phenylpyrrolidin-1-yl)methyl)-1H-indol-5-yl)-2-oxo-1,2-dihydropyridine-3-carboxylic acid<br>$^1$H NMR (500 MHz, DMSO-$d_6$) δ ppm 1.01 (t, J = 7.49 Hz, 3 H) 1.64-1.85 (m, 2 H) 2.13-2.26 (m, 1 H) 2.26-2.37 (m, 1 H) 2.44 (q, J = 7.49 Hz, 2 H) 2.91-3.01 (m, 1 H) 3.35-3.44 (m, 2 H) 3.57-3.64 (m, 1 H) 3.60 (s, 3 H) 3.71-3.81 (m, 1 H) 6.46 (s, 1 H) 7.18 (dd, J = 8.43, 1.73 Hz, 1 H) 7.23-7.31 (m, 1 H) 7.36 (t, J = 7.57 Hz, 2 H) 7.43-7.52 (m, 3 H) 7.60 (d, J = 1.18 Hz, 1 H) 8.31 (br. s., 1 H). LC-MS 454.0 [M − H]$^-$, 456.4 [M + H]$^+$, RT 0.93 min. |
| 132 | (R)-5-ethyl-6-(2-((2-(hydroxymethyl)pyrrolidin-1-yl)methyl)-1-methyl-1H-indol-5-yl)-2-oxo-1,2-dihydropyridine-3-carboxylic acid<br>$^1$H NMR (500 MHz, MeOH-$d_4$) δ ppm 1.11 (t, J = 7.53 Hz, 3 H) 1.68-1.88 (m, 3 H) 2.00-2.10 (m, 1 H) 2.56 (q, J = 7.51 Hz, 2 H) 3.04-3.10 (m, 1 H) 3.31-3.34 (m, 1 H) 3.57 (d, J = 5.36 Hz, 2 H) 3.80-3.92 (m, 2 H) 3.90 (s, 3 H) 4.42 (d, J = 13.71 Hz, 1 H) 6.58 (s, 1 H) 7.26 (dd, J = 8.51, 1.73 Hz, 1 H) 7.53 (d, J = 8.59 Hz, 1 H) 7.64 (d, J = 1.10 Hz, 1 H) 8.39 (s, 1 H). LC-MS 408.2 [M − H]$^-$, 410.5 [M + H]$^+$, RT 0.75 min. |

| Cpd | Name |
|---|---|
| 133 | 5-ethyl-6-(1-methyl-2-(piperidin-1-ylmethyl)-1H-indol-5-yl)-2-oxo-1,2-dihydropyridine-3-carboxylic acid<br>$^1$H NMR (500 MHz, DMSO-d$_6$) δ ppm 1.02 (t, J = 7.53 Hz, 3 H) 1.40 (br. s., 2 H) 1.45-1.56 (m, 4 H) 2.38-2.45 (m, 4 H) 2.45 (q, J = 7.53 Hz, 2 H) 3.64 (br. s., 2 H) 3.82 (s, 3 H) 6.45 (s, 1 H) 7.21 (dd, J = 8.47, 1.69 Hz, 1 H) 7.55 (d, J = 8.35 Hz, 1 H) 7.62 (s, 1 H) 8.32 (s, 1 H). LC-MS 392.2 [M − H]$^−$, 394.4 [M + H]$^+$, RT 0.77 min. |
| 134 | 6-(2-((3,4-dihydroisoquinolin-2(1H)-yl)methyl)-1-methyl-1H-indol-5-yl)-5-ethyl-2-oxo-1,2-dihydropyridine-3-carboxylic acid<br>$^1$H NMR (500 MHz, DMSO-d$_6$) δ ppm 1.04 (t, J = 7.49 Hz, 3 H) 2.47-2.53 (m, 2 H) 2.76 (t, J = 5.64 Hz, 2 H) 2.82 (t, J = 5.60 Hz, 2 H) 3.64 (s, 2 H) 3.82 (s, 3 H) 3.85 (s, 2 H) 6.52 (s, 1 H) 6.98-7.06 (m, 1 H) 7.06-7.14 (m, 3 H) 7.22 (dd, J = 8.51, 1.66 Hz, 1 H) 7.51 (d, J = 8.51 Hz, 1 H) 7.62 (s, 1 H) 8.15 (d, J = 4.57 Hz, 1 H). LC-MS 440.4 [M − H]$^−$, 442.5 [M + H]$^+$, RT 0.89 min. |
| 135 | 6-(2-((5H-pyrrolo[3,4-b]pyridin-6(7H)-yl)methyl)-1-methyl-1H-indol-5-yl)-5-ethyl-2-oxo-1,2-dihydropyridine-3-carboxylic acid<br>$^1$H NMR (500 MHz, MeOH-d$_4$) δ ppm 1.11 (t, J = 7.53 Hz, 3 H) 2.55-2.63 (m, 2 H) 3.88 (s, 3 H) 4.03 (d, J = 5.75 Hz, 4 H) 4.16 (s, 2 H) 6.56 (s, 1 H) 7.25 (dd, J = 7.49, 4.89 Hz, 2 H) 7.46 (d, J = 8.12 Hz, 1 H) 7.61 (s, 1 H) 7.68 (d, J = 7.57 Hz, 1 H) 8.24 (br. s., 1 H) 8.32 (d, J = 4.34 Hz, 1 H). LC-MS 427.0 [M − H]$^−$, 429.0 [M + H]$^+$, RT 0.53 min (1 min Method). |
| 136 | 5-ethyl-6-(1-methyl-2-((tetrahydro-1H-pyrrolo[3,4-b]pyridin-6(2H,7H,7aH)-yl)methyl)-1H-indol-5-yl)-2-oxo-1,2-dihydropyridine-3-carboxylic acid<br>$^1$H NMR (500 MHz, MeOH-d$_4$) δ ppm 1.10 (t, J = 7.57 Hz, 3 H) 1.81 (br. s., 2 H) 1.96 (br. s., 3 H) 2.52 (q, J = 7.25 Hz, 2 H) 3.05 (br. s., 2 H) 3.40-3.47 (m, 1 H) 3.60-3.90 (m, 3 H) 3.94-4.25 (m, 2 H) 4.00 (s, 3 H) 4.85-5.15 (m, 1 H) 7.03 (br. s., 1 H) 7.38 (d, J = 8.20 Hz, 1 H) 7.67 (d, J = 8.83 Hz, 1 H) 7.77 (s, 1 H) 8.49 (s, 1 H). LC-MS 433.0 [M − H]$^−$, 435.0 [M + H]$^+$, RT 0.49 min. (1 min Method). |
| 137 | 5-Ethyl-6-(1-methyl-2-(morpholinomethyl)-1H-indol-5-yl)-2-oxo-1,2-dihydropyridine-3-carboxylic acid<br>$^1$H NMR (500 MHz, DMSO-d$_6$) δ ppm 1.02 (t, J = 7.49 Hz, 3 H) 2.37-2.45 (m, 4 H) 2.46 (q, J = 7.49 Hz, 2 H) 3.57 (t, J = 4.45 Hz, 4 H) 3.67 (s, 2 H) 3.83 (s, 3 H) 6.47 (s, 1 H) 7.21 (dd, J = 8.51, 1.66 Hz, 1 H) 7.55 (d, J = 8.59 Hz, 1 H) 7.62 (s, 1 H) 8.29 (br. s., 1 H). LC-MS 394.5 [M − H]$^−$, 396.5 [M + H]$^+$, RT 0.76 min. |
| 138 | 6-(2-((cis-2,6-Dimethylmorpholino)methyl)-1-methyl-1H-indol-5-yl)-5-ethyl-2-oxo-1,2-dihydropyridine-3-carboxylic acid<br>$^1$H NMR (500 MHz, MeOH-d$_4$) δ ppm 1.10 (t, J = 7.49 Hz, 3 H) 1.10-1.13 (m, 6 H) 1.73-1.84 (m, 2 H) 2.56 (q, J = 7.49 Hz, 2 H) 2.78-2.82 (m, 2 H) 3.62-3.71 (m, 2 H) 3.69 (s, 2 H) 3.86 (s, 3 H) 6.47 (s, 1 H) 7.23 (dd, J = 8.47, 1.46 Hz, 1 H) 7.49 (d, J = 8.51 Hz, 1 H) 7.59-7.64 (m, 1 H) 8.36 (s, 1 H). LC-MS 423.0 [M − H]$^−$, 425.0 [M + H]$^+$, RT 0.54 min. (1 min Method). |
| 139 | 5-Ethyl-6-(1-methyl-2-(piperazin-1-ylmethyl)-1H-indol-5-yl)-2-oxo-1,2-dihydropyridine-3-carboxylic acid<br>$^1$H NMR (500 MHz, MeOH-d$_4$) δ ppm 1.10 (t, J = 7.45 Hz, 3 H) 2.46-2.59 (m, 2 H) 3.28-3.34 (m, 4 H) 3.34-3.41 (m, 4 H) 3.53 (s, 2 H) 3.92 (s, 3 H) 6.71 (br. s., 1 H) 7.31 (d, J = 7.64 Hz, 1 H) 7.60 (d, J = 8.51 Hz, 1 H) 7.70 (s, 1 H) 8.48 (s, 1 H). LC-MS 393.0 [M − H]$^−$, RT 0.55 min. (1 min Method). |
| 140 | 5-ethyl-6-(1-methyl-2-((4-methylpiperazin-1-yl)methyl)-1H-indol-5-yl)-2-oxo-1,2-dihydropyridine-3-carboxylic acid<br>$^1$H NMR (500 MHz, MeOH-d$_4$) δ ppm 1.10 (t, J = 7.57 Hz, 3 H) 2.41 (s, 3 H) 2.56 (q, J = 7.78 Hz, 2 H) 2.45-2.70 (m, 6 H) 3.07-3.11 (m, 2 H) 3.75 (s, 2 H) 3.86 (s, 3 H) 6.49 (s, 1 H) 7.24 (dd, J = 8.51, 1.58 Hz, 1 H) 7.50 (d, J = 8.51 Hz, 1 H) 7.62 (d, J = 1.26 Hz, 1 H) 8.36 (s, 1 H). LC-MS 407.3 [M − H]$^−$, 409.7 [M + H]$^+$, RT 0.77 min. |
| 141 | 5-ethyl-6-(2-((4-isopropylpiperazin-1-yl)methyl)-1-methyl-1H-indol-5-yl)-2-oxo-1,2-dihydropyridine-3-carboxylic acid<br>$^1$H NMR (500 MHz, MeOH-d$_4$) δ ppm 1.10 (t, J = 7.57 Hz, 3 H) 1.41 (d, J = 6.62 Hz, 6 H) 2.53 (q, J = 7.54 Hz, 2 H) 3.18-3.30 (m, 2 H) 3.42-3.53 (m, 5 H) 3.57-3.76 (m, 5 H) 3.96 (s, 3 H) 4.47 (br. s., 2 H) 6.87 (br. s., 1 H) 7.35 (dd, J = 8.55, 1.69 Hz, 1 H) 7.65 (d, J = 8.59 Hz, 1 H) 7.75 (d, J = 1.18 Hz, 1 H) 8.49 (s, 1 H). LC-MS 435.3 [M − H]$^−$, 437.3 [M + H]$^+$, RT 0.84 min. |
| 142 | 6-(2-(2,5-diazabicyclo[2.2.1]heptan-2-ylmethyl)-1-methyl-1H-indol-5-yl)-5-ethyl-2-oxo-1,2-dihydropyridine-3-carboxylic acid<br>$^1$H NMR (500 MHz, MeOH-d$_4$) δ ppm 1.10 (t, J = 7.53 Hz, 3 H) 1.87-1.92 (m, 1 H) 2.25-2.31 (m, 1 H) 2.54 (q, J = 7.36 Hz, 2 H) 3.04 (br. s., 1 H) 3.21-3.27 (m, 1 H) 3.29-3.34 (m, 2 H) 3.90 (s, 3 H) 3.99-4.06 (m, 1 H) 4.15 (d, J = 13.95 Hz, 1 H) 4.31 (br. s., 2 H) 6.61 (s, 1 H) 7.27 (d, J = 8.12 Hz, 1 H) 7.57 (d, J = 8.51 Hz, 1 H) 7.66 (s, 1 H) 8.48 (s, 1 H). LC-MS 405.1 [M − H]$^−$, 407.1 [M + H]$^+$, RT 0.74 min. |
| 143 | 6-(2-(((1R,5S,6s)-6-(dibenzylamino)-3-azabicyclo[3.1.0]hexan-3-yl)methyl)-1-methyl-1H-indol-5-yl)-5-ethyl-2-oxo-1,2-dihydropyridine-3-carboxylic acid<br>$^1$H NMR (500 MHz, DMSO-d$_6$) δ ppm 1.03 (t, J = 7.53 Hz, 3 H) 1.25 (s, 2 H) 1.96-2.03 (m, 1 H) 2.31 (d, J = 8.51 Hz, 2 H) 2.46 (q, J = 7.51 Hz, 2 H) 2.77 (d, J = 8.83 Hz, 2 H) 3.55 (s, 4 H) 3.70 (s, 2 H) 3.72 (s, 3 H) 6.39 (s, 1 H) 7.18-7.28 (m, 7 H) 7.28-7.34 (m, 4 H) 7.57 (d, J = 8.51 Hz, 1 H) 7.62 (d, J = 1.58 Hz, 1 H) 8.35 (s, 1 H). LC-MS 585.3 [M − H]$^−$, 587.4 [M + H]$^+$, RT 1.13 min. |

-continued

| Cpd | Name |
|---|---|
| 144 | 6-(2-((4-acetylpiperazin-1-yl)methyl)-1-methyl-1H-indol-5-yl)-5-ethyl-2-oxo-1,2-dihydropyridine-3-carboxylic acid<br>$^1$H NMR (500 MHz, MeOH-d$_4$) δ ppm 1.10 (t, J = 7.53 Hz, 3 H) 2.16 (s, 3 H) 2.52 (q, J = 7.51 Hz, 2 H) 3.06-3.35 (m, 4 H) 3.45-3.75 (m, 4 H) 3.97 (s, 3 H) 4.73 (s, 2 H) 7.00 (br. s., 1 H) 7.40 (dd, J = 8.59, 1.58 Hz, 1 H) 7.70 (d, J = 8.59 Hz, 1 H) 7.80 (s, 1 H) 8.49 (s, 1 H). LC-MS 435.2 [M − H]$^-$, 437.2 [M + H]$^+$, RT 0.73 min. |
| 145 | 5-Ethyl-6-(1-methyl-2-((N-methylacetamido)methyl)-1H-indol-5-yl)-2-oxo-1,2-dihydropyridine-3-carboxylic acid<br>$^1$H NMR (500 MHz, DMSO-d$_6$) δ ppm 1.01 (t, J = 7.41 Hz, 3 H) 2.02-2.14 (m, 3 H) 2.44 (q, J = 7.41 Hz, 2 H) 2.89 (s, 0.75 H) 2.95 (s, 2.25 H) 3.70-3.78 (m, 3 H) 4.74 (s, 1.5 H) 4.82 (s, 0.5 H) 6.30 (s, 0.25 H) 6.51 (s, 0.75 H) 7.22 (dd, J = 8.47, 1.69 Hz, 1 H) 7.50-7.62 (m, 1 H) 7.62-7.68 (m, 1 H) 8.34 (s, 1 H) 13.20 (br. s., 1 H). The amide exists as a 3:1 mixture of two rotamers. LC-MS 380.2 [M − H]$^-$, 382.2 [M + H]$^+$, RT 0.97 min. |
| 146 | 6-(2-(((3aR,4R,7aS)-4-(benzyl(methyl)amino)-1H-isoindol-2(3H,3aH,4H,5H,6H,7H,7aH)-yl)methyl)-1-methyl-1H-indol-5-yl)-5-ethyl-2-oxo-1,2-dihydropyridine-3-carboxylic acid<br>LC-MS 553.5 [M + H]$^+$, RT 1.25 min. |
| 147 | 6-(2-(((3aR,4R,6aS)-4-(dimethylamino)hexahydrocyclopenta[c]pyrrol-2(1H)-yl)methyl)-1-methyl-1H-indol-5-yl)-5-ethyl-2-oxo-1,2-dihydropyridine-3-carboxylic acid<br>LC-MS 463.2 [M + H]$^+$, RT 0.62 min. |
| 148 | 5-ethyl-6-(1-methyl-2-(((3aR,4R,7aS)-4-(methylamino)-1H-isoindol-2(3H,3aH,4H,5H,6H,7H,7aH)-yl)methyl)-1H-indol-5-yl)-2-oxo-1,2-dihydropyridine-3-carboxylic acid<br>LC-MS 463.5 [M + H]$^+$, RT 0.59 min. |
| 149 | 6-(2-(((3aR,4R,7aS)-4-(dimethylamino)-1H-isoindol-2(3H,3aH,4H,5H,6H,7H,7aH)-yl)methyl)-1-methyl-1H-indol-5-yl)-5-ethyl-2-oxo-1,2-dihydropyridine-3-carboxylic acid<br>$^1$H NMR (500 MHz, MeOH-d$_4$) δ ppm 8.50 (s, 1 H) 7.77 (s, 1 H) 7.66 (d, J = 8.59 Hz, 1 H) 7.37 (d, J = 8.59 Hz, 1 H) 7.07 (s, 1 H) 3.97 (d, J = 5.36 Hz, 4 H) 3.22-3.36 (m, 13 H) 2.98 (s, 2 H) 2.85-2.94 (m, 5 H) 2.52 (d, J = 7.41 Hz, 2 H) 1.09 (t, J = 7.41 Hz, 3 H). LC-MS 477.3 [M + H]$^+$, RT 0.60 min. |
| 150 | 6-(2-(aminomethyl)-1-methyl-1H-indol-5-yl)-5-ethyl-2-oxo-1,2-dihydropyridine-3-carboxylic acid<br>LC-MS 326.2 [M + H]$^+$, RT 0.67 min. |

Example 151

5-ethyl-2-oxo-6-(1-(pyrrolidin-1-yl)-2,3-dihydro-1H-pyrrolo[1,2-a]indol-7-yl)-1,2-dihydropyridine-3-carboxylic acid

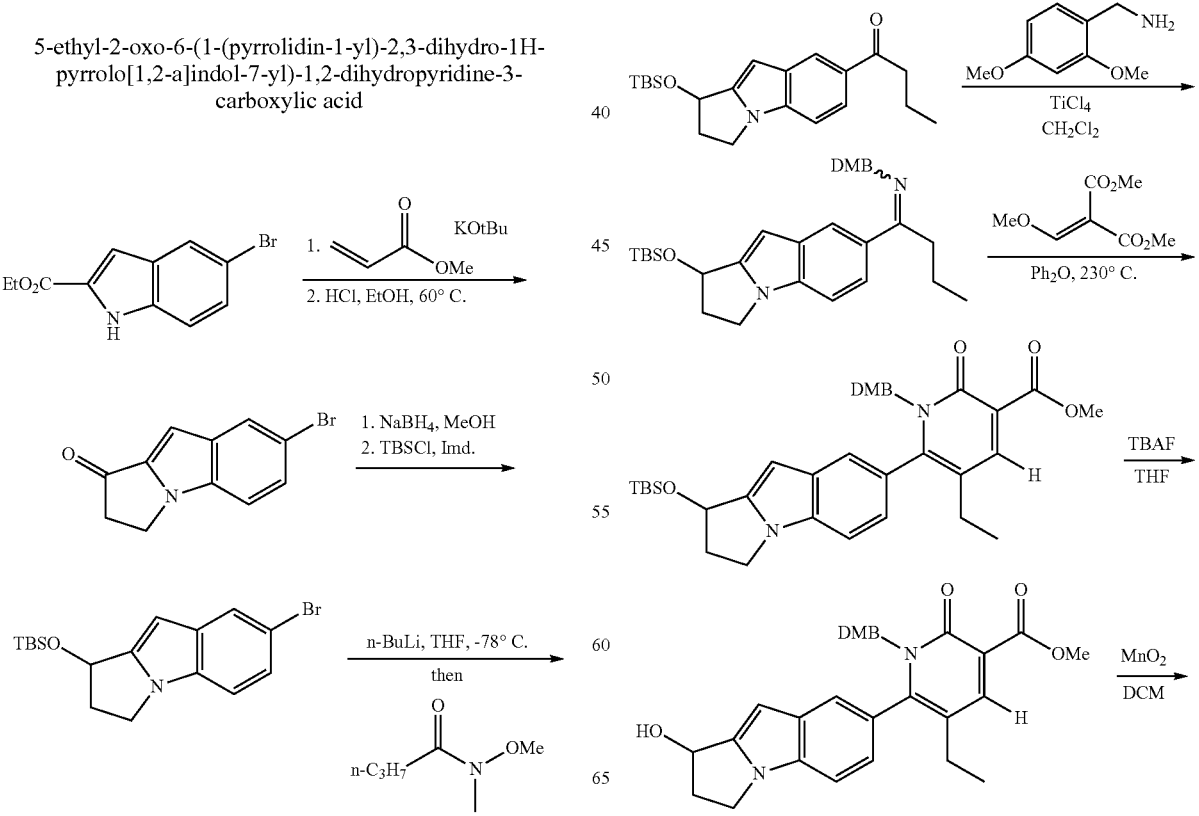

233
-continued

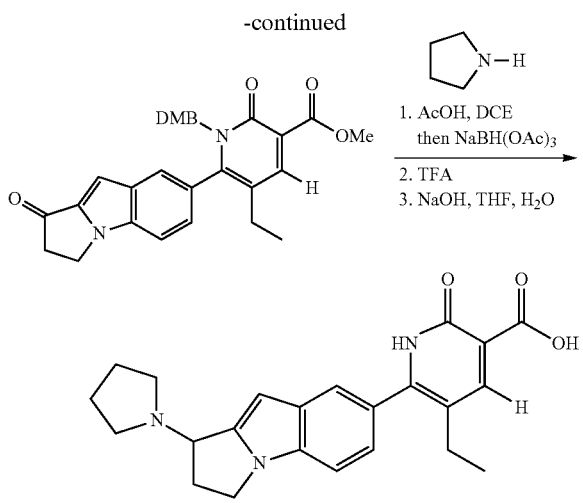

Step 1-2:
7-bromo-2,3-dihydro-1H-pyrrolo[1,2-a]indol-1-one

To a solution of KOtBu (1.0 g, 8.9 mmol) in benzene (20 mL) was added ethyl 5-bromo-1H-indole-2-carboxylate (2.3 g, 8.6 mmol) as a solution in benzene (40 mL) at room temperature. To the resulting white slurry was added methyl acrylate (1.5 mL, 17.1 mmol). The combined solution was heated at 80° C. for 1 h then cooled to room temperature and stirred for an additional 16 h. The reaction mixture was then poured into H$_2$O (100 mL) and the pH was adjusted to 4 with concentrated HCl. The aqueous phase was then extracted with CH$_2$Cl$_2$ (2×200 mL). The combined organic phases were washed with H$_2$O, dried over Na$_2$SO$_4$, filtered and concentrated. The crude residue was then dissolved in EtOH (30 mL), 4M HCl (10 mL) was added, and the mixture was heated to reflux. After stirring at reflux for 3.5 h, the reaction mixture was cooled to room temperature and neutralized with saturated aqueous NaHCO$_3$. The aqueous phase was then washed with Et$_2$O (2×100 mL). The combined organic phase was dried over MgSO$_4$, filtered, and concentrated to afford the title compound as an off white solid (1.3 g, 61%).
$^1$H NMR (500 MHz, CHCl$_3$-d) δ ppm 3.22-3.29 (m, 2H) 4.42-4.49 (m, 2H) 6.95 (d, J=0.71 Hz, 1H) 7.31-7.36 (m, 1H) 7.45 (dd, J=8.83, 1.81 Hz, 1H) 7.92 (d, J=1.42 Hz, 1H). LC-MS 252.2 [M+H]$^+$, RT 1.22 min.

Step 3-4: 7-bromo-1-(tert-butyldimethylsilyloxy)-2,3-dihydro-1H-pyrrolo[1,2-a]indole To a suspension of 7-bromo-2,3-dihydro-1H-pyrrolo[1,2-a]indol-1-one (1.1 g, 4.4 mmol) in MeOH (20 mL), cooled to 0° C., was added NaBH$_4$ (0.33 g, 8.8 mmol). After stirring at 0° C. for 1 h, the reaction was quenched with H$_2$O and then extracted with CH$_2$Cl$_2$. The combined organic phases were dried over Na$_2$SO$_4$, filtered, and concentrated to afford a white solid which was used without further purification. The crude solid was dissolved in CH$_2$Cl$_2$ (20 mL) and TBSCl (0.7 g, 4.4 mmol) and imidazole (0.33 g, 4.4 mmol) were added. After stirring at room temperature for 1 h, the reaction mixture was poured into H$_2$O and extracted with CH$_2$Cl$_2$. The combined organic phases were dried over Na$_2$SO$_4$, filtered, and concentrated to afford the title compound as a white solid (1.26 g, 79%).
$^1$H NMR (500 MHz, CHCl$_3$-d) δ ppm –0.05 (s, 3H) 0.00 (s, 3H) 0.72-0.76 (m, 9H) 2.28-2.36 (m, 1H) 2.61-2.70 (m, 1H) 3.76-3.83 (m, 1H) 3.99-4.08 (m, 1H) 5.14-5.19 (m, 1H) 6.06 (t, J=0.75 Hz, 1H) 6.92-6.96 (m, 1H) 7.04 (dd, J=8.59, 1.89 Hz, 1H) 7.52 (dd, J=1.85, 0.43 Hz, 1H). LC-MS 368.7 [M+H]$^+$, RT 1.14 min.

Step 5: 1-(1-(tert-butyldimethylsilyloxy)-2,3-dihydro-1H-pyrrolo[1,2-a]indol-7-yl)butan-1-one To a solution of 7-bromo-1-(tert-butyldimethylsilyloxy)-2,3-dihydro-1H-pyrrolo[1,2-a]indole (4.1 g, 11.2 mmol) in THF (60 mL), cooled to –78° C., was added n-BuLi (7.7 mL, 1.6M, 12.3 mmol) dropwise. The reaction mixture was allowed to stir at –78° C. for 5 minutes before N-methoxy-N-methylbutyramide (1.6 g, 12.3 mmol) was added. The resulting orange solution was allowed to slowly warm to room temperature then quenched with the addition of a saturated solution of NH$_4$Cl. The reaction mixture was poured into H$_2$O (100 mL) and extracted with Et$_2$O (2×100 mL). The combined organic phases were dried over MgSO$_4$, filtered, and concentrated in vacuo to afford the title compound as a white solid (4.0 g, 99%).
$^1$H NMR (500 MHz, CHCl$_3$-d) δ ppm –0.06 (s, 3H) 0.00 (s, 3H) 0.73 (s, 9H) 0.83 (t, J=7.41 Hz, 3H) 1.57-1.64 (m, 2H) 2.27-2.36 (m, 1H) 2.59-2.69 (m, 1H) 2.78-2.84 (m, 2H) 3.80-3.87 (m, 1H) 4.04-4.11 (m, 1H) 5.13-5.19 (m, 1H) 6.23 (t, J=0.71 Hz, 1H) 7.04-7.10 (m, 1H) 7.65 (dd, J=8.59, 1.66 Hz, 1H) 8.09 (d, J=1.10 Hz, 1H). LC-MS 358.6 [M+H]$^+$, RT 1.09 min.

Step 6: N-(1-(1-(tert-butyldimethylsilyloxy)-2,3-dihydro-1H-pyrrolo[1,2-a]indol-7-yl)butylidene)-1-(2,4-dimethoxyphenyl)methanamine To a solution of 1-(1-(tert-butyldimethylsilyloxy)-2,3-dihydro-1H-pyrrolo[1,2-a]indol-7-yl)butan-1-one (4.0 g, 11.2 mmol) in CH$_2$Cl$_2$ (50 mL), cooled to 0° C., was added dimethoxybenzyl amine (1.9 mL, 12.3 mmol) and Et$_3$N (4.7 mL, 34 mmol). To this mixture was added a solution of TiCl$_4$ (6.8 mL, 1M, 6.8 mmol) in CH$_2$Cl$_2$ dropwise via an addition funnel. Upon completion of addition, the reaction was stirred at room temperature for 6 h before it was quenched with a saturated solution of NaHCO$_3$. The aqueous phase was extracted with CH$_2$Cl$_2$ and the combined organic phases were dried over Na$_2$SO$_4$, filtered, and concentrated to give a crude product that was used immediately without further purification. LC-MS 507.8 [M+H]$^+$, RT 0.90 min.

Step 7: methyl 6-(1-(tert-butyldimethylsilyloxy)-2,3-dihydro-1H-pyrrolo[1,2-a]indol-7-yl)-1-(2,4-dimethoxybenzyl)-5-ethyl-2-oxo-1,2-dihydropyridine-3-carboxylate A solution of 4 N-(1-(1-(tert-butyldimethylsilyloxy)-2,3-dihydro-1H-pyrrolo[1,2-a]indol-7-yl)butylidene)-1-(2,4-dimethoxyphenyl)methanamine (5.7 g, 11.2 mmol) and dimethyl 2-(methoxymethylene)malonate (2.55 g. 14.4 mmol) in Ph$_2$O (10 mL) was heated at 220° C. for 30 min. The reaction mixture was then cooled to room temperature and loaded directly on silica gel eluting with hexanes/EtOAc (9:1) to afford the title compound as an orange foam (1.7 g, 25%).
$^1$H NMR (500 MHz, CHCl$_3$-d) δ ppm –0.04 (s, 3H) –0.01 (d, J=5.28 Hz, 3H) 0.71-0.78 (m, 12H) 1.85-1.94 (m, 2H) 2.26-2.37 (m, 1H) 2.60-2.70 (m, 1H) 2.96 (s, 1H) 3.02 (s, 1H) 3.55 (d, J=1.73 Hz, 3H) 3.74 (d, J=4.65 Hz, 3H) 3.77-3.88 (m, 1H) 4.01-4.11 (m, 1H) 4.70-4.80 (m, 1H) 4.81-4.95 (m, 1H) 5.11-5.22 (m, 1H) 5.95 (dd, J=15.64, 2.40 Hz, 1H) 6.03 (d, J=7.17 Hz, 1H) 6.14-6.19 (m, 1H) 6.51-6.56 (m, 1H) 6.57-6.64 (m, 1H) 6.81-6.94 (m, 1H) 6.97-7.02 (m, 1H) 8.02 (d, J=1.18 Hz, 1H).

Step 8: methyl 1-(2,4-dimethoxybenzyl)-5-ethyl-6-(1-hydroxy-2,3-dihydro-1H-pyrrolo[1,2-a]indol-7-yl)-2-oxo-1,2-dihydropyridine-3-carboxylate To a solution of methyl 6-(1-(tert-butyldimethylsilyloxy)-2,3-dihydro-1H-pyrrolo[1,2-a]indol-7-yl)-1-(2,4-dimethoxybenzyl)-5-ethyl-2-oxo-1,2-dihydropyridine-3-carboxylate (1.7 g, 2.8 mmol) in THF (40 mL) was added a solution of TBAF (2.9 mL, 1M, 2.9 mmol). The dark red solution was stirred for 1 h at room temperature and then concentrated. The crude residue was purified on silica gel eluting with EtOAc to afford the title compound as yellow oil (1.3 g, 93%).

$^1$H NMR (500 MHz, CHCl$_3$-d) δ ppm 0.92-0.96 (m, 3H) 1.25 (t, J=7.13 Hz, 1H) 2.30 (br. s., 1H) 2.58 (ddd, J=13.60, 7.25, 3.59 Hz, 1H) 2.82-2.93 (m, 1H) 3.16-3.21 (m, 3H) 3.73 (d, J=1.34 Hz, 3H) 3.88-3.95 (m, 3H) 4.02-4.09 (m, 1H) 4.19-4.29 (m, 1H) 4.89-5.09 (m, 2H) 5.36 (td, J=6.09, 2.72 Hz, 1H) 6.14 (t, J=2.56 Hz, 1H) 6.28-6.39 (m, 2H) 6.65-6.80 (m, 2H) 7.11 (d, J=4.73 Hz, 1H) 7.19 (dd, J=13.95, 8.35 Hz, 1H) 8.21 (d, J=0.79 Hz, 1H). LC-MS 503.6 [M+H]$^+$, RT 0.73 min.

Step 9: methyl 1-(2,4-dimethoxybenzyl)-5-ethyl-2-oxo-6-(1-oxo-2,3-dihydro-1H-pyrrolo[1,2-a]indol-7-yl)-1,2-dihydropyridine-3-carboxylate (922-148)

To a solution of methyl 1-(2,4-dimethoxybenzyl)-5-ethyl-6-(1-hydroxy-2,3-dihydro-1H-pyrrolo[1,2-a]indol-7-yl)-2-oxo-1,2-dihydropyridine-3-carboxylate (1.3 g, 2.6 mmol) in CH$_2$Cl$_2$ (20 mL) was added MnO$_2$ in two batches over 2 hrs (2.3 g, 26 mmol). The reaction mixture was then filtered through celite and concentrated to afford the title compound as an orange solid (1.1 g, 85%).

$^1$H NMR (500 MHz, CHCl$_3$-d) δ ppm 0.86 (t, J=7.49 Hz, 3H) 1.92-2.01 (m, 2H) 3.04 (s, 3H) 3.14-3.20 (m, 2H) 3.66 (s, 3H) 3.86 (s, 3H) 4.39 (t, J=6.27 Hz, 2H) 4.78-4.90 (m, 1H) 4.98-5.08 (m, 1H) 6.03 (d, J=2.21 Hz, 1H) 6.28 (d, J=5.52 Hz, 1H) 6.67-6.77 (m, 1H) 6.80-6.88 (m, 2H) 7.30 (d, J=8.51 Hz, 1H) 8.12 (s, 1H). LC-MS 499.4 [M–H]$^-$, RT 1.22 min.

Step 10-12: 5-ethyl-2-oxo-6-(1-(pyrrolidin-1-yl)-2,3-dihydro-1H-pyrrolo[1,2-a]indol-7-yl)-1,2-dihydropyridine-3-carboxylic acid To a solution of methyl 1-(2,4-dimethoxybenzyl)-5-ethyl-2-oxo-6-(1-oxo-2,3-dihydro-1H-pyrrolo[1,2-a]indol-7-yl)-1,2-dihydropyridine-3-carboxylate (0.11 g, 0.22 mmol) in DCE (2 mL) was added pyrrolidine (80 μL, 0.88 mmol) and AcOH (30 μL). After stirring at room temperature for 1 h, NaBH(OAc)$_3$ (0.1 g, 0.44 mmol) was added and the reaction mixture was stirred for an additional 2 h before TFA (1.5 mL) was added. After stirring for 30 min, the reaction mixture was concentrated and the crude residue was dissolved in THF (1 mL) and aqueous NaOH (2 mL, 4M) was added and the resulting mixture was heated to 60° C. for 15 h. The reaction mixture was then poured into H$_2$O, acidified with 4M HCl, and extracted with CH$_2$Cl$_2$ (2×30 mL). The combined organic phases were dried over Na$_2$SO$_4$, filtered, and concentrated in vacuo to afford a crude oil which was triturated with Et$_2$O to afford the title compound as an orange solid (35 mg, 41% over 3 steps).

$^1$H NMR (500 MHz, CHCl$_3$-d) δ ppm 1.19-1.23 (t, J=7.49 Hz, 3H) 2.15-2.29 (m, 4H) 2.57-2.71 (m, 4H) 3.27 (d, J=7.96 Hz, 1H) 3.31-3.37 (m, 1H) 3.69-3.76 (m, 1H) 3.94-4.02 (m, 1H) 4.29-4.37 (m, 1H) 4.42 (s, 1H) 5.11-5.16 (m, 1H) 6.74 (s, 1H) 7.35 (dd, J=8.47, 1.69 Hz, 1H) 7.50 (d, J=8.51 Hz, 1H) 7.84 (d, J=1.18 Hz, 1H) 8.52-8.56 (m, 1H). LC-MS 390.0 [M–H]$^-$, RT 0.57 min.

Using the procedures described above, additional compounds described herein may be prepared by substituting the appropriate starting materials, reagents and reaction conditions and include compounds selected from:

| Cpd | Name |
| --- | --- |
| 152 | 6-(1-(dimethylamino)-2,3-dihydro-1H-pyrrolo[1,2-a]indol-7-yl)-5-ethyl-2-oxo-1,2-dihydropyridine-3-carboxylic acid<br>$^1$H NMR (500 MHz, DMSO-d$_6$) δ ppm 1.02 (t, J = 7.49 Hz, 3 H) 2.44 (q, J = 7.41 Hz, 2 H) 2.72-2.88 (m, 6 H) 2.89-2.99 (m, 1 H) 3.02-3.13 (m, 1 H) 4.21-4.38 (m, 3 H) 5.11-5.20 (m, 1 H) 6.79 (s, 1 H) 7.31 (dd, J = 8.47, 1.54 Hz, 1 H) 7.62 (d, J = 8.43 Hz, 1 H) 7.80 (d, J = 0.95 Hz, 1 H) 8.40 (s, 1 H) 10.52-10.65 (m, 1 H) 13.21-13.35 (m, 1 H). LC-MS 364.2 [M – H]$^-$, RT 0.50 min. |
| 153 | 6-(1-(3-(dimethylamino)pyrrolidin-1-yl)-2,3-dihydro-1H-pyrrolo[1,2-a]indol-7-yl)-5-ethyl-2-oxo-1,2-dihydropyridine-3-carboxylic acid<br>$^1$H NMR (500 MHz, DMSO-d$_6$) δ ppm 1.03 (t, J = 7.49 Hz, 3 H) 1.60-1.71 (m, 1 H) 1.86-1.97 (m, 1 H) 2.24 (d, J = 1.81 Hz, 6 H) 2.60-2.85 (m, 4 H) 2.86-2.96 (m, 2 H) 4.06-4.15 (m, 2 H) 4.16-4.24 (m, 2 H) 4.24-4.30 (m, 1 H) 6.36-6.42 (m, 1 H) 7.15-7.21 (m, 1 H) 7.42-7.47 (m, 1 H) 7.60-7.64 (m, 1 H) 8.16-8.22 (m, 1 H). LC-MS 433.2 [M – H]$^-$, RT 0.50 min. |
| 154 | 5-ethyl-2-oxo-6-(1-(piperidin-1-yl)-2,3-dihydro-1H-pyrrolo[1,2-a]indol-7-yl)-1,2-dihydropyridine-3-carboxylic acid<br>$^1$H NMR (500 MHz, DMSO-d$_6$) δ ppm 1.02 (t, J = 7.49 Hz, 3 H) 1.32-1.40 (m, 1 H) 1.70 (br. s., 2 H) 1.79-1.92 (m, 1 H) 2.44 (m, J = 7.50 Hz, 2 H) 2.96-3.04 (m, 2 H) 3.05-3.16 (m, 2 H) 3.36-3.46 (m, 2 H) 3.52-3.61 (m, 2 H) 4.30 (s, 2 H) 5.10-5.16 (m, 1 H) 6.80 (s, 1 H) 7.31 (dd, J = 8.47, 1.54 Hz, 1 H) 7.62 (d, J = 8.43 Hz, 1 H) 7.80 (d, J = 0.87 Hz, 1 H) 8.40 (s, 1 H). LC-MS 406.2 [M + H]$^+$, RT 0.54 min. |
| 155 | 5-ethyl-6-(1-morpholino-2,3-dihydro-1H-pyrrolo[1,2-a]indol-7-yl)-2-oxo-1,2-dihydropyridine-3-carboxylic acid<br>$^1$H NMR (500 MHz, DMSO-d$_6$) δ ppm 1.02 (t, J = 7.49 Hz, 3 H) 2.44 (q, J = 7.46 Hz, 2 H) 2.96-3.14 (m, 6 H) 3.65-3.81 (m, 2 H) 4.23-4.35 (m, 5 H) 6.81 (br. s., 1 H) 7.30 (dd, J = 8.43, 1.26 Hz, 1 H) 7.62 (d, J = 8.43 Hz, 1 H) 7.80 (s, 1 H) 8.40 (s, 1 H) 13.23-13.35 (m, 1 H). LC-MS 408.2 [M + H]$^+$, RT 0.50 min. |

Example 156

5-ethyl-6-(1-methyl-2-(pyrrolidin-3-yl)-1H-indol-5-yl)-2-oxo-1,2-dihydropyridine-3-carboxylic acid hydrochloride

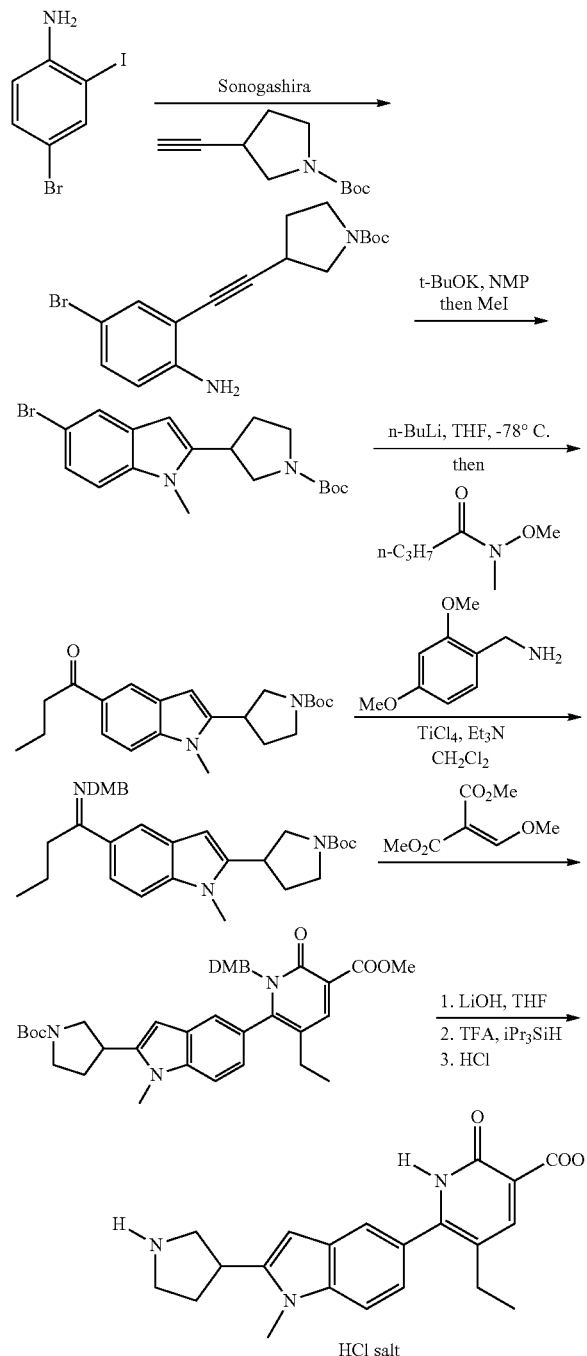

Step 1: tert-butyl 3-((2-amino-5-bromophenyl)ethynyl)pyrrolidine-1-carboxylate

4-Bromo-2-iodoaniline (3.88 g, 19.88 mmol), tert-butyl 3-ethynylpyrrolidine-1-carboxylate (4.90 g, 16.45 mmol), CuI (65 mg, 0.34 mmol, 2 mol %) and Pd(PPh$_3$)$_2$Cl$_2$ (115 mg, 0.16 mmol, 1 mol %) were mixed together under argon in a heat-gun dried flask. Acetonitrile (17 mL) and NEt$_3$ (4.60 mL, 33.00 mmol) were added to the mixture and reaction was heated at 70° C. for 1.5 h. TLC showed complete consumption of the alkyne. Acetonitrile was concentrated under reduced pressure and EtOAc (100 mL) was added to the residue. Triethylamine salt was filtered off and washed with EtOAc. Mother liquor was concentrated and residue was purified by column chromatography using EtOAc/hexanes (gradient 0-40%) to afford tert-butyl 3-((2-amino-5-bromophenyl)ethynyl)pyrrolidine-1-carboxylate (5.69 g) in 95% yield.

$^1$H NMR (500 MHz, CHCl$_3$-d) δ ppm 1.48 (s, 9H) 1.95-2.09 (m, 1H) 2.18-2.29 (m, 1H) 3.16-3.28 (m, 1H) 3.30-3.46 (m, 2H) 3.48-3.64 (m, 1H) 3.66-3.76 (m, 1H) 4.15 (br. s., 2H) 6.57 (d, J=8.8 Hz, 1H) 7.18 (dd, J=8.8, 2.2 Hz, 1H) 7.35 (d, J=2.2 Hz, 1H).

Step 2: tert-butyl 3-(5-bromo-1-methyl-1H-indol-2-yl)pyrrolidine-1-carboxylate

To degassed with argon solution of tert-butyl 3-((2-amino-5-bromophenyl)ethynyl)pyrrolidine-1-carboxylate (5.69 g, 15.58 mmol) in NMP (30 mL) was added t-BuOK (3.9 g, 34.75 mmol). Mixture was heated at 780° C. for 45 min before it was cooled to 0° C. in an ice-bath. MeI (3.0 mL, 48.08 mmol) was added dropwise and reaction was allowed to warm to room temperature and stirred 30 min. Then reaction was diluted with H$_2$O (100 mL) and acidified with 1M aqueous HCl to pH~2. Product was extracted with EtOAc (3×150 mL). Combined organics were washed with NaCl (aqueous saturated) and dried over Na$_2$SO$_4$. Upon solvent removal residue was purified by column chromatography using EtOAc/hexanes (gradient 0-40%) to afford tert-butyl 3-(5-bromo-1-methyl-1H-indol-2-yl)pyrrolidine-1-carboxylate (5.17 g) in 87% yield.

$^1$H NMR (500 MHz, CHCl$_3$-d) δ ppm 1.50 (s, 9H) 2.00-2.16 (m, 1H) 2.28-2.40 (m, 1H) 3.35-3.68 (m, 4H) 3.71 (br. s, 3H) 3.79-3.96 (m, 1H) 6.27 (s, 1H) 7.15 (d, J=8.5 Hz, 1H) 7.27 (dd, J=8.5, 1.9 Hz, 1H) 7.67 (d, J=1.9 Hz, 1H). LC-MS 379.2/381.2 [M+H]$^+$, RT 1.60 min.

Step 3: tert-butyl 3-(5-butyryl-1-methyl-1H-indol-2-yl)pyrrolidine-1-carboxylate To solution of tert-butyl 3-(5-bromo-1-methyl-1H-indol-2-yl)pyrrolidine-1-carboxylate (1.207 g, 3.18 mmol) in THF (13 mL) at −78° C. was added solution of n-BuLi (2.5M hexanes, 1.50 mL, 3.75 mmol) dropwise over 10 min. The reaction was stirred at −78° C. for 10 min, then a solution of N-methoxy-N-methylbutyramide (0.50 g, 3.81 mmol) in THF (2.0 mL) was added dropwise. The reaction was slowly allowed to warm to −50° C. before it was quenched with NH$_4$Cl (aqueous saturated, 10 mL). Once ambient temperature was reached in the reaction mixture, the product was extracted with EtOAc (3×20 mL). Combined organics were washed with NaCl (aqueous saturated) and dried over Na$_2$SO$_4$. Upon solvent removal residue was purified by column chromatography using EtOAc/hexanes (gradient 0-60%) to afford tert-butyl 3-(5-butyryl-1-methyl-1H-indol-2-yl)pyrrolidine-1-carboxylate (0.823 g) in 70% yield.

$^1$H NMR (500 MHz, CHCl$_3$-d) δ ppm 1.03 (t, J=7.4 Hz, 3H) 1.50 (s, 9H) 1.81 (sxt, J=7.4 Hz, 2H) 2.11 (dq, J=12.5, 8.3 Hz, 1H) 2.17-2.52 (m, 1H) 3.02 (t, J=7.4 Hz, 2H) 3.41-3.56 (m, 3H) 3.59-3.65 (m, 1H) 3.77 (s, 3H) 3.90 (dd, J=10.2, 7.1 Hz, 1H) 6.44 (s, 1H) 7.31 (d, J=8.8 Hz, 1H) 7.89 (dd, J=8.8, 1.7 Hz, 1H) 8.23 (d, J=1.7 Hz, 1H). LC-MS 371.3 [M+H]$^+$, RT 1.50 min.

Step 4: tert-butyl 3-(5-(1-(2,4-dimethoxybenzylimino)butyl)-1-methyl-1H-indol-2-yl)pyrrolidine-1-carboxylate To solution of tert-butyl 3-(5-butyryl-1-methyl-1H-indol-2-yl)pyrrolidine-1-carboxylate (0.823 g, 2.22 mmol) in DCM (5 mL) was added 2,4-dimethoxybenzylamine (0.38 mL, 2.53 mmol) and NEt$_3$ (0.90 mL, 6.45 mmol). Mixture was cooled to 0° C. before TiCl$_4$ solution (1M DCM, 1.45 mL, 1.45 mmol) was added dropwise via syringe pump over 30 min. Reaction was allowed to warm to room temperature and stirred overnight. Mixture was diluted with DCM (10 mL) and then quenched with NaHCO$_3$ (aqueous saturated, 10 mL). Upon vigorous shaking organic phase was separated using a PTFE phase separator, dried over Na$_2$SO$_4$. Removal of the solvent afforded product (1.15 g, quant) as yellow oil, which was taken directly into next steps without purification.

Step 5: methyl 6-(2-(1-(tert-butoxycarbonyl)pyrrolidin-3-yl)-1-methyl-1H-indol-5-yl)-1-(2,4-dimethoxybenzyl)-5-ethyl-2-oxo-1,2-dihydropyridine-3-carboxylate Crude tert-butyl 3-(5-(1-(2,4-dimethoxybenzylimino)butyl)-1-methyl-1H-indol-2-yl)pyrrolidine-1-carboxylate (0.620 g, 1.19 mmol) and dimethyl 2-(methoxymethylene)malonate (0.350 g, 2.01 mmol) were mixed together in Ph$_2$O (2.5 mL). Stirred mixture was heated at 180-190° C. for 1.5 h. Reaction mixture was then cooled to room temperature and loaded directly on the column. It was eluted first with hexanes to separate Ph$_2$O and then EtOAc/hexanes gradient (0-80%) to yield product as yellow foam (0.247 g, 33%). LC-MS 630.5 [M+H]$^+$, RT 1.33, 1.34 min. (2 atropisomers)

Step 6-8: 5-ethyl-6-(1-methyl-2-(pyrrolidin-3-yl)-1H-indol-5-yl)-2-oxo-1,2-dihydropyridine-3-carboxylic acid hydrochloride To solution of methyl 6-(2-(1-(tert-butoxycarbonyl)pyrrolidin-3-yl)-1-methyl-1H-indol-5-yl)-1-(2,4-dimethoxybenzyl)-5-ethyl-2-oxo-1,2-dihydropyridine-3-carboxylate (0.245 g, 0.40 mmol) in THF (1.5 mL) was added solution of LiOH (1M aqueous, 0.80 ml, 0.80 mmol). Reaction mixture was heated at 50° C. 30 min. Reaction was then cooled to room temperature and acidified with 1M HCl to pH~2. Product was extracted with DCM (3×10 mL). Combined organic were washed with brine and dried over Na$_2$SO$_4$. Upon removal of the solvent residue was purified by column chromatography using MeOH/DCM (gradient 0-2.5%) to 6-(2-(1-(tert-butoxycarbonyl)pyrrolidin-3-yl)-1-methyl-1H-indol-5-yl)-1-(2,4-dimethoxybenzyl)-5-ethyl-2-oxo-1,2-dihydropyridine-3-carboxylic acid (0.1514 g) in 63% yield. LC-MS 616.5 [M+H]$^+$, RT 1.54 min.

To 6-(2-(1-(tert-butoxycarbonyl)pyrrolidin-3-yl)-1-methyl-1H-indol-5-yl)-1-(2,4-dimethoxybenzyl)-5-ethyl-2-oxo-1,2-dihydropyridine-3-carboxylic acid (0.151 g, 0.25 mmol) obtained above was added i-Pr$_3$SiH (0.30 mL) followed by TFA (0.60 mL). Mixture was heated at 50° C. for 15 min until complete consumption of starting material was observed. TFA was concentrated under reduced pressure. Addition of HCl solution (2M Et$_2$O, 1.0 mL) to the oily residue resulted in precipitate formation. Mixture was diluted with Et$_2$O; solid was filtered and washed with Et$_2$O. Product was obtained as pale yellow solid (77.3 mg, 78%) as an HCl salt $^1$H NMR (500 MHz, MeOH-d$_4$) δ ppm 1.10 (t, J=7.6 Hz, 3H) 2.15-2.29 (m, 1H) 2.53 (q, J=7.6 Hz, 2H) 2.57-2.67 (m, 1H) 3.40-3.53 (m, 2H) 3.54-3.63 (m, 1H) 3.82-3.87 (m, 1H) 3.86 (s, 3H) 3.93 (t, J=7.1 Hz, 1H) 6.59 (s, 1H) 7.29 (dd, J=8.5, 1.6 Hz, 1H) 7.59 (d, J=8.5 Hz, 1H) 7.68 (d, J=1.6 Hz, 1H) 8.48 (s, 1H). LC-MS 364.2 [M−H]$^-$, 366.3 [M+H]$^+$, RT 0.79 min.

Using the procedures described above, additional compounds described herein may be prepared by substituting the appropriate starting materials, reagents and reaction conditions and include compounds selected from:

| Cpd | Name |
|---|---|
| 157 | 5-ethyl-6-(1-methyl-2-(1-(pyrrolidin-1-yl)ethyl)-1H-indol-5-yl)-2-oxo-1,2-dihydropyridine-3-carboxylic acid<br>LC-MS 392.3 [M − H]$^-$, 394.4 [M + H]$^+$, RT 0.94 min. (Method A) |
| 158 | 5-ethyl-6-(4-fluoro-1-methyl-2-(pyrrolidin-1-ylmethyl)-1H-indol-5-yl)-2-oxo-1,2-dihydropyridine-3-carboxylic acid<br>LC-MS 396.2 [M − H]$^-$, 398.4 [M + H]$^+$, RT 0.68 min. (Method A) |

Example 159

5-ethyl-6-(1-methyl-2-(2-(pyrrolidin-1-yl)ethyl)-1H-indol-5-yl)-2-oxo-1,2-dihydropyridine-3-carboxylic acid (Cpd 159)

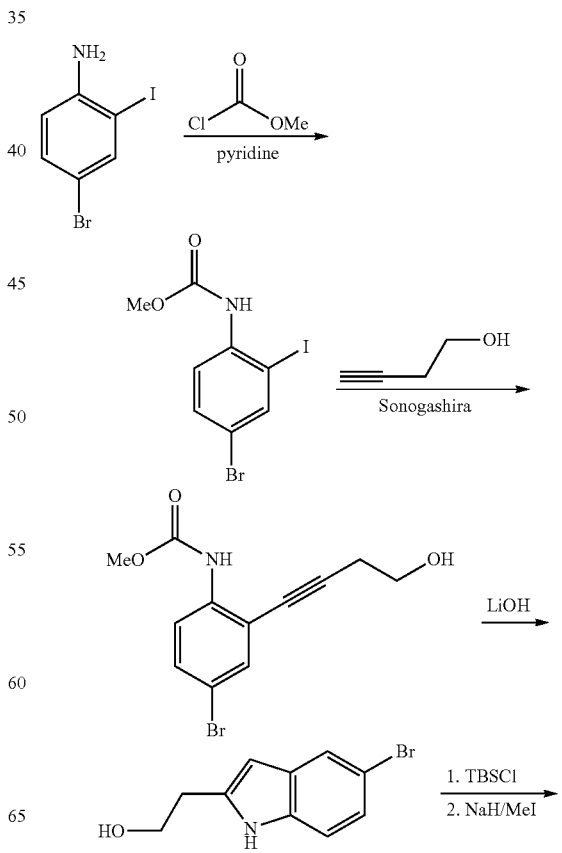

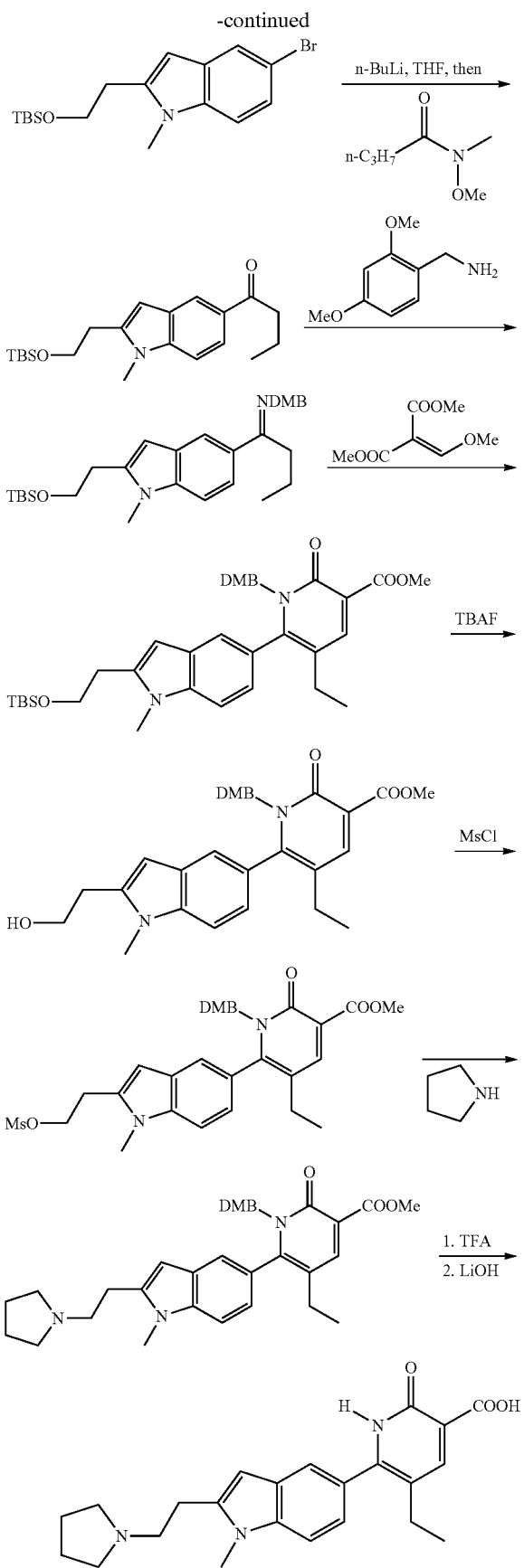

Step 1: Methyl 4-bromo-2-iodophenylcarbamate

To solution of 4-bromo-2-iodoaniline (18.50 g, 62.08 mmol) in pyridine (120 mL) at −10° C. was added methyl chloroformate (7.50 mL, 97.46 mmol) over 30 min via syringe pump. Reaction was allowed to warm to room temperature and was diluted with $H_2O$ (450 mL). Solid which was formed was collected by filtration, washed with $H_2O$ and dried in dessicator. Methyl 4-bromo-2-iodophenylcarbamate (21.59 g, 98%) was obtained as colorless solid.

$^1$H NMR (500 MHz, CHCl$_3$-d) δ ppm 3.81 (s, 3H) 6.95 (br. s., 1H) 7.46 (dd, J=8.5, 2.2 Hz, 1H) 7.89 (d, J=2.2 Hz, 1H) 7.96 (d, J=8.5 Hz, 1H). LC-MS 356.0/358.0 [M+H]$^+$, RT 1.40 min.

Step 2: Methyl 4-bromo-2-(4-hydroxybut-1-ynyl)phenylcarbamate

CuI (230 mg, 1.21 mmol, 2 mol %) and Pd(PPh$_3$)$_2$Cl$_2$ (426 mg, 0.61 mmol, 1 mol %) were mixed together under argon in a heat-gun dried flask. NEt$_3$ (60 mL) was added and mixture was heated to 120° C. for 15 min. After cooling to room temperature methyl 4-bromo-2-iodophenylcarbamate (21.54 g, 60.50 mmol) was added. Flask was resealed under argon and heated at 120° C. for 15 min. LC/MS indicated complete conversion to the product. Upon cooling to room temperature EtOAc (~400 mL) was added to the mixture. Triethylamine salt was filtered off and washed with EtOAc. Mother liquor was concentrated to afford methyl 4-bromo-2-(4-hydroxybut-1-ynyl)phenylcarbamate as oil which was pure enough to be taken to the next step without purification. LC-MS 298.0/300.0 [M+H]$^+$, RT 1.21 min.

Step 3: 2-(5-Bromo-1H-indol-2-yl)ethanol

To solution of 4-bromo-2-(4-hydroxybut-1-ynyl)phenylcarbamate (ca. 60.50 mmol) obtained above in DMSO (160 mL) were added $H_2O$ (16 mL) and LiOH monohydrate (7.80 g, 185.89 mmol). Mixture was heated to 70° C. and monitored by LC/MS. Upon complete consumption of starting material (~40 min) mixture was cooled to room temperature and diluted with $H_2O$ (~400 mL). Reaction mixture was made acidic (pH~2) with 1M HCl. Product was extracted with DCM (3×200 mL). Combined organics were washed with NaCl (aqueous saturated, 100 mL) and dried over Na$_2$SO$_4$. After concentration of the solvent residue was purified by column chromatography (EtOAc/hexanes, 0-80% gradient) to yield 2-(5-bromo-1H-indol-2-yl)ethanol (11.37 g) in 78% yield over 2 steps.

$^1$H NMR (500 MHz, CHCl$_3$-d) δ ppm 1.79 (t, J=5.4 Hz, 1H) 3.01 (t, J=5.4 Hz, 2H) 3.99 (q, J=5.4 Hz, 2H) 6.23 (s, 1H) 7.19 (d, J=8.5 Hz, 1H) 7.23 (dd, J=8.5, 1.6 Hz, 1H) 7.67 (s, 1H) 8.61 (br. s., 1H). LC-MS 240.1/242.1 [M+H]$^+$, RT 1.14 min.

Step 4-5: 5-Bromo-2-(2-(tert-butyldimethylsilyloxy)ethyl)-1-methyl-1H-indole

To solution of 2-(5-bromo-1H-indol-2-yl)ethanol (11.37 g, 47.36 mmol) in DCM (150 mL) was added imidazole (4.0 g, 58.75 mmol). Reaction mixture was cooled to 0° C. before solution of TBSCl (8.60 g, 57.06 mmol) was added dropwise. The reaction mixture was allowed to warm to room temperature and stirred for 30 min. The mixture was then diluted with DCM (150 mL), washed with $H_2O$ (100 mL) and NaCl (aqueous saturated, 100 mL) and the organic phase was dried over Na$_2$SO$_4$. The solvent was concentrated to afford 5-bromo-2-

(2-(tert-butyldimethylsilyloxy)ethyl)-1H-indole which was used directly in the next step. LC-MS 354.2/356.2 [M+H]⁺, RT 1.85 min.

To a solution of 5-bromo-2-(2-(tert-butyldimethylsilyloxy)ethyl)-1H-indole (ca. 47.36 mmol) obtained above in DMF (200 mL) at 0° C. was added NaH (60%, 2.90 g, 72.50 mmol) in portions. The reaction mixture was stirred at 0° C. for 15 min before MeI (4.50 mL, 72.10 mmol) was added. It was then allowed to warm to room temperature and was stirred 30 min. Reaction mixture was diluted with $H_2O$ (~400 mL) and product was extracted with $Et_2O$ (3×200 mL). Combined organics were washed with NaCl (aqueous saturated, 100 mL) and dried over $MgSO_4$. After concentration of the solvent residue was purified by column chromatography (EtOAc/hexanes, 0-20% gradient) to yield 5-bromo-2-(2-(tert-butyldimethylsilyloxy)ethyl)-1-methyl-1H-indole (14.49 g) in 83% yield over 2 steps.

$^1$H NMR (500 MHz, $CHCl_3$-d) δ ppm 0.03 (s, 6H) 0.89 (s, 9H) 2.98 (t, J=7.1 Hz, 2H) 3.69 (s, 3H) 3.92 (t, J=7.1 Hz, 2H) 6.23 (s, 1H) 7.14 (d, J=8.8 Hz, 1H) 7.23 (dd, J=8.8, 1.9 Hz, 1H) 7.65 (d, J=1.9 Hz, 1H). LC-MS 368.2/370.2 [M+H]⁺, RT 1.93 min.

Step 6: 1-(2-(2-(tert-Butyldimethylsilyloxy)ethyl)-1-methyl-1H-indol-5-yl)butan-1-one To solution of 5-bromo-2-(2-(tert-butyldimethylsilyloxy)ethyl)-1-methyl-1H-indole (9.963 g, 27.04 mmol) in THF (100 mL) at −78° C. was added solution of n-BuLi (2.5M hexanes, 13.0 mL, 32.50 mmol) dropwise over 10 min. Reaction was stirred at −78° C. for 10 min before solution of N-methoxy-N-methylbutyramide (4.30 g, 32.78 mmol) in THF (10 mL) was added dropwise. Reaction was stirred at −78° C. for 15 min and then quenched with $NH_4Cl$ (aqueous saturated, 30 mL). Once ambient temperature was reached in the reaction mixture product was extracted with EtOAc (2×100 mL). Combined organics were washed with NaCl (aqueous saturated) and dried over $Na_2SO_4$. Upon solvent removal residue was purified by column chromatography using EtOAc/hexanes (gradient 0-30%) to afford 1-(2-(2-(tert-butyldimethylsilyloxy)ethyl)-1-methyl-1H-indol-5-yl)butan-1-one (6.620 g, 68%) as white solid.

$^1$H NMR (500 MHz, $CHCl_3$-d) δ ppm 0.03 (s, 6H) 0.89 (s, 9H) 1.03 (t, J=7.4 Hz, 3H) 1.81 (sxt, J=7.4 Hz, 2H) 2.98-3.05 (m, 4H) 3.74 (s, 3H) 3.95 (t, J=7.1 Hz, 2H) 6.40 (s, 1H) 7.29 (d, J=8.8 Hz, 1H) 7.86 (dd, J=8.8, 1.7 Hz, 1H) 8.22 (d, J=1.7 Hz, 1H). LC-MS 360.3 [M+H]⁺, RT 1.73 min.

Step 7: N-(1-(2-(2-(tert-butyldimethylsilyloxy)ethyl)-1-methyl-1H-indol-5-yl)butylidene)-1-(2,4-dimethoxyphenyl)methanamine To solution of 1-(2-(2-(tert-butyldimethylsilyloxy)ethyl)-1-methyl-1H-indol-5-yl)butan-1-one (6.62 g, 18.41 mmol) in DCM (35 mL) was added 2,4-dimethoxybenzylamine (3.20 mL, 21.30 mmol) and $NEt_3$ (7.0 mL, 50.22 mmol). Mixture was cooled to 0° C. before $TiCl_4$ solution (1M DCM, 12.0 mL, 12.0 mmol) was added dropwise via syringe pump over 30 min. Reaction was allowed to warm to room temperature and stirred overnight. Mixture was diluted with DCM (100 mL) and then quenched with $NaHCO_3$ (aqueous saturated, ~30 mL). Upon vigorous shaking organic phase was separated using PTFE phase separator and dried over $Na_2SO_4$. Removal of the solvent afforded N-(1-(2-(2-(tert-butyldimethylsilyloxy)ethyl)-1-methyl-1H-indol-5-yl)butylidene)-1-(2,4-dimethoxyphenyl)methanamine as yellow oil, which was taken directly into next step without purification.

Step 8: Methyl 6-(2-(2-(tert-butyldimethylsilyloxy)ethyl)-1-methyl-1H-indol-5-yl)-1-(2,4-dimethoxybenzyl)-5-ethyl-2-oxo-1,2-dihydropyridine-3-carboxylate Crude N-(1-(2-(2-(tert-butyldimethylsilyloxy)ethyl)-1-methyl-1H-indol-5-yl)butylidene)-1-(2,4-dimethoxyphenyl)methanamine (ca. 18.41 mmol) obtained above and dimethyl 2-(methoxymethylene)malonate (5.50 g, 31.58 mmol) were mixed together in $Ph_2O$ (20 mL). Stirred mixture was heated at 190° C. for 1.5 h. Reaction mixture was then cooled to room temperature and loaded directly on the column. It was eluted first with hexanes to separate $Ph_2O$ and then EtOAc/hexanes gradient (0-100%) to yield methyl 6-(2-(2-(tert-butyldimethylsilyloxy)ethyl)-1-methyl-1H-indol-5-yl)-1-(2,4-dimethoxybenzyl)-5-ethyl-2-oxo-1,2-dihydropyridine-3-carboxylate (6.10 g, 54%) as brownish foam.

$^1$H NMR (500 MHz, $CHCl_3$-d) δ ppm 0.05 (s, 3H) 0.05 (s, 3H) 0.89 (s, 9H) 0.96 (t, J=7.6 Hz, 3H) 2.09 (qd, J=7.6, 3.0 Hz, 1H) 3.00 (t, J=7.1 Hz, 2H) 3.22 (s, 3H) 3.72 (s, 3H) 3.76 (s, 3H) 3.93 (t, J=7.1 Hz, 2H) 3.95 (s, 3H) 4.98 (br. d, J=15.8 Hz, 1H) 5.07 (br. d, J=15.8 Hz, 1H) 6.16 (d, J=3.0 Hz, 1H) 6.23 (s, 1H) 6.37 (dd, J=8.5, 2.2 Hz, 1H) 6.74 (dd, J=8.5, 1.4 Hz, 1H) 6.80 (d, J=8.5 Hz, 1H) 7.06 (s, 1H) 7.20 (d, J=8.5 Hz, 1H) 8.22 (s, 1H). LC-MS 619.5 [M+H]⁺, RT 1.87 min.

Step 9: Methyl 1-(2,4-dimethoxybenzyl)-5-ethyl-6-(2-(2-hydroxyethyl)-1-methyl-1H-indol-5-yl)-2-oxo-1,2-dihydropyridine-3-carboxylate To solution of methyl 6-(2-(2-(tert-butyldimethylsilyloxy)ethyl)-1-methyl-1H-indol-5-yl)-1-(2,4-dimethoxybenzyl)-5-ethyl-2-oxo-1,2-dihydropyridine-3-carboxylate (6.10 g, 9.84 mmol) in THF (60 mL) was added TBAF solution (1M THF, 15.0 mL, 15.0 mmol). Reaction mixture was stirred at room temperature for 30 min until starting material was completely consumed. THF was then concentrated and residue was purified by column chromatography (EtOAc/DCM, 0-100% gradient). Methyl 1-(2,4-dimethoxybenzyl)-5-ethyl-6-(2-(2-hydroxyethyl)-1-methyl-1H-indol-5-yl)-2-oxo-1,2-dihydropyridine-3-carboxylate was obtained as yellow solid (4.56 g, 92%).

$^1$H NMR (500 MHz, $CHCl_3$-d) δ ppm 0.96 (t, J=7.6 Hz, 3H) 1.80 (t, J=6.1 Hz, 1H) 2.10 (qd, J=7.6, 2.5 Hz, 2H) 3.06 (t, J=6.1 Hz, 2H) 3.24 (s, 3H) 3.72 (s, 3H) 3.75 (s, 3H) 3.94 (s, 3H) 3.98 (q, J=6.1 Hz, 2H) 4.97 (br. d, J=15.1 Hz, 1H) 5.04 (br. d, J=15.1 Hz, 1H) 6.16 (d, J=2.5 Hz, 1H) 6.28 (s, 1H) 6.37 (dd, J=8.5, 2.2 Hz, 1H) 6.62-6.89 (m, 2H) 7.08 (s, 1H) 7.22 (d, J=8.5 Hz, 1H) 8.23 (s, 1H). LC-MS 505.5 [M+H]⁺, RT 1.24 min.

Step 10: Methyl 1-(2,4-dimethoxybenzyl)-5-ethyl-6-(1-methyl-2-(2-(methylsulfonyloxy)ethyl)-1H-indol-5-yl)-2-oxo-1,2-dihydropyridine-3-carboxylate To solution of methyl 1-(2,4-dimethoxybenzyl)-5-ethyl-6-(2-(2-hydroxyethyl)-1-methyl-1H-indol-5-yl)-2-oxo-1,2-dihydropyridine-3-carboxylate (1.142 g, 2.26 mmol) in DCM (10 mL) was added $NEt_3$ (0.45 mL, 3.23 mmol) and mixture was cooled to 0° C. Methanesulfonyl chloride (0.22 mL, 2.84 mmol) was added dropwise and reaction mixture was stirred at 0° C. 15 min. LC/MS indicated complete consumption of the starting material. Reaction was diluted with DCM (20 mL) and washed with $H_2O$ (10 mL). Organic phase was dried over Na₂SO₄ and solvent was removed under reduced pressure. Methyl 1-(2,4-dimethoxybenzyl)-5-ethyl-6-(1-methyl-2-(2-(methylsulfonyloxy)ethyl)-1H-indol-5-yl)-2-oxo-1,2-dihydropyridine-3-carboxylate (1.30 g) was obtained in nearly quantitative yield as yellow solid and was pure enough to be used in the next step without purification.

¹H NMR (500 MHz, CHCl₃-d) δ ppm 0.96 (t, J=7.6 Hz, 3H) 2.09 (qd, J=7.6, 1.9 Hz, 2H) 3.02 (s, 3H) 3.20 (s, 3H) 3.27 (t, J=6.8 Hz, 2H) 3.74 (s, 3H) 3.76 (s, 3H) 3.95 (s, 3H) 4.54 (t, J=6.8 Hz, 2H) 4.95 (br. d, J=15.1 Hz, 1H) 5.07 (br. d, J=15.1 Hz, 1H) 6.16 (d, J=1.9 Hz, 1H) 6.30 (s, 1H) 6.38 (dd, J=8.4, 2.4 Hz, 1H) 6.76-6.85 (m, 2H) 7.07 (s, 1H) 7.24 (d, J=8.4 Hz, 1H) 8.22 (s, 1H). LC-MS 583.5 [M+H]⁺, RT 1.32 min.

Step 11-13: 5-Ethyl-6-(1-methyl-2-(2-(pyrrolidin-1-yl)ethyl)-1H-indol-5-yl)-2-oxo-1,2-dihydropyridine-3-carboxylic acid To solution of methyl 1-(2,4-dimethoxybenzyl)-5-ethyl-6-(1-methyl-2-(2-(methylsulfonyloxy)ethyl)-1H-indol-5-yl)-2-oxo-1,2-dihydropyridine-3-carboxylate (0.233 g, 0.40 mmol) in CH₃CN (2 mL) was added pyrrolidine (0.15 mL, 1.83 mmol). Reaction mixture was heated at 80° C. for 1.5 h until complete consumption of starting material was observed. Then NaHCO₃ (aqueous saturated, 5 mL) was added to the reaction and product was extracted with DCM (3×10 mL). Combined organics were washed with NaCl (aqueous saturated, 5 mL) and dried over Na₂SO₄. Upon solvent removal residue was purified by column chromatography using MeOH/DCM (gradient 0-10%) to afford methyl 1-(2,4-dimethoxybenzyl)-5-ethyl-6-(1-methyl-2-(2-(pyrrolidin-1-yl)ethyl)-1H-indol-5-yl)-2-oxo-1,2-dihydropyridine-3-carboxylate (0.140 g) in 62% yield.

¹H NMR (500 MHz, CHCl₃-d) δ ppm 0.96 (t, J=7.6 Hz, 3H) 1.77-1.92 (m, 4H) 2.09 (qd, J=7.4, 2.4 Hz, 2H) 2.59-2.70 (m, 4H) 2.81-2.88 (m, 2H) 2.97-3.04 (m, 2H) 3.22 (s, 3H) 3.71 (s, 3H) 3.76 (s, 3H) 3.94 (s, 3H) 4.97 (br. d, J=15.4 Hz, 1H) 5.06 (br. d, J=15.4 Hz, 1H) 6.17 (d, J=2.4 Hz, 1H) 6.22 (s, 1H) 6.37 (dd, J=8.4, 2.4 Hz, 1H) 6.75 (dd, J=8.4, 1.4 Hz, 1H) 6.80 (d, J=8.4 Hz, 1H) 7.05 (s, 1H) 7.20 (d, J=8.4 Hz, 1H) 8.22 (s, 1H). LC-MS 558.5 [M+H]⁺, RT 1.04 min.

1-(2,4-dimethoxybenzyl)-5-ethyl-6-(1-methyl-2-(2-(pyrrolidin-1-yl)ethyl)-1H-indol-5-yl)-2-oxo-1,2-dihydropyridine-3-carboxylate (0.135 g, 0.24 mmol) obtained above was mixed together with i-Pr₃SiH (0.50 mL) and TFA (1.0 mL). Reaction mixture was heated at 50° C. 15 min. TFA was removed under reduced pressure and residue was treated with NaHCO₃ (aqueous saturated, 5 mL). Product was extracted with DCM (3×5 mL). Organic phase was dried over Na₂SO₄ and solvent was concentrated. Obtained material was dissolved in THF (2.0 mL) and solution of LiOH (1M aqueous saturated, 2.0 mL, 2.0 mmol) was added. Reaction was heated at 50° C. for 2 h until ester mass was not detected by LC/MS. Reaction was acidified with 1M HCl to pH~2. Then excess of NaHCO₃ (aqueous saturated, ~3 mL) was added. Product was extensively extracted with DCM (4×10 mL), organic phase was dried over Na₂SO₄ and solvent was concentrated. Residue was triturated with Et₂O then pale yellow powder was collected by filtration and washed with Et₂O. 5-Ethyl-6-(1-methyl-2-(2-(pyrrolidin-1-yl)ethyl)-1H-indol-5-yl)-2-oxo-1,2-dihydropyridine-3-carboxylic acid (57.0 mg) was obtained in 57% yield over 2 steps.

¹H NMR (500 MHz, MeOH-d₄) δ ppm 1.10 (t, J=7.6 Hz, 3H) 1.97-2.15 (m, 2H) 2.16-2.29 (m, 2H) 2.54 (q, J=7.6 Hz, 2H) 3.19-3.26 (m, 2H) 3.31-3.36 (m, 2H) 3.66 (t, J=7.7 Hz, 2H) 3.73-3.81 (m, 2H) 3.85 (s, 3H) 6.55 (s, 1H) 7.28 (dd, J=8.5, 1.3 Hz, 1H) 7.59 (d, J=8.5 Hz, 1H) 7.67 (s, 1H) 8.48 (s, 1H). LC-MS 392.4 [M−H]⁻, 394.4 [M+H]⁺, RT 0.84 min.

Using the procedures described above, additional compounds described herein may be prepared by substituting the appropriate starting materials, reagents and reaction conditions and include compounds selected from:

| Cpd | Name |
|---|---|
| 160 | 5-ethyl-6-(1-methyl-2-(2-(piperidin-1-yl)ethyl)-1H-indol-5-yl)-2-oxo-1,2-dihydropyridine-3-carboxylic acid<br>¹H NMR (500 MHz, DMSO-d₆) δ ppm 1.02 (t, J = 7.6 Hz, 3 H) 1.36-1.45 (m, 2 H) 1.48-1.58 (m, 4 H) 2.45-2.55 (m, 6 H) 2.65 (m, J = 8.2 Hz, 2 H) 2.94 (t, J = 8.2 Hz, 2 H) 3.72 (s, 3 H) 6.29 (s, 1 H) 7.15 (dd, J = 8.4, 1.4 Hz, 2 H) 7.43 (d, J = 8.4 Hz, 1 H) 7.50 (d, J = 1.4 Hz, 1 H) 7.98 (s, 1 H). LC-MS 406.4 [M − H]⁻, 408.4 [M + H]⁺, RT 0.88 min. |
| 161 | 6-(2-(2-(dimethylamino)ethyl)-1-methyl-1H-indol-5-yl)-5-ethyl-2-oxo-1,2-dihydropyridine-3-carboxylic acid<br>¹H NMR (500 MHz, DMSO-d₆) δ ppm 1.02 (t, J = 7.4 Hz, 3 H) 2.40 (s, 6 H) 2.46 (q, J = 7.4 Hz, 2 H) 2.80 (t, J = 8.2 Hz, 2 H) 2.98 (t, J = 8.2 Hz, 2 H) 3.74 (s, 3 H) 6.36 (s, 1 H) 7.18 (dd, J = 8.5, 1.6 Hz, 1 H) 7.52 (d, J = 8.5 Hz, 1 H) 7.57 (d, J = 1.6 Hz, 1 H) 8.24 (s, 1 H) 15.66 (br. s., 1 H). LC-MS 366.3 [M − H]⁻, 368.4 [M + H]⁺, RT 0.81 min. |
| 162 | 5-ethyl-6-(1-methyl-2-(2-morpholinoethyl)-1H-indol-5-yl)-2-oxo-1,2-dihydropyridine-3-carboxylic acid<br>¹H NMR (500 MHz, DMSO-d₆) δ ppm 1.01 (t, J = 7.6 Hz, 3 H) 2.45 (q, J = 7.6 Hz, 2 H) 2.67 (t, J = 7.6 Hz, 2 H) 2.97 (t, J = 7.6 Hz, 2 H) 3.27-3.46 (m, 4 H) 3.53-3.66 (m, 4 H) 3.74 (s, 3 H) 6.37 (s, 1 H) 7.17 (dd, J = 8.5, 1.3 Hz, 1 H) 7.53 (d, J = 8.5 Hz, 1 H) 7.58 (s, 1 H) 8.31 (s, 1 H) 13.19 (br. s., 1 H) 15.30 (br. s., 1 H). LC-MS 408.3 [M − H]⁻, 410.4 [M + H]⁺, RT 0.83 min. |

Example 163

6-(2-(2-aminoethyl)-1-methyl-1H-indol-5-yl)-5-ethyl-2-oxo-1,2-dihydropyridine-3

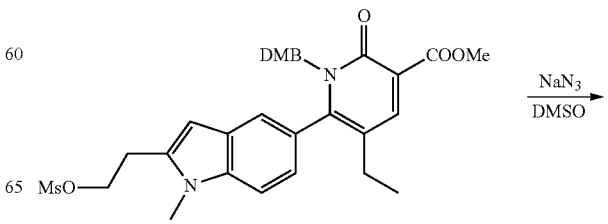

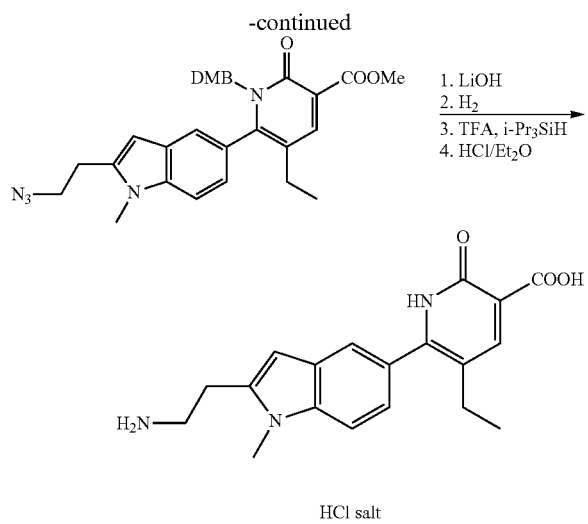

HCl salt

Step 1: methyl 6-(2-(2-azidoethyl)-1-methyl-1H-indol-5-yl)-1-(2,4-dimethoxybenzyl)-5-ethyl-2-oxo-1,2-dihydropyridine-3-carboxylate To solution of methyl 1-(2,4-dimethoxybenzyl)-5-ethyl-6-(1-methyl-2-(2-(methylsulfonyloxy)ethyl)-1H-indol-5-yl)-2-oxo-1,2-dihydropyridine-3-carboxylate (309.6 mg, 0.53 mmol), prepared according to procedure described in Example 159 Step 10, in DMSO (2 mL) was added NaN₃ (100 mg, 1.54 mmol). The reaction mixture was heated at 80° C. for 1.5 h until complete consumption of starting material was observed. The reaction mixture was then diluted with H₂O and the product was extracted with DCM (3×10 mL). The combined organics were washed with NaCl (aqueous saturated, 5 mL) and dried over Na₂SO₄. Upon solvent removal, the residue was purified by column chromatography using EtOAc/hexanes (gradient 0-80%) to afford methyl 6-(2-(2-azidoethyl)-1-methyl-1H-indol-5-yl)-1-(2,4-dimethoxybenzyl)-5-ethyl-2-oxo-1,2-dihydropyridine-3-carboxylate (204.0 mg) in 73% yield. The product could not be completely separated from mesylate elimination by-product.

LC-MS 530.5 [M+H]⁺, RT 1.47 min.

Step 2-4: 6-(2-(2-aminoethyl)-1-methyl-1H-indol-5-yl)-5-ethyl-2-oxo-1,2-dihydropyridine-3-carboxylic acid hydrochloride Obtained methyl 6-(2-(2-azidoethyl)-1-methyl-1H-indol-5-yl)-1-(2,4-dimethoxybenzyl)-5-ethyl-2-oxo-1,2-dihydropyridine-3-carboxylate (204.0 mg, 0.39 mmol) was dissolved in THF (1.5 mL) and solution of LiOH (1M aqueous, 1.5 mL, 1.5 mmol) was added. Reaction was stirred at room temperature for 1 h until ester mass was not detected by LC/MS. Reaction was then acidified with 1M HCl to pH~2 and product was extracted with DCM (3×7 mL). Organic phase was dried over Na₂SO₄ and solvent was concentrated. Residue was taken up in MeOH (5 mL) and DCM (5 mL) and hydrogenated over Pd/C (10%, Degussa type, 20 mg) and Pd(OH)₂/C (20%, Degussa type, 20 mg) at 1 atm H₂ for 1 h. Catalyst was filtered off and washed with DCM. Mother liquor was concentrated and obtained material was mixed with i-Pr₃SiH (0.50 mL) and TFA (1.0 mL). Reaction mixture was heated at 50° C. 15 min. TFA was removed under reduced pressure and residue was treated with HCl (2M Et₂O, 2 mL). Mixture was diluted with Et₂O and solid was filtered. It was then washed several times with Et₂O and finally with DCM (~5 mL). Upon drying in the dessicator 6-(2-(2-aminoethyl)-1-methyl-1H-indol-5-yl)-5-ethyl-2-oxo-1,2-dihydropyridine-3-carboxylic acid (25.0 mg) was obtained as hydrochloride salt in 13% overall yield over 4 steps.

¹H NMR (500 MHz, DMSO-d₆) δ ppm 1.01 (t, J=7.6 Hz, 3H) 2.43 (q, J=7.6 Hz, 2H) 3.15 (br. s., 4H) 3.77 (s, 3H) 6.47 (s, 1H) 7.22 (dd, J=8.5, 1.6 Hz, 1H) 7.59 (d, J=8.5 Hz, 1H) 7.63 (d, J=1.6 Hz, 1H) 8.19 (br. s., 3H) 8.37 (s, 1H) 13.24 (br. s., 1H). LC-MS 338.3 [M−H]⁻, 340.3 [M+H]⁺, RT 0.81 min.

Example 164

5-ethyl-4-hydroxy-6-(1-methyl-2-(pyrrolidin-1-ylmethyl)-1H-indol-5-yl)-2-oxo-1,2-dihydropyridine-3-carboxylic acid

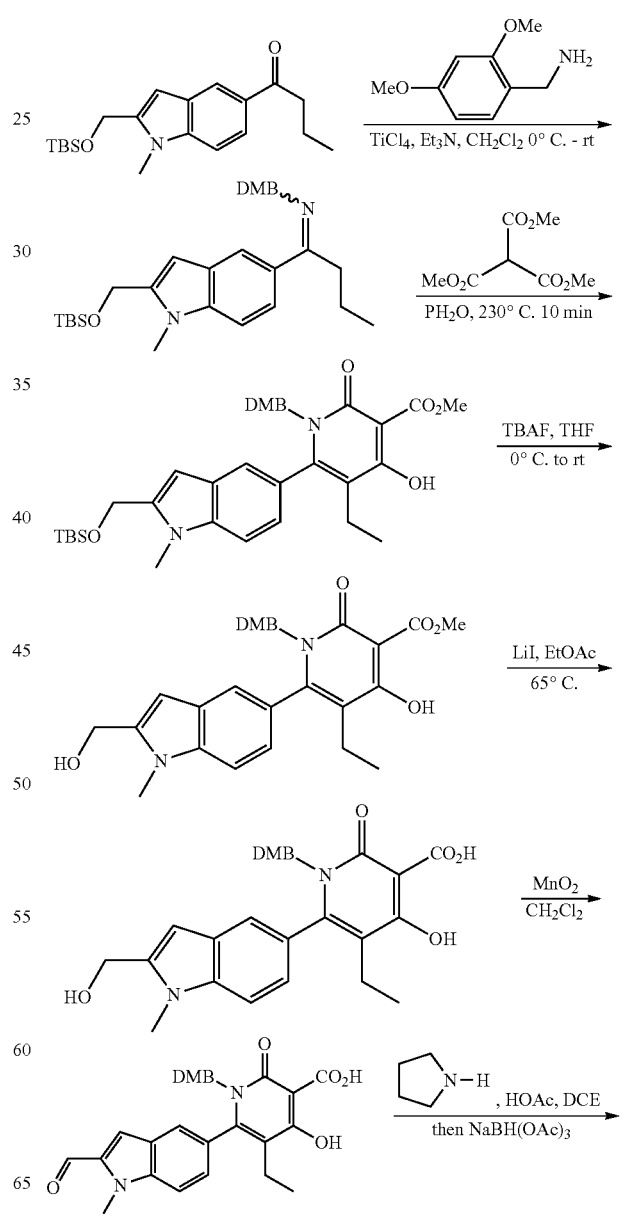

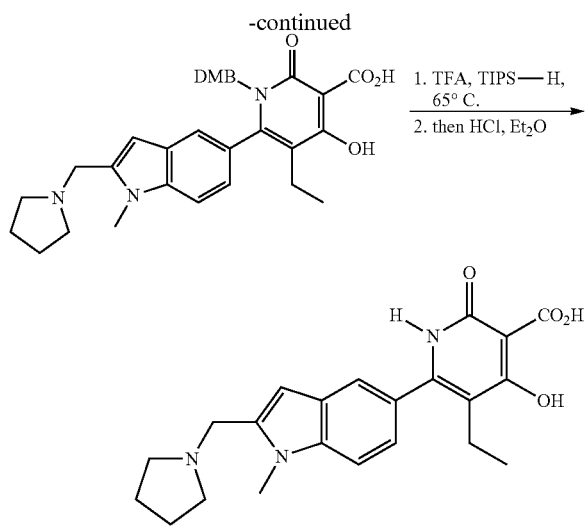

Step 1: N-(1-(2-((tert-Butyldimethylsilyloxy)methyl)-1-methyl-1H-indol-5-yl)butylidene)-1-(2,4-dimethoxyphenyl)methanamine To a stirred solution of ketone (4.14 g, 12.0 mmol), prepared according to procedure described in Example 39 Step 4, in CH$_2$Cl$_2$ (12 mL) was added 2,4-dimethoxybenzylamine (1.98 mL, 13.2 mmol, 1.1 eq) and Et$_3$N (4.5 mL, 32.4 mmol, 2.7 eq) sequentially at 0° C. Then a solution of TiCl$_4$ (7.8 mL, 1.0M in CH$_2$Cl$_2$, 7.8 mmol, 0.65 eq) was added to mixture via syringe pump over 30 min. The reaction was allowed to warm to room temperature and stirred overnight. The mixture was quenched with saturated aqueous NaHCO$_3$ solution and extracted by CH$_2$Cl$_2$ (5×30 mL). The combined organic layers were dried over Na$_2$SO$_4$ then concentrated under reduced pressure to give the crude product (5.94 g) which was carried over to next step without further purification. LC-MS 495.3 [M+H]$^+$, RT 1.43 min.

Step 2: Methyl 6-(2-((tert-butyldimethylsilyloxy)methyl)-1-methyl-1H-indol-5-yl)-1-(2,4-dimethoxybenzyl)-5-ethyl-4-hydroxy-2-oxo-1,2-dihydropyridine-3-carboxylate The crude imine (5.94 g, ca. 12.0 mmol) obtained above was dissolved in Ph$_2$O (20 mL) then trimethyl methanetricarboxylate (3.88 g, 20.4 mmol, 1.7 eq) was added. Distillation apparatus was set up then attached to the flask containing reaction mixture. The reaction was heated to 230° C. for 10 min. The heating was removed once distillation of methanol ceased. The mixture was cooled to room temperature then purified by flash column chromatography (0-50% EtOAc in CH$_2$Cl$_2$) to give desired product (4.17 g, 56%) as yellow foam.

$^1$H NMR (500 MHz, CHCl$_3$-d) δ ppm 0.08-0.14 (m, 6H) 0.85-0.94 (m, 12H) 2.13 (m, 2H) 3.16 (s, 3H) 3.76 (s, 3H) 3.78-3.81 (m, 3H) 3.99-4.03 (m, 3H) 4.78-4.87 (m, 2H) 6.13 (d, J=2.29 Hz, 1H) 6.30 (s, 1H) 6.39 (dd, J=8.39, 2.40 Hz, 1H) 6.79 (d, J=7.49 Hz, 1H) 6.84 (d, J=8.43 Hz, 1H) 7.06 (s, 1H) 7.22 (d, J=8.51 Hz, 1H). LC-MS 621.3 [M+H]$^+$, RT 1.84 min.

Step 3: Methyl 1-(2,4-dimethoxybenzyl)-5-ethyl-4-hydroxy-6-(2-(hydroxymethyl)-1-methyl-1H-indol-5-yl)-2-oxo-1,2-dihydropyridine-3-carboxylate To a stirred solution of cycloadduct (4.17 g, 6.72 mmol) obtained above in THF (10 mL) was added TBAF (8.1 mL, 8.1 mmol, 1.2 eq) at 0° C. The mixture was allowed to warm to room temperature and stirred for 30 min. Additional TBAF (5.4 mL, 5.4 mmol, 0.8 eq) was added and reaction was complete. The solvent was removed under reduced pressure then crude product was purified by flash column chromatography (0-50% EtOAc in CH$_2$Cl$_2$) to give the title compound (3.13 g, 92%).

$^1$H NMR (500 MHz, CHCl$_3$-d) δ ppm 0.86-0.95 (m, 3H) 2.07-2.21 (m, 2H) 3.21 (s, 3H) 3.74-3.78 (m, 3H) 3.82-3.86 (m, 3H) 3.99-4.03 (m, 3H) 4.83 (s, 2H) 4.88-4.98 (m, 2H) 6.15 (d, J=2.36 Hz, 1H) 6.36-6.42 (m, 2H) 6.78-6.88 (m, 2H) 7.12 (s, 1H) 7.25 (m, 1H). LC-MS 505.1 [M–H]$^-$, 507.2 [M+H]$^+$, RT 1.28 min.

Step 4: 1-(2,4-Dimethoxybenzyl)-5-ethyl-4-hydroxy-6-(2-(hydroxymethyl)-1-methyl-1H-indol-5-yl)-2-oxo-1,2-dihydropyridine-3-carboxylic acid To a suspension of ester (3.13 g, 6.18 mmol) obtained above in EtOAc (15 mL) was added LiI (2.48 g, 18.5 mmol, 3.0 eq) at room temperature. The mixture heated to 65° C. and stirred for 1 h. The reaction mixture was diluted by EtOAc (30 mL) then quenched with saturated aqueous Na$_2$S$_2$O$_3$ (30 mL). The organic phase was separated then aqueous layer was extracted by EtOAc (4×30 mL). The combined organic layers were dried over Na$_2$SO$_4$ then concentrated to give the title compound (2.89 g, 95%) which was carried over to next step without further purification.

$^1$H NMR (500 MHz, CHCl$_3$-d) δ ppm 0.88-0.99 (m, 3H) 2.11-2.27 (m, 2H) 3.29 (s, 3H) 3.78 (s, 3H) 3.85 (s, 3H) 4.81-4.87 (m, 2H) 4.90 (d, J=15.76 Hz, 1H) 4.99 (d, J=15.84 Hz, 1H) 6.21 (d, J=2.36 Hz, 1H) 6.35-6.46 (m, 2H) 6.69 (d, J=8.43 Hz, 1H) 6.85 (dd, J=8.43, 1.66 Hz, 1H) 7.16 (d, J=1.26 Hz, 1H) 7.29-7.33 (m, 1H) 13.97 (s, 1H) 15.96 (s, 1H). LC-MS 491.2 [M–H]$^-$, 493.2 [M+H]$^+$, RT 1.37 min.

Step 5: 1-(2,4-Dimethoxybenzyl)-5-ethyl-6-(2-formyl-1-methyl-1H-indol-5-yl)-4-hydroxy-2-oxo-1,2-dihydropyridine-3-carboxylic acid To a suspension of alcohol (2.89 g, 5.87 mmol) obtained above in CH$_2$Cl$_2$ (30 mL) was added MnO$_2$ (5.1 g, 58.7 mmol, 10 eq) at room temperature. After 1 h, MnO$_2$ (5.1 g, 58.7 mmol, 10 eq) was added. The reaction was monitored by LC-MS. Upon completion, reaction mixture was filtered through celite to remove solid waste. The filtrate was concentrated to give a crude aldehyde (2.45 g, 4.99 mmol) which was used in next step without further purification.

$^1$H NMR (500 MHz, CHCl$_3$-d) δ ppm 0.93 (t, J=7.41 Hz, 3H) 2.11-2.26 (m, 2H) 3.19 (s, 3H) 3.79 (s, 3H) 4.14 (s, 3H) 4.88 (d, J=15.76 Hz, 1H) 5.04 (d, J=15.84 Hz, 1H) 6.18 (d, J=2.36 Hz, 1H) 6.42 (dd, J=8.43, 2.36 Hz, 1H) 6.73 (d, J=8.35 Hz, 1H) 7.03 (dd, J=8.67, 1.58 Hz, 1H) 7.21 (s, 1H) 7.40 (d, J=8.67 Hz, 1H) 9.94 (s, 1H) 14.03 (s, 1H) 15.88 (s, 1H). LC-MS 489.3 [M–H]$^-$, 491.3 [M+H]$^+$, RT 1.46 min.

Step 6-8: 5-Ethyl-4-hydroxy-6-(1-methyl-2-(pyrrolidin-1-ylmethyl)-1H-indol-5-yl)-2-oxo-1,2-dihydropyridine-3-carboxylic acid To a solution of crude aldehyde (200 mg, 0.41 mmol) obtained above in DCE (2.0 mL) was added pyrrolidine (0.07 mL, 0.85 mmol, 2.0 eq) and HOAc (0.05 mL, 0.82 mmol, 2.0 eq) at room temperature. The reaction was stirred for 1 h before NaBH(OAc)$_3$ (174 mg, 0.82 mmol, 2.0 eq) was added. Upon completion, solvent was removed under reduced pressure then water was added. The crude product was collected through filtration and purified by preparative HPLC (40-90% MeCN in H₂O) to afford the intermediate for final deprotection. To a suspension of above intermediate in TIPS-H (1.5 mL) was added TFA (1.5 mL) then reaction mixture was heated to 65° C. for 1 h. The reaction was monitored by LC-MS. Upon completion, the solvent was removed under reduced pressure. The residue was dissolved in CH₂Cl₂ (1.5 mL), then HCl (2.0M/Et₂O, 2.0 mL) was added. The white precipitate was collected by filtration and washed by Et₂O (3×3 mL) then dried under nitrogen flow overnight to afford the title compound as a light yellow solid.

$^1$H NMR (500 MHz, MeOH-d₄) δ ppm 1.04 (t, J=7.25 Hz, 3H) 1.81-1.86 (m, 4H) 2.41 (q, J=7.57 Hz, 2H) 2.62-2.67 (m, 4H) 3.84 (s, 3H) 3.86 (s, 2H) 6.48 (s, 1H) 7.18 (d, J=9.46 Hz, 1H) 7.45 (d, J=8.51 Hz, 1H) 7.55 (s, 1H). LC-MS 394.0 [M−H]⁻, 396.1 [M+H]⁺, RT 0.88 min.

Using the procedures described above, additional compounds described herein may be prepared by substituting the appropriate starting materials, reagents and reaction conditions and include compounds selected from:

| Cpd | Name |
|---|---|
| 165 | 5-Ethyl-6-(2-((ethylamino)methyl)-1-methyl-1H-indol-5-yl)-4-hydroxy-2-oxo-1,2-dihydropyridine-3-carboxylic acid<br>$^1$H NMR (500 MHz, DMSO-d₆) δ ppm 0.98 (t, J = 7.41 Hz, 3 H) 1.28 (t, J = 7.25 Hz, 3 H) 2.33 (q, J = 7.33 Hz, 2 H) 2.98-3.13 (m, 2 H) 3.87 (s, 3 H) 4.43 (t, J = 5.12 Hz, 2 H) 5.76 (s, 1 H) 6.82 (s, 1 H) 7.28 (dd, J = 8.51, 1.66 Hz, 1 H) 7.67 (d, J = 8.59 Hz, 1 H) 7.73 (d, J = 1.26 Hz, 1 H) 9.26 (br. s., 2 H) 12.79 (s, 1 H) 13.90 (s, 1 H). LC-MS 368.2 [M − H]⁻, 370.1 [M + H]⁺, RT 0.78 min. |
| 166 | 6-(2-((Dimethylamino)methyl)-1-methyl-1H-indol-5-yl)-5-ethyl-4-hydroxy-2-oxo-1,2-dihydropyridine-3-carboxylic acid<br>$^1$H NMR (500 MHz, MeOH-d₄) δ ppm 1.06 (t, J = 7.28 Hz, 3 H) 2.45 (q, J = 7.28 Hz, 2 H) 2.97 (s, 6 H) 3.93 (s, 3 H) 4.68 (br. s., 2 H) 6.95 (br. s., 1 H) 7.37 (d, J = 8.20 Hz, 1 H) 7.67 (d, J = 8.51 Hz, 1 H) 7.76 (s, 1 H). LC-MS 368.2 [M − H]⁻, 370.2 [M + H]⁺, RT 0.57 min. (1 min Method). |
| 167 | 6-(2-((Diethylamino)methyl)-1-methyl-1H-indol-5-yl)-5-ethyl-4-hydroxy-2-oxo-1,2-dihydropyridine-3-carboxylic acid<br>$^1$H NMR (500 MHz, MeOH-d₄) δ ppm 1.07 (t, J = 7.37 Hz, 3 H) 1.42 (t, J = 6.58 Hz, 6 H) 2.45 (q, J = 7.33 Hz, 2 H) 3.33-3.42 (m, 4 H) 3.94 (s, 3 H) 4.69 (br. s., 2 H) 6.97 (br. s., 1 H) 7.37 (d, J = 8.43 Hz, 1 H) 7.68 (d, J = 8.43 Hz, 1 H) 7.76 (s, 1 H). LC-MS 396.2 [M − H]⁻, 398.2 [M + H]⁺, RT 0.59 min. (1 min Method). |
| 168 | 5-ethyl-4-hydroxy-6-(1-methyl-2-(morpholinomethyl)-1H-indol-5-yl)-2-oxo-1,2-dihydropyridine-3-carboxylic acid<br>$^1$H NMR (500 MHz, DMSO-d₆) δ ppm 0.99 (t, J = 7.41 Hz, 3 H) 2.27-2.40 (m, 2 H) 3.23 (br. s., 2 H) 3.33-3.46 (m, 2 H) 3.75-3.88 (m, 2 H) 3.89-4.03 (m, 2 H) 3.93 (s, 3 H) 4.65 (br. s., 2 H) 6.92 (br. s., 1 H) 7.31 (d, J = 8.20 Hz, 1 H) 7.68 (d, J = 8.20 Hz, 1 H) 7.75 (s, 1 H) 10.91 (br. s., 1 H) 12.77 (br. s., 1 H) 13.91 (s, 1 H) 16.32 (br. s., 1 H). LC-MS 410.1 [M − H]⁻, 412.2 [M + H]⁺, RT 1.00 min. |
| 169 | 5-Ethyl-4-hydroxy-6-(1-methyl-2-((4-methylpiperazin-1-yl)methyl)-1H-indol-5-yl)-2-oxo-1,2-dihydropyridine-3-carboxylic acid<br>$^1$H NMR (500 MHz, MeOH-d₄) δ ppm 1.07 (t, J = 7.41 Hz, 3 H) 2.46 (q, J = 7.46 Hz, 2 H) 2.94 (s, 3 H) 3.32-3.35 (m, 8 H) 3.91 (s, 3 H) 4.12 (br. s., 2 H) 6.68 (s, 1 H) 7.28 (dd, J = 8.51, 1.58 Hz, 1 H) 7.59 (d, J = 8.59 Hz, 1 H) 7.67 (s, 1 H). LC-MS 423.1 [M − H]⁻, 425.2 [M + H]⁺, RT 0.92 min. |
| 170 | 5-ethyl-4-hydroxy-6-(1-methyl-2-(((3S,5R)-3,4,5-trimethylpiperazin-1-yl)methyl)-1H-indol-5-yl)-2-oxo-1,2-dihydropyridine-3-carboxylic acid<br>$^1$H NMR (500 MHz, MeOH-d₄) δ ppm 1.07 (t, J = 7.41 Hz, 3 H) 1.42 (br. s., 6 H) 2.46 (q, J = 7.25 Hz, 2 H) 2.66 (br. s., 2 H) 2.95 (br. s., 3 H) 3.33-3.43 (m, 2 H) 3.46-3.60 (m, 2 H) 3.92 (s, 3 H) 4.11 (br. s., 2 H) 6.71 (br. s., 1 H) 7.29 (d, J = 8.83 Hz, 1 H) 7.59 (d, J = 8.83 Hz, 1 H) 7.68 (br. s., 1 H). LC-MS 451.4 [M − H]⁻, 453.4 [M + H]⁺, RT 1.00 min. |
| 171 | 5-ethyl-4-hydroxy-6-(1-methyl-2-(piperazin-1-ylmethyl)-1H-indol-5-yl)-2-oxo-1,2-dihydropyridine-3-carboxylic acid<br>$^1$H NMR (500 MHz, MeOH-d₄) δ ppm 1.06 (t, J = 7.41 Hz, 3 H) 2.45 (q, J = 6.94 Hz, 2 H) 3.17-3.35 (m, 4 H) 3.39-3.52 (m, 4 H) 3.94 (s, 3 H) 4.33 (br. s., 2 H) 6.79 (br. s., 1 H) 7.31 (d, J = 7.57 Hz, 1 H) 7.61 (d, J = 8.51 Hz, 1 H) 7.69 (s, 1 H). LC-MS 409.0 [M − H]⁻, RT 0.66 min. (1 min Method). |
| 172 | 6-(2-(((2S,6R)-2,6-Dimethylmorpholino)methyl)-1-methyl-1H-indol-5-yl)-5-ethyl-4-hydroxy-2-oxo-1,2-dihydropyridine-3-carboxylic acid<br>$^1$H NMR (500 MHz, MeOH-d₄) δ ppm 1.06 (t, J = 7.37 Hz, 3 H) 1.23-1.27 (m, 6 H) 2.45 (q, J = 7.30 Hz, 2 H) 2.89 (t, J = 11.19 Hz, 2 H) 3.51-3.57 (m, 2 H) 3.90-4.00 (m, 5 H) 4.70 (br. s., 2 H) 7.00 (br. s., 1 H) 7.36 (d, J = 8.43 Hz, 1 H) 7.68 (d, J = 8.51 Hz, 1 H) 7.76 (s, 1 H). LC-MS 438.0 [M − H]⁻, 440.0 [M + H]⁺, RT 0.62 min. (1 min Method). |
| 173 | 5-Ethyl-4-hydroxy-6-(1-methyl-2-((2-methylpyrrolidin-1-yl)methyl)-1H-indol-5-yl)-2-oxo-1,2-dihydropyridine-3-carboxylic acid<br>$^1$H NMR (500 MHz, DMSO-d₆) δ ppm 0.99 (t, J = 7.41 Hz, 3 H) 1.44 (d, J = 6.46 Hz, 3 H) 1.64-1.75 (m, 1 H) 1.86-2.01 (m, 2 H) 2.25 (dt, J = 7.80, 4.73 Hz, 1 H) 2.33 (q, J = 7.33 Hz, 2 H) 3.20-3.30 (m, 1 H) 3.30-3.55 (m, 2 H) 3.92 (s, 3 H) 4.51 (dd, J = 14.58, 7.33 Hz, 1 H) 4.81 (dd, J = 14.62, 2.72 Hz, 1 H) 6.93 (s, 1 H) 7.30 (dd, J = 8.55, 1.69 Hz, 1 H) 7.69 (d, J = 8.59 Hz, 1 H) 7.74 (d, J = 1.18 Hz, 1 H) 10.40 (br. s., 1 H) 12.77 (s, 1 H) 13.90 (s, 1 H). LC-MS 408.3 [M − H]⁻, 410.3 [M + H]⁺, RT 0.86 min. |
| 174 | 5-Ethyl-6-(2-((4-isopropylpiperazin-1-yl)methyl)-1-methyl-1H-indol-5-yl)-2-oxo-1,2-dihydropyridine-3-carboxylic acid<br>$^1$H NMR (500 MHz, MeOH-d₄) δ ppm 1.06 (t, J = 7.41 Hz, 3 H) 1.39-1.45 (m, 6 H) 2.45 (q, J = 7.41 Hz, 2 H) 3.34-3.80 (m, 9 H) 3.98 (s, 3 H) 4.60 (br. s., 2 H) 6.93 (br. s., 1 H) 7.34 (dd, J = 8.59, 1.66 Hz, 1 H) 7.65 (d, J = 8.59 Hz, 1 H) 7.69-7.77 (m, 1 H). LC-MS 451.2 [M − H]⁻, 453.2 [M + H]⁺, RT 0.99 min. |

| Cpd | Name |
|---|---|
| 175 | 6-(2-((4-acetylpiperazin-1-yl)methyl)-1-methyl-1H-indol-5-yl)-5-ethyl-4-hydroxy-2-oxo-1,2-dihydropyridine-3-carboxylic acid<br>$^1$H NMR (500 MHz, DMSO-d$_6$) δ ppm 0.99 (t, J = 7.41 Hz, 3 H) 2.04 (s, 3 H) 2.34 (q, J = 7.46 Hz, 2 H) 2.98-3.26 (m, 3 H) 3.37-3.54 (m, 2 H) 3.54-3.67 (m, 1 H) 3.93 (s, 3 H) 3.93-4.06 (m, 1 H) 4.44 (br. s., 1 H) 4.63 (br. s., 2 H) 6.93 (br. s., 1 H) 7.30 (d, J = 8.51 Hz, 1 H) 7.68 (d, J = 8.83 Hz, 1 H) 7.75 (s, 1 H) 11.39 (br. s., 1 H) 12.76 (br. s., 1 H) 13.90 (br. s., 1 H) 16.32 (br. s., 1 H). LC-MS 451.5 [M − H]$^-$, 453.6 [M + H]$^+$, RT 0.60 min. (1 min Method). |
| 176 | 6-(2-((3,3-Difluoropyrrolidin-1-yl)methyl)-1-methyl-1H-indol-5-yl)-5-ethyl-4-hydroxy-2-oxo-1,2-dihydropyridine-3-carboxylic acid<br>$^1$H NMR (500 MHz, MeOH-d$_4$) δ ppm 1.07 (t, J = 7.29 Hz, 3 H) 2.35-2.50 (m, 2 H) 2.65-2.80 (m, 2 H) 3.60-4.05 (m, 6 H) 3.95 (s, 3 H) 6.97 (br. s., 1 H) 7.37 (d, J = 8.35 Hz, 1 H) 7.68 (d, J = 8.28 Hz, 1 H) 7.76 (s, 1 H). LC-MS 430.3 [M − H]$^-$, 432.4 [M + H]$^+$, RT 1.29 min. |
| 177 | (R)-5-ethyl-6-(2-((3-fluoropyrrolidin-1-yl)methyl)-1-methyl-1H-indol-5-yl)-4-hydroxy-2-oxo-1,2-dihydropyridine-3-carboxylic acid<br>$^1$H NMR (500 MHz, MeOH-d$_4$) δ ppm 1.07 (t, J = 7.41 Hz, 3 H) 2.45 (q, J = 7.36 Hz, 2 H) 3.48-4.00 (m, 6 H) 3.94 (s, 3 H) 4.82 (br. s., 2 H) 5.50 (d, J = 55.0 Hz, 1 H) 6.96 (br. s., 1 H) 7.37 (d, J = 8.67 Hz, 1 H) 7.68 (d, J = 8.67 Hz, 1 H) 7.76 (s, 1 H). LC-MS 412.3 [M − H]$^-$, 414.4 [M + H]$^+$, RT 1.29 min. |
| 178 | 5-ethyl-4-hydroxy-6-(2-((3-hydroxypyrrolidin-1-yl)methyl)-1-methyl-1H-indol-5-yl)-2-oxo-1,2-dihydropyridine-3-carboxylic acid<br>$^1$H NMR (500 MHz, DMSO-d$_6$) δ ppm 0.99 (t, J = 7.41 Hz, 3 H) 1.81-2.10 (m, 2 H) 2.34 (q, J = 7.46 Hz, 2 H) 3.07-3.18 (m, 1 H) 3.25-3.38 (m, 2 H) 3.55-3.64 (m, 1 H) 3.86-3.93 (m, 3 H) 4.41-4.51 (m, 1 H) 4.65-4.75 (m, 2 H) 5.42-5.62 (m, 1 H) 6.92 (d, J = 7.88 Hz, 1 H) 7.30 (dd, J = 8.51, 1.58 Hz, 1 H) 7.67 (d, J = 8.83 Hz, 1 H) 7.74 (d, J = 1.26 Hz, 1 H) 10.55-10.85 (m, 1 H) 12.76 (br. s., 1 H) 13.91 (s, 1 H) 16.32 (br. s., 1 H). LC-MS 410.2 [M − H]$^-$, 412.2 [M + H]$^+$, RT 0.80 min. |
| 179 | 5-ethyl-4-hydroxy-6-(2-((3-methoxypyrrolidin-1-yl)methyl)-1-methyl-1H-indol-5-yl)-2-oxo-1,2-dihydropyridine-3-carboxylic acid<br>$^1$H NMR (500 MHz, DMSO-d$_6$) δ ppm 0.99 (t, J = 7.41 Hz, 3 H) 1.95-2.20 (m, 2 H) 2.34 (q, J = 7.67 Hz, 3 H) 3.21-3.33 (m, 4 H) 3.50-3.60 (m, 2 H) 3.65-3.73 (m, 1 H) 3.86-3.94 (m, 3 H) 4.10-4.21 (m, 1 H) 4.68 (br. s., 2 H) 6.93 (d, J = 9.46 Hz, 1 H) 7.30 (dd, J = 8.51, 1.58 Hz, 1 H) 7.67 (d, J = 8.83 Hz, 1 H) 7.74 (s, 1 H) 10.74 (br. s., 1 H) 11.18 (br. s., 1 H) 12.76 (br. s., 1 H) 13.91 (s, 1 H) 16.34 (br. s., 1 H). LC-MS 424.3 [M − H]$^-$, 426.3 [M + H]$^+$, RT 0.85 min. |
| 180 | (S)-6-(2-((3-aminopyrrolidin-1-yl)methyl)-1-methyl-1H-indol-5-yl)-5-ethyl-4-hydroxy-2-oxo-1,2-dihydropyridine-3-carboxylic acid<br>$^1$H NMR (500 MHz, MeOH-d$_4$) δ ppm 1.07 (t, J = 7.41 Hz, 3 H) 2.27 (br. s., 2 H) 2.45 (q, J = 7.25 Hz, 2 H) 2.66 (br. s., 2 H) 3.66-3.89 (m, 2 H) 3.98 (s, 3 H) 4.19 (br. s., 2 H) 4.78 (br. s., 1 H) 6.95 (br. s., 1 H) 7.35 (dd, J = 8.51, 1.58 Hz, 1 H) 7.66 (d, J = 8.51 Hz, 1 H) 7.74 (s, 1 H). LC-MS 410.0 [M − H]$^-$, 412.0 [M + H]$^+$, RT 0.56 min. (1 min Method). |
| 181 | 5-ethyl-4-hydroxy-6-(1-methyl-2-((3-(methylamino)pyrrolidin-1-yl)methyl)-1H-indol-5-yl)-2-oxo-1,2-dihydropyridine-3-carboxylic acid<br>$^1$H NMR (500 MHz, MeOH-d$_4$) δ ppm 1.07 (t, J = 7.41 Hz, 3 H) 2.38 (br. s., 1 H) 2.45 (q, J = 7.25 Hz, 2 H) 2.73-2.86 (m, 1 H) 2.78 (s, 3 H) 3.68-3.95 (m, 3 H) 3.99 (s, 3 H) 4.15 (br. s., 2 H) 4.84 (br. s., 2 H) 6.99 (br. s., 1 H) 7.36 (d, J = 8.51 Hz, 1 H) 7.66 (d, J = 8.51 Hz, 1 H) 7.75 (s, 1 H). LC-MS 423.2 [M − H]$^-$, 425.2 [M + H]$^+$, RT 0.83 min. |
| 182 | 6-(2-(2,5-diazabicyclo[2.2.1]heptan-2-ylmethyl)-1-methyl-1H-indol-5-yl)-5-ethyl-4-hydroxy-2-oxo-1,2-dihydropyridine-3-carboxylic acid<br>$^1$H NMR (500 MHz, DMSO-d$_6$) δ ppm 0.99 (t, J = 7.41 Hz, 3 H) 2.05-2.20 (m, 1 H) 2.34 (q, J = 7.46 Hz, 2 H) 2.66-2.81 (m, 1 H) 3.73-4.10 (m, 4 H) 3.94 (s, 3 H) 4.40-5.00 (m, 4 H) 6.99 (br. s., 1 H) 7.29 (d, J = 8.20 Hz, 1 H) 7.67 (d, J = 8.51 Hz, 1 H) 7.73 (br. s., 1 H) 9.69 (br. s., 1 H) 10.10 (br. s., 1 H) 11.86 (br. s., 1 H) 12.75 (br. s., 1 H) 13.90 (br. s., 1 H) 16.35 (br. s., 1 H). LC-MS 421.2 [M − H]$^-$, 423.2 [M + H]$^+$, RT 0.86 min. |
| 183 | 6-(2-((3-acetamidopyrrolidin-1-yl)methyl)-1-methyl-1H-indol-5-yl)-5-ethyl-4-hydroxy-2-oxo-1,2-dihydropyridine-3-carboxylic acid<br>$^1$H NMR (500 MHz, MeOH-d$_4$) δ ppm 1.07 (t, J = 7.41 Hz, 3 H) 1.95 (s, 3 H) 2.05-2.22 (m, 2 H) 2.33-2.42 (m, 1 H) 2.45 (q, J = 7.36 Hz, 2 H) 2.56-2.65 (m, 1 H) 3.52-3.61 (m, 2 H) 3.82-3.92 (m, 1 H) 3.94 (s, 3 H) 4.33-4.43 (m, 1 H) 4.73-4.83 (m, 2 H) 6.93 (s, 1 H) 7.36 (d, J = 8.20 Hz, 1 H) 7.67 (d, J = 8.20 Hz, 1 H) 7.75 (br. s., 1 H). LC-MS 451.2 [M − H]$^-$, 453.1 [M + H]$^+$, RT 0.84 min. |
| 184 | 5-ethyl-4-hydroxy-6-(1-methyl-2-((tetrahydro-1H-pyrrolo[3,4-b]pyridin-6(2H,7H,7aH)-yl)methyl)-1H-indol-5-yl)-2-oxo-1,2-dihydropyridine-3-carboxylic acid<br>$^1$H NMR (500 MHz, DMSO-d$_6$) δ ppm 0.99 (t, J = 7.41 Hz, 3 H) 1.63 (br. s., 2 H) 1.69-1.89 (m, 3 H) 2.34 (q, J = 7.36 Hz, 2 H) 2.62-2.70 (m, 1 H) 2.87 (br. s., 2 H) 3.42-3.53 (m, 1 H) 3.83-4.12 (m, 3 H) 3.97 (s, 3 H) 4.85 (br. s., 1 H) 5.08 (d, J = 18.60 Hz, 2 H) 6.99 (br. s., 1 H) 7.30 (d, J = 7.88 Hz, 1 H) 7.68 (d, J = 8.51 Hz, 1 H) 7.75 (br. s., 1 H) 9.35 (br. s., 1 H) 10.34 (br. s., 1 H) 11.80 (br. s., 1 H) 12.75 (br. s., 1 H) 13.91 (br. s., 1 H) 16.31 (br. s., 1 H). LC-MS 449.1 [M − H]$^-$, 451.2 [M + H]$^+$, RT 0.96 min. |
| 185 | 6-(2-((3-(2-Aminopropan-2-yl)pyrrolidin-1-yl)methyl)-1-methyl-1H-indol-5-yl)-5-ethyl-4-hydroxy-2-oxo-1,2-dihydropyridine-3-carboxylic acid<br>$^1$H NMR (500 MHz, MeOH-d$_4$) δ ppm 1.07 (t, J = 7.41 Hz, 3 H) 1.41 (s, 6 H) 1.94-2.34 (m, 2 H) 2.45 (q, J = 7.36 Hz, 2 H) 2.75-3.10 (m, 1 H) 3.40-3.54 (m, 1 H) 3.55-3.88 (m, 3 H) 3.98 (s, 3 H) 4.83 (br. s., 2 H) 7.01 (br. s., 1 H) 7.35 (dd, J = 8.51, 1.58 Hz, 1 H) 7.66 (d, J = 8.51 Hz, 1 H) 7.75 (s, 1 H). LC-MS 451.1 [M − H]$^-$, 453.2 [M + H]$^+$, RT 0.77 min. |

| Cpd | Name |
|---|---|
| 186 | 6-(2-(Azetidin-1-ylmethyl)-1-methyl-1H-indol-5-yl)-5-ethyl-4-hydroxy-2-oxo-1,2-dihydropyridine-3-carboxylic acid<br>$^1$H NMR (500 MHz, MeOH-d$_4$) δ ppm 1.06 (t, J = 7.41 Hz, 3 H) 2.44 (q, J = 7.38 Hz, 2 H) 2.47-2.56 (m, 1 H) 2.57-2.67 (m, 1 H) 3.89 (s, 3 H) 4.18-4.35 (m, 4 H) 4.73 (s, 2 H) 6.85 (s, 1 H) 7.34 (dd, J = 8.59, 1.73 Hz, 1 H) 7.64 (d, J = 8.59 Hz, 1 H) 7.73 (d, J = 1.10 Hz, 1 H). LC-MS 380.2 [M − H]$^-$, 382.2 [M + H]$^+$, RT 0.84 min. |
| 187 | 5-Ethyl-4-hydroxy-6-(2-((3-hydroxyazetidin-1-yl)methyl)-1-methyl-1H-indol-5-yl)-2-oxo-1,2-dihydropyridine-3-carboxylic acid<br>$^1$H NMR (500 MHz, MeOH-d$_4$) δ ppm 1.06 (t, J = 7.41 Hz, 3 H) 2.44 (q, J = 7.33 Hz, 2 H) 3.89 (br. s., 3 H) 4.07 (br. s., 2 H) 4.44 (br. s., 2 H) 4.64-4.80 (m, 3 H) 6.88 (br. s., 1 H) 7.34 (d, J = 7.96 Hz, 1 H) 7.65 (d, J = 8.43 Hz, 1 H) 7.73 (br. s., 1 H). LC-MS 396.2 [M − H]$^-$, 398.3 [M + H]$^+$, RT 0.82 min. |
| 188 | 6-(2-((3-aminoazetidin-1-yl)methyl)-1-methyl-1H-indol-5-yl)-5-ethyl-4-hydroxy-2-oxo-1,2-dihydropyridine-3-carboxylic acid<br>$^1$H NMR (500 MHz, DMSO-d$_6$) δ ppm 0.99 (t, J = 7.41 Hz, 3 H) 2.33 (q, J = 7.36 Hz, 2 H) 3.88 (s, 3 H) 4.01-4.62 (m, 5 H) 4.72-4.96 (m, 2 H) 6.85 (br. s., 1 H) 7.29 (dd, J = 8.51, 1.58 Hz, 1 H) 7.66 (d, J = 8.51 Hz, 1 H) 7.73 (s, 1 H) 8.79 (br. s., 3 H) 11.69 (br. s., 1 H) 12.77 (br. s., 1 H) 13.89 (br. s., 1 H). LC-MS 395.2 [M − H]$^-$, 397.3 [M + H]$^+$, RT 0.73 min. |
| 189 | 6-(2-((3-(dimethylamino)azetidin-1-yl)methyl)-1-methyl-1H-indol-5-yl)-5-ethyl-4-hydroxy-2-oxo-1,2-dihydropyridine-3-carboxylic acid<br>$^1$H NMR (500 MHz, DMSO-d$_6$) δ ppm 0.99 (t, J = 7.25 Hz, 3 H) 2.33 (q, J = 7.36 Hz, 2 H) 2.74 (br. s., 6 H) 3.90 (s, 3 H) 4.15-4.40 (m, 3 H) 4.50-4.75 (m, 2 H) 4.97 (br. s., 2 H) 6.89 (br. s., 1 H) 7.27-7.37 (m, 1 H) 7.67 (d, J = 8.51 Hz, 1 H) 7.74 (s, 1 H) 11.80 (br. s., 1 H) 12.28 (br. s., 1 H) 12.77 (br. s., 1 H) 13.90 (br. s., 1 H). LC-MS 423.3 [M − H]$^-$, 425.3 [M + H]$^+$, RT 0.89 min. |
| 190 | (S)-5-ethyl-4-hydroxy-6-(2-((2-(methoxycarbonyl)pyrrolidin-1-yl)methyl)-1-methyl-1H-indol-5-yl)-2-oxo-1,2-dihydropyridine-3-carboxylic acid<br>$^1$H NMR (500 MHz, MeOH-d$_4$) δ ppm 1.06 (t, J = 7.41 Hz, 3 H) 2.01-2.22 (m, 2 H) 2.22-2.32 (m, 1 H) 2.44 (q, J = 7.33 Hz, 2 H) 2.60-2.70 (m, 1 H) 3.43-3.57 (m, 1 H) 3.68 (s, 3 H) 3.70-3.80 (m, 1 H) 3.99 (s, 3 H) 4.57 (t, J = 8.83 Hz, 1 H) 4.75 (d, J = 14.27 Hz, 1 H) 4.86-4.90 (m, 1H) 6.94 (s, 1 H) 7.37 (d, J = 8.67 Hz, 1 H) 7.68 (d, J = 8.59 Hz, 1 H) 7.75 (s, 1 H). LC-MS 452.2 [M − H]$^-$, 454.3 [M + H]$^+$, RT 0.97 min. |
| 191 | 6-(2-((3-(Dimethylcarbamoyl)pyrrolidin-1-yl)methyl)-1-methyl-1H-indol-5-yl)-5-ethyl-4-hydroxy-2-oxo-1,2-dihydropyridine-3-carboxylic acid<br>$^1$H NMR (500 MHz, DMSO-d$_6$) δ ppm 0.99 (t, J = 7.41 Hz, 3 H) 1.80-2.15 (m, 1 H) 2.24-2.32 (m, 1 H) 2.34 (q, J = 7.38 Hz, 2 H) 2.78-2.94 (m, 3 H) 2.94-3.10 (m, 3 H) 3.48-3.64 (m, 4 H) 3.64-3.81 (m, 3 H) 3.83-3.98 (m, 3 H) 4.68-4.79 (m, 2 H) 6.93 (s, 1 H) 7.30 (d, J = 8.51 Hz, 1 H) 7.68 (d, J = 8.59 Hz, 1 H) 7.74 (br. s., 1 H) 12.77 (s, 1 H) 13.90 (s, 1 H). LC-MS 465.4 [M − H]$^-$, 467.4 [M + H]$^+$, RT 0.85 min. |
| 192 | 5-Ethyl-4-hydroxy-6-(1-methyl-2-(piperidin-1-ylmethyl)-1H-indol-5-yl)-2-oxo-1,2-dihydropyridine-3-carboxylic acid<br>$^1$H NMR (500 MHz, MeOH-d$_4$) δ ppm 1.06 (t, J = 7.37 Hz, 3 H) 1.47-1.61 (m, 1 H) 1.71-1.90 (m, 3 H) 1.94-2.03 (m, 2 H) 2.45 (q, J = 7.36 Hz, 2 H) 3.11 (t, J = 11.63 Hz, 2 H) 3.56-3.64 (m, 2 H) 3.93 (s, 3 H) 4.63 (s, 2 H) 6.94 (br. s., 1 H) 7.37 (d, J = 8.67 Hz, 1 H) 7.68 (d, J = 8.59 Hz, 1 H) 7.76 (s, 1 H). LC-MS 408.3 [M − H]$^-$, 410.3 [M + H]$^+$, RT 0.88 min. |
| 193 | 6-(2-((tert-Butylamino)methyl)-1-methyl-1H-indol-5-yl)-5-ethyl-4-hydroxy-2-oxo-1,2-dihydropyridine-3-carboxylic acid<br>$^1$H NMR (500 MHz, DMSO-d$_6$) δ ppm 0.98 (t, J = 7.37 Hz, 3 H) 1.43 (s, 9 H) 2.32 (q, J = 7.38 Hz, 2 H) 3.87 (s, 3 H) 4.35-4.47 (m, 2 H) 6.83 (s, 1 H) 7.28 (dd, J = 8.55, 1.62 Hz, 1 H) 7.68 (d, J = 8.59 Hz, 1 H) 7.74 (d, J = 1.18 Hz, 1 H) 9.22 (br. s., 2 H) 12.82 (s, 1 H) 13.90 (s, 1 H). LC-MS 396.4 [M − H]$^-$, 398.4 [M + H]$^+$, RT 0.89 min. |
| 194 | 5-ethyl-6-(2-((3-fluoroazetidin-1-yl)methyl)-1-methyl-1H-indol-5-yl)-4-hydroxy-2-oxo-1,2-dihydropyridine-3-carboxylic acid<br>$^1$H NMR (500 MHz, MeOH-d$_4$) δ ppm 1.06 (t, J = 7.37 Hz, 3 H) 2.44 (q, J = 7.30 Hz, 2 H) 3.90 (br. s., 3 H) 4.46 (br. s., 2 H) 4.66 (br. s., 2 H) 4.75-4.90 (m, 2 H) 5.35-5.60 (m, 1 H) 6.91 (br. s., 1 H) 7.35 (d, J = 7.25 Hz, 1 H) 7.66 (d, J = 7.57 Hz, 1 H) 7.74 (br. s., 1 H). LC-MS 398.3 [M − H]$^-$, 400.3 [M + H]$^+$, RT 0.84 min. |
| 195 | 6-(2-((3,3-Difluoroazetidin-1-yl)methyl)-1-methyl-1H-indol-5-yl)-5-ethyl-4-hydroxy-2-oxo-1,2-dihydropyridine-3-carboxylic acid<br>$^1$H NMR (500 MHz, MeOH-d$_4$) δ ppm 1.06 (t, J = 7.37 Hz, 3 H) 2.44 (q, J = 7.30 Hz, 2 H) 3.92 (s, 3 H) 4.75-4.90 (m, 6 H) 6.92 (br. s., 1 H) 7.36 (d, J = 8.28 Hz, 1 H) 7.66 (d, J = 8.43 Hz, 1 H) 7.75 (br. s., 1 H). LC-MS 416.3 [M − H]$^-$, 418.3 [M + H]$^+$, RT 1.25 min. |
| 196 | 6-(2-(((1R,5S,6s)-6-(dibenzylamino)-3-azabicyclo[3.1.0]hexan-3-yl)methyl)-1-methyl-1H-indol-5-yl)-5-ethyl-4-hydroxy-2-oxo-1,2-dihydropyridine-3-carboxylic acid<br>$^1$H NMR (500 MHz, MeOH-d$_4$) δ ppm 1.00-1.12 (m, 1 H) 1.08 (t, J = 7.37 Hz, 3 H) 1.89 (br. s., 2 H) 2.46 (q, J = 7.30 Hz, 2 H) 3.41-3.64 (m, 4 H) 3.92 (br. s., 3 H) 4.46 (br. s., 4 H) 4.62 (br. s., 2 H) 6.92 (br. s., 1 H) 7.35 (d, J = 8.20 Hz, 1 H) 7.49 (br. s., 6 H) 7.57 (br. s., 4 H) 7.64 (d, J = 8.51 Hz, 1 H) 7.74 (br. s., 1 H). LC-MS 601.3 [M − H]$^-$, 603.3 [M + H]$^+$, RT 1.28 min. |
| 197 | 6-(2-(((1R,5S,6s)-6-(dimethylamino)-3-azabicyclo[3.1.0]hexan-3-yl)methyl)-1-methyl-1H-indol-5-yl)-5-ethyl-4-hydroxy-2-oxo-1,2-dihydropyridine-3-carboxylic acid<br>$^1$H NMR (500 MHz, DMSO-d$_6$) δ ppm 0.99 (t, J = 7.25 Hz, 3 H) 2.33 (q, J = 7.25 Hz, 2 H) 2.48-2.55 (m, 2 H) 2.79 (br. s., 6 H) 2.84 (br. s., 1 H) 3.55-3.75 (m, 4 H) 3.90 (br. s., 3 H) 4.55-4.70 (m, 2 H) 6.96 (br. s., 1 H) 7.29 (br. s., 1 H) 7.65 (br. s., 1 H) 7.71 (br. s., 1 H) 11.08 (br. s., 1 H) 11.41 (br. s., 1 H) 12.75 (br. s., 1 H) 13.90 (br. s., 1 H). LC-MS 449.4 [M − H]$^-$, 451.4 [M + H]$^+$, RT 0.67 min. |

-continued

| Cpd | Name |
|---|---|
| 198 | 6-(2-(((1R,5S,6s)-3-azabicyclo[3.1.0]hexan-6-ylamino)methyl)-1-methyl-1H-indol-5-yl)-5-ethyl-4-hydroxy-2-oxo-1,2-dihydropyridine-3-carboxylic acid<br>$^1$H NMR (500 MHz, MeOH-d$_4$) δ ppm 1.07 (t, J = 7.37 Hz, 3 H) 2.45 (q, J = 7.30 Hz, 2 H) 2.45-2.53 (m, 2 H) 2.99 (br. s., 1 H) 3.59 (s, 4 H) 3.94 (s, 3 H) 4.71 (s, 2 H) 6.91 (s, 1 H) 7.35 (dd, J = 8.67, 1.73 Hz, 1 H) 7.66 (d, J = 8.51 Hz, 1 H) 7.73-7.76 (m, 1 H). LC-MS 421.2 [M − H]$^-$, 423.2 [M + H]$^+$, RT 0.71 min. |
| 199 | 5-Ethyl-4-hydroxy-6-(2-((isopropylamino)methyl)-1-methyl-1H-indol-5-yl)-2-oxo-1,2-dihydropyridine-3-carboxylic acid<br>$^1$H NMR (500 MHz, DMSO-d$_6$) δ ppm 0.98 (t, J = 7.37 Hz, 3 H) 1.35 (d, J = 7.21 Hz, 6 H) 2.32 (q, J = 7.25 Hz, 2 H) 3.41-3.51 (m, 1 H) 3.87 (s, 3 H) 4.45 (t, J = 5.44 Hz, 2 H) 6.81 (s, 1 H) 7.28 (dd, J = 8.55, 1.22 Hz, 1 H) 7.67 (d, J = 8.51 Hz, 1 H) 7.73 (s, 1 H) 9.10 (br. s., 2 H) 12.80 (s, 1 H) 13.90 (s, 1 H). LC-MS 382.3 [M − H]$^-$, 384.3 [M + H]$^+$, RT 0.74 min. |
| 200 | 6-(2-((3-(Dimethylamino)pyrrolidin-1-yl)methyl)-1-methyl-1H-indol-5-yl)-5-ethyl-4-hydroxy-2-oxo-1,2-dihydropyridine-3-carboxylic acid<br>$^1$H NMR (500 MHz, DMSO-d$_6$) δ ppm 0.99 (t, J = 7.37 Hz, 3 H) 2.34 (q, J = 7.30 Hz, 2 H) 2.80 (br. s., 8 H) 3.48-3.80 (m, 5 H) 3.93 (br. s., 3 H) 3.95-4.06 (m, 2 H) 7.29 (d, J = 7.17 Hz, 1 H) 7.68 (d, J = 7.49 Hz, 1 H) 7.73 (br. s., 1 H) 12.77 (br. s., 1 H) 13.90 (s, 1 H). LC-MS 437.2 [M − H]$^-$, 439.2 [M + H]$^+$, RT 0.96 min. |
| 201 | 5-Ethyl-6-(2-((2-fluoroethylamino)methyl)-1-methyl-1H-indol-5-yl)-4-hydroxy-2-oxo-1,2-dihydropyridine-3-carboxylic acid<br>$^1$H NMR (500 MHz, DMSO-d$_6$) δ ppm 0.98 (t, J = 7.37 Hz, 3 H) 2.33 (q, J = 7.30 Hz, 2 H) 3.35-3.50 (m, 2 H) 3.87 (s, 3 H) 4.51 (s, 2 H) 4.82 (dt, J = 49.50, 5.10 Hz, 2 H) 6.85 (s, 1 H) 7.29 (dd, J = 8.55, 1.62 Hz, 1 H) 7.67 (d, J = 8.59 Hz, 1 H) 7.74 (d, J = 1.34 Hz, 1 H) 9.66 (br. s., 2 H). LC-MS 386.3 [M − H]$^-$, 388.3 [M + H]$^+$, RT 0.82 min. |
| 202 | 6-(2-((2-((Dimethylamino)methyl)pyrrolidin-1-yl)methyl)-1-methyl-1H-indol-5-yl)-5-ethyl-4-hydroxy-2-oxo-1,2-dihydropyridine-3-carboxylic acid<br>$^1$H NMR (500 MHz, MeOH-d$_4$) δ ppm 1.07 (t, J = 7.37 Hz, 3 H) 2.00-2.30 (m, 4 H) 2.45 (q, J = 7.33 Hz, 2 H) 2.57 (br. s., 1 H) 2.95 (br. s., 6 H) 3.56-3.80 (m, 4 H) 3.99 (s, 3 H) 4.13 (br. s., 1 H) 4.65 (br. s., 2 H) 7.36 (d, J = 8.67 Hz, 1 H) 7.67 (d, J = 8.59 Hz, 1 H) 7.75 (br. s., 1 H). LC-MS 451.4 [M − H]$^-$, 453.4 [M + H]$^+$, RT 0.84 min. |
| 203 | 5-Ethyl-4-hydroxy-6-(1-methyl-2-((methylamino)methyl)-1H-indol-5-yl)-2-oxo-1,2-dihydropyridine-3-carboxylic acid<br>$^1$H NMR (500 MHz, DMSO-d$_6$) δ ppm 0.98 (t, J = 7.37 Hz, 3 H) 2.32 (q, J = 7.33 Hz, 2 H) 2.65 (br. s., 3 H) 3.86 (s, 3 H) 4.44 (br. s., 2 H) 6.79 (s, 1 H) 7.29 (dd, J = 8.51, 1.50 Hz, 1 H) 7.67 (d, J = 8.43 Hz, 1 H) 7.74 (s, 1 H) 12.78 (br. s., 1 H) 13.90 (br. s., 1 H). LC-MS 354.3 [M − H]$^-$, 356.3 [M + H]$^+$, RT 0.80 min. |
| 204 | 5-Ethyl-4-hydroxy-6-(1-methyl-2-((2-(methylamino)ethylamino)methyl)-1H-indol-5-yl)-2-oxo-1,2-dihydropyridine-3-carboxylic acid<br>$^1$H NMR (500 MHz, DMSO-d$_6$) δ ppm 0.99 (t, J = 7.37 Hz, 3 H) 2.32 (q, J = 7.33 Hz, 2 H) 2.61 (s, 3 H) 3.35-3.45 (m, 4 H) 3.90 (s, 3 H) 4.53 (br. s., 2 H) 6.86 (s, 1 H) 7.29 (dd, J = 8.55, 1.62 Hz, 1 H) 7.68 (d, J = 8.59 Hz, 1 H) 7.74 (d, J = 1.18 Hz, 1 H) 9.21 (br. s., 2 H) 9.84 (br. s., 2 H) 12.80 (br. s., 1 H). LC-MS 397.3 [M − H]$^-$, 399.3 [M + H]$^+$, RT 0.60 min. |
| 205 | 6-(2-((2-Aminoethylamino)methyl)-1-methyl-1H-indol-5-yl)-5-ethyl-4-hydroxy-2-oxo-1,2-dihydropyridine-3-carboxylic acid<br>$^1$H NMR (500 MHz, DMSO-d$_6$) δ ppm 0.99 (t, J = 7.37 Hz, 3 H) 2.33 (q, J = 7.33 Hz, 2 H) 3.20-3.35 (m, 4 H) 3.90 (s, 3 H) 4.53 (br. s., 2 H) 6.85 (s, 1 H) 7.29 (dd, J = 8.55, 1.69 Hz, 1 H) 7.67 (d, J = 8.59 Hz, 1 H) 7.74 (d, J = 1.18 Hz, 1 H) 12.78 (br. s., 1 H). LC-MS 383.3 [M − H]$^-$, 385.3 [M + H]$^+$, RT 0.70 min. |
| 206 | 6-(2-((3-(Benzyl(methyl)amino)azetidin-1-yl)methyl)-1-methyl-1H-indol-5-yl)-5-ethyl-4-hydroxy-2-oxo-1,2-dihydropyridine-3-carboxylic acid<br>$^1$H NMR (500 MHz, DMSO-d$_6$) δ ppm 0.99 (t, J = 7.37 Hz, 3 H) 2.33 (q, J = 7.33 Hz, 2 H) 3.88 (s, 3 H) 3.90-5.00 (m, 12 H) 6.86 (br. s., 1 H) 7.29 (dd, J = 8.55, 1.62 Hz, 1 H) 7.45 (br. s., 3 H) 7.57 (br. s., 2 H) 7.66 (d, J = 8.59 Hz, 1 H) 7.73 (s, 1 H) 12.76 (s, 1 H) 13.91 (br. s., 1 H). LC-MS 499.4 [M − H]$^-$, 501.4 [M + H]$^+$, RT 0.88 min. |
| 207 | 6-(2-((3-((2-(Dimethylamino)ethyl)(methyl)amino)azetidin-1-yl)methyl)-1-methyl-1H-indol-5-yl)-5-ethyl-4-hydroxy-2-oxo-1,2-dihydropyridine-3-carboxylic acid<br>$^1$H NMR (500 MHz, MeOH-d$_4$) δ ppm 1.06 (t, J = 7.37 Hz, 3 H) 2.45 (q, J = 7.38 Hz, 2 H) 2.44 (br. s., 2 H) 3.03-3.10 (m, 1 H) 3.12-3.20 (m, 1 H) 3.23 (s, 3 H) 3.35 (s, 6 H) 3.37-3.43 (m, 1 H) 3.46-3.55 (m, 2 H) 3.56-3.67 (m, 2 H) 3.96 (s, 3 H) 4.65 (d, J = 15.00 Hz, 1 H) 4.69 (d, J = 15.00 Hz, 1 H) 7.00 (s, 1 H) 7.35 (dd, J = 8.55, 1.69 Hz, 1 H) 7.63-7.70 (m, 1 H) 7.74 (d, J = 1.10 Hz, 1 H). LC-MS 482.5 [M + H]$^+$, RT 0.70 min. |
| 208 | 5-Ethyl-4-hydroxy-6-(1-methyl-2-(((1R,5S,6s)-6-(methylamino)-3-azabicyclo[3.1.0]hexan-3-yl)methyl)-1H-indol-5-yl)-2-oxo-1,2-dihydropyridine-3-carboxylic acid<br>$^1$H NMR (500 MHz, MeOH-d$_4$) δ ppm 1.07 (t, J = 7.41 Hz, 3 H) 1.18 (t, J = 7.01 Hz, 1 H) 2.11 (br. s., 1 H) 2.46 (q, J = 7.38 Hz, 2 H) 2.77 (s, 3 H) 3.01 (br. s., 1 H) 3.30-3.35 (m, 4 H) 3.84 (s, 3 H) 4.15 (br. s., 2 H) 6.63 (br. s., 1 H) 7.27 (dd, J = 8.47, 1.69 Hz, 1 H) 7.57 (d, J = 8.59 Hz, 1 H) 7.65 (d, J = 1.26 Hz, 1 H). LC-MS 435.4 [M − H]$^-$, 437.4 [M + H]$^+$, RT 0.74 min. |
| 209 | 6-(2-((cyclobutyl(methyl)amino)methyl)-1-methyl-1H-indol-5-yl)-5-ethyl-4-hydroxy-2-oxo-1,2-dihydropyridine-3-carboxylic acid hydrochloride<br>$^1$H NMR (500 MHz, DMSO-d$_6$) δ ppm 0.99 (t, J = 7.4 Hz, 3 H) 1.64-1.81 (m, 2 H) 2.12-2.23 (m, 2 H) 2.25-2.41 (m, 4 H) 2.62 (br. s., 3 H) 3.80-3.88 (m, 1 H) 3.91 (s, 3 H) 4.34-4.44 (m, 1 H) 4.57 (br. d, J = 14.5 Hz, 1 H) 6.92 (s, 1 H) 7.31 (dd, J = 8.5, 1.6 Hz, 1 H) 7.69 (d, J = 8.5 Hz, 1 H) 7.75 (s, 1 H) 10.52 (br. s., 1 H) 12.75 (br. s., 1 H) 13.91 (br. s, 1 H). LC-MS 408.3 [M − H]$^-$, 410.4 [M + H]$^+$, RT 0.95 min. |

| Cpd | Name |
|---|---|
| 210 | 6-(2-(((cyclopropylmethyl)(methyl)amino)methyl)-1-methyl-1H-indol-5-yl)-5-ethyl-4-hydroxy-2-oxo-1,2-dihydropyridine-3-carboxylic acid hydrochloride<br>¹H NMR (500 MHz, DMSO-d₆) δ ppm 0.38-0.50 (m, 2 H) 0.64-0.73 (m, 2 H) 1.00 (t, J = 7.4 Hz, 3 H) 1.19-1.29 (m, 1 H) 2.34 (q, J = 7.4 Hz, 2 H) 2.80 (d, J = 4.1 Hz, 3 H) 2.96-3.07 (m, 1 H) 3.16-3.28 (m, 1 H) 4.52 (dd, J = 14.2, 6.3 Hz, 1 H) 4.75 (br. d, J = 14.2 Hz, 1 H) 6.94 (s, 1 H) 7.31 (dd, J = 8.5, 1.6 Hz, 1 H) 7.69 (d, J = 8.5 Hz, 1 H) 7.76 (d, J = 1.6 Hz, 1 H) 10.41 (br. s., 1 H) 12.76 (br. s., 1 H) 13.91 (br. s, 1 H). LC-MS 408.4 [M − H]⁻, 410.4 [M + H]⁺, RT 0.95 min. |
| 211 | 6-(2-((cyclopentyl(methyl)amino)methyl)-1-methyl-1H-indol-5-yl)-5-ethyl-4-hydroxy-2-oxo-1,2-dihydropyridine-3-carboxylic acid hydrochloride<br>¹H NMR (500 MHz, DMSO-d₆) δ ppm 0.99 (t, J = 7.4 Hz, 3 H) 1.49-1.67 (m, 2 H) 1.70-1.83 (m, 2 H) 1.84-1.96 (m, 2 H) 1.99-2.10 (m, 1 H) 2.13-2.24 (m, 1 H) 2.34 (q, J = 7.4 Hz, 2 H) 2.71 (d, J = 4.4 Hz, 3 H) 3.68-3.81 (m, 1 H) 3.91 (s, 3 H) 4.47 (dd, J = 14.3, 7.4 Hz, 1 H) 4.73 (br. d, J = 14.3 Hz, 1 H) 6.94 (s, 1 H) 7.32 (dd, J = 8.7, 1.4 Hz, 1 H) 7.70 (d, J = 8.7 Hz, 1 H) 7.76 (d, J = 1.4 Hz, 1 H) 10.32 (br. s., 1 H) 12.76 (br. s., 1 H) 13.91 (br. s, 1 H). LC-MS 422.4 [M − H]⁻, 424.4 [M + H]⁺, RT 0.98 min. |
| 212 | 6-(2-((cyclopropyl(methyl)amino)methyl)-1-methyl-1H-indol-5-yl)-5-ethyl-4-hydroxy-2-oxo-1,2-dihydropyridine-3-carboxylic acid hydrochloride<br>¹H NMR (500 MHz, DMSO-d₆) δ ppm 0.72-0.89 (m, 4 H) 1.00 (t, J = 7.3 Hz, 3 H) 2.34 (q, J = 7.3 Hz, 2 H) 2.87 (br. s., 3 H) 2.91-3.00 (m, 1 H) 3.92 (s, 3 H) 4.73 (br. s., 2 H) 6.91 (br. s., 1 H) 7.31 (d, J = 8.8 Hz, 1 H) 7.69 (d, J = 8.8 Hz, 1 H) 7.75 (s, 1 H) 10.32 (br. s., 1 H) 12.76 (br. s., 1 H) 13.91 (s, 1 H). LC-MS 394.3 [M − H]⁻, 396.3 [M + H]⁺, RT 0.96 min. |
| 213 | 5-ethyl-4-hydroxy-6-(1-methyl-2-((phenylamino)methyl)-1H-indol-5-yl)-2-oxo-1,2-dihydropyridine-3-carboxylic acid<br>¹H NMR (500 MHz, CHCl₃-d) δ ppm 1.14 (t, J = 7.3 Hz, 3 H) 2.53 (q, J = 7.3 Hz, 2 H) 3.78 (s, 3 H) 4.54 (s, 2 H) 6.63 (s, 1 H) 6.91 (d, J = 7.9 Hz, 2 H) 6.96 (t, J = 7.9 Hz, 1 H) 7.24 (dd, J = 8.5, 1.6 Hz, 1 H) 7.29 (t, J = 7.9 Hz, 2 H) 7.44 (d, J = 8.5 Hz, 1 H) 7.62 (d, J = 1.6 Hz, 1 H) 10.08 (br. s., 1 H) 13.83 (br. s., 1 H). LC-MS 416.2 [M − H]⁻, 418.3 [M + H]⁺, RT 1.42 min. |
| 214 | 6-(2-((benzylamino)methyl)-1-methyl-1H-indol-5-yl)-5-ethyl-4-hydroxy-2-oxo-1,2-dihydropyridine-3-carboxylic acid hydrochloride<br>¹H NMR (500 MHz, MeOH-d₄) δ ppm 1.06 (q, J = 7.4 Hz, 2 H) 2.45 (q, J = 7.4 Hz, 2 H) 3.84 (s, 3 H) 4.39 (br. s., 2 H) 4.58 (br. s., 2 H) 6.88 (br. s., 1 H) 7.34 (d, J = 8.2 Hz, 1 H) 7.46-7.58 (m, 5 H) 7.64 (d, J = 8.2 Hz, 1 H) 7.73 (s, 1 H). LC-MS 430.2 [M − H]⁻, 432.2 [M + H]⁺, RT 0.98 min. |
| 215 | (R)-5-ethyl-4-hydroxy-6-(1-methyl-2-((1-phenylethylamino)methyl)-1H-indol-5-yl)-2-oxo-1,2-dihydropyridine-3-carboxylic acid hydrochloride<br>¹H NMR (500 MHz, MeOH-d₄) δ ppm 1.05 (q, J = 7.4 Hz, 2 H) 1.77 (d, J = 6.6 Hz, 3 H) 2.43 (d, J = 7.4 Hz, 2 H) 3.68 (s, 3 H) 4.24 (d, J = 14.5 Hz, 1 H) 4.47 (d, J = 14.5 Hz, 1 H) 4.61 (q, J = 6.6 Hz, 1 H) 6.81 (s, 1 H) 7.32 (d, J = 8.5 Hz, 1 H) 7.49-7.59 (m, 5 H) 7.61 (d, J = 8.5 Hz, 1 H) 7.71 (s, 1 H). LC-MS 444.2 [M − H]⁻, 446.2 [M + H]⁺, RT 1.01 min. |
| 216 | (S)-5-ethyl-4-hydroxy-6-(1-methyl-2-((1-phenylethylamino)methyl)-1H-indol-5-yl)-2-oxo-1,2-dihydropyridine-3-carboxylic acid hydrochloride<br>¹H NMR (500 MHz, MeOH-d₄) δ ppm 1.05 (q, J = 7.4 Hz, 2 H) 1.77 (d, J = 6.6 Hz, 3 H) 2.43 (d, J = 7.4 Hz, 2 H) 3.68 (s, 3 H) 4.24 (d, J = 14.5 Hz, 1 H) 4.47 (d, J = 14.5 Hz, 1 H) 4.61 (q, J = 6.6 Hz, 1 H) 6.81 (s, 1 H) 7.32 (d, J = 8.5 Hz, 1 H) 7.49-7.59 (m, 5 H) 7.61 (d, J = 8.5 Hz, 1 H) 7.71 (s, 1 H). LC-MS 444.2 [M − H]⁻, 446.2 [M + H]⁺, RT 1.01 min. |
| 217 | 5-ethyl-4-hydroxy-6-(1-methyl-2-((2-phenylpropan-2-ylamino)methyl)-1H-indol-5-yl)-2-oxo-1,2-dihydropyridine-3-carboxylic acid hydrochloride<br>¹H NMR (500 MHz, MeOH-d₄) δ ppm 1.04 (t, J = 7.4 Hz, 3 H) 1.94 (s, 6 H) 2.42 (q, J = 7.4 Hz, 2 H) 3.57 (s, 3 H) 4.18 (s, 2 H) 6.74 (s, 1 H) 7.32 (dd, J = 8.7, 1.4 Hz, 1 H) 7.51-7.57 (m, 1 H) 7.58-7.63 (m, 3 H) 7.69-7.75 (m, 3 H). LC-MS 458.2 [M − H]⁻, 460.3 [M + H]⁺, RT 0.99 min. |
| 218 | 6-(2-((benzyl(methyl)amino)methyl)-1-methyl-1H-indol-5-yl)-5-ethyl-4-hydroxy-2-oxo-1,2-dihydropyridine-3-carboxylic acid hydrochloride<br>¹H NMR (500 MHz, MeOH-d₄) δ ppm 1.06 (t, J = 7.3 Hz, 3 H) 2.45 (d, J = 7.3 Hz, 2 H) 2.90 (s, 3 H) 3.75 (s, 3 H) 4.39-4.67 (m, 3 H) 4.74-4.82 (m, 1 H) 6.98 (br. s., 1 H) 7.36 (d, J = 8.5 Hz, 1 H) 7.55 (br. s., 5 H) 7.65 (d, J = 8.5 Hz, 1 H) 7.76 (s, 1 H). LC-MS 444.1 [M − H]⁻, 446.3 [M + H]⁺, RT 0.98 min. |
| 219 | 5-ethyl-4-hydroxy-6-(1-methyl-2-((pyridin-2-ylmethylamino)methyl)-1H-indol-5-yl)-2-oxo-1,2-dihydropyridine-3-carboxylic acid hydrochloride<br>¹H NMR (500 MHz, MeOH-d₄) δ ppm 1.07 (t, J = 7.3 Hz, 3 H) 2.45 (q, J = 7.3 Hz, 2 H) 3.93 (s, 3 H) 4.55 (s, 2 H) 4.67 (s, 2 H) 6.91 (s, 1 H) 7.34 (dd, J = 8.5, 1.6 Hz, 1 H) 7.46 (dd, J = 7.7, 5.2 Hz, 1 H) 7.52 (d, J = 7.7 Hz, 1 H) 7.65 (d, J = 8.5 Hz, 1 H) 7.73 (d, J = 1.6 Hz, 1 H) 7.92 (td, J = 7.7, 1.9 Hz, 1 H) 8.70 (d, J = 5.2 Hz, 1 H). LC-MS 431.2 [M − H]⁻, 433.2 [M + H]⁺, RT 0.90 min. |
| 220 | 5-ethyl-4-hydroxy-6-(1-methyl-2-((pyridin-3-ylmethylamino)methyl)-1H-indol-5-yl)-2-oxo-1,2-dihydropyridine-3-carboxylic acid hydrochloride<br>¹H NMR (500 MHz, MeOH-d₄) δ ppm 1.06 (t, J = 7.4 Hz, 3 H) 2.44 (q, J = 7.4 Hz, 2 H) 3.96 (br. s., 3 H) 4.63-4.82 (m, 4 H) 6.97 (br. s., 1 H) 7.35 (d, J = 8.2 Hz, 1 H) 7.66 (d, J = 8.2 Hz, 1 H) 7.74 (br. s., 1 H) 8.13 (br. s., 1 H) 8.78 (br. s., 1 H) 8.94 (br. s., 1 H) 9.16 (br. s., 1 H). LC-MS 431.3 [M − H]⁻, 433.2 [M + H]⁺, RT 0.82 min. |

| Cpd | Name |
|---|---|
| 221 | 5-ethyl-4-hydroxy-6-(1-methyl-2-((pyridin-4-ylmethylamino)methyl)-1H-indol-5-yl)-2-oxo-1,2-dihydropyridine-3-carboxylic acid hydrochloride<br>$^1$H NMR (500 MHz, MeOH-d$_4$) δ ppm 1.06 (t, J = 7.4 Hz, 3 H) 2.45 (q, J = 7.4 Hz, 2 H) 3.96 (s, 3 H) 4.74 (br. s., 2 H) 4.75 (br. s., 2 H) 6.97 (br. s., 1 H) 7.36 (d, J = 8.5 Hz, 1 H) 7.67 (d, J = 8.5 Hz, 1 H) 7.75 (s, 1 H) 8.19 (d, J = 5.4 Hz, 2 H) 8.93 (d, J = 5.4 Hz, 2 H). LC-MS 431.2 [M − H]$^-$, 433.2 [M + H]$^+$, RT 0.81 min. |
| 222 | 6-(2-((cyclohexylmethylamino)methyl)-1-methyl-1H-indol-5-yl)-5-ethyl-4-hydroxy-2-oxo-1,2-dihydropyridine-3-carboxylic acid hydrochloride<br>$^1$H NMR (500 MHz, DMSO-d$_6$) δ ppm 0.90-0.97 (m, 2 H) 0.98 (t, J = 7.3 Hz, 3 H) 1.08-1.27 (m, 3 H) 1.57-1.85 (m, 6 H) 2.33 (q, J = 7.3 Hz, 2 H) 2.89 (br. s., 2 H) 3.86 (s, 3 H) 4.44 (br. s., 2 H) 6.85 (s, 1 H) 7.28 (dd, J = 8.5, 1.3 Hz, 1 H) 7.66 (d, J = 8.5 Hz, 1 H) 7.73 (d, J = 1.3 Hz, 1 H) 9.03-9.25 (m, 2 H) 12.78 (br. s., 1 H) 13.90 (br. s., 1 H). LC-MS 436.2 [M − H]$^-$, 438.3 [M + H]$^+$, RT 1.00 min. |
| 223 | 6-(2-((cyclopropylmethylamino)methyl)-1-methyl-1H-indol-5-yl)-5-ethyl-4-hydroxy-2-oxo-1,2-dihydropyridine-3-carboxylic acid hydrochloride<br>$^1$H NMR (500 MHz, DMSO-d$_6$) δ ppm 0.39-0.44 (m, 2 H) 0.56-0.64 (m, 2 H) 0.99 (t, J = 7.3 Hz, 3 H) 1.13-1.25 (m, 1 H) 2.33 (q, J = 7.3 Hz, 2 H) 2.94 (d, J = 6.6 Hz, 2 H) 3.88 (s, 3 H) 4.44 (br. s., 2 H) 6.85 (s, 1 H) 7.28 (dd, J = 8.5, 1.6 Hz, 1 H) 7.66 (d, J = 8.5 Hz, 1 H) 7.73 (d, J = 1.6 Hz, 1 H) 9.49 (br. s., 2 H) 12.77 (br. s., 1 H) 13.91 (br. s., 1 H). LC-MS 394.2 [M − H]$^-$, 396.2 [M + H]$^+$, RT 0.90 min. |
| 224 | 5-ethyl-4-hydroxy-6-(1-methyl-2-((methyl(pyridin-3-ylmethyl)amino)methyl)-1H-indol-5-yl)-2-oxo-1,2-dihydropyridine-3-carboxylic acid hydrochloride<br>$^1$H NMR (500 MHz, MeOH-d$_4$) δ ppm 1.07 (t, J = 7.0 Hz, 3 H) 2.45 (q, J = 7.0 Hz, 2 H) 2.89 (br. s., 3 H) 3.96 (br. s., 3 H) 4.70-4.95 (m, 4 H) 7.04 (br. s., 1 H) 7.37 (d, J = 8.2 Hz, 1 H) 7.67 (d, J = 8.2 Hz, 1 H) 7.76 (br. s., 1 H) 8.09 (br. s., 1 H) 8.77 (br. s., 1 H) 8.92 (br. s., 1 H) 9.16 (br. s., 1 H). LC-MS 445.1 [M − H]$^-$, 447.3 [M + H]$^+$, RT 0.91 min. |
| 225 | 5-ethyl-4-hydroxy-6-(1-methyl-2-((methyl(pyridin-4-ylmethyl)amino)methyl)-1H-indol-5-yl)-2-oxo-1,2-dihydropyridine-3-carboxylic acid hydrochloride<br>$^1$H NMR (500 MHz, MeOH-d$_4$) δ ppm 1.08 (t, J = 7.4 Hz, 3 H) 2.45 (q, J = 7.3 Hz, 2 H) 2.87 (br. s., 3 H) 3.95 (s., 3 H) 4.56-4.81 (m, 4 H) 6.96 (br. s., 1 H) 7.35 (d, J = 7.3 Hz, 1 H) 7.63 (d, J = 7.3 Hz, 1 H) 7.73 (br. s., 1 H) 8.09-8.50 (m, 2 H) 8.74-8.98 (m, 2 H). LC-MS 445.1 [M − H]$^-$, 447.2 [M + H]$^+$, RT 1.00 min. |
| 226 | 5-ethyl-4-hydroxy-6-(1-methyl-2-((1-(pyridin-4-yl)ethylamino)methyl)-1H-indol-5-yl)-2-oxo-1,2-dihydropyridine-3-carboxylic acid hydrochloride<br>$^1$H NMR (500 MHz, MeOH-d$_4$) δ ppm 1.07 (t, J = 7.4 Hz, 3 H) 1.88 (br. s., 3 H) 2.44 (q, J = 7.4 Hz, 2 H) 3.90 (br. s., 3 H) 4.48-5.12 (m, 3 H) 6.95 (br. s., 1 H) 7.34 (d, J = 6.9 Hz, 1 H) 7.63 (d, J = 6.9 Hz, 1 H) 7.73 (br. s., 1 H) 8.24-8.58 (m, 2 H) 8.83-9.20 (m, 2 H). LC-MS 445.1 [M − H]$^-$, 447.2 [M + H]$^+$, RT 0.91 min. |
| 227 | 5-ethyl-4-hydroxy-6-(1-methyl-2-(((tetrahydro-2H-pyran-4-yl)methylamino)methyl)-1H-indol-5-yl)-2-oxo-1,2-dihydropyridine-3-carboxylic acid hydrochloride<br>$^1$H NMR (500 MHz, DMSO-d$_6$) δ ppm 0.98 (t, J = 7.3 Hz, 3 H) 1.24 (qd, J = 12.6, 3.8 Hz, 2 H) 1.70 (br. d, J = 13.6 Hz, 2 H) 1.93-2.09 (m, 1 H) 2.33 (q, J = 7.3 Hz, 2 H) 2.96 (br. s., 2 H) 3.29 (td, J = 11.7, 1.7 Hz, 3 H) 3.83-3.89 (m, 2 H) 3.87 (s, 3 H) 4.45 (br. s., 2 H) 6.85 (s, 1 H) 7.29 (dd, J = 8.5, 1.6 Hz, 1 H) 7.67 (d, J = 8.5 Hz, 1 H) 7.74 (d, J = 1.6 Hz, 1 H) 9.08-9.35 (m, 2 H) 12.78 (br. s., 1 H) 13.89 (br. s., 1 H). LC-MS 438.1 [M − H]$^-$, 440.3 [M + H]$^+$, RT 0.90 min. |
| 228 | 6-(2-((cyclopropylamino)methyl)-1-methyl-1H-indol-5-yl)-5-ethyl-4-hydroxy-2-oxo-1,2-dihydropyridine-3-carboxylic acid hydrochloride<br>$^1$H NMR (500 MHz, DMSO-d$_6$) δ ppm 0.79 (q, J = 6.6 Hz, 2 H) 0.91-0.96 (m, 2 H) 0.98 (t, J = 7.3 Hz, 3 H) 2.32 (q, J = 7.4 Hz, 2 H) 2.80 (br. s., 1 H) 3.88 (s, 3 H) 4.54 (br. s., 2 H) 6.81 (s, 1 H) 7.28 (dd, J = 8.5, 1.6 Hz, 1 H) 7.67 (d, J = 8.5 Hz, 1 H) 7.73 (d, J = 1.6 Hz, 1 H) 9.40-9.66 (m, 2 H) 12.77 (br. s., 1 H) 13.90 (br. s., 1 H). LC-MS 380.1 [M − H]$^-$, 382.2 [M + H]$^+$, RT 0.90 min. |
| 229 | 6-(2-((cyclopentylamino)methyl)-1-methyl-1H-indol-5-yl)-5-ethyl-4-hydroxy-2-oxo-1,2-dihydropyridine-3-carboxylic acid hydrochloride<br>$^1$H NMR (500 MHz, DMSO-d$_6$) δ ppm 0.98 (t, J = 7.4 Hz, 3 H) 1.50-1.61 (m, 2 H) 1.68-1.81 (m, 4 H) 1.94-2.11 (m, 2 H) 2.32 (q, J = 7.3 Hz, 2 H) 3.61 (br. s., 1 H) 3.88 (s, 3 H) 4.44 (br. s, 2 H) 6.84 (s, 1 H) 7.28 (dd, J = 8.7, 1.7 Hz, 1 H) 7.67 (d, J = 8.7 Hz, 1 H) 7.73 (d, J = 1.7 Hz, 1 H) 9.33 (br. s., 2 H) 12.79 (s, 1 H) 13.90 (s, 1 H). LC-MS 408.1 [M − H]$^-$, 410.2 [M + H]$^+$, RT 0.93 min. |
| 230 | 5-ethyl-6-(2-(((1-ethylpyrrolidin-2-yl)methylamino)methyl)-1-methyl-1H-indol-5-yl)-4-hydroxy-2-oxo-1,2-dihydropyridine-3-carboxylic acid dihydrochloride<br>$^1$H NMR (500 MHz, MeOH-d$_4$) δ ppm 1.07 (t, J = 7.3 Hz, 3 H) 1.42 (t, J = 7.1 Hz, 3 H) 2.00-2.11 (m, 1 H) 2.11-2.26 (m, 2 H) 2.45 (q, J = 7.3 Hz, 2 H) 2.47-2.54 (m, 1 H) 3.15-3.25 (m, 1 H) 3.26-3.35 (m, 1 H) 3.53-3.67 (m, 2 H) 3.70-3.79 (m, 1 H) 3.79-3.86 (m, 1 H) 3.87-3.95 (m, 1 H) 3.97 (s, 3 H) 4.67 (s, 2 H) 6.99 (s, 1 H) 7.34 (dd, J = 8.5, 1.9 Hz, 1 H) 7.66 (d, J = 8.5 Hz, 1 H) 7.74 (d, J = 1.9 Hz, 1 H). LC-MS 451.2 [M − H]$^-$, 453.3 [M + H]$^+$, RT 0.83 min. |
| 231 | 5-ethyl-4-hydroxy-6-(1-methyl-2-(((1-methylpiperidin-3-yl)methylamino)methyl)-1H-indol-5-yl)-2-oxo-1,2-dihydropyridine-3-carboxylic acid dihydrochloride<br>$^1$H NMR (500 MHz, MeOH-d$_4$) δ ppm 1.06 (t, J = 7.3 Hz, 3 H) 1.32-1.42 (m, 1 H) 1.80-1.95 (m, 1 H) 2.06 (br. d, J = 11.3 Hz, 2 H) 2.45 (q, J = 7.3 Hz, 2 H) 2.45-2.53 (m, 1 H) 2.84 (t, J = 12.1 Hz, 1 H) 2.90 (s, 3 H) 2.91-2.98 (m, 1 H) 3.10-3.26 (m, 2 H) 3.53 (br. d, J = 12.6 Hz, 1 H) 3.65 (br. d, J = 12.6 Hz, 1 H) 3.94 (s, 3 H) 4.61 (s, 2 H) 6.94 (s, 1 H) 7.34 (dd, J = 8.7, 1.7 Hz, 1 H) 7.66 (d, J = 8.7 Hz, 1 H) 7.74 (d, J = 1.7 Hz, 1 H). LC-MS 451.2 [M − H]$^-$, 453.3 [M + H]$^+$, RT 0.75 min. |

| Cpd | Name |
|---|---|
| 232 | 6-(2-((cyclobutylamino)methyl)-1-methyl-1H-indol-5-yl)-5-ethyl-4-hydroxy-2-oxo-1,2-dihydropyridine-3-carboxylic acid hydrochloride
$^1$H NMR (500 MHz, DMSO-d$_6$) δ ppm 0.98 (t, J = 7.3 Hz, 3 H) 1.73-1.89 (m, 2 H) 2.13-2.38 (m, 6 H) 3.76-3.84 (m, 1 H) 3.87 (s, 3 H) 4.32 (br. s., 2 H) 6.81 (s, 1 H) 7.28 (dd, J = 8.5, 1.6 Hz, 1 H) 7.66 (d, J = 8.5 Hz, 1 H) 7.73 (d, J = 1.6 Hz, 1 H) 9.63 (br. s., 2 H) 12.78 (br. s., 1 H) 13.90 (br. s., 1 H). LC-MS 394.1 [M − H]$^-$, 396.2 [M + H]$^+$, RT 0.90 min. |
| 233 | 5-ethyl-4-hydroxy-6-(1-methyl-2-((((1-methylpiperidin-2-yl)methyl)amino)methyl)-1H-indol-5-yl)-2-oxo-1,2-dihydropyridine-3-carboxylic acid dihydrochloride
$^1$H NMR (500 MHz, DMSO-d$_6$) δ ppm 0.98 (t, J = 7.4 Hz, 3 H) 1.37-1.58 (m, 1 H) 1.62-1.94 (m, 3 H) 2.14-2.27 (m, 1 H) 2.33 (q, J = 7.4 Hz, 2 H) 2.88 (br. s., 3 H) 3.00-3.26 (m, 2 H) 3.44-3.61 (m, 2 H) 3.71-3.80 (m, 1 H) 3.83-3.89 (m, 1 H) 3.90 (s, 3 H) 4.54 (br. s., 2 H) 6.91 (s., 1 H) 7.29 (dd, J = 8.5, 1.3 Hz, 1 H) 7.67 (d, J = 8.5 Hz, 1 H) 7.74 (s, 1 H) 9.35-10.05 (m, 2 H) 10.92 (br. s., 1 H) 12.79 (br. s., 1 H) 13.90 (br. s., 1 H). LC-MS 451.3 [M − H]$^-$, 453.3 [M + H]$^+$, RT 0.84 min. |
| 234 | 5-ethyl-4-hydroxy-6-(1-methyl-2-((((1-methylpiperidin-4-yl)methyl)amino)methyl)-1H-indol-5-yl)-2-oxo-1,2-dihydropyridine-3-carboxylic acid dihydrochloride
$^1$H NMR (500 MHz, DMSO-d$_6$) δ ppm 0.98 (t, J = 7.4 Hz, 3 H) 1.42-1.61 (m, 2 H) 1.97-2.09 (m, 2 H) 2.33 (q, J = 7.4 Hz, 2 H) 2.71 (br. d, J = 3.2 Hz, 3 H) 2.83-3.02 (m, 3 H) 3.36-3.45 (m, 4 H) 3.88 (s, 3 H) 4.44 (br. s., 2 H) 6.88 (s, 1 H) 7.28 (dd, J = 8.5, 1.6 Hz, 1 H) 7.67 (d, J = 8.5 Hz, 1 H) 7.73 (s, 1 H) 9.37-9.61 (m, 2 H) 10.26 (br. s., 1 H) 12.78 (br. s., 1 H) 13.91 (br. s., 1 H). LC-MS 451.2 [M − H]$^-$, 453.3 [M + H]$^+$, RT 0.74 min. |
| 235 | 6-(2-((cyclobutylmethylamino)methyl)-1-methyl-1H-indol-5-yl)-5-ethyl-4-hydroxy-2-oxo-1,2-dihydropyridine-3-carboxylic acid hydrochloride
$^1$H NMR (500 MHz, DMSO-d$_6$) δ ppm 0.98 (t, J = 7.3 Hz, 3 H) 1.74-1.94 (m, 4 H) 2.02-2.14 (m, 2 H) 2.33 (q, J = 7.3 Hz, 2 H) 2.66-2.77 (m, 1 H) 3.08 (br. s., 2 H) 3.86 (s, 3 H) 4.41 (br. s., 2 H) 6.83 (s, 1 H) 7.28 (dd, J = 8.5, 1.6 Hz, 1 H) 7.66 (d, J = 8.5 Hz, 1 H) 7.73 (d, J = 1.6 Hz, 1 H) 9.13 (br. s., 2 H) 12.77 (br. s., 1 H) 13.90 (br. s., 1 H). LC-MS 408.1 [M − H]$^-$, 410.3 [M + H]$^+$, RT 0.95 min. |
| 236 | 6-(2-((cyclopentylmethylamino)methyl)-1-methyl-1H-indol-5-yl)-5-ethyl-4-hydroxy-2-oxo-1,2-dihydropyridine-3-carboxylic acid hydrochloride
$^1$H NMR (500 MHz, DMSO-d$_6$) δ ppm 0.98 (t, J = 7.4 Hz, 3 H) 1.21-1.31 (m, 2 H) 1.46-1.68 (m, 4 H) 1.73-1.86 (m, 2 H) 2.26 (dt, J = 15.4, 7.7 Hz, 1 H) 2.33 (q, J = 7.4 Hz, 2 H) 3.00 (br. s., 2 H) 3.87 (s, 3 H) 4.45 (br. s., 2 H) 6.85 (s, 1 H) 7.28 (dd, J = 8.5, 1.6 Hz, 1 H) 7.67 (d, J = 8.5 Hz, 1 H) 7.73 (d, J = 1.6 Hz, 1 H) 9.17 (br. s., 2 H) 12.78 (br. s., 1 H) 13.90 (br. s., 1 H). LC-MS 422.1 [M − H]$^-$, 424.3 [M + H]$^+$, RT 1.00 min. |
| 237 | 5-ethyl-4-hydroxy-6-(1-methyl-2-((neopentylamino)methyl)-1H-indol-5-yl)-2-oxo-1,2-dihydropyridine-3-carboxylic acid hydrochloride
$^1$H NMR (500 MHz, DMSO-d$_6$) δ ppm 0.99 (t, J = 7.4 Hz, 3 H) 1.01 (s, 9 H) 2.33 (q, J = 7.4 Hz, 2 H) 2.87 (br. s., 2 H) 3.87 (s, 3 H) 4.48 (br. s., 2 H) 6.91 (s, 1 H) 7.29 (dd, J = 8.5, 0.9 Hz, 1 H) 7.67 (d, J = 8.5 Hz, 1 H) 7.74 (s, 1 H) 9.01 (br. s., 2 H) 12.77 (br. s., 1 H) 13.91 (br. s., 1 H). LC-MS 410.3 [M − H]$^-$, 412.4 [M + H]$^+$, RT 1.00 min. |
| 238 | 5-ethyl-4-hydroxy-6-(1-methyl-2-((4-methyl-1,4-diazepan-1-yl)methyl)-1H-indol-5-yl)-2-oxo-1,2-dihydropyridine-3-carboxylic acid dihydrochloride
$^1$H NMR (500 MHz, DMSO-d$_6$) δ ppm 0.99 (t, J = 7.4 Hz, 3 H) 2.11-2.38 (m, 2 H) 2.34 (q, J = 7.4 Hz, 2 H) 2.78 (br. s., 3 H) 3.11-3.90 (m, 8 H) 3.93 (br. s., 3 H) 4.68 (br. s., 2 H) 6.97 (br. s., 1 H) 7.30 (d, J = 7.3 Hz, 1 H) 7.68 (d, J = 7.3 Hz, 1 H) 7.74 (br. s., 1 H) 10.98-11.46 (br m, 1 H) 11.55-12.01 (br m, 1 H) 12.75 (br. s., 1 H) 13.91 (br. s., 1 H). LC-MS 437.3 [M − H]$^-$, 439.4 [M + H]$^+$, RT 0.93 min. |
| 239 | 6-(2-((1,4-diazepan-1-yl)methyl)-1-methyl-1H-indol-5-yl)-5-ethyl-4-hydroxy-2-oxo-1,2-dihydropyridine-3-carboxylic acid dihydrochloride
$^1$H NMR (500 MHz, DMSO-d$_6$) δ ppm 0.99 (t, J = 7.4 Hz, 3 H) 2.12-2.30 (m, 2 H) 2.34 (q, J = 7.4 Hz, 2 H) 3.11-3.83 (m, 8 H) 3.93 (br. s., 3 H) 4.69 (br. s., 2 H) 6.98 (br. s., 1 H) 7.30 (d, J = 8.2 Hz, 1 H) 7.68 (d, J = 8.2 Hz, 1 H) 7.75 (br. s., 1 H) 8.97-9.91 (br m, 2 H) 11.69 (br. s., 1 H) 12.76 (br. s., 1 H) 13.91 (br. s., 1 H). LC-MS 423.2 [M − H]$^-$, 425.2 [M + H]$^+$, RT 0.79 min. |
| 240 | 5-ethyl-4-hydroxy-6-(1-methyl-2-(((2-methylcyclopropyl)methyl)-1H-indol-5-yl)-2-oxo-1,2-dihydropyridine-3-carboxylic acid hydrochloride
$^1$H NMR (500 MHz, DMSO-d$_6$) δ ppm 0.36-0.41 (m, 1 H) 0.52-0.60 (m, 1 H) 0.73-0.91 (m, 2 H) 0.98 (t, J = 7.3 Hz, 3 H) 1.05 (d, J = 5.7 Hz, 3 H) 2.33 (q, J = 7.3 Hz, 2 H) 2.85-3.03 (m, 2 H) 3.87 (s, 3 H) 4.43 (br. s., 2 H) 6.83 (s, 1 H) 7.29 (d, J = 8.5 Hz, 1 H) 7.67 (d, J = 8.5 Hz, 1 H) 7.73 (s, 1 H) 9.28 (br. s., 2 H) 12.78 (br. s., 1 H) 13.91 (br. s., 1 H). LC-MS 408.3 [M − H]$^-$, 410.4 [M + H]$^+$, RT 0.99 min. |
| 241 | 6-(2-((cyclohexylamino)methyl)-1-methyl-1H-indol-5-yl)-5-ethyl-4-hydroxy-2-oxo-1,2-dihydropyridine-3-carboxylic acid hydrochloride
$^1$H NMR (500 MHz, DMSO-d$_6$) δ ppm 0.98 (t, J = 7.4 Hz, 3 H) 1.15 (tt, J = 12.9, 3.0 Hz, 1 H) 1.27 (br. q, J = 12.9 Hz, 2 H) 1.45 (qd, J = 12.1, 3.0 Hz, 2 H) 1.64 (br. d, J = 12.9 Hz, 1 H) 1.81 (d, J = 13.6 Hz, 2 H) 2.19 (d, J = 10.7 Hz, 2 H) 2.32 (q, J = 7.4 Hz, 2 H) 3.11-3.21 (m, 1 H) 3.87 (s, 3 H) 4.45 (br. s., 2 H) 6.83 (s, 1 H) 7.28 (dd, J = 8.5, 1.6 Hz, 1 H) 7.67 (d, J = 8.5 Hz, 1 H) 7.73 (d, J = 1.6 Hz, 1 H) 9.30 (br. s., 2 H) 12.79 (br. s., 1 H) 13.90 (br. s., 1 H). LC-MS 422.3 [M − H]$^-$, 424.4 [M + H]$^+$, RT 1.06 min. |

| Cpd | Name |
|---|---|
| 242 | 5-ethyl-4-hydroxy-6-(1-methyl-2-((1-(pyridin-3-yl)ethylamino)methyl)-1H-indol-5-yl)-2-oxo-1,2-dihydropyridine-3-carboxylic acid hydrochloride<br>$^1$H NMR (500 MHz, DMSO-d$_6$) δ ppm 0.98 (t, J = 7.4 Hz, 3 H) 1.75 (d, J = 6.6 Hz, 3 H) 2.32 (q, J = 7.4 Hz, 2 H) 3.77 (s, 3 H) 4.20 (br. d, J = 13.6 Hz, 1 H) 4.46 (br. d, J = 13.6 Hz, 1 H) 4.74 (br. s., 1 H) 6.81 (s, 1 H) 7.27 (dd, J = 8.5, 1.6 Hz, 1 H) 7.64 (d, J = 8.5 Hz, 1 H) 7.71 (s, 1 H) 7.75 (dd, J = 7.6, 5.0 Hz, 1 H) 8.44 (d, J = 7.6 Hz, 1 H) 8.76 (d, J = 5.0 Hz, 1 H) 8.97 (s, 1 H) 10.03 (br. s., 1 H) 10.33 (br. s., 1 H) 12.79 (br. s., 1 H) 13.90 (br. s., 1 H). LC-MS 445.4 [M − H]$^−$, 447.4 [M + H]$^+$, RT 0.96 min. |
| 243 | 6-(2-((allylamino)methyl)-1-methyl-1H-indol-5-yl)-5-ethyl-4-hydroxy-2-oxo-1,2-dihydropyridine-3-carboxylic acid hydrochloride<br>$^1$H NMR (500 MHz, DMSO-d$_6$) δ ppm 0.98 (t, J = 7.4 Hz, 3 H) 2.33 (q, J = 7.4 Hz, 2 H) 3.71 (br. s., 2 H) 3.86 (s, 3 H) 4.42 (br. s., 2 H) 5.45 (dd, J = 10.4, 1.4 Hz, 1 H) 5.52 (dd, J = 17.2, 1.4 Hz, 1 H) 6.00 (ddt, J = 17.2, 10.4, 6.7 Hz, 1 H) 6.82 (s, 1 H) 7.28 (dd, J = 8.5, 1.6 Hz, 1 H) 7.67 (d, J = 8.5 Hz, 1 H) 7.73 (d, J = 1.6 Hz, 1 H) 9.51 (br. s., 2 H) 12.79 (br. s., 1 H) 13.90 (br. s., 1 H). LC-MS 380.3 [M − H]$^−$, 382.3 [M + H]$^+$, RT 0.83 min. |
| 244 | 6-(2-((azetidin-3-ylamino)methyl)-1-methyl-1H-indol-5-yl)-5-ethyl-4-hydroxy-2-oxo-1,2-dihydropyridine-3-carboxylic acid dihydrochloride<br>$^1$H NMR (500 MHz, DMSO-d$_6$) δ ppm 0.99 (t, J = 7.4 Hz, 3 H) 2.33 (q, J = 7.4 Hz, 2 H) 3.90 (s, 3 H) 4.04-4.17 (m, 2 H) 4.21-4.40 (m, 3 H) 4.45 (br. s, 2 H) 6.82 (br. s., 1 H) 7.29 (dd, J = 8.5, 1.6 Hz, 1 H) 7.67 (d, J = 8.5 Hz, 1 H) 7.73 (d, J = 1.6 Hz, 1 H) 9.06 (br. s., 1 H) 9.34 (br. s., 1 H) 10.59 (br. s., 2 H) 12.78 (br. s., 1 H) 13.91 (br. s., 1 H). LC-MS 395.4 [M − H]$^−$, 397.3 [M + H]$^+$, RT 0.80 min. |
| 245 | 5-ethyl-4-hydroxy-6-(1-methyl-2-((1-methylcyclobutylamino)methyl)-1H-indol-5-yl)-2-oxo-1,2-dihydropyridine-3-carboxylic acid hydrochloride<br>$^1$H NMR (500 MHz, DMSO-d$_6$) δ ppm 0.98 (t, J = 7.3 Hz, 3 H) 1.61 (s, 3 H) 1.78-2.01 (m, 4 H) 2.32 (q, J = 7.6 Hz, 2 H) 2.51-2.56 (m, 2 H) 3.88 (s, 3 H) 4.32 (t, J = 5.5 Hz, 2 H) 6.83 (s, 1 H) 7.28 (dd, J = 8.5, 1.6 Hz, 1 H) 7.67 (d, J = 8.5 Hz, 1 H) 7.74 (d, J = 1.6 Hz, 1 H) 9.62 (br. s., 2 H) 12.81 (br. s, 1 H) 13.90 (br. s., 1 H). LC-MS 408.4 [M − H]$^−$, 410.4 [M + H]$^+$, RT 0.86 min. |
| 246 | 5-ethyl-4-hydroxy-6-(1-methyl-2-((1-methylazetidin-3-ylamino)methyl)-1H-indol-5-yl)-2-oxo-1,2-dihydropyridine-3-carboxylic acid dihydrochloride<br>$^1$H NMR (500 MHz, DMSO-d$_6$) δ ppm 0.99 (t, J = 7.4 Hz, 3 H) 2.33 (q, J = 7.4 Hz, 2 H) 2.94 (br. s., 3 H) 3.92 (s, 3 H) 4.10-4.62 (m, 7 H) 6.84 (s, 1 H) 7.28 (dd, J = 8.5, 1.6 Hz, 1 H) 7.67 (d, J = 8.5 Hz, 1 H) 7.73 (d, J = 1.6 Hz, 1 H) 8.85 (br. s., 1 H) 11.03 (br. s., 2 H) 12.77 (br. s., 1 H) 13.90 (br. s., 1 H). LC-MS 409.3 [M − H]$^−$, 411.4 [M + H]$^+$, RT 0.81 min. |
| 247 | 5-ethyl-4-hydroxy-6-(1-methyl-2-((4-methylpiperidin-1-yl)methyl)-1H-indol-5-yl)-2-oxo-1,2-dihydropyridine-3-carboxylic acid<br>$^1$H NMR (500 MHz, MeOH-d$_4$) δ ppm 1.04 (d, J = 6.46 Hz, 3 H) 1.09 (t, J = 1.00 Hz, 3 H) 1.40-1.55 (m, 2 H) 1.70-1.83 (m, 1 H) 1.93-2.02 (m, 2 H) 2.47 (q, J = 7.28 Hz, 2 H) 3.16 (t, J = 12.10 Hz, 2 H) 3.64 (d, J = 11.98 Hz, 2 H) 3.96 (s, 3 H) 4.66 (br. s., 2 H) 6.98 (br. s., 1 H) 7.39 (d, J = 8.43 Hz, 1 H) 7.70 (d, J = 8.59 Hz, 1 H) 7.78 (s, 1 H). LC-MS 424.5 [M + H]$^+$, RT 0.54 min. |
| 248 | 6-(2-((4-(dimethylamino)piperidin-1-yl)methyl)-1-methyl-1H-indol-5-yl)-5-ethyl-4-hydroxy-2-oxo-1,2-dihydropyridine-3-carboxylic acid<br>$^1$H NMR (500 MHz, MeOH-d$_4$) δ ppm 1.05-1.13 (m, 7 H) 2.47 (d, J = 6.86 Hz, 2 H) 2.95 (br. s., 4 H) 3.33-3.35 (m, 6 H) 4.00 (br. s., 3 H) 7.35-7.43 (m, 1 H) 7.67-7.74 (m, 1 H) 7.76-7.82 (m, 1 H). LC-MS 453.2 [M + H]$^+$, RT 0.43 min. |
| 249 | 6-(2-((4,4-difluoropiperidin-1-yl)methyl)-1-methyl-1H-indol-5-yl)-5-ethyl-4-hydroxy-2-oxo-1,2-dihydropyridine-3-carboxylic acid<br>$^1$H NMR (500 MHz, MeOH-d$_4$) δ ppm 1.13-1.25 (m, 7 H) 2.52-2.63 (m, 4 H) 4.10 (br. s., 2 H) 4.84-4.97 (m, 1 H) 7.52 (br. s., 1 H) 7.79-7.86 (m, 1 H) 7.87-7.95 (m, 1 H). LC-MS 446.2 [M + H]$^+$, RT 0.67 min. |
| 250 | 6-(2-((3-(dimethylamino)piperidin-1-yl)methyl)-1-methyl-1H-indol-5-yl)-5-ethyl-4-hydroxy-2-oxo-1,2-dihydropyridine-3-carboxylic acid<br>$^1$H NMR (500 MHz, MeOH-d$_4$) δ ppm 1.05-1.13 (m, 3 H) 1.83-2.02 (m, 1 H) 2.16-2.40 (m, 2 H) 2.41-2.54 (m, 2 H) 3.01 (br. s., 6 H) 3.03-3.03 (m, 1 H) 3.16-3.31 (m, 2 H) 3.55-3.72 (m, 2 H) 3.94-4.12 (m, 5 H) 6.89 (s, 1 H) 7.39 (br. s., 1 H) 7.70 (br. s., 2 H). LC-MS 453.2 [M + H]$^+$, RT 0.85 min. |
| 251 | 6-(2-(1,4'-bipiperidin-1'-ylmethyl)-1-methyl-1H-indol-5-yl)-5-ethyl-4-hydroxy-2-oxo-1,2-dihydropyridine-3-carboxylic acid<br>$^1$H NMR (500 MHz, MeOH-d$_4$) δ ppm 0.91-0.97 (m, 5 H) 1.36-1.48 (m, 2 H) 1.66-1.79 (m, 4 H) 1.82-1.92 (m, 2 H) 2.02-2.18 (m, 2 H) 2.26-2.38 (m, 4 H) 2.88-2.99 (m, 2 H) 3.39-3.51 (m, 4 H) 3.65-3.75 (m, 2 H) 3.86 (s, 3 H) 4.60 (s, 2 H) 6.89 (s, 1 H) 7.25 (dd, J = 8.59, 1.73 Hz, 1 H) 7.57 (d, J = 8.59 Hz, 1 H) 7.65 (d, J = 1.18 Hz, 1 H). LC-MS 493.3 [M + H]$^+$, RT 1.15 min. |
| 252 | 6-(2-((4-aminopiperidin-1-yl)methyl)-1-methyl-1H-indol-5-yl)-5-ethyl-4-hydroxy-2-oxo-1,2-dihydropyridine-3-carboxylic acid<br>$^1$H NMR (500 MHz, MeOH-d$_4$) δ ppm 1.06-1.12 (m, 3 H) 2.06-2.21 (m, 2 H) 2.32 (d, J = 11.82 Hz, 2 H) 2.47 (q, J = 7.41 Hz, 2 H) 3.34-3.42 (m, 2 H) 3.51-3.59 (m, 1 H) 3.71-3.83 (m, 2 H) 3.99 (s, 3 H) 4.73 (br. s., 2 H) 7.04 (br. s., 1 H) 7.38 (dd, J = 8.59, 1.66 Hz, 1 H) 7.70 (d, J = 8.67 Hz, 1 H) 7.78 (s, 1 H). LC-MS 425.2 [M + H]$^+$, RT 0.76 min. |

| Cpd | Name |
|---|---|
| 253 | (S)-6-(2-((3-aminopiperidin-1-yl)methyl)-1-methyl-1H-indol-5-yl)-5-ethyl-4-hydroxy-2-oxo-1,2-dihydropyridine-3-carboxylic acid<br>$^1$H NMR (500 MHz, MeOH-d$_4$) δ ppm 1.07-1.10 (m, 3 H) 1.70-1.78 (m, 1 H) 1.96-2.10 (m, 1 H) 2.11-2.27 (m, 2 H) 2.47 (q, J = 7.38 Hz, 2 H) 3.15-3.28 (m, 2 H) 3.56-3.67 (m, 1 H) 3.68-3.82 (m, 2 H) 4.00 (s, 3 H) 4.76 (d, J = 9.54 Hz, 2 H) 7.02 (s, 1 H) 7.38 (dd, J = 8.59, 1.66 Hz, 1 H) 7.69 (d, J = 8.59 Hz, 1 H) 7.78 (d, J = 1.18 Hz, 1 H). LC-MS 425.2 [M + H]$^+$, RT 0.5 min. |
| 254 | 5-ethyl-4-hydroxy-6-(2-((4-hydroxypiperidin-1-yl)methyl)-1-methyl-1H-indol-5-yl)-2-oxo-1,2-dihydropyridine-3-carboxylic acid<br>$^1$H NMR (500 MHz, MeOH-d$_4$) δ ppm 1.06-1.10 (m, 3 H) 1.95-2.09 (m, 2 H) 2.16-2.24 (m, 1 H) 2.43-2.52 (m, 2 H) 3.19-3.28 (m, 2 H) 3.44-3.49 (m, 1 H) 3.62-3.71 (m, 1 H) 3.97 (s, 4 H) 4.10-4.16 (m, 1 H) 4.65-4.73 (m, 2 H) 6.95-7.02 (m, 1 H) 7.36-7.41 (m, 1 H) 7.67-7.72 (m, 1 H) 7.76-7.80 (m, 1 H). LC-MS 426.1 [M + H]$^+$, RT 0.85 min. |
| 255 | 5-ethyl-4-hydroxy-6-(2-((3-hydroxypiperidin-1-yl)methyl)-1-methyl-1H-indol-5-yl)-2-oxo-1,2-dihydropyridine-3-carboxylic acid<br>$^1$H NMR (500 MHz, MeOH-d$_4$) δ ppm 0.84-0.88 (m, 3 H) 1.54-1.65 (m, 1 H) 1.83-1.90 (m, 1 H) 2.25 (d, J = 7.41 Hz, 4 H) 2.92-3.05 (m, 1 H) 3.34-3.46 (m, 1 H) 3.57-3.63 (m, 2 H) 3.73 (s, 3 H) 3.91-4.00 (m, 3 H) 6.72-6.79 (m, 2 H) 7.12-7.19 (m, 1 H) 7.44-7.49 (m, 1 H) 7.55 (s, 1 H). LC-MS 426.2 [M + H]$^+$, RT 0.74 min. |
| 256 | 5-ethyl-4-hydroxy-6-(1-methyl-2-((4-(methylamino)piperidin-1-yl)methyl)-1H-indol-5-yl)-2-oxo-1,2-dihydropyridine-3-carboxylic acid<br>$^1$H NMR (500 MHz, MeOH-d$_4$) δ ppm 0.92-0.96 (m, 3 H) 1.87-2.00 (m, 2 H) 2.32 (d, J = 7.41 Hz, 3 H) 2.62 (s, 3 H) 3.18 (m, J = 3.30, 1.60, 1.60 Hz, 2 H) 3.66 (br. s., 2 H) 3.85 (s, 3 H) 4.59 (s, 2 H) 6.89 (s, 1 H) 7.24 (dd, J = 8.59, 1.66 Hz, 1 H) 7.55 (d, J = 8.59 Hz, 1 H) 7.64 (d, J = 1.10 Hz, 1 H). LC-MS 439.2 [M + H]$^+$, RT 0.84 min. |
| 257 | (S)-5-ethyl-4-hydroxy-6-(1-methyl-2-((3-(methylamino)piperidin-1-yl)methyl)-1H-indol-5-yl)-2-oxo-1,2-dihydropyridine-3-carboxylic acid<br>$^1$H NMR (500 MHz, DMSO-d$_6$) δ ppm 0.97-1.03 (m, 3 H) 2.30-2.40 (m, 4 H) 2.54-2.61 (m, 4 H) 3.66-3.78 (m, 5 H) 3.91-3.99 (m, 3 H) 6.89 (s, 1 H) 7.27-7.36 (m, 1 H) 7.67-7.73 (m, 1 H) 7.73-7.79 (m, 1 H). LC-MS 439.3 [M + H]$^+$, RT 0.90 min. |
| 258 | 5-ethyl-4-hydroxy-6-(1-methyl-2-((2-(trifluoromethyl)piperidin-1-yl)methyl)-1H-indol-5-yl)-2-oxo-1,2-dihydropyridine-3-carboxylic acid<br>$^1$H NMR (500 MHz, DMSO-d$_6$) δ ppm 1.01 (t, J = 1.00 Hz, 3 H) 1.75-1.82 (m, 1 H) 1.82-1.90 (m, 1 H) 1.99-2.06 (m, 1 H) 2.33-2.40 (m, 3 H) 2.72-2.81 (m, 1 H) 2.96-3.06 (m, 1 H) 3.31-3.37 (m, 1 H) 3.82 (s, 3 H) 4.06-4.12 (m, 4 H) 6.52-6.56 (m, 1 H) 7.19-7.24 (m, 1 H) 7.54-7.57 (m, 1 H) 7.58-7.62 (m, 1 H) 7.62-7.65 (m, 1 H). LC-MS 478.2 [M + H]$^+$, RT 1.01 min. |
| 259 | 5-ethyl-4-hydroxy-6-(2-((2-(2-methoxyethyl)piperidin-1-yl)methyl)-1-methyl-1H-indol-5-yl)-2-oxo-1,2-dihydropyridine-3-carboxylic acid<br>$^1$H NMR (500 MHz, DMSO-d$_6$) δ ppm 1.01 (t, J = 1.00 Hz, 3 H) 1.69-1.81 (m, 2 H) 1.98-2.10 (m, 2 H) 2.30-2.40 (m, 2 H) 3.11-3.18 (m, 1 H) 3.18-3.26 (m, 1 H) 3.31 (s, 3 H) 3.40-3.47 (m, 1 H) 3.47-3.58 (m, 4 H) 3.58-3.66 (m, 1 H) 3.94 (s, 3 H) 4.37-4.49 (m, 1 H) 4.59-4.65 (m, 1 H) 4.91-5.02 (m, 1 H) 6.96 (s, 2 H) 7.27-7.35 (m, 2 H) 7.67-7.73 (m, 2 H) 7.73-7.79 (m, 2 H) 12.69-12.81 (m, 1 H) 13.87-13.96 (m, 1 H). LC-MS 468.3 [M + H]$^+$, RT 0.56 min. |
| 260 | 5-ethyl-4-hydroxy-6-(2-((2-(3-methoxypropyl)piperidin-1-yl)methyl)-1-methyl-1H-indol-5-yl)-2-oxo-1,2-dihydropyridine-3-carboxylic acid<br>$^1$H NMR (500 MHz, DMSO-d$_6$) δ ppm 0.97-1.03 (m, 3 H) 1.61-1.79 (m, 3 H) 1.79-1.88 (m, 1 H) 1.91-1.99 (m, 1 H) 2.00-2.08 (m, 1 H) 2.18-2.28 (m, 1 H) 2.31-2.40 (m, 2 H) 3.11-3.19 (m, 1 H) 3.28 (s, 3 H) 3.41 (m, 4 H) 3.88-3.95 (m, 5 H) 4.43-4.52 (m, 1 H) 4.57-4.65 (m, 1 H) 4.84-4.95 (m, 1 H) 6.95 (s, 1 H) 7.28-7.36 (m, 1 H) 7.69 (s, 1 H) 7.73-7.78 (m, 1 H) 12.69-12.81 (m, 1 H) 13.85-13.97 (m, 1 H). LC-MS 482.2 [M + H]$^+$, RT 0.56 min. |
| 261 | 5-ethyl-4-hydroxy-6-(1-methyl-2-((methyl(piperidin-4-yl)amino)methyl)-1H-indol-5-yl)-2-oxo-1,2-dihydropyridine-3-carboxylic acid<br>$^1$H NMR (500 MHz, MeOH-d$_4$) δ ppm 1.10 (t, J = 1.00 Hz, 3 H) 2.26 (d, J = 11.19 Hz, 2 H) 2.48 (q, J = 7.36 Hz, 2 H) 2.56 (d, J = 12.45 Hz, 2 H) 2.93 (s, 3 H) 3.24 (t, J = 12.37 Hz, 2 H) 3.69 (d, J = 12.53 Hz, 2 H) 3.93-4.02 (m, 6 H) 7.06 (s, 1 H) 7.40 (dd, J = 8.59, 1.58 Hz, 1 H) 7.71 (d, J = 8.59 Hz, 1 H) 7.79 (s, 1 H). LC-MS 439.2 [M + H]$^+$, RT 0.77 min. |
| 262 | 5-ethyl-4-hydroxy-6-(1-methyl-2-((methyl(piperidin-3-yl)amino)methyl)-1H-indol-5-yl)-2-oxo-1,2-dihydropyridine-3-carboxylic acid<br>$^1$H NMR (500 MHz, MeOH-d$_4$) δ ppm 1.10 (t, J = 1.00 Hz, 3 H) 1.90-2.02 (m, 2 H) 2.04-2.15 (m, 2 H) 2.19-2.29 (m, 2 H) 2.43-2.53 (m, 2 H) 2.95 (s, 3 H) 3.03-3.13 (m, 2 H) 3.94-4.03 (m, 6 H) 7.05-7.09 (m, 1 H) 7.39 (dd, J = 8.59, 1.66 Hz, 1 H) 7.71 (d, J = 8.59 Hz, 1 H) 7.79 (d, J = 1.10 Hz, 1 H). LC-MS 439.2 [M + H]$^+$, RT 0.85 min. |
| 263 | 5-ethyl-4-hydroxy-6-(1-methyl-2-((piperidin-4-ylamino)methyl)-1H-indol-5-yl)-2-oxo-1,2-dihydropyridine-3-carboxylic acid<br>$^1$H NMR (500 MHz, MeOH-d$_4$) δ ppm 1.06-1.12 (m, 3 H) 2.05-2.17 (m, 2 H) 2.47 (q, J = 7.36 Hz, 2 H) 2.55 (d, J = 11.59 Hz, 2 H) 3.22 (br. s., 2 H) 3.60-3.68 (m, 2 H) 3.78 (s, 1 H) 3.96 (s, 3 H) 4.68 (br. s., 2 H) 6.93-6.99 (m, 1 H) 7.36 (dd, J = 8.55, 1.54 Hz, 1 H) 7.68 (d, J = 8.59 Hz, 1 H) 7.76 (s, 1 H). LC-MS 425.2 [M + H]$^+$, RT 0.74 min. |

| Cpd | Name |
|---|---|
| 264 | 6-(2-(((cyclopropylmethyl)(piperidin-4-yl)amino)methyl)-1-methyl-1H-indol-5-yl)-5-ethyl-4-hydroxy-2-oxo-1,2-dihydropyridine-3-carboxylic acid<br>$^1$H NMR (500 MHz, MeOH-d$_4$) δ ppm 0.50 (m, 2 H) 0.84 (m, 2 H) 1.07-1.11 (m, 3 H) 1.18-1.28 (m, 1 H) 2.33 (m, 2 H) 2.48 (m, 4 H) 3.27 (br. s., 3 H) 3.68 (m, 3 H) 4.01 (s, 3 H) 4.13 (m, 1 H) 4.86 (br. s., 2 H) 7.09 (br. s., 1 H) 7.40 (dd, J = 8.55, 1.38 Hz, 1 H) 7.72 (d, J = 8.59 Hz, 1 H) 7.80 (s, 1 H). LC-MS 479.6 [M + H]$^+$, RT 0.82 min. |
| 265 | 6-(2-(((cyclopropylmethyl)(piperidin-3-yl)amino)methyl)-1-methyl-1H-indol-5-yl)-5-ethyl-4-hydroxy-2-oxo-1,2-dihydropyridine-3-carboxylic acid<br>$^1$H NMR (500 MHz, MeOH-d$_4$) δ ppm 0.32 (br. s., 2 H) 0.65 (t, J = 7.80 Hz, 2 H) 0.86-0.89 (m, 3 H) 1.04-1.13 (m, 1 H) 1.68-1.81 (m, 1 H) 1.83-1.95 (m, 1 H) 1.98-2.09 (m, 2 H) 2.21-2.31 (m, 3 H) 2.86 (br. s., 2 H) 3.21-3.30 (m, 2 H) 3.74-3.83 (m, 5 H) 4.59-4.66 (m, 2 H) 6.89 (br. s., 1 H) 7.18 (dd, J = 8.59, 1.26 Hz, 1 H) 7.50 (d, J = 8.59 Hz, 1 H) 7.58 (s, 1 H). LC-MS 479.6 [M + H]$^+$, RT 0.82 min. |
| 266 | (S)-5-ethyl-4-hydroxy-6-(1-methyl-2-((2-((phenylamino)methyl)pyrrolidin-1-yl)methyl)-1H-indol-5-yl)-2-oxo-1,2-dihydropyridine-3-carboxylic acid<br>$^1$H NMR (500 MHz, MeOH-d$_4$) δ ppm 1.07-1.11 (t, 3 H) 1.97-2.07 (m, 1 H) 2.09-2.19 (m, 1 H) 2.23-2.32 (m, 1 H) 2.44-2.53 (m, 3 H) 3.47-3.55 (m, 3 H) 3.62-3.69 (m, 1 H) 3.89 (s, 3 H) 4.12 (s, 1 H) 4.70 (d, J = 14.34 Hz, 1 H) 4.91 (d, J = 14.30 Hz, 1 H) 6.75 (d, J = 7.72 Hz, 2 H) 6.79 (t, J = 7.33 Hz, 1 H) 6.96 (s, 1 H) 7.14-7.20 (m, 2 H) 7.37 (dd, J = 8.59, 1.66 Hz, 1 H) 7.63 (d, J = 8.59 Hz, 1 H) 7.74 (d, J = 1.26 Hz, 1 H). LC-MS 501.6 [M + H]$^+$, RT 1.08 min. |
| 267 | 5-ethyl-4-hydroxy-6-(1-methyl-2-((3-(pyridin-2-yl)pyrrolidin-1-yl)methyl)-1H-indol-5-yl)-2-oxo-1,2-dihydropyridine-3-carboxylic acid<br>$^1$H NMR (500 MHz, MeOH-d$_4$) δ ppm 1.09 (t, J = 7.30 Hz, 3 H) 2.47 (q, J = 7.40 Hz, 2 H) 3.58-3.65 (m, 1 H) 3.86-3.99 (m, 2 H) 4.03 (s, 4 H) 4.14-4.22 (m, 2 H) 4.24-4.32 (m, 2 H) 7.05 (br. s., 1 H) 7.38 (dd, J = 8.59, 1.42 Hz, 1 H) 7.70 (d, J = 8.59 Hz, 1 H) 7.77 (s, 1 H) 7.93 (br. s., 1 H) 8.18 (d, J = 7.64 Hz, 1 H) 8.49-8.57 (m, 1 H) 8.81 (d, J = 4.34 Hz, 1 H). LC-MS 473.4 [M + H]$^+$, RT 0.89 min. |
| 268 | 5-ethyl-4-hydroxy-6-(1-methyl-2-((3-(pyridin-4-yl)pyrrolidin-1-yl)methyl)-1H-indol-5-yl)-2-oxo-1,2-dihydropyridine-3-carboxylic acid<br>$^1$H NMR (500 MHz, MeOH-d$_4$) δ ppm 1.09 (t, J = 7.30 Hz, 3 H) 2.47 (q, J = 7.40 Hz, 2 H) 3.58-3.65 (m, 1 H) 3.86-3.99 (m, 2 H) 4.03 (s, 4 H) 4.14-4.22 (m, 2 H) 4.24-4.32 (m, 2 H) 7.02-7.09 (m, 1 H) 7.38 (dd, J = 8.59, 1.58 Hz, 1 H) 7.70 (d, J = 8.59 Hz, 1 H) 7.77 (d, J = 1.10 Hz, 1 H) 8.23 (br. s., 2 H) 8.83-8.94 (m, 2 H). LC-MS 473.4 [M + H]$^+$, RT 0.73 min. |
| 269 | 6-(2-((3-carboxyazetidin-1-yl)methyl)-1-methyl-1H-indol-5-yl)-5-ethyl-4-hydroxy-2-oxo-1,2-dihydropyridine-3-carboxylic acid<br>$^1$H NMR (500 MHz, MeOH-d$_4$) δ ppm 0.96 (t, J = 7.40 Hz, 3 H) 2.35 (q, J = 7.38 Hz, 2 H) 3.65 (d, J = 2.99 Hz, 1 H) 3.80 (br. s., 3 H) 4.36 (br. s., 4 H) 4.69 (br. s., 2 H) 6.79 (s, 1 H) 7.25 (dd, J = 8.55, 1.69 Hz, 1 H) 7.55 (d, J = 8.59 Hz, 1 H) 7.64 (d, J = 1.18 Hz, 1 H). LC-MS 426.3 [M + H]$^+$, RT 0.83 min. |
| 270 | 6-(2-((3-(dimethylcarbamoyl)azetidin-1-yl)methyl)-1-methyl-1H-indol-5-yl)-5-ethyl-4-hydroxy-2-oxo-1,2-dihydropyridine-3-carboxylic acid<br>$^1$H NMR (500 MHz, MeOH-d$_4$) δ ppm 1.08 (t, J = 7.41 Hz, 3 H) 2.47 (q, J = 7.40 Hz, 2 H) 3.02 (br. s, 6 H) 3.93 (br. s., 4 H) 4.37-4.53 (m, 4 H) 4.78-4.84 (m, 2 H) 6.91 (s, 1 H) 7.35-7.40 (m, 1 H) 7.67 (s, 1 H) 7.76 (d, J = 1.18 Hz, 1 H). LC-MS 453.2 [M + H]$^+$, RT 0.81 min. |
| 271 | 5-ethyl-4-hydroxy-6-(2-((3-(hydroxymethyl)azetidin-1-yl)methyl)-1-methyl-1H-indol-5-yl)-2-oxo-1,2-dihydropyridine-3-carboxylic acid<br>$^1$H NMR (500 MHz, MeOH-d$_4$) δ ppm 1.09 (t, J = 7.40 Hz, 3 H) 2.47 (d, J = 7.41 Hz, 2 H) 3.68 (br. s., 1 H) 3.74-3.80 (m, 1 H) 3.92 (m, J = 5.10 Hz, 5 H) 4.12-4.20 (m, 1 H) 4.21-4.28 (m, 1 H) 4.28-4.37 (m, 1 H) 4.76 (br. s., 2 H) 6.86-6.94 (m, 1 H) 7.37 (d, J = 8.43 Hz, 1 H) 7.67 (d, J = 8.43 Hz, 1 H) 7.76 (br. s., 1 H). LC-MS 412.3 [M + H]$^+$, RT 0.91 min. |
| 272 | (R)-5-ethyl-4-hydroxy-6-(1-methyl-2-((1,1,1-trifluoropropan-2-ylamino)methyl)-1H-indol-5-yl)-2-oxo-1,2-dihydropyridine-3-carboxylic acid<br>$^1$H NMR (500 MHz, DMSO-d$_6$) δ ppm 1.01 (t, J = 7.40 Hz, 3 H) 1.25 (d, J = 6.78 Hz, 3 H) 2.30-2.39 (m, 4 H) 3.82 (s, 3 H) 4.03-4.14 (m, 3 H) 6.51-6.57 (m, 1 H) 7.17-7.25 (m, 1 H) 7.57-7.62 (m, 1 H) 7.62-7.66 (m, 1 H) 12.72-12.77 (m, 1 H). LC-MS 438.3 [M + H]$^+$, RT 1.38 min. |
| 273 | (S)-5-ethyl-4-hydroxy-6-(1-methyl-2-((1,1,1-trifluoropropan-2-ylamino)methyl)-1H-indol-5-yl)-2-oxo-1,2-dihydropyridine-3-carboxylic acid<br>$^1$H NMR (500 MHz, DMSO-d$_6$) δ ppm 1.01 (t, J = 7.40 Hz, 3 H) 1.25 (d, J = 6.78 Hz, 3 H) 2.30-2.39 (m, 4 H) 3.82 (s, 3 H) 4.03-4.14 (m, 3 H) 6.51-6.57 (m, 1 H) 7.17-7.25 (m, 1 H) 7.57-7.62 (m, 1 H) 7.62-7.66 (m, 1 H) 12.72-12.77 (m, 1 H). LC-MS 438.3 [M + H]$^+$, RT 1.41 min. |
| 274 | 6-(2-(((1,3-difluoropropan-2-ylamino)methyl)-1-methyl-1H-indol-5-yl)-5-ethyl-4-hydroxy-2-oxo-1,2-dihydropyridine-3-carboxylic acid<br>$^1$H NMR (500 MHz, DMSO-d$_6$) δ ppm 0.99 (t, J = 7.37 Hz, 3 H) 2.34 (q, J = 7.50 Hz, 2 H) 3.65 (br. s., 1 H) 3.89 (s, 3 H) 4.60 (br. s., 2 H) 4.83-5.09 (m, 4 H) 6.89 (s, 1 H) 7.30 (dd, J = 8.51, 1.58 Hz, 1 H) 7.69 (d, J = 8.59 Hz, 1 H) 7.76 (d, J = 1.10 Hz, 1 H) 12.78-12.86 (m, 1 H). LC-MS 420.3 [M + H]$^+$, RT 0.97 min. |

-continued

| Cpd | Name |
|---|---|
| 275 | 5-ethyl-4-hydroxy-6-(1-methyl-2-((1-methylcyclopropylamino)methyl)-1H-indol-5-yl)-2-oxo-1,2-dihydropyridine-3-carboxylic acid<br>$^1$H NMR (500 MHz, MeOH-d$_4$) δ ppm 0.91-0.99 (m, 2 H) 1.08 (t, J = 7.40 Hz, 3 H) 1.16-1.20 (m, 2 H) 1.67 (s, 3 H) 2.40-2.51 (m, 2 H) 3.93 (s, 3 H) 4.67-4.73 (m, 2 H) 6.85-6.91 (m, 1 H) 7.34-7.40 (m, 1 H) 7.66-7.72 (m, 1 H) 7.73-7.79 (m, 1 H). LC-MS 396.3 [M + H]$^+$, RT 0.82 min. |
| 276 | 6-(2-(((3aR,4R,6aS)-4-aminohexahydrocyclopenta[c]pyrrol-2(1H)-yl)methyl)-1-methyl-1H-indol-5-yl)-5-ethyl-4-hydroxy-2-oxo-1,2-dihydropyridine-3-carboxylic acid<br>$^1$H NMR (500 MHz, MeOH-d$_4$) δ ppm 1.09 (t, J = 7.37 Hz, 3 H) 1.76-1.96 (m, 2 H) 2.08-2.20 (m, 2 H) 2.47 (q, J = 7.40 Hz, 2 H) 3.00-3.30 (m, 4 H) 3.39-3.48 (m, 2 H) 3.78 (s, 3 H) 4.01 (s, 4 H) 6.99-7.07 (m, 1 H) 7.38 (dd, J = 8.55, 1.54 Hz, 1 H) 7.69 (d, J = 8.51 Hz, 1 H) 7.77 (s, 1 H). LC-MS 451.4 [M + H]$^+$, RT 0.67 min. |
| 277 | 5-ethyl-4-hydroxy-6-(1-methyl-2-((prop-2-ynylamino)methyl)-1H-indol-5-yl)-2-oxo-1,2-dihydropyridine-3-carboxylic acid hydrochloride<br>$^1$H NMR (500 MHz, MeOH-d$_4$) δ ppm 1.09 (t, J = 7.37 Hz, 3 H) 2.41-2.52 (m, 2 H) 3.39 (s, 1 H) 3.94 (s, 3 H) 4.12 (br. s., 2 H) 4.67 (br. s., 2 H) 6.85-6.96 (m, 1 H) 7.37 (d, J = 8.43 Hz, 1 H) 7.68 (d, J = 8.51 Hz, 1 H) 7.76 (s, 1 H). LC-MS 380.4 [M + H]$^+$, RT 0.54 min. |
| 278 | 6-(2-(((3aR,4R,6aS)-4-(dimethylamino)hexahydrocyclopenta[c]pyrrol-2(1H)-yl)methyl)-1-methyl-1H-indol-5-yl)-5-ethyl-4-hydroxy-2-oxo-1,2-dihydropyridine-3-carboxylic acid<br>LC-MS 479.2 [M + H]$^+$, RT 0.75 min. |
| 279 | 6-(2-(((3aR,4R,7aS)-4-(dimethylamino)-1H-isoindol-2(3H,3aH,4H,5H,6H,7H,7aH)-yl)methyl)-1-methyl-1H-indol-5-yl)-5-ethyl-4-hydroxy-2-oxo-1,2-dihydropyridine-3-carboxylic acid<br>LC-MS 493.3 [M + H]$^+$, RT 0.78 min. |
| 280 | 6-(2-(((3aR,4R,7aS)-4-(benzyl(methyl)amino)-1H-isoindol-2(3H,3aH,4H,5H,6H,7H,7aH)-yl)methyl)-1-methyl-1H-indol-5-yl)-5-ethyl-4-hydroxy-2-oxo-1,2-dihydropyridine-3-carboxylic acid<br>LC-MS 569.3 [M + H]$^+$, RT 0.81 min. |
| 281 | 6-(2-(((3aR,4R,6aS)-4-(dibenzylamino)hexahydrocyclopenta[c]pyrrol-2(1H)-yl)methyl)-1-methyl-1H-indol-5-yl)-5-ethyl-4-hydroxy-2-oxo-1,2-dihydropyridine-3-carboxylic acid<br>LC-MS 631.3 [M + H]$^+$, RT 1.27 min. |
| 282 | 5-ethyl-4-hydroxy-6-(1-methyl-2-(((3aR,4R,7aS)-4-(methylamino)-1H-isoindol-2(3H,3aH,4H,5H,6H,7H,7aH)-yl)methyl)-1H-indol-5-yl)-2-oxo-1,2-dihydropyridine-3-carboxylic acid<br>LC-MS 479.4 [M + H]$^+$, RT 0.76 min. |
| 283 | 6-(2-(((3aR,4R,7aS)-4-(dibenzylamino)-1H-isoindol-2(3H,3aH,4H,5H,6H,7H,7aH)-yl)methyl)-1-methyl-1H-indol-5-yl)-5-ethyl-4-hydroxy-2-oxo-1,2-dihydropyridine-3-carboxylic acid<br>LC-MS 645.6 [M + H]$^+$, RT 1.17 min. |
| 284 | 6-(2-(((3aR,4R,7aS)-4-amino-1H-isoindol-2(3H,3aH,4H,5H,6H,7H,7aH)-yl)methyl)-1-methyl-1H-indol-5-yl)-5-ethyl-4-hydroxy-2-oxo-1,2-dihydropyridine-3-carboxylic acid<br>LC-MS 465.3 [M + H]$^+$, RT 0.76 min. |
| 285 | 6-(2-(((3aR,5r,6aS)-5-(dimethylamino)hexahydrocyclopenta[c]pyrrol-2(1H)-yl)methyl)-1-methyl-1H-indol-5-yl)-5-ethyl-4-hydroxy-2-oxo-1,2-dihydropyridine-3-carboxylic acid<br>LC-MS 479.4 [M + H]$^+$, RT 0.75 min. |
| 286 | 6-(2-(((3aR,5r,6aS)-5-(dibenzylamino)hexahydrocyclopenta[c]pyrrol-2(1H)-yl)methyl)-1-methyl-1H-indol-5-yl)-5-ethyl-4-hydroxy-2-oxo-1,2-dihydropyridine-3-carboxylic acid<br>LC-MS 631.3 [M + H]$^+$, RT 0.93 min. |
| 287 | 6-(2-(((3aR,5r,6aS)-5-aminohexahydrocyclopenta[c]pyrrol-2(1H)-yl)methyl)-1-methyl-1H-indol-5-yl)-5-ethyl-4-hydroxy-2-oxo-1,2-dihydropyridine-3-carboxylic acid<br>LC-MS 451.4 [M + H]$^+$, RT 0.85 min. |
| 288 | 6-(2-(((3aR,5r,6aS)-5-(benzyl(methyl)amino)hexahydrocyclopenta[c]pyrrol-2(1H)-yl)methyl)-1-methyl-1H-indol-5-yl)-5-ethyl-4-hydroxy-2-oxo-1,2-dihydropyridine-3-carboxylic acid<br>LC-MS 555.3 [M + H]$^+$, RT 0.82 min. |
| 289 | 5-ethyl-4-hydroxy-6-(1-methyl-2-(((3aR,5r,6aS)-5-(methylamino)hexahydrocyclopenta[c]pyrrol-2(1H)-yl)methyl)-1H-indol-5-yl)-2-oxo-1,2-dihydropyridine-3-carboxylic acid<br>LC-MS 465.3 [M + H]$^+$, RT 0.73 min. |
| 290 | 6-(2-(aminomethyl)-1-methyl-1H-indol-5-yl)-5-ethyl-4-hydroxy-2-oxo-1,2-dihydropyridine-3-carboxylic acid<br>$^1$H NMR (500 MHz, CHCl$_3$-d) δ ppm 7.68-7.75 (m, 1 H) 7.51-7.58 (m, 1 H) 7.33-7.40 (m, 1 H) 6.76-6.86 (m, 1 H) 4.56-4.71 (m, 2 H) 3.88 (s, 3 H) 3.63 (s, 1 H) 2.53-2.66 (m, 2 H) 1.19-1.19 (m, 1 H) 1.16 (s, 3 H). LC-MS 340.2 [M − H]$^-$, RT 0.81 min. |
| 291 | 5-ethyl-4-hydroxy-6-(2-((4-methoxybenzylamino)methyl)-1-methyl-1H-indol-5-yl)-2-oxo-1,2-dihydropyridine-3-carboxylic acid<br>LC-MS 460.3 [M − H]$^-$, 462.4 [M + H]$^+$, RT 0.87 min. (Method A) |
| 292 | 5-ethyl-6-(2-((4-fluorobenzylamino)methyl)-1-methyl-1H-indol-5-yl)-4-hydroxy-2-oxo-1,2-dihydropyridine-3-carboxylic acid<br>LC-MS 448.3 [M − H]$^-$, 450.5 [M + H]$^+$, RT 0.88 min. (Method A) |
| 293 | 5-ethyl-4-hydroxy-6-(2-((2-methoxybenzylamino)methyl)-1-methyl-1H-indol-5-yl)-2-oxo-1,2-dihydropyridine-3-carboxylic acid<br>LC-MS 460.4 [M − H]$^-$, 462.5 [M + H]$^+$, RT 0.90 min. (Method A) |

| Cpd | Name |
|---|---|
| 294 | 5-ethyl-4-hydroxy-6-(1-methyl-2-((3-methylbenzylamino)methyl)-1H-indol-5-yl)-2-oxo-1,2-dihydropyridine-3-carboxylic acid<br>LC-MS 444.2 [M − H]⁻, 446.4 [M + H]⁺, RT 0.93 min. (Method A) |
| 295 | 5-ethyl-4-hydroxy-6-(1-methyl-2-((2-methylbenzylamino)methyl)-1H-indol-5-yl)-2-oxo-1,2-dihydropyridine-3-carboxylic acid<br>LC-MS 444.3 [M − H]⁻, 446.5 [M + H]⁺, RT 0.92 min. (Method A) |
| 296 | 5-ethyl-4-hydroxy-6-(2-((3-methoxybenzylamino)methyl)-1-methyl-1H-indol-5-yl)-2-oxo-1,2-dihydropyridine-3-carboxylic acid<br>LC-MS 460.4 [M − H]⁻, 462.5 [M + H]⁺, RT 0.87 min. (Method A) |
| 297 | 5-ethyl-4-hydroxy-6-(1-methyl-2-((4-methylbenzylamino)methyl)-1H-indol-5-yl)-2-oxo-1,2-dihydropyridine-3-carboxylic acid<br>LC-MS 444.3 [M − H]⁻, 446.5 [M + H]⁺, RT 0.92 min. (Method A) |
| 298 | 5-ethyl-6-(2-((3-fluorobenzylamino)methyl)-1-methyl-1H-indol-5-yl)-4-hydroxy-2-oxo-1,2-dihydropyridine-3-carboxylic acid<br>LC-MS 448.2 [M − H]⁻, 450.5 [M + H]⁺, RT 0.89 min. (Method A) |
| 299 | 5-ethyl-6-(2-((2-fluorobenzylamino)methyl)-1-methyl-1H-indol-5-yl)-4-hydroxy-2-oxo-1,2-dihydropyridine-3-carboxylic acid<br>LC-MS 448.3 [M − H]⁻, 450.4 [M + H]⁺, RT 0.88 min. (Method A) |
| 300 | 5-ethyl-4-hydroxy-6-(2-(((2-methoxyethyl)(methyl)amino)methyl)-1-methyl-1H-indol-5-yl)-2-oxo-1,2-dihydropyridine-3-carboxylic acid<br>LC-MS 412.3 [M − H]⁻, 414.4 [M + H]⁺, RT 0.80 min. (Method A) |
| 301 | 6-(2-((cycloheptylmethylamino)methyl)-1-methyl-1H-indol-5-yl)-5-ethyl-4-hydroxy-2-oxo-1,2-dihydropyridine-3-carboxylic acid<br>LC-MS 450.3 [M − H]⁻, 452.5 [M + H]⁺, RT 0.98 min. (Method A) |
| 302 | 6-(2-((2-(dimethylamino)ethylamino)methyl)-1-methyl-1H-indol-5-yl)-5-ethyl-4-hydroxy-2-oxo-1,2-dihydropyridine-3-carboxylic acid<br>LC-MS 411.3 [M − H]⁻, 413.4 [M + H]⁺, RT 0.64 min. (Method A) |
| 303 | 6-(2-(((2-(dimethylamino)ethyl)(methyl)amino)methyl)-1-methyl-1H-indol-5-yl)-5-ethyl-4-hydroxy-2-oxo-1,2-dihydropyridine-3-carboxylic acid<br>LC-MS 425.3 [M − H]⁻, 427.5 [M + H]⁺, RT 0.79 min. (Method A) |
| 333 | 6-(2-((butylamino)methyl)-1-methyl-1H-indol-5-yl)-5-ethyl-4-hydroxy-2-oxo-1,2-dihydropyridine-3-carboxylic acid<br>¹H NMR (500 MHz, DMSO-d₆) δ ppm 0.86-0.95 (m, 3 H) 0.98 (t, J = 7.41 Hz, 3 H) 1.36 (s × t, J = 7.44 Hz, 2 H) 1.68 (dt, J = 15.53, 7.84 Hz, 2 H) 2.27-2.39 (m, 2 H) 2.92-3.08 (m, 2 H) 3.87 (s, 3 H) 4.44 (br. s., 2 H) 6.83 (s, 1 H) 7.28 (dd, J = 8.51, 1.58 Hz, 1 H) 7.66 (d, J = 8.51 Hz, 1 H) 7.73 (d, J = 1.26 Hz, 1 H) 9.24 (br. s., 2 H) 12.78 (s, 1 H) 13.90 (s, 1 H). LC-MS 396.3 [M − H]⁻, 398.3 [M + H]⁺, RT 1.05 min. |
| 334 | 5-ethyl-4-hydroxy-6-(1-methyl-2-((pentylamino)methyl)-1H-indol-5-yl)-2-oxo-1,2-dihydropyridine-3-carboxylic acid<br>¹H NMR (500 MHz, DMSO-d₆) δ ppm 0.83-0.93 (m, 3 H) 0.98 (t, J = 7.25 Hz, 3 H) 1.24-1.36 (m, 4 H) 1.62-1.76 (m, 2 H) 2.33 (q, J = 7.25 Hz, 2 H) 2.94-3.05 (m, 2 H) 3.87 (s, 3 H) 4.44 (br. s., 2 H) 6.82 (s, 1 H) 7.28 (dd, J = 8.51, 1.58 Hz, 1 H) 7.66 (d, J = 8.51 Hz, 1 H) 7.70-7.77 (m, 1 H) 9.23 (br. s., 2 H) 12.78 (s, 1 H) 13.90 (s, 1 H). LC-MS 410.3 [M − H]⁻, 412.3 [M + H]⁺, RT 1.10 min. |
| 335 | 5-ethyl-6-(2-((hexylamino)methyl)-1-methyl-1H-indol-5-yl)-4-hydroxy-2-oxo-1,2-dihydropyridine-3-carboxylic acid<br>¹H NMR (500 MHz, DMSO-d₆) δ ppm 0.87 (t, J = 6.78 Hz, 3 H) 0.98 (t, J = 7.41 Hz, 3 H) 1.22-1.37 (m, 6 H) 1.69 (quin, J = 7.49 Hz, 2 H) 2.33 (q, J = 7.25 Hz, 2 H) 3.00 (br. s., 2 H) 3.87 (s, 3 H) 4.43 (br. s., 2 H) 6.83 (s, 1 H) 7.22-7.32 (m, 1 H) 7.66 (d, J = 8.51 Hz, 1 H) 7.73 (s, 1 H) 9.29 (br. s., 2 H) 12.77 (s, 1 H) 13.90 (br. s., 1 H). LC-MS 424.3 [M − H]⁻, 426.3 [M + H]⁺, RT 1.20 min. |
| 336 | 5-ethyl-6-(2-((heptylamino)methyl)-1-methyl-1H-indol-5-yl)-4-hydroxy-2-oxo-1,2-dihydropyridine-3-carboxylic acid<br>¹H NMR (500 MHz, DMSO-d₆) δ ppm 0.83-0.91 (m, 3 H) 0.98 (t, J = 7.41 Hz, 3 H) 1.20-1.38 (m, 8 H) 1.63-1.76 (m, 2 H) 2.33 (q, J = 7.25 Hz, 2 H) 2.92-3.05 (m, 2 H) 3.87 (s, 3 H) 4.43 (br. s., 2 H) 6.83 (s, 1 H) 7.28 (dd, J = 8.51, 1.58 Hz, 1 H) 7.66 (d, J = 8.51 Hz, 1 H) 7.73 (d, J = 1.26 Hz, 1 H) 9.30 (br. s., 2 H) 12.78 (s, 1 H) 13.91 (s, 1 H). LC-MS 438.3 [M − H]⁻, 440.3 [M + H]⁺, RT 1.20 min. |
| 337 | 5-ethyl-4-hydroxy-6-(1-methyl-2-((octylamino)methyl)-1H-indol-5-yl)-2-oxo-1,2-dihydropyridine-3-carboxylic acid<br>¹H NMR (500 MHz, DMSO-d₆) δ ppm 0.86 (t, J = 6.62 Hz, 3 H) 0.98 (t, J = 7.25 Hz, 3 H) 1.26 (br. s., 10 H) 1.61-1.76 (m, 2 H) 2.33 (q, J = 7.25 Hz, 2 H) 3.00 (br. s., 2 H) 3.86 (s, 3 H) 4.43 (br. s., 2 H) 6.82 (s, 1 H) 7.28 (d, J = 8.20 Hz, 1 H) 7.66 (d, J = 8.51 Hz, 1 H) 7.73 (s, 1 H) 9.23 (br. s., 2 H) 12.77 (br. s., 1 H) 13.90 (br. s., 1 H). LC-MS 452.3 [M − H]⁻, 454.3 [M + H]⁺, RT 1.28 min. |
| 338 | 5-ethyl-4-hydroxy-6-(1-methyl-2-((nonylamino)methyl)-1H-indol-5-yl)-2-oxo-1,2-dihydropyridine-3-carboxylic acid<br>¹H NMR (500 MHz, DMSO-d₆) δ ppm 0.81-0.90 (m, 3 H) 0.98 (t, J = 7.41 Hz, 3 H) 1.18-1.38 (m, 12 H) 1.62-1.76 (m, 2 H) 2.32 (q, J = 7.25 Hz, 2 H) 2.92-3.05 (m, 2 H) 3.87 (s, 3 H) 4.43 (br. s., 2 H) 6.82 (s, 1 H) 7.28 (dd, J = 8.67, 1.42 Hz, 1 H) 7.66 (d, J = 8.83 Hz, 1 H) 7.69-7.76 (m, 1 H) 9.28 (br. s., 2 H) 12.77 (s, 1 H) 13.90 (s, 1 H). LC-MS 466.4 [M − H]⁻, 468.4 [M + H]⁺, RT 1.32 min. |

| Cpd | Name |
|---|---|
| 339 | 5-allyl-6-(2-((dimethylamino)methyl)-1-methyl-1H-indol-5-yl)-4-hydroxy-2-oxo-1,2-dihydropyridine-3-carboxylic acid<br>$^1$H NMR (500 MHz, DMSO-d$_6$) δ ppm 2.82 (s, 6 H), 3.08 (d, J = 5.7 Hz, 2 H), 3.88 (s, 3 H), 4.60 (s, 2 H), 4.89 (dd, J = 7.0, 1.7 Hz, 1 H), 5.01 (dd, J = 10.4, 1.7 Hz, 1 H), 5.81-5.90 (m, 1 H), 6.84-6.88 (m, 1 H), 7.33 (dd, J = 8.5, 1.9 Hz, 1 H), 7.68 (d, J = 8.5 Hz, 1 H), 7.76 (d, J = 1.3 Hz, 1 H), 9.87-9.96 (br s, 1 H), 12.80-12.86 (br s, 1 H), 13.83-13.88 (br s, 1 H), 16.21-16.30 (br s, 1 H). LC-MS 337.1 [M + H]$^+$, RT 0.99 min. |

Example 304

5-ethyl-4-hydroxy-2-oxo-6-(1-(pyrrolidin-1-yl)-2,3-dihydro-1H-pyrrolo[1,2-a]indol-7-yl)-1,2-dihydropyridine-3-carboxylic acid

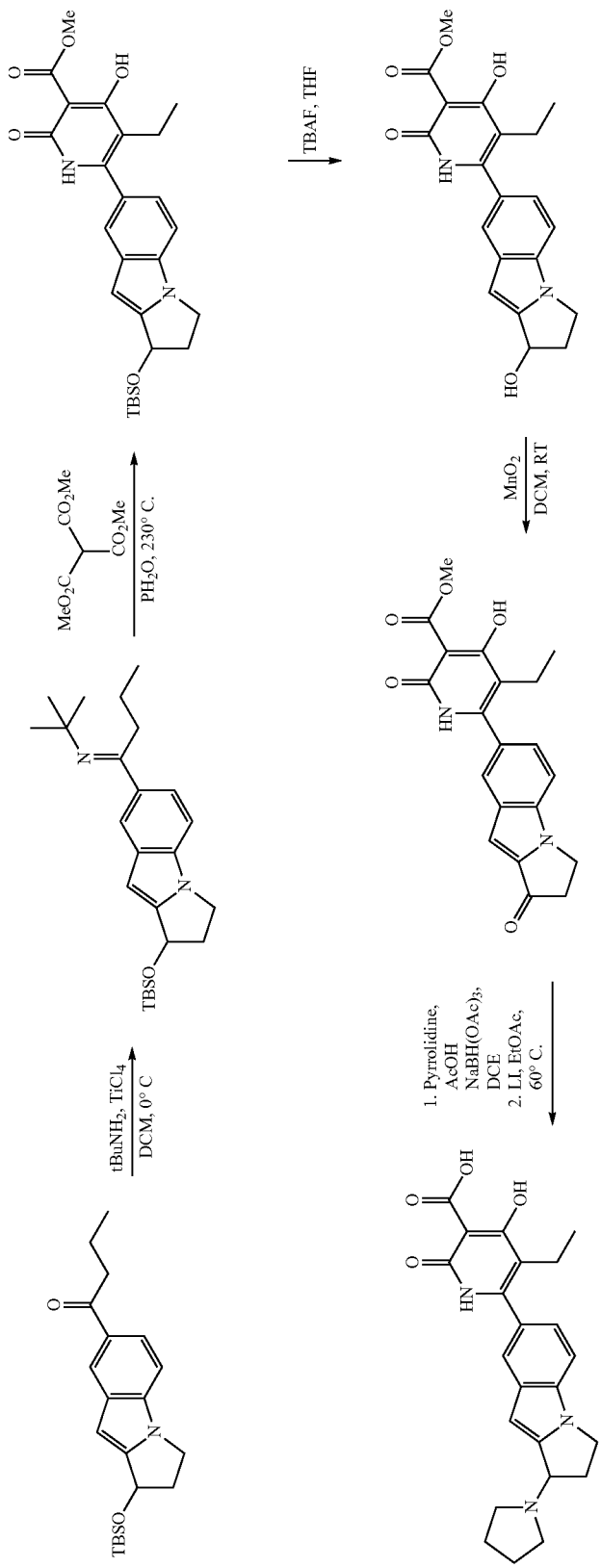

Step 1: N-(1-(1-(tert-Butyldimethylsilyloxy)-2,3-dihydro-1H-pyrrolo[1,2-a]indol-7-yl)butylidene)-2-methylpropan-2-amine To a solution of 1-(1-(tert-butyldimethylsilyloxy)-2,3-dihydro-1H-pyrrolo[1,2-a]indol-7-yl)butan-1-one (3.2 g, 9.0 mmol), prepared according to procedure described in Example 151 Step 5, in $CH_2Cl_2$ (40 mL), cooled to 0° C., was added $tBuNH_2$ (3.0 mL, 27.0 mmol). To this mixture was added a solution of $TiCl_4$ (5.4 mL, 1M, 5.4 mmol) in $CH_2Cl_2$ dropwise via an addition funnel. Upon completion of addition, the reaction was stirred at room temperature for 24 hrs before it was quenched with a saturated solution of $NaHCO_3$. The aqueous phase was extracted with $CH_2Cl_2$ and the combined organic phases were dried over $Na_2SO_4$, filtered, and concentrated to give a crude product that was used immediately without further purification. LC-MS 413.5 [M+H]$^+$, RT 0.98 min.

Step 2: Methyl 6-(1-(tert-butyldimethylsilyloxy)-2,3-dihydro-1H-pyrrolo[1,2-a]indol-7-yl)-5-ethyl-4-hydroxy-2-oxo-1,2-dihydropyridine-3-carboxylate A solution of N-(1-(1-(tert-butyldimethylsilyloxy)-2,3-dihydro-1H-pyrrolo[1,2-a]indol-7-yl)butylidene)-2-methylpropan-2-amine (3.8 g, 9.0 mmol) and trimethyl methanetricarboxylate (2.6 g. 13.5 mmol) in $Ph_2O$ (10 mL) was heated at 220° C. for 30 min. The reaction mixture was then cooled to room temperature and triturated with $Et_2O$ to afford the title compound as an off-white solid (1.2 g, 30%).

$^1$H NMR (500 MHz, DMSO-$d_6$) δ ppm 0.90 (t, J=6.82 Hz, 3H) 2.03-2.12 (m, 2H) 3.49-3.56 (m, 2H) 3.67 (s, 3H) 3.87-3.96 (m, 1H) 4.01-4.10 (m, 1H) 5.19-5.27 (m, 1H) 6.14-6.19 (m, 1H) 6.89-6.93 (m, 1H) 7.24-7.29 (m, 1H) 7.36-7.43 (m, 1H) 11.18-11.25 (m, 1H) 13.35-13.42 (m, 1H). LC-MS 483.5 [M+H]$^+$, RT 1.05 min.

Step 3: Methyl 5-ethyl-4-hydroxy-6-(1-hydroxy-2,3-dihydro-1H-pyrrolo[1,2-a]indol-7-yl)-2-oxo-1,2-dihydropyridine-3-carboxylate To a suspension of methyl 6-(1-(tert-butyldimethylsilyloxy)-2,3-dihydro-1H-pyrrolo[1,2-a]indol-7-yl)-5-ethyl-4-hydroxy-2-oxo-1,2-dihydropyridine-3-carboxylate (1.4 g, 3.0 mmol) in THF (20 mL) was added a solution of TBAF (3.2 mL, 1M, 3.2 mmol) in THF. The reaction mixture was stirred at room temperature for 1 h and then concentrated. The crude residue was triturated with THF to afford the title compound as an off-white solid (0.9 g, 80%).

$^1$H NMR (500 MHz, DMSO-$d_6$) δ ppm 0.84-0.91 (m, 3H) 2.07-2.14 (m, 2H) 3.23-3.28 (m, 2H) 3.32-3.49 (m, 2H) 3.58 (s, 3H) 4.53 (t, J=6.07 Hz, 1H) 7.03 (s, 1H) 7.30 (dd, J=8.59, 1.42 Hz, 1H) 7.64-7.73 (m, 2H). LC-MS 369.3 [M+H]$^+$, RT 0.75 min.

Step 4: Methyl 5-ethyl-4-hydroxy-2-oxo-6-(1-oxo-2,3-dihydro-1H-pyrrolo[1,2-a]indol-7-yl)-1,2-dihydropyridine-3-carboxylate To a solution of methyl 5-ethyl-4-hydroxy-6-(1-hydroxy-2,3-dihydro-1H-pyrrolo[1,2-a]indol-7-yl)-2-oxo-1,2-dihydropyridine-3-carboxylate (1.4 g, 3.8 mmol) in $CH_2Cl_2$ (20 mL) was added $MnO_2$ (2.2 g, 25 mmol). After stirring at room temperature for 2 h, the reaction mixture was filtered through celite and concentrated to afford the title compound as a brown solid (1.0 g, 72%).

$^1$H NMR (500 MHz, DMSO-$d_6$) δ ppm 0.78 (t, J=6.82 Hz, 3H) 2.06 (m, J=6.90 Hz, 2H) 3.04 (br. s., 2H) 3.67 (br. s., 3H) 4.33 (br. s., 2H) 6.86 (s, 1H) 7.16 (d, J=8.28 Hz, 1H) 7.55 (d, J=8.75 Hz, 1H) 7.64 (br. s., 1H) 11.31 (br. s., 1H) 13.37 (br. s., 1H). LC-MS 367.2 [M+H]$^+$, RT 0.79 min.

Step 5-6: 5-Ethyl-4-hydroxy-2-oxo-6-(1-(pyrrolidin-1-yl)-2,3-dihydro-1H-pyrrolo[1,2-a]indol-7-yl)-1,2-dihydropyridine-3-carboxylic acid To a solution of methyl 5-ethyl-4-hydroxy-2-oxo-6-(1-oxo-2,3-dihydro-1H-pyrrolo[1,2-a]indol-7-yl)-1,2-dihydropyridine-3-carboxylate (0.13 g, 0.37 mmol) in DCE (3 mL) was added pyrrolidine (60 µL, 0.8 mmol) and AcOH (30 µL). After stirring at room temperature for 1 h, $NaBH(OAc)_3$ (0.17 g, 0.8 mmol) was added and stirred for an additional 1 h. The reaction mixture was then concentrated and to the crude residue was added $H_2O$. The resulting precipitate was filtered and dried over $N_2$ stream. The crude solid was dissolved in EtOAc (3 mL) and LiI (0.2 g, 1.6 mmol) was added. The resulting suspension was heated to 60° C. for 1 h. The reaction mixture was then cooled to room temperature and acidified with 4M HCl (1 mL). The resulting precipitate was filtered and rinsed with $Et_2O$ to afford the title compound as an orange solid (25 mg, 20%).

$^1$H NMR (500 MHz, MeOH-$d_4$) δ ppm 1.93 (t, J=6.70 Hz, 3H) 2.25 (s, 4H) 2.70-2.78 (m, 1H) 3.00-3.09 (m, 1H) 3.26-3.43 (m, 4H) 4.11 (s, 1H) 4.23 (s, 1H) 4.93-4.99 (m, 1H) 6.62 (s, 1H) 7.11 (dd, J=8.47, 1.69 Hz, 1H) 7.38-7.40 (m, 1H) 7.56 (dd, J=1.62, 0.67 Hz, 1H). LC-MS 406.3 [M−H]$^-$, RT 0.70 min.

Example 305

5-ethyl-4-hydroxy-2-oxo-6-(1,2,3,4-tetrahydropyrazino[1,2-a]indol-8-yl)-1,2-dihydropyridine-3-carboxylic acid

Step 1: tert-Butyl 8-butyryl-3,4-dihydropyrazino[1,2-a]indole-2(1H)-carboxylate To a vial was added tert-butyl 8-bromo-3,4-dihydropyrazino[1,2-a]indole-2(1H)-carboxylate (1.4 g, 4.0 mmol), Pd(dba)$_2$ (75 mg, 2 mol %), BINAP (75 mg, 3 mol %), and crushed 4 Å MS (2.0 g). The vial was evacuated and backfilled under argon. To the vial was then added DMF (15 mL), pyrrolidine (660 µL, 8.0 mmol), and butyraldehyde (1.0 mL, 12 mmol). The vial was then sealed under argon and heated to 115° C. for 6 h. The reaction mixture was then cooled to room temperature, diluted with EtOAc (50 mL), and filtered through celite. The filtrate was washed with $H_2O$ (50 mL) and brine (50 mL). The organic layer was dried over $Na_2SO_4$, filtered, and concentrated to afford a crude residue that was purified on silica gel (1:1 hexanes/EtOAc) to afford the title compound as a white solid (1.0 g, 73%).

$^1$H NMR (500 MHz, CHCl$_3$-d) δ ppm 1.05 (t, J=7.41 Hz, 3H) 1.53 (s, 9H) 1.78-1.88 (m, 2H) 3.00-3.09 (m, 2H) 3.97 (br. s., 2H) 4.15 (d, J=5.60 Hz, 2H) 4.86 (s, 2H) 6.42 (d, J=0.63 Hz, 1H) 7.33 (s, 1H) 7.89 (dd, J=8.63, 1.69 Hz, 1H) 8.27 (d, J=1.34 Hz, 1H).

Step 2: tert-Butyl-8-(1-(2,4-dimethoxybenzylimino)butyl)-3,4-dihydropyrazino[1,2-a]indole-2(1H)-carboxylate To a solution of tert-butyl 8-butyryl-3,4-dihydropyrazino[1,2-a]indole-2(1H)-carboxylate (1.0 g, 2.9 mmol) in $CH_2Cl_2$ (20 mL), cooled to 0° C., was added 2,4-dimethoxybenzyl amine (0.5 mL, 3.2 mmol) and Et₃N (1.2 mL, 9 mmol). To this mixture was added a solution of TiCl₄ (1.8 mL, 1M, 1.8 mmol) in CH₂Cl₂ dropwise via an addition funnel. Upon completion of addition, the reaction was stirred at room temperature for 6 h before it was quenched with a saturated solution of NaHCO₃. The aqueous phase was extracted with CH₂Cl₂ and the combined organic phases were dried over Na₂SO₄, filtered, and concentrated to give a crude product that was used immediately without further purification.

Step 3: tert-Butyl-8-(1-(2,4-dimethoxybenzyl)-3-ethyl-4-hydroxy-5-(methoxycarbonyl)-6-oxo-1,6-dihydropyridin-2-yl)-3,4-dihydropyrazino[1,2-a]indole-2(1H)-carboxylate To a solution of the crude product from the above procedure in Ph₂O (5 mL) was added trimethyl methanetricarboxylate (0.9 g, 4.3 mmol). The reaction mixture was heated to 210° C. for 15 min and then allowed to cool to room temperature. The crude reaction mixture was purified on silica gel (1:1 hexanes/EtOAc) to afford the title compound as an orange foam (0.8 g, 43%).

¹H NMR (500 MHz, CHCl₃-d) δ ppm 1.29 (t, J=7.17 Hz, 3H) 1.53 (s, 9H) 2.10-2.18 (m, 2H) 3.79 (s, 6H) 3.95-4.00 (m, 2H) 4.02 (s, 3H) 4.11-4.15 (m, 2H) 4.82-4.87 (m, 2H) 6.16-6.22 (m, 1H) 6.23-6.28 (m, 1H) 6.36-6.51 (m, 2H) 6.78-6.90 (m, 2H) 7.19-7.26 (m, 1H). LC-MS 618.6 [M+H]⁺, RT 1.58 min.

Step 4: 5-ethyl-4-hydroxy-2-oxo-6-(1,2,3,4-tetrahydropyrazino[1,2-a]indol-8-yl)-1,2-dihydropyridine-3-carboxylic acid To a solution of tert-butyl-8-(1-(2,4-dimethoxybenzyl)-3-ethyl-4-hydroxy-5-(methoxycarbonyl)-6-oxo-1,6-dihydropyridin-2-yl)-3,4-dihydropyrazino[1,2-a]indole-2(1H)-carboxylate (0.5 g, 0.8 mmol) in EtOAc (8 mL) was added lithium iodide (0.33 g, 2.4 mmol). The solution was heated at 60° C. for 1.5 h then cooled to room temperature and diluted with EtOAc (20 mL). The reaction mixture was washed with 1M HCl (20 mL), 10% Na₂S₂O₃ (20 mL), and brine (20 mL). The organic layer was then dried over Na₂SO₄, filtered, and concentrated. To the crude residue was added TIPS-H (1 mL) and TFA (1 mL), and the reaction mixture was heated at 60° C. for 1 h. The reaction mixture was allowed to cool to room temperature and the solvents were removed in vacuo. To the crude residue was added HCl/Et₂O (1 mL, 2.0 M) and the precipitate was collected by filtration to afford the title compound as a light brown solid (60 mg, 21%).

¹H NMR (500 MHz, MeOH-d₄) δ ppm 1.09 (t, J=7.41 Hz, 3H) 2.47 (d, J=7.41 Hz, 2H) 3.90 (s, 2H) 4.48 (s, 2H) 4.72 (s, 2H) 6.66 (d, J=0.71 Hz, 1H) 7.30-7.38 (m, 1H) 7.62-7.67 (m, 1H) 7.73 (d, J=1.18 Hz, 1H). LC-MS 354.3 [M+H]⁺, RT 0.78 min.

Example 306

5-ethyl-4-hydroxy-6-(1-methyl-2-(pyrrolidin-3-yl)-1H-indol-5-yl)-2-oxo-1,2-dihydropyridine-3-carboxylic acid hydrochloride

Step 1: Methyl 6-(2-(1-(tert-butoxycarbonyl)pyrrolidin-3-yl)-1-methyl-1H-indol-5-yl)-1-(2,4-dimethoxybenzyl)-5-ethyl-4-hydroxy-2-oxo-1,2-dihydropyridine-3-carboxylate Crude tert-butyl 3-(5-(1-(2,4-dimethoxybenzylimino)butyl)-1-methyl-1H-indol-2-yl)pyrrolidine-1-carboxylate (0.537 g, 1.03 mmol) and trimethyl methanetricarboxylate (0.33 g, 1.70 mmol) were mixed together in Ph₂O (2 mL). Stirred mixture was heated at 180-190° C. for 1.5 h. Reaction mixture was then cooled to room temperature and loaded directly on the column. It was eluted first with hexanes to separate Ph₂O and then EtOAc/hexanes gradient (0-70%) to yield product as yellow foam (0.322 g, 48%). LC-MS 646.5 [M+H]⁺, RT 1.45, 1.46 min. (2 atropisomers).

Step 2: 6-(2-(1-(tert-Butoxycarbonyl)pyrrolidin-3-yl)-1-methyl-1H-indol-5-yl)-1-(2,4-dimethoxybenzyl)-5-ethyl-4-hydroxy-2-oxo-1,2-dihydropyridine-3-carboxylic acid To solution of methyl 6-(2-(1-(tert-butoxycarbonyl)pyrrolidin-3-yl)-1-methyl-1H-indol-5-yl)-1-(2,4-dimethoxybenzyl)-5-ethyl-4-hydroxy-2-oxo-1,2-dihydropyridine-3-carboxylate (0.322 g, 0.45 mmol) in EtOAc (2 mL) was added LiI (0.17 g, 1.27 mmol). Reaction mixture was stirred and heated at 60° C. for 1.5 h until complete consumption of starting material was observed. Mixture was then cooled to room temperature and acidified with aqueous HCl (1M, 10 mL). Product was extracted with DCM (3×10 mL). Organic phase was washed with NaCl (aqueous saturated, 10 mL) and dried over Na₂SO₄. Upon removal of the solvent product was obtained as yellow foam (0.276 g, 88%) in 88% LC/MS purity. It was further purified by column chromatography using MeOH/DCM (gradient 0-2.5%) to yield 6-(2-(1-(tert-butoxycarbonyl)pyrrolidin-3-yl)-1-methyl-1H-indol-5-yl)-1-(2,4-dimethoxybenzyl)-5-ethyl-4-hydroxy-2-oxo-1,2-dihydropyridine-3-carboxylic acid (0.161 g) in 93% purity. LC-MS 632.5 [M+H]⁺, RT 1.68 min.

Step 3: 5-Ethyl-4-hydroxy-6-(1-methyl-2-(pyrrolidin-3-yl)-1H-indol-5-yl)-2-oxo-1,2-dihydropyridine-3-carboxylic acid hydrochloride To 6-(2-(1-(tert-butoxycarbonyl)pyrrolidin-3-yl)-1-methyl-1H-indol-5-yl)-1-(2,4-dimethoxybenzyl)-5-ethyl-4-hydroxy-2-oxo-1,2-dihydropyridine-3-carboxylic acid (0.161 g, 0.25 mmol) obtained above was added i-Pr₃SiH (0.30 mL) followed by TFA (0.60 mL). Mixture was heated at 60° C. for 2 h until complete consumption of starting material was observed. TFA was concentrated under reduced pressure. Addition of HCl solution (2M Et₂O, 1.0 mL) to the oily residue resulted in precipitate formation. Mixture was diluted with Et₂O; solid was filtered and washed with Et₂O. Product was obtained as pale yellow solid (82.2 mg, 77%) as an HCl salt ¹H NMR (500 MHz, MeOH-d₄) δ ppm 1.07 (t, J=7.4 Hz, 3H) 2.16-2.28 (m, 1H) 2.45 (q, J=7.4 Hz, 2H) 2.57-2.67 (m, 1H) 3.37-3.53 (m, 2H) 3.54-3.63 (m, 1H) 3.78-3.87 (m, 1H) 3.85 (s, 3H) 3.88-3.99 (m, 1H) 6.57 (s, 1H) 7.25 (dd, J=8.7, 1.1 Hz, 1H) 7.57 (d, J=8.7 Hz, 1H) 7.64 (s, 1H). LC-MS 380.2 [M−H]⁻, 382.4 [M+H]⁺, RT 0.94 min.

Using the procedures described above, additional compounds described herein may be prepared by substituting the appropriate starting materials, reagents and reaction conditions and include compounds selected from:

| Cpd | Name |
|---|---|
| 307 | 5-ethyl-4-hydroxy-6-(1-methyl-2-(2-(pyrrolidin-1-yl)propan-2-yl)-1H-indol-5-yl)-2-oxo-1,2-dihydropyridine-3-carboxylic acid LC-MS 422.3 [M−H]⁻, RT 0.83 min (Method A) |

283
-continued

| Cpd | Name |
|---|---|
| 308 | 6-(2-(2-(dimethylamino)propan-2-yl)-1-methyl-1H-indol-5-yl)-5-ethyl-4-hydroxy-2-oxo-1,2-dihydropyridine-3-carboxylic acid LC-MS 396.3 [M−H]⁻, RT 0.81 min (Method A) |

Example 309

5-(4-Fluorophenyl)-4-hydroxy-6-(1-methyl-2-(pyrrolidin-1-ylmethyl)-1H-indol-5-yl)-2-oxo-1,2-dihydropyridine-3-carboxylic acid (Cpd 309)

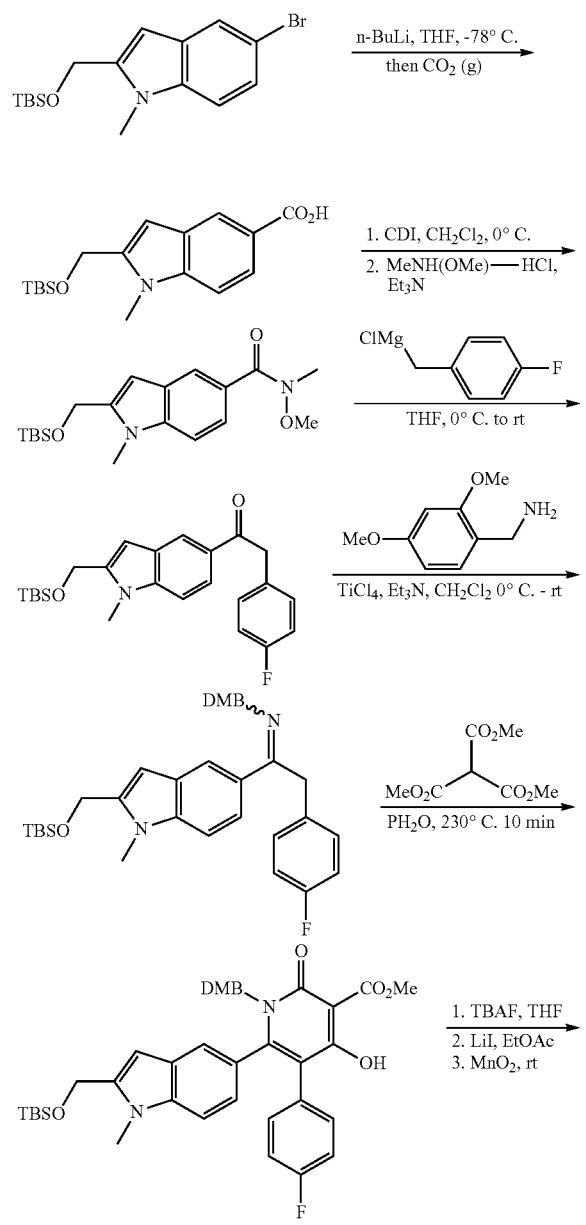

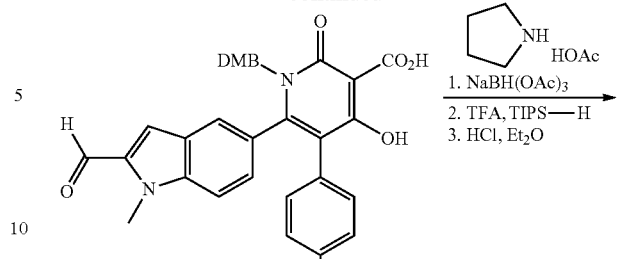

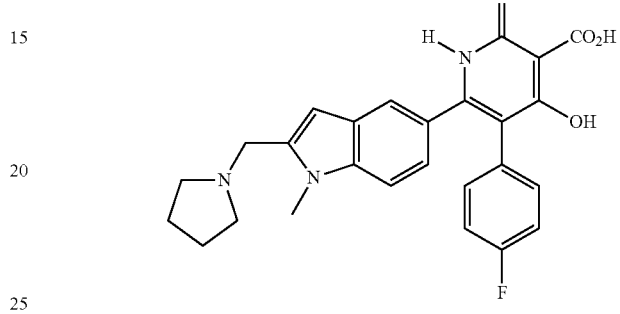

Step 1: 2-((tert-Butyldimethylsilyloxy)methyl)-1-methyl-1H-indole-5-carboxylic acid To a stirred solution of 5-bromo-2-((tert-butyldimethylsilyloxy)methyl)-1-methyl-1H-indole (5.32 g, 15.0 mmol), prepared according to procedure described in Example 39, Step 3, in THF (30 mL) was added n-BuLi (2.5 M solution in hexanes, 7.30 mL, 18.25 mmol, 1.2 eq) at −78° C. dropwise. The mixture was stirred for 30 min at −78° C. before dry $CO_2$ (g) was bubbled into reaction for 10 min. The reaction was quenched with saturated aqueous $NH_4Cl$ then extracted by $CH_2Cl_2$ (3×50 mL). The combined organic layers were dried over $Na_2SO_4$ then concentrated under reduced pressure to give the title compound (4.80 g, ca. 15.0 mmol) in quantitative yield. The acid was carried over to next step without further purification.

$^1$H NMR (500 MHz, DMSO-$d_6$) δ ppm 0.06 (s, 6H) 0.87 (s, 9H) 3.77 (s, 3H) 4.86 (s, 2H) 6.48-6.60 (m, 1H) 7.49 (d, J=8.67 Hz, 1H) 7.75 (dd, J=8.67, 1.66 Hz, 1H) 8.11-8.24 (m, 1H) 12.40 (br. s., 1H). LC-MS 318.3 [M−H]⁻, 320.3 [M+H]⁺, RT 1.52 min.

Step 2: 2-((tert-Butyldimethylsilyloxy)methyl)-N-methoxy-N,1-dimethyl-1H-indole-5-carboxamide To a suspension of acid (4.80 g, ca. 15.0 mmol) obtained above in $CH_2Cl_2$ (30 mL) was added CDI (2.43 g, 15.0 mmol, 1.0 eq) at 0° C. The mixture was allowed to warm to room temperature and stirred for 1 h. The homogeneous reaction mixture was observed then cooled to 0° C. Then N,O-dimethylhydroxylamine hydrochloride (1.95 g, 20.0 mmol, 1.3 eq) and $Et_3N$ (2.8 mL, 20.1 mmol, 1.3 eq) was added to reaction mixture sequentially at 0° C. The mixture was allowed to warm to room temperature and stirred overnight. The reaction was quenched with saturated aqueous $NaHCO_3$ then extracted by $CH_2Cl_2$ (3×50 mL). Solvent was removed to give the crude product which was purified by flash chromatography (0-50% EtOAc in hexanes) to afford the title compound (3.92 g, 72%).

¹H NMR (500 MHz, CHCl₃-d) δ ppm 0.08 (s, 6H) 0.91 (s, 9H) 3.39 (s, 3H) 3.59 (s, 3H) 3.81 (s, 3H) 4.84 (s, 2H) 6.44 (s, 1H) 7.30 (d, J=8.59 Hz, 1H) 7.60 (dd, J=8.59, 1.58 Hz, 1H) 8.00 (d, J=1.10 Hz, 1H). LC-MS 363.3 [M+H]⁺, RT 1.57 min.

Step 3: 1-(2-((tert-Butyldimethylsilyloxy)methyl)-1-methyl-1H-indol-5-yl)-2-(4-fluorophenyl)ethanone To a stirred solution of Weinreb amide (2.91 g, 8.0 mmol) obtained above in THF (20 mL) was added (4-fluorobenzyl) magnesium chloride (0.25 M solution in THF, 48.0 mL, 12.0 mmol, 1.5 eq) at 0° C. The mixture was allowed to warm to room temperature and stirred for 1 h. Reaction was quenched with saturated aqueous NH₄Cl then extracted by EtOAc (3×30 mL). Solvent was removed to give the crude product which was purified by flash chromatography (0-15% EtOAc in hexanes) to afford the title compound (3.30 g, 8.0 mmol) in nearly quantitative yield.

¹H NMR (500 MHz, CHCl₃-d) δ ppm 0.08 (s, 6H) 0.91 (s, 9H) 3.82 (s, 3H) 4.33 (s, 2H) 4.84 (s, 2H) 6.50 (s, 1H) 7.01 (t, J=8.75 Hz, 2H) 7.25-7.29 (m, 2H) 7.33 (d, J=8.67 Hz, 1H) 7.92 (dd, J=8.71, 1.69 Hz, 1H) 8.31 (d, J=1.34 Hz, 1H). LC-MS 412.3 [M+H]⁺, RT 1.73 min.

Step 4: N-(1-(2-((tert-Butyldimethylsilyloxy)methyl)-1-methyl-1H-indol-5-yl)-2-(4-fluorophenyl) ethylidene)-1-(2,4-dimethoxyphenyl)methanamine To a stirred solution of ketone (3.30 g, 8.0 mmol) obtained above in CH₂Cl₂ (10 mL) was added 2,4-dimethoxybenzylamine (1.25 mL, 8.3 mmol, 1.04 eq) and Et₃N (3.0 mL, 21.5 mmol, 2.7 eq) sequentially at 0° C. Then TiCl₄ (1.0M solution in CH₂Cl₂, 5.4 mL, 5.4 mmol, 0.67 eq) was added to mixture via syringe pump over 30 min. The reaction was allowed to warm to room temperature and stirred overnight. The mixture was quenched with saturated aqueous NaHCO₃ solution then extracted by CH₂Cl₂ (5×30 mL). The combined organic layers were dried over Na₂SO₄ then concentrated under reduced pressure to give the crude product (4.52 g, ca. 8.0 mmol) which was carried over to next step without further purification. LC-MS 561.4 [M+H]⁺, RT 1.45 min.

Step 5: Methyl 6-(2-((tert-butyldimethylsilyloxy) methyl)-1-methyl-1H-indol-5-yl)-1-(2,4-dimethoxybenzyl)-5-(4-fluorophenyl)-4-hydroxy-2-oxo-1,2-dihydropyridine-3-carboxylate To a suspension of crude imine (4.52 g, ca. 8.0 mmol) in Ph₂O (15 mL) was added trimethyl methanetricarboxylate (2.75 g, 14.5 mmol, 1.8 eq). Distillation apparatus was set up then attached to the flask containing reaction mixture. The reaction was heated to 230° C. for 10 min. The heating was removed once distillation of methanol ceased. The mixture was allowed to cool down to room temperature then purified by flash chromatography (0-25% EtOAc in CH₂Cl₂) to give the title compound (2.76 g, 50%). LC-MS 685.4 [M−H]⁻, 687.5 [M+H]⁺, RT 1.75 min.

Step 6-8: 1-(2,4-Dimethoxybenzyl)-5-(4-fluorophenyl)-6-(2-formyl-1-methyl-1H-indol-5-yl)-4-hydroxy-2-oxo-1,2-dihydropyridine-3-carboxylic acid To a stirred solution of cycloadduct (2.76 g, 4.02 mmol) obtained above in THF (10 mL) was added TBAF (8.0 mL, 1.0 M/THF, 8.0 mmol, 2.0 eq) at 0° C. The mixture was allowed to warm to room temperature and stirred for 30 min. Upon completion, solvent was removed then crude product was purified by flash column chromatography (0-50% EtOAc in CH₂Cl₂) to give the alcohol (2.07 g, 90%). LC-MS 571.4 [M−H]⁻, 573.3 [M+H]⁺, RT 1.25 min. To a suspension of methyl ester (2.07 g, 3.60 mmol) obtained above in EtOAc (15 mL) was added LiI (1.4 g, 10.5 mmol, 2.9 eq) at room temperature. The mixture heated to 65° C. and stirred for 1 h. The reaction mixture was diluted by EtOAc (30 mL) then quenched with saturated aqueous Na₂S₂O₃ (30 mL). The organic phase was separated then aqueous layer was extracted by EtOAc (4×30 mL). The combined organic layers were dried over Na₂SO₄ then concentrated under reduced pressure to give a crude acid (1.94 g, 96%) which was carried over to next step without further purification. LC-MS 557.4 [M−H]⁻, 559.3 [M+H]⁺, RT 1.35 min.

To a suspension of alcohol (1.94 g, 3.47 mmol) obtained above in CH₂Cl₂ (20 mL) was added MnO₂ (3.1 g, 35.7 mmol, 10.3 eq) at room temperature. After 1 h, MnO₂ (3.1 g, 35.7 mmol, 10.3 eq) was added. The reaction was monitored by LC-MS. Upon completion, reaction mixture was filtered through celite to remove solid waste. The filtrate was concentrated under reduced pressure to give the title compound (1.23 g, 64%). The material was used in next step without further purification. LC-MS 555.4 [M−H]⁻, 557.2 [M+H]⁺, RT 1.45 min.

Step 9-11: 5-(4-Fluorophenyl)-4-hydroxy-6-(1-methyl-2-(pyrrolidin-1-ylmethyl)-1H-indol-5-yl)-2-oxo-1,2-dihydropyridine-3-carboxylic acid To a solution of crude aldehyde (200 mg, 0.36 mmol) obtained above in 1,2-dichloroethane (2.0 mL) was added pyrrolidine (0.06 mL, 0.72 mmol, 2.0 eq) and HOAc (0.04 mL, 0.72 mmol, 2.0 eq) at room temperature. The reaction was stirred for 1 h before NaBH(OAc)₃ (152 mg, 0.72 mmol, 2.0 eq) was added. Upon completion, solvent was removed under reduced pressure then water was added to quench the reaction. The crude product was collected through filtration and purified by preparative HPLC (40-90% MeCN in H₂O).

To a suspension of above intermediate in TIPS-H (1.5 mL) was added TFA (1.5 mL) then reaction mixture was heated to 65° C. for 1 h. The progress was monitored by LC-MS. Upon completion, the solvent was removed under reduced pressure. The residue was dissolved in CH₂Cl₂ (1.5 mL), then HCl (2.0 mL, 2.0M/Et₂O) was added. The white precipitate was collected by filtration and washed by Et₂O (3×3 mL) then dried under nitrogen flow overnight to afford the title compound as a yellow solid.

¹H NMR (500 MHz, DMSO-d₆) δ ppm 1.82-1.96 (m, 2H) 1.96-2.13 (m, 2H) 3.10-3.20 (m, 2H) 3.35-3.50 (m, 2H) 3.81 (s, 3H) 4.60 (br. s., 2H) 6.80 (s, 1H) 6.96 (dd, J=8.67, 1.73 Hz, 1H) 7.06 (t, J=8.87 Hz, 2H) 7.15 (dd, J=8.75, 5.60 Hz, 2H) 7.40 (d, J=8.67 Hz, 1H) 7.61 (d, J=1.34 Hz, 1H) 12.98 (br. s., 1H) 13.78 (br. s., 1H). LC-MS 460.3 [M−H]⁻, 462.3 [M+H]⁺, RT 0.90 min.

Using the procedures described above, additional compounds described herein may be prepared by substituting the appropriate starting materials, reagents and reaction conditions and include compounds selected from:

| Cpd | Name |
|---|---|
| 310 | 6-(2-((Dimethylamino)methyl)-1-methyl-1H-indol-5-yl)-5-(4-fluorophenyl)-4-hydroxy-2-oxo-1,2-dihydropyridine-3-carboxylic acid
$^1$H NMR (500 MHz, DMSO-$d_6$) δ ppm 2.77 (s, 6 H) 3.80 (s, 3 H) 4.53 (br. s., 2 H) 6.78 (s, 1 H) 6.97 (dd, J = 8.71, 1.62 Hz, 1 H) 7.06 (t, J = 8.87 Hz, 2 H) 7.15 (dd, J = 8.63, 5.64 Hz, 2 H) 7.41 (d, J = 8.67 Hz, 1 H) 7.63 (d, J = 1.26 Hz, 1 H) 12.98 (br. s., 1 H) 13.78 (br. s., 1 H). LC-MS 434.3 [M − H]$^-$, 436.3 [M + H]$^+$, RT 0.87 min. |
| 311 | 6-(2-((Cyclopropylmethylamino)methyl)-1-methyl-1H-indol-5-yl)-5-(4-fluorophenyl)-4-hydroxy-2-oxo-1,2-dihydropyridine-3-carboxylic acid
$^1$H NMR (500 MHz, DMSO-$d_6$) δ ppm 0.39 (d, J = 3.70 Hz, 2 H) 0.59 (d, J = 7.41 Hz, 2 H) 1.13 (br. s., 1 H) 2.91 (br. s., 2 H) 3.76 (s, 3 H) 4.37 (br. s., 2 H) 6.69 (s, 1 H) 6.97 (d, J = 8.43 Hz, 1 H) 7.01-7.09 (m, 2 H) 7.09-7.19 (m, 2 H) 7.40 (d, J = 8.43 Hz, 1 H) 7.56 (s, 1 H) 9.28 (br. s., 1 H) 13.00 (br. s., 1 H) 13.78 (br. s., 1 H). LC-MS 460.3 [M − H]$^-$, 462.3 [M + H]$^+$, RT 0.92 min. |
| 312 | 6-(2-(Azetidin-1-ylmethyl)-1-methyl-1H-indol-5-yl)-5-(4-fluorophenyl)-4-hydroxy-2-oxo-1,2-dihydropyridine-3-carboxylic acid
$^1$H NMR (500 MHz, DMSO-$d_6$) δ ppm 3.74 (s, 3 H) 3.90 (s, 2 H) 3.99-4.15 (m, 4 H) 4.61 (br. s., 2 H) 6.70 (s, 1 H) 6.94 (d, J = 7.88 Hz, 1 H) 6.98-7.10 (m, 2 H) 7.14 (br. s., 2 H) 7.38 (d, J = 8.20 Hz, 1 H) 7.59 (s, 1 H) 12.96 (br. s., 1 H) 13.77 (br. s., 1 H). LC-MS 446.4 [M − H]$^-$, 448.4 [M + H]$^+$, RT 0.92 min. |

Example 313

4-hydroxy-5-methyl-6-(1-methyl-2-(pyrrolidin-1-ylmethyl)-1H-indol-5-yl)-2-oxo-1,2-dihydropyridine-3-carboxylic acid

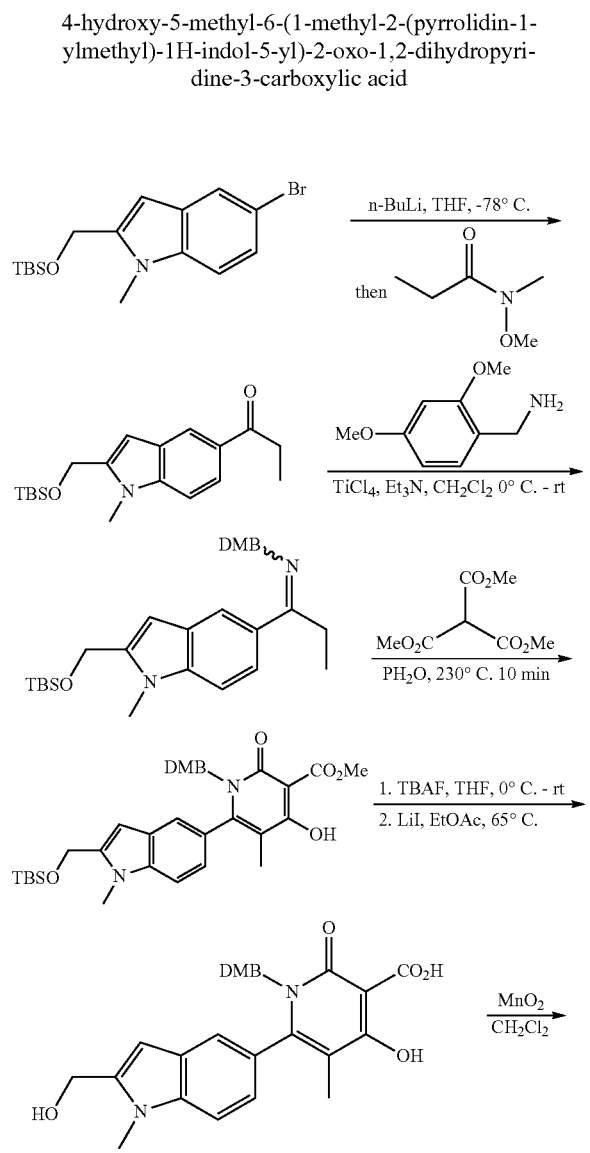

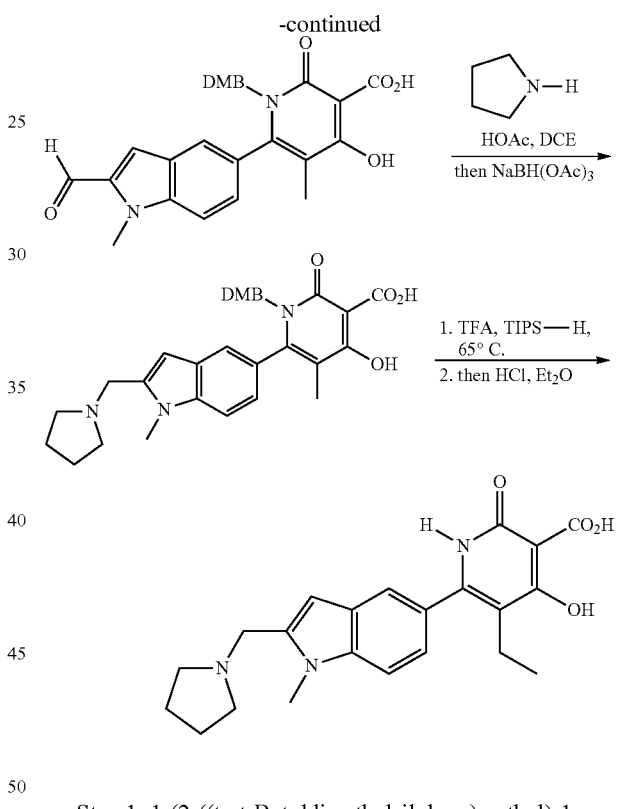

Step 1: 1-(2-((tert-Butyldimethylsilyloxy)methyl)-1-methyl-1H-indol-5-yl)propan-1-one To a stirred solution of 5-bromo-2-((tert-butyldimethylsilyloxy)methyl)-1-methyl-1H-indole (3.76 g, 10.6 mmol), prepared according to procedure described in Example 39 Step 3, in THF (15 mL) was added n-BuLi (2.5 M solution in hexanes, 5.1 mL, 12.7 mmol, 1.2 eq) at −78° C. dropwise. The mixture was stirred for 30 min at −78° C. before a solution of N-methoxy-N-methylpropionamide (1.49 g, 12.7 mmol, 1.2 eq) in THF (5 mL) was added. After stirred at −78° C. for 10 min, the reaction was quenched with saturated aqueous NH$_4$Cl solution. The resulting mixture was extracted by ether (3×30 mL) and combined organic layers were dried over Na$_2$SO$_4$. The crude product was purified by flash chromatography (0-10% EtOAc in hexanes) to give the title compound (2.70 g, 77%).

¹H NMR (500 MHz, CHCl₃-d) δ ppm 0.04-0.10 (m, 6H) 0.88-0.93 (m, 9H) 1.26 (t, J=7.29 Hz, 3H) 3.09 (q, J=7.30 Hz, 2H) 3.82 (s, 3H) 4.84 (s, 2H) 6.47-6.53 (m, 1H) 7.33 (d, J=8.75 Hz, 1H) 7.91 (dd, J=8.67, 1.73 Hz, 1H) 8.27 (d, J=1.18 Hz, 1H). LC-MS 332.2 [M+H]⁺, RT 1.72 min.

Step 2: N-(1-(2-((tert-Butyldimethylsilyloxy)methyl)-1-methyl-1H-indol-5-yl)propylidene)-1-(2,4-dimethoxyphenyl)methanamine To a stirred solution of above ketone (2.70 g, 8.14 mmol) in CH₂Cl₂ (12 mL) was added (2,4-dimethoxyphenyl)methanamine (1.23 mL, 8.19 mmol, 1.0 eq) and Et₃N (2.96 mL, 21.2 mmol, 2.6 eq) sequentially. The mixture was cooled to 0° C. and TiCl₄ (5.7 mL, 1.0M in CH₂Cl₂, 5.7 mmol, 0.70 eq) was added to mixture via syringe pump over 30 min. The reaction was allowed to warm to room temperature and stirred overnight. The reaction mixture was quenched with saturated aqueous NaHCO₃ solution (15 mL) then extracted by CH₂Cl₂ (5×25 mL). The combined organic layers were dried over Na₂SO₄ then concentrated under reduced pressure to give the crude product which was carried over to next step without further purification. LC-MS 481.3 [M+H]⁺, RT 1.60 min.

Step 3: Methyl 6-(2-((tert-butyldimethylsilyloxy)methyl)-1-methyl-1H-indol-5-yl)-1-(2,4-dimethoxybenzyl)-4-hydroxy-5-methyl-2-oxo-1,2-dihydropyridine-3-carboxylate To a suspension of crude imine (4.11 g, ca. 8.5 mmol) obtained above in Ph₂O (20 mL) was added trimethyl methanetricarboxylate (2.76 g, 14.5 mmol, 1.7 eq). Distillation apparatus was set up then attached to the flask containing reaction mixture. The reaction was stirred at 230° C. for 10 min then heating was removed. The mixture was allowed to cool down to room temperature then purified by flash chromatography (0-50% EtOAc in CH₂Cl₂) to give the title compound (2.41 g, 49%). LC-MS 605.3 [M−H]⁻, 607.4 [M+H]⁺, RT 1.80 min.

Step 4-5: 1-(2,4-Dimethoxybenzyl)-4-hydroxy-6-(2-(hydroxymethyl)-1-methyl-1H-indol-5-yl)-5-methyl-2-oxo-1,2-dihydropyridine-3-carboxylic acid To a stirred solution of above cycloadduct (2.41 g, 3.97 mmol) in THF (6 mL) was added TBAF (1.0 M in THF, 6.0 mL, 6.0 mmol, 1.5 eq) at 0° C. The mixture was allowed to warm to room temperature and stirred for 1 h. The reaction was monitored by LC-MS. Upon completion, solvent was removed under reduced pressure then crude product was purified by flash chromatography (0-50% EtOAc in CH₂Cl₂) to give pure alcohol intermediate (1.52 g, 78%). LC-MS 491.3 [M−H]⁻, 493.3 [M+H]⁺, RT 1.21 min.

To a suspension of above intermediate (1.52 g, 3.08 mmol) in EtOAc (15 mL) was added lithium iodide (1.23 g, 9.19 mmol, 3.0 eq) at room temperature. The mixture was heated to 65° C. and stirred for 1 h. The reaction mixture was diluted by EtOAc (15 mL) then quenched with 1N HCl (10 mL). The organic phase was separated then aqueous layer was extracted by EtOAc (4×30 mL). The combined organic layers were washed by saturated aqueous Na₂S₂O₃ (15 mL) then dried over Na₂SO₄. Solvent was removed under reduced pressure to give the title compound (1.40 g, 95%) which was carried over to next step without further purification. LC-MS 477.2 [M−H]⁻, 479.2 [M+H]⁺, RT 1.30 min.

Step 6: 1-(2,4-Dimethoxybenzyl)-6-(2-formyl-1-methyl-1H-indol-5-yl)-4-hydroxy-5-methyl-2-oxo-1,2-dihydropyridine-3-carboxylic acid To a suspension of above acid (1.40 g, 2.92 mmol) in CH₂Cl₂ (15 mL) was added MnO₂ (2.6 g, 29.9 mmol, 10 eq) at room temperature. After 1 h, more MnO₂ (2.6 g, 29.9 mmol, 10 eq) was added. The reaction was monitored by LC-MS. Upon completion, reaction mixture was filtered through celite to remove solid waste. The filtrate was concentrated under reduced pressure to afford the title compound (1.06 g, 76%) which was used in next step without further purification. LC-MS 475.3 [M−H]⁻, 477.3 [M+H]⁺, RT 1.43 min.

Step 7-9: 4-hydroxy-5-methyl-6-(1-methyl-2-(pyrrolidin-1-ylmethyl)-1H-indol-5-yl)-2-oxo-1,2-dihydropyridine-3-carboxylic acid To a solution of crude aldehyde (170 mg, 0.36 mmol) obtained above in 1,2-dichloroethane (2.0 mL) was added pyrrolidine (0.06 mL, 0.72 mmol, 2.0 eq) and HOAc (0.04 mL, 0.72 mmol, 2.0 eq) at room temperature. The reaction was stirred for 1 h before NaBH(OAc)₃ (152 mg, 0.72 mmol, 2.0 eq) was added. Upon completion, solvent was removed under reduced pressure then water was added. The crude product was collected through filtration and purified by preparative HPLC (40-90% MeCN in H₂O).

To a suspension of above intermediate in TIPS-H (1.5 mL) was added TFA (1.5 mL) then reaction mixture was heated to 65° C. for 1 h. The progress was monitored by LC-MS. Upon completion, the solvent was removed under reduced pressure. The residue was dissolved in CH₂Cl₂ (1.5 mL), then HCl (2.0 mL, 2.0M/Et₂O) was added. The white precipitate was collected by filtration and washed by Et₂O (3×3 mL) then dried under nitrogen flow overnight to afford the title compound as a yellow solid.

¹H NMR (500 MHz, DMSO-d₆) δ ppm 1.88-1.96 (m, 2H) 1.93 (s, 3H) 2.00-2.10 (m, 2H) 3.18 (br. s., 2H) 3.48 (br. s., 2H) 3.91 (s, 3H) 4.67 (br. s., 2H) 6.91 (s, 1H) 7.34 (dd, J=8.59, 1.66 Hz, 1H) 7.67 (d, J=8.59 Hz, 1H) 7.77 (d, J=1.18 Hz, 1H) 12.77 (br. s., 1H) 13.86 (s, 1H). LC-MS 380.3 [M−H]⁻, 382.3 [M+H]⁺, RT 0.79 min.

Using the procedures described above, additional compounds described herein may be prepared by substituting the appropriate starting materials, reagents and reaction conditions and include compounds selected from:

| Cpd | Name |
|---|---|
| 314 | 6-(2-((Dimethylamino)methyl)-1-methyl-1H-indol-5-yl)-4-hydroxy-5-methyl-2-oxo-1,2-dihydropyridine-3-carboxylic acid<br>¹H NMR (500 MHz, MeOH-d₄) δ ppm 2.01 (s, 3 H) 2.97 (s, 6 H) 3.93 (s, 3 H) 4.68 (br. s., 2 H) 6.94 (br. s., 1 H) 7.39 (d, J = 8.75 Hz, 1 H) 7.68 (d, J = 8.51 Hz, 1 H) 7.79 (s, 1 H). LC-MS 354.3 [M − H]⁻, 356.3 [M + H]⁺, RT 0.76 min. |

| Cpd | Name |
|---|---|
| 315 | 6-(2-((Cyclopropylmethylamino)methyl)-1-methyl-1H-indol-5-yl)-4-hydroxy-5-methyl-2-oxo-1,2-dihydropyridine-3-carboxylic acid<br>$^1$H NMR (500 MHz, MeOH-d$_4$) δ ppm 0.45 (br. s., 2 H) 0.76 (d, J = 6.86 Hz, 2 H) 1.17 (br. s., 1 H) 2.00 (s, 3 H) 3.08 (d, J = 5.75 Hz, 2 H) 3.90 (s, 3 H) 4.55 (br. s., 2 H) 6.87 (br. s., 1 H) 7.35 (d, J = 7.72 Hz, 1 H) 7.65 (d, J = 8.12 Hz, 1 H) 7.75 (br. s., 1 H). LC-MS 380.4 [M − H]$^-$, 382.4 [M + H]$^+$, RT 0.83 min. |
| 316 | 6-(2-(Azetidin-l-ylmethyl)-1-methyl-1H-indol-5-yl)-4-hydroxy-5-methyl-2-oxo-1,2-dihydropyridine-3-carboxylic acid<br>$^1$H NMR (500 MHz, MeOH-d$_4$) δ ppm 2.00 (s, 3 H) 2.58-2.67 (m, 2 H) 3.89 (s, 3 H) 4.18-4.38 (m, 4 H) 4.73 (br. s., 2 H) 6.86 (br. s., 1 H) 7.37 (d, J = 8.04 Hz, 1 H) 7.65 (d, J = 8.35 Hz, 1 H) 7.76 (s, 1 H). LC-MS 366.4 [M − H]$^-$, 368.3 [M + H]$^+$, RT 0.73 min. |
| 317 | 4-Hydroxy-5-methyl-6-(1-methyl-2-((methylamino)methyl)-1H-indol-5-yl)-2-oxo-1,2-dihydropyridine-3-carboxylic acid<br>$^1$H NMR (500 MHz, DMSO-d$_6$) δ ppm 1.93 (s, 3 H) 2.64 (br. s., 3 H) 3.87 (s, 3 H) 4.43 (br. s., 2 H) 6.81 (s, 1 H) 7.32 (d, J = 8.43 Hz, 1 H) 7.66 (d, J = 8.43 Hz, 1 H) 7.77 (s, 1 H) 9.29 (br. s., 2 H) 12.76 (br. s., 1 H) 13.87 (br. s., 1 H). LC-MS 340.3 [M − H]$^-$, 342.2 [M + H]$^+$, RT 0.74 min. |
| 318 | 6-(2-((dimethylamino)methyl)-1-methyl-1H-indol-5-yl)-4-hydroxy-5-isopropyl-2-oxo-1,2-dihydropyridine-3-carboxylic acid<br>$^1$H NMR (500 MHz, MeOH-d$_4$) δ ppm 1.30 (d, J = 7.09 Hz, 6 H) 2.85-2.94 (m, 1 H) 3.00 (s, 6 H) 3.96 (s, 3 H) 4.70 (s, 2 H) 6.96 (s, 1 H) 7.35 (dd, J = 8.55, 1.69 Hz, 1 H) 7.69 (d, J = 8.59 Hz, 1 H) 7.73-7.75 (m, 1 H). LC-MS 382.1 [M − H]$^-$, RT 0.56 min. |
| 319 | 4-hydroxy-5-isopropyl-6-(1-methyl-2-(pyrrolidin-l-ylmethyl)-1H-indol-5-yl)-2-oxo-1,2-dihydropyridine-3-carboxylic acid<br>$^1$H NMR (500 MHz, MeOH-d$_4$) δ ppm 1.30 (d, J = 7.09 Hz, 6 H) 2.10 (dd, J = 7.25, 4.49 Hz, 2 H) 2.21-2.30 (m, 2 H) 2.85-2.93 (m, 1 H) 3.34-3.39 (m, 2 H) 3.63-3.71 (m, 2 H) 3.94-3.98 (m, 3 H) 4.77 (s, 2 H) 6.95 (s, 1 H) 7.33 (dd, J = 8.55, 1.69 Hz, 1 H) 7.68 (d, J = 8.59 Hz, 1 H) 7.71-7.74 (m, 1 H). LC-MS 410.3 [M + H]$^+$, RT 0.56 min. |
| 320 | 6-(2-(azetidin-l-ylmethyl)-1-methyl-1H-indol-5-yl)-4-hydroxy-5-isopropyl-2-oxo-1,2-dihydropyridine-3-carboxylic acid<br>$^1$H NMR (500 MHz, MeOH-d$_4$) δ ppm 1.30 (d, J = 7.09 Hz, 6 H) 2.48-2.58 (m, 1 H) 2.63-2.64 (m, 1 H) 2.88 (m, 1 H) 3.91 (s, 3 H) 4.31 (s, 4 H) 4.75 (s, 2 H) 6.87 (s, 1 H) 7.32 (dd, J = 8.55, 1.69 Hz, 1 H) 7.66 (d, J = 8.59 Hz, 1 H) 7.71 (dd, J = 1.66, 0.63 Hz, 1 H). LC-MS 396.3 [M + H]$^+$, RT 0.90 min. |
| 321 | 6-(2-((cyclopropylmethylamino)methyl)-1-methyl-1H-indol-5-yl)-4-hydroxy-5-isopropyl-2-oxo-1,2-dihydropyridine-3-carboxylic acid<br>$^1$H NMR (500 MHz, MeOH-d$_4$) δ ppm 0.46-0.52 (m, 2 H) 0.76-0.82 (m, 2 H) 1.17-1.24 (m, 1 H) 1.30 (d, J = 7.09 Hz, 6 H) 2.88 (m, 1 H) 3.12 (d, J = 7.49 Hz, 2 H) 3.94 (s, 3 H) 4.59 (s, 2 H) 6.89 (s, 1 H) 7.32 (dd, J = 8.55, 1.69 Hz, 1 H) 7.67 (d, J = 8.59 Hz, 1 H) 7.71 (d, J = 1.10 Hz, 1 H). LC-MS 408.2 [M − H]$^-$, RT 0.55 min. |
| 322 | 5-cyclopropyl-6-(2-((dimethylamino)methyl)-1-methyl-1H-indol-5-yl)-4-hydroxy-2-oxo-1,2-dihydropyridine-3-carboxylic acid<br>$^1$H NMR (500 MHz, MeOH-d$_4$) δ ppm 0.01 (dd, J = 5.44, 1.34 Hz, 2 H) 0.52 (dd, J = 8.39, 1.54 Hz, 2 H) 1.53-1.62 (m, 1 H) 2.87 (s, 6 H) 3.83 (s, 3 H) 4.57 (s, 2 H) 6.84 (s, 1 H) 7.40 (dd, J = 8.59, 1.73 Hz, 1 H) 7.54 (d, J = 8.67 Hz, 1 H) 7.76 (d, J = 1.18 Hz, 1 H). LC-MS 380.3 [M − H]$^-$, RT 0.83 min. |
| 323 | 5-cyclopropyl-4-hydroxy-6-(1-methyl-2-(pyrrolidin-l-ylmethyl)-1H-indol-5-yl)-2-oxo-1,2-dihydropyridine-3-carboxylic acid<br>$^1$H NMR (500 MHz, MeOH-d$_4$) δ ppm 0.01 (dd, J = 5.44, 1.34 Hz, 2 H) 0.48-0.56 (m, 2 H) 1.58 (m, 1 H) 1.91-2.02 (m, 2 H) 2.08-2.18 (m, 2 H) 3.22-3.28 (m, 2 H) 3.51-3.60 (m, 2 H) 3.84 (s, 3 H) 4.65 (s, 2 H) 6.84 (s, 1 H) 7.39 (dd, J = 8.67, 1.66 Hz, 1 H) 7.54 (d, J = 8.67 Hz, 1 H) 7.75 (d, J = 1.26 Hz, 1 H). LC-MS 406.3 [M − H]$^-$, RT 0.86 min. |
| 324 | 6-(2-(azetidin-l-ylmethyl)-1-methyl-1H-indol-5-yl)-5-cyclopropyl-4-hydroxy-2-oxo-1,2-dihydropyridine-3-carboxylic acid<br>LC-MS 394.3 [M + H]$^+$, RT 0.85 min. |
| 325 | 5-cyclopropyl-6-(2-((cyclopropylmethylamino)methyl)-1-methyl-1H-indol-5-yl)-4-hydroxy-2-oxo-1,2-dihydropyridine-3-carboxylic acid<br>$^1$H NMR (500 MHz, MeOH-d$_4$) δ ppm 0.01 (dd, J = 5.44, 1.34 Hz, 2 H) 0.33-0.42 (m, 2 H) 0.52 (dd, J = 8.39, 1.54 Hz, 2 H) 0.68 (dd, J = 8.00, 1.38 Hz, 2 H) 1.05-1.13 (m, 1 H) 1.55-1.64 (m, 1 H) 3.01 (d, J = 7.49 Hz, 2 H) 3.82 (s, 3 H) 4.47 (s, 2 H) 6.79 (s, 1 H) 7.38 (dd, J = 8.59, 1.73 Hz, 1 H) 7.54 (d, J = 8.67 Hz, 1 H) 7.76 (d, J = 1.18 Hz, 1 H). LC-MS 406.3 [M − H]$^-$, RT 0.87 min. |
| 326 | 6-(2-((dimethylamino)methyl)-1-methyl-1H-indol-5-yl)-4-hydroxy-2-oxo-1,2-dihydropyridine-3-carboxylic acid<br>LC-MS 342.2 [M + H]$^+$, RT 0.73 min. |
| 327 | 4-hydroxy-6-(1-methyl-2-(pyrrolidin-l-ylmethyl)-1H-indol-5-yl)-2-oxo-1,2-dihydropyridine-3-carboxylic acid<br>LC-MS 368.3 [M + H]$^+$, RT 0.76 min. |
| 328 | 6-(2-(azetidin-l-ylmethyl)-1-methyl-1H-indol-5-yl)-4-hydroxy-2-oxo-1,2-dihydropyridine-3-carboxylic acid<br>LC-MS 354.2 [M + H]$^+$, RT 0.74 min. |
| 341 | 4-hydroxy-6-(2-((2-methoxyethylamino)methyl)-1-methyl-1H-indol-5-yl)-5-methyl-2-oxo-1,2-dihydropyridine-3-carboxylic acid<br>$^1$H NMR (500 MHz, DMSO-d$_6$) δ ppm 1.93 (s, 3 H) 3.22 (br. s., 2 H) 3.33 (s, 3 H) 3.66 (t, J = 5.04 Hz, 2 H) 3.85 (s, 3 H) 4.46 (br. s., 2 H) 6.83 (s, 1 H) 7.32 (dd, J = 8.51, 1.58 Hz, 1 H) 7.66 (d, J = 8.51 Hz, 1 H) 7.77 (d, J = 1.26 Hz, 1 H) 9.27 (br. s., 2 H) 12.77 (br. s., 1 H) 13.87 (br. s., 1 H). LC-MS 384.0 [M − H]$^-$, 386.1 [M + H]$^+$, RT 0.93 min. |

| Cpd | Name |
|---|---|
| 342 | 6-(2-((ethylamino)methyl)-1-methyl-1H-indol-5-yl)-4-hydroxy-5-methyl-2-oxo-1,2-dihydropyridine-3-carboxylic acid<br>$^1$H NMR (500 MHz, DMSO-d$_6$) δ ppm 1.27 (t, J = 7.25 Hz, 3 H) 1.93 (s, 3 H) 3.02-3.12 (m, 2 H) 3.87 (s, 3 H) 4.43 (br. s., 2 H) 6.82 (s, 1 H) 7.32 (dd, J = 8.51, 1.58 Hz, 1 H) 7.66 (d, J = .51 Hz, 1 H) 7.77 (d, J = 1.26 Hz, 1 H) 9.24 (br. s., 2 H) 12.77 (br. s., 1 H) 13.87 (br. s., 1 H). LC-MS 354.3 [M − H]$^-$, 356.2 [M + H]$^+$, RT 0.86 min. |
| 343 | 6-(2-((2-aminoethylamino)methyl)-1-methyl-1H-indol-5-yl)-4-hydroxy-5-methyl-2-oxo-1,2-dihydropyridine-3-carboxylic acid<br>$^1$H NMR (500 MHz, DMSO-d$_6$) δ ppm 1.93 (s, 3 H) 3.29 (br. s., 4 H) 3.91 (s, 3 H) 4.53 (br. s., 2 H) 6.87 (s, 1 H) 7.32 (d, J = 7.57 Hz, 1 H) 7.67 (d, J = 8.51 Hz, 1 H) 7.77 (s, 1 H) 8.33 (br. s., 3 H) 9.95 (br. s., 2 H) 12.77 (br. s., 1 H) 13.87 (br. s., 1 H). LC-MS 369.3 [M − H]$^-$, 371.3 [M + H]$^+$, RT 0.75 min. |
| 344 | 4-hydroxy-5-methyl-6-(1-methyl-2-42-(methylamino)ethylamino)methyl)-1H-indol-5-yl)-2-oxo-1,2-dihydropyridine-3-carboxylic acid<br>$^1$H NMR (500 MHz, DMSO-d$_6$) δ ppm 1.93 (s, 3 H) 2.61 (s, 3 H) 3.30-3.42 (m, 4 H) 3.91 (s, 3 H) 4.54 (br. s., 2 H) 6.88 (s, 1 H) 7.32 (dd, J = 8.67, 1.73 Hz, 1 H) 7.67 (d, J = 8.83 Hz, 1 H) 7.77 (d, J = 1.26 Hz, 1 H) 9.26 (br. s., 2 H) 9.89 (br. s., 2 H) 12.78 (br. s., 1 H) 13.87 (br. s., 1 H). LC-MS 383.1 [M − H]$^-$, 385.1 [M + H]$^+$, RT 0.75 min. |
| 345 | 6-(2-((2-(dimethylamino)ethylamino)methyl)-1-methyl-1H-indol-5-yl)-4-hydroxy-5-methyl-2-oxo-1,2-dihydropyridine-3-carboxylic acid<br>$^1$H NMR (500 MHz, DMSO-d$_6$) δ ppm 1.93 (s, 3 H) 2.85 (s, 6 H) 3.52 (br. s., 4 H) 3.91 (s, 3 H) 4.53 (br. s., 2 H) 6.88 (s, 1 H) 7.32 (dd, J = 8.51, 1.58 Hz, 1 H) 7.67 (d, J = 8.51 Hz, 1 H) 7.72-7.82 (m, 1 H) 9.88 (br. s., 2 H) 10.81 (br. s., 1 H) 12.77 (br. s., 1 H) 13.86 (br. s., 1 H). LC-MS 397.2 [M − H]$^-$, 399.1 [M + H]$^+$, RT 0.77 min. |
| 346 | 4-hydroxy-6-(2-((l-methoxypropan-2-ylamino)methyl)-1-methyl-1H-indol-5-yl)-5-methyl-2-oxo-1,2-dihydropyridine-3-carboxylic acid<br>$^1$H NMR (500 MHz, DMSO-d6) δ ppm 1.33 (d, J = 6.62 Hz, 3 H) 1.93 (s, 3 H) 3.36 (s, 3 H) 3.55 (br. s., 1 H) 3.61 (dd, J = 10.40, 5.67 Hz, 2 H) 3.65 (dd, J = 10.56, 4.26 Hz, 1 H) 3.86 (s, 3 H) 4.47 (br. s., 2 H) 6.85 (s, 1 H) 7.32 (dd, J = 8.51, 1.58 Hz, 1 H) 7.66 (d, J = 8.51 Hz, 1 H) 7.77 (d, J = 1.26 Hz, 1 H) 9.20 (br. s., 1 H) 9.35 (br. s., 1 H) 12.77 (br. s., 1 H) 13.88 (s, 1 H). LC-MS 398.3 [M − H]$^-$, 400.2 [M + H]$^+$, RT 0.53 min. (1 min Method). |
| 347 | 6-(2-((sec-butylamino)methyl)-1-methyl-1H-indol-5-yl)-4-hydroxy-5-methyl-2-oxo-1,2-dihydropyridine-3-carboxylic acid<br>$^1$H NMR (500 MHz, DMSO-d$_6$) δ ppm 0.94 (t, J = 7.41 Hz, 3 H) 1.34 (d, J = 6.31 Hz, 3 H) 1.58 (ddd, J = 13.56, 9.30, 7.41 Hz, 1 H) 1.88-1.96 (m, 1 H) 1.93 (s, 3 H) 3.25 (br. s., 1 H) 3.88 (s, 3 H) 4.45 (br. s., 2 H) 6.85 (s, 1 H) 7.32 (dd, J = 8.67, 1.42 Hz, 1 H) 7.67 (d, J = 8.83 Hz, 1 H) 7.72-7.81 (m, 1 H) 9.19 (br. s., 1 H) 9.29 (br. s., 1 H) 12.77 (s, 1 H) 13.87 (s, 1 H). LC-MS 382.3 [M − H]$^-$, 384.3 [M + H]$^+$, RT 0.53 min. (1 min Method). |
| 348 | 4-hydroxy-6-(2-((isopropylamino)methyl)-1-methyl-1H-indol-5-yl)-5-methyl-2-oxo-1,2-dihydropyridine-3-carboxylic acid<br>$^1$H NMR (500 MHz, DMSO-d$_6$) δ ppm 1.36 (d, J = 6.31 Hz, 6 H) 1.93 (s, 3 H) 3.44-3.51 (1, 2 H) 3.87 (s, 3 H) 4.44 (t, J = 5.67 Hz, 2 H) 6.83 (s, 1 H) 7.32 (dd, J = 8.51, 1.58 Hz, 1 H) 7.67 (d, J = 8.51 Hz, 1 H) 7.75-7.81 (m, 1 H) 9.18 (br. s., 2 H) 12.78 (s, 1 H) 13.87 (s, 1 H). LC-MS 368.2 [M − H]$^-$, 370.2 [M + H]$^+$, RT 0.50 min. (1 min Method). |
| 349 | 4-hydroxy-6-(2-((l-hydroxypropan-2-ylamino)methyl)-1-methyl-1H-indol-5-yl)-5-methyl-2-oxo-1,2-dihydropyridine-3-carboxylic acid<br>$^1$H NMR (500 MHz, DMSO-d$_6$) δ ppm 1.30 (d, J = 6.94 Hz, 3 H) 1.93 (s, 3 H) 2.52-2.57 (m, 1 H) 3.61 (dd, J = 11.66, 5.36 Hz, 1 H) 3.68-3.78 (m, 1 H) 3.86 (s, 3 H) 4.49 (br. s., 2 H) 5.48 (br. s., 1 H) 6.84 (s, 1 H) 7.32 (dd, J = 8.51, 1.58 Hz, 1 H) 7.67 (d, J = 8.51 Hz, 1 H) 7.77 (d, J = 1.26 Hz, 1 H) 9.00 (br. s., 1 H) 9.17 (br. s., 1 H) 12.79 (s, 1 H) 13.86 (br. s., 1 H). LC-MS 384.3 [M − H]$^-$, 386.2 [M + H]$^+$, RT 0.49 min. (1 min Method). |
| 350 | 4-hydroxy-6-(24(2-hydroxyethylamino)methyl)-1-methyl-1H-indol-5-yl)-5-methyl-2-oxo-1,2-dihydropyridine-3-carboxylic acid<br>$^1$H NMR (500 MHz, DMSO-d$_6$) δ ppm 1.93 (s, 3 H) 3.10 (br. s., 2 H) 3.69-3.77 (m, 2 H) 3.86 (s, 3 H) 4.48 (br. s., 2 H) 5.30 (br. s., 1 H) 6.84 (s, 1 H) 7.32 (dd, J = 8.67, 1.73 Hz, 1 H) 7.66 (d, J = 8.83 Hz, 1 H) 7.77 (d, J = 1.58 Hz, 1 H) 9.25 (br. s., 2 H) 12.77 (br. s., 1 H) 13.87 (br. s., 1 H). LC-MS 370.2 [M − H]$^-$, 372.2 [M + H]$^+$, RT 0.49 min. (1 min Method). |
| 351 | 6-(2-((tert-butylamino)methyl)-1-methyl-1H-indol-5-yl)-4-hydroxy-5-methyl-2-oxo-1,2-dihydropyridine-3-carboxylic acid<br>$^1$H NMR (500 MHz, DMSO-d$_6$) δ ppm 1.43 (s, 9 H) 1.93 (s, 3 H) 3.87 (s, 3 H) 4.36-4.48 (m, 2 H) 6.83 (s, 1 H) 7.32 (d, J = 8.51 Hz, 1 H) 7.68 (d, J = 8.51 Hz, 1 H) 7.78 (s, 1 H) 9.17 (br. s., 2 H) 12.79 (br. s., 1 H) 13.87 (br. s., 1 H). LC-MS 382.3 [M − H]$^-$, 384.3 [M + H]$^+$, RT 0.52 min. (1 min Method). |
| 352 | 4-hydroxy-5-methyl-6-(1-methyl-2-((propylamino)methyl)-1H-indol-5-yl)-2-oxo-1,2-dihydropyridine-3-carboxylic acid<br>$^1$H NMR (500 MHz, DMSO-d$_6$) δ ppm 0.93 (t, J = 7.41 Hz, 3 H) 1.71 (dq, J = 15.61, 7.62 Hz, 2 H) 1.93 (s, 3 H) 2.97 (br. s., 2 H) 3.87 (s, 3 H) 4.44 (br. s., 2 H) 6.83 (s, 1 H) 7.32 (dd, J = 8.51, 1.26 Hz, 1 H) 7.66 (d, J = 8.51 Hz, 1 H) 7.77 (s, 1 H) 9.27 (br. s., 2 H) 12.78 (br. s., 1 H) 13.86 (br. s., 1 H). LC-MS 368.2 [M − H]$^-$, 370.2 [M + H]$^+$, RT 0.92 min. |
| 353 | 4-hydroxy-6-(2-((isobutylamino)methyl)-1-methyl-1H-indol-5-yl)-5-methyl-2-oxo-1,2-dihydropyridine-3-carboxylic acid<br>$^1$H NMR (500 MHz, DMSO-d$_6$) δ ppm 0.97 (d, J = 6.62 Hz, 6 H) 1.93 (s, 3 H) 2.06 (dt, J = 13.40, 6.86 Hz, 1 H) 2.88 (br. s., 2 H) 3.87 (s, 3 H) 4.45 (br. s., 2 H) 6.86 (s, 1 H) 7.32 (d, J = 8.51 Hz, 1 H) 7.67 (d, J = 8.51 Hz, 1 H) 7.78 (s, 1 H) 9.10 (br. s., 2 H) 12.79 (br. s., 1 H) 13.86 (br. s., 1 H). LC-MS 382.3 [M − H]$^-$, 384.1 [M + H]$^+$, RT 0.92 min. |

| Cpd | Name |
|---|---|
| 354 | 6-(2-((cyclobutylamino)methyl)-1-methyl-1H-indol-5-yl)-4-hydroxy-5-methyl-2-oxo-1,2-dihydropyridine-3-carboxylic acid<br>$^1$H NMR (500 MHz, DMSO-$d_6$) δ ppm 1.72-1.88 (m, 2 H) 1.93 (s, 3 H) 2.20 (br. s., 2 H) 2.23-2.32 (m, 2 H) 3.79 (br. s., 1 H) 3.86 (s, 3 H) 4.32 (br. s., 2 H) 6.81 (s, 1 H) 7.31 (d, J = 8.20 Hz, 1 H) 7.66 (d, J = 8.51 Hz, 1 H) 7.76 (s, 1 H) 9.59 (br. s., 2 H) 12.77 (br. s., 1 H) 13.86 (br. s., 1 H). LC-MS 380.1 [M − H]$^−$, 382.1 [M + H]$^+$, RT 0.92 min. |
| 355 | 6-(2-((cyclopropylamino)methyl)-1-methyl-1H-indol-5-yl)-4-hydroxy-5-methyl-2-oxo-1,2-dihydropyridine-3-carboxylic acid<br>$^1$H NMR (500 MHz, DMSO-$d_6$) δ ppm 0.69-0.86 (m, 2 H) 0.86-0.99 (m, 2 H) 1.93 (s, 3 H) 2.79 (br. s., 1 H) 3.88 (s, 3 H) 4.53 (s, 2 H) 6.82 (s, 1 H) 7.32 (dd, J = 8.67, 1.73 Hz, 1 H) 7.67 (d, J = 8.51 Hz, 1 H) 7.76 (d, J = 1.26 Hz, 1 H) 9.58 (br. s., 2 H) 12.77 (br. s., 1 H) 13.87 (br. s., 1 H). LC-MS 366.1 [M − H]$^−$, 368.1 [M + H]$^+$, RT 0.90 min. |
| 356 | 4-hydroxy-5-methyl-6-(1-methyl-2-((1-methylcyclopropylamino)methyl)-1H-indol-5-yl)-2-oxo-1,2-dihydropyridine-3-carboxylic acid<br>$^1$H NMR (500 MHz, DMSO-$d_6$) δ ppm 0.67-0.78 (m, 2 H) 1.10-1.20 (m, 2 H) 1.53 (s, 3 H) 1.92 (s, 3 H) 3.87 (s, 3 H) 4.54 (br. s., 2 H) 6.82 (s, 1 H) 7.28-7.37 (m, 1 H) 7.67 (d, J = 8.51 Hz, 1 H) 7.77 (s, 1 H) 9.51 (br. s., 2 H) 12.79 (br. s., 1 H) 13.86 (br. s., 1 H). LC-MS 380.4 [M − H]$^−$, 382.3 [M + H]$^+$, RT 0.50 min. (1 min Method). |
| 357 | 6-(2-((diethylamino)methyl)-1-methyl-1H-indol-5-yl)-4-hydroxy-5-methyl-2-oxo-1,2-dihydropyridine-3-carboxylic acid<br>$^1$H NMR (500 MHz, DMSO-$d_6$) δ ppm 1.30 (t, J = 7.09 Hz, 6 H) 1.93 (s, 3 H) 3.14-3.25 (m, 4 H) 3.91 (s, 3 H) 4.52-4.66 (m, 2 H) 6.93 (s, 1 H) 7.35 (d, J = 8.51 Hz, 1 H) 7.69 (d, J = 8.51 Hz, 1 H) 7.79 (s, 1 H) 10.08 (br. s., 1 H) 12.78 (br. s., 1 H) 13.86 (br. s., 1 H). LC-MS 382.4 [M − H]$^−$, 384.4 [M + H]$^+$, RT 0.50 min. (1 min Method). |
| 358 | 6-(2-(aminomethyl)-1-methyl-1H-indol-5-yl)-4-hydroxy-5-methyl-2-oxo-1,2-dihydropyridine-3-carboxylic acid<br>$^1$H NMR (500 MHz, DMSO-$d_6$) δ ppm 1.92 (s, 3 H) 3.83 (s, 3 H) 4.26-4.38 (m, 2 H) 6.70 (s, 1 H) 7.29 (d, J = 8.51 Hz, 1 H) 7.64 (d, J = 8.51 Hz, 1 H) 7.75 (s, 1 H) 8.53 (br. s., 3 H) 12.78 (br. s., 1 H) 13.85 (br. s., 1 H). LC-MS 326.3 [M − H]$^−$, 328.3 [M + H]$^+$, RT 0.47 min (1 min Method). |

Example 329

4-amino-5-ethyl-6-(1-methyl-2-(pyrrolidin-1-ylmethyl)-1H-indol-5-yl)-2-oxo-1,2-dihydropyridine-3-carboxylic acid (Cpd 329)

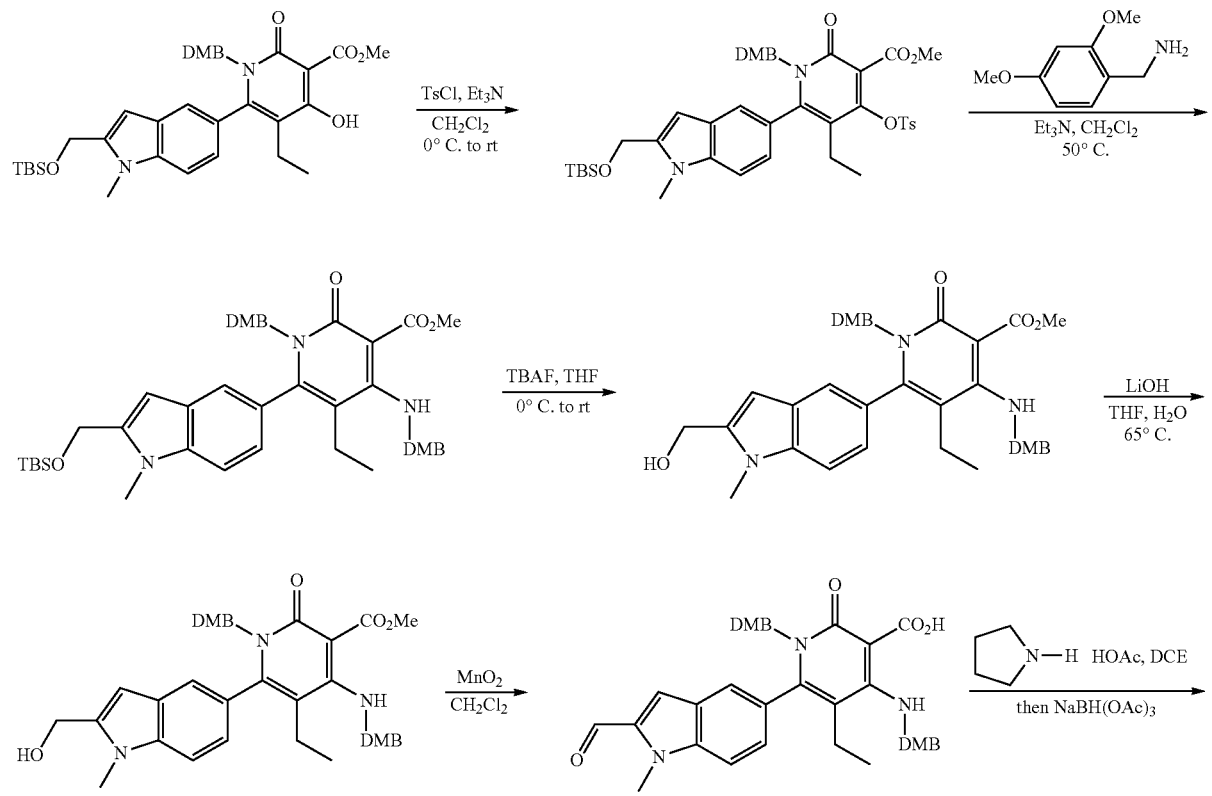

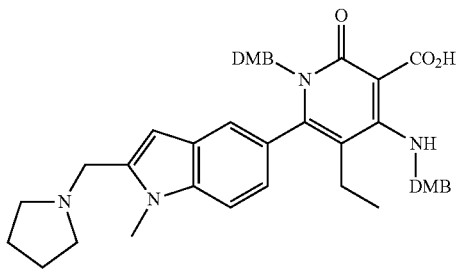

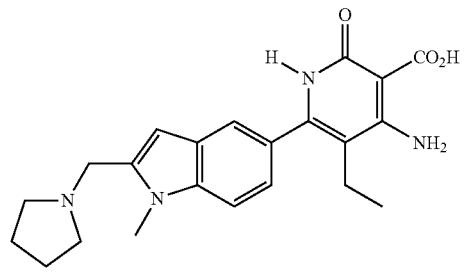 [SMILES: CCc1c(-c2ccc3c(c2)cc(CN2CCCC2)n3C)[nH]c(=O)c(C(=O)O)c1O]

TFA, TIPS—H, 65° C.
then Prep-HPLC

Step 1: Methyl 6-(2-((tert-butyldimethylsilyloxy) methyl)-1-methyl-1H-indol-5-yl)-1-(2,4-dimethoxybenzyl)-5-ethyl-2-oxo-4-(tosyloxy)-1,2-dihydropyridine-3-carboxylate To a stirred solution of methyl 6-(2-((tert-butyldimethylsilyloxy)methyl)-1-methyl-1H-indol-5-yl)-1-(2,4-dimethoxybenzyl)-5-ethyl-4-hydroxy-2-oxo-1,2-dihydropyridine-3-carboxylate (2.0 g, 3.2 mmol), prepared according to procedure described in Example 164, Step 2, in CH$_2$Cl$_2$ (15 mL) was added Et$_3$N (0.68 mL, 4.9 mmol, 1.5 eq) and TsCl (0.74 g, 3.9 mmol, 1.2 eq) at 0° C. The mixture was allowed to warm to room temperature then stirred for 2 h. The solvent was removed and the residue was purified by flash column chromatography (0-25% EtOAc in CH$_2$Cl$_2$) to give the title compound (2.12 g, 85%). LC-MS 775.3 [M+H]$^+$, RT 1.80 min.

Step 2: Methyl 6-(2-((tert-butyldimethylsilyloxy) methyl)-1-methyl-1H-indol-5-yl)-1-(2,4-dimethoxybenzyl)-4-(2,4-dimethoxybenzylamino)-5-ethyl-2-oxo-1,2-dihydropyridine-3-carboxylate To a stirred solution of tosylate (1.70 g, 2.2 mmol) obtained above in CH$_2$Cl$_2$ (8 mL) was added Et$_3$N (0.61 mL, 4.4 mmol, 2.0 eq) and 2,4-dimethoxybenzylamine (0.50 mL, 3.3 mmol, 1.5 eq) at room temperature. The mixture was heated to 50° C. then stirred for 1 h. The reaction was monitored by LC-MS then more Et$_3$N (0.20 mL) and 2,4-dimethoxybenzylamine (0.20 mL) was added. After 5 h, solvent was removed then residue was purified by flash column chromatography (0-50% EtOAc in CH$_2$Cl$_2$) to give the title compound (1.45 g, 86%).

$^1$H NMR (500 MHz, CHCl$_3$-d) δ ppm 0.10 (s, 3H) 0.11 (s, 3H) 0.79 (t, J=7.45 Hz, 3H) 0.91 (s, 9H) 1.88-2.02 (m, 2H) 3.07 (s, 3H) 3.77 (s, 3H) 3.78 (s, 3H) 3.81 (s, 3H) 3.82 (s, 3H) 3.96 (s, 3H) 4.32 (s, 2H) 4.71-4.86 (m, 3H) 4.93 (d, J=15.05 Hz, 1H) 6.08 (d, J=2.36 Hz, 1H) 6.27 (s, 1H) 6.39 (dd, J=8.43, 2.44 Hz, 1H) 6.44-6.51 (m, 2H) 6.74 (d, J=8.20 Hz, 1H) 6.91-7.01 (m, 2H) 7.18 (dd, J=8.35, 6.15 Hz, 2H). LC-MS 770.4 [M+H]$^+$, RT 1.76 min.

Step 3: Methyl 1-(2,4-dimethoxybenzyl)-4-(2,4-dimethoxybenzylamino)-5-ethyl-6-(2-(hydroxymethyl)-1-methyl-1H-indol-5-yl)-2-oxo-1,2-dihydropyridine-3-carboxylate To a stirred solution of silylether (1.76 g, 2.28 mmol) obtained above in THF (10 mL) was added TBAF (3.5 mL, 1.0 M in THF, 3.5 mmol, 1.5 eq) at 0° C. The mixture was allowed to warm to room temperature and stirred for 30 min. The solvent was removed under reduced pressure then residue was purified by flash column chromatography (10-50% EtOAc in CH$_2$Cl$_2$) to give the title compound (1.45 g, 97%).

$^1$H NMR (500 MHz, CHCl$_3$-d) δ ppm 0.80 (t, J=7.45 Hz, 3H) 1.95 (quin, J=7.09 Hz, 2H) 3.12 (s, 3H) 3.77 (s, 3H) 3.81 (s, 3H) 3.82 (s, 6H) 3.96 (s, 3H) 4.32 (s, 2H) 4.71-4.79 (m, 1H) 4.82 (s, 2H) 4.87-4.94 (m, 1H) 6.08-6.12 (m, 1H) 6.36 (s, 1H) 6.40 (dd, J=8.28, 2.05 Hz, 1H) 6.44-6.51 (m, 2H) 6.78 (d, J=8.51 Hz, 1H) 6.93 (d, J=8.28 Hz, 1H) 7.03 (s, 1H) 7.20 (t, J=8.47 Hz, 2H). LC-MS 654.2 [M−H]$^-$, 656.3 [M+H]$^+$, RT 1.27 min.

Step 4: 1-(2,4-Dimethoxybenzyl)-4-(2,4-dimethoxybenzylamino)-5-ethyl-6-(2-(hydroxymethyl)-1-methyl-1H-indol-5-yl)-2-oxo-1,2-dihydropyridine-3-carboxylic acid To a stirred solution of above ester (1.45 g, 2.21 mmol) in THF (6 mL) and H$_2$O (3 mL) was added LiOH—H$_2$O (450 mg, 10.7 mmol, 4.9 eq) at room temperature. The mixture was heated to 65° C. then stirred overnight. The reaction was quenched with 1N aqueous HCl (12 mL) then extracted with CH$_2$Cl$_2$ (4×25 mL). Solvent was removed under reduced pressure then residue was purified by flash column chromatography (10-50% EtOAc in CH$_2$Cl$_2$) to give the title compound (1.12 g, 79%).

$^1$H NMR (500 MHz, CHCl$_3$-d) δ ppm 0.93 (t, J=7.45 Hz, 3H) 2.21-2.35 (m, 2H) 3.26 (s, 3H) 3.78 (s, 3H) 3.82 (s, 6H) 3.84 (s, 3H) 4.65 (d, J=5.91 Hz, 2H) 4.77 (d, J=15.45 Hz, 1H) 4.84 (d, J=5.67 Hz, 2H) 4.90 (d, J=15.45 Hz, 1H) 6.17-6.21 (m, 1H) 6.38-6.44 (m, 2H) 6.46-6.51 (m, 2H) 6.73 (d, J=8.43 Hz, 1H) 6.84 (dd, J=8.51, 1.42 Hz, 1H) 7.11 (s, 1H) 7.21 (d, J=9.06 Hz, 1H) 7.25-7.27 (m, 1H). LC-MS 640.4 [M−H]$^-$, 642.6 [M+H]$^+$, RT 1.36 min.

Step 5: 1-(2,4-Dimethoxybenzyl)-4-(2,4-dimethoxybenzylamino)-5-ethyl-6-(2-formyl-1-methyl-1H-indol-5-yl)-2-oxo-1,2-dihydropyridine-3-carboxylic acid To a suspension of alcohol (1.12 g, 1.75 mmol) in CH$_2$Cl$_2$ (12 mL) was added MnO$_2$ (1.55 g, 17.8 mmol, 10 eq) at room temperature. After 1 h, MnO$_2$ (1.55 g, 17.8 mmol, 10 eq) was added. The reaction was monitored by LC-MS. Upon completion, reaction mixture was filtered to remove solid waste. The filtrate was concentrated under reduced pressure to give the title compound (0.96 g, 86%). Crude material was used in next step without further purification. LC-MS 638.5 [M−H]$^-$, 640.5 [M+H]$^+$, RT 1.48 min.

Step 6-7: 4-Amino-5-ethyl-6-(1-methyl-2-(pyrrolidin-1-ylmethyl)-1H-indol-5-yl)-2-oxo-1,2-dihydropyridine-3-carboxylic acid To a solution of crude aldehyde (240 mg, 0.38 mmol) in 1,2-dichloroethane (2.0 mL) was added pyrrolidine (0.06 mL, 0.73 mmol, ca. 2.0 eq), and acetic acid (0.04 mL, 0.69 mmol, ca. 2.0 eq) at room temperature. The mixture was stirred for 30 min before NaBH(OAc)₃ (174 mg, 0.82 mmol, 2.2 eq) was added. Upon completion, solvent was removed under reduced pressure then water was added to quench the reaction. The crude product was collected through filtration then purified by preparative HPLC (40%-90% MeCN/H₂O) to give desired product carried over to final deprotection.

To a suspension of above reductive amination product in TIPS-H (1.0 mL) was added TFA (1.0 mL) then reaction mixture was heated to 65° C. for 3 h. Upon completion, the solvent was removed under reduced pressure then residue was purified by preparative HPLC (20%-75% MeCN/H₂O) to give desired product (12.8 mg, 7% over three steps).

¹H NMR (500 MHz, MeOH-d₄) δ ppm 1.03 (t, J=7.41 Hz, 3H) 2.06 (br. s., 2H) 2.23 (br. s., 2H) 2.37 (q, J=7.41 Hz, 2H) 3.26-3.35 (br. s., 2H) 3.65 (br. s., 2H) 3.92 (s, 3H) 4.74 (s, 2H) 6.90 (s, 1H) 7.26-7.35 (m, 1H) 7.64 (d, J=8.51 Hz, 1H) 7.69 (s, 1H). LC-MS 393.5 [M−H]⁻, 395.4 [M+H]⁺, RT 0.73 min.

Using the procedures described above, additional compounds described herein may be prepared by substituting the appropriate starting materials, reagents and reaction conditions and include compounds selected from:

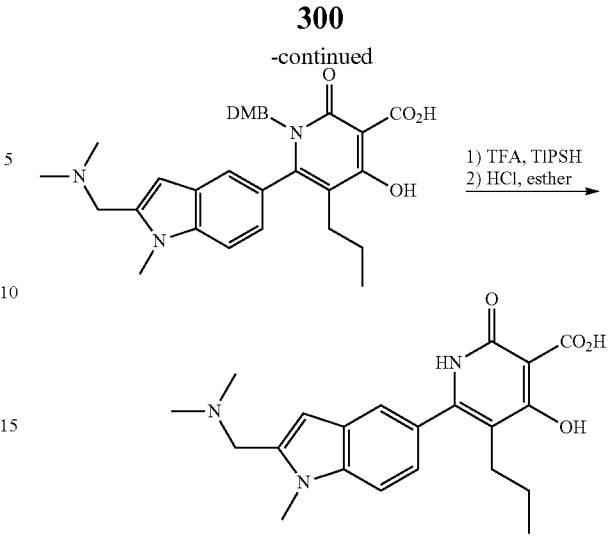

A mixture of 5-allyl-1-(2,4-dimethoxybenzyl)-6-(2-((dimethylamino)methyl)-1H-indol-5-yl)-4-hydroxy-2-oxo-1,2-dihydropyridine-3-carboxylic acid (45 mg, 0.085 mmol), prepared according to the procedure described in Example 164, Steps 1-6, and Pd/C (10 mg, 10%) in EtOAc (1 mL) was stirred under H₂ (1 atm) at room temperature for 2 h. The

| Cpd | Name |
|---|---|
| 330 | 4-amino-6-(2-((dimethylamino)methyl)-1-methyl-1H-indol-5-yl)-5-ethyl-2-oxo-1,2-dihydropyridine-3-carboxylic acid<br>¹H NMR (500 MHz, MeOH-d₄) δ ppm 1.03 (t, J = 7.41 Hz, 3 H) 2.37 (q, J = 7.59 Hz, 2 H) 2.97 (s, 6 H) 3.92 (s, 3 H) 4.67 (s, 2 H) 6.92 (s, 1 H) 7.33 (dd, J = 8.51, 1.66 Hz, 1 H) 7.66 (d, J = 8.43 Hz, 1 H) 7.71 (d, J = 1.50 Hz, 1 H). LC-MS 367.1 [M − H]⁻, 369.2 [M + H]⁺, RT 0.69 min. |
| 331 | 4-amino-5-ethyl-6-(1-methyl-2-(piperidin-l-ylmethyl)-1H-indol-5-yl)-2-oxo-1,2-dihydropyridine-3-carboxylic acid<br>¹H NMR (500 MHz, MeOH-d₄) δ ppm 1.03 (t, J = 7.45 Hz, 3 H) 1.93-2.05 (m, 2 H) 2.36 (q, J = 7.41 Hz, 2 H) 3.04-3.15 (m, 2 H) 3.27-3.35 (m, 4 H) 3.55-3.65 (m, 2 H) 3.92 (s, 3 H) 4.62 (s, 2 H) 6.91 (s, 1 H) 7.33 (dd, J = 8.55, 1.69 Hz, 1 H) 7.65 (d, J = 8.59 Hz, 1 H) 7.71 (d, J = 1.10 Hz, 1 H). LC-MS 407.1 [M − H]⁻, 409.2 [M + H]⁺, RT 0.74 min. |
| 332 | 4-amino-6-(24(3-(dimethylamino)pyrrolidin-l-yl)methyl)-1-methyl-1H-indol-5-yl)-5-ethyl-2-oxo-1,2-dihydropyridine-3-carboxylic acid<br>¹H NMR (500 MHz, MeOH-d₄) δ ppm 1.04 (t, J = 7.45 Hz, 3 H) 1.99-2.14 (m, 1 H) 2.32-2.45 (m, 1 H) 2.38 (q, J = 7.49 Hz, 2 H) 2.87 (s, 6 H) 3.29-3.37 (m, 4 H) 3.87 (s, 3 H) 3.90-3.98 (m, 1 H) 4.03 (s, 2 H) 6.59 (s, 1 H) 7.21 (dd, J = 8.47, 1.69 Hz, 1 H) 7.54 (d, J = 8.51 Hz, 1 H) 7.60 (d, J = 1.42 Hz, 1 H). LC-MS 436.2 [M − H]⁻, 438.3 [M + H]⁺, RT 0.65 min. |

Example 340

6-(2-((dimethylamino)methyl)-1-methyl-1H-indol-5-yl)-4-hydroxy-2-oxo-5-propyl-1,2-dihydropyridine-3-carboxylic acid

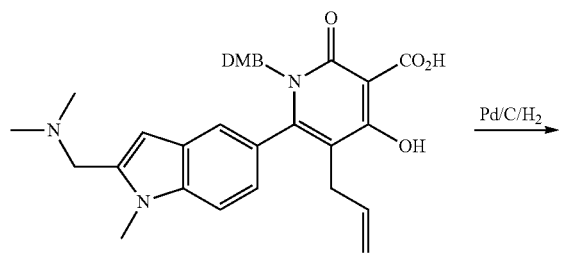

solvent was evaporated and the residue was chromatographed (0-2.5% MeOH in CH₂Cl₂) to give the intermediate of 1-(2,4-dimethoxybenzyl)-6-(2-((dimethylamino)methyl)-1H-indol-5-yl)-4-hydroxy-2-oxo-5-propyl-1,2-dihydropyridine-3-carboxylic acid. LC-MS 489.2 [M+H]⁺, RT 1.17 min. This intermediate was stirred in TFA (0.5 mL) and TIPS-H (0.5 mL) at room temperature for 15 h, and then the mixture was concentrated to dryness. The residue was dissolved in CH₂Cl₂ (0.5 mL), then HCl (2.0M in Et₂O, 1.0 mL) was added. The precipitate was collected by filtration and washed by ether to afford the title compound as an off-white solid (15 mg, 44% over 2 steps).

¹H NMR (500 MHz, DMSO-d₆) δ ppm 0.70 (t, J=7.3 Hz, 3H), 1.35-1.45 (m, 2H), 2.28-2.35 (m, 2H), 2.83 (s, 6H), 3.88 (s, 3H), 4.61 (s, 2H), 6.87 (s, 1H), 7.31 (dd, J=8.5, 1.6 Hz, 1H), 7.68 (d, J=8.5 Hz, 1H), 7.75 (d, J=1.2 Hz, 1H), 9.84-9.98 (br s, 1H), 12.72-12.80 (br s, 1H), 13.89-13.95 (br s, 1H), 16.27-16.38 (br s, 1H). LC-MS 339.2 [M+H]⁺, RT 1.03 min.

Example 359

6-(3-cyano-1-methyl-1H-indol-5-yl)-5-ethyl-4-hydroxy-2-oxo-1,2-dihydropyridine-3-carboxylic acid

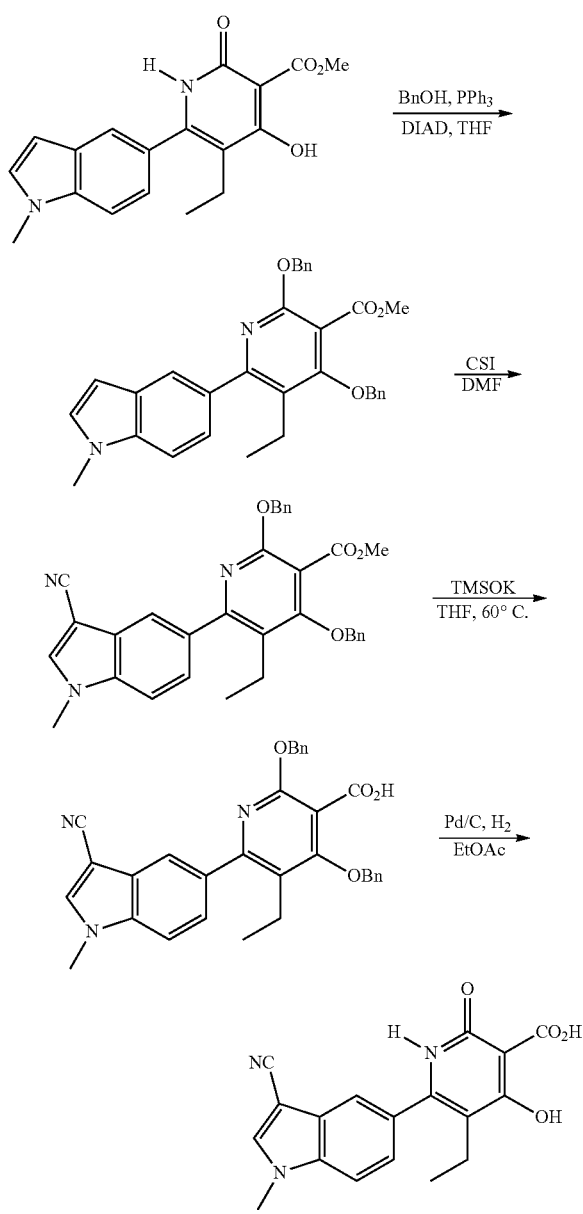

Step 1: methyl 2,4-bis(benzyloxy)-5-ethyl-6-(1-methyl-1H-indol-5-yl)nicotinate To a solution of methyl 5-ethyl-4-hydroxy-6-(1-methyl-1H-indol-5-yl)-2-oxo-1,2-dihydropyridine-3-carboxylate (1.15 g, 3.52 mmol), prepared according to the procedure described in Example 22 step 1, in THF (20 mL) was added triphenylphosphine (2.31 g, 8.81 mmol, 2.5 eq) and benzyl alcohol (0.92 mL, 8.88 mmol, 2.5 eq) at room temperature. The reaction mixture was cooled to 0° C. before DIAD (1.73 mL, 8.79 mmol, 2.5 eq) was added. The reaction was stirred at 0° C. for 1 h before it was allowed to warm to room temperature. The reaction was monitored by LC-MS. Upon completion, the solvents were removed under reduced pressure to give a crude product which was purified by flash column chromatography (0-15% EtOAc in hexanes) to afford the title compound (1.00 g, 56%).

$^1$H NMR (500 MHz, CHLOROFORM-d) δ ppm 1.05 (t, J=7.25 Hz, 3H) 2.65 (q, J=7.25 Hz, 2H) 3.85 (s, 3H) 3.91 (s, 3H) 5.13 (s, 2H) 5.46 (s, 2H) 6.55 (dd, J=3.15, 0.63 Hz, 1H) 7.12 (d, J=3.15 Hz, 1H) 7.28-7.50 (m, 12H) 7.71 (d, J=0.95 Hz, 1H). LC-MS 507.3 [M+H]$^+$, RT 1.73 min.

Step 2: methyl 2,4-bis(benzyloxy)-6-(3-cyano-1-methyl-1H-indol-5-yl)-5-ethylnicotinate To a solution of methyl 2,4-bis(benzyloxy)-5-ethyl-6-(1-methyl-1H-indol-5-yl)nicotinate (880 mg, 1.74 mmol) in DMF (10 mL) was added chlorosulfonyl isocyanate (0.18 mL, 2.07 mmol, 1.2 eq) at 0° C. The reaction was monitored by LC-MS and starting material was completely consumed within 5 min. The reaction was quenched with water then extracted by CH$_2$Cl$_2$ (3×30 mL). The combined organic layers were dried over Na$_2$SO$_4$ and then concentrated to give a crude product which was purified by trituration with hexanes and CH$_2$Cl$_2$ to afford the title compound (732 mg, 79%).

$^1$H NMR (500 MHz, CHLOROFORM-d) δ ppm 1.02 (t, J=7.41 Hz, 3H) 2.60 (q, J=7.25 Hz, 2H) 3.91 (s, 3H) 3.92 (s, 3H) 5.14 (s, 2H) 5.44 (s, 2H) 7.28-7.34 (m, 1H) 7.34-7.50 (m, 11H) 7.64 (s, 1H) 7.85 (t, J=1.10 Hz, 1H). LC-MS 532.4 [M+H]$^+$, RT 1.65 min.

Step 3: 2,4-bis(benzyloxy)-6-(3-cyano-1-methyl-1H-indol-5-yl)-5-ethylnicotinic acid To a solution of methyl 2,4-bis(benzyloxy)-6-(3-cyano-1-methyl-1H-indol-5-yl)-5-ethylnicotinate (130 mg, 0.24 mmol) in THF (2.5 mL) was added potassium trimethylsilanolate (80 mg, 0.62 mmol, 2.6 eq) at room temperature. Then the reaction mixture was heated to 60° C. and stirred for 8 h. Upon completion of the reaction, the solvents were removed under reduced pressure. The reaction was acidified with 1N HCl (1 mL) and then the reaction mixture was extracted with CH$_2$Cl$_2$ (3×20 mL). The solvent was removed to give a crude product which was purified by flash column chromatography (0-15% EtOAc in CH$_2$Cl$_2$) to afford the title compound (99 mg, 78%).

$^1$H NMR (500 MHz, CHLOROFORM-d) δ ppm 1.02 (t, J=7.41 Hz, 3H) 2.60 (q, J=7.57 Hz, 2H) 3.93 (s, 3H) 5.18 (s, 2H) 5.54 (s, 2H) 7.30-7.45 (m, 6H) 7.45-7.51 (m, 6H) 7.66 (s, 1H) 7.88 (t, J=1.10 Hz, 1H). LC-MS 518.3 [M+H]$^+$, RT 1.50 min.

Step 4: 6-(3-cyano-1-methyl-1H-indol-5-yl)-5-ethyl-4-hydroxy-2-oxo-1,2-dihydropyridine-3-carboxylic acid To a solution of 2,4-bis(benzyloxy)-6-(3-cyano-1-methyl-1H-indol-5-yl)-5-ethylnicotinic acid (123 mg, 0.24 mmol) in EtOAc (4 mL) was added Pd/C (10% Degussa type, 30 mg) at room temperature. The flask was evacuated then back-filled with H$_2$ (1 atm) over three cycles. The reaction was monitored by LC-MS. Upon completion, the reaction mixture was filtered through celite then washed with MeOH (ca. 25 mL) thoroughly. The filtrated was concentrated to afford the title compound (58 mg, 72%).

¹H NMR (500 MHz, DMSO-d₆) δ ppm 0.99 (t, J=7.25 Hz, 3H) 2.32 (q, J=6.94 Hz, 2H) 3.93 (s, 3H) 7.42 (d, J=8.51 Hz, 1H) 7.74 (s, 1H) 7.78 (d, J=8.51 Hz, 1H) 8.37 (s, 1H) 12.76 (br. s., 1H) 14.58 (br. s., 1H) 15.88 (br. s., 1H). LC-MS 336.1 [M−H]⁻, 338.1 [M+H]⁺, RT 1.29 min.

Example 360

6-(3-cyano-1-methyl-2-(pyrrolidin-1-yl)-1H-indol-5-yl)-5-ethyl-4-hydroxy-2-oxo-1,2-dihydropyridine-3-carboxylic acid

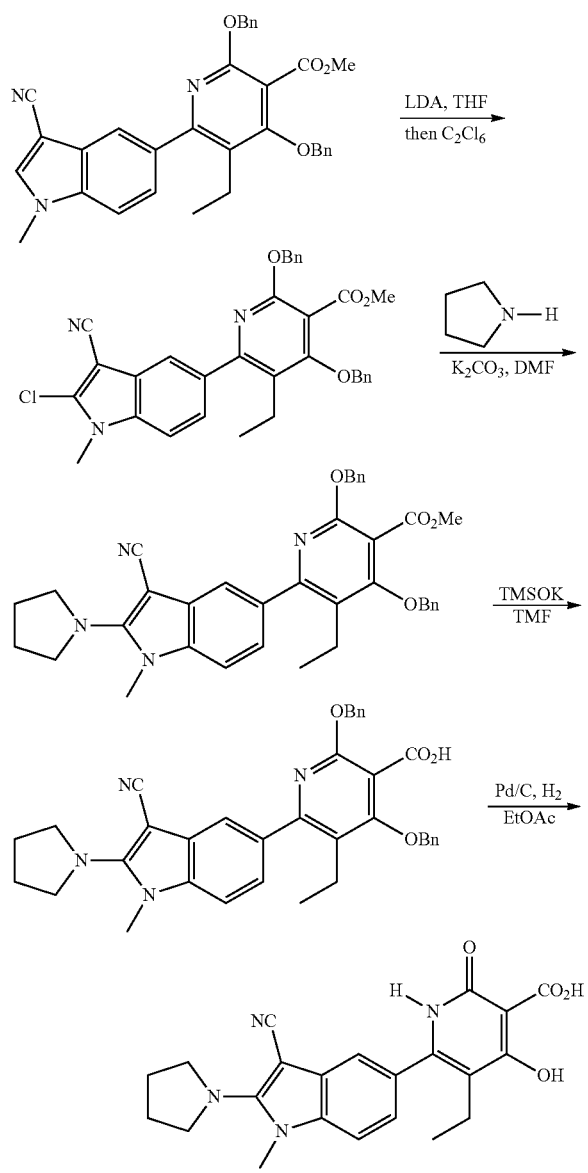

Step 1: methyl 2,4-bis(benzyloxy)-6-(2-chloro-3-cyano-1-methyl-1H-indol-5-yl)-5-ethylnicotinate To a solution of methyl 2,4-bis(benzyloxy)-6-(3-cyano-1-methyl-1H-indol-5-yl)-5-ethylnicotinate (1.80 g, 3.39 mmol), prepared in Example 359 step 2, in THF (24 mL) was added LDA solution (1.5M in cyclohexane, 3.40 mL, 5.10 mmol, 1.5 eq) dropwise at −78° C. The reaction mixture was stirred for 15 min before a solution of hexachloroethane (1.21 g, 5.1 mmol, 1.5 eq) in THF (6 mL) was added dropwise at −78° C. The reaction progress was monitored by LC-MS. Upon completion, the reaction was quenched with sat. NH₄Cl solution then extracted with Et₂O (4×30 mL). The combined organic layers were dried over Na₂SO₄ then concentrated to give a crude product which was purified by flash column chromatography (0-10% EtOAc in 1/1 CH₂Cl₂/hexanes) to afford the title compound (1.58 g, 82%).

¹H NMR (500 MHz, CHLOROFORM-d) δ ppm 1.01 (t, J=7.41 Hz, 3H) 2.58 (q, J=7.46 Hz, 2H) 3.86 (s, 3H) 3.92 (s, 3H) 5.13 (s, 2H) 5.44 (s, 2H) 7.27-7.49 (m, 12H) 7.71-7.79 (m, 1H). LC-MS 566.3/568.3 [M+H]⁺, RT 1.73 min.

Step 2: methyl 2,4-bis(benzyloxy)-6-(3-cyano-1-methyl-2-(pyrrolidin-1-yl)-1H-indol-5-yl)-5-ethylnicotinate To a solution of methyl 2,4-bis(benzyloxy)-6-(2-chloro-3-cyano-1-methyl-1H-indol-5-yl)-5-ethylnicotinate (143 mg, 0.25 mmol) in DMF (2 mL) was added potassium carbonate (70 mg, 0.50 mmol, 2.0 eq) followed by pyrrolidine (0.05 mL, 0.61 mmol, 2.4 eq) at room temperature. The reaction was heated to 60° C. and the progress was monitored by LC-MS. Upon completion, the reaction was quenched with water then extracted with EtOAc (3×25 mL). The solvent was removed under reduced pressure and the crude product was purified by flash column chromatography (0-10% EtOAc in 1/1 CH₂Cl₂/hexanes) to afford the title compound (134 mg, 89%).

¹H NMR (500 MHz, CHLOROFORM-d) δ ppm 1.02 (t, J=7.41 Hz, 3H) 2.02-2.10 (m, 4H) 2.62 (q, J=7.57 Hz, 2H) 3.67 (s, 3H) 3.69-3.77 (m, 4H) 3.90 (s, 3H) 5.12 (s, 2H) 5.45 (s, 2H) 7.17-7.23 (m, 1H) 7.23-7.32 (m, 2H) 7.32-7.49 (m, 9H) 7.57-7.64 (m, 1H). LC-MS 601.4 [M+H]⁺, RT 1.74 min.

Step 3: 2,4-bis(benzyloxy)-6-(3-cyano-1-methyl-2-(pyrrolidin-1-yl)-1H-indol-5-yl)-5-ethylnicotinic acid The title compound (98 mg, 0.17 mmol) was prepared according to procedure described in Example 359, Step 3 from methyl 2,4-bis(benzyloxy)-6-(3-cyano-1-methyl-2-(pyrrolidin-1-yl)-1H-indol-5-yl)-5-ethylnicotinate (134 mg, 0.22 mmol) in 76% yield. LC-MS 585.4 [M−H]⁻, 587.4 [M+H]⁺, RT 1.61 min.

Step 4: 6-(3-cyano-1-methyl-2-(pyrrolidin-1-yl)-1H-indol-5-yl)-5-ethyl-4-hydroxy-2-oxo-1,2-dihydropyridine-3-carboxylic acid The title compound (60 mg, 0.15 mmol) was prepared according to the procedure described in Example 359 Step 4 from 2,4-bis(benzyloxy)-6-(3-cyano-1-methyl-2-(pyrrolidin-1-yl)-1H-indol-5-yl)-5-ethylnicotinic acid (98 mg, 0.17 mmol) in 87% yield.

¹H NMR (500 MHz, DMSO-d₆) δ ppm 1.00 (t, J=7.41 Hz, 3H) 1.98 (dt, J=6.23, 3.35 Hz, 4H) 2.33 (q, J=6.94 Hz, 2H) 3.67-3.80 (m, 7H) 7.17 (dd, J=8.20, 1.58 Hz, 1H) 7.31 (s, 1H) 7.48 (d, J=8.20 Hz, 1H) 12.74 (br. s., 1H) 14.20 (br. s., 1H). LC-MS 405.2 [M−H]⁻, 407.2 [M+H]⁺, RT 1.42 min.

Using the procedures described above, additional compounds described herein may be prepared by substituting the appropriate starting materials, reagents and reaction conditions and include compounds selected from:

| Cpd | Name |
|---|---|
| 361 | 6-(3-cyano-2-(dimethylamino)-1-methyl-1H-indol-5-yl)-5-ethyl-4-hydroxy-2-oxo-1,2-dihydropyridine-3-carboxylic acid<br>$^1$H NMR (500 MHz, DMSO-$d_6$) δ ppm 0.99 (t, J = 7.41 Hz, 3 H) 2.33 (q, J = 7.25 Hz, 2 H) 3.08 (s, 6 H) 3.66 (s, 3 H) 7.26 (dd, J = 8.20, 1.58 Hz, 1 H) 7.45 (s, 1 H) 7.55 (d, J = 8.20 Hz, 1 H) 12.76 (br. s., 1 H) 14.34 (br. s., 1 H) 16.11 (br. s., 1 H). LC-MS 379.1 [M − H]$^-$, 381.1 [M + H]$^+$, RT 1.38 min. |
| 362 | 6-(3-cyano-2-methoxy-1-methyl-1H-indol-5-yl)-5-ethyl-4-hydroxy-2-oxo-1,2-dihydropyridine-3-carboxylic acid<br>$^1$H NMR (500 MHz, DMSO-$d_6$) δ ppm 1.00 (t, J = 7.25 Hz, 3 H) 2.33 (q, J = 7.25 Hz, 2 H) 3.62 (s, 3 H) 4.38 (s, 3 H) 7.24-7.34 (m, 1 H) 7.50 (s, 1 H) 7.58 (d, J = 8.51 Hz, 1 H) 12.75 (br. s., 1 H) 14.68 (br. s., 1 H). LC-MS 366.1 [M − H]$^-$, 368.1 [M + H]$^+$, RT 1.38 min. |

Example 363

6-(3-chloro-1-methyl-1H-indol-5-yl)-5-ethyl-4-hydroxy-2-oxo-1,2-dihydropyridine-3-carboxylic acid

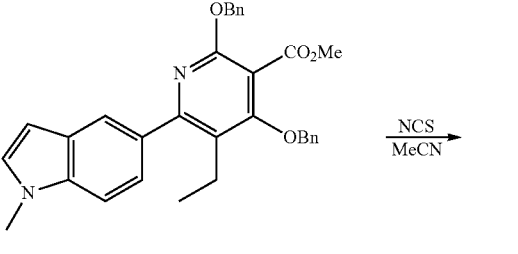

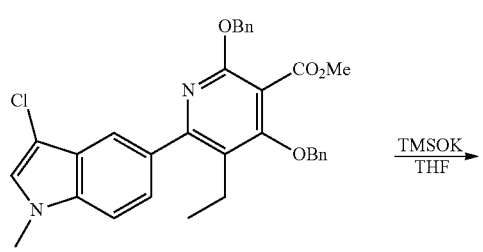

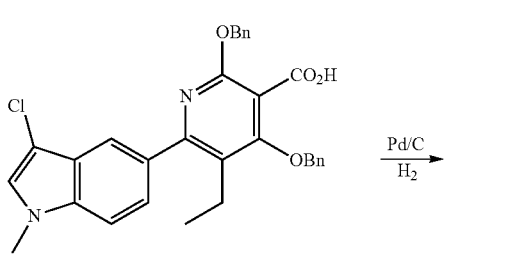

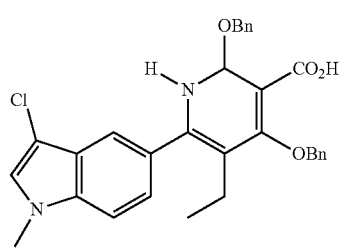

Step 1: methyl 2,4-bis(benzyloxy)-6-(3-chloro-1-methyl-1H-indol-5-yl)-5-ethylnicotinate To a solution of methyl 2,4-bis(benzyloxy)-5-ethyl-6-(1-methyl-1H-indol-5-yl)nicotinate (131 mg, 0.26 mmol), prepared in Example 359, step 1, in MeCN (2 mL) was added NCS (35 mg, 0.26 mmol) at 0° C. The reaction was stirred at 0° C. for 1 h before it was allowed to warm to room temperature. The reaction progress was monitored by LC-MS. Upon completion, the reaction was quenched with water then extracted by $CH_2Cl_2$ (3×20 mL). The solvent was removed to give the crude product which was purified by flash column chromatography (0-10% EtOAc in hexanes) to afford the desired product (100 mg, 71%).

$^1$H NMR (500 MHz, CHLOROFORM-d) δ ppm 1.05 (t, J=7.41 Hz, 3H) 2.62 (q, J=7.25 Hz, 2H) 3.82 (s, 3H) 3.91 (s, 3H) 5.13 (s, 2H) 5.48 (s, 2H) 7.10 (s, 1H) 7.28-7.33 (m, 1H) 7.33-7.50 (m, 11H) 7.70 (t, J=1.10 Hz, 1H). LC-MS 541.3/543.3 [M+H]$^+$, RT 1.81 min.

Step 2: 2,4-bis(benzyloxy)-6-(3-chloro-1-methyl-1H-indol-5-yl)-5-ethylnicotinic acid The title compound (87 mg, 0.17 mmol) was prepared according to procedure described in Example 359 Step 3 from methyl 2,4-bis(benzyloxy)-6-(3-chloro-1-methyl-1H-indol-5-yl)-5-ethylnicotinate (100 mg, 0.18 mmol) in 89% yield.

$^1$H NMR (500 MHz, CHLOROFORM-d) δ ppm 1.05 (t, J=7.41 Hz, 3H) 2.63 (q, J=7.36 Hz, 2H) 3.83 (s, 3H) 5.17 (s, 2H) 5.56 (s, 2H) 7.12 (s, 1H) 7.31-7.45 (m, 8H) 7.46-7.52 (m, 4H) 7.74 (dd, J=1.42, 0.79 Hz, 1H). LC-MS 527.3/529.2 [M+H]$^+$, RT 1.65 min.

Step 3: 6-(3-chloro-1-methyl-1H-indol-5-yl)-5-ethyl-4-hydroxy-2-oxo-1,2-dihydropyridine-3-carboxylic acid The title compound (25 mg, 0.072 mmol) was prepared according to procedure described in Example 359 Step 4 from 2,4-bis(benzyloxy)-6-(3-chloro-1-methyl-1H-indol-5-yl)-5-ethylnicotinic acid (87 mg, 0.17 mmol) in 44% yield.

$^1$H NMR (500 MHz, DMSO-$d_6$) δ ppm 1.00 (t, J=7.25 Hz, 3H) 2.32 (q, J=7.25 Hz, 2H) 3.85 (s, 3H) 7.33 (dd, J=8.51, 1.58 Hz, 1H) 7.57-7.65 (m, 1H) 7.65-7.73 (m, 2H) 12.77 (br. s., 1H) 13.92 (br. s., 1H). LC-MS 345.1/347.1 [M−H]$^-$, 347.1/349.1 [M+H]$^+$, RT 1.47 min.

Example 364

6-(benzofuran-5-yl)-5-ethyl-2-oxo-1,2-dihydropyridine-3-carboxylic acid

Step 1: N-methoxy-N-methylbenzofuran-5-carboxamide

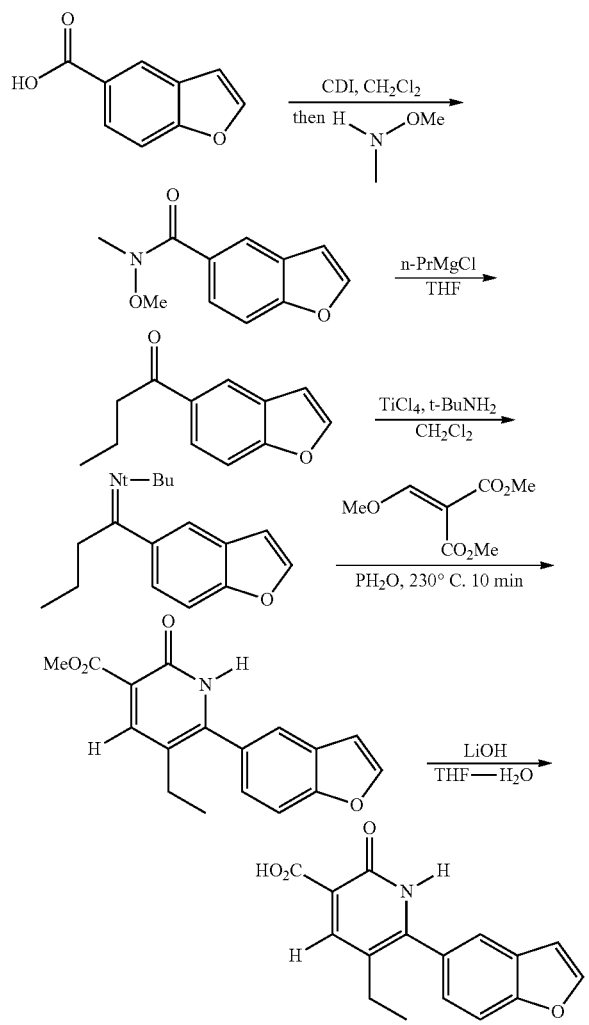

The title compound (1.28 g, 6.25 mmol) was prepared according to the procedure described in Example 15, Step 3 from benzofuran-5-carboxylic acid (1.10 g, 6.78 mmol) in 92% yield.

$^1$H NMR (500 MHz, CHLOROFORM-d) δ ppm 3.40 (s, 3H) 3.56 (s, 3H) 6.83 (dd, J=2.05, 1.10 Hz, 1H) 7.49-7.55 (m, 1H) 7.65-7.71 (m, 2H) 8.00 (d, J=1.58 Hz, 1H). LC-MS 206.2 [M+H]$^+$, RT 0.99 min.

Step 2: 1-(benzofuran-5-yl)butan-1-one

The title compound (903 mg, 4.80 mmol) was prepared according to the procedure described in Example 15, Step 4 from N-methoxy-N-methylbenzofuran-5-carboxamide (1.28 g, 6.25 mmol) in 77% yield.

$^1$H NMR (500 MHz, CHLOROFORM-d) δ ppm 1.04 (t, J=7.41 Hz, 3H) 1.81 (sxt, J=7.38 Hz, 2H) 3.02 (t, J=7.41 Hz, 2H) 6.87 (dd, J=2.21, 0.95 Hz, 1H) 7.55 (d, J=8.51 Hz, 1H) 7.70 (d, J=2.21 Hz, 1H) 7.98 (dd, J=8.83, 1.89 Hz, 1H) 8.27 (d, J=1.58 Hz, 1H). LC-MS 189.2 [M+H]$^+$, RT 1.28 min.

Step 3: N-(1-(benzofuran-5-yl)butylidene)-2-methylpropan-2-amine

The title compound (1.22 g, ca. 4.80 mmol) was prepared according to the procedure described in Example 1, Step 6 from 1-(benzofuran-5-yl)butan-1-one (903 mg, 4.80 mmol) in quantitative yield. LC-MS 244.3 [M+H]$^+$, RT 0.89 min.

Step 4-5: 6-(benzofuran-5-yl)-5-ethyl-2-oxo-1,2-dihydropyridine-3-carboxylic acid The title compound (106 mg, 0.37 mmol) was prepared according to the procedure described in Example 1, Step 7-8 from N-(1-(benzofuran-5-yl)butylidene)-2-methylpropan-2-amine (0.61 g, ca. 2.40 mmol) in 15% yield over three steps.

$^1$H NMR (500 MHz, DMSO-d$_6$) δ ppm 1.02 (t, J=7.57 Hz, 3H) 2.39 (q, J=7.57 Hz, 2H) 7.08 (dd, J=2.21, 0.95 Hz, 1H) 7.43 (dd, J=8.51, 1.89 Hz, 1H) 7.77 (d, J=8.51 Hz, 1H) 7.83 (d, J=1.26 Hz, 1H) 8.14 (d, J=2.21 Hz, 1H) 8.40 (s, 1H) 13.31 (br. s., 1H) 15.04 (br. s., 1H). LC-MS 282.3 [M−H]$^−$, 284.3 [M+H]$^+$, RT 1.07 min.

Example 365

6-(benzofuran-5-yl)-5-ethyl-4-hydroxy-2-oxo-1,2-dihydropyridine-3-carboxylic acid

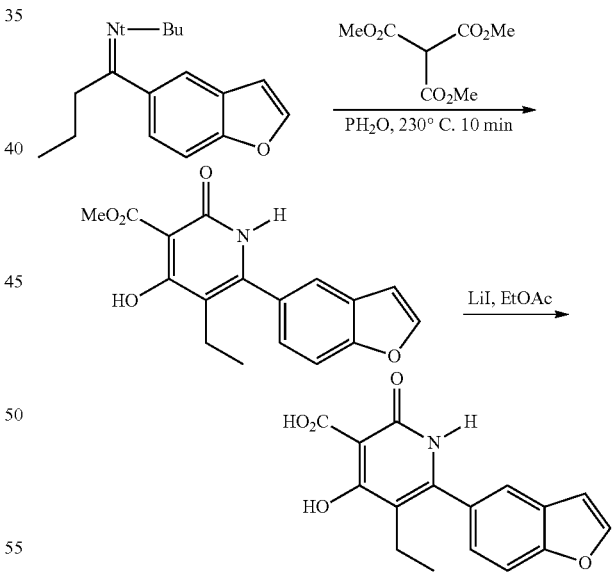

Step 1-2: 6-(benzofuran-5-yl)-5-ethyl-4-hydroxy-2-oxo-1,2-dihydropyridine-3-carboxylic acid The title compound (123 mg, 0.41 mmol) was prepared according to the procedure described in Example 2, Step 1-2 from N-(1-(benzofuran-5-yl)butylidene)-2-methylpropan-2-amine (0.61 g, ca. 2.40 mmol) in 17% yield over three steps.

$^1$H NMR (500 MHz, DMSO-d$_6$) δ ppm 0.98 (t, J=7.25 Hz, 3H) 2.29 (q, J=7.25 Hz, 2H) 7.09 (d, J=1.58 Hz, 1H) 7.41 (dd, J=8.51, 1.58 Hz, 1H) 7.77 (d, J=8.51 Hz, 1H) 7.80-7.84 (m, 1H) 8.14 (d, J=1.89 Hz, 1H) 12.81 (br. s., 1H) 13.92 (br. s., 1H) 16.29 (br. s., 1H). LC-MS 298.3 [M−H]⁻, 300.3 [M+H]⁺, RT 1.23 min.

Example 366

6-(benzo[b]thiophen-5-yl)-5-ethyl-2-oxo-1,2-dihydropyridine-3-carboxylic acid

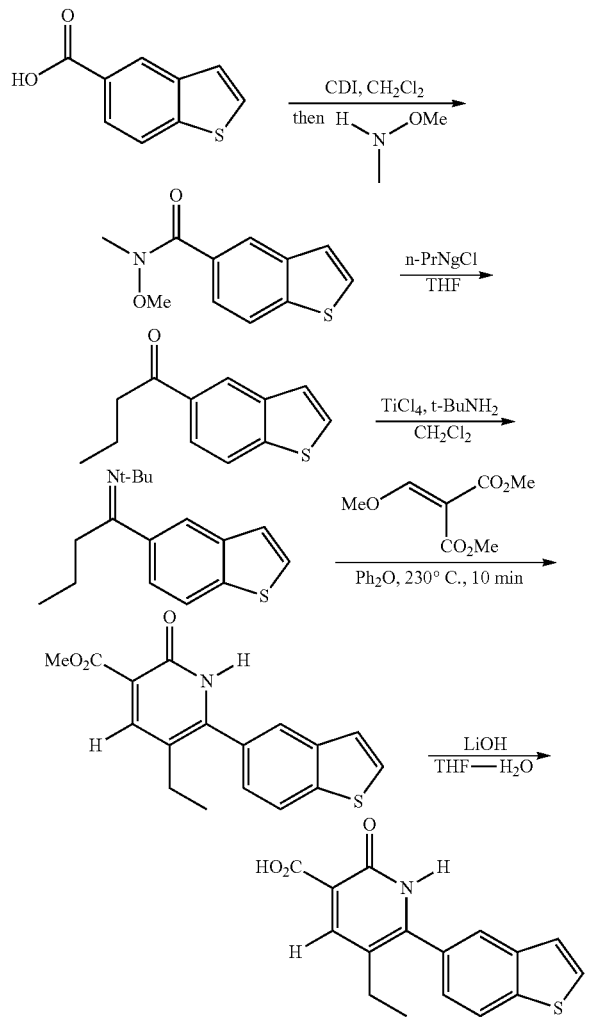

Step 1: N-methoxy-N-methylbenzo[b]thiophene-5-carboxamide

The title compound (1.33 g, 6.01 mmol) was prepared according to the procedure described in Example 15, Step 3 from benzo[b]thiophene-5-carboxylic acid (1.10 g, 6.17 mmol) in 97% yield.

¹H NMR (500 MHz, CHLOROFORM-d) δ ppm 3.41 (s, 3H) 3.57 (s, 3H) 7.38-7.42 (m, 1H) 7.51 (d, J=5.67 Hz, 1H) 7.68 (dd, J=8.35, 1.42 Hz, 1H) 7.89-7.94 (m, 1H) 8.20 (d, J=1.26 Hz, 1H). LC-MS 222.1 [M+H]⁺, RT 1.22 min.

Step 2: 1-(benzo[b]thiophen-5-yl)butan-1-one

The title compound (1.14 g, 5.58 mmol) was prepared according to the procedure described in Example 15, Step 4 from N-methoxy-N-methylbenzo[b]thiophene-5-carboxamide (1.33 g, 6.01 mmol) in 93% yield.

¹H NMR (500 MHz, CHLOROFORM-d) δ ppm 1.05 (t, J=7.41 Hz, 3H) 1.83 (sxt, J=7.38 Hz, 2H) 3.05 (t, J=7.41 Hz, 2H) 7.45 (d, J=5.36 Hz, 1H) 7.54 (d, J=5.36 Hz, 1H) 7.91-8.01 (m, 2H) 8.45 (s, 1H). LC-MS 205.1 [M+H]⁺, RT 1.51 min.

Step 3: N-(1-(benzo[b]thiophen-5-yl)butylidene)-2-methylpropan-2-amine

The title compound (1.50 g, ca. 5.58 mmol) was prepared according to the procedure described in Example 1, Step 6 from 1-(benzo[b]thiophen-5-yl)butan-1-one (1.14 g, 5.58 mmol) in quantitative yield. LC-MS 260.2 [M+H]⁺, RT 1.09 min.

Step 4-5: 6-(benzo[b]thiophen-5-yl)-5-ethyl-2-oxo-1,2-dihydropyridine-3-carboxylic acid The title compound (129 mg, 0.43 mmol) was prepared according to the procedure described in Example 1, Step 7-8 from N-(1-(benzo[b]thiophen-5-yl)butylidene)-2-methylpropan-2-amine (0.75 g, ca. 2.79 mmol) in 15% yield over three steps.

¹H NMR (500 MHz, DMSO-d₆) δ ppm 1.02 (t, J=7.41 Hz, 3H) 2.41 (q, J=7.36 Hz, 2H) 7.46 (dd, J=8.20, 1.58 Hz, 1H) 7.58 (d, J=5.67 Hz, 1H) 7.92 (d, J=5.36 Hz, 1H) 8.04 (d, J=1.58 Hz, 1H) 8.19 (d, J=8.20 Hz, 1H) 8.41 (s, 1H) 13.34 (br. s., 1H) 15.02 (br. s., 1H). LC-MS 298.1 [M−H]⁻, 300.1 [M+H]⁺, RT 1.28 min.

Example 367

6-(benzo[b]thiophen-5-yl)-5-ethyl-4-hydroxy-2-oxo-1,2-dihydropyridine-3-carboxylic acid

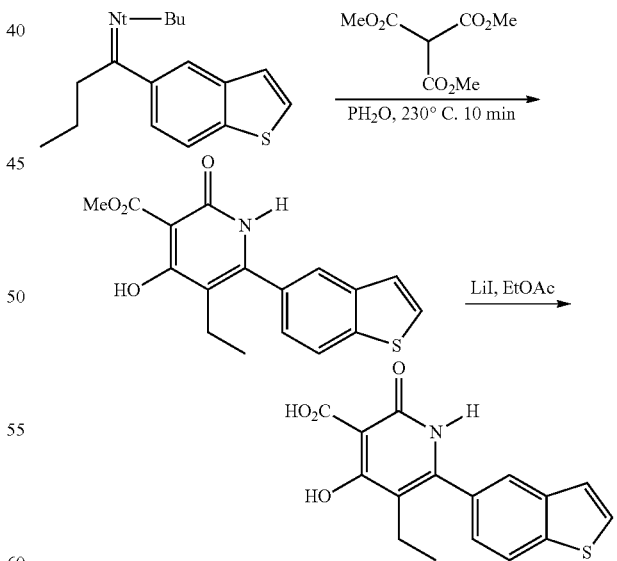

Step 1-2: 6-(benzo[b]thiophen-5-yl)-5-ethyl-4-hydroxy-2-oxo-1,2-dihydropyridine-3-carboxylic acid The title compound (140 mg, 0.44 mmol) was prepared according to the procedure described in Example 2, Step 1-2 from N-(1-(benzo[b]thiophen-5-yl)butylidene)-2-methyl-propan-2-amine (0.75 g, ca. 2.79 mmol) in 16% yield over three steps.

$^1$H NMR (500 MHz, DMSO-d$_6$) δ ppm 0.99 (t, J=7.25 Hz, 3H) 2.31 (q, J=7.04 Hz, 2H) 7.44 (d, J=7.88 Hz, 1H) 7.58 (d, J=5.04 Hz, 1H) 7.91 (d, J=5.04 Hz, 1H) 8.02 (s, 1H) 8.19 (d, J=8.20 Hz, 1H) 12.83 (br. s., 1H) 13.93 (br. s., 1H) 16.27 (br. s., 1H). LC-MS 314.1 [M−H]$^-$, 316.1 [M+H]$^+$, RT 1.44 min.

Example 368

5-ethyl-6-(3-fluoro-1-methyl-2-((methylamino)methyl)-1H-indol-5-yl)-4-hydroxy-2-oxo-1,2-dihydro-pyridine-3-carboxylic acid

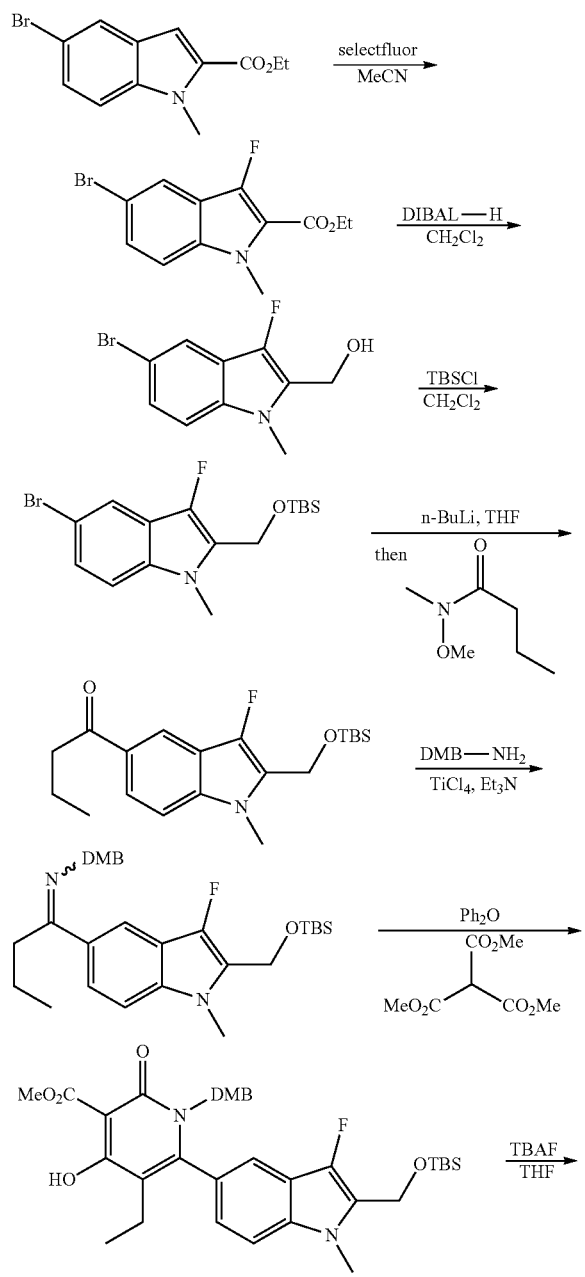

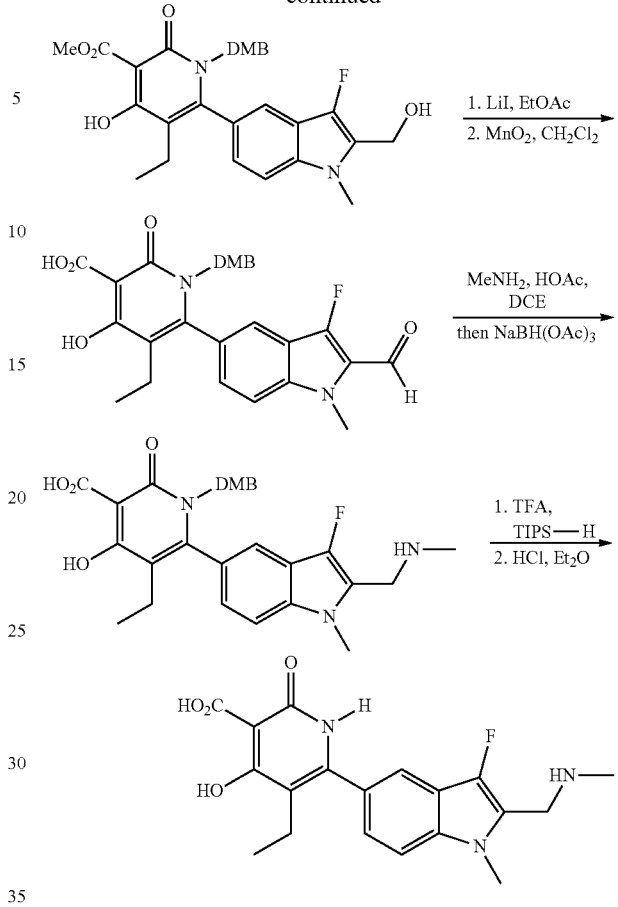

Step 1: ethyl 5-bromo-3-fluoro-1-methyl-1H-indole-2-carboxylate

To a stirred solution of ethyl 5-bromo-1-methyl-1H-indole-2-carboxylate (2.93 g, 10.39 mmol) in MeCN (52 mL) was added Selectfluor® (3.87 g, 10.92 mmol, 1.05 eq) at 0° C. in three portions with an interval of 10 min. The reaction was stirred at 0° C. for 30 min before it was allowed to warm to room temperature then stirred for an additional 30 min. The reaction was monitored by TLC analysis. Once the starting material was completely consumed, the reaction was quenched with sat. NaHCO$_3$ and then extracted by CH$_2$Cl$_2$ (4×25 mL). The solvent was removed to give a crude product which was purified by flash column chromatography (0-10% EtOAc in hexanes) to afford the desired product (860 mg, 2.87 mmol) in 28% yield.

$^1$H NMR (500 MHz, CHLOROFORM-d) δ ppm 1.44 (t, J=7.09 Hz, 3H) 3.97-4.01 (m, 3H) 4.43 (q, J=7.25 Hz, 2H) 7.24 (dd, J=9.14, 1.89 Hz, 1H) 7.44 (dd, J=8.83, 1.89 Hz, 1H) 7.83 (dd, J=1.89, 0.63 Hz, 1H).

Step 2: (5-bromo-3-fluoro-1-methyl-1H-indol-2-yl)methanol

The title compound (734 mg, 2.84 mmol) was prepared according to the procedure described in Example 39, Step 2 from ethyl 5-bromo-3-fluoro-1-methyl-1H-indole-2-carboxylate (860 mg, 2.87 mmol) in 99% yield.

$^1$H NMR (500 MHz, CHLOROFORM-d) δ ppm 3.77 (d, J=0.63 Hz, 3H) 4.86 (d, J=1.26 Hz, 2H) 7.17 (dd, J=8.83, 2.21

Hz, 1H) 7.33 (dd, J=8.83, 1.89 Hz, 1H) 7.73 (d, J=1.58 Hz, 1H). LC-MS 240.1/242.1 [M+H−H$_2$O]$^+$, RT 1.20 min.

Step 3: 5-bromo-2-((tert-butyldimethylsilyloxy)methyl)-3-fluoro-1-methyl-1H-indole The title compound (1.02 g, 2.75 mmol) was prepared according to the procedure described in Example 39, Step 3 from (5-bromo-3-fluoro-1-methyl-1H-indol-2-yl)methanol (734 mg, 2.84 mmol) in 97% yield.

$^1$H NMR (500 MHz, CHLOROFORM-d) δ ppm 0.06 (s, 6H) 0.88 (s, 9H) 3.74 (d, J=0.63 Hz, 3H) 4.85 (d, J=1.58 Hz, 2H) 7.15 (dd, J=8.83, 2.21 Hz, 1H) 7.30 (dd, J=8.67, 2.05 Hz, 1H) 7.72 (d, J=1.89 Hz, 1H).

Step 4: 1-(2-((tert-butyldimethylsilyloxy)methyl)-3-fluoro-1-methyl-1H-indol-5-yl)butan-1-one The title compound (820 mg, 2.26 mmol) was prepared according to the procedure described in Example 21, Step 1 from 5-bromo-2-((tert-butyldimethylsilyloxy)methyl)-3-fluoro-1-methyl-1H-indole (1.02 g, 2.75 mmol) in 82% yield.

$^1$H NMR (500 MHz, CHLOROFORM-d) δ ppm 0.08 (s, 6H) 0.89 (s, 9H) 1.04 (t, J=7.44 Hz, 3H) 1.82 (sxt, J=7.44 Hz, 2H) 2.98-3.05 (m, 2H) 3.79 (s, 3H) 4.88 (d, J=1.58 Hz, 2H) 7.31 (dd, J=8.83, 1.89 Hz, 1H) 7.92 (dd, J=8.83, 1.58 Hz, 1H) 8.27 (d, J=1.26 Hz, 1H). LC-MS 364.3 [M+H]$^+$, RT 1.71 min.

Step 5: N-(1-(2-((tert-butyldimethylsilyloxy)methyl)-3-fluoro-1-methyl-1H-indol-5-yl)butylidene)-1-(2,4-dimethoxyphenyl)methanamine The title compound (1.20 g, ca. 2.26 mmol) was prepared according to the procedure described in Example 164, Step 1 from 1-(2-((tert-butyldimethylsilyloxy)methyl)-3-fluoro-1-methyl-1H-indol-5-yl)butan-1-one (820 mg, 2.26 mmol) in quantitative yield. LC-MS 513.5 [M+H]$^+$, RT 1.71 min.

Step 6: methyl 6-(2-((tert-butyldimethylsilyloxy)methyl)-3-fluoro-1-methyl-1H-indol-5-yl)-1-(2,4-dimethoxybenzyl)-5-ethyl-4-hydroxy-2-oxo-1,2-dihydropyridine-3-carboxylate The title compound (513 mg, 0.80 mmol) was prepared according to the procedure described in Example 164, Step 2 from N-(1-(2-((tert-butyldimethylsilyloxy)methyl)-3-fluoro-1-methyl-1H-indol-5-yl)butylidene)-1-(2,4-dimethoxyphenyl)methanamine (1.20 g, ca. 2.26 mmol) in 35% yield over two steps.

$^1$H NMR (500 MHz, CHLOROFORM-d) δ ppm 0.11 (s, 3H) 0.12 (s, 3H) 0.91 (s, 9H) 2.03-2.22 (m, 2H) 3.19 (s, 3H) 3.76 (s, 6H) 4.02 (s, 3H) 4.79-4.92 (m, 3H) 4.92-5.01 (m, 1H) 6.14 (d, J=2.52 Hz, 1H) 6.34-6.44 (m, 1H) 6.79 (dd, J=8.51, 1.26 Hz, 1H) 6.84 (d, J=8.51 Hz, 1H) 7.09 (s, 1H) 7.16-7.23 (m, 1H) 13.73 (s, 1H). LC-MS 639.5 [M+H]$^+$, RT 1.75 min.

Step 7: methyl 1-(2,4-dimethoxybenzyl)-5-ethyl-6-(3-fluoro-2-(hydroxymethyl)-1-methyl-1H-indol-5-yl)-4-hydroxy-2-oxo-1,2-dihydropyridine-3-carboxylate The title compound (400 mg, 0.76 mmol) was prepared according to the procedure described in Example 164, Step 3 from methyl 6-(2-((tert-butyldimethylsilyloxy)methyl)-3-fluoro-1-methyl-1H-indol-5-yl)-1-(2,4-dimethoxybenzyl)-5-ethyl-4-hydroxy-2-oxo-1,2-dihydropyridine-3-carboxylate (513 mg, 0.80 mmol) in 95% yield. LC-MS 523.3 [M−H]$^-$, 525.3 [M+H]$^+$, RT 1.28 min.

Step 8-9: 1-(2,4-dimethoxybenzyl)-5-ethyl-6-(3-fluoro-2-formyl-1-methyl-1H-indol-5-yl)-4-hydroxy-2-oxo-1,2-dihydropyridine-3-carboxylic acid The title compound (255 mg, 0.50 mmol) was prepared according to the procedure described in Example 164, Step 4-5 from methyl 1-(2,4-dimethoxybenzyl)-5-ethyl-6-(3-fluoro-2-(hydroxymethyl)-1-methyl-1H-indol-5-yl)-4-hydroxy-2-oxo-1,2-dihydropyridine-3-carboxylate (400 mg, 0.76 mmol) in 66% yield over two steps. LC-MS 507.2 [M−H]$^-$, 509.2 [M+H]$^+$, RT 1.58 min.

Step 10-12: 5-ethyl-6-(3-fluoro-1-methyl-2-((methylamino)methyl)-1H-indol-5-yl)-4-hydroxy-2-oxo-1,2-dihydropyridine-3-carboxylic acid The title compound (6 mg, 0.015 mmol) was prepared according to the procedure described in Example 164, Step 6-8 from 1-(2,4-dimethoxybenzyl)-5-ethyl-6-(3-fluoro-2-formyl-1-methyl-1H-indol-5-yl)-4-hydroxy-2-oxo-1,2-dihydropyridine-3-carboxylic acid (64 mg, 0.126 mmol) in 12% yield over three steps.

$^1$H NMR (500 MHz, DMSO-d$_6$) δ ppm 0.98 (t, J=7.09 Hz, 3H) 2.32 (q, J=6.94 Hz, 2H) 2.63 (br. s., 3H) 3.88 (br. s., 3H) 4.47 (br. s., 2H) 7.36 (d, J=8.51 Hz, 1H) 7.67-7.79 (m, 2H) 9.38 (br. s., 2H) 12.81 (br. s., 1H) 13.91 (s, 1H). LC-MS 372.2 [M−H]$^-$, 374.3 [M+H]$^+$, RT 0.93 min.

Using the procedures described above, additional compounds described herein may be prepared by substituting the appropriate starting materials, reagents and reaction conditions and include compounds selected from:

| Cpd | Name |
| --- | --- |
| 369 | 5-ethyl-6-(2-((ethylamino)methyl)-3-fluoro-1-methyl-1H-indol-5-yl)-4-hydroxy-2-oxo-1,2-dihydropyridine-3-carboxylic acid<br>$^1$H NMR (500 MHz, DMSO-d6) δ ppm 0.98 (t, J = 7.25 Hz, 3 H) 1.27 (t, J = 7.09 Hz, 3 H) 2.32 (q, J = 6.83 Hz, 2 H) 3.07 (d, J = 4.41 Hz, 2 H) 3.88 (s, 3 H) 4.47 (br. s., 2 H) 7.37 (d, J = 8.51 Hz, 1 H) 7.67-7.70 (m, 2 H) 9.22 (br. s., 2 H) 12.81 (br. s., 1 H) 13.91 (s, 1H). LC-MS 386.3 [M − H]$^-$, 388.3 [M + H]$^+$, RT 0.94 min. |
| 370 | 5-ethyl-6-(3-fluoro-2-((isopropylamino)methyl)-1-methyl-1H-indol-5-yl)-4-hydroxy-2-oxo-1,2-dihydropyridine-3-carboxylic acid<br>$^1$H NMR (500 MHz, DMSO-d$_6$) δ ppm 0.98 (t, J = 7.09 Hz, 3 H) 1.36 (d, J = 6.31 Hz, 6 H) 2.31 (q, J = 7.25 Hz, 2 H) 3.47 (br. s., 1 H) 3.89 (s, 3 H) 4.46 (br. s., 2 H) 7.36 (d, J = 8.51 Hz, 1 H) 7.69-7.80 (m, 2 H) 9.30 (br. s., 2 H) 12.82 (br. s., 1 H) 13.91 (s, 1 H). LC-MS 400.2 [M − H]$^-$, 402.2 [M + H]$^+$, RT 0.94 min. |

| Cpd | Name |
|---|---|
| 371 | 6-(2-((tert-butylamino)methyl)-3-fluoro-1-methyl-1H-indol-5-yl)-5-ethyl-4-hydroxy-2-oxo-1,2-dihydropyridine-3-carboxylic acid<br>¹H NMR (500 MHz, DMSO-d₆) δ ppm 0.97 (t, J = 7.09 Hz, 3 H) 1.44 (s, 9 H) 2.31 (q, J = 6.62 Hz, 2 H) 3.92 (s, 3 H) 4.42 (br. s., 2 H) 7.36 (d, J = 8.20 Hz, 1 H) 7.69-7.77 (m, 2 H) 9.41 (br. s., 2 H) 12.84 (br. s., 1 H) 13.91 (br. s., 1 H). LC-MS 414.2 [M − H]⁻, 416.2 [M + H]⁺, RT 0.96 min. |

Example 372

6-(4-(Benzyloxy)-1-methyl-1H-indol-5-yl)-5-ethyl-2-oxo-1,2-dihydropyridine-3-carboxylic acid

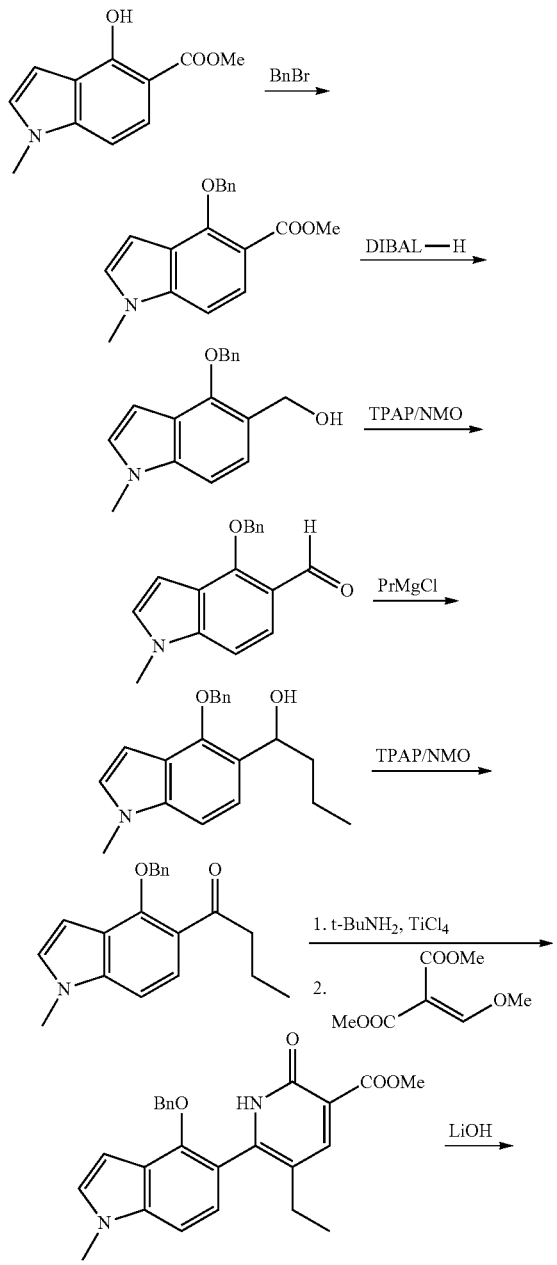

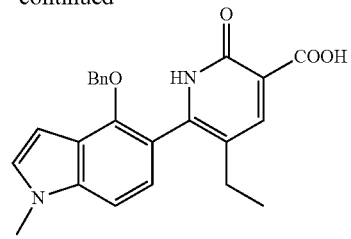

Step 1

Methyl 4-(benzyloxy)-1-methyl-1H-indole-5-carboxylate

To a solution of methyl 4-hydroxy-1-methyl-1H-indole-5-carboxylate (7.70 g, 37.52 mmol), prepared according to the literature (*Bioorg. Med. Chem.* 2005, 13, 1497-1505), in CH₃CN (150 mL) was added K₂CO₃ (8.80 g, 63.67 mmol), NaI (200 mg, cat.) and BnBr (6.70 mL, 56.41 mmol). The mixture was heated at 70° C. overnight. The solids were filtered off and the mother liquor was concentrated. The residue was purified by column chromatography using EtOAc/hexanes (gradient 10-30%) to afford methyl 4-(benzyloxy)-1-methyl-1H-indole-5-carboxylate (7.10 g) in 85% yield based on recovered starting material (1.90 g).

¹H NMR (500 MHz, CHLOROFORM-d) δ ppm 3.80 (s, 3H) 3.90 (s, 3H) 5.28 (s, 2H) 6.64 (dd, J=3.2, 0.9 Hz, 1H) 7.02 (d, J=3.2 Hz, 1H) 7.10 (dd, J=8.5, 0.9 Hz, 1H) 7.35 (t, J=7.6 Hz, 1H) 7.42 (t, J=7.6 Hz, 2H) 7.57 (d, J=7.6 Hz, 2H) 7.79 (d, J=8.5 Hz, 1H). LC-MS 296.3 [M+H]⁺, RT 1.32 min.

Step 2-3

4-(benzyloxy)-1-methyl-1H-indole-5-carbaldehyde

To a solution of ethyl methyl 4-(benzyloxy)-1-methyl-1H-indole-5-carboxylate (7.09 g, 24.0 mmol) in DCM (100 mL) at −78° C. was added a solution of DIBAL-H (1M hexanes, 53.0 mL, 53.0 mmol). The reaction mixture was stirred for 1 h at −78° C. before it was quenched with Na—K-tartrate (aqueous saturated, 50 mL). The mixture was allowed to warm to room temperature and was stirred vigorously for 3 h. The organic phase was separated and the aqueous phase was extracted with DCM (2×100 mL). The combined organics were washed with NaCl (aqueous saturated, 100 mL) and dried over Na₂SO₄. The solvent was concentrated to yield (4-(benzyloxy)-1-methyl-1H-indol-5-yl)methanol as an oil which was pure enough to be used in the next step without purification.

To activated 4 Å molecular sieves (6.0 g, 250 mg/mmol) was added a solution of 4-(benzyloxy)-1-methyl-1H-indol-5-yl)methanol obtained above (ca 24 mmol) in DCM (120 mL). The mixture was cooled to 0° C. before NMO (4.20 g, 35.86 mmol) and TPAP (420 mg, 1.20 mmol, 5 mol %) were added subsequently. The reaction was stirred at 0° C. for 15 min and then allowed to warm to room temperature. After 2 h complete conversion of staring material was observed. Molecular sieves were filtered off and were washed with DCM. The mother liquor was concentrated and the residue was purified by column chromatography (EtOAc/hexanes, 0-15% gradient). 4-(Benzyloxy)-1-methyl-1H-indole-5-carbaldehyde was obtained as a solid (4.57 g) in 72% yield over 2 steps.

$^1$H NMR (500 MHz, Acetone) δ ppm 3.88 (s, 3H) 5.55 (s, 2H) 6.87 (dd, J=3.3, 0.8 Hz, 1H) 7.22 (d, J=8.5 Hz, 1H) 7.33-7.38 (m, 2H) 7.39-7.44 (m, 2H) 7.52 (dd, J=7.7, 1.1 Hz, 2H) 7.59 (d, J=8.5 Hz, 1H) 10.38 (d, J=0.6 Hz, 1H)

Step 4-5

1-(4-(benzyloxy)-1-methyl-1H-indol-5-yl)butan-1-one

To a solution of 4-(benzyloxy)-1-methyl-1H-indole-5-carbaldehyde (4.57 g, 17.22 mmol) in THF (60 mL) at −78° C. was slowly added a solution of n-PrMgCl (2M Et$_2$O, 13.00 mL, 26 mmol). The mixture was stirred at this temperature for 15 min and then allowed to warm to 0° C. After 1 h the reaction was quenched with NH$_4$Cl (aqueous saturated, 50 mL) and the product was extracted with EtOAc (3×100 mL). The combined organics were washed with NaCl (aqueous saturated, 100 mL) and dried over Na$_2$SO$_4$. The solvents were concentrated to yield 1-(4-(benzyloxy)-1-methyl-1H-indol-5-yl)butan-1-ol as an oil which was used directly in the next step without purification.

To activated 4 Å molecular sieves (4.3 g, 250 mg/mmol) was added a solution of 1-(4-(benzyloxy)-1-methyl-1H-indol-5-yl)butan-1-ol obtained above (ca. 17.22 mmol) in DCM (90 mL). The mixture was cooled to 0° C. before NMO (3.00 g, 25.61 mmol) and TPAP (300 mg, 0.85 mmol, 5 mol %) were added subsequently. The reaction was stirred at 0° C. for 15 min and then allowed to warm to room temperature. After 2 h complete conversion of staring material was observed. Molecular sieves were filtered off and were washed with DCM. The mother liquor was concentrated and the residue was purified by column chromatography (EtOAc/hexanes, 5-15% gradient). 1-(4-(Benzyloxy)-1-methyl-1H-indol-5-yl) butan-1-one was obtained as a white solid (4.85 g) in 92% yield over 2 steps.

$^1$H NMR (500 MHz, Acetone) δ ppm 0.82 (t, J=7.4 Hz, 3H) 1.60 (sxt, J=7.4 Hz, 2H) 2.94 (t, J=7.4 Hz, 2H) 3.86 (s, 3H) 5.41 (s, 2H) 6.74 (dd, J=3.2, 0.9 Hz, 1H) 7.19 (dd, J=8.7, 0.9 Hz, 1H) 7.29 (d, J=3.2 Hz, 1H) 7.34-7.39 (m, 1H) 7.40-7.45 (m, 2H) 7.53-7.58 (m, 3H). LC-MS 308.2 [M+H]$^+$, RT 1.50 min.

Step 6

N-(1-(4-(benzyloxy)-1-methyl-1H-indol-5-yl)butylidene)-2-methylpropan-2-amine

To a solution of 1-(4-(benzyloxy)-1-methyl-1H-indol-5-yl)butan-1-one (0.260 g, 0.85 mmol) in DCE (4 mL) was added t-BuNH$_2$ (0.40 mL, 3.79 mmol). The mixture was cooled to 0° C. before TiCl$_4$ solution (1M DCE, 0.55 mL, 0.55 mmol) was added dropwise via syringe pump over 30 min. The reaction was allowed to warm to room temperature and then heated at 50° C. for 6 h. The mixture was then diluted with DCM (15 mL) and quenched with NaHCO$_3$ (aqueous saturated, 5 mL). Upon vigorous shaking, the organic phase was separated using a PTFE phase separator and dried over Na$_2$SO$_4$. Removal of the solvent afforded N-(1-(4-(benzyloxy)-1-methyl-1H-indol-5-yl)butylidene)-2-methylpropan-2-amine as a yellow oil, which was taken directly into next step without purification.

Step 7

Methyl 6-(4-(benzyloxy)-1-methyl-1H-indol-5-yl)-5-ethyl-2-oxo-1,2-dihydropyridine-3-carboxylate Crude N-(1-(4-(benzyloxy)-1-methyl-1H-indol-5-yl)butylidene)-2-methylpropan-2-amine (ca. 0.43 mmol) obtained above and dimethyl 2-(methoxymethylene)malonate (0.13 g, 0.75 mmol) were mixed together in Ph$_2$O (1.0 mL). The stirred mixture was placed onto a pre-heated heat block at 210° C. and heated for 15 min after initial bubbling of MeOH was observed (occurs at −160° C. internal reaction temperature). The reaction mixture was cooled to room temperature and was loaded directly on a silica gel column. It was eluted first with hexanes to separate Ph$_2$O and then an EtOAc/hexanes gradient (0-80%) to yield product as a yellow foam (88.8 mg, 50% 2 steps).

$^1$H NMR (500 MHz, CHLOROFORM-d) δ ppm 1.04 (t, J=7.6 Hz, 3H) 2.35 (q, J=7.6 Hz, 2H) 3.85 (s, 3H) 3.97 (s, 3H) 5.16 (s, 2H) 6.68 (dd, J=3.2, 0.6 Hz, 1H) 7.02 (d, J=8.2 Hz, 1H) 7.09 (d, J=6.9 Hz, 2H) 7.13 (d, J=3.2 Hz, 1H) 7.16 (dd, J=8.2, 0.6 Hz, 1H) 7.21-7.31 (m, 3H) 8.25 (s, 1H). LC-MS 417.2 [M+H]$^+$, RT 1.36 min.

Step 8

6-(4-(benzyloxy)-1-methyl-1H-indol-5-yl)-5-ethyl-2-oxo-1,2-dihydropyridine-3-carboxylic acid To a solution of methyl 6-(4-(benzyloxy)-1-methyl-1H-indol-5-yl)-5-ethyl-2-oxo-1,2-dihydropyridine-3-carboxylate (0.0888 g, 0.21 mmol) in THF (1.5 mL) was added a solution of LiOH (1M aqueous saturated, 0.60 ml, 0.60 mmol). The reaction mixture was heated at 50° C. for 1 h until starting material was consumed. The reaction was then cooled to room temperature and acidified with 1M HCl to pH~2. The product was extracted with DCM (3×10 mL). The combined organic phases were washed with brine and dried over Na$_2$SO$_4$. Upon removal of the solvent product (0.0757 g, 88%) was obtained as yellow solid.

$^1$H NMR (500 MHz, DMSO-d$_6$) δ ppm 0.93 (t, J=7.6 Hz, 3H) 2.24 (q, J=7.6 Hz, 2H) 3.84 (s, 3H) 5.24 (s, 2H) 6.75 (dd, J=3.2, 0.8 Hz, 1H) 7.07 (d, J=8.4 Hz, 1H) 7.17-7.22 (m, 2H) 7.22-7.28 (m, 3H) 7.31 (dd, J=8.4, 0.8 Hz, 1H) 7.44 (d, J=3.2 Hz, 1H) 8.32 (s, 1H) 13.23 (br. s., 1H) 15.16 (s, 1H). LC-MS 401.2 [M−H]$^+$, 403.3 [M+H]$^+$, RT 1.36 min.

Example 373

6-(4-(Benzyloxy)-1-methyl-1H-indol-5-yl)-5-ethyl-4-hydroxy-2-oxo-1,2-dihydropyridine-3-carboxylic acid

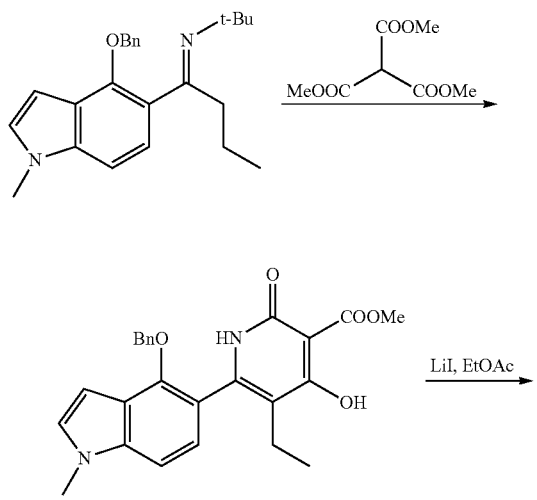

Step 1

Methyl 6-(4-(benzyloxy)-1-methyl-1H-indol-5-yl)-5-ethyl-4-hydroxy-2-oxo-1,2-dihydropyridine-3-carboxylate Crude N-(1-(4-(benzyloxy)-1-methyl-1H-indol-5-yl)butylidene)-2-methylpropan-2-amine (Example 372, step 6, ca. 0.43 mmol) and trimethyl methanetricarboxylate (0.14 g, 0.74 mmol) were mixed together in Ph$_2$O (1.0 mL). The stirred mixture was placed onto a pre-heated heat block at 230° C. and heated for 10 min after initial bubbling of MeOH was observed (occurs at ~160° C. internal reaction temperature). The reaction mixture was cooled to room temperature and was loaded directly on a silica gel column. It was eluted first with hexanes to separate Ph$_2$O and then EtOAc/hexanes gradient (0-80%) to yield product as yellow foam (0.0867 g, 47% over 2 steps).

$^1$H NMR (500 MHz, CHLOROFORM-d) δ ppm 1.00 (t, J=7.4 Hz, 3H) 2.30 (q, J=7.4 Hz, 2H) 3.85 (s, 3H) 4.02 (s, 3H) 6.67 (dd, J=3.2, 0.9 Hz, 1H) 7.01 (d, J=8.4 Hz, 1H) 7.12 (d, J=3.2 Hz, 1H) 7.14 (dd, J=8.4, 0.9 Hz, 1H) 7.17-7.20 (m, 2H) 7.24-7.29 (m, 3H) 8.81 (br. s., 1H) 13.77 (s, 1H). LC-MS 431.3 [M−H]$^+$, 433.3 [M+H]$^+$, RT 1.40 min.

Step 2

6-(4-(Benzyloxy)-1-methyl-1H-indol-5-yl)-5-ethyl-4-hydroxy-2-oxo-1,2-dihydropyridine-3-carboxylic acid To a solution of methyl 6-(4-(benzyloxy)-1-methyl-1H-indol-5-yl)-5-ethyl-4-hydroxy-2-oxo-1,2-dihydropyridine-3-carboxylate (0.0387 g, 0.09 mmol) in EtOAc (0.5 mL) was added LiI (0.0360 g, 0.27 mmol). The reaction mixture was stirred and heated at 60° C. for 1 h until complete consumption of starting material was observed. The mixture was then cooled to room temperature and acidified with aqueous HCl (1M, 1.0 mL) to pH~2. The product was extracted with EtOAc (3×3 mL). The organic phase was dried over Na$_2$SO$_4$. Upon removal of the solvent 6-(4-(benzyloxy)-1-methyl-1H-indol-5-yl)-5-ethyl-4-hydroxy-2-oxo-1,2-dihydropyridine-3-carboxylic acid was obtained as a yellow foam (0.0352 g, 94%).

$^1$H NMR (500 MHz, DMSO-d$_6$) δ ppm 0.88 (t, J=7.4 Hz, 3H) 2.16 (br. s., 2H) 3.84 (s, 3H) 6.73 (d, J=3.2 Hz, 1H) 7.06 (d, J=8.2 Hz, 1H) 7.21-7.28 (m, 5H) 7.30 (d, J=8.2 Hz, 1H) 7.43 (d, J=3.2 Hz, 1H) 12.72 (br. s., 1H) 14.00 (br. s., 1H). LC-MS 417.3 [M−H]$^+$, 419.3 [M+H]$^+$, RT 1.37 min.

Example 374

5-ethyl-4-hydroxy-6-(4-hydroxy-1-methyl-1H-indol-5-yl)-2-oxo-1,2-dihydropyridine-3-carboxylic acid

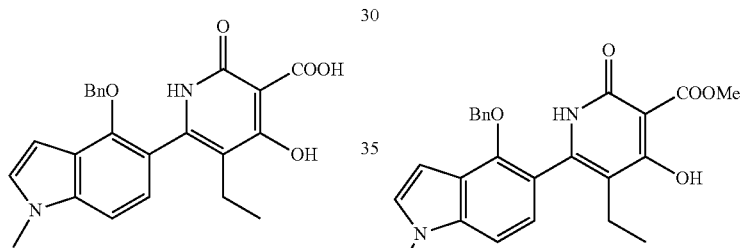

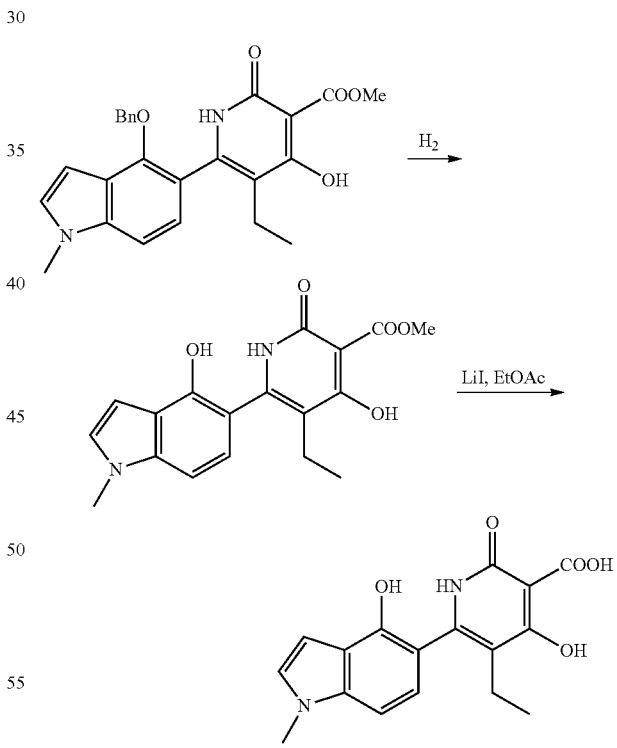

Step 1

Methyl 5-ethyl-4-hydroxy-6-(4-hydroxy-1-methyl-1H-indol-5-yl)-2-oxo-1,2-dihydropyridine-3-carboxylate A solution of methyl 6-(4-(benzyloxy)-1-methyl-1H-indol-5-yl)-5-ethyl-4-hydroxy-2-oxo-1,2-dihydropyridine-3- carboxylate (Example 373, step 1, 0.086 g, 0.20 mmol) in DCM (5 mL) and EtOAc (2 mL) was hydrogenated under a H₂-filled balloon over Pd/C (10% Degussa type, 20 mg) until complete consumption of staring material was observed. The catalyst was filtered off and washed with DCM and EtOAc. The mother liquor was concentrated and the residue was purified by column chromatography (MeOH/DCM, 0-5% gradient). Methyl 5-ethyl-4-hydroxy-6-(4-hydroxy-1-methyl-1H-indol-5-yl)-2-oxo-1,2-dihydropyridine-3-carboxylate was obtained as a yellowish solid (0.0466 g, 68%).

$^1$H NMR (500 MHz, DMSO-$d_6$) δ ppm 0.87 (t, J=7.4 Hz, 3H) 2.18 (q, J=7.4 Hz, 2H) 3.76 (s, 3H) 3.85 (s, 3H) 6.71 (dd, J=3.2, 0.9 Hz, 1H) 6.86 (d, J=8.2 Hz, 1H) 6.97 (dd, J=8.2, 0.9 Hz, 1H) 7.23 (d, J=3.2 Hz, 1H) 9.57 (br. s., 1H) 11.21 (br. s., 1H) 13.46 (br. s., 1H). LC-MS 343.1 [M+H]⁺, RT 1.20 min.

Step 2

5-Ethyl-4-hydroxy-6-(4-hydroxy-1-methyl-1H-indol-5-yl)-2-oxo-1,2-dihydropyridine-3-carboxylic acid To a solution of methyl 5-ethyl-4-hydroxy-6-(4-hydroxy-1-methyl-1H-indol-5-yl)-2-oxo-1,2-dihydropyridine-3-carboxylate (0.045 g, 0.12 mmol) in EtOAc (1.0 mL) was added LiI (0.050 g, 0.37 mmol). The reaction mixture was stirred and heated at 60° C. for 1 h until complete consumption of starting material was observed. The mixture was then cooled to room temperature and acidified with aqueous HCl (1M, 1.0 mL) to pH~2. The product was extracted with EtOAc (3×5 mL). The organic phase was dried over Na₂SO₄. Upon removal of the solvent the residue was triturated with Et₂O. The solid was collected by filtration affording product (0.018 g, 42%) as a solid.

$^1$H NMR (500 MHz, Acetone) δ ppm 1.00 (t, J=7.4 Hz, 3H) 2.41 (q, J=7.4 Hz, 2H) 3.86 (s, 3H) 6.72 (d, J=2.8 Hz, 1H) 7.01-7.11 (m, 2H) 7.24 (d, J=2.8 Hz, 1H) 9.98 (br. s., 2H) 14.07 (br. s., 1H) 16.01 (br. s., 1H). LC-MS 327.1 [M–H]⁺, 329.1 [M+H]⁺, RT 1.25 min.

Example 375

4-Hydroxy-6-(1-methyl-1H-indol-5-yl)-2-oxo-5-vinyl-1,2,5,6-tetrahydropyridine-3-carboxylic acid (Cpd 375)

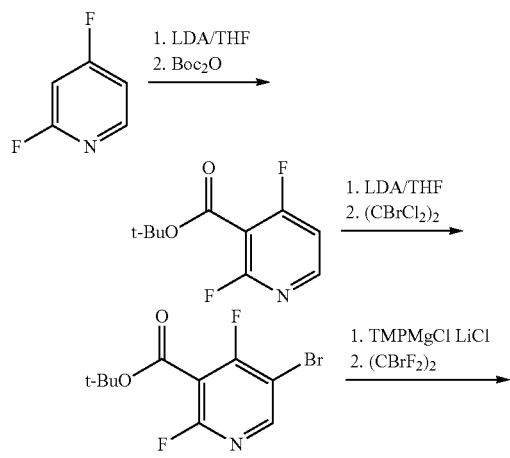

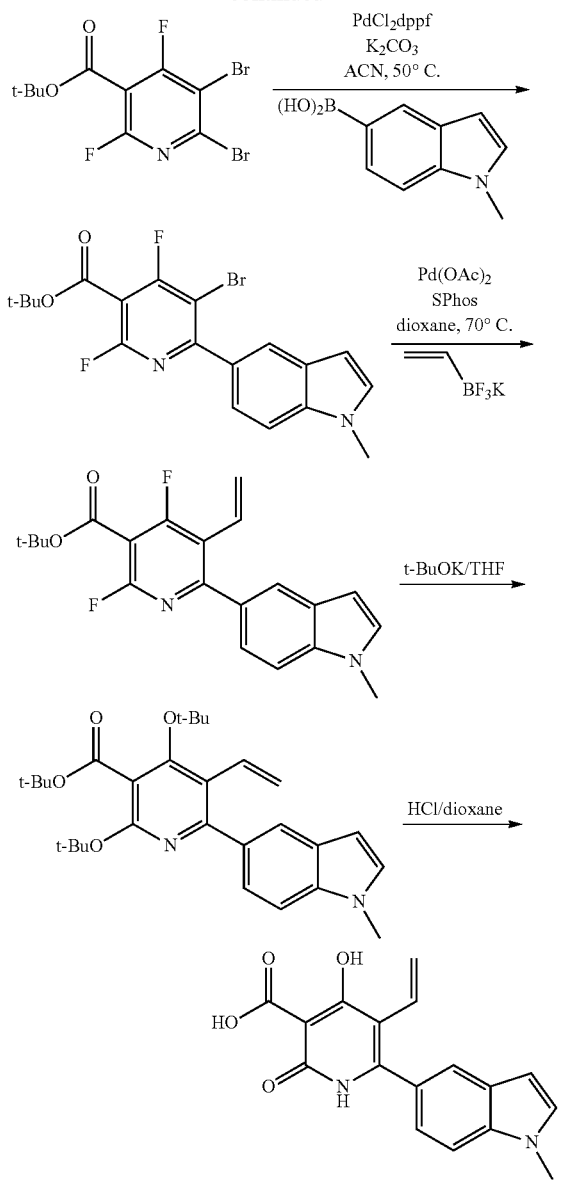

Step 1: Preparation of tert-butyl 2,4-difluoronicotinate

Into a solution of 2,4-difluoropyridine (1.38 g, 12.1 mmol) in THF (20 mL) at −78° C. was added dropwise a solution of LDA in heptane (1.5 M×8.9 mL, 13.3 mmol). The mixture was stirred at −78° C. for 10 min. Then a solution of Boc₂O in THF (2.0 M×6.35 mL, 12.7 mmol) was added dropwise. After 15 min, the reaction was quenched with saturated NH₄Cl and extracted with ethyl acetate. The combined organic layers were dried over sodium sulfate and evaporated to give a residue, which was purified by silica chromatography (0-10% EtOAc in hexanes) to give tert-butyl 2,4-difluoronicotinate (1.9 g, 73%).

$^1$H NMR (500 MHz, CHCl₃-d) δ ppm 1.61 (s, 9H), 6.96-7.07 (dd, J=6.0, 8.2 Hz, 1H), 8.21-8.29 (ddd, J=0.6, 5.7, 7.9 Hz, 1H).

Step 2: Preparation of tert-butyl 5-bromo-2,4-difluoronicotinate

Into a solution of tert-butyl 2,4-difluoronicotinate (0.95 g, 4.4 mmol) in THF (15 mL) at −78° C. was added a solution of LDA in heptane (1.5 M×3.5 mL, 5.3 mmol) dropwise. The mixture was stirred for 10 min. Then a solution of dibromotetrachloroethane (1.86 g, 5.7 mmol) in THF (4.0 mL) was added dropwise. After 15 min, the temperature was allowed to rise to room temperature slowly. The reaction was quenched with saturated NH$_4$Cl. The mixture was extracted with ethyl acetate. The combined organic layers were dried over sodium sulfate and evaporated to give a residue, which was purified by silica chromatography (5-50% dichloromethane in hexanes) to give tert-butyl 5-bromo-2,4-difluoronicotinate (0.55 g, 42%).

$^1$H NMR (500 MHz, CHLOROFORM-d) δ ppm 1.61 (s, 9H), 8.37-8.40 (dd, J=0.6, 8.5 Hz, 1H).

Step 3: Preparation of tert-butyl 5,6-dibromo-2,4-difluoronicotinate

Into a solution of TMPMgCl LiCl (1.0 M×6.8 mL, 6.8 mmol) in THF (5.0 mL) at −45° C. was added dropwise a solution of tert-butyl 5-bromo-2,4-difluoronicotinate (1.32 g, 4.5 mmol) in THF (5.0 mL). The mixture was stirred for 15 min then dibromotetrafluoroethane (1.0 mL, 6.8 mmol) was added. After 15 min at −45° C., the temperature was allowed to rise to room temperature. The reaction was quenched with saturated NH$_4$Cl and extracted with ethyl acetate. The organic layers were combined, dried over sodium sulfate and evaporated. The residue was purified by silica chromatography (0-10% ethyl acetate in hexanes) to give tert-butyl 5,6-dibromo-2,4-difluoronicotinate (1.29 g, 77%).

$^1$H NMR (500 MHz, CHLOROFORM-d) δ ppm 1.60 (s, 9H).

Step 4: Preparation of tert-butyl 5-bromo-2,4-difluoro-6-(1-methyl-1H-indol-5-yl)nicotinate A mixture of tert-butyl 5,6-dibromo-2,4-difluoronicotinate (156 mg, 0.42 mmol), 1-methyl-1H-indol-5-ylboronic acid (80 mg, 0.46 mmol), PdCl$_2$dppf (34 mg, 0.042 mmol), aqueous K$_2$CO$_3$ (2.0 M×0.6 mL, 1.2 mmol) in acetonitrile (1.8 mL) was stirred at 50° C. overnight. The mixture was cooled and extracted with ethyl acetate. The organic layers were combined and dried over sodium sulfate, then evaporated and purified by silica chromatography (0-5% ethyl acetate in hexanes) to give tert-butyl 5-bromo-2,4-difluoro-6-(1-methyl-1H-indol-5-yl)nicotinate (128 mg, 73%).

$^1$H NMR (500 MHz, CHLOROFORM-d) δ ppm 1.63 (s, 9H), 3.85 (s, 3H), 6.59 (dd, J=0.7, 3.2 Hz, 1H), 7.13 (d, J=3.2 Hz, 1H), 7.41 (d, J=8.5 Hz, 1H), 7.63 (dd, J=1.6, 8.5 Hz, 1H), 8.07 (dd, J=0.6, 1.9 Hz, 1H).

Step 5: Preparation of tert-butyl 2,4-difluoro-6-(1-methyl-1H-indol-5-yl)-5-vinylnicotinate A mixture of tert-butyl 5-bromo-2,4-difluoro-6-(1-methyl-1H-indol-5-yl)nicotinate (128 mg, 0.30 mmol), potassium vinyltrifluoroborate (80 mg, 0.60 mmol), Pd(OAc)$_2$ (4.7 mg, 0.012 mmol), SPhos (17 mg, 0.024 mmol), aqueous K$_2$CO$_3$ (2.0 M×0.45 mL, 0.9 mmol) and dioxane (2.0 mL) was stirred at 70° C. under Ar overnight. The mixture was cooled and extracted with ethyl acetate. The organic layers were combined, evaporated, and purified by silica chromatography (0-5% ethyl acetate in hexanes) to give tert-butyl 2,4-difluoro-6-(1-methyl-1H-indol-5-yl)-5-vinylnicotinate (72 mg, 64%).

$^1$H NMR (500 MHz, CHLOROFORM-d) δ ppm 1.64 (s, 9H), 3.85 (s, 3H), 5.58 (dt, J=1.6, 11.7 Hz, 1H), 5.88 (ddd, J=1.3, 2.5, 18.0 Hz, 1H), 6.50 (dd, J=11.7, 18.0 Hz, 1H), 6.56 (dd, J=1.0, 3.2 Hz, 1H), 7.12 (d, J=3.2 Hz, 1H), 7.36-7.40 (m, 1H), 7.51 (dd, J=1.6, 8.5 Hz, 1H), 7.89 (dd, J=0.6, 1.6 Hz, 1H).

Step 6: Preparation of tert-butyl 2,4-di-tert-butoxy-6-(1-methyl-1H-indol-5-yl)-5-vinylnicotinate Into a solution of tert-butyl 2,4-difluoro-6-(1-methyl-1H-indol-5-yl)-5-vinylnicotinate (72 mg, 0.2 mmol) in THF (1.0 mL) at −78° C. was added a solution of potassium tert-butoxide (1.0 M×0.48 mL, 0.48 mmol). The temperature was allowed to rise to room temperature and the reaction was quenched with saturated NH$_4$Cl. The mixture was extracted with ethyl acetate. The organic layers were combined, dried, evaporated and purified by silica chromatography (0-10% ethyl acetate in hexanes) to give tert-butyl 2,4-di-tert-butoxy-6-(1-methyl-1H-indol-5-yl)-5-vinylnicotinate (94 mg, 47%).

$^1$H NMR (500 MHz, CHLOROFORM-d) δ ppm 1.40 (s, 9H), 1.60 (d, 9H), 1.61 (d, 9H), 3.82 (s, 3H), 5.26 (dd, J=2.2, 11.7 Hz, 1H), 5.33 (dd, J=2.2, 18.0 Hz, 1H), 6.53 (dd, J=0.6, 3.2 Hz, 1H), 6.64 (dd, J=11.7, 18.0 Hz, 1H), 7.08 (d, J=3.2 Hz, 1H), 7.32 (d, J=8.5 Hz, 1H), 7.42 (dd, J=1.6, 8.5 Hz, 1H), 7.79 (dd, J=1.6, 8.5 Hz, 1H).

Step 7: Preparation of 4-hydroxy-6-(1-methyl-1H-indol-5-yl)-2-oxo-5-vinyl-1,2,5,6-tetrahydropyridine-3-carboxylic acid Into a solution of tert-butyl 2,4-di-tert-butoxy-6-(1-methyl-1H-indol-5-yl)-5-vinylnicotinate (44 mg, 0.092 mmol) in dioxane (1.0 mL) was added a solution of HCl in dioxane (4.0 M×1.0 mL, 4.0 mmol). After 1 min, the mixture was evaporated to dryness. The residue was treated with ether and filtered. The solid was collected as 4-hydroxy-6-(1-methyl-1H-indol-5-yl)-2-oxo-5-vinyl-1,2,5,6-tetrahydropyridine-3-carboxylic acid (26 mg, 97%).

$^1$H NMR (500 MHz, DMSO-d$_6$) δ ppm 3.85 (s, 3H), 5.26 (dd, J=2.2, 12.0 Hz, 1H), 5.80 (dd, J=2.2, 18.0 Hz, 1H), 6.17 (dd, J=12.0, 18.0 Hz, 1H), 6.56 (dd, J=0.6, 3.2 Hz, 1H), 7.23 (dd, J=1.5, 8.5 Hz, 1H), 7.48 (d, J=3.2 Hz, 1H), 7.59 (d, J=8.5 Hz, 1H), 7.70 (d, J=0.9 Hz, 1H), 12.95 (br s, 1H), 14.44 (br s, 1H), 16.24 (br s, 1H). LC-MS 291.0 [M−H]$^−$, 293.1 [M+H]$^+$, RT 1.24 min.

Example 376

5-chloro-4-hydroxy-6-(1-methyl-1H-indol-5-yl)-2-oxo-1,2-dihydropyridine-3-carboxylic acid

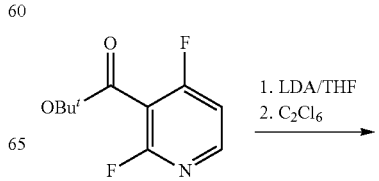

-continued

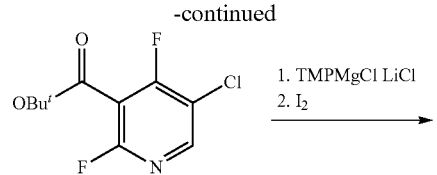

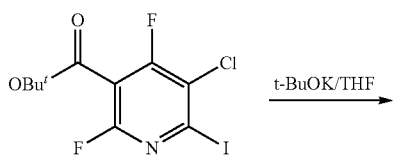

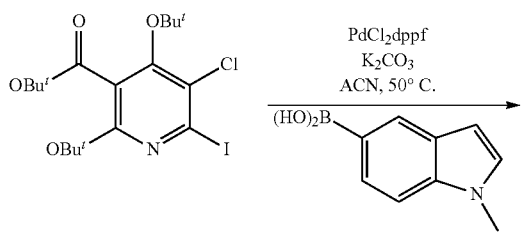

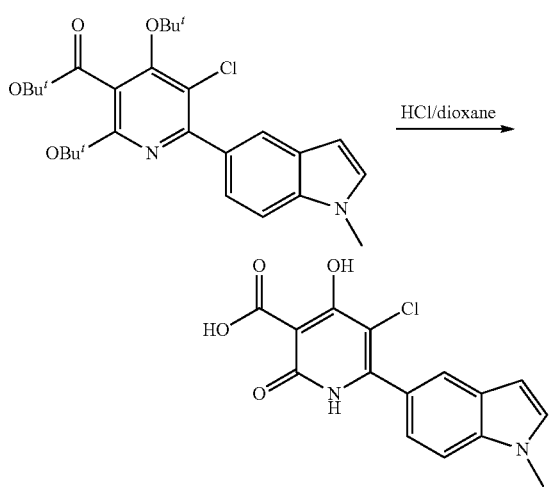

Step 1: Preparation of tert-butyl 5-chloro-2,4-difluoronicotinate

Into a solution of LDA in THF (20 mL, 12 mmol) was added a solution of tert-butyl 2,4-difluoronicotinate (2.14 g, 10 mmol) in THF (12 mL) at −78° C. The mixture was stirred for 30 min and then a solution of hexachloroethane (2.96 g, 12.5 mmol) in THF (7.0 mL) was added. The temperature was allowed to rise to 0° C. The reaction was then quenched with saturated NH$_4$Cl. The mixture was extracted with ethyl acetate and the organic layers were combined, dried over sodium sulfate, evaporated and purified by silica chromatography (0-8% ethyl acetate in hexanes) to give tert-butyl 5-chloro-2,4-difluoronicotinate (1.2 g, 48%).

$^1$H NMR (500 MHz, CHLOROFORM-d) δ ppm 1.61 (s, 9H), 8.28 (dd, J=0.9, 7.8 Hz, 1H).

Step 2: Preparation of tert-butyl 5-chloro-2,4-difluoro-6-iodonicotinate

Into a solution of TMPMgCl LiCl (1.0 M×2.4 mL, 2.4 mmol) in THF at −45° C. was added dropwise a solution of tert-butyl 5-chloro-2,4-difluoronicotinate (0.4 g, 1.6 mmol) in THF (3.0 mL). The mixture was stirred for 20 min then iodine (0.61 g, 2.4 mmol) was added. After 15 min at −45° C., the temperature was allowed to warm to 0° C. The reaction was quenched with saturated NH$_4$Cl and extracted with ethyl acetate. The organic layers were combined, dried over sodium sulfate and evaporated. The residue was purified by silica chromatography (0-5% ethyl acetate in hexanes) to give tert-butyl 5-chloro-2,4-difluoro-6-iodonicotinate (0.4 g, 67%).

$^1$H NMR (500 MHz, Acetone) S ppm 1.59 (s, 9H).

Step 3: Preparation of tert-butyl 2,4-di-tert-butoxy-5-chloro-6-iodonicotinate

Into a solution of tert-butyl 5-chloro-2,4-difluoro-6-iodonicotinate (0.4 g, 1.1 mmol) in THF (2.3 mL) at −78° C. was added a solution of potassium tert-butoxide (1.0 M×2.3 mL, 2.3 mmol). The temperature was allowed to rise to room temperature and the reaction was quenched with saturated NH$_4$Cl. The mixture was extracted with ethyl acetate. The organic layers were combined, dried, evaporated and purified by silica chromatography (0-20% ethyl acetate in hexanes) to give tert-butyl 2,4-di-tert-butoxy-5-chloro-6-iodonicotinate (0.23 g, 44%).

$^1$H NMR (500 MHz, Acetone) δ ppm 1.46 (s, 9H), 1.56 (s, 9H), 1.57 (s, 9H).

Step 4: Preparation of tert-butyl 2,4-di-tert-butoxy-5-chloro-6-(1-methyl-1H-indol-5-yl)nicotinate A mixture of tert-butyl 2,4-di-tert-butoxy-5-chloro-6-iodonicotinate (103 mg, 0.2 mmol), 1-methyl-1H-indol-5-ylboronic acid (53 mg, 0.3 mmol), PdCl$_2$dppf (16 mg, 0.02 mmol), aqueous K$_2$CO$_3$ (2.0 M×0.4 mL, 0.8 mmol) in acetonitrile (1.0 mL) was stirred at 80° C. for 3 h and then extracted with ethyl acetate. The organic layers were combined and dried over sodium sulfate, evaporated and purified by silica chromatography (0-5% ethyl acetate in hexanes) to give tert-butyl 2,4-di-tert-butoxy-5-chloro-6-(1-methyl-1H-indol-5-yl)nicotinate (103 mg, 100%).

$^1$H NMR (500 MHz, CHLOROFORM-d) δ ppm 1.53 (s, 9H), 1.60 (s, 9H), 1.61 (s, 9H), 3.84 (s, 3H), 6.57 (dd, J=0.9, 3.1 Hz, 1H), 7.10 (d, J=3.1 Hz, 1H), 7.38 (d, J=8.5 Hz, 1H), 7.60 (dd, J=1.6, 8.5 Hz, 1H), 8.01 (dd, J=0.6, 1.6 Hz, 1H).

Step 5: Preparation of 5-chloro-4-hydroxy-6-(1-methyl-1H-indol-5-yl)-2-oxo-1,2-dihydropyridine-3-carboxylic acid Following the procedure of Example 375 step 7, treatment of tert-butyl 2,4-di-tert-butoxy-5-chloro-6-(1-methyl-1H-indol-5-yl)nicotinate (27 mg, 0.055 mmol) with HCl in dioxane (4.0 M×1.0 mL, 4.0 mmol) provided 5-chloro-4-hydroxy-6-(1-methyl-1H-indol-5-yl)-2-oxo-1,2-dihydropyridine-3-carboxylic acid (12 mg, 68%).

$^1$H NMR (500 MHz, DMSO-d$_6$) δ ppm 3.86 (s, 3H), 6.58 (dd, J=3.2, 0.9 Hz, 1H), 7.37 (dd, J=8.5, 1.6 Hz, 1H), 7.48 (d, J=3.2 Hz, 1H), 7.61 (d, J=8.8 Hz, 1H), 7.81-7.85 (m, 1H), 12.84-13.67 (br s, 1H), 14.10-14.57 (br s, 1H), 15.32-16.22 (br s, 1H). LC-MS 318.9, 320.9 [M+H]$^+$, RT 1.23 min.

Example 377

4-hydroxy-5-methoxy-6-(1-methyl-1H-indol-5-yl)-2-oxo-1,2-dihydropyridine-3-carboxylic acid

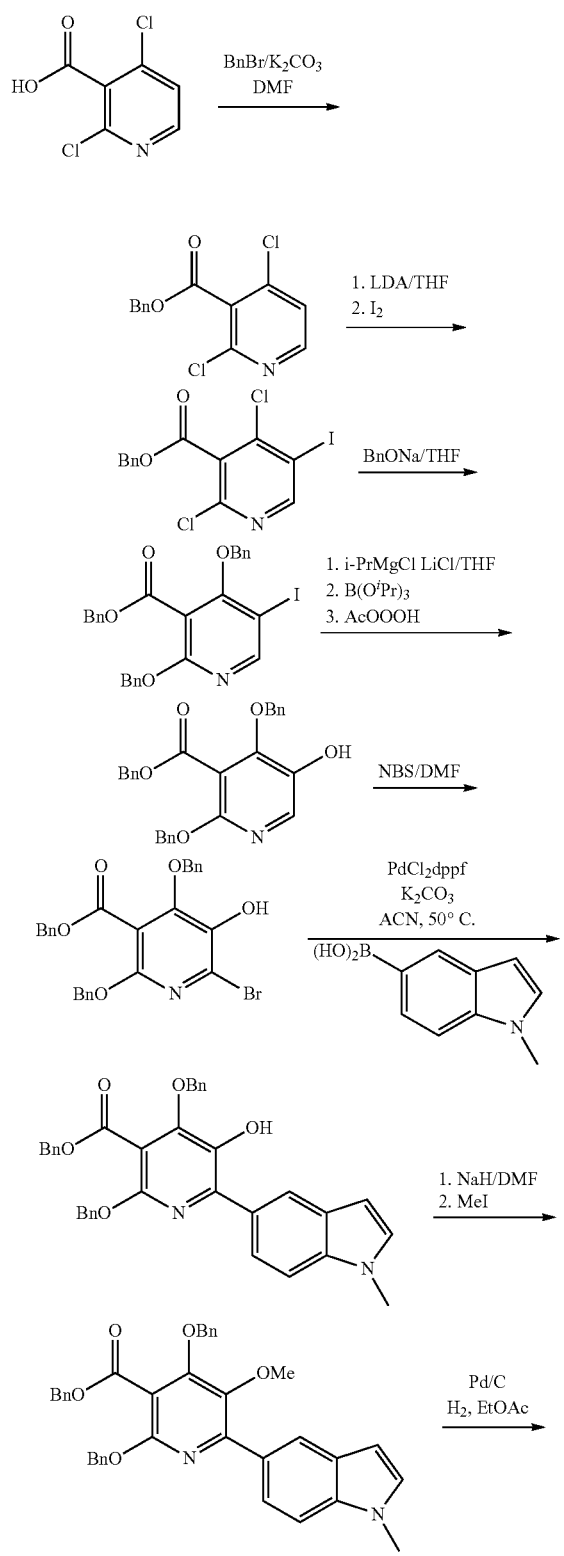

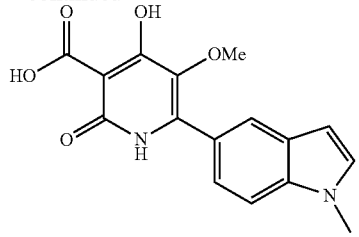

Step 1: benzyl 2,4-dichloronicotinate

A mixture of 2,4-dichloronicotinic acid (5.0 g, 26 mmol), benzyl bromide (3.7 mL, 31 mmol) and $K_2CO_3$ (7.2 g, 52 mmol) in DMF (50 mL) was stirred at room temperature overnight. Water was added and the mixture was extracted with ethyl acetate. The organic layers were combined and washed with water, brine, dried over sodium sulfate, evaporated and then purified by silica chromatography (0-7% ethyl acetate in hexanes) to give benzyl 2,4-dichloronicotinate (7.0 g, 96%).

$^1$H NMR (500 MHz, CHLOROFORM-d) δ ppm 5.44 (s, 2H), 7.33 (d, J=5.4 Hz, 1H), 7.36-7.43 (m, 3H), 7.44-7.49 (m, 2H), 8.34 (d, J=5.4 Hz, 1H). LC-MS 282.0, 284.0 [M+H]$^+$, RT 1.32 min.

Step 2: Preparation of benzyl 2,4-dichloro-5-iodonicotinate

Into a solution of benzyl 2,4-dichloronicotinate (4.35 g, 15.4 mmol) in THF (40 mL) at −78° C. was added LDA (1.5 M×11.8 mL, 17.7 mmol) dropwise. The mixture was stirred at −78° C. for 30 min. Iodine (4.7 g, 18.5 mmol) was added portionwise. The temperature was then allowed to rise to room temperature slowly and the reaction was quenched with saturated NH$_4$Cl solution. The mixture was extracted with ethyl acetate. The organic layers were combined and washed with brine, dried over sodium sulfate, evaporated and purified by silica chromatography (0-7% ethyl acetate in hexanes) to give benzyl 2,4-dichloro-5-iodonicotinate (3.8 g, 60%).

$^1$H NMR (500 MHz, CHLOROFORM-d) δ ppm 5.44 (s, 2H), 7.34-7.50 (m, 5H), 8.75 (s, 1H). LC-MS 408.0, 410.0 [M+H]$^+$, RT 1.47 min.

Step 3: Preparation of benzyl 2,4-bis(benzyloxy)-5-iodonicotinate

Into a solution of benzyl 2,4-dichloro-5-iodonicotinate (3.7 g, 9.1 mmol) in THF (20 mL) was added a solution of sodium benzoxide in THF (1.0 M×20 mL, 20 mmol). The mixture was stirred at room temperature overnight. The reaction was quenched with saturated NH$_4$Cl. The mixture was extracted with ethyl acetate. The organic layers were combined and washed with brine, dried over sodium sulfate, evaporated and purified by silica chromatography (0-7% ethyl acetate in hexanes) to give benzyl 2,4-bis(benzyloxy)-5-iodonicotinate (2.55 g, 51%).

$^1$H NMR (500 MHz, CHLOROFORM-d) δ ppm 5.08 (s, 2H), 5.31 (s, 2H), 5.41 (s, 2H), 7.23-7.43 (m, 15H), 8.44 (s, 1H). LC-MS 552.1 [M+H]$^+$, RT 1.80 min.

Step 4: Preparation of benzyl 2,4-bis(benzyloxy)-5-hydroxynicotinate

Into a solution of benzyl 2,4-bis(benzyloxy)-5-iodonicotinate (1.0 g, 1.8 mmol) in THF (8.0 mL) at −45° C. was added a solution of i-PrMgCl—LiCl (1.3 M×2.8 mL, 3.6 mmol) dropwise. The mixture was stirred at −45° C. for 30 min, into which triisopropyl borate (0.87 mL, 3.78 mmol) was added dropwise. After stirring at −45° C. for 15 min, the temperature was allowed to rise to room temperature slowly. The mixture was stirred at room temperature for 1.5 h then cooled to −20° C., into which peracetic acid (32%, 0.79 mL, 3.78 mmol) was added. The mixture was stirred at room temperature for another 30 min before it was treated with water (50 mL). The mixture was extracted with ethyl acetate. The organic layers were combined and washed with brine, dried over sodium sulfate, evaporated and purified by silica chromatography (0-30% ethyl acetate in hexanes) to give benzyl 2,4-bis(benzyloxy)-5-hydroxynicotinate (0.29 g, 36%).

$^1$H NMR (500 MHz, CHLOROFORM-d) δ ppm 5.03 (s, 2H), 5.35 (s, 2H), 5.37 (s, 2H), 7.27-7.40 (m, 15H), 7.85 (s, 1H). LC-MS 476.3 [M+H]$^+$, RT 0.94 min. (1 min Method).

Step 5: Preparation of benzyl 2,4-bis(benzyloxy)-6-bromo-5-hydroxynicotinate

A mixture of benzyl 2,4-bis(benzyloxy)-5-hydroxynicotinate (0.29 g, 0.66 mmol) and NBS (0.13 g, 0.72 mmol) in DMF (1.2 mL) was stirred at room temperature for 5 min then treated with water. The mixture was extracted with ethyl acetate. The organic layers were combined and washed with brine, dried over sodium sulfate, evaporated and purified by silica chromatography (0-30% ethyl acetate in hexanes) to give benzyl 2,4-bis(benzyloxy)-6-bromo-5-hydroxynicotinate (0.23 g, 68%).

$^1$H NMR (500 MHz, CHLOROFORM-d) δ ppm 5.15 (s, 2H), 5.30 (s, 2H), 5.34 (s, 2H), 7.24-7.40 (m, 15H). LC-MS 522.2 [M+H]$^+$, RT 0.95 min. (1 min Method).

Step 6: Preparation of benzyl 2,4-bis(benzyloxy)-5-hydroxy-6-(1-methyl-1H-indol-5-yl)nicotinate A mixture of benzyl 2,4-bis(benzyloxy)-6-bromo-5-hydroxynicotinate (0.23 g, 0.44 mol), 1-methyl-1H-indol-5-yl-boronic acid (90 mg, 0.51 mmol), Pd$_2$(dba)$_3$ (20 mg, 0.022 mmol), tri-tert-butylphosphonium tetrafluoroborate (13 mg, 0.044 mmol) and KF (0.26 g, 4.4 mmol) in THF (2.0 mL) was stirred at 60° C. overnight under an Ar atmosphere. The mixture was filtered. The filtrate was evaporated and purified by silica chromatography (2-30% ethyl acetate in hexanes) to give benzyl 2,4-bis(benzyloxy)-5-hydroxy-6-(1-methyl-1H-indol-5-yl)nicotinate (0.24 g, 96%).

$^1$H NMR (500 MHz, CHLOROFORM-d) δ ppm 3.83 (s, 3H), 5.08 (s, 2H), 5.39 (s, 2H), 5.52 (s, 2H), 6.56 (dd, J=0.6, 3.2 Hz, 1H), 7.09 (d, J=3.2 Hz, 1H), 7.28-7.47 (m, 15H), 7.93 (dd, J=1.6, 8.8 Hz, 1H), 8.33 (dd, J=0.6, 1.9 Hz, 1H). LC-MS 571.2 [M+H]$^+$, RT 1.65 min.

Step 7: Preparation of benzyl 2,4-bis(benzyloxy)-5-methoxy-6-(1-methyl-1H-indol-5-yl)nicotinate Into a solution of benzyl 2,4-bis(benzyloxy)-5-hydroxy-6-(1-methyl-1H-indol-5-yl)nicotinate (80 mg, 0.14 mmol) in DMF (0.3 mL) was added 60% NaH (7.3 mg, 0.18 mmol). After 15 min, iodomethane (13 μL, 0.20 mmol) was added. The mixture was stirred at room temperature for another 30 min and then loaded directly onto a silica column and chromatographed to give benzyl 2,4-bis(benzyloxy)-5-methoxy-6-(1-methyl-1H-indol-5-yl)nicotinate (73 mg, 89%).

$^1$H NMR (500 MHz, CHLOROFORM-d) δ ppm 3.59 (s, 3H), 3.85 (s, 3H), 5.29 (s, 2H), 5.31 (s, 2H), 5.51 (s, 2H), 6.59 (dd, J=3.2, 0.9 Hz, 1H), 7.11 (d, J=3.2 Hz, 1H), 7.27-7.45 (m, 16H), 7.92 (dd, J=8.5, 1.6 Hz, 1H), 8.32 (dd, J=1.6, 0.6 Hz, 1H). LC-MS 585.4 [M+H]$^+$, RT 1.06 min. (1 min Method).

Step 8: Preparation of 4-hydroxy-5-methoxy-6-(1-methyl-1H-indol-5-yl)-2-oxo-1,2-dihydropyridine-3-carboxylic acid A mixture of benzyl 2,4-bis(benzyloxy)-5-methoxy-6-(1-methyl-1H-indol-5-yl)nicotinate (73 mg, 0.12 mmol) and 10% Pd/C (18 mg) in ethyl acetate (3.0 mL) was stirred for 2 h at room temperature under a hydrogen balloon. The mixture was then filtered. The filtrate was evaporated and the residue was triturated with ether to give 4-hydroxy-5-methoxy-6-(1-methyl-1H-indol-5-yl)-2-oxo-1,2-dihydropyridine-3-carboxylic acid (27 mg, 69%).

$^1$H NMR (500 MHz, DMSO-d$_6$) δ ppm 3.52 (s, 3H), 3.85 (s, 3H), 6.57 (dd, J=3.2, 0.9 Hz, 1H), 7.44 (dd, J=8.5, 1.6 Hz, 1H), 7.46 (d, J=3.2 Hz, 1H), 7.59 (d, J=8.5 Hz, 1H), 7.86-7.89 (m, 1H), 12.78 (br s, 1H), 13.91 (br s, 1H), 16.19 (br s, 1H). LC-MS 313.2 [M−H]$^−$, 315.2 [M+H]$^+$, RT 0.67 min. (1 min Method).

Using the procedures described above, additional compounds described herein may be prepared by substituting the appropriate starting materials, reagents and reaction conditions and include compounds selected from:

| Cpd | Name |
|---|---|
| 378 | 4-hydroxy-5-ethoxy-6-(1-methyl-1H-indol-5-yl)-2-oxo-1,2-dihydropyridine-3-carboxylic acid<br>$^1$H NMR (500 MHz, DMSO-d$_6$) δ ppm 1.00 (t, J = 7.1 Hz, 3 H), 3.72 (d, J = 6.9 Hz, 2 H), 3.85 (s, 3 H), 6.57 (dd, J = 3.2, 0.9 Hz, 1 H), 7.44-7.48 (m, 2 H), 7.58 (d, J = 8.8 Hz, 1 H), 7.89 (d, J = 1.3 Hz, 1 H), 12.66-12.88 (br s, 1 H), 13.81-14.02 (br s, 1 H), 16.06-16.38 (br s, 1 H). LC-MS 329.2 [M − H]$^−$, 327.2 [M + H]$^+$, RT 0.71 min. (1 min Method). |

Example 379

5-ethyl-4-hydroxy-6-(6-methoxy-1H-indol-2-yl)-2-oxo-1,2-dihydropyridine-3-carboxylic acid

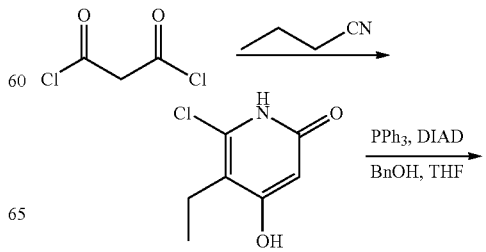

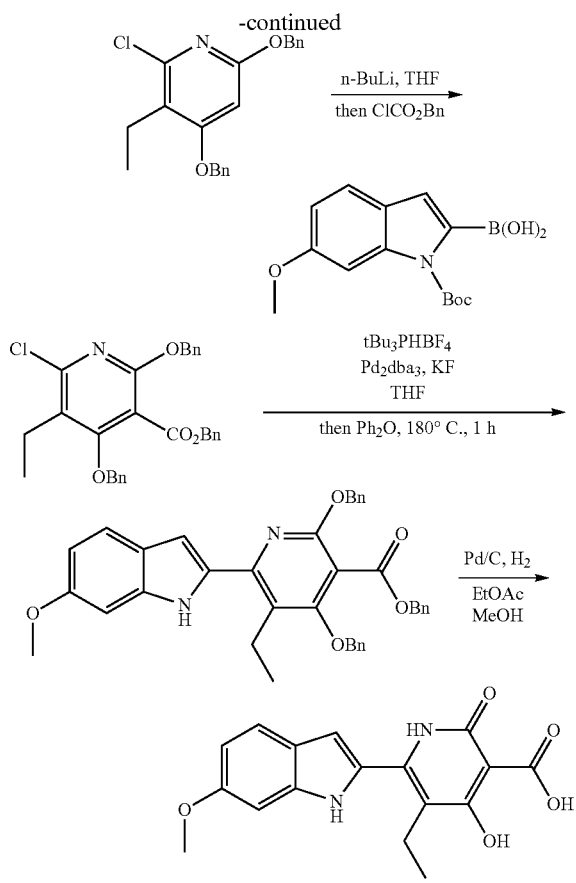

Step 1:
6-chloro-5-ethyl-4-hydroxypyridin-2(1H)-one

A mixture of butyronitrile (30 mL) and malonyl dichloride (25.0 g, 177 mmol) was stirred at room temperature under a $N_2$ atmosphere for 3 days. This was diluted with dioxane (100 mL) and filtered. The precipitate was washed with dioxane (20 mL), then ethyl ether (2×30 mL) and dried in air to provide 6-chloro-5-ethyl-4-hydroxypyridin-2(1H)-one (12.7 g, 67% pure, contains 33% of 6-chloro-2-propyl-1,2-dihydropyrimidin-4-ol by-product, based on $^1$H NMR).

$^1$H NMR (500 MHz, METHANOL-$d_4$) δ ppm 6.43 (1H, s), 2.72 (2H, q, J=7.36 Hz), 1.09-1.19 (3H, m). This was used directly in next step.

Step 2: 4,6-bis(benzyloxy)-2-chloro-3-ethylpyridine

The intermediate obtained in Step 1 (12.7 g) was dissolved in THF (250 mL) followed by the addition of $Ph_3P$ (54.0 g, 210 mmol) and the mixture was cooled in an ice-water bath. DIAD (42 mL, 211 mmol) was added dropwise. After the addition, the mixture was stirred for 5 min, followed by the addition of benzyl alcohol (23.6 mL, 228 mmol) dropwise. The cooling bath was removed and the mixture was stirred for 4 hr. The solvents were removed on a rotovap and the residue was treated with 1:1 hexanes and ethyl ether (600 mL) and stirred for 0.5 hr. The precipitate was filtered and washed with more hexanes-ether mixture until no desired product was found in the wash. All the filtrates were combined, concentrated and chromatographed (silica gel, ethyl acetate in hexanes 0-3% gradient) to furnish the dibenzylated intermediate, 4,6-bis(benzyloxy)-2-chloro-3-ethylpyridine, as a colorless oil (7.7 g, yield: 12.3%, two steps).

$^1$H NMR (500 MHz, CHLOROFORM-d) δ ppm 7.28-7.56 (10H, m), 6.27 (1H, s), 5.30-5.39 (2H, m), 5.08 (2H, s), 2.75 (2H, q, J=7.25 Hz), 1.08-1.19 (3H, m).

Step 3: benzyl 2,4-bis(benzyloxy)-6-chloro-5-ethylnicotinate

To a solution of the intermediate obtained in Step 2 (7.7 g, 21.8 mmol) in THF (80 mL), at −78° C. was added n-BuLi (21.8 mL, 54.4 mmol) dropwise, and stirred for additional 15 min. at −78° C. after the addition. Benzyl chloroformate (4.7 mL, 32.6 mmol) was then added and the resulting mixture was stirred for 10 min before the cooling bath was removed. The mixture was allowed to warm to room temperature while stirring. The reaction was quenched with a solution of $NH_4Cl$ (5 mL), diluted with ethyl ether (150 mL), washed with water (2×30 mL) and brine (30 mL). After drying with $Na_2SO_4$, the solvent was removed and the residue was chromatographed (silica gel, ethylacetate in hexanes, 0-5%) to provide product as white crystalline material (6.9 g, yield: 65%).

$^1$H NMR (500 MHz, CHLOROFORM-d) δ ppm 7.24-7.43 (15H, m), 5.39 (2H, s), 5.30 (2H, s), 4.97 (2H, s), 2.66 (2H, q, J=7.57 Hz), 1.10 (3H, t, J=7.41 Hz).

Step 4: benzyl 2,4-bis(benzyloxy)-5-ethyl-6-(6-methoxy-1H-indol-2-yl)nicotinate A mixture of (1-(tert-butoxycarbonyl)-6-methoxy-1H-indol-2-yl)boronic acid (437 mg, 1.5 mmol), $Pd_2dba_3$ (23 mg, 0.025 mmol), KF (174 mg, 3.0 mmol), t-$Bu_3PHBF_4$ (17.4 mg, 0.06 mmol) and benzyl 2,4-bis(benzyloxy)-6-chloro-5-ethylnicotinate (488 mg, 1.0 mmol) in THF (2.0 mL) was stirred at 60° C. under argon overnight. The solvent was then replaced with diphenyl ether (2.0 mL) and the mixture was stirred at 180° C. for 1 h. After cooling, the reaction mixture was loaded on a silica gel column and the product was eluted with ethyl acetate in hexanes (0-30% gradient) to furnish benzyl 2,4-bis(benzyloxy)-5-ethyl-6-(6-methoxy-1H-indol-2-yl)nicotinate (380 mg) in 64% yield.

$^1$H NMR (500 MHz, CHLOROFORM-d) δ ppm 9.15-9.24 (1H, m), 7.26-7.56 (18H, m), 6.90 (1H, d, J=2.21 Hz), 6.89 (1H, d, J=2.21 Hz), 6.79 (1H, dd, J=8.83, 2.21 Hz), 5.52 (2H, s), 5.35 (2H, s), 5.03 (2H, s), 3.90 (3H, s), 2.93 (2H, q, J=7.46 Hz), 1.25 (3H, t, J=7.41 Hz). LC-MS 599.3 [M+H]$^+$, RT 1.84 min.

Step 5: 5-ethyl-4-hydroxy-6-(6-methoxy-1H-indol-2-yl)-2-oxo-1,2-dihydropyridine-3-carboxylic acid The intermediate obtained in Step 4 (170 mg, 0.24 mmol) was dissolved in a mixed solvent of MeOH (0.5 mL) and ethyl acetate (2.0 mL) and hydrogenated with 10% Pd on charcoal (50 mg) using a balloon at room temperature. LC/MS showed complete conversion was achieved overnight. The catalyst was filtered over Celite and washed with 5% MeOH in DCM. The filtrate was concentrated to dryness and the residue was triturated with DCM and dried to provide the title compound as a pale yellow powder (27 mg) in 34% yield.

$^1$H NMR (500 MHz, DMSO-$d_6$) δ ppm 16.18 (1H, br. s), 13.96 (1H, br. s), 12.63 (1H, br. s), 11.53 (1H, s), 7.55 (1H, d, J=8.83 Hz), 6.92 (1H, d, J=2.21 Hz), 6.84 (1H, d, J=1.26 Hz), 6.76 (1H, dd, J=8.83, 2.21 Hz), 3.80 (3H, s), 2.62 (2H, q, J=7.25 Hz), 1.10 (3H, t, J=7.41 Hz). LC-MS 329.2 [M+H]$^+$, RT 1.33 min.

Using the procedures described above, additional compounds described herein may be prepared by substituting the appropriate starting materials, reagents and reaction conditions and include compounds selected from:

| Cpd | Name |
|---|---|
| 380 | 5-ethyl-6-(5-fluoro-1H-indol-2-yl)-4-hydroxy-2-oxo-1,2-dihydropyridine-3-carboxylic acid<br>$^1$H NMR (500 MHz, DMSO-$d_6$) δ ppm 16.15 (1 H, br. s), 13.98 (1 H, br. s.), 12.79 (1 H, br. s), 11.86 (1 H, s), 7.48 (1 H, dd, J = 8.83, 4.73 Hz), 7.44 (1 H, dd, J = 9.77, 2.52 Hz), 7.09 (1 H, td, J = 9.30, 2.52 Hz), 6.87 (1 H, dd, J = 2.21, 0.95 Hz), 2.57 (2 H, q, J = 7.25 Hz), 1.09 (3 H, t, J = 7.41 Hz), RT 1.33 min. |
| 381 | 5-ethyl-6-(5-ethyl-1H-indol-2-yl)-4-hydroxy-2-oxo-1,2-dihydropyridine-3-carboxylic acid<br>$^1$H NMR (500 MHz, DMSO-$d_6$) δ ppm 16.20 (1 H, br. s), 13.95 (1 H, br. s.), 12.72 (1 H, br. s), 11.61 (1 H, s), 7.44-7.48 (1 H, m), 7.38 (1 H, d, J = 8.51 Hz), 7.10 (1 H, dd, J = 8.35, 1.73 Hz), 6.81 (1 H, dd, J = 2.05, 0.79 Hz), 2.69 (2 H, q, J = 7.57 Hz), 2.60 (2 H, q, J = 7.25 Hz), 1.23 (3 H, t, J = 7.57 Hz), 1.09 (3 H, t, J = 7.41 Hz), RT 1.48 min. |
| 382 | 5-ethyl-6-(6-ethyl-1H-indol-2-yl)-4-hydroxy-2-oxo-1,2-dihydropyridine-3-carboxylic acid<br>$^1$H NMR (500 MHz, DMSO-$d_6$) δ ppm 15.99-16.39 (1 H, m), 13.95 (1 H, br. s.), 12.52-12.84 (1 H, m), 11.58 (1 H, s), 7.57 (1 H, d, J = 7.88 Hz), 7.27 (1 H, s), 6.98 (1 H, dd, J = 8.20, 1.26 Hz), 6.84 (1 H, dd, J = 2.05, 0.79 Hz), 2.72 (2 H, q, J = 7.57 Hz), 2.60 (2 H, q, J = 7.25 Hz), 1.23 (3 H, t, J = 7.57 Hz), 1.09 (3 H, t, J = 7.41 Hz), RT 1.47 min. |
| 383 | 5-ethyl-4-hydroxy-2-oxo-6-(5-propyl-1H-indol-2-yl)-1,2-dihydropyridine-3-carboxylic acid<br>$^1$H NMR (500 MHz, DMSO-$d_6$) δ ppm 16.16 (1 H, br. s), 13.98 (1 H, br. s.), 12.67 (1 H, br. s), 11.61 (1 H, s), 7.44 (1 H, s), 7.38 (1 H, d, J = 8.20 Hz), 7.08 (1 H, dd, J = 8.51, 1.58 Hz), 6.81 (1 H, dd, J = 2.05, 0.79 Hz), 2.56-2.67 (4 H, m), 1.63 (2 H, sxt, J = 7.38 Hz), 1.09 (3 H, t, J = 7.57 Hz), 0.91 (3 H, t, J = 7.25 Hz), RT 1.55 min. |
| 384 | 5-ethyl-4-hydroxy-2-oxo-6-(6-propyl-1H-indol-2-yl)-1,2-dihydropyridine-3-carboxylic acid<br>$^1$H NMR (500 MHz, DMSO-$d_6$) δ ppm 16.17 (1 H, br. s), 13.95 (1 H, br. s.), 12.67 (1 H, br. s.), 11.58 (1 H, s), 7.56 (1 H, d, J = 8.20 Hz), 7.25 (1 H, s), 6.96 (1 H, dd, J = 8.20, 1.58 Hz), 6.84 (1 H, dd, J = 2.05, 0.79 Hz), 2.64-2.71 (2 H, m), 2.61 (2 H, q, J = 7.57 Hz), 1.64 (2 H, sxt, J = 7.44 Hz), 1.10 (3 H, t, J = 7.41 Hz), 0.92 (3 H, t, J = 7.41 Hz), RT 1.54 min. |
| 385 | 5-ethyl-6-(5-fluoro-6-methyl-1H-indol-2-yl)-4-hydroxy-2-oxo-1,2-dihydropyridine-3-carboxylic acid<br>$^1$H NMR (500 MHz, DMSO-$d_6$) δ ppm 16.12 (1 H, br. s), 14.01 (1 H, br. s), 12.73 (1 H, br. s), 11.70 (1 H, br. s.), 7.38 (1 H, d, J = 10.40 Hz), 7.34 (1 H, d, J = 6.62 Hz), 6.82 (1 H, d, J = 1.26 Hz), 2.58 (2 H, q. J = 7.25 Hz), 2.35 (3 H, d, J = 1.58 Hz), 1.08 (3 H, t, J = 7.41 Hz), RT 1.40 min. |
| 386 | 6-(5-ethyl-1H-indol-2-yl)-4-hydroxy-5-methyl-2-oxo-1,2-dihydropyridine-3-carboxylic acid<br>$^1$H NMR (500 MHz, DMSO-$d_6$) δ ppm 15.26 (1 H, br. s), 11.28 (1 H, br. s), 8.36 (1 H, br. s), 7.36-7.43 (2 H, m), 7.02 (1 H, d, J = 8.83 Hz), 6.81 (1 H, s), 2.70 (3 H, q, J = 7.57 Hz), 2.24 (3 H, s), 1.25 (3 H, t, J = 7.57 Hz), RT 0.81 min. (1 min method). |
| 387 | 6-(6-ethyl-1H-indol-2-yl)-4-hydroxy-5-methyl-2-oxo-1,2-dihydropyridine-3-carboxylic acid<br>$^1$H NMR (500 MHz, DMSO-$d_6$) δ ppm 16.10 (1 H, br. s), 13.99 (1 H, br. s), 12.62 (1 H, br. s), 11.54 (1 H, br. s.), 7.56 (1 H, d, J = 7.88 Hz), 7.28 (1 H, s), 6.98 (1 H, dd, J = 8.20, 1.26 Hz), 6.93 (1 H, d, J = 1.26 Hz), 2.72 (2 H, q, J = 7.57 Hz), 2.17 (3 H, s), 1.23 (4 H, t, J = 7.57 Hz), RT 0.80 min. (1 min method). |
| 388 | 6-(5-fluoro-6-methyl-1H-indol-2-yl)-4-hydroxy-5-methyl-2-oxo-1,2-dihydropyridine-3-carboxylic acid<br>$^1$H NMR (500 MHz, DMSO-$d_6$) δ ppm 16.11 (1 H, br. s), 14.00 (1 H, br. s), 12.70 (1 H, br. s), 11.67 (1 H, s), 7.32-7.41 (2 H, m), 6.90 (1 H, d, J = 1.26 Hz), 2.35 (3 H, d, J = 1.58 Hz), 2.14 (3 H, s), RT 0.76 min. (1 min method). |
| 389 | 5-ethyl-4-hydroxy-6-(2-methyl-2H-indazol-6-yl)-2-oxo-1,2-dihydropyridine-3-carboxylic acid<br>$^1$H NMR (500 MHz, DMSO-$d_6$) δ ppm 16.28 (1 H, br. s), 13.96 (1 H, br. s), 12.82 (1 H, br. s), 8.46 (1 H, s), 7.85 (1 H, dd, J = 8.67, 0.79 Hz), 7.70-7.78 (1 H, m), 7.06 (1 H, dd, J = 8.51, 1.26 Hz), 4.22 (3 H, s), 2.32 (2 H, q, J = 7.25 Hz), 0.99 (3 H, t, J = 7.30 Hz), RT 0.65 min. (1 min method). |
| 390 | 5-ethyl-4-hydroxy-6-(1-methyl-1H-indazol-6-yl)-2-oxo-1,2-dihydropyridine-3-carboxylic acid<br>$^1$H NMR (500 MHz, DMSO-$d_6$) δ ppm 16.24 (1 H, br. s), 13.99 (1 H, br. s), 12.86 (1 H, br. s), 8.17 (1 H, d, J = 0.95 Hz), 7.92 (1 H, dd, J = 8.35, 0.79 Hz), 7.87 (1 H, d, J = 0.95 Hz), 7.21 (1 H, dd, J = 8.35, 1.42 Hz), 4.10 (3 H, s), 2.32 (2 H, q, J = 7.57 Hz), 1.00 (3 H, t, J = 7.30 Hz), RT 0.69 min. (1 min method). |
| 391 | 5-ethyl-4-hydroxy-6-(1H-indazol-6-yl)-2-oxo-1,2-dihydropyridine-3-carboxylic acid<br>$^1$H NMR (500 MHz, DMSO-$d_6$) δ ppm 16.23 (1 H, br. s), 14.03 (1 H, br. s), 13.36 (1 H, s), 12.82 (1 H, br. s), 8.20 (1 H, s), 7.92 (1 H, dd, J = 8.20, 0.63 Hz), 7.68 (1 H, s), 7.17 (1 H, dd, J = 8.51, 1.26 Hz), 2.31 (2 H, q, J = 7.36 Hz), 1.00 (3 H, t, J = 7.41 Hz), RT 0.64 min. (1 min method). |
| 392 | 5-ethyl-4-hydroxy-6-(1H-indazol-5-yl)-2-oxo-1,2-dihydropyridine-3-carboxylic acid<br>$^1$H NMR (500 MHz, DMSO-$d_6$) δ ppm 16.28 (1 H, br. s), 13.96 (1 H, br. s), 13.35 (1 H, br. s.), 12.79 (1 H, br. s), 8.22 (1 H, s), 7.93 (1 H, s), 7.69 (1 H, d, J = 8.51 Hz), 7.42 (1 H, dd, J = 8.83, 1.58 Hz), 2.32 (2 H, q, J = 7.25 Hz), 1.00 (3 H, t, J = 7.41 Hz), RT 0.62 min. (1 min method). |
| 393 | 5-ethyl-4-hydroxy-6-(2-methyl-2H-indazol-5-yl)-2-oxo-1,2-dihydropyridine-3-carboxylic acid<br>$^1$H NMR (500 MHz, DMSO-$d_6$) δ ppm 16.30 (1 H, br. s), 13.93 (1 H, s), 12.82 (1 H, br. s), 8.51 (1 H, s), 7.88 (1 H, dd, J = 1.58, 0.95 Hz), 7.72 (1 H, dt, J = 9.14, 0.95 Hz), 7.27 (1 H, dd, J = 8.83, 1.89 Hz), 4.22 (3 H, s), 2.33 (2 H, q, J = 7.25 Hz), 1.00 (3 H, t, J = 7.41 Hz), RT 0.64 min. (1 min method). |

| Cpd | Name |
|---|---|
| 394 | 4-hydroxy-5-methyl-6-(1-methyl-1H-indazol-5-yl)-2-oxo-1,2-dihydropyridine-3-carboxylic acid <br> $^1$H NMR (500 MHz, DMSO-d$_6$) δ ppm 16.18 (1 H, br. s), 14.03 (1 H, br. s), 12.83 (1 H, br. s), 8.19 (1 H, d, J = 0.63 Hz), 7.90-8.02 (1 H, m), 7.79 (1 H, d, J = 8.83 Hz), 7.50 (1 H, dd, J = 8.83, 1.58 Hz), 4.11 (3 H, s), 1.92 (3 H, s), RT 0.63 min. (1 min method). |
| 395 | 4-hydroxy-5-methyl-6-(2-methyl-2H-indazol-5-yl)-2-oxo-1,2-dihydropyridine-3-carboxylic acid <br> $^1$H NMR (500 MHz, DMSO-d$_6$) δ ppm 16.21 (1 H, br. s), 14.01 (1 H, br. s), 12.77 (1 H, br. s), 8.51 (1 H, s), 7.84-7.99 (1 H, m), 7.71 (1 H, d, J = 9.14 Hz), 7.30 (1 H, dd, J = 8.98, 1.73 Hz), 4.22 (3 H, s), 1.93 (3 H, s), RT 0.59 min. (1 min method). |
| 396 | 4-hydroxy-5-methyl-6-(1-methyl-1H-indazol-6-yl)-2-oxo-1,2-dihydropyridine-3-carboxylic acid <br> $^1$H NMR (500 MHz, DMSO-d$_6$) δ ppm 16.21 (1 H, br. s), 13.96 (1 H, br. s.), 12.88 (1 H, br. s), 8.17 (1 H, d, J = 0.95 Hz), 7.89-7.93 (2 H, m), 7.23 (1 H, dd, J = 8.20, 1.58 Hz), 4.10 (3 H, s), 1.93 (3 H, s), RT 0.64 min. (1 min method). |
| 397 | 4-hydroxy-5-methyl-6-(2-methyl-2H-indazol-6-yl)-2-oxo-1,2-dihydropyridine-3-carboxylic acid <br> $^1$H NMR (500 MHz, DMSO-d$_6$) δ ppm 16.16 (1 H, br. s), 14.08 (1 H, br. s), 12.87 (1 H, br. s), 8.45 (1 H, s), 7.84 (1 H, dd, J = 8.67, 0.79 Hz), 7.76 (1 H, s), 7.09 (1 H, dd, J = 8.51, 1.58 Hz), 4.22 (3 H, s), 1.92 (3 H, s), RT 0.60 min. (1 min method). |
| 398 | 4-hydroxy-6-(1H-indazol-5-yl)-5-methyl-2-oxo-1,2-dihydropyridine-3-carboxylic acid <br> $^1$H NMR (500 MHz, DMSO-d$_6$) δ ppm 16.28 (1 H, br. s), 13.89 (1 H, s), 13.35 (1 H, s), 12.80 (1 H, br. s), 8.22 (1 H, s), 7.97 (1 H, s), 7.68 (1 H, d, J = 8.83 Hz), 7.45 (1 H, dd, J = 8.51, 1.58 Hz), 1.92 (3 H, s), RT 0.58 min. (1 min method). |
| 399 | 4-hydroxy-6-(1H-indazol-6-yl)-5-methyl-2-oxo-1,2-dihydropyridine-3-carboxylic acid <br> $^1$H NMR (500 MHz, DMSO-d$_6$) δ ppm 16.17 (1 H, br. s), 14.03 (1 H, br. s), 13.38 (1 H, br. s.), 12.79 (1 H, br. s), 8.20 (1 H, s), 7.91 (1 H, dd, J = 8.35, 0.79 Hz), 7.70 (1 H, d, J = 0.95 Hz), 7.20 (1 H, dd, J = 8.35, 1.42 Hz), 1.91 (3 H, s), RT 0.59 min. (1 min method). |
| 400 | 5-ethyl-4-hydroxy-6-(imidazo[1,2-a]pyridin-2-yl)-2-oxo-1,2-dihydropyridine-3-carboxylic acid <br> $^1$H NMR (500 MHz, METHANOL-d$_4$) δ ppm 1.20 (3 H, t, J = 7.41 Hz), 2.67 (2 H, q, J = 7.25 Hz), 7.44-7.49 (1 H, m), 7.92-7.96 (2 H, m), 8.59 (1 H, s), 8.79-8.83 (1 H, m). LC-MS 300.1 [M + H]$^+$, RT 0.69 min. (1 min Method). |
| 401 | 6-(4-(dimethylamino)-6-methylpyrazolo[1,5-a]pyrazin-2-yl)-5-ethyl-4-hydroxy-2-oxo-1,2-dihydropyridine-3-carboxylic acid <br> $^1$H NMR (500 MHz, DMSO-d$_6$) δ ppm 1.08-1.13 (3 H, m), 2.24 (3 H, d, J = 0.95 Hz), 2.73-2.83 (2 H, m), 3.32 (6 H, s, obscured by water), 7.49 (1 H, s), 7.89 (1 H, s). (acidic protons not observed). LC-MS 358.2 [M + H]$^+$, RT 0.68 min. (1 min Method). |
| 402 | 5-ethyl-4-hydroxy-6-(6-methyl-4-(pyrrolidin-1-yl)pyrazolo[1,5-a]pyrazin-2-yl)-2-oxo-1,2-dihydropyridine-3-carboxylic acid <br> $^1$H NMR (500 MHz, DMSO-d$_6$) δ ppm 1.12 (3 H, t, J = 7.41 Hz), 2.05 (4 H, br. s.), 2.29 (3 H, s), 2.75 (2 H, q, J = 7.25 Hz), 3.79-3.94 (4 H, m), 7.73 (1 H, s), 8.00 (1 H, s), 12.71 (1 H, br. s), 13.92 (1 H, br. s.), 16.10 (1 H, br. s). LC-MS 384.3 [M + H]$^+$, RT 0.60 min. (1 min Method). |
| 403 | 5-ethyl-4-hydroxy-6-(1-methyl-1H-indol-4-yl)-2-oxo-1,2-dihydropyridine-3-carboxylic acid <br> $^1$H NMR (500 MHz, DMSO-d$_6$) δ ppm 0.85 (3 H, t, J = 7.41 Hz), 2.50 (2H, m, obscured by DMSO-d$_6$), 3.86 (3 H, s), 6.24 (1 H, dd, J = 3.15, 0.95 Hz), 7.10 (1 H, dd, J = 7.09, 0.79 Hz), 7.30 (1 H, dd, J = 8.20, 7.25 Hz), 7.45 (1 H, d, J = 2.84 Hz), 7.64 (1 H, d, J = 8.20 Hz), 12.79 (1 H, br. s), 13.93 (1 H, br. s), 16.37 (1 H, br. s). LC-MS 313.2 [M + H]$^+$, RT 0.76 min. (1 min Method). |
| 404 | 4-hydroxy-5-methyl-6-(1-methyl-1H-indol-4-yl)-2-oxo-1,2-dihydropyridine-3-carboxylic acid <br> $^1$H NMR (500 MHz, DMSO-d$_6$) δ ppm 1.76 (3 H, s), 3.86 (3 H, s), 6.25 (1 H, dd, J = 3.15, 0.95 Hz), 7.13 (1 H, dd, J = 7.25, 0.95 Hz), 7.31 (1 H, dd, J = 8.20, 7.25 Hz), 7.47 (1 H, d, J = 3.15 Hz), 7.65 (1 H, d, J = 8.51 Hz), 12.81 (1 H, br. s), 13.93 (1 H, br. s), 16.34 (1 H, br. s). LC-MS 299.1 [M + H]$^+$, RT 0.71 min. (1min Method). |

Example 405

5-ethyl-4-hydroxy-6-(6-methoxy-1-methyl-1H-indol-2-yl)-2-oxo-1,2-dihydropyridine-3-carboxylic acid

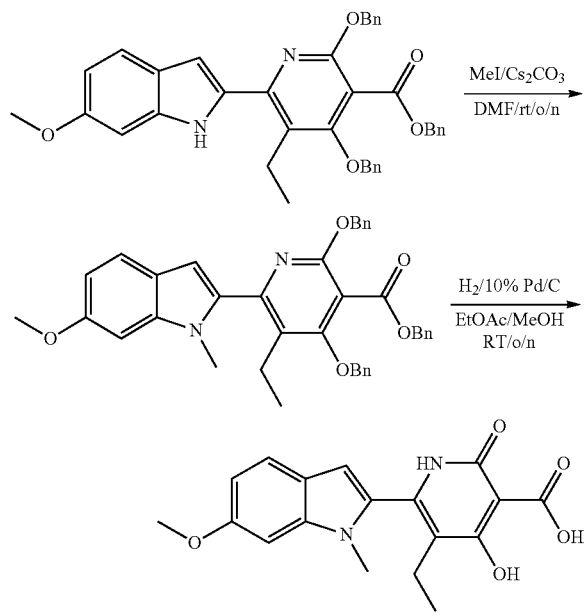

Step 1

A mixture of benzyl 2,4-bis(benzyloxy)-5-ethyl-6-(6-methoxy-1H-indol-2-yl)nicotinate (220 mg, 0.37 mmol), prepared in Example 379, $Cs_2CO_3$ (163 mg, 0.5 mmol), MeI (71 mg, 31 µL, 0.5 mmol) in DMF (1.0 mL) was stirred at room temperature overnight. The mixture was then diluted with water (5 mL) and extracted with ethylacetate (3×5 mL). The combined extract was washed with water (5 mL), brine (5 mL) and dried over $Na_2SO_4$ (anhydrous), which was then discarded by filtration. The solvent was removed and the residue was chromatographed on a silica gel column (ethyl acetate in hexanes, 0-30% gradient).

Step 2

The methylated intermediate above was dissolved in a mixture of MeOH (0.5 mL) and ethyl acetate (2.0 mL) and hydrogenated with 10% Pd on charcoal (50 mg) using a balloon at room temperature. LC/MS showed a complete conversion was achieved overnight. The catalyst was filtered over Celite and washed with 5% MeOH in DCM. The filtrate was concentrated to dryness and the residue was triturated with DCM and dried to provide the title compound as a pale yellow powder (24 mg) in 19% yield.

$^1$H NMR (500 MHz, DMSO-$d_6$) δ ppm 16.22 (1H, br. s), 13.99 (1H, br. s.), 12.85 (1H, br. s), 7.53 (1H, d, J=8.51 Hz), 7.08 (1H, d, J=2.21 Hz), 6.78 (1H, dd, J=8.51, 2.21 Hz), 6.70 (1H, d, J=0.63 Hz), 3.84 (3H, s), 3.60 (3H, s), 2.26-2.46 (2H, m), 0.99 (3H, t, J=7.41 Hz). LC-MS 343.2 [M+H]$^+$, RT 1.38 min.

Using the procedures described above, additional compounds described herein may be prepared by substituting the appropriate starting materials, reagents and reaction conditions and include compounds selected from:

| Cpd | Name |
|---|---|
| 406 | 5-ethyl-6-(5-fluoro-1-methyl-1H-indol-2-yl)-4-hydroxy-2-oxo-1,2-dihydropyridine-3-carboxylic acid<br>$^1$H NMR (500 MHz, DMSO-$d_6$) δ ppm 16.17 (1 H, br. s), 14.00 (1 H, br. s.), 12.92 (1 H, br. s), 7.59 (1 H, dd, J = 8.98, 4.57 Hz), 7.44 (1 H, dd, J = 9.62, 2.36 Hz), 7.15 (1 H, td, J = 9.30, 2.52 Hz), 6.77 (1 H, d, J = 0.63 Hz), 3.64 (3 H, s), 2.16-2.47 (2 H, m), 0.99 (3 H, t, J = 7.41 Hz), Rt 1.39 min. |
| 407 | 5-ethyl-6-(5-ethyl-1-methyl-1H-indol-2-yl)-4-hydroxy-2-oxo-1,2-dihydropyridine-3-carboxylic acid<br>$^1$H NMR (500 MHz, DMSO-$d_6$) δ ppm 16.19 (1 H, br. s), 13.99 (1 H, br. s.), 12.90 (1 H, br. s), 7.44-7.48 (2 H, m), 7.14-7.17 (1 H, m), 6.69 (1 H, d, J = 0.63 Hz), 3.61 (3 H, s), 2.70 (2 H, q, J = 7.57 Hz), 2.16-2.48 (2 H, m), 1.23 (3 H, t, J = 7.57 Hz), 0.99 (3 H, t, J = 7.41 Hz), RT 1.53 min. |
| 408 | 5-ethyl-6-(6-ethyl-1-methyl-1H-indol-2-yl)-4-hydroxy-2-oxo-1,2-dihydropyridine-3-carboxylic acid<br>$^1$H NMR (500 MHz, DMSO-$d_6$) δ ppm 16.21 (1 H, br. s), 13.99 (1 H, br. s.), 12.89 (1 H, br. s), 7.55 (1 H, d, J = 8.20 Hz), 7.37 (1 H, s), 7.02 (1 H, dd, J = 8.04, 1.42 Hz), 6.71 (1 H, d, J = 0.95 Hz), 3.61 (3 H, s), 2.75 (2 H, q, J = 7.57 Hz), 2.15-2.48 (2 H, m), 1.26 (3 H, t, J = 7.57 Hz), 0.99 (3 H, t, J = 7.41 Hz), RT 1.53 min. |
| 409 | 5-ethyl-4-hydroxy-6-(1-methyl-5-propyl-1H-indol-2-yl)-2-oxo-1,2-dihydropyridine-3-carboxylic acid<br>$^1$H NMR (500 MHz, DMSO-$d_6$) δ ppm 16.23 (1 H, br. s), 13.99 (1 H, br. s.), 12.87 (1 H, br. s.), 7.46 (1 H, d, J = 8.51 Hz), 7.44 (1 H, d, J = 0.95 Hz), 7.13 (1 H, dd, J = 8.51, 1.58 Hz), 6.69 (1 H, d, J = 0.63 Hz), 3.61 (3 H, s), 2.65 (2 H, t, J = 7.41 Hz), 2.09-2.46 (2 H, m), 1.64 (2 H, sxt, J = 7.38 Hz), 0.99 (3 H, t, J = 7.41 Hz), 0.90 (3 H, t, J = 7.25 Hz), RT 1.61 min. |
| 410 | 5-ethyl-4-hydroxy-6-(1-methyl-6-propyl-1H-indol-2-yl)-2-oxo-1,2-dihydropyridine-3-carboxylic acid<br>$^1$H NMR (500 MHz, DMSO-$d_6$) δ ppm 16.09-16.33 (1 H, m), 13.99 (1 H, br. s.), 12.87 (1 H, br. s), 7.55 (1 H, d, J = 7.57 Hz), 7.35 (1 H, s), 7.00 (2 H, dd, J = 8.20, 1.26 Hz), 6.71 (1 H, d, J = 0.63 Hz), 3.60 (3 H, s), 2.65-2.76 (2 H, m), 2.14-2.47 (2 H, m), 1.67 (2 H, sxt, J = 7.44 (Hz), 0.99 (3 H, t, J = 7.41 Hz), 0.93 (3 H, t , J = 7.25 Hz), RT 1.60 min. |

-continued

| Cpd | Name |
|---|---|
| 411 | 5-ethyl-6-(5-fluoro-1,6-dimethyl-1H-indol-2-yl)-4-hydroxy-2-oxo-1,2-dihydropyridine-3-carboxylic acid<br>$^1$H NMR (500 MHz, DMSO-d$_6$) δ ppm 16.19 (1 H, br. s), 13.99 (1 H, s), 12.91 (1 H, br. s), 7.47 (1 H, d, J = 6.31 Hz), 7.38 (1 H, d, J = 10.40 Hz), 6.71 (1 H, d, J = 0.63 Hz), 3.60 (3 H, s), 2.15-2.44 (5 H, m), 0.98 (3 H, t, J = 7.41 Hz), RT 1.346 min. |

Example 412

6-(2-Amino-2,3-dihydro-1H-pyrrolo[1,2-a]indol-7-yl)-4-hydroxy-5-methyl-2-oxo-1,2-dihydropyridine-3-carboxylic acid hydrochloride

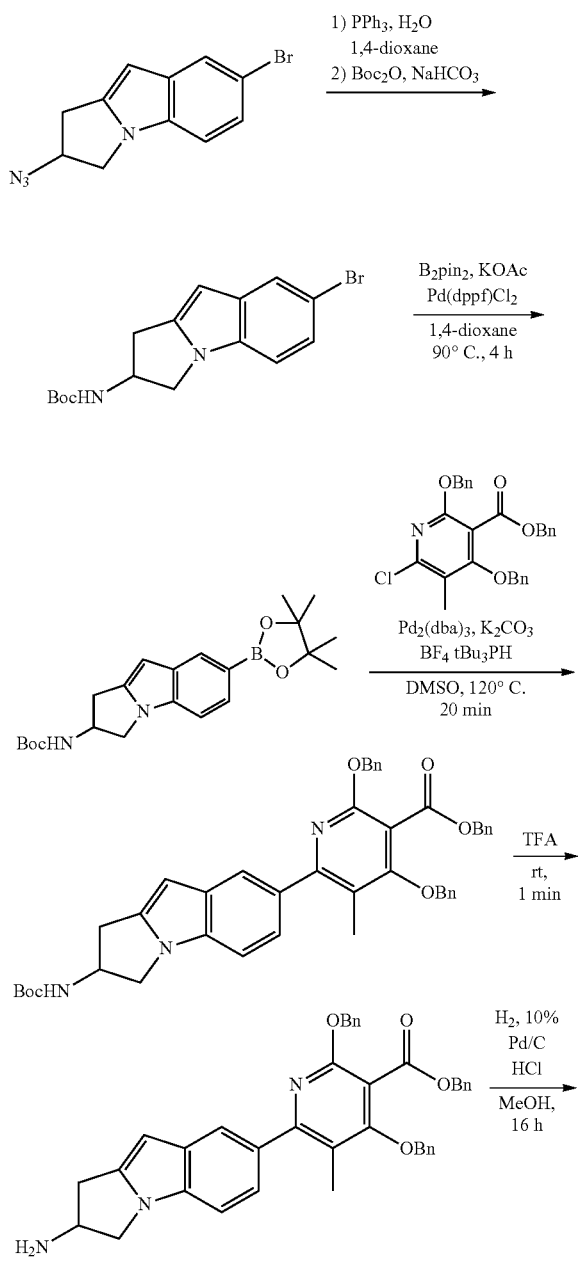

Step 1: Preparation of tert-butyl (7-bromo-2,3-dihydro-1H-pyrrolo[1,2-a]indol-2-yl)carbamate 2-Azido-7-bromo-2,3-dihydro-1H-pyrrolo[1,2-a]indole (1.96 g, 7.1 mmol, prepared according to the procedure in *Tetrahedron*, 2004, 7367) was dissolved in 1,4-dioxane (15 mL). Triphenylphosphine (2.05 g, 7.8 mmol) was added to the solution. Nitrogen gas evolution was observed. The mixture stirred at room temperature for 10 min. To the mixture was added water (1.28 mL, 71 mmol). The mixture was stirred at 90° C. for 2 h. After cooling the mixture to room temperature, aqueous saturated NaHCO$_3$ (5 mL) was added, followed by di-tert-butyl dicarbonate (1.7 g, 7.8 mmol). The mixture was stirred at room temperature for 3 h. The mixture was partitioned in EtOAc (100 mL) and H$_2$O (100 mL). The organic layer was washed with brine, dried over Na$_2$SO$_4$, filtered and concentrated. The residue was chromatographed on silica gel (0-30% EtOAc in hexanes) to afford the product as a white powder (2.33 g, 93%).

$^1$H NMR (500 MHz, acetone-d$_6$) δ ppm 1.44 (s, 9H), 3.01 (dd, J=16.3, 5.8 Hz, 1H), 3.39 (dd, J=16.5, 7.7 Hz, 1H), 3.96 (dd, J=10.4, 5.3 Hz, 1H), 4.43 (dd, J=10.4, 7.8 Hz, 1H), 4.89 (m, 1H), 6.16 (s, 1H), 6.68 (br, 1H), 7.18 (dd, J=8.6, 1.8 Hz, 1H), 7.26 (d, J=8.5 Hz, 1H), 7.64 (d, J=1.9 Hz, 1H). LC-MS 351.0, 353.0 [M+H]$^+$, RT 1.51 min.

Step 2: Preparation of tert-butyl (7-(4,4,5,5-tetramethyl-1,3,2-dioxaborolan-2-yl)-2,3-dihydro-1H-pyrrolo[1,2-a]indol-2-yl)carbamate The intermediate from Step 1 (2.33 g, 6.6 mmol) was combined with bis(pinacolato)diboron (2.51 g, 9.9 mmol), potassium acetate (1.3 g, 13.2 mmol) and [1,1'-bis(diphenylphosphino)ferrocene]dichloropalladium(II) (270 mg, 0.33 mmol) in 1,4-dioxane (15 mL). The mixture was heated at 90° C. for 4 h. The mixture was partitioned in EtOAc (100 mL) and H$_2$O (100 mL). The organic layer was washed with brine, dried over Na$_2$SO$_4$, filtered and concentrated. The residue was chromatographed on silica gel (0-30% EtOAc in hexanes) to afford the product as a tan powder (2.4 g, 91%).

$^1$H NMR (500 MHz, CHCl$_3$-d) δ ppm 1.39 (s, 9H), 1.48 (s, 12H), 2.87 (dd, J=16.3, 6.9 Hz), 3.41 (dd, J=16.3, 6.9 Hz, 1H), 3.93 (d, J=9.6 Hz, 1H), 4.37 (dd, J=10.7, 6.0 Hz, 1H), 4.94 (br s, 1H), 6.22 (br s, 1H), 7.24 (d, J=8.2 Hz, 1H), 7.61 (d, J=8.2 Hz, 1H), 8.09 (s, 1H). LC-MS 399.1 [M+H]$^+$, RT 1.58 min.

Step 3: Preparation of benzyl 2,4-bis(benzyloxy)-6-(2-((tert-butoxycarbonyl)amino)-2,3-dihydro-1H-pyrrolo[1,2-a]indol-7-yl)-5-methylnicotinate The intermediate from Step 2 (280 mg, 0.7 mmol) was combined with benzyl 2,4-bis(benzyloxy)-6-chloro-5-methylnicotinate (332 mg, 0.7 mmol, prepared according to Example 379, Step 3), potassium carbonate (193 mg, 1.4 mmol), tris(dibenzylideneacetone) dipalladium(0) (32 mg, 0.035 mmol) and tri-tert-butylphosphine tetrafluoroborate (41 mg, 0.14 mmol) in DMSO (3 mL). The mixture was heated under Ar at 120° C. for 20 min. The mixture was cooled to room temperature and partitioned in CH$_2$Cl$_2$ (10 mL) and saturated aqueous NaHCO$_3$ (10 mL). The organic layer was removed, concentrated and chromatographed on silica gel (0-30% EtOAc in hexanes) to provide the product as a white powder (274 mg, 55%).

LC-MS 710.3 [M+H]$^+$, RT 1.73 min.

Step 4: Preparation of benzyl 6-(2-amino-2,3-dihydro-1H-pyrrolo[1,2-a]indol-7-yl)-2,4-bis(benzyloxy)-5-methylnicotinate The intermediate from Step 3 (65 mg, 0.09 mmol) was dissolved in trifluoroacetic acid (1 mL). After 1 min of stirring at room temperature, the mixture was partitioned in CH$_2$Cl$_2$ and aqueous 1 M K$_2$CO$_3$. The organic layer was removed, concentrated and chromatographed on silica gel (0-8% MeOH in CH$_2$Cl$_2$) to provide the product as a white powder (36 mg, 64%).

LC-MS 610.3 [M+H], RT 1.18 min.

Step 5: Preparation of 6-(2-amino-2,3-dihydro-1H-pyrrolo[1,2-a]indol-7-yl)-4-hydroxy-5-methyl-2-oxo-1,2-dihydropyridine-3-carboxylic acid hydrochloride The intermediate from Step 4 (36 mg, 0.06 mmol) was dissolved in MeOH (2 mL). To the solution was added 10% Pd/C (20 mg) and 3 N HCl in MeOH (0.1 mL). The mixture stirred under H$_2$ (1 atm) at room temperature for 16 h. The mixture was filtered through a 5 μm cartridge. The filtrate was concentrated, leaving the product (21 mg, 49%) as an off white powder.

$^1$H NMR (500 MHz, DMSO-d$_6$) δ ppm 1.94 (s, 3H), 3.14 (dd, J=17.3, 3.4 Hz, 1H), 3.48 (dd, J=17.7, 7.5 Hz, 1H), 4.20 (dd, J=11.4, 3.7 Hz, 1H), 4.49 (dd, J=11.3, 7.0 Hz, 1H), 4.55 (m, 1H), 6.35 (s, 1H), 7.21 (dd, J=8.4, 1.7 Hz, 1H), 7.55 (d, J=8.4 Hz, 1H), 7.67 (d, J=1.7 Hz, 1H), 8.57 (br s, 2H), 12.76 (br s, 1H), 13.91 (br s, 1H), 16.32 (br s, 1H). LC-MS 340.1 [M+H]$^+$, RT 0.86 min.

Using the procedures described above, additional compounds described herein may be prepared by substituting the appropriate starting materials, reagents and reaction conditions and include compounds selected from:

| Cpd | Name |
|---|---|
| 413 | 6-(2-amino-2,3-dihydro-1H-pyrrolo[1,2-a]indol-7-yl)-5-ethyl-4-hydroxy-2-oxo-1,2-dihydropyridine-3-carboxylic acid hydrochloride<br>$^1$H NMR (500 MHz, DMSO-d$_6$) δ ppm 0.98 (t, J = 7.4 Hz, 3H), 2.33 (q, J = 7.4 Hz, 2H), 3.14 (dd, J = 17.0, 3.2 Hz, 1H), 3.48 (m, 1H), 4.18 (dd, J = 11.4, 3.7 Hz, 1H), 4.49 (dd, J = 11.3, 7.0 Hz, 1H), 4.55 (m, 1H), 6.35 (s, 1H), 7.16 (dd, J = 8.4, 1.7 Hz, 1H), 7.55 (d, J = 8.4 Hz, 1H), 7.62 (d, J = 1.7 Hz, 1H), 8.46 (br s, 2H), 12.67 (br s, 1H), 13.82 (br s, 1H), 16.50 (br s, 1H). LC-MS 354.2 [M + H]$^+$, RT 0.51 min (1 min Method). |
| 414 | 5-ethyl-4-hydroxy-6-(7-(methylamino)-6,7,8,9-tetrahydropyrido[1,2-a]indol-2-yl)-2-oxo-1,2-dihydropyridine-3-carboxylic acid hydrochloride<br>$^1$H NMR (500 MHz, CH$_3$OH-d$_4$) δ ppm 1.09 (t, J = 7.5 Hz, 3H), 2.29 (m, 1H), 2.48 (q, J = 7.5 Hz, 2H), 2.56 (m, 1H), 3.12 (m, 1H), 3.53 (m, 1H), 3.80 (m, 1H), 4.12 (br, 1H), 4.53 (br, 1H), 6.46 (s, 1H), 7.24 (m, 1H), 7.55 (m, 1H), 7.63 (s, 1H). LC-MS 368.2 [M + H]$^+$, RT 0.53 min (1 min Method). |

Example 415

4-Hydroxy-5-methyl-6-(2-(methylamino)-2,3-dihydro-1H-pyrrolo[1,2-a]indol-7-yl)-2-oxo-1,2-dihydropyridine-3-carboxylic acid hydrochloride

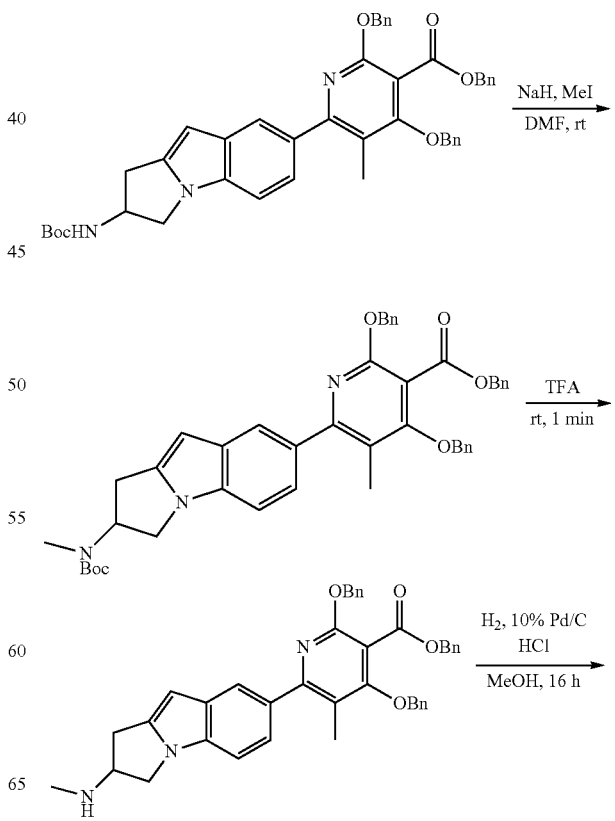

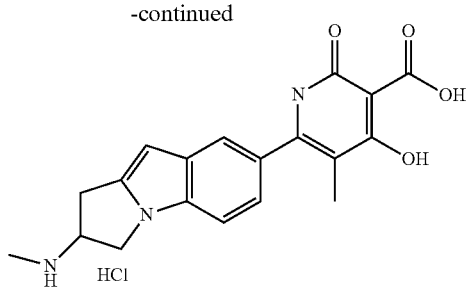

Step 1: Preparation of benzyl 2,4-bis(benzyloxy)-6-(2-((tert-butoxycarbonyl)(methyl)amino)-2,3-dihydro-1H-pyrrolo[1,2-a]indol-7-yl)-5-methylnicotinate The product from Example 412, Step 3 (130 mg, 0.18 mmol) was dissolved in DMF (1 mL). Sodium hydride (60% dispersion in mineral oil, 15 mg, 0.36 mmol) was added to the mixture. After 10 min of vigorous stirring at room temperature, iodomethane (35 µL, 0.54 mmol) was added to the mixture. The mixture was stirred an additional 10 min at room temperature, and then was quenched with the addition of aqueous saturated NH$_4$Cl solution (5 mL). The mixture was extracted with CH$_2$Cl$_2$ (5 mL). The organic extracts were concentrated. The residue was 97% pure by UPLC analysis and used without further purification.

LC-MS 724.6 [M+H]$^+$, RT 1.72 min.

Step 2: Preparation of benzyl 2,4-bis(benzyloxy)-5-methyl-6-(2-(methylamino)-2,3-dihydro-1H-pyrrolo[1,2-a]indol-7-yl)nicotinate The intermediate from Step 1 (~0.18 mmol) was dissolved in trifluoroacetic acid (1 mL). After 1 min of stirring at room temperature, the mixture was partitioned in CH$_2$Cl$_2$ and aqueous 1 M K$_2$CO$_3$. The organic layer was removed, concentrated and chromatographed on silica gel (0-8% MeOH in CH$_2$Cl$_2$) to provide the product as a white powder (70 mg, 55%).

LC-MS 624.5 [M+H]$^+$, RT 0.81 min. (1 min Method).

Step 3: Preparation of 4-hydroxy-5-methyl-6-(2-(methylamino)-2,3-dihydro-1H-pyrrolo[1,2-a]indol-7-yl)-2-oxo-1,2-dihydropyridine-3-carboxylic acid hydrochloride The intermediate from Step 2 (70 mg, 0.11 mmol) was dissolved in MeOH (2 mL). To the solution was added 10% Pd/C (20 mg) and 3 N HCl in MeOH (0.1 mL). The mixture was stirred under H$_2$ (1 atm) at room temperature for 16 h. The mixture was filtered through a 5 µm cartridge. The filtrate was concentrated, leaving the product (21 mg, 49%) as an off white powder.

$^1$H NMR (500 MHz, DMSO-d$_6$) δ ppm 1.94 (s, 3H), 2.67 (s, 3H), 3.28 (dd, J=17.3, 3.2 Hz, 1H), 3.51 (dd, J=17.3, 7.5 Hz, 1H), 4.36 (m, 1H), 4.53 (m, 2H), 6.36 (s, 1H), 7.21 (dd, J=8.4, 1.7 Hz, 1H), 7.52 (d, J=8.4 Hz, 1H), 7.67 (d, J=1.7 Hz, 1H), 9.49 (br s, 2H), 12.76 (br s, 1H), 13.87 (br s, 1H), 16.35 (br s, 1H). LC-MS 354.1 [M+H]$^+$, RT 0.86 min.

Using the procedures described above, additional compounds described herein may be prepared by substituting the appropriate starting materials, reagents and reaction conditions and include compounds selected from:

| Cpd | Name |
|---|---|
| 416 | 5-ethyl-4-hydroxy-6-(2-(methylamino)-2,3-dihydro-1H-pyrrolo[1,2-a]indol-7-yl)-2-oxo-1,2-dihydropyridine-3-carboxylic acid hydrochloride<br>$^1$H NMR (500 MHz, CH$_3$OH-d$_4$) δ ppm 1.09 (m, 3H), 2.47 (m, 2H), 2.85 (s, 3H), 3.28 (m, 1H), 3.74 (m, 1H), 4.36 (m, 1H), 4.60 (m, 2H), 7.11 (s, 1H), 7.26 (m, 1H), 7.48 (m, 1H), 7.67 (s, 1H). LC-MS 368.0 [M + H]$^+$, RT 0.92 min. |

Example 417

6-(2-(Dimethylamino)-2,3-dihydro-1H-pyrrolo[1,2-a]indol-7-yl)-4-hydroxy-5-methyl-2-oxo-1,2-dihydropyridine-3-carboxylic acid hydrochloride

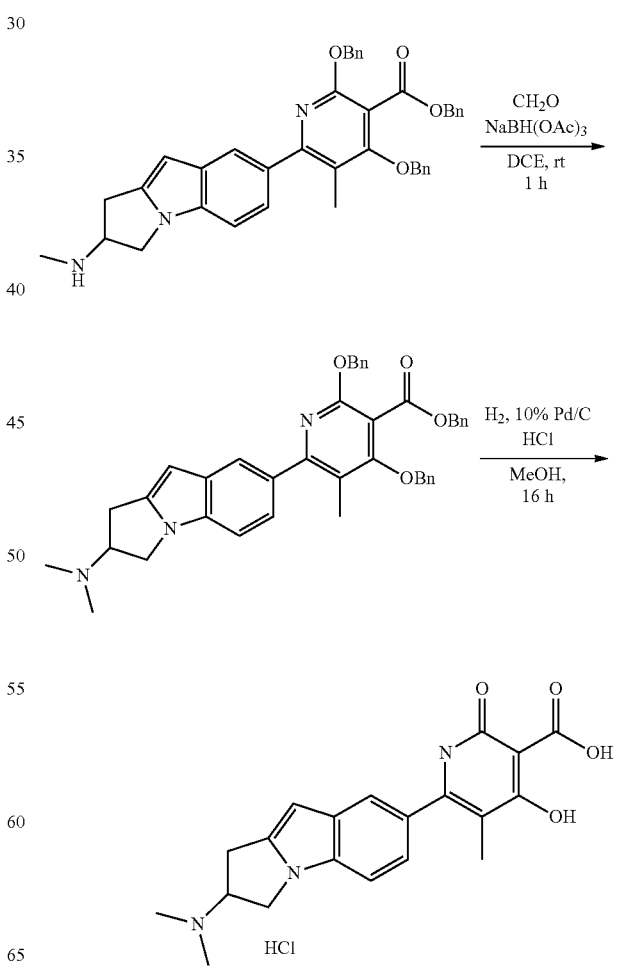

Step 1: benzyl 2,4-bis(benzyloxy)-6-(2-(dimethylamino)-2,3-dihydro-1H-pyrrolo[1,2-a]indol-7-yl)-5-methylnicotinate The product from Example 415, Step 2 (31 mg, 0.05 mmol) was dissolved in 1,2-dichloroethane (1 mL). Aqueous 30% formaldehyde (1 drop, ~0.2 mmol) was added to the mixture, followed by sodium triacetoxyborohydride (21 mg, 0.1 mmol). The mixture stirred at room temperature for 30 min. The mixture was loaded directly to silica gel, eluting with 0-8% MeOH in CH$_2$Cl$_2$ to afford product (25 mg, 78%). LC-MS 638.3 [M+H]$^+$, RT 1.21 min.

Step 2: Preparation of 6-(2-(dimethylamino)-2,3-dihydro-1H-pyrrolo[1,2-a]indol-7-yl)-4-hydroxy-5-methyl-2-oxo-1,2-dihydropyridine-3-carboxylic acid hydrochloride The title compound was prepared according to Example 412, Step 5 (11 mg, 91%).

$^1$H NMR (500 MHz, DMSO-d$_6$) δ ppm 1.94 (s, 3H), 2.81 (s, 6H), 3.45 (dd, J=17.2, 5.5 Hz, 1H), 3.53 (dd, J=17.1, 7.7 Hz, 1H), 4.52 (dd, J=11.6, 5.4 Hz, 1H), 4.60 (dd, J=11.5, 7.4 Hz, 1H), 4.67 (m, 1H), 6.36 (s, 1H), 7.22 (dd, J=8.4, 1.7 Hz, 1H), 7.50 (d, J=8.4 Hz, 1H), 7.67 (d, J=1.7 Hz, 1H), 11.34 (br s, 1H), 12.76 (br s, 1H), 13.87 (br s, 1H), 16.35 (br s, 1H). LC-MS 368.1 [M+H]$^+$, RT 0.87 min.

Using the procedures described above, additional compounds described herein may be prepared by substituting the appropriate starting materials, reagents and reaction conditions and include compounds selected from:

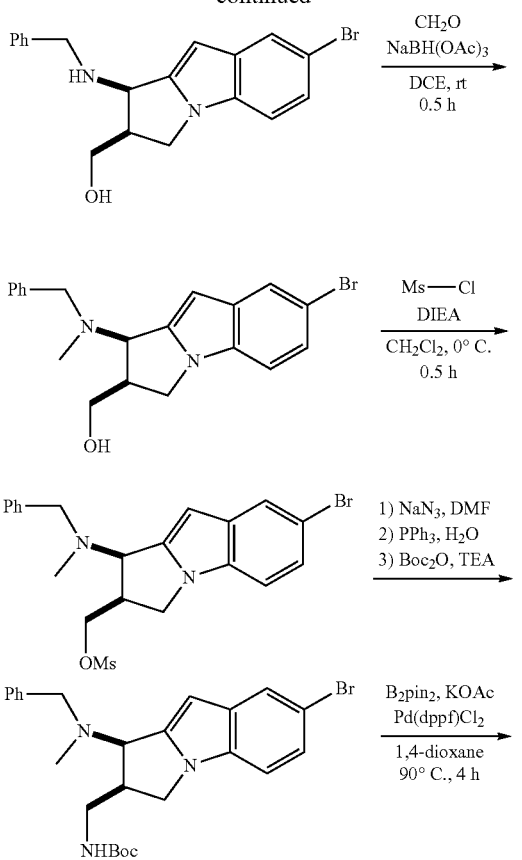

| Cpd | Name |
|---|---|
| 418 | 6-(2-(dimethylamino)-2,3-dihydro-1H-pyrrolo[1,2-a]indol-7-yl)-5-ethyl-4-hydroxy-2-oxo-1,2-dihydropyridine-3-carboxylic acid hydrochloride<br>$^1$H NMR (500 MHz, DMSO-d$_6$) δ ppm 1.00 (t, J = 7.4 Hz, 3H), 2.33 (q, J = 7.4 Hz, 2H), 2.79 (s, 6H), 3.48 (m, 2H), 4.52 (m, 1H), 4.58 (m, 2H), 6.36 (s, 1H), 7.19 (dd, J = 8.4, 1.7 Hz, 1H), 7.50 (d, J = 8.4 Hz, 1H), 7.63 (d, J = 1.7 Hz, 1H), 11.57 (br s, 1H), 12.78 (br s, 1H), 13.91 (br s, 1H), 16.33 (br s, 1H). LC-MS 382.3 [M + H]$^+$, RT 0.53 min (1 min). |
| 419 | 5-ethyl-6-(2-(ethyl(methyl)amino)-2,3-dihydro-1H-pyrrolo[1,2-a]indol-7-yl)-4-hydroxy-2-oxo-1,2-dihydropyridine-3-carboxylic acid<br>$^1$H NMR (500 MHz, CH$_3$OH-d$_4$) δ ppm 0.97 (t, J = 7.4 Hz, 3H), 1.08 (t, J = 7.2 Hz, 3H), 1.50 (m, 2H), 2.25 (s, 3H), 2.37 (q, J = 7.4 Hz, 2H), 2.44 (q, J = 7.2 Hz, 2H), 2.96 (m, 1H), 3.22 (m, 1H), 3.97 (m, 2H), 4.30 (m, 1H), 6.17 (s, 1H), 7.05 (dd, J = 8.4, 1.7 Hz, 1H), 7.34 (d, J = 8.4 Hz, 1H), 7.47 (d, J = 1.7 Hz, 1H). LC-MC 396.3 [M + H]$^+$, RT 0.89 min. |
| 420 | 5-ethyl-4-hydroxy-6-(2-(methyl(propyl)amino)-2,3-dihydro-1H-pyrrolo[1,2-a]indol-7-yl)-2-oxo-1,2-dihydropyridine-3-carboxylic acid<br>$^1$H NMR (500 MHz, CH$_3$OH-d$_4$) δ ppm 0.86 (t, J = 7.4 Hz, 3H), 0.97 (t, J = 7.4 Hz, 3H), 2.25 (s, 3H), 2.37 (q, J = 7.4 Hz, 2H), 2.58 (q, J = 7.2 Hz, 2H), 2.96 (m, 1H), 3.22 (m, 1H), 3.97 (m, 2H), 4.30 (m, 1H), 6.17 (s, 1H), 7.05 (dd, J = 8.4, 1.7 Hz, 1H), 7.34 (d, J = 8.4 Hz, 1H), 7.47 (d, J = 1.7 Hz, 1H). LC-MS 410.3 [M + H]$^+$, RT 0.91 min. |

Example 421

6-(cis-2-(aminomethyl)-1-(methylamino)-2,3-dihydro-1H-pyrrolo[1,2-a]indol-7-yl)-5-ethyl-4-hydroxy-2-oxo-1,2-dihydropyridine-3-carboxylic acid bis-hydrochloride

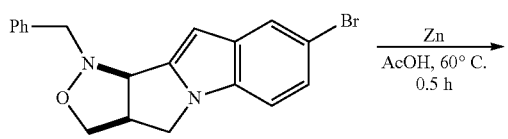

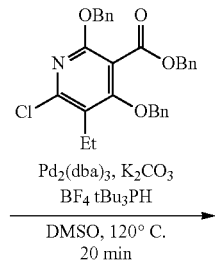

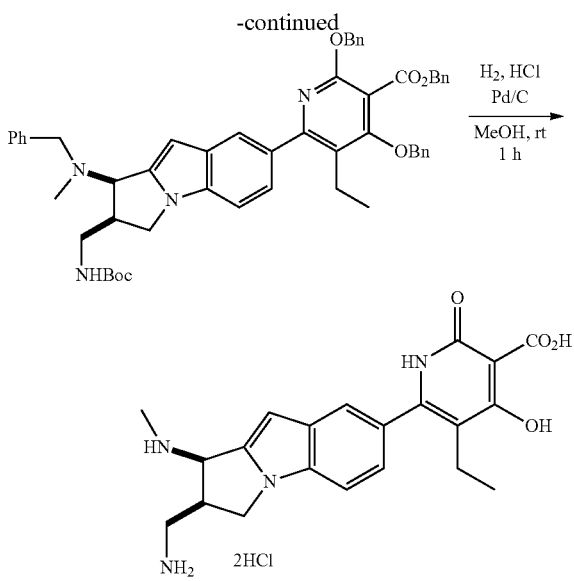

Step 1: (cis-1-(benzylamino)-7-bromo-2,3-dihydro-1H-pyrrolo[1,2-a]indol-2-yl)methanol (cis-3a,10b)-1-Benzyl-8-bromo-3,3a,4,10b-tetrahydro-1H-isoxazolo[3',4':3,4]pyrrolo[1,2-a]indole (2.3 g, 6.2 mmol, prepared according to the procedure in *J. Org. Chem.* 2000, 65, 8924-8932) was suspended in AcOH:$H_2O$ (5:1, 60 mL). Zinc dust (4.1 g, 62 mmol) was added to the mixture. The mixture was heated at 50° C. for 20 min with vigorous stirring. After cooling to room temperature, the mixture was filtered through a 5 μm fritted funnel. The filtrate was concentrated. The residue was partitioned in $CH_2Cl_2$ (100 mL) and aqueous $K_2CO_3$ (1M, 100 mL). The organic layer was collected and concentrated, providing the product as a white powder (2.24 g, quant.).

LC-MS 264.1, 266.1 [M+H-benzyl]$^+$, RT 1.04 min.

Step 2: (cis-1-(benzyl(methyl)amino)-7-bromo-2,3-dihydro-1H-pyrrolo[1,2-a]indol-2-yl)methanol The product of Step 1 (710 mg, 2 mmol) was suspended in 1,2-dichloroethane with formaldehyde (0.4 mL of 37% aqueous solution, 5 mmol). Sodium triacetoxyborohydride (848 mg, 4 mmol) was added to the mixture. The mixture stirred vigorously at room temperature for 30 min. The mixture was washed with aqueous saturated $NaHCO_3$ and run through a plug of silica gel, eluting with EtOAc, to give the product (690 mg, 90%).

LC-MS 385.2, 387.2 [M+H]$^+$, RT 0.58 min. (1 min Method).

Step 3: (cis-1-(benzyl(methyl)amino)-7-bromo-2,3-dihydro-1H-pyrrolo[1,2-a]indol-2-yl)methyl methanesulfonate The product from Step 2 (690 mg, 1.8 mmol) was dissolved in $CH_2Cl_2$ (10 mL) with N,N-diisopropylethylamine (0.94 mL, 5.4 mmol). The mixture was cooled to 0° C., before adding methanesulfonyl chloride (0.21 mL, 2.7 mmol). After 30 min, the mixture was washed with water, dried over $Na_2SO_4$ and concentrated. The crude mixture was carried on without further purification.

Step 4: tert-butyl ((cis-1-(benzyl(methyl)amino)-7-bromo-2,3-dihydro-1H-pyrrolo[1,2-a]indol-2-yl)methyl)carbamate The crude material from Step 3 was dissolved in DMF (5 mL) and treated with $NaN_3$ (234 mg, 3.6 mmol). The mixture was heated at 80° C. for 2 h. To the mixture was added $H_2O$ (1 mL) and triphenylphosphine (524 mg, 2 mmol). The mixture stirred at 80° C. for 1 h. After cooling the mixture to room temperature, triethylamine (0.5 mL, 3.6 mmol) and di-tert-butyldicarbonate (436 mg, 2.0 mmol) were added sequentially. The mixture was stirred at room temperature for 1 h. The mixture was concentrated and chromatographed on silica gel (0-8% MeOH in $CH_2Cl_2$) to afford the product (300 mg, 35%).

LC-MS 484.3, 486.3 [M+H]$^+$, RT 0.69 min. (1 min Method).

Step 5: tert-butyl ((cis-1-(benzyl(methyl)amino)-7-(4,4,5,5-tetramethyl-1,3,2-dioxaborolan-2-yl)-2,3-dihydro-1H-pyrrolo[1,2-a]indol-2-yl)methyl)carbamate The title compound was prepared from the product of Step 4 (242 mg, 0.5 mmol), according to Example 412, Step 2 (113 mg, 43%).

LC-MS 532.4 [M+H]$^+$, RT 0.73 min. (1 min Method).

Step 6: benzyl 6-(cis-1-(benzyl(methyl)amino)-2-(((tert-butoxycarbonyl)amino)methyl)-2,3-dihydro-1H-pyrrolo[1,2-a]indol-7-yl)-2,4-bis(benzyloxy)-5-ethylnicotinate The title compound was prepared from the product of Step 5 (113 mg, 0.2 mmol), according to Example 412, Step 3 (117 mg, 69%). RT 0.90 min. (1 min Method).

Step 7: 6-(cis-2-(aminomethyl)-1-(methylamino)-2,3-dihydro-1H-pyrrolo[1,2-a]indol-7-yl)-5-ethyl-4-hydroxy-2-oxo-1,2-dihydropyridine-3-carboxylic acid bis-hydrochloride The product of step 6 (110 mg, 0.13 mmol) was combined with 10% Pd/C (20 mg) in MeOH (10 mL). The mixture stirred under $H_2$ (1 atm) for 18 h at room temperature. The mixture was filtered over a 5 μm frit. The filtrate was concentrated and dissolved in TFA (1 mL). The mixture sat 10 min, and then was concentrated. The residue was dissolved in 3 N HCl in MeOH (1 mL). The solvents were removed providing the title compound (27 mg, 69%).

$^1$H NMR (500 MHz, CHCl$_3$-d) δ ppm 0.98 (t, J=7.4 Hz, 3H), 2.33 (q, J=7.3 Hz, 2H), 2.65 (s, 3H), 3.32 (m, 1H), 3.47 (m, 2H), 4.18 (m, 1H), 4.56 (m, 1H), 5.00 (m, 1H), 6.66 (s, 1H), 7.26 (d, J=8.2 Hz, 1H), 7.55 (d, J=8.4 Hz, 1H), 7.76 (s, 1H), 8.96-9.32 (br, 5H), 12.81 (s, 1H), 13.91 (s, 1H), 16.35 (br s, 1H). LC-MS 397.3 [M+H]$^+$.

Using the procedures described above, additional compounds described herein may be prepared by substituting the appropriate starting materials, reagents and reaction conditions and include compounds selected from:

| Cpd | Name |
|---|---|
| 422 | 6-(trans-7-amino-9-(methylamino)-6,7,8,9-tetrahydropyrido[1,2-a]indol-2-yl)-5-ethyl-4-hydroxy-2-oxo-1,2-dihydropyridine-3-carboxylic acid bis-hydrochloride<br>¹H NMR (500 MHz, CHCl₃-d) δ ppm 1.00 (t, J = 7.4 Hz, 3H), 2.33 (q, J = 7.3 Hz, 2H), 2.35 (m, 1H), 2.46 (m, 1H), 2.66 (m, 1H), 2.69 (s, 3H), 4.06 (m, 1H), 4.61 (m, 1H), 4.91 (m, 1H), 6.96 (s, 1H), 7.34 (d, J = 8.2 Hz, 1H), 7.65 (d, J = 8.4 Hz, 1H), 7.80 (s, 1H), 8.59-8.81 (br, 3H), 9.61-9.82 (br, 2H), 12.82 (s, 1H), 13.92 (s, 1H), 16.35 (br s, 1H). LC-MS 397.3 [M + H]⁺. |

Example 423

5-Ethyl-4-hydroxy-6-(1H-indol-6-yl)-2-oxo-1,2-dihydropyridine-3-carboxylic

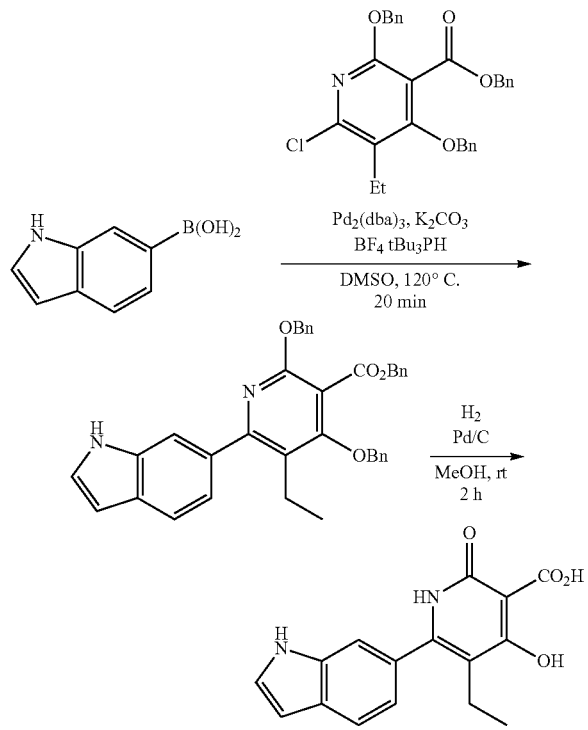

Step 1: Preparation of benzyl 2,4-bis(benzyloxy)-5-ethyl-6-(1H-indol-6-yl)nicotinate The title compound was prepared from (1H-indol-6-yl) boronic acid (32 mg, 0.2 mmol), according to Example 412, Step 3 (104 mg, 92%).

LC-MS 569.2 [M+H]⁺, RT 1.78 min.

Step 2: Preparation of 5-ethyl-4-hydroxy-6-(1H-indol-6-yl)-2-oxo-1,2-dihydropyridine-3-carboxylic acid The product from Step 1 (104 mg, 0.18 mmol) was combined with 10% Pd/C (20 mg) in MeOH (3 mL). The mixture stirred under H₂ (1 atm) for 2 h. The mixture was filtered over a 5 μm frit. The filtrate was concentrated, suspended in CH₃CN. The solid was collected and dried to provide the title compound as a tan powder (26 mg, 56%).

¹H NMR (500 MHz, CHCl₃-d) δ ppm 1.04 (t, J=7.4 Hz, 3H), 2.37 (q, J=7.3 Hz, 2H), 6.55 (s, 1H), 7.07 (d, J=8.2 Hz, 1H), 7.51-7.55 (m, 2H), 7.70 (d, J=8.2 Hz, 1H), 11.44 (s, 1H), 12.72 (br s, 1H), 13.97 (br s, 1H), 16.35 (br s, 1H). LC-MS 299.0 [M+H]⁺, RT 1.27 min.

Using the procedures described above, additional compounds described herein may be prepared by substituting the appropriate starting materials, reagents and reaction conditions and include compounds selected from:

| Cpd | Name |
|---|---|
| 424 | 4-hydroxy-6-(1H-indol-6-yl)-5-methyl-2-oxo-1,2-dihydropyridine-3-carboxylic acid<br>¹H NMR (500 MHz, CHCl₃-d) δ ppm 1.96 (s, 3H), 6.55 (s, 1H), 7.11 (d, J = 8.2 Hz, 1H), 7.52-7.57 (m, 2H), 7.69 (d, J = 8.2 Hz, 1H), 11.47 (s, 1H), 12.74 (br s, 1H), 13.91 (br s, 1H), 16.35 (br s, 1H). LC-MS 285.2 [M + H]⁺, RT 1.09 min |
| 425 | 5-ethyl-4-hydroxy-6-(1H-indol-5-yl)-2-oxo-1,2-dihydropyridine-3-carboxylic acid<br>¹H NMR (500 MHz, DMSO-d₆) δ ppm 13.92 (1 H, br. s), 12.71 (1 H, br. s), 11.41 (1 H, br. s), 7.65-7.71 (1 H, m), 7.53 (1 H, d, J = 8.53 Hz), 7.48 (1 H, t, J = 2.80 Hz), 7.16 (1 H, dd, J = 8.53, 1.65 Hz), 6.53-6.57 (1 H, m), 2.35 (2 H, d, J = 7.43 Hz), 1.01 (3H, t, J = 7.29 Hz), RT 1.25 min. |
| 426 | 4-hydroxy-6-(1H-indol-5-yl)-5-methyl-2-oxo-1,2-dihydropyridine-3-carboxylic acid<br>¹H NMR (500 MHz, DMSO-d₆) δ ppm 1.94 (s, 3 H), 6.55 (br. s., 1 H), 7.17-7.22 (m, 1 H), 7.48 (s, 1 H), 7.53 (d, J = 8.5 Hz, 1 H), 7.71 (d, J = 1.6 Hz, 1 H), 11.36-11.45 (br s, 1 H), 12.60-12.80 (br s, 1 H), 13.84-13.97 (br s, 1 H), 16.18-16.45 (br s, 1 H). LC-MS 285.2 [M − H]⁻, 283.2 [M + H]⁺, RT 0.66 min. (1 min Method). |
| 427 | 4-hydroxy-5-methyl-2-oxo-6-(2-oxoindolin-5-yl)-1,2-dihydropyridine-3-carboxylic acid<br>¹H NMR (500 MHz, DMSO-d₆) δ ppm 1.92 (s, 3 H), 3.56 (s, 2 H), 6.95 (d, J = 7.9 Hz, 1 H), 7.33 (d, J = 8.2 Hz, 1 H), 7.36 (s, 1 H), 10.62-10.70 (br s, 1 H), 12.58-12.80 (br s, 1 H), 13.77-13.92 (br s, 1 H), 16.10-16.41 (br s, 1 H). LC-MS 299.1 [M − H]⁻, 301.0 [M + H]⁺, RT 0.70 min. |

-continued

| Cpd | Name |
|---|---|
| 428 | 6-(6-(dimethylamino)naphthalen-2-yl)-5-ethyl-4-hydroxy-2-oxo-1,2-dihydropyridine-3-carboxylic acid<br>$^1$H NMR (500 MHz, DMSO-d$_6$) δ ppm 1.03 (t, J = 7.4 Hz, 3 H), 2.37 (d, J = 7.3 Hz, 2 H), 3.05 (s, 6 H), 7.00 (d, J = 2.5 Hz, 1H), 7.31 (dd, J = 9.1, 1.5 Hz, 1 H), 7.39 (dd, J = 8.5, 1.5 Hz, 1 H), 7.77 (d, J = 8.5 Hz, 1 H), 7.84 (d, J = 9.1 Hz, 1H), 7.85 (s, 1 H), 12.63-12.99 (br s, 1 H), 13.85-14.23 (br s, 1 H), 15.98-16.42 (br s, 1 H). LC-MS 351.1 [M − H]$^−$, 353.0 [M + H]$^+$, RT 1.48 min. |
| 429 | 5-ethyl-4-hydroxy-6-(2-methylindolizin-6-yl)-2-oxo-1,2-dihydropyridine-3-carboxylic acid<br>$^1$H NMR (500 MHz, DMSO-d$_6$) δ ppm 1.04 (t, J = 7.6 Hz, 3 H), 2.27 (s, 3 H), 2.40 (q, J = 7.6 Hz, 2 H), 6.33 (s, 1 H), 6.67 (d, J = 9.1 Hz, 1 H), 7.40 (d, J = 9.1 Hz, 1 H), 7.45 (s, 1 H), 8.41 (s, 1 H), 12.30-13.29 (br s, 1 H), 13.96-14.50 (br s, 1 H), 15.53-16.41 (br s, 1 H). LC-MS 311.2 [M − H]$^−$, 313.2 [M + H]$^+$, RT 1.32 min. |
| 430 | 5-ethyl-4-hydroxy-2-oxo-6-(1H-pyrrolo[3,2-b]pyridin-6-yl)-1,2-dihydropyridine-3-carboxylic acid<br>$^1$H NMR (500 MHz, DMSO-d$_6$) δ ppm 1.02 (t, J = 7.41 Hz, 3 H) 2.34 (q, J = 6.94 Hz, 2 H) 6.99 (br. s., 1 H) 8.40 (br. s., 1 H) 8.76 (s, 1 H) 8.91 (s, 1 H) 13.30 (br. s., 1 H) 13.95 (br. s, 1 H). LC-MS: 300.2 [M + H]$^+$, RT 0.45 min. |
| 431 | 4-hydroxy-5-methyl-2-oxo-6-(1H-pyrrolo[3,2-b]pyridin-6-yl)-1,2-dihydropyridine-3-carboxylic acid<br>$^1$H NMR (500 MHz, DMSO-d$_6$) δ ppm 1.96 (s, 3 H) 6.73 (br. s., 1 H) 7.95 (t, J = 2.84 Hz, 1 H) 8.11 (s, 1 H) 8.52 (d, J = 1.26 Hz, 1 H) 12.02 (br. s, 1 H) 13.90 br. s, 1 H). LC-MS: 286.2 [M + H]$^+$, RT 0.39 min. |
| 432 | 6-(9H-carbazol-2-yl)-5-ethyl-4-hydroxy-2-oxo-1,2-dihydropyridine-3-carboxylic acid<br>$^1$H NMR (500 MHz, MeOD) δ ppm 1.15 (t, J = 7 Hz, 3 H), 2.53 (q, J = 7 Hz, 2 H), 7.23-7.27 (m, 2 H), 7.47 (dt, J = 7, 1 Hz, 1 H), 7.53 (d, J = 8.5 Hz, 1 H), 7.58 (d, J = 1 Hz, 1 H), 8.15 (d, J = 7.5 Hz, 1 H), 8.25 (d, J = 8 Hz, 1 H). LC-MS 347.3 [M − H]$^−$, 349.2 [M + H]$^+$, RT 1.30 min. |
| 433 | 5-ethyl-4-hydroxy-2-oxo-6-(1H-pyrrolo[2,3-b]pyridin-6-yl)-1,2-dihydropyridine-3-carboxylic acid<br>$^1$H NMR (500 MHz, DMSO-d$_6$) δ ppm 1.06 (t, J = 7.41 Hz, 3 H) 2.43 (q, J = 7.36 Hz, 2 H) 6.59 (dd, J = 3.47, 1.89 Hz, 1 H) 7.35 (d, J = 8.20 Hz, 1 H) 7.61-7.77 (m, 1 H) 8.16 (d, J = 7.88 Hz, 1 H) 12.00 (br. s., 1 H) 12.79 (br. s., 1 H) 13.95 (br. s., 1 H). LC-MS: 300.2 [M + H]$^+$, RT 0.42 min. |
| 434 | 4-hydroxy-5-methyl-2-oxo-6-(1H-pyrrolo[2,3-b]pyridin-6-yl)-1,2-dihydropyridine-3-carboxylic acid<br>$^1$H NMR (500 MHz, DMSO-d$_6$) δ ppm 2.03 (s, 3 H) 6.54-6.61 (m, 1 H) 7.36-7.43 (m, 1 H) 7.68-7.72 (m, 1 H) 8.13-8.19 (m, 1 H) 12.05 (br. s, 1 H) 12.74 (br. s, 1 H) 13.96 (br. s, 1 H). LC-MS: 286.2 [M + H]$^+$, RT 0.40 min. |
| 435 | 5-ethyl-4-hydroxy-2-oxo-6-(1-phenyl-1H-indol-5-yl)-1,2-dihydropyridine-3-carboxylic acid<br>$^1$H NMR (500 MHz, DMSO-d$_6$) δ ppm 13.95 (1 H, br. s), 12.79 (1 H, br. s), 7.82 (1 H, d, J = 3.30 Hz), 7.81 (1 H, d, J = 1.38 Hz), 7.68 (1 H, d, J = 8.53 Hz), 7.63 (4 H, d, J = 0.55 Hz), 7.42-7.50 (1 H, m), 7.28 (1 H, dd, J = 8.53, 1.65 Hz), 6.84 (1 H, dd, J = 3.16, 0.69 Hz), 2.51-2.53 (2 H, m), 1.02 (3 H, t, J = 7.29 Hz), RT 1.52 min. |
| 436 | 5-ethyl-4-hydroxy-2-oxo-6-(1-(pyridin-2-yl)-1H-indol-5-yl)-1,2-dihydropyridine-3-carboxylic acid<br>$^1$H NMR (500 MHz, DMSO-d$_6$) δ ppm 13.95 (1 H, br. s), 12.82 (1 H, br. s), 8.61 (1 H, m, J = 2.48, 2.48, 0.83 Hz), 8.55 (1 H, d, J = 8.80 Hz), 8.18 (1 H, d, J = 3.58 Hz), 8.04 (1 H, ddd, J = 8.25, 7.43, 1.93 Hz), 7.84 (1 H, d, J = 8.53 Hz), 7.79 (1 H, d, J = 1.38 Hz), 7.33-7.40 (2 H, m), 6.90 (1 H, dd, J = 3.44, 0.69 Hz), 2.51-2.53 (2 H, m), 1.02 (3 H, t, J = 7.43 Hz), RT 1.42 min. |
| 437 | 5-ethyl-4-hydroxy-2-oxo-6-(1-(4-(trifluoromethyl)phenyl)-1H-indol-5-yl)-1,2-dihydropyridine-3-carboxylic acid<br>$^1$H NMR (500 MHz, DMSO-d$_6$) δ ppm 12.82 (1 H, br. s), 11.95 (1 H, br. s), 7.87-8.01 (5 H, m), 7.76-7.84 (2 H, m), 7.32 (1 H, dd, J = 8.53, 1.38 Hz), 6.90 (1 H, d, J = 3.03 Hz), 2.51-2.53 (2 H, m), 1.02 (3 H, t, J = 7.43 Hz), RT 1.59 min. |
| 438 | 5-ethyl-6-(1-(4-fluorophenyl)-1H-indol-5-yl)-4-hydroxy-2-oxo-1,2-dihydropyridine-3-carboxylic acid<br>$^1$H NMR (500 MHz, DMSO-d$_6$) δ ppm 13.95 (1 H, br. s), 12.76 (1 H, br. s), 7.80 (1 H, d, J = 1.10 Hz), 7.78 (1 H, d, J = 3.30 Hz), 7.65-7.70 (2 H, m), 7.62 (1 H, d, J = 8.53 Hz), 7.46 (2 H, t, J = 8.80 Hz), 7.28 (1 H, dd, J = 8.67, 1.79 Hz), 6.83 (1 H, dd, J = 3.30, 0.83 Hz), 2.51-2.53 (2 H, m), 1.02 (3 H, t, J = 7.43 Hz), RT 1.51 min. |
| 439 | 5-ethyl-4-hydroxy-2-oxo-6-(1-(3-(pyrrolidin-1-yl)phenyl)-1H-indol-5-yl)-1,2-dihydropyridine-3-carboxylic acid<br>$^1$H NMR (500 MHz, DMSO-d$_6$) δ ppm 16.18-16.43 (1 H, m), 13.76-14.01 (1 H, m), 12.48-12.95 (1 H, m), 7.70-7.81 (2 H, m), 7.24-7.39 (2 H, m), 7.12-7.19 (1 H, m), 6.22-6.82 (4 H, m), 3.22-3.34 (3 H, m), 2.51-2.53 (1 H, m), 1.89-2.02 (3 H, m), 1.00-1.07 (3 H, m), RT 1.58 min. |
| 440 | 5-ethyl-4-hydroxy-2-oxo-6-(1-(4-(pyrrolidin-1-yl)phenyl)-1H-indol-5-yl)-1,2-dihydropyridine-3-carboxylic acid<br>$^1$H NMR (500 MHz, CHLOROFORM-d) δ ppm 14.84-15.03 (1 H, m), 13.82-13.95 (1 H, m), 8.73-8.95 (1 H, m), 7.73 (1 H, dd, J = 1.89, 0.63 Hz), 7.54 (1 H, d, J = 8.51 Hz), 7.41 (1 H, d, J = 3.15 Hz), 7.33 (2 H, d, J = 9.14 Hz), 7.18 (1 H, dd, J = 8.51, 1.89 Hz), 6.72 (1 H, dd, J = 3.15, 0.95 Hz), 6.70 (2 H, d, J = 8.83 Hz), 3.34-3.41 (4 H, m), 2.56 (2 H, q, J = 7.25 Hz), 2.05-2.12 (4 H, m), 1.16 (3 H, t, J = 7.41 Hz), RT 1.58 min. |

Example 441

6-(2-((Dimethylamino)methyl)-1H-indol-6-yl)-5-ethyl-4-hydroxy-2-oxo-1,2-dihydropyridine-3-carboxylic acid hydrochloride

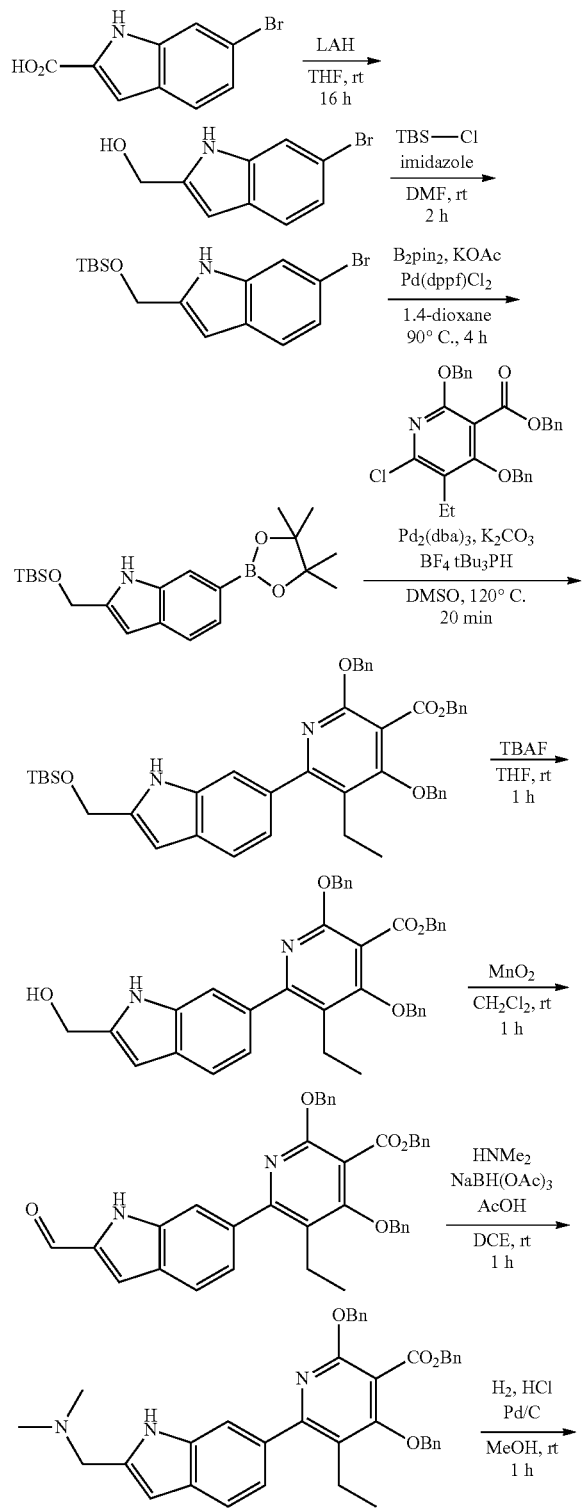

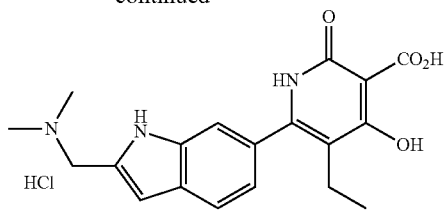

Step 1: Preparation of (6-bromo-1H-indol-2-yl)methanol

6-Bromo-1H-indole-2-carboxylic acid (2.4 g, 10 mmol) was dissolved in THF (20 mL) and cooled to 0° C. Lithium aluminum hydride (20 mmol, 1 M in THF) was added to the solution via syringe. The mixture was stirred overnight at room temperature. The excess reagent was quenched with the slow addition of aqueous KOH (10 mL, 1 M). The mixture was stirred vigorously for 30 min. The mixture was filtered through Celite. The filtrate was concentrated and chromatographed (0-20% EtOAc in $CH_2Cl_2$) to afford the product as a yellow powder (1.87 g, 83%). LC-MS 224.1, 226.1 $[M+H]^+$, RT 1.03 min.

Step 2: Preparation of 6-bromo-2-(((tert-butyldimethylsilyl)oxy)methyl)-1H-indole The product from Step 1 (1.87 g, 8.3 mmol) was combined with t-butyldimethylsilyl chloride (1.38 g, 9.1 mmol) and imidazole (734 mg, 10.8 mmol) in DMF (15 mL). The mixture was stirred 2 h at room temperature. The solvents were removed by rotary evaporation under reduced pressure. The resulting residue was partitioned in EtOAc and saturated aqueous ammonium chloride. The organic layer was washed with brine, dried over $Na_2SO_4$, concentrated and chromatographed on silica gel (0-15% EtOAC in hexanes) to give the product (2.7 g, 96%). LC-MS 340.2, 342.2 $[M+H]^+$, RT 1.62 min.

Step 3: Preparation of 2-(((tert-butyldimethylsilyl)oxy)methyl)-6-(4,4,5,5-tetramethyl-1,3,2-dioxaborolan-2-yl)-1H-indole The title compound was prepared from the product of Step 2 (2.7 g, 7.9 mmol), according to Example 412, Step 2 (2.0 g, 65%).

$^1$H NMR (500 MHz, $CHCl_3$-d) δ ppm 0.06 (s, 6H), 0.88 (s, 9H), 1.30 (s, 12H), 4.81 (s, 2H), 6.32 (s, 1H), 7.26 (d, J=7.9 Hz, 1H), 7.45 (d, J=7.9 Hz, 1H), 7.71 (s, 1H), 11.12 (s, 1H). LC-MS 388.4 $[M+H]^+$, RT 1.65 min.

Step 4: Preparation of benzyl 2,4-bis(benzyloxy)-6-(2-(((tert-butyldimethylsilyl)oxy)methyl)-1H-indol-6-yl)-5-ethylnicotinate The title compound was prepared from the product of Step 3 (388 mg, 1 mmol), according to Example 412, Step 3 (450 mg, 63%).

LC-MS 713.6 $[M+H]^+$, RT 2.05 min.

Step 5: Preparation of benzyl benzyl 2,4-bis(benzyloxy)-5-ethyl-6-(2-(hydroxymethyl)-1H-indol-6-yl)nicotinate The product from Step 4 (714 mg, 1.0 mmol) was dissolved in THF (5 mL). Tetrabutylammonium fluoride (2.0 mmol, 1 M in THF) was added to the solution. The solution was stirred at room temperature for 1 h. The mixture was partitioned in EtOAC (50 mL) and saturated aqueous NaHCO$_3$ (50 mL). The organic layer was washed with brine, dried over Na$_2$SO$_4$, concentrated and chromatographed on silica gel (0-60% EtOAC in hexanes) to give the product (520 mg, 86%).
LC-MS 599.2 [M+H]$^+$, RT 1.67 min

Step 6: Preparation of benzyl 2,4-bis(benzyloxy)-5-ethyl-6-(2-formyl-1H-indol-6-yl)nicotinate The product from Step 5 (520 mg, 0.86 mmol) was dissolved in CH$_2$Cl$_2$ (10 mL).
Manganese(IV) oxide (1.48 g, 17.2 mmol) was added to the mixture. The mixture was stirred 1 h at room temperature. The mixture was filtered, concentrated and chromatographed on silica gel (0-40% EtOAC in hexanes) to provide the title compound (330 mg, 63%).

$^1$H NMR (500 MHz, CHCl$_3$-d) δ ppm 1.00 (t, J=7.4 Hz, 3H), 2.53 (q, J=7.4 Hz, 2H), 5.08 (s, 2H), 5.37 (s, 2H), 5.60 (s, 2H), 7.26-7.45 (17H), 7.52 (s, 1H), 7.82 (d, J=8.5 Hz, 1H), 9.31 (br s, 1H), 10.07 (s, 1H). LC-MS 597.5 [M+H]$^+$, RT 1.74 min.

Step 7: Preparation of benzyl 2,4-bis(benzyloxy)-6-(2-((dimethylamino)methyl)-1H-indol-6-yl)-5-ethylnicotinate The product from Step 6 (40 mg, 0.067 mmol) was combined with dimethylamine (0.13 mmol, 2 M in THF) and AcOH (7.5 μL, 0.13 mmol) in 1,2-dichloroethane (1 mL). The mixture was stirred at room temperature for 30 min. Sodium triacetyoxyborohydride (28 mg, 0.13 mmol) was added to the solution. The mixture stirred 30 min at room temperature, and then was partitioned between CH$_2$Cl$_2$ (4 mL) and aqueous 1 M K$_2$CO$_3$ (4 mL). The organic layer was loaded onto silica gel and eluted with 0-10% MeOH in CH$_2$Cl$_2$ to afford the title compound (36 mg, 86%). LC-MS 626.6 [M+H]$^+$, RT 1.26 min.

Step 8: Preparation of 6-(2-((dimethylamino)methyl)-1H-indol-6-yl)-5-ethyl-4-hydroxy-2-oxo-1,2-dihydropyridine-3-carboxylic acid hydrochloride The product from Step 7 (36 mg, 0.058 mmol) was dissolved in MeOH (3 mL) with 3 drops of 3 N HCl in MeOH. 10% Pd/C was added to the mixture. The mixture stirred under H$_2$ (1 atm) for 1 h. The mixture was filtered over a 5 μm frit. The filtrate was concentrated to provide the title compound as a tan powder (18 mg, 87%).

$^1$H NMR (500 MHz, CHCl$_3$-d) δ ppm 1.03 (t, J=7.4 Hz, 3H), 2.35 (q, J=7.3 Hz, 2H), 2.78 (s, 6H), 4.47 (s, 2H), 6.79 (s, 1H), 7.14 (d, J=8.2 Hz, 1H), 7.61 (s, 1H), 7.75 (d, J=8.2 Hz, 1H), 10.52 (br s, 1H), 11.72 (s, 1H), 12.78 (br s, 1H), 13.93 (s, 1H), 16.35 (br s, 1H). LC-MS 356.3 [M+H]$^+$, RT 0.86 min.

Using the procedures described above, additional compounds described herein may be prepared by substituting the appropriate starting materials, reagents and reaction conditions and include compounds selected from:

| Cpd | Name |
|---|---|
| 442 | 5-ethyl-6-(2-((ethylamino)methyl)-1H-indol-6-yl)-4-hydroxy-2-oxo-1,2-dihydropyridine-3-carboxylic acid hydrochloride<br>$^1$H NMR (500 MHz, CHCl$_3$-d) δ ppm 1.03 (t, J = 7.4 Hz, 3H), 1.25 (t, J = 7.3 Hz, 3H), 2.35 (q, J = 7.3 Hz, 2H), 3.02 (q, J = 7.3 Hz, 2H), 4.35 (s, 2H), 6.73 (s, 1H), 7.12 (d, J = 8.1 Hz, 1H), 7.58 (s, 1 H), 7.72 (d, J = 8.2 Hz, 1H), 9.27 (br s, 2H), 11.64 (s, 1H), 12.78 (br s, 1H), 13.97 (br s, 1H), 16.35 (br s, 1H). LC-MS 356.3 [M + H]$^+$, RT 0.85 min. |
| 443 | 6-(2-((sec-butylamino)methyl)-1H-indol-6-yl)-5-ethyl-4-hydroxy-2-oxo-1,2-dihydropyridine-3-carboxylic acid hydrochloride<br>$^1$H NMR (500 MHz, CHCl$_3$-d) δ ppm 0.93 (t, J = 7.5 Hz, 3H), 1.01 (t, J = 7.4 Hz, 3H), 1.30 (d, J = 6.6 Hz, 3H), 1.55 (m, 1H), 1.88 (m, 1H), 2.35 (q, J = 7.3 Hz, 2H), 3.12 (m, 1H), 4.36 (d, J = 14.1 Hz, 1H), 4.41 (d, J = 14.1 Hz, 1H), 6.76 (s, 1H), 7.12 (d, J = 8.1 Hz, 1H), 7.58 (s, 1 H), 7.73 (d, J = 8.2 Hz, 1H), 9.31 (br s, 2H), 11.71 (s, 1H), 12.78 (br s, 1H), 13.97 (br s, 1H), 16.35 (br s, 1H). LC-MS 384.4 [M + H]$^+$, RT 0.91 min. |
| 444 | 6-(2-((ethylamino)methyl)-1H-indol-6-yl)-4-hydroxy-5-methyl-2-oxo-1,2-dihydropyridine-3-carboxylic acid hydrochloride<br>$^1$H NMR (500 MHz, CHCl$_3$-d) δ ppm 1.25 (t, J = 7.3 Hz, 3H), 1.94 (s, 3H), 3.02 (q, J = 7.3 Hz, 2H), 4.35 (s, 2H), 6.72 (s, 1H), 7.15 (d, J = 8.1 Hz, 1H), 7.60 s, 1 H), 7.71 (d, J = 8.2 Hz, 1H), 9.22 (br s, 2H), 11.64 (s, 1H), 12.79 (br s, 1H), 13.93 (br s, 1H), 16.32 (br s, 1H). LC-MS 342.3 [M + H]$^+$, RT 0.81 min. |

Example 445

5-ethyl-4-hydroxy-2-oxo-6-(2,3,4,9-tetrahydro-1H-pyrido[3,4-b]indol-7-yl)-1,2-dihydropyridine-3-carboxylic acid

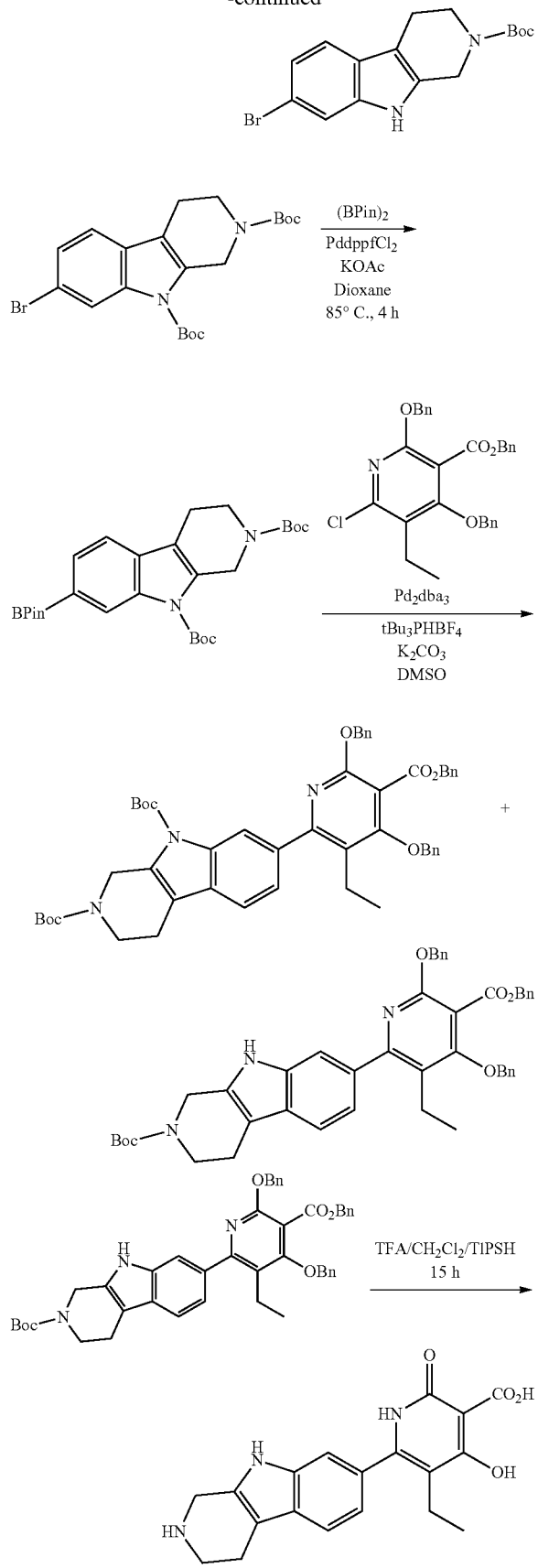

Step 1: di-tert-butyl 7-bromo-3,4-dihydro-1H-pyrido[3,4-b]indole-2,9-dicarboxylate To a solution of crude 7-bromo-2,3,4,9-tetrahydro-1H-pyrido[3,4-b]indole (<15.6 mmol), prepared from 6-bromo-indole according to the procedure in *Tetrahedron*, 1999, 935, in THF (20 mL) and $CH_2Cl_2$ (40 mL) was added di-tert-butyl dicarbonate (3.40 g, 15.6 mmol) and DMAP (95 mg, 0.78 mmol) at room temperature. After 7 h, the mixture was concentrated and chromatographed (0-20% EtOAc in hexanes) to give the title compound (1.663 g, 23.7% from 6-bromo-indole), LC-MS no ionization, RT 1.11 min, and tert-butyl 7-bromo-3,4-dihydro-1H-pyrido[3,4-b]indole-2(9H)-carboxylate (0.42 g, 7.7%) as white foams. LC-MS 295.1 $[M+H]^+$, 297.1 $[M+2+H]^+$, RT 0.90 min.

Step 2-3: di-tert-butyl 7-(4,6-bis(benzyloxy)-5-(benzyloxycarbonyl)-3-ethylpyridin-2-yl)-3,4-dihydro-1H-pyrido[3,4-b]indole-2,9-dicarboxylate and tert-butyl 7-(4,6-bis(benzyloxy)-5-(benzyloxycarbonyl)-3-ethylpyridin-2-yl)-3,4-dihydro-1H-pyrido[3,4-b]indole-2(9H)-carboxylate The title compounds, di-tert-butyl 7-(4,6-bis(benzyloxy)-5-(benzyloxycarbonyl)-3-ethylpyridin-2-yl)-3,4-dihydro-1H-pyrido[3,4-b]indole-2,9-dicarboxylate (231 mg, 0.28 mmol) and tert-butyl 7-(4,6-bis(benzyloxy)-5-(benzyloxycarbonyl)-3-ethylpyridin-2-yl)-3,4-dihydro-1H-pyrido[3,4-b]indole-2(9H)-carboxylate (130 mg, 0.18 mmol) were prepared according to the procedures in Example 412, Steps 2-3 from di-tert-butyl 7-bromo-3,4-dihydro-1H-pyrido[3,4-b]indole-2,9-dicarboxylate (244 mg, 0.5 mmol) over 2 steps in 48% and 31% yield respectively. Di-tert-butyl 7-(4,6-bis(benzyloxy)-5-(benzyloxycarbonyl)-3-ethylpyridin-2-yl)-3,4-dihydro-1H-pyrido[3,4-b]indole-2,9-dicarboxylate: LC-MS no ionization, RT 1.88 min. tert-Butyl 7-(4,6-bis(benzyloxy)-5-(benzyloxycarbonyl)-3-ethylpyridin-2-yl)-3,4-dihydro-1H-pyrido[3,4-b]indole-2(9H)-carboxylate:

$^1$H NMR (500 MHz, DMSO-$d_6$) δ ppm 0.93 (3H, t, J=7.41 Hz), 1.44 (9H, s), 2.54-2.60 (2H, m), 2.70-2.75 (2H, m), 3.69 (2H, t, J=5.52 Hz), 4.59 (2H, br. s), 5.02 (2H, s), 5.37 (2H, s), 5.38 (2H, s), 7.09 (1H, dd, J=8.04, 1.42 Hz), 7.38 (13H, m, J=12.60 Hz), 7.46 (1H, d, J=7.88 Hz). LC-MS 724.7 $[M+H]^+$, RT 1.74 min.

Step 4: 5-ethyl-4-hydroxy-2-oxo-6-(2,3,4,9-tetrahydro-1H-pyrido[3,4-b]indol-7-yl)-1,2-dihydropyridine-3-carboxylic acid A mixture of tert-butyl 7-(4,6-bis(benzyloxy)-5-(benzyloxycarbonyl)-3-ethylpyridin-2-yl)-3,4-dihydro-1H-pyrido[3,4-b]indole-2(9H)-carboxylate (20 mg, 0.027 mmol) in TFA (0.2 mL) and TIPSH (0.2 mL) was stirred at room temperature for 15 h. The solvents were removed and the residue was stirred in 10% MeOH in $CH_2Cl_2$ (0.5 mL). The resulting solid was collected by filtration and washed with $CH_2Cl_2$ to give the title compound as an off-white solid (10 mg, TFA salt, 78%).

$^1$H NMR (500 MHz, DMSO-$d_6$) δ ppm 1.00 (3H, t, J=7.41 Hz), 2.33 (2H, q, J=7.57 Hz), 2.93-3.04 (2H, m), 3.44-3.55 (2H, m), 7.11 (1H, dd, J=8.20, 1.58 Hz), 7.52 (1H, d, J=0.95 Hz), 7.61 (1H, d, J=8.20 Hz), 9.11 (2H, br. s), 11.38 (1H, br.

s), 12.78 (1H, br. s), 13.91 (1H, br. s), 16.33 (1H, br. s). LC-MS 354.3 [M+H]+, RT 0.83 min.

Example 446

5-ethyl-4-(hydroxy)-6-(2-methyl-2,3,4,9-tetrahydro-1H-pyrido[3,4-b]indol-7-yl)-2-oxo-1,2-dihydropyridine-3-carboxylic acid

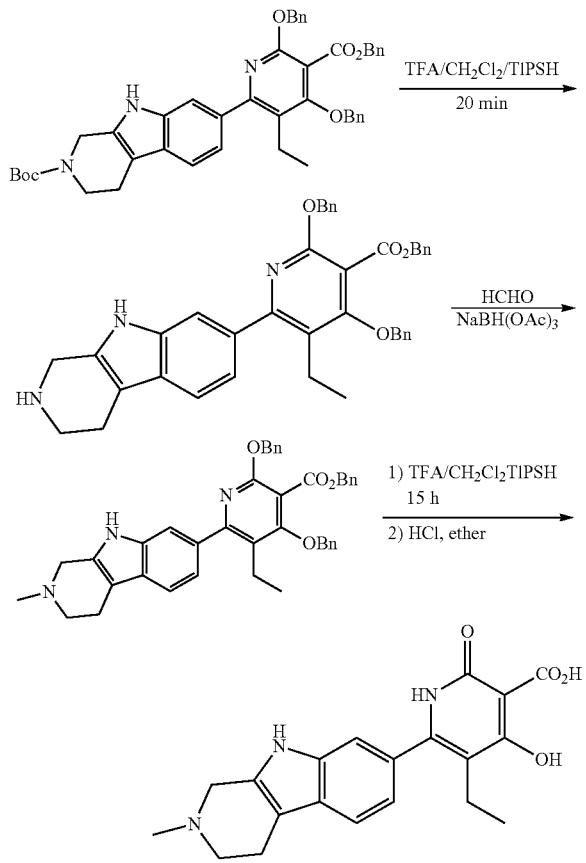

Step 1: benzyl 2,4-bis(benzyloxy)-5-ethyl-6-(2,3,4,9-tetrahydro-1H-pyrido[3,4-b]indol-7-yl)nicotinate To a solution of tert-butyl 7-(4,6-bis(benzyloxy)-5-(benzyloxycarbonyl)-3-ethylpyridin-2-yl)-3,4-dihydro-1H-pyrido[3,4-b]indole-2(9H)-carboxylate (130 mg, 0.18 mmol) in $CH_2Cl_2$ (0.3 mL) and TIPSH (0.3 mL) was added TFA (0.3 mL). The mixture was stirred at room temperature for 20 min. The solvents were removed and the residue was treated with 2N $NH_3$ in MeOH (0.5 mL). The mixture was concentrated and chromatographed (0-5% 2N $NH_3$ in MeOH/$CH_2Cl_2$) to give the title compound (111 mg, 99%) as a white solid.

$^1$H NMR (500 MHz, DMSO-$d_6$) δ ppm 0.93 (3H, t, J=7.41 Hz), 1.07 (9H, s), 2.51-2.53 (2H, m), 2.53-2.60 (2H, m), 2.83-2.90 (2H, m), 4.24 (2H, br. s), 5.02 (2H, s), 5.37 (2H, s), 5.38 (2H, s), 7.11 (1H, m, J=1.26 Hz), 7.27-7.45 (13H, m), 7.51 (1H, d, J=8.20 Hz), 11.08 (1H, br. s). LC-MS 624.6 [M+H]+, RT 1.24 min.

Step 2: benzyl 2,4-bis(benzyloxy)-5-ethyl-6-(2-methyl-2,3,4,9-tetrahydro-1H-pyrido[3,4-b]indol-7-yl)nicotinate The title compound (19 mg, 0.030 mmol) was prepared according to the procedures in Example 417, Step 1 from the intermediate in Step 1 (44 mg, 0.07 mmol) as an off-white solid in 43% yield. LC-MS 638.6 [M+H]+, RT 1.26 min.

Step 3: 5-ethyl-4-(hydroxy)-6-(2-methyl-2,3,4,9-tetrahydro-1H-pyrido[3,4-b]indol-7-yl)-2-oxo-1,2-dihydropyridine-3-carboxylic acid The intermediate from Step 2 (19 mg, 0.030 mmol) was stirred in TFA (0.2 mL), $CH_2Cl_2$ (0.2 mL) and TIPSH (0.2 mL) at room temperature for 15 h. The solvents were removed and the residue was dissolved in $CH_2Cl_2$ (0.5 mL), then HCl (2.0M in $Et_2O$, 1.0 mL) was added. The precipitate was collected by filtration and washed by ether to afford the title compound as an off-white solid (12 mg, 0.030 mmol, HCl salt) in 100% yield.

$^1$H NMR (500 MHz, DMSO-$d_6$) δ ppm 0.99 (3H, t, J=7.41 Hz), 2.29-2.34 (2H, m), 3.01 (3H, br. s.), 3.03-3.09 (1H, m), 3.36-3.41 (2H, m), 3.71-3.83 (1H, m), 4.34-4.50 (1H, m), 4.56-4.69 (1H, m), 7.11 (1H, dd, J=8.04, 1.42 Hz), 7.51 (1H, d, J=0.95 Hz), 7.62 (1H, d, J=8.20 Hz), 10.33-10.48 (1H, m), 11.38-11.48 (1H, m), 12.74-12.84 (1H, m), 13.83-13.95 (1H, m), 16.24-16.39 (1H, m). LC-MS 368.1 [M+H]+, RT 0.91 min.

Using the procedures described above, additional compounds described herein may be prepared by substituting the appropriate starting materials, reagents and reaction conditions and include compounds selected from:

| Cpd | Name |
|---|---|
| 447 | 5-ethyl-6-(2-ethyl-2,3,4,9-tetrahydro-1H-pyrido[3,4-b]indol-7-yl)-4-hydroxy-2-oxo-1,2-dihydropyridine-3-carboxylic acid<br>$^1$H NMR (500 MHz, DMSO-$d_6$) δ ppm 1.00 (3 H, t, J = 7.41 Hz), 1.37 (3 H, t, J = 7.25 Hz), 2.33 (2 H, m, J = 7.60 Hz), 2.99-3.14 (2 H, m), 3.31-3.40 (3 H, m), 3.76-3.84 (1 H, m), 4.39-4.47 (1 H, m), 4.55-4.63 (1 H, m), 7.11 (1 H, dd, J = 8.20, 1.58 Hz), 7.52 (1 H, d, J = 0.95 Hz), 7.62 (1 H, d, J = 8.20 Hz), 10.74 (1 H, br. s), 11.45 (1 H, s), 12.79 (1 H, br. s), 13.90 (1 H, s), 16.34 (1 H, br. s). LC-MS 382.1 [M + H]+, RT 0.94 min. |
| 448 | 5-ethyl-4-hydroxy-2-oxo-6-(2-propyl-2,3,4,9-tetrahydro-1H-pyrido[3,4-b]indol-7-yl)-1,2-dihydropyridine-3-carboxylic acid<br>$^1$H NMR (500 MHz, DMSO-$d_6$) δ ppm 0.96 (3 H, t, J = 7.41 Hz), 1.00 (3 H, t, J = 7.25 Hz), 1.77-1.89 (2 H, m), 2.33 (2 H, m, J = 7.30 Hz), 2.99-3.15 (2 H, m), 3.20-3.28 (2 H, m), 3.38-3.45 (1 H, m), 3.70 (1 H, m), 4.39-4.49 (1 H, m), 4.56-4.64 (1 H, m), 7.11 (1 H, dd, J = 8.20, 1.60 Hz), 7.52 (1 H, d, J = 0.95 Hz), 7.62 (1 H, d, J = 8.20 Hz), 10.72 (1 H, br. s), 11.44 (1 H, s), 12.78 (1 H, br. s), 13.90 (1 H, br. s), 16.34 (1 H, br. s). LC-MS 396.1 [M + H]+, RT 0.96 min. |

| Cpd | Name |
|---|---|
| 449 | 5-ethyl-4-hydroxy-6-(2-isopropyl-2,3,4,9-tetrahydro-1H-pyrido[3,4-b]indol-7-yl)-2-oxo-1,2-dihydropyridine-3-carboxylic acid
$^1$H NMR (500 MHz, DMSO-d$_6$) δ ppm 1.00 (3 H, t, J = 7.41 Hz), 1.40 (6 H, d, J = 6.62, Hz), 2.33 (2 H, m, J = 7.30 Hz), 2.98-3.16 (2 H, m), 3.29-3.38 (1 H, m), 3.70-3.85 (2 H, m), 4.36-4.46 (1 H, m), 4.51-4.62 (1 H, m), 7.11 (1 H, dd, J = 8.20, 1.58 Hz), 7.52 (1 H, d, J = 0.63 Hz), 7.63 (1 H, d, J = 8.20 Hz), 10.51 (1 H, br. s), 11.45 (1 H, s), 12.77 (1 H, br. s), 16.32 (1 H, br. s), 13.90 (1 H, s). LC-MS 396.1 [M + H]$^+$, RT 0.95 min. |

Example 450

5-ethyl-4-hydroxy-2-oxo-6-(2,3,4,5-tetrahydro-1H-pyrido[4,3-b]indol-7-yl)-1,2-dihydropyridine-3-carboxylic acid

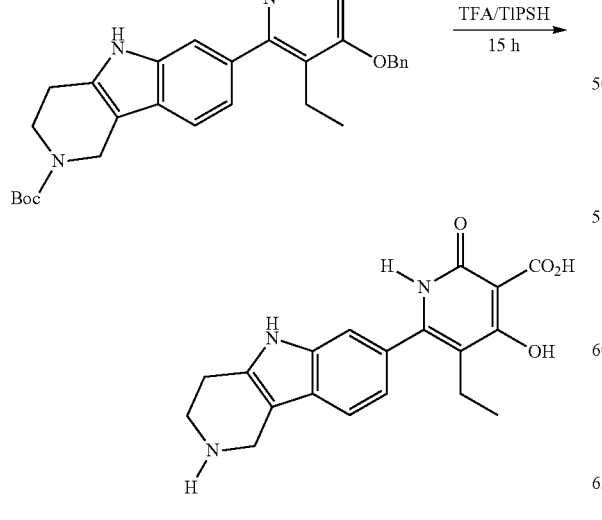

Steps 1-2: tert-butyl 7-(4,6-bis(benzyloxy)-5-(benzyloxycarbonyl)-3-ethylpyridin-2-yl)-3,4-dihydro-1H-pyrido[4,3-b]indole-2(5H)-carboxylate The title compound (188 mg, 0.26 mmol) was prepared according the procedure described in Example 412, Steps 2-3 from tert-butyl 7-bromo-3,4-dihydro-1H-pyrido[4,3-b]indole-2(5H)-carboxylate, which was prepared by following the procedure in WO2009089482, as a light yellow solid in 39% yield over 2 steps.

$^1$H NMR (500 MHz, DMSO-d$_6$) δ ppm 0.93 (3H, t, J=7.25 Hz), 1.07 (9H, s), 2.54-2.60 (2H, m), 2.78-2.85 (2H, m), 3.69-3.75 (2H, m), 4.57 (2H, br. s), 5.02 (2H, s), 5.36 (2H, s), 5.38 (2H, s), 7.05-7.11 (1H, m), 7.28-7.43 (13H, m), 7.44-7.49 (1H, m), 11.09 (1H, br. s). LC-MS 724.4 [M+H]$^+$, RT 1.86 min.

Step 3: 5-ethyl-4-hydroxy-2-oxo-6-(2,3,4,5-tetrahydro-1H-pyrido[4,3-b]indol-7-yl)-1,2-dihydropyridine-3-carboxylic acid The title compound (14 mg, 0.030 mmol, TFA salt) was prepared according the procedure in Example 445, Step 4 from the intermediate in Step 2 (30 mg, 0.041 mmol) as an off-white solid in 73% yield.

$^1$H NMR (500 MHz, DMSO-d$_6$) δ ppm 1.00 (3H, t, J=7.41 Hz), 2.28-2.35 (2H, m), 3.02-3.10 (2H, m), 3.47-3.56 (2H, m), 4.33-4.41 (2H, m), 7.10 (1H, dd, J=8.20, 1.58 Hz), 7.48 (1H, d, J=0.63 Hz), 7.60 (1H, d, J=8.20 Hz), 8.94-9.15 (2H, m), 11.50 (1H, s), 12.79 (1H, br. s), 13.90 (1H, br. s), 16.34 (1H, br. s). LC-MS 354.3 [M+H]$^+$, RT 0.78 min.

Example 451

5-ethyl-4-hydroxy-6-(2-methyl-2,3,4,5-tetrahydro-1H-pyrido[4,3-b]indol-7-yl)-2-oxo-1,2-dihydropyridine-3-carboxylic acid

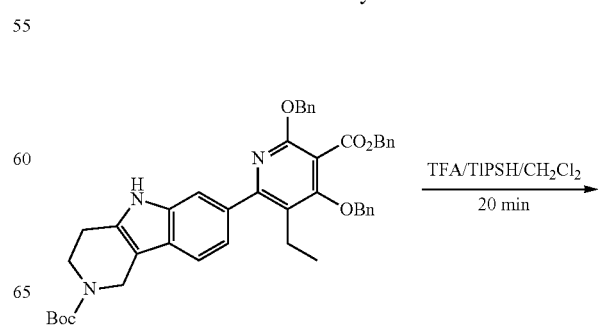

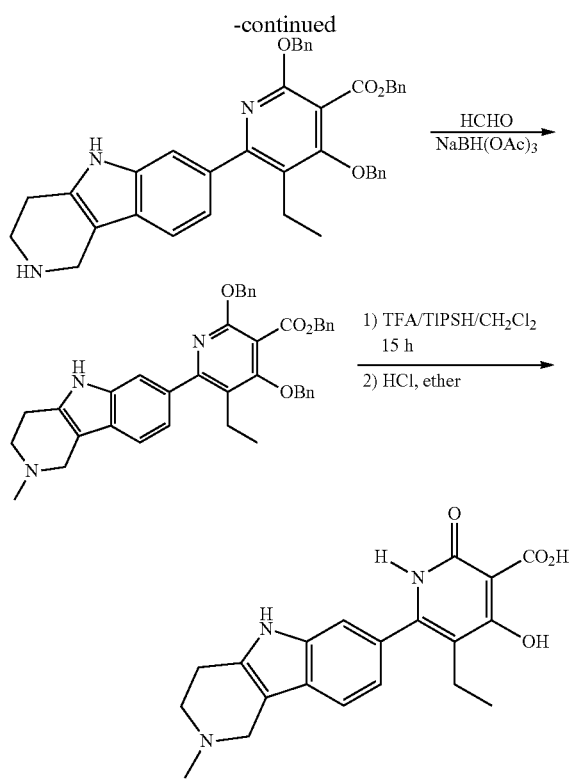

tert-butyl 7-(4,6-bis(benzyloxy)-5-(benzyloxycarbonyl)-3-ethylpyridin-2-yl)-3,4-dihydro-1H-pyrido[4,3-b]indole-2(5H)-carboxylate as an off-white solid.

$^1$H NMR (500 MHz, DMSO-$d_6$) δ ppm 1.00 (3H, t, J=7.41 Hz), 2.30-2.35 (1H, m), 3.01 (3H, s), 3.07-3.23 (2H, m), 3.43-3.56 (1H, m), 3.72-3.81 (1H, m), 4.25-4.37 (1H, m), 4.58-4.73 (1H, m), 7.11 (1H, dd, J=8.20, 1.58 Hz), 7.49 (1H, d, J=0.95 Hz), 7.57 (1H, d, J=8.20 Hz), 10.29 (1H, br. s), 11.56 (1H, br. s), 12.78 (1H, br. s), 13.89 (1H, br. s), 16.32 (1H, br. s). LC-MS 382.3 [M+H]$^+$, RT 0.82 min.

Using the procedures described above, additional compounds described herein may be prepared by substituting the appropriate starting materials, reagents and reaction conditions and include compounds selected from:

| Cpd | Name |
| --- | --- |
| 452 | 5-ethyl-6-(2-ethyl-2,3,4,5-tetrahydro-1H-pyrido[4,3-b]indol-7-yl)-4-hydroxy-2-oxo-1,2-dihydropyridine-3-carboxylic acid<br>$^1$H NMR (500 MHz, DMSO-$d_6$) δ ppm 1.00 (3 H, t, J = 7.41 Hz), 1.38 (3 H, t, J = 7.25 Hz), 2.29-2.36 (2 H, m), 3.06-3.17 (1 H, m), 3.17-3.28 (1 H, m), 3.28-3.35 (2 H, m), 3.42-3.53 (1 H, m), 3.73-3.85 (1 H, m), 4.22-4.35 (1 H, m), 4.61-4.75 (1 H, m), 7.11 (1 H, dd, J = 8.20, 1.58 Hz), 7.49 (1 H, d, J = 0.95 Hz), 7.61 (1 H, d, J = 7.88 Hz), 10.26 (1 H, br. s), 11.56 (1 H, br. s), 12.78 (1 H, br. s), 13.90 (1 H, br. s), 16.32 (1 H, br. s). LC-MS 382.3 [M + H]$^+$, RT 0.83 min. |

Example 453

6-(2-(4-cyanophenyl)-1H-indol-5-yl)-5-ethyl-4-hydroxy-2-oxo-1,2-dihydropyridine-3-carboxylic acid The title compound (14 mg, 0.033 mmol) was prepared according to the procedures in Example 446, Steps 1-3 from

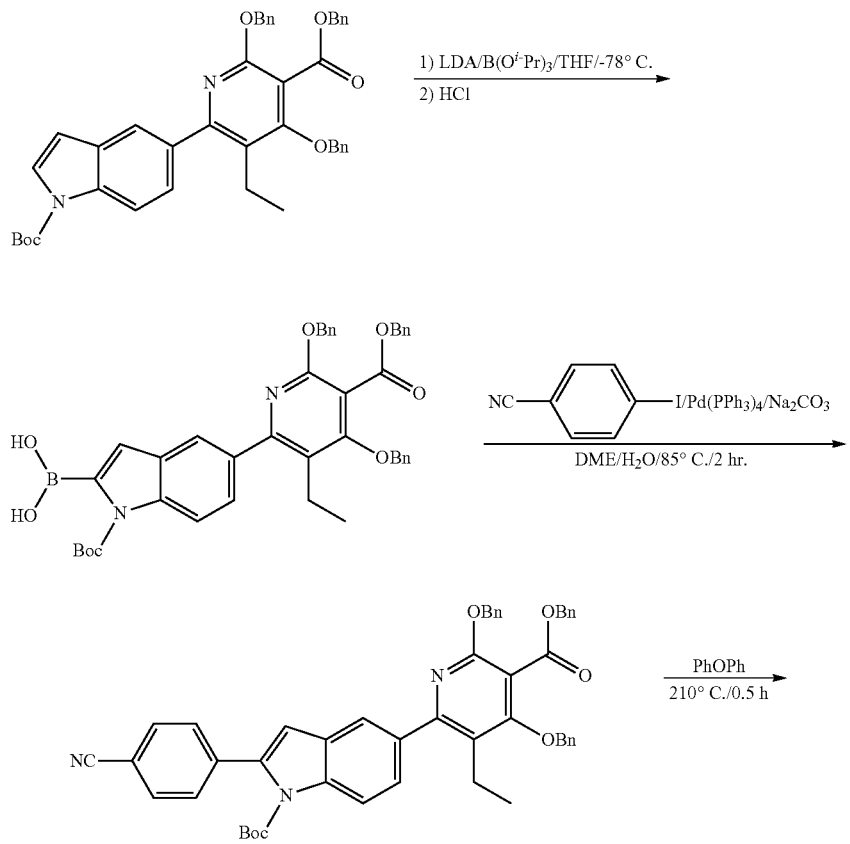

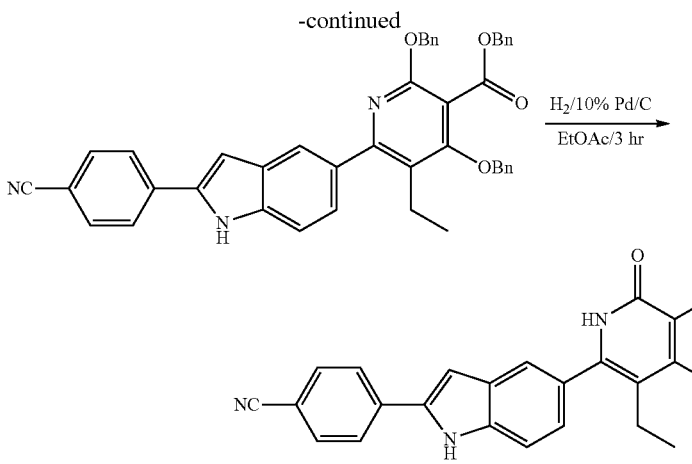

Step 1: (5-(4,6-bis(benzyloxy)-5-((benzyloxy)carbonyl)-3-ethylpyridin-2-yl)-1-(tert-butoxycarbonyl)-1H-indol-2-yl)boronic acid To a solution of tert-butyl 5-(4,6-bis(benzyloxy)-5-((benzyloxy)carbonyl)-3-ethylpyridin-2-yl)-1H-indole-1-carboxylate, prepared according to the protocol described in Example 412, step 3 (3.07 g, 4.59 mmol), triisopropylborate (1.17 mL, 5.51 mmol) in THF (15 mL), at −78° C. was added while stirring, LDA (3.67 mL, 1.5 M in cyclohexane, 5.51 mmol). The mixture was stirred for 0.5 h after the addition and the cooling bath was removed to allow the reaction mixture to warm to room temperature and stirred for an additional 0.5 h. The reaction was quenched with 6 N HCl at 0° C. and acidified to pH 4 and the mixture was diluted with DCM and water. The organic layer was separated, washed with water, brine and dried over anhydrous $Na_2SO_4$. The filtrate was concentrated and chromatographed (ethyl acetate in DCM, 0-40%) to give the boronic acid intermediate as light yellow powder (0.78 g) in 24% yield.
LC-MS 713.3 [M+H]$^+$, RT 1.74 min.

Step 2: tert-butyl 5-(4,6-bis(benzyloxy)-5-((benzyloxy)carbonyl)-3-ethylpyridin-2-yl)-2-(4-cyanophenyl)-1H-indole-1-carboxylate A mixture of the boronic acid obtained in Step 1 (75 mg, 0.10 mmol), 4-cyanoiodobenzene (24 mg, 0.10 mmol) Pd(PPh$_3$)$_4$ (12 mg, 0.01 mmol), Na$_2$CO$_3$ (33 mg, 0.30 mmol), DME (0.9 mL) and H$_2$O (0.1 mL) was stirred under argon at 85° C. for 2 hr. The mixture was then concentrated to dryness and chromatographed (silica gel, ethyl acetate in hexanes 0-15% gradient) to provide tert-butyl 5-(4,6-bis(benzyloxy)-5-((benzyloxy)carbonyl)-3-ethylpyridin-2-yl)-2-(4-cyanophenyl)-1H-indole-1-carboxylate (42 mg, yield: 55%). LC-MS 770.6 [M+H]$^+$, RT 1.16 min. (1 min. Method). This was dissolved in diphenyl ether (1 mL) and heated to 210° C. for 0.5 hr. After cooling the mixture was chromatographed (silica gel, ethyl acetate in hexanes 0-50% gradient) to furnish 6-(2-(4-cyanophenyl)-1H-indol-5-yl)-5-ethyl-4-hydroxy-2-oxo-1,2-dihydropyridine-3-carboxylic acid (29 mg, yield: 80%).
LC-MS 670.5 [M+H]$^+$, RT 1.06 min. (1 min. method).

Step 3: 6-(2-(4-cyanophenyl)-1H-indol-5-yl)-5-ethyl-4-hydroxy-2-oxo-1,2-dihydropyridine-3-carboxylic acid The intermediate obtained in Step 2 (29 mg, 0.04 mmol) was dissolved in ethyl acetate (1.0 mL) and hydrogenated with 10% Pd on charcoal (10 mg) under a H$_2$-filled balloon at room temperature for 3 hr. The catalyst was filtered over Celite and washed with ethyl acetate and dried to provide the title compound as a tan solid (7.5 mg) in 50% yield.
$^1$H NMR (500 MHz, DMSO-d$_6$) δ ppm 16.36 (1H, br. s), 13.94 (1H, br. s), 12.76 (1H, br. s), 12.10 (1H, br. s), 8.10 (2H, d, J=8.83 Hz), 7.95 (2H, d, J=8.51 Hz), 7.73 (1H, s), 7.57 (1H, d, J=8.51 Hz), 7.28 (1H, d, J=1.26 Hz), 7.24 (1H, dd, J=1.60 Hz), 2.51-2.53 (2H, m), 1.02 (3H, t, J=7.41 Hz). LC-MS 400.3 [M+H]$^+$, RT 0.80 min. (1 min. method).

Using the procedures described above, additional compounds described herein may be prepared by substituting the appropriate starting materials, reagents and reaction conditions and include compounds selected from:

| Cpd | Name |
| --- | --- |
| 454 | 5-ethyl-4-hydroxy-2-oxo-6-(2-phenyl-1H-indol-5-yl)-1,2-dihydropyridine-3-carboxylic acid, and<br>$^1$H NMR (500 MHz, CHLOROFORM-d) δ ppm 14.74 (1 H, br. s), 13.82 (1 H, s), 10.19 (1 H, br. s), 8.67 (1 H, br. s), 7.68-7.75 (3 H, m), 7.56 (1 H, d, J = 8.51 Hz), 7.50 (2 H, t, J = 7.72 Hz), 7.40 (1 H, t, J = 7.60 Hz), 7.22 (1 H, dd, J = 8.35, 1.73 Hz), 6.92 (1 H, dd, J = 2.05, 0.79 Hz), 2.58 (2 H, q, J = 7.25 Hz), 1.17 (3 H, t, J = 7.41 Hz), RT 0.80 min. (1 min. method). |
| 455 | 5-ethyl-4-hydroxy-2-oxo-6-(2-(4-(trifluoromethyl)phenyl)-1H-indol-5-yl)-1,2-dihydropyridine-3-carboxylic acid;<br>$^1$H NMR (500 MHz, CHLOROFORM-d) δ ppm 14.73 (1 H, br. s), 13.85 (1 H, s), 10.00 (1 H, br. s), 8.73 (1 H, br. s), 7.70-7.84 (5 H, m), 7.59 (1 H, d, J = 8.20 Hz), 7.52-7.56 (1 H, m), 7.25-7.28 (1 H, m), 7.02 (1 H, d, J = 1.26 Hz), 2.56 (2 H, q, J = 7.25 Hz), 1.16 (3 H, t, J = 7.41 Hz), RT 0.89 min. (1 min. method). |

Biological Examples

The following biological examples demonstrate the usefulness of the compounds described herein for treating bacterial infections.

Example 1

The antibacterial activity from a microbroth dilution method may be presented as the minimum inhibitory concentration (MIC in μg/mL). The MIC value is the lowest concentration of drug which prevents macroscopically visible growth under test conditions.

In the following tables, an MIC value between >12.5 μg/mL and ≤150 μg/mL is indicated by a single star (*), an MIC value between >3.5 μg/mL and ≤12.5 μg/mL is indicated by two stars (), an MIC value between >1.0 μg/mL and ≤3.5 μg/mL is indicated by three stars (*) and an MIC value of ≤1.0 μg/mL is indicated by four stars (****). The term ND indicates that the MIC value was Not Determined.

Antibacterial activity of test compounds against the super sensitive Gram-negative *Escherichia coli* (*E. coli*) BAS849 bacterium, the control Gram-negative *E. coli* 25922 strain and the Gram-positive *Staphylococcus aureus* (*S. aureus*) 29213 bacterium are shown in Table 1.

TABLE 1

| Cpd | BAS849 | 25922 | 29213 |
|---|---|---|---|
| 1 | **** | *** | * |
| 2 | **** | * | ** |
| 3 | **** | *** | * |
| 4 | **** | ** | ** |
| 5 | **** | ** | * |
| 6 | **** | ** | ** |
| 7 | *** | * | * |
| 8 | *** | * | ** |
| 9 | **** | *** | * |
| 10 | **** | ** | *** |
| 11 | **** | *** | * |
| 12 | *** | * | * |
| 13 | ** | * | * |
| 14 | *** | * | ** |
| 15 | *** | * | * |
| 16 | ** | * | *** |
| 17 | ** | * | *** |
| 18 | ** | * | *** |
| 19 | * | * | * |
| 20 | *** | * | * |
| 21 | **** | **** | ** |
| 22 | **** | **** | *** |
| 23 | **** | ** | * |
| 24 | **** | ** | ** |
| 25 | **** | * | * |
| 26 | **** | * | ** |
| 27 | **** | * | ** |
| 28 | * | * | **** |
| 29 | **** | * | * |
| 30 | *** | * | *** |
| 31 | *** | * | * |
| 32 | **** | * | ** |
| 33 | **** | ** | * |
| 34 | **** | ** | *** |
| 35 | **** | *** | * |
| 36 | *** | * | ** |
| 37 | **** | **** | *** |
| 38 | **** | *** | *** |
| 39 | **** | *** | ** |
| 40 | **** | *** | *** |
| 41 | **** | ** | * |
| 42 | **** | ** | * |
| 49 | * | * | * |
| 50 | * | * | * |
| 51 | * | * | * |

TABLE 1-continued

| Cpd | BAS849 | 25922 | 29213 |
|---|---|---|---|
| 52 | * | * | * |
| 53 | ** | * | * |
| 54 | *** | * | * |
| 55 | * | * | * |
| 56 | ** | * | * |
| 57 | * | * | * |
| 58 | ** | * | * |
| 59 | * | * | * |
| 60 | * | * | * |
| 61 | * | * | * |
| 62 | * | * | * |
| 63 | * | * | * |
| 64 | **** | * | * |
| 65 | **** | ** | * |
| 66 | **** | **** | * |
| 67 | **** | *** | * |
| 68 | **** | *** | * |
| 69 | **** | *** | * |
| 70 | ** | * | * |
| 71 | ** | * | * |
| 72 | ** | * | * |
| 73 | * | * | * |
| 74 | * | * | * |
| 75 | * | * | * |
| 76 | * | * | * |
| 77 | ** | * | ** |
| 84 | *** | ** | * |
| 85 | *** | * | * |
| 86 | * | * | * |
| 87 | **** | ** | * |
| 88 | **** | ** | * |
| 89 | * | * | * |
| 90 | * | * | * |
| 91 | * | * | * |
| 92 | * | * | * |
| 93 | * | * | * |
| 94 | * | * | * |
| 95 | * | * | * |
| 96 | * | * | * |
| 97 | **** | *** | * |
| 98 | **** | ** | * |
| 99 | **** | ** | * |
| 100 | **** | ** | * |
| 101 | **** | ** | * |
| 102 | **** | ** | * |
| 103 | **** | * | * |
| 104 | **** | ** | * |
| 105 | **** | ** | * |
| 106 | **** | *** | * |
| 107 | * | * | * |
| 108 | * | * | * |
| 109 | * | * | * |
| 110 | * | * | * |
| 111 | * | * | * |
| 112 | **** | **** | * |
| 113 | **** | **** | * |
| 114 | **** | **** | ** |
| 115 | **** | **** | *** |
| 116 | **** | **** | *** |
| 117 | **** | **** | * |
| 118 | **** | *** | *** |
| 119 | **** | *** | ** |
| 120 | **** | **** | ** |
| 121 | **** | *** | ** |
| 122 | **** | **** | * |
| 123 | **** | **** | * |
| 124 | **** | **** | * |
| 125 | **** | *** | * |
| 126 | ** | * | * |
| 127 | *** | * | * |
| 128 | **** | *** | * |
| 129 | **** | **** | ** |
| 130 | **** | **** | * |
| 131 | **** | *** | *** |
| 132 | **** | **** | * |
| 133 | **** | **** | * |
| 134 | **** | *** | ** |
| 135 | **** | ** | * |

TABLE 1-continued

| Cpd | BAS849 | 25922 | 29213 |
|---|---|---|---|
| 136 | *** | ** | * |
| 137 | **** | *** | * |
| 138 | **** | ** | * |
| 139 | *** | * | * |
| 140 | **** | *** | * |
| 141 | **** | *** | * |
| 142 | ** | * | * |
| 143 | **** | * | ** |
| 144 | **** | ** | * |
| 145 | **** | ** | * |
| 146 | **** | *** | * |
| 147 | **** | **** | * |
| 148 | *** | ** | * |
| 149 | **** | *** | * |
| 150 | **** | *** | * |
| 151 | **** | *** | * |
| 152 | **** | **** | * |
| 153 | **** | ** | * |
| 154 | **** | *** | * |
| 155 | **** | ** | * |
| 156 | ** | * | * |
| 157 | **** | ** | * |
| 158 | **** | *** | * |
| 159 | **** | **** | * |
| 160 | **** | **** | * |
| 161 | **** | **** | * |
| 162 | **** | *** | * |
| 163 | **** | * | * |
| 164 | **** | **** | ** |
| 165 | **** | **** | ** |
| 166 | **** | **** | ** |
| 167 | **** | **** | * |
| 168 | **** | *** | *** |
| 169 | **** | *** | ** |
| 170 | **** | ** | * |
| 171 | **** | *** | * |
| 172 | **** | * | ** |
| 173 | **** | **** | ** |
| 174 | **** | *** | ** |
| 175 | **** | ** | *** |
| 176 | **** | * | *** |
| 177 | **** | *** | ** |
| 178 | **** | **** | ** |
| 179 | **** | *** | ** |
| 180 | **** | *** | * |
| 181 | **** | *** | * |
| 182 | *** | * | * |
| 183 | **** | *** | * |
| 184 | **** | *** | * |
| 185 | **** | *** | * |
| 186 | **** | **** | ** |
| 187 | **** | **** | * |
| 188 | **** | **** | * |
| 189 | **** | *** | ** |
| 190 | **** | * | ** |
| 191 | **** | *** | ** |
| 192 | **** | **** | ** |
| 193 | **** | **** | ** |
| 194 | **** | *** | ** |
| 195 | **** | ** | *** |
| 196 | ** | * | * |
| 197 | **** | *** | ** |
| 198 | *** | * | * |
| 199 | **** | **** | ** |
| 200 | **** | *** | ** |
| 201 | **** | **** | ** |
| 202 | **** | ** | * |
| 203 | **** | **** | ** |
| 204 | *** | ** | * |
| 205 | *** | * | * |
| 206 | **** | ** | ** |
| 207 | *** | * | * |
| 208 | **** | **** | ** |
| 209 | **** | **** | ** |
| 210 | **** | **** | ** |
| 211 | **** | *** | ** |
| 212 | **** | *** | *** |
| 213 | **** | * | *** |
| 214 | **** | **** | *** |
| 215 | **** | *** | *** |
| 216 | **** | *** | *** |
| 217 | **** | *** | *** |
| 218 | **** | * | ** |
| 219 | **** | *** | *** |
| 220 | **** | **** | *** |
| 221 | **** | *** | *** |
| 222 | **** | **** | *** |
| 223 | **** | **** | ** |
| 224 | **** | *** | ** |
| 225 | **** | ** | ** |
| 226 | **** | *** | *** |
| 227 | **** | *** | ** |
| 228 | **** | **** | ** |
| 229 | **** | **** | ** |
| 230 | **** | ** | * |
| 231 | **** | *** | * |
| 232 | **** | **** | ** |
| 233 | **** | *** | * |
| 234 | **** | *** | * |
| 235 | **** | **** | ** |
| 236 | **** | **** | ** |
| 237 | **** | *** | ** |
| 238 | **** | *** | ** |
| 239 | *** | ** | * |
| 240 | **** | **** | ** |
| 241 | **** | **** | ** |
| 242 | **** | *** | *** |
| 243 | **** | **** | ** |
| 244 | *** | * | * |
| 245 | **** | **** | ** |
| 246 | *** | * | * |
| 247 | **** | **** | ** |
| 248 | **** | **** | ** |
| 249 | **** | * | *** |
| 250 | **** | *** | ** |
| 251 | **** | *** | ** |
| 252 | **** | *** | * |
| 253 | **** | *** | * |
| 254 | **** | *** | ** |
| 255 | **** | *** | ** |
| 256 | **** | *** | * |
| 257 | **** | ** | * |
| 258 | **** | * | ** |
| 259 | **** | ** | ** |
| 260 | **** | ** | ** |
| 261 | *** | ** | * |
| 262 | *** | ** | * |
| 263 | ** | * | * |
| 264 | *** | ** | ** |
| 265 | *** | * | *** |
| 266 | **** | * | **** |
| 267 | **** | *** | ** |
| 268 | **** | ** | ** |
| 269 | ** | * | * |
| 270 | **** | ** | ** |
| 271 | **** | **** | * |
| 272 | **** | * | *** |
| 273 | **** | * | ** |
| 274 | **** | *** | ** |
| 275 | **** | **** | ** |
| 276 | **** | *** | ** |
| 277 | **** | **** | *** |
| 278 | **** | *** | ** |
| 279 | **** | *** | ** |
| 280 | **** | * | *** |
| 281 | * | * | * |
| 282 | **** | **** | * |
| 283 | * | * | * |
| 284 | **** | *** | * |
| 285 | **** | *** | * |
| 286 | * | * | * |
| 287 | **** | ** | ** |
| 288 | **** | *** | ** |
| 289 | *** | * | * |
| 290 | **** | **** | ** |
| 291 | **** | **** | ** |

TABLE 1-continued

| Cpd | BAS849 | 25922 | 29213 |
|---|---|---|---|
| 292 | **** | *** | ** |
| 293 | **** | **** | ** |
| 294 | **** | **** | *** |
| 295 | **** | ** | *** |
| 296 | **** | **** | ** |
| 297 | **** | **** | *** |
| 298 | **** | *** | *** |
| 299 | **** | *** | *** |
| 300 | **** | ** | * |
| 301 | **** | * | ** |
| 302 | **** | *** | * |
| 303 | **** | ** | * |
| 304 | **** | **** | * |
| 305 | **** | **** | ** |
| 306 | *** | ** | * |
| 307 | **** | * | *** |
| 308 | **** | * | *** |
| 309 | **** | ** | * |
| 310 | **** | ** | * |
| 311 | **** | *** | * |
| 312 | **** | ** | * |
| 313 | **** | ** | * |
| 314 | **** | ** | * |
| 315 | **** | *** | * |
| 316 | **** | *** | * |
| 317 | **** | *** | * |
| 318 | **** | *** | * |
| 319 | **** | *** | ** |
| 320 | **** | *** | ** |
| 321 | **** | *** | ** |
| 322 | *** | * | * |
| 323 | *** | * | * |
| 324 | *** | * | * |
| 325 | ** | * | * |
| 326 | * | * | * |
| 327 | ** | * | * |
| 328 | ** | * | * |
| 329 | **** | ** | * |
| 330 | **** | ** | * |
| 331 | **** | ** | * |
| 332 | ** | * | * |
| 333 | **** | **** | ** |
| 334 | **** | **** | * |
| 335 | **** | **** | *** |
| 336 | **** | ** | **** |
| 337 | **** | * | *** |
| 338 | *** | * | ** |
| 339 | **** | **** | ** |
| 340 | **** | ** | * |
| 341 | **** | ** | * |
| 342 | **** | *** | * |
| 343 | * | * | * |
| 344 | * | * | * |
| 345 | ** | * | * |
| 346 | **** | * | * |
| 347 | **** | ** | * |
| 348 | **** | ** | * |
| 349 | *** | * | * |
| 350 | ** | * | * |
| 351 | **** | *** | * |
| 352 | **** | ** | * |
| 353 | **** | ** | * |
| 354 | **** | *** | * |
| 355 | **** | ** | * |
| 356 | **** | ** | ** |
| 357 | **** | ** | * |
| 358 | *** | ** | * |
| 359 | ** | * | * |
| 360 | ** | * | *** |
| 361 | *** | * | ** |
| 362 | *** | * | ** |
| 363 | **** | * | *** |
| 364 | *** | * | * |
| 365 | **** | * | ** |
| 366 | **** | ** | * |
| 367 | **** | * | *** |
| 368 | **** | *** | * |
| 369 | **** | *** | * |
| 370 | **** | **** | ** |
| 371 | **** | *** | * |
| 372 | * | * | * |
| 373 | ** | * | *** |
| 374 | * | * | * |
| 375 | **** | * | * |
| 376 | ** | * | * |
| 377 | **** | * | * |
| 378 | ** | * | * |
| 379 | ** | * | * |
| 380 | ** | * | * |
| 381 | **** | * | ** |
| 382 | **** | * | ** |
| 383 | **** | * | ** |
| 384 | **** | * | * |
| 385 | **** | * | ** |
| 386 | ** | * | * |
| 387 | *** | * | * |
| 388 | ** | * | * |
| 389 | ** | * | * |
| 390 | * | * | * |
| 391 | ** | * | * |
| 392 | ** | * | * |
| 393 | **** | ** | * |
| 394 | ** | * | * |
| 395 | * | * | ** |
| 396 | * | * | * |
| 397 | * | * | * |
| 398 | * | * | * |
| 399 | * | * | * |
| 400 | *** | * | * |
| 401 | ** | * | ** |
| 402 | * | * | ** |
| 403 | ** | * | * |
| 404 | ** | * | * |
| 405 | ** | * | ** |
| 406 | *** | * | ** |
| 407 | *** | * | *** |
| 408 | *** | * | *** |
| 409 | *** | * | ** |
| 410 | *** | * | ** |
| 411 | *** | * | ** |
| 412 | *** | ** | * |
| 413 | **** | **** | * |
| 414 | **** | *** | * |
| 415 | *** | ** | * |
| 416 | ** | * | * |
| 417 | *** | * | * |
| 418 | ** | ** | * |
| 419 | **** | ** | ** |
| 420 | **** | ** | ** |
| 421 | *** | ** | * |
| 422 | *** | * | * |
| 423 | **** | **** | *** |
| 424 | ** | * | ** |
| 425 | **** | *** | ** |
| 426 | ** | * | * |
| 427 | * | * | * |
| 428 | **** | * | **** |
| 429 | * | * | * |
| 430 | * | * | * |
| 431 | * | * | * |
| 432 | **** | ** | **** |
| 433 | **** | * | * |
| 434 | * | * | * |
| 435 | **** | * | **** |
| 436 | **** | * | *** |
| 437 | **** | * | ** |
| 438 | **** | * | **** |
| 439 | *** | * | ** |
| 440 | * | * | * |
| 441 | **** | **** | *** |
| 442 | *** | ** | * |
| 443 | *** | ** | ** |
| 444 | * | * | * |
| 445 | ** | * | * |
| 446 | **** | *** | * |
| 447 | **** | **** | * |

TABLE 1-continued

| Cpd | BAS849 | 25922 | 29213 |
|---|---|---|---|
| 448 | **** | **** | * |
| 449 | **** | **** | * |
| 450 | ** | * | * |
| 451 | **** | **** | * |
| 452 | **** | **** | * |
| 453 | **** | * | *** |
| 454 | **** | * | **** |
| 455 | **** | * | ** |

Example 2

Antibacterial activity of test compounds against the quinolone resistant *E. coli* LZ3111 bacterium is shown in Table 2. The *E. coli* LZ3111 strain is genetically engineered and possesses double mutations in both the gyrase A and par C regions of the topoisomerase subunits. Mutations in these regions are known to confer a high level resistance to the quinolone class of antibiotics.

TABLE 2

| Cpd | LZ3111 |
|---|---|
| 1 | * |
| 3 | * |
| 4 | ** |
| 5 | * |
| 6 | * |
| 7 | * |
| 8 | ** |
| 9 | * |
| 10 | * |
| 11 | * |
| 12 | * |
| 14 | * |
| 18 | * |
| 20 | ** |
| 21 | * |
| 22 | *** |
| 23 | * |
| 24 | * |
| 28 | * |
| 30 | * |
| 31 | * |
| 32 | *** |
| 33 | * |
| 35 | * |
| 36 | ** |
| 37 | * |
| 38 | * |
| 39 | * |
| 40 | ** |
| 41 | * |
| 42 | *** |
| 49 | * |
| 50 | * |
| 51 | * |
| 52 | * |
| 53 | * |
| 54 | * |
| 55 | * |
| 56 | * |
| 57 | * |
| 58 | * |
| 59 | * |
| 60 | * |
| 61 | * |
| 62 | * |
| 63 | * |
| 64 | * |
| 65 | * |
| 66 | * |
| 67 | * |
| 68 | * |
| 69 | * |
| 70 | * |
| 71 | * |
| 72 | * |
| 73 | * |
| 74 | * |
| 75 | * |
| 76 | * |
| 77 | * |
| 84 | * |
| 85 | * |
| 86 | * |
| 87 | * |
| 88 | * |
| 89 | * |
| 90 | * |
| 91 | * |
| 92 | * |
| 93 | * |
| 94 | * |
| 95 | * |
| 96 | * |
| 97 | * |
| 98 | * |
| 99 | * |
| 100 | * |
| 101 | * |
| 102 | * |
| 103 | * |
| 104 | * |
| 105 | * |
| 106 | * |
| 107 | * |
| 108 | * |
| 109 | * |
| 110 | * |
| 111 | * |
| 112 | * |
| 113 | * |
| 114 | * |
| 115 | * |
| 116 | * |
| 117 | * |
| 118 | * |
| 119 | * |
| 120 | * |
| 121 | * |
| 122 | * |
| 123 | * |
| 124 | * |
| 125 | * |
| 126 | * |
| 127 | * |
| 128 | * |
| 129 | * |
| 130 | * |
| 131 | * |
| 132 | * |
| 133 | * |
| 134 | * |
| 135 | * |
| 136 | * |
| 137 | * |
| 138 | * |
| 139 | * |
| 140 | * |
| 141 | * |
| 142 | * |
| 143 | * |
| 144 | * |
| 145 | * |
| 146 | * |
| 147 | * |
| 148 | * |
| 149 | * |
| 150 | * |
| 151 | * |

TABLE 2-continued

| Cpd | LZ3111 |
|---|---|
| 152 | * |
| 153 | * |
| 154 | * |
| 155 | * |
| 156 | * |
| 157 | * |
| 158 | * |
| 159 | * |
| 160 | * |
| 161 | * |
| 162 | * |
| 163 | * |
| 164 | ** |
| 165 | *** |
| 166 | ** |
| 167 | ** |
| 168 | ** |
| 169 | ** |
| 170 | * |
| 171 | *** |
| 172 | * |
| 173 | ** |
| 174 | * |
| 175 | * |
| 176 | * |
| 177 | ** |
| 178 | ** |
| 179 | ** |
| 180 | *** |
| 181 | *** |
| 182 | ** |
| 183 | * |
| 184 | *** |
| 185 | *** |
| 186 | *** |
| 187 | *** |
| 188 | *** |
| 189 | ** |
| 190 | * |
| 191 | * |
| 192 | *** |
| 193 | ** |
| 194 | ** |
| 195 | * |
| 196 | * |
| 197 | * |
| 198 | * |
| 199 | *** |
| 200 | *** |
| 201 | *** |
| 202 | ** |
| 203 | *** |
| 204 | * |
| 205 | * |
| 206 | * |
| 207 | * |
| 208 | ** |
| 209 | ** |
| 210 | ** |
| 211 | ** |
| 212 | * |
| 213 | * |
| 214 | * |
| 215 | * |
| 216 | * |
| 217 | * |
| 218 | * |
| 219 | ** |
| 220 | * |
| 221 | * |
| 222 | * |
| 223 | *** |
| 224 | * |
| 225 | * |
| 226 | * |
| 227 | * |
| 228 | *** |
| 229 | ** |
| 230 | ** |
| 231 | *** |
| 232 | *** |
| 233 | *** |
| 234 | *** |
| 235 | ** |
| 236 | ** |
| 237 | * |
| 238 | *** |
| 239 | ** |
| 240 | ** |
| 241 | ** |
| 242 | * |
| 243 | *** |
| 244 | * |
| 245 | *** |
| 246 | ** |
| 247 | ** |
| 248 | ** |
| 249 | * |
| 250 | ** |
| 251 | ** |
| 252 | *** |
| 253 | ** |
| 254 | * |
| 255 | * |
| 256 | *** |
| 257 | ** |
| 258 | * |
| 259 | * |
| 260 | * |
| 261 | ** |
| 262 | ** |
| 263 | * |
| 264 | *** |
| 265 | * |
| 266 | * |
| 267 | * |
| 268 | * |
| 269 | * |
| 270 | * |
| 271 | ** |
| 272 | * |
| 273 | * |
| 274 | ** |
| 275 | **** |
| 276 | ** |
| 277 | *** |
| 278 | ** |
| 279 | *** |
| 280 | * |
| 281 | * |
| 282 | *** |
| 283 | * |
| 284 | ** |
| 285 | *** |
| 286 | * |
| 287 | ** |
| 288 | * |
| 289 | ** |
| 290 | *** |
| 291 | *** |
| 292 | * |
| 293 | * |
| 294 | * |
| 295 | * |
| 296 | * |
| 297 | * |
| 298 | * |
| 299 | * |
| 300 | * |
| 301 | * |
| 302 | ** |
| 303 | * |
| 304 | ** |
| 305 | ** |
| 306 | ** |
| 307 | * |

TABLE 2-continued

| Cpd | LZ3111 |
|---|---|
| 308 | * |
| 309 | * |
| 310 | * |
| 311 | * |
| 312 | * |
| 313 | *** |
| 314 | *** |
| 315 | **** |
| 316 | **** |
| 317 | **** |
| 318 | * |
| 319 | * |
| 320 | * |
| 321 | * |
| 322 | * |
| 323 | ** |
| 324 | ** |
| 325 | ** |
| 326 | * |
| 327 | * |
| 328 | ** |
| 329 | * |
| 330 | * |
| 331 | * |
| 332 | * |
| 333 | ** |
| 334 | * |
| 335 | *** |
| 336 | **** |
| 337 | ** |
| 338 | * |
| 339 | ** |
| 340 | ** |
| 341 | **** |
| 342 | **** |
| 343 | * |
| 344 | * |
| 345 | *** |
| 346 | ** |
| 347 | *** |
| 348 | *** |
| 349 | ** |
| 350 | ** |
| 351 | ** |
| 352 | **** |
| 353 | *** |
| 354 | **** |
| 355 | **** |
| 356 | **** |
| 357 | *** |
| 358 | *** |
| 359 | *** |
| 360 | * |
| 361 | * |
| 362 | * |
| 363 | *** |
| 364 | * |
| 365 | ** |
| 366 | * |
| 367 | ** |
| 368 | ** |
| 369 | ** |
| 370 | ** |
| 371 | * |
| 372 | * |
| 373 | * |
| 374 | * |
| 375 | *** |
| 376 | * |
| 377 | ** |
| 378 | ** |
| 379 | * |
| 380 | * |
| 381 | * |
| 382 | * |
| 383 | * |
| 384 | * |
| 385 | * |

TABLE 2-continued

| Cpd | LZ3111 |
|---|---|
| 386 | * |
| 387 | * |
| 388 | * |
| 389 | ** |
| 390 | ** |
| 391 | ** |
| 392 | ** |
| 393 | ** |
| 394 | **** |
| 395 | *** |
| 396 | *** |
| 397 | *** |
| 398 | ** |
| 399 | * |
| 400 | * |
| 401 | * |
| 402 | * |
| 403 | * |
| 404 | * |
| 405 | * |
| 406 | * |
| 407 | * |
| 408 | * |
| 409 | * |
| 410 | * |
| 411 | * |
| 412 | *** |
| 413 | ** |
| 414 | ** |
| 415 | **** |
| 416 | * |
| 417 | **** |
| 418 | **** |
| 419 | *** |
| 420 | ** |
| 421 | * |
| 422 | * |
| 423 | *** |
| 424 | **** |
| 425 | *** |
| 426 | **** |
| 427 | * |
| 428 | * |
| 429 | * |
| 430 | * |
| 431 | * |
| 432 | * |
| 433 | * |
| 434 | * |
| 435 | * |
| 436 | * |
| 437 | * |
| 438 | * |
| 439 | * |
| 440 | * |
| 441 | * |
| 442 | * |
| 443 | ** |
| 444 | * |
| 445 | * |
| 446 | *** |
| 447 | ** |
| 448 | ** |
| 449 | ** |
| 450 | * |
| 451 | ** |
| 452 | * |
| 453 | * |
| 454 | * |
| 455 | * |

Example 3

Antibacterial activity of test compounds against *E. coli* ELZ4000 and *E. coli* ELZ4251 multi-drug resistant clinical isolates is shown in Table 3.

TABLE 3

| Cpd | ELZ4251 | ELZ4000 |
|---|---|---|
| 1 | * | * |
| 3 | * | * |
| 4 | ** | ** |
| 5 | * | * |
| 6 | * | * |
| 8 | * | * |
| 9 | * | * |
| 10 | * | * |
| 11 | * | * |
| 20 | ** | * |
| 21 | * | * |
| 22 | ** | ** |
| 24 | * | * |
| 32 | **** | *** |
| 33 | * | * |
| 35 | * | * |
| 36 | *** | ** |
| 37 | * | * |
| 38 | * | * |
| 39 | * | * |
| 40 | ** | * |
| 41 | * | * |
| 42 | ** | ** |
| 122 | * | * |
| 124 | * | * |
| 129 | * | * |
| 130 | * | * |
| 132 | * | * |
| 133 | * | * |
| 152 | * | * |
| 159 | * | * |
| 160 | * | * |
| 161 | * | * |
| 164 | * | * |
| 165 | *** | ** |
| 166 | ** | * |
| 167 | ** | * |
| 168 | * | * |
| 169 | * | * |
| 171 | * | * |
| 173 | ** | * |
| 177 | ** | * |
| 178 | * | * |
| 179 | ** | * |
| 180 | ** | * |
| 181 | * | * |
| 182 | * | * |
| 184 | ** | * |
| 185 | * | * |
| 186 | ** | ** |
| 187 | ** | * |
| 188 | * | * |
| 189 | ** | * |
| 192 | ** | * |
| 193 | ** | ** |
| 194 | * | * |
| 199 | ** | ** |
| 200 | * | * |
| 201 | ** | ** |
| 202 | * | * |
| 203 | *** | ** |
| 209 | * | * |
| 210 | ** | * |
| 211 | * | * |
| 219 | * | * |
| 223 | * | ** |
| 227 | * | * |
| 228 | *** | ** |
| 229 | ** | * |
| 230 | * | * |
| 231 | * | * |
| 232 | ** | ** |
| 233 | * | * |
| 234 | * | * |
| 235 | ** | * |
| 236 | * | * |
| 238 | * | * |
| 239 | ** | * |
| 240 | ** | * |
| 241 | ** | * |
| 243 | *** | ** |
| 245 | *** | ** |
| 247 | * | * |
| 248 | * | * |
| 250 | * | * |
| 251 | * | * |
| 252 | * | * |
| 253 | * | * |
| 255 | * | * |
| 256 | * | * |
| 257 | * | * |
| 261 | * | * |
| 262 | * | * |
| 264 | ** | * |
| 271 | ** | * |
| 274 | ** | * |
| 275 | *** | *** |
| 276 | * | * |
| 277 | ** | * |
| 278 | * | * |
| 279 | * | * |
| 282 | ** | * |
| 284 | * | * |
| 285 | ** | * |
| 287 | * | * |
| 288 | * | * |
| 289 | * | * |
| 290 | ** | ** |
| 291 | * | * |
| 302 | ** | * |
| 304 | * | * |
| 305 | ** | * |
| 313 | *** | ** |
| 314 | *** | ** |
| 315 | **** | *** |
| 316 | ** | ** |
| 317 | **** | *** |
| 323 | ** | * |
| 324 | ** | ** |
| 325 | *** | ** |
| 328 | * | * |
| 331 | * | * |
| 333 | * | ND |
| 334 | * | ND |
| 335 | * | ND |
| 336 | * | ND |
| 337 | * | ND |
| 338 | * | ND |
| 354 | **** | ** |
| 362 | * | ND |
| 364 | * | ND |
| 365 | ** | ND |
| 366 | * | ND |
| 367 | * | ND |
| 412 | ** | ** |
| 415 | *** | ** |
| 423 | *** | ** |

Example 4

Antibacterial activity of test compounds against the Gram-negative *Acinetobacter baumannii* (*A. baumannii*) BAA747 and *Klebsiella pneumoniae* (*K. pneumoniae*) 35657 bacterium and the resistant *A. baumannii* MXX2240 and *K. pneumoniae* MXX1232 strains are shown in Table 4. The MMX strains are multi-drug resistant clinical isolates.

TABLE 4

| Cpd | BAA747 | MMX2240 | 35657 | MMX1232 |
|---|---|---|---|---|
| 3 | ** | * | ** | * |
| 4 | *** | *** | ** | * |
| 5 | *** | * | ** | * |
| 6 | *** | *** | * | * |
| 8 | * | * | * | * |
| 14 | * | * | * | * |
| 21 | **** | * | **** | * |
| 22 | **** | **** | *** | * |
| 24 | ** | * | ND | * |
| 31 | * | * | * | * |
| 32 | * | **** | * | * |
| 36 | * | *** | * | * |
| 40 | *** | ** | ND | * |
| 41 | * | * | * | * |
| 42 | *** | ** | ** | * |
| 49 | * | * | * | * |
| 50 | * | * | * | * |
| 51 | * | * | * | * |
| 52 | * | * | * | * |
| 53 | * | * | * | * |
| 121 | *** | * | ** | * |
| 122 | **** | * | **** | * |
| 123 | *** | * | **** | * |
| 124 | **** | * | *** | * |
| 125 | * | ND | **** | ND |
| 129 | ** | * | *** | * |
| 130 | *** | * | **** | * |
| 131 | ** | ND | * | ND |
| 132 | ** | * | **** | * |
| 133 | *** | * | **** | * |
| 137 | ** | * | *** | * |
| 140 | ** | * | *** | * |
| 152 | ** | * | **** | * |
| 154 | ** | * | *** | * |
| 155 | * | ND | ** | ND |
| 159 | ** | * | **** | * |
| 160 | *** | * | **** | * |
| 161 | ** | * | **** | * |
| 162 | ** | ND | *** | ND |
| 164 | **** | ** | ** | * |
| 165 | **** | ** | **** | * |
| 166 | **** | *** | **** | * |
| 167 | *** | ** | *** | * |
| 168 | *** | ** | *** | * |
| 169 | *** | * | *** | * |
| 171 | * | * | *** | * |
| 173 | *** | * | *** | * |
| 177 | ND | ND | *** | * |
| 178 | *** | * | ** | * |
| 179 | *** | ** | ND | * |
| 180 | * | * | ** | * |
| 181 | ** | * | *** | * |
| 184 | ** | * | *** | * |
| 185 | * | * | *** | * |
| 186 | **** | *** | **** | * |
| 187 | *** | * | *** | * |
| 188 | * | * | * | * |
| 189 | *** | * | *** | * |
| 192 | *** | *** | *** | * |
| 193 | **** | *** | **** | * |
| 194 | *** | ** | ND | * |
| 199 | **** | *** | **** | * |
| 200 | ** | * | * | * |
| 201 | **** | ** | **** | * |
| 202 | * | ND | ND | ND |
| 203 | **** | ** | ND | * |
| 208 | ND | * | ND | * |
| 209 | *** | ** | *** | * |
| 210 | *** | * | ** | * |
| 214 | ND | ND | * | * |
| 220 | ND | ND | ** | * |
| 221 | ND | ND | *** | * |
| 223 | **** | *** | ** | * |
| 228 | **** | *** | *** | * |
| 229 | **** | *** | **** | * |
| 230 | * | * | *** | * |
| 231 | ** | * | *** | * |
| 232 | **** | *** | *** | * |

TABLE 4-continued

| Cpd | BAA747 | MMX2240 | 35657 | MMX1232 |
|---|---|---|---|---|
| 233 | * | * | *** | * |
| 234 | * | * | *** | * |
| 235 | **** | ** | *** | * |
| 236 | *** | *** | *** | * |
| 238 | ** | * | *** | * |
| 240 | **** | *** | **** | * |
| 243 | **** | ND | **** | * |
| 245 | **** | *** | **** | * |
| 247 | *** | *** | *** | * |
| 248 | *** | * | *** | * |
| 250 | ** | * | ** | * |
| 251 | ** | * | *** | * |
| 252 | * | * | *** | * |
| 253 | * | * | *** | * |
| 254 | ND | ND | ** | * |
| 256 | * | * | *** | * |
| 257 | * | * | ** | * |
| 271 | *** | * | ND | * |
| 274 | ** | ** | ND | * |
| 275 | **** | **** | *** | * |
| 276 | * | * | *** | * |
| 277 | *** | * | *** | * |
| 279 | *** | * | *** | * |
| 282 | * | * | *** | * |
| 285 | ** | * | *** | * |
| 289 | * | ND | ND | ND |
| 290 | *** | * | ** | * |
| 291 | *** | *** | ** | * |
| 302 | ** | ND | ND | ND |
| 304 | *** | * | ** | * |
| 305 | *** | * | **** | * |
| 306 | * | ND | ** | ND |
| 313 | ** | *** | ND | * |
| 314 | ** | *** | ** | * |
| 315 | *** | *** | *** | * |
| 316 | ** | *** | ** | * |
| 317 | ** | *** | *** | ** |
| 318 | * | * | * | * |
| 322 | * | * | ND | ND |
| 323 | * | ND | ND | ND |
| 324 | * | ND | ND | ND |
| 325 | * | ND | ND | ND |
| 328 | * | ND | ND | ND |
| 333 | **** | *** | **** | * |
| 334 | *** | * | *** | * |
| 335 | ** | * | *** | * |
| 336 | * | * | * | * |
| 337 | * | * | * | * |
| 338 | * | * | * | * |
| 339 | ** | ** | *** | * |
| 340 | * | ** | ** | * |
| 341 | ** | *** | ** | * |
| 342 | ** | *** | **** | * |
| 343 | * | * | * | * |
| 344 | * | * | * | * |
| 345 | * | * | * | * |
| 346 | ** | ** | ** | * |
| 347 | **** | **** | *** | * |
| 348 | *** | *** | *** | * |
| 349 | * | * | ** | * |
| 350 | * | * | * | * |
| 351 | **** | *** | *** | * |
| 352 | ** | *** | *** | * |
| 353 | ** | **** | ** | * |
| 354 | *** | **** | ** | * |
| 355 | ** | **** | ** | * |
| 356 | **** | **** | ** | * |
| 357 | ** | ** | ** | * |
| 358 | * | ** | *** | * |
| 362 | * | * | * | * |
| 364 | * | * | * | * |
| 365 | * | *** | * | * |
| 366 | * | * | * | * |
| 367 | * | * | * | * |
| 368 | *** | ** | *** | * |
| 369 | *** | ** | **** | * |
| 370 | *** | ** | ** | * |
| 371 | ** | ** | *** | * |

TABLE 4-continued

| Cpd | BAA747 | MMX2240 | 35657 | MMX1232 |
| --- | --- | --- | --- | --- |
| 372 | * | * | * | * |
| 373 | * | * | * | * |
| 374 | * | * | * | * |
| 375 | * | *** | * | * |
| 376 | * | * | * | * |
| 377 | * | ** | * | * |
| 378 | * | ** | * | * |
| 379 | * | * | * | * |
| 380 | * | * | * | * |
| 381 | * | * | * | * |
| 382 | * | * | * | * |
| 383 | * | * | * | * |
| 384 | * | * | * | * |
| 385 | * | * | * | * |
| 386 | * | * | * | * |
| 387 | * | * | * | * |
| 388 | * | * | * | * |
| 389 | * | ** | * | * |
| 390 | * | ** | * | * |
| 391 | * | * | ** | * |
| 392 | * | * | ** | * |
| 393 | ** | ** | * | * |
| 394 | * | **** | * | * |
| 395 | * | ** | * | * |
| 396 | * | ** | * | * |
| 397 | * | ** | * | * |
| 398 | * | * | * | * |
| 399 | * | * | * | * |
| 400 | * | * | * | * |
| 401 | * | * | * | * |
| 402 | * | * | * | * |
| 403 | * | * | * | * |
| 404 | * | * | * | * |
| 405 | * | * | * | * |
| 406 | * | * | * | * |
| 407 | * | * | * | * |
| 408 | * | * | * | * |
| 409 | * | * | * | * |
| 410 | * | * | * | * |
| 411 | * | * | * | * |
| 412 | * | * | ** | * |
| 413 | ** | * | **** | * |
| 414 | ** | * | **** | * |
| 415 | * | ** | ** | * |
| 416 | * | * | * | * |
| 417 | ** | **** | * | * |
| 418 | ** | ** | ** | * |
| 419 | ** | ** | ** | * |
| 420 | * | ** | * | * |
| 421 | * | * | * | * |
| 422 | * | * | ** | * |
| 423 | **** | *** | **** | * |
| 424 | * | **** | * | * |
| 425 | ** | **** | *** | * |
| 426 | * | **** | * | * |
| 427 | * | * | * | * |
| 428 | * | * | * | * |
| 429 | * | * | * | * |
| 430 | * | * | * | * |
| 431 | * | * | * | * |
| 432 | *** | * | ** | * |
| 433 | ** | * | ** | * |
| 434 | * | * | * | * |
| 435 | * | * | * | * |
| 436 | * | * | * | * |
| 437 | * | * | * | * |
| 438 | * | * | * | * |
| 439 | * | * | * | * |
| 440 | * | * | * | * |
| 441 | *** | ** | **** | * |
| 442 | * | * | ** | * |
| 443 | * | ** | ** | * |
| 444 | * | * | * | * |
| 445 | * | * | ** | * |
| 446 | ** | * | **** | * |
| 447 | ** | * | **** | * |
| 448 | ** | ** | *** | * |
| 449 | ** | ** | **** | * |
| 450 | * | * | ** | * |
| 451 | ** | * | **** | * |
| 452 | * | * | *** | * |
| 453 | * | * | * | * |
| 454 | * | * | * | * |
| 455 | * | * | * | * |

Example 5

Antibacterial activity of test compounds against the Gram-negative bacterium *Pseudomonas aeruginosa* (*P. aeruginosa*) 27853 is shown in Table 5.

TABLE 5

| Cpd | 27853 |
| --- | --- |
| 1 | * |
| 3 | * |
| 4 | * |
| 5 | * |
| 6 | * |
| 8 | * |
| 14 | * |
| 20 | * |
| 21 | * |
| 22 | * |
| 31 | * |
| 32 | * |
| 36 | * |
| 40 | ** |
| 41 | * |
| 42 | * |
| 49 | * |
| 50 | * |
| 51 | * |
| 52 | * |
| 53 | * |
| 121 | * |
| 122 | ** |
| 123 | * |
| 124 | ** |
| 125 | * |
| 129 | * |
| 130 | * |
| 131 | * |
| 132 | * |
| 133 | * |
| 137 | * |
| 140 | * |
| 152 | * |
| 154 | * |
| 155 | * |
| 159 | ** |
| 160 | * |
| 161 | ** |
| 162 | * |
| 164 | ** |
| 165 | ** |
| 166 | ** |
| 167 | * |
| 168 | * |
| 169 | * |
| 171 | * |
| 173 | * |
| 177 | * |
| 178 | ** |
| 179 | * |
| 180 | * |
| 181 | * |
| 182 | * |
| 184 | * |
| 185 | ** |
| 186 | ** |

TABLE 5-continued

| Cpd | 27853 |
|---|---|
| 187 | ** |
| 188 | * |
| 189 | * |
| 192 | * |
| 193 | ** |
| 194 | * |
| 199 | ** |
| 200 | * |
| 201 | ** |
| 202 | * |
| 203 | *** |
| 209 | * |
| 210 | * |
| 211 | * |
| 219 | * |
| 223 | ** |
| 227 | * |
| 228 | ** |
| 229 | ** |
| 230 | * |
| 231 | * |
| 232 | ** |
| 233 | * |
| 234 | * |
| 235 | * |
| 236 | * |
| 238 | * |
| 239 | * |
| 240 | ** |
| 241 | * |
| 243 | ** |
| 245 | ** |
| 247 | * |
| 248 | * |
| 250 | * |
| 251 | * |
| 252 | ** |
| 253 | * |
| 255 | * |
| 256 | ** |
| 257 | * |
| 261 | * |
| 262 | * |
| 264 | * |
| 271 | ** |
| 274 | * |
| 275 | ** |
| 276 | * |
| 277 | * |
| 278 | * |
| 279 | * |
| 282 | * |
| 284 | ** |
| 285 | * |
| 287 | * |
| 288 | * |
| 289 | * |
| 290 | *** |
| 291 | * |
| 302 | * |
| 304 | * |
| 305 | ** |
| 306 | * |
| 313 | * |
| 314 | * |
| 315 | * |
| 316 | * |
| 317 | * |
| 318 | * |
| 322 | * |
| 323 | * |
| 324 | * |
| 325 | * |
| 328 | * |
| 331 | * |
| 333 | * |
| 334 | * |
| 335 | * |

TABLE 5-continued

| Cpd | 27853 |
|---|---|
| 336 | * |
| 337 | * |
| 338 | * |
| 339 | * |
| 340 | * |
| 341 | * |
| 342 | * |
| 343 | * |
| 344 | * |
| 345 | * |
| 346 | * |
| 347 | * |
| 348 | * |
| 349 | * |
| 350 | * |
| 351 | * |
| 352 | * |
| 353 | * |
| 354 | * |
| 355 | * |
| 356 | * |
| 357 | * |
| 358 | * |
| 362 | * |
| 364 | * |
| 365 | * |
| 366 | * |
| 367 | * |
| 368 | * |
| 369 | * |
| 370 | * |
| 371 | * |
| 372 | * |
| 373 | * |
| 374 | * |
| 375 | * |
| 376 | * |
| 377 | * |
| 378 | * |
| 379 | * |
| 380 | * |
| 381 | * |
| 382 | * |
| 383 | * |
| 384 | * |
| 385 | * |
| 386 | * |
| 387 | * |
| 388 | * |
| 389 | * |
| 390 | * |
| 391 | * |
| 392 | * |
| 393 | * |
| 394 | * |
| 395 | * |
| 396 | * |
| 397 | * |
| 398 | * |
| 399 | * |
| 400 | * |
| 401 | * |
| 402 | * |
| 403 | * |
| 404 | * |
| 405 | * |
| 406 | * |
| 407 | * |
| 408 | * |
| 409 | * |
| 410 | * |
| 411 | * |
| 412 | * |
| 413 | * |
| 414 | * |
| 415 | * |
| 416 | * |
| 417 | * |

TABLE 5-continued

| Cpd | 27853 |
|-----|-------|
| 418 | * |
| 419 | * |
| 420 | * |
| 421 | * |
| 422 | * |
| 423 | ** |
| 424 | * |
| 425 | * |
| 426 | * |
| 427 | * |
| 428 | * |
| 429 | * |
| 430 | * |
| 431 | * |
| 432 | * |
| 433 | * |
| 434 | * |
| 435 | * |
| 436 | * |
| 437 | * |
| 438 | * |
| 439 | * |
| 440 | * |
| 441 | * |
| 442 | * |
| 443 | * |
| 444 | * |
| 445 | * |
| 446 | ** |
| 447 | * |
| 448 | * |
| 449 | * |
| 450 | * |
| 451 | * |
| 452 | * |
| 453 | * |
| 454 | * |
| 455 | * |

Example 6

Antibacterial activity of test compounds against the Gram-negative bacteria *Haemophilus influenzae* (*H. influenzae*) 49247 is shown in Table 6, *Moraxella catarrhalis* (*M. catarrhalis*) 25238 is shown in Table 7 and *Neisseria meningitidis* (*N. meningitidis*) 13090 is shown in Table 8.

TABLE 6

| Cpd | 49247 |
|-----|-------|
| 1 | **** |
| 2 | **** |
| 3 | **** |
| 4 | **** |
| 5 | **** |
| 6 | **** |
| 9 | **** |
| 10 | **** |
| 11 | **** |
| 21 | **** |
| 22 | **** |
| 32 | *** |
| 33 | **** |
| 35 | **** |
| 36 | ** |
| 37 | **** |
| 38 | **** |
| 39 | **** |
| 40 | **** |
| 41 | **** |
| 42 | **** |
| 165 | **** |
| 166 | **** |
| 167 | **** |
| 168 | **** |
| 169 | *** |
| 171 | *** |
| 173 | **** |
| 180 | *** |
| 181 | *** |
| 184 | *** |
| 185 | *** |
| 186 | **** |
| 187 | **** |
| 188 | ** |
| 189 | **** |
| 192 | **** |
| 193 | **** |
| 199 | **** |
| 200 | *** |
| 201 | **** |
| 203 | **** |
| 209 | **** |
| 210 | *** |
| 223 | **** |
| 228 | **** |
| 229 | **** |
| 230 | ** |
| 231 | *** |
| 232 | **** |
| 233 | ** |
| 234 | *** |
| 235 | **** |
| 236 | *** |
| 238 | **** |
| 240 | **** |
| 243 | **** |
| 245 | **** |
| 247 | *** |
| 248 | **** |
| 250 | ** |
| 251 | *** |
| 252 | *** |
| 253 | ** |
| 256 | *** |
| 257 | ** |
| 275 | **** |
| 276 | *** |
| 277 | **** |
| 279 | *** |
| 282 | *** |
| 285 | *** |
| 290 | *** |
| 291 | **** |
| 305 | **** |
| 314 | *** |
| 315 | *** |
| 316 | *** |
| 317 | *** |

TABLE 7

| Cpd | 25238 |
|-----|-------|
| 22 | **** |
| 32 | *** |
| 36 | *** |
| 42 | **** |
| 165 | **** |
| 166 | **** |
| 167 | **** |
| 168 | **** |
| 169 | **** |
| 171 | ** |
| 173 | **** |
| 180 | ** |
| 181 | *** |
| 184 | *** |

TABLE 7-continued

| Cpd | 25238 |
|---|---|
| 185 | *** |
| 186 | **** |
| 187 | **** |
| 188 | ** |
| 189 | **** |
| 192 | **** |
| 193 | **** |
| 199 | **** |
| 200 | *** |
| 201 | **** |
| 203 | **** |
| 209 | **** |
| 210 | **** |
| 223 | **** |
| 275 | **** |
| 228 | **** |
| 229 | **** |
| 230 | ** |
| 231 | ** |
| 232 | **** |
| 233 | ** |
| 234 | ** |
| 235 | **** |
| 236 | **** |
| 238 | *** |
| 240 | **** |
| 243 | **** |
| 245 | **** |
| 247 | **** |
| 248 | *** |
| 250 | *** |
| 251 | **** |
| 252 | ** |
| 253 | ** |
| 256 | *** |
| 257 | ** |
| 276 | *** |
| 277 | **** |
| 279 | *** |
| 282 | ** |
| 285 | *** |
| 290 | *** |
| 291 | **** |
| 305 | **** |
| 314 | ** |
| 315 | ** |
| 316 | ** |
| 317 | ** |

TABLE 8

| Cpd | 13090 |
|---|---|
| 1 | **** |
| 2 | **** |
| 5 | **** |
| 6 | **** |
| 10 | **** |
| 21 | **** |
| 22 | **** |
| 32 | **** |
| 33 | **** |
| 35 | **** |
| 36 | **** |
| 37 | **** |
| 38 | **** |
| 39 | **** |
| 40 | **** |
| 41 | **** |
| 42 | **** |
| 122 | **** |
| 124 | **** |
| 165 | **** |
| 166 | **** |
| 167 | **** |
| 168 | **** |
| 169 | **** |
| 171 | *** |
| 173 | **** |
| 180 | *** |
| 181 | *** |
| 184 | **** |
| 185 | **** |
| 186 | ** |
| 187 | **** |
| 188 | ** |
| 189 | **** |
| 192 | **** |
| 193 | **** |
| 199 | **** |
| 200 | **** |
| 201 | **** |
| 203 | **** |
| 209 | **** |
| 210 | **** |
| 223 | **** |
| 228 | **** |
| 229 | **** |
| 230 | *** |
| 231 | *** |
| 232 | **** |
| 233 | *** |
| 234 | *** |
| 235 | **** |
| 236 | **** |
| 238 | **** |
| 240 | **** |
| 243 | **** |
| 245 | **** |
| 247 | **** |
| 248 | **** |
| 250 | **** |
| 251 | **** |
| 252 | *** |
| 253 | *** |
| 256 | *** |
| 257 | *** |
| 275 | **** |
| 276 | **** |
| 277 | **** |
| 279 | **** |
| 282 | *** |
| 285 | **** |
| 290 | **** |
| 291 | **** |
| 305 | **** |
| 314 | **** |
| 315 | **** |
| 316 | * |
| 317 | **** |
| 354 | **** |
| 412 | *** |
| 415 | *** |
| 423 | **** |

Example 7

Combinations with Antibacterial Agents

The in vitro effects of compounds described herein in combination with ciprofloxacin are investigated in various organisms using the microdilution checkerboard method for the measurement of antibiotic synergy. Assays can be performed in a 96-well checkerboard titration format, with serial dilutions of each compound to identify the lowest MIC value (μg/mL) for each drug where the bacterial culture is completely inhibited. The ability of compounds to either act synergistically, additively, or antagonistically can be determined. Synergy is defined such that when the elements A and B are combined, the result is greater than the expected arithmetic sum A+B. The calculated fractional inhibitory concentration (FIC) is a quantitative measure of drug interactions: where values ≤0.5=synergy, values between >0.5 and <2=additive, values between ≥2 and ≤4=indifference, and values >4=antagonism. The fractional inhibition indices are calculated using the checkerboard method in a 96-well microtiter plate. Combinations that demonstrated no difference (Indiff) in the resulting activity and those that demonstrated synergistic (Syn) or additive (Add) activity are indicated.

Development of a combination therapy is an option to treat certain infections.

Combination therapy can be applied with any quinolone antibiotic including, without limitation, one or more of Ciprofloxacin, Enoxacin, Gatifloxacin, Levofloxacin, Lomefloxacin, Moxifloxacin, Nalidixic acid, Norfloxacin or Ofloxacin.

In addition, combination therapy can be applied with any non-quinolone antibiotic including, without limitation, one or more of Amikacin, Amoxicillin, Ampicillin, Arsphenamine, Azithromycin, Azlocillin, Aztreonam, Bacitracin, Capreomycin, Carbenicillin, Cefaclor, Cefadroxil, Cefalexin, Cefalotin (Cefalothin), Cefamandole, Cefazolin, Cefdinir, Cefditoren, Cefixime, Cefoperazone, Cefotaxime, Cefoxitin, Cefpodoxime, Cefprozil, Ceftazidime, Ceftibuten, Ceftizoxime, Ceftriaxone, Cefuroxime, Chloramphenicol, Cilastatin, Clarithromycin, Clavulanate, Clindamycin, Clofazimine, Cloxacillin, Colistin, Cycloserine, Dalfopristin, Dapsone, Daptomycin, Dicloxacillin, Dirithromycin, Doripenem, Doxycycline, Erythromycin, Ethambutol, Ethionamide, Flucloxacillin, Fosfomycin, Furazolidone, Fusidic acid, Gentamicin, Imipenem, Isoniazid, Kanamycin, Lincomycin, Linezolid, Loracarbef, Mafenide, Meropenem, Methicillin, Metronidazole, Mezlocillin, Minocycline, Mupirocin, Nafcillin, Neomycin, Netilmicin, Nitrofurantoin, Oxacillin, Oxytetracycline, Paromomycin, Penicillin G, Penicillin V, Piperacillin, Platensimycin, Polymyxin B, Pyrazinamide, Quinupristin, Rapamycin, Rifabutin, Rifampicin, Rifampin, Rifapentine, Rifaximin, Roxithromycin, Silver sulfadiazine, Spectinomycin, Streptomycin, Sulbactam, Sulfacetamide, Sulfadiazine, Sulfamethizole, Sulfamethoxazole, Sulfanilimide, Sulfasalazine, Sulfisoxazole, Tazobactam, Teicoplanin, Telavancin, Telithromycin, Temocillin, Tetracycline, Thiamphenicol, Ticarcillin, Tigecycline, Timidazole, Tobramycin, Trimethoprim, Troleandomycin or Vancomycin.

Without regard to whether a document cited herein was specifically and individually indicated as being incorporated by reference, all documents referred to herein are incorporated by reference into the present application for any and all purposes to the same extent as if each individual reference was fully set forth herein.

Although certain embodiments have been described in detail above, those having ordinary skill in the art will clearly understand that many modifications are possible in the embodiments without departing from the teachings thereof. All such modifications are intended to be encompassed within the claims included herein.

What is claimed is:
1. A compound of Formula (I):

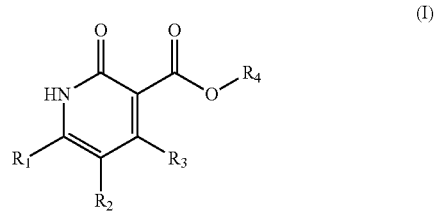

or a form thereof, wherein
$R_1$ is aryl, heterocyclyl or heteroaryl each optionally substituted with one, two or three substituents each selected from $R_5$ and one additional substituent selected from $R_6$, wherein aryl and heteroaryl are selected from a bicyclic or tricyclic ring system, and wherein heterocyclyl is selected from the group consisting of dihydro-indolyl, indolinyl, tetrahydro-indolyl, dihydro-indazolyl, tetrahydro-indazolyl, dihydro-isoindolyl, dihydro-benzofuranyl, tetrahydro-benzofuranyl, dihydro-benzothienyl, tetrahydro-benzothienyl, dihydro-benzimidazolyl, tetrahydro-benzimidazolyl, dihydro-benzooxazolyl, 2,3-dihydrobenzo[d]oxazolyl, tetrahydro-benzooxazolyl, dihydro-benzooxazinyl, 3,4-dihydro-2H-benzo[b][1,4]oxazinyl, tetrahydro-benzooxazinyl, dihydropurinyl, tetrahydro-purinyl, dihydro-quinolinol, tetrahydro-quinolinyl, 1,2,3,4-tetrahydroquinolinyl, dihydro-isoquinolinyl, 3,4-dihydroisoquinolin-(1H)-yl, tetrahydro-isoquinolinyl, 1,2,3,4-tetrahydroisoquinolinyl, dihydro-quinazolinyl, tetrahydro-quinazolinyl, dihydro-quinoxalinyl, tetrahydro-quinoxalinyl, 1,2,3,4-tetrahydroquinoxalinyl, 2,5-dihydro-1H-pyrrolyl, hexahydropyrrolo[3,4-b][1,4]oxazin-(2H)-yl, (4aR,7aS)-hexahydropyrrolo[3,4-b][1,4]oxazin-(4aH)-yl, 3,4-dihydro-2H-pyrido[3,2-b][1,4]oxazinyl, (cis)-octahydrocyclopenta[c]pyrrolyl, hexahydropyrrolo[3,4-b]pyrrol-(1H)-yl, (3aR,6aR)-hexahydropyrrolo[3,4-b]pyrrol-(1H)-yl, (3aR,6aS)-hexahydropyrrolo[3,4-c]pyrrol-(1H)-yl, 5H-pyrrolo[3,4-b]pyridin-(7H)-yl, 5,7-dihydro-6Hpyrrolo[3,4-b]pyridinyl, tetrahydro-1H-pyrrolo[3,4-b]pyridin-(2H,7H,7aH)-yl, hexahydro-1H-pyrrolo[3,4-b]pyridin-(2H)-yl, (4aR,7aR)-hexahydro-1H-pyrrolo[3,4-b]pyridin-(2H)-yl, octahydro-6H-pyrrolo[3,4-b]pyridinyl, 2,3,4,9-tetrahydro-1H-carbazolyl, 1,2,3,4-tetrahydropyrazino[1,2-a]indolyl, 2,3-dihydro-1H-pyrrolo[1,2-a]indolyl, (3aR,6aR)-hexahydrocyclopenta[c]pyrrol-(1H)-yl, (3aR,4R,6aS)-hexahydrocyclopenta[c]pyrrol-(1H)-yl, (3aR,4S,6aS)-hexahydrocyclopenta[c]pyrrol-(1H)-yl, (3aR,5r,6aS)-hexahydrocyclopenta[c]pyrrol-(1H)-yl, 1,3-dihydro-2H-isoindolyl, octahydro-2H-isoindolyl, (3aS)-1,3,3a,4,5,6-hexahydro-2H-isoindolyl, (3aR,4R,7aS)-1H-isoindol-(3H,3aH,4H,5H,6H,7H,7aH)-yl, (3aR,7aS)-octahydro-2H-isoindolyl, (3aR,4R,7aS)-octahydro-2H-isoindolyl, (3aR,4S,7aS)-octahydro-2H-isoindolyl, 2,5-diazabicyclo[2.2.1]heptanyl, 2-azabicyclo[2.2.1]hept-5-enyl, 3-azabicyclo[3.1.0]hexanyl, 3,6-diazabicyclo[3.1.0]hexanyl, (1R,5S,6s)-3-azabicyclo[3.1.0]hexanyl, (1S,5R,6R)-3-azabicyclo[3.2.0]heptanyl, (1S,5R,6S)-3-azabicyclo[3.2.0]heptanyl, 5-azaspiro[2.4]heptanyl, 2,6-diazaspiro[3.3]heptanyl, 2,5-diazaspiro[3.4]octanyl, 2,6-diazaspiro[3.4]octanyl, 2,7-diazaspiro[3.5]nonanyl, 2,7-diazaspiro[4.4]nonanyl, 2-azaspiro[4.5]

decanyl, 2,8-diazaspiro[4.5]decanyl, 6,7,8,9-tetrahydropyrido[1,2-a]indolyl, 2,3,4,9-tetrahydro-1H-pyrido[3,4-b]indolyl and 2,3,4,5-tetrahydro-1H-pyrido[4,3-b]indolyl;

$R_2$ is fluorine, chlorine, iodine, cyano, $C_{1-8}$alkyl, halo-$C_{1-8}$alkyl, hydroxyl-$C_{1-8}$ alkyl, formyl-$C_{1-8}$alkyl, $C_{1-8}$alkoxy-$C_{1-8}$ alkyl, $C_{2-8}$ alkenyl, $C_{2-8}$alkynl, carboxy, amino, $C_{1-8}$alkyl-amino, ($C_{1-8}$ alkyl)$_2$-amino, amino-$C_{1-8}$alkyl, $C_{1-8}$ alkyl-amino-$C_{1-8}$ alkyl, ($C_{1-8}$ alkyl)$_2$-amino-$C_{1-8}$ alkyl, $C_{3-14}$cycloalkyl, $C_{3-8}$cycloalkyl-oxy or aryl-$C_{1-8}$alkyl, wherein each instance of aryl is optionally substituted with one halogen substituent;

$R_3$ is hydrogen, halogen, hydroxyl, $C_{1-8}$alkyl, $C_{1-8}$alkoxy, carboxyl, amino, $C_{1-8}$alkyl-amino, ($C_{1-8}$alkyl)$_2$-amino or $C_{1-8}$ alkyl-SO$_2$-amino;

$R_4$ is hydrogen;

$R_5$ is halogen, hydroxyl, oxo, cyano, nitro, $C_{1-8}$alkyl, hydroxyl-$C_{1-8}$alkyl, halo-$C_{1-8}$alkyl, $C_{1-8}$alkoxy, $C_{1-8}$alkyl-thio, carboxyl, $C_{1-8}$ alkyl-carbonyl, $C_{1-8}$ alkoxy-carbonyl, amino-carbonyl, amino, $C_{1-8}$ alkyl-amino, ($C_{1-8}$alkyl)$_2$-amino, $C_{2-8}$alkenyl-amino, ($C_{2-8}$alkenyl)$_2$-amino, $C_{2-8}$ alkynyl-amino, ($C_{2-8}$ alkynyl)$_2$-amino, amino-$C_{1-8}$ alkyl, $C_{1-10}$alkyl-amino-$C_{1-8}$ alkyl, ($C_{1-8}$ alkyl)$_2$-amino-$C_{1-8}$ alkyl, $C_{2-8}$alkenyl-amino-$C_{1-8}$alkyl, ($C_{2-8}$alkenyl)$_2$-amino-$C_{1-8}$alkyl, $C_{2-8}$alkynyl-amino-$C_{1-8}$ alkyl, ($C_{2-8}$alkynyl)$_2$-amino-$C_{1-8}$alkyl, halo-$C_{1-8}$alkyl-amino, (halo-$C_{1-8}$alkyl)$_2$-amino, halo-$C_{1-8}$ alkyl-amino-$C_{1-8}$ alkyl, (halo-$C_{1-8}$alkyl)$_2$-amino-$C_{1-8}$alkyl, $C_{1-8}$ alkoxy-$C_{1-8}$ alkyl-amino, ($C_{1-8}$alkoxy-$C_{1-8}$alkyl, $C_{1-8}$alkyl)-amino, ($C_{1-8}$alkoxy-$C_{1-8}$alkyl)$_2$-amino, $C_{1-8}$alkoxy-$C_{1-8}$alkyl-amino-$C_{1-8}$ alkyl, ($C_{1-8}$ alkoxy-$C_{1-8}$ alkyl, $C_{1-8}$ alkyl)-amino-$C_{1-8}$ alkyl, ($C_{1-8}$ alkoxy-$C_{1-8}$alkyl)$_2$-amino-$C_{1-8}$alkyl, amino-$C_{1-8}$ alkyl-amino, (amino-$C_{1-8}$alkyl, $C_{1-8}$alkyl)amino, $C_{1-8}$alkyl-amino-$C_{1-8}$alkyl-amino, ($C_{1-8}$alkyl-amino-$C_{1-8}$alkyl, $C_{1-8}$alkyl)amino, ($C_{1-8}$ alkyl)$_2$-amino-$C_{1-8}$ alkyl-amino, [($C_{1-8}$ alkyl)$_2$-amino-$C_{1-8}$alkyl, $C_{1-8}$alkyl]amino, amino-$C_{1-8}$ alkyl-amino-$C_{1-8}$ alkyl, (amino-$C_{1-8}$alkyl, $C_{1-8}$alkyl)amino-$C_{1-8}$alkyl, $C_{1-8}$alkyl-amino-$C_{1-8}$alkyl-amino-$C_{1-8}$ alkyl, ($C_{1-8}$alkyl-amino-$C_{1-8}$ alkyl, $C_{1-8}$ alkyl)amino-$C_{1-8}$alkyl, ($C_{1-8}$ alkyl)$_2$-amino-$C_{1-8}$ alkyl-amino-$C_{1-8}$ alkyl, [($C_{1-8}$ alkyl)$_2$-amino-$C_{1-8}$alkyl, $C_{1-8}$ alkyl]amino-$C_{1-8}$alkyl, hydroxyl-amino, hydroxyl-$C_{1-8}$ alkyl-amino, (hydroxyl-$C_{1-8}$alkyl, $C_{1-8}$alkyl)amino, (hydroxyl-$C_{1-8}$alkyl)$_2$-amino, hydroxyl-$C_{1-8}$alkyl-amino-$C_{1-8}$alkyl, (hydroxyl-$C_{1-8}$ alkyl, $C_{1-8}$ alkyl)amino-$C_{1-8}$ alkyl, hydroxyl-$C_{1-8}$alkyl-amino-$C_{1-8}$alkyl-amino, (hydroxyl-$C_{1-8}$alkyl-amino-$C_{1-8}$alkyl, $C_{1-8}$alkyl)amino, (hydroxyl-$C_{1-8}$ alkyl, $C_{1-8}$ alkyl)amino-$C_{1-8}$ alkyl-amino, [(hydroxyl-$C_{1-8}$alkyl, $C_{1-8}$alkyl)amino-$C_{1-8}$alkyl, $C_{1-8}$alkyl]amino, ($C_{1-8}$alkyl-carbonyl, $C_{1-8}$alkyl)amino-$C_{1-8}$alkyl, $C_{1-8}$alkyl-amino-carbonyl, ($C_{1-8}$alkyl)$_2$-amino-carbonyl or ($C_{1-8}$alkyl)$_2$-amino-carbonyl-$C_{1-8}$alkyl-amino-$C_{1-8}$alkyl;

$R_6$ is $C_{3-14}$cycloalkyl, $C_{3-14}$cycloalkyl-$C_{1-8}$alkyl, $C_{3-14}$cycloalkyl-oxy, $C_{3-14}$cycloalkyl-$C_{1-8}$alkoxy, $C_{3-14}$cycloalkyl-amino, $C_{3-14}$cycloalkyl-amino-$C_{1-8}$alkyl, ($C_{3-14}$cycloalkyl, $C_{1-8}$alkyl)amino-$C_{1-8}$alkyl, ($C_{3-14}$cycloalkyl)$_2$-amino-$C_{1-8}$alkyl, $C_{3-14}$cycloalkyl-$C_{1-8}$alkyl-amino-$C_{1-8}$alkyl, ($C_{3-14}$cycloalkyl-$C_{1-8}$alkyl, $C_{1-8}$alkyl)amino-$C_{1-8}$alkyl, ($C_{3-14}$cycloalkyl-$C_{1-8}$alkyl)$_2$-amino-$C_{1-8}$alkyl, aryl, aryl-$C_{1-8}$alkyl, aryl-$C_{1-8}$alkoxy, aryl-amino, (aryl,$C_{1-8}$alkyl)amino, (aryl)$_2$-amino, aryl-amino-$C_{1-8}$alkyl, (aryl,$C_{1-8}$alkyl)amino-$C_{1-8}$alkyl, (aryl)$_2$-amino-$C_{1-8}$alkyl, aryl-$C_{1-8}$alkyl-amino, (aryl-$C_{1-8}$alkyl, $C_{1-8}$alkyl)amino, (aryl-$C_{1-8}$alkyl)$_2$-amino, aryl-$C_{1-8}$alkyl-amino-$C_{1-8}$alkyl, (aryl-$C_{1-8}$alkyl, $C_{1-8}$alkyl)amino-$C_{1-8}$alkyl, (aryl-$C_{1-8}$alkyl)$_2$-amino-$C_{1-8}$alkyl, heteroaryl, heteroaryl-$C_{1-8}$alkyl, heteroaryl-amino, heteroaryl-$C_{1-8}$alkyl-amino, (heteroaryl-$C_{1-8}$alkyl, $C_{1-8}$alkyl)amino, (heteroaryl-$C_{1-8}$alkyl)$_2$-amino, heteroaryl-$C_{1-8}$alkyl-amino-$C_{1-8}$alkyl, (heteroaryl-$C_{1-8}$alkyl, $C_{1-8}$alkyl)amino-$C_{1-8}$alkyl, heterocyclyl, heterocyclyl-$C_{1-8}$alkyl, heterocyclyl-oxy, heterocyclyl-$C_{1-8}$alkoxy, heterocyclyl-amino, (heterocyclyl, $C_{1-8}$alkyl)amino, (heterocyclyl)$_2$-amino, heterocyclyl-amino-$C_{1-8}$alkyl, (heterocyclyl, $C_{1-8}$alkyl)amino-$C_{1-8}$alkyl, (heterocyclyl)$_2$-amino-$C_{1-8}$alkyl, (heterocyclyl, $C_{3-14}$cycloalkyl-$C_{1-8}$alkyl)amino-$C_{1-8}$alkyl, heterocyclyl-$C_{1-8}$alkyl-amino-$C_{1-8}$alkyl, (heterocyclyl-$C_{1-8}$alkyl, $C_{1-8}$alkyl)amino-$C_{1-8}$alkyl, (heterocyclyl-$C_{1-8}$alkyl)$_2$-amino-$C_{1-8}$ alkyl, heterocyclyl-oxy-amino, (heterocyclyl-oxy, $C_{1-8}$alkyl)amino, (heterocyclyl-oxy)$_2$-amino, (heterocyclyl-oxy-$C_{1-8}$alkyl, $C_{1-8}$alkyl)amino, heterocyclyl-carbonyl or heterocyclyl-carbonyl-oxy;

wherein each instance of heterocyclyl is optionally substituted with one, two or three substituents each selected from $R_7$; and, wherein each instance of $C_{3-14}$cycloalkyl, aryl and heteroaryl is optionally substituted with one, two or three substituents each selected from $R_8$;

$R_7$ is azido, halogen, hydroxyl, oxo, cyano, nitro, $C_{1-8}$alkyl, halo-$C_{1-8}$alkyl, hydroxyl-$C_{1-8}$alkyl, $C_{1-8}$alkoxy-$C_{1-8}$alkyl, $C_{1-8}$alkoxy, halo-$C_{1-8}$alkoxy, hydroxyl-$C_{1-8}$alkoxy, carboxyl, $C_{1-8}$alkyl-carbonyl, $C_{1-8}$alkoxy-carbonyl, amino, $C_{1-8}$alkyl-amino, ($C_{1-8}$alkyl)$_2$-amino, halo-$C_{1-8}$alkyl-amino, (halo-$C_{1-8}$alkyl)$_2$-amino, halo-$C_{1-8}$alkyl-amino-$C_{1-8}$alkyl, (halo-$C_{1-8}$alkyl)$_2$-amino-$C_{1-8}$alkyl, amino-$C_{1-8}$alkyl, $C_{1-8}$alkyl-amino-$C_{1-8}$alkyl, ($C_{1-8}$alkyl)$_2$-amino-$C_{1-8}$alkyl, [($C_{1-8}$alkyl)$_2$-amino-$C_{1-8}$alkyl, $C_{1-8}$alkyl]amino-$C_{1-8}$alkyl $C_{1-8}$alkyl-thio, amino-carbonyl, $C_{1-8}$alkyl-amino-carbonyl, ($C_{1-8}$alkyl)$_2$-amino-carbonyl, $C_{1-8}$alkyl-carbonyl-amino, (carboxyl-$C_{1-8}$alkyl, $C_{1-8}$alkyl)amino-carbonyl-amino, $C_{3-14}$cycloalkyl, $C_{3-14}$cycloalkyl-amino, aryl, aryl-$C_{1-8}$alkyl, aryl-amino, (aryl,$C_{1-8}$alkyl)amino, (aryl)$_2$-amino, aryl-$C_{1-8}$alkyl-amino, (aryl-$C_{1-8}$alkyl, $C_{1-8}$alkyl)amino, (aryl-$C_{1-8}$alkyl)$_2$-amino, aryl-$C_{1-8}$alkyl-amino-$C_{1-8}$alkyl, (aryl-$C_{1-8}$alkyl, $C_{1-8}$alkyl)amino-$C_{1-8}$alkyl, (aryl-$C_{1-8}$alkyl)$_2$-amino-$C_{1-8}$alkyl, aryl-amino-$C_{1-8}$alkyl, (aryl,$C_{1-8}$alkyl)amino-$C_{1-8}$alkyl, (aryl)$_2$-amino-$C_{1-8}$alkyl, aryl-amino-carbonyl, aryl-$C_{1-8}$alkoxy, aryl-$C_{1-8}$alkoxy-carbonyl-amino, heteroaryl, heteroaryl-$C_{1-8}$alkyl, heteroaryl-amino, (heteroaryl)$_2$-amino, heteroaryl-$C_{1-8}$alkyl-amino, (heteroaryl-$C_{1-8}$alkyl, $C_{1-8}$alkyl)amino, (heteroaryl-$C_{1-8}$alkyl)$_2$-amino, heteroaryl-$C_{1-8}$alkyl-amino-$C_{1-8}$alkyl, (heteroaryl-$C_{1-8}$alkyl, $C_{1-8}$alkyl)amino-$C_{1-8}$alkyl, (heteroaryl-$C_{1-8}$alkyl)$_2$-amino-$C_{1-8}$alkyl, heterocyclyl, heterocyclyl-$C_{1-8}$alkyl, heterocyclyl-amino-$C_{1-8}$alkyl or heterocyclyl-oxy;

wherein each instance of $C_{3-14}$cycloalkyl is optionally substituted with one substituent selected from $R_9$;

wherein each instance of aryl is optionally substituted with one substituent selected from $R_{10}$; and, wherein each instance of heterocyclyl and heteroaryl is optionally substituted with one substituent selected from $R_{11}$;

$R_8$ is azido, halogen, hydroxyl, cyano, nitro, $C_{1-8}$alkyl, halo-$C_{1-8}$alkyl, $C_{1-8}$alkoxy, $C_{1-8}$alkoxy-$C_{1-8}$alkyl, halo-$C_{1-8}$alkoxy, carboxyl, $C_{1-8}$alkoxy-carbonyl, amino, $C_{1-8}$alkyl-amino, ($C_{1-8}$alkyl)$_2$-amino, $C_{1-8}$alkyl-thio, aryl, aryl-$C_{1-8}$ alkoxy, heteroaryl, heterocyclyl, heterocyclyl-$C_{1-8}$alkyl or heterocyclyl-oxy;

$R_9$ is amino, $C_{1-8}$alkyl-amino, $(C_{1-8}alkyl)_2$-amino, amino-$C_{1-8}$alkyl, $C_{1-8}$alkyl-amino-$C_{1-8}$alkyl, $(C_{1-8}alkyl)_2$-amino-$C_{1-8}$alkyl or aryl-$C_{1-8}$alkyl-amino;

$R_{10}$ is halogen; and, $R_{11}$ is halogen, hydroxyl, $C_{1-8}$alkyl, halo-$C_{1-8}$alkyl, $C_{1-8}$alkoxy, $C_{1-8}$ alkoxy-$C_{1-8}$alkyl, halo-$C_{1-8}$alkoxy, amino, $C_{1-8}$alkyl-amino or $(C_{1-8}alkyl)_2$-amino.

2. The compound of claim 1, wherein $R_1$ is aryl selected from naphthalenyl;

heterocyclyl selected from indolinyl, 1,2,3,4-tetrahydroquinolinyl, 3,4-dihydro-2H-benzo[b][1,4]oxazinyl, 2,3-dihydrobenzo[d]oxazolyl, 2,3,4,9-tetrahydro-1H-carbazolyl, 1,2,3,4-tetrahydroquinoxalinyl, 3,4-dihydro-2H-pyrido[3,2-b][1,4]oxazinyl, 6,7,8,9-tetrahydropyrido[1,2-a]indolyl, 2,3,4,9-tetrahydro-1H-pyrido[3,4-b]indolyl, 2,3,4,5-tetrahydro-1H-pyrido[4,3-b]indolyl, 1,2,3,4-tetrahydropyrazino[1,2-a]indolyl and 2,3-dihydro-1H-pyrrolo[1,2-a]indolyl; and, heteroaryl selected from 1H-indolyl, 1H-indazolyl, 2H-indazolyl, indolizinyl, benzofuranyl, benzo[b]thienyl, benzo[d]oxazolyl, quinolinyl, quinoxalinyl, 9H-carbazolyl, 1H-pyrrolo[2,3-b]pyridinyl, pyrazolo[1,5-a]pyrazinyl, [1,2,4]triazolo[1,5-a]pyridinyl, [1,2,4]triazolo[4,3-a]pyridinyl, imidazo[1,2-a]pyridinyl, 3H-imidazo[4,5-b]pyridinyl, 1H-benzo[d]imidazolyl, 1H-pyrrolo[2,3-c]pyridinyl, 6H-thieno[2,3-b]pyrrolyl and 1H-pyrrolo[3,2-b]pyridinyl.

3. The compound of claim 1, wherein $R_2$ is cyano, $C_{1-8}$alkyl, halo-$C_{1-8}$alkyl, hydroxyl-$C_{1-8}$alkyl, formyl-$C_{1-8}$alkyl, $C_{1-8}$ alkoxy-$C_{1-8}$ alkyl, $C_{2-8}$alkenyl, $C_{2-8}$alkynl, carboxy, $C_{3-14}$cycloalkyl or aryl-$C_{1-8}$alkyl, wherein each instance of aryl is optionally substituted with one halogen substituent;

$R_3$ is hydrogen, hydroxyl, $C_{1-8}$alkoxy, carboxyl or amino;

$R_4$ is hydrogen;

$R_5$ is halogen, oxo, cyano, $C_{1-8}$alkyl, hydroxyl-$C_{1-8}$alkyl, $C_{1-8}$alkoxy, carboxyl, amino-carbonyl, amino, $C_{1-8}$alkyl-amino, $(C_{1-8}alkyl)_2$-amino, $(C_{2-8}alkenyl)_2$-amino, amino-$C_{1-8}$alkyl, $C_{1-8}$alkyl-amino-$C_{1-8}$alkyl, $(C_{1-8}alkyl)_2$-amino-$C_{1-8}$alkyl, $C_{2-8}$alkenyl-amino-$C_{1-8}$alkyl, $C_{2-8}$alkynyl-amino-$C_{1-8}$alkyl, halo-$C_{1-8}$alkyl-amino, halo-$C_{1-8}$alkyl-amino-$C_{1-8}$alkyl, (hydroxyl-$C_{1-8}$alkyl, $C_{1-8}$alkyl)amino, $(C_{1-8}$alkoxy-$C_{1-8}$alkyl, $C_{1-8}$alkyl)-amino-$C_{1-8}$alkyl, $(C_{1-8}alkyl)_2$-amino-$C_{1-8}$alkyl-amino, $[(C_{1-8}alkyl)_2$-amino-$C_{1-8}$alkyl, $C_{1-8}$alkyl]amino, amino-$C_{1-8}$alkyl-amino-$C_{1-8}$alkyl, $C_{1-8}$alkyl-amino-$C_{1-8}$alkyl-amino-$C_{1-8}$alkyl, $(C_{1-8}alkyl)_2$-amino-$C_{1-8}$alkyl-amino-$C_{1-8}$alkyl, $[(C_{1-8}alkyl)_2$-amino-$C_{1-8}$alkyl, $C_{1-8}$alkyl]amino-$C_{1-8}$alkyl or $(C_{1-8}$alkyl-carbonyl, $C_{1-8}$alkyl)amino-$C_{1-8}$alkyl;

$R_6$ is $C_{3-14}$cycloalkyl-amino-$C_{1-8}$alkyl, $(C_{3-14}$cycloalkyl, $C_{1-8}$alkyl)amino-$C_{1-8}$ alkyl, $C_{3-14}$cycloalkyl-$C_{1-8}$alkyl-amino-$C_{1-8}$alkyl, aryl, aryl-amino, (aryl,$C_{1-8}$ alkyl)amino, aryl-amino-$C_{1-8}$alkyl, aryl-$C_{1-8}$alkyl-amino-$C_{1-8}$alkyl, (aryl-$C_{1-8}$alkyl, $C_{1-8}$alkyl)amino-$C_{1-8}$alkyl, (aryl-$C_{1-8}$alkyl)$_2$-amino-$C_{1-8}$alkyl, heteroaryl, heteroaryl-$C_{1-8}$alkyl-amino-$C_{1-8}$alkyl, (heteroaryl-$C_{1-8}$alkyl, $C_{1-8}$alkyl)amino-$C_{1-8}$alkyl, heterocyclyl, heterocyclyl-$C_{1-8}$alkyl, heterocyclyl-amino-$C_{1-8}$alkyl, (heterocyclyl, $C_{1-8}$alkyl)amino-$C_{1-8}$alkyl, (heterocyclyl, $C_{3-14}$cycloalkyl-$C_{1-8}$alkyl)amino-$C_{1-8}$alkyl, heterocyclyl-$C_{1-8}$alkyl-amino-$C_{1-8}$alkyl or (heterocyclyl-oxy-$C_{1-8}$alkyl, $C_{1-8}$alkyl)amino;

wherein each instance of heterocyclyl is optionally substituted with one, two or three substituents each selected from $R_7$; and, wherein each instance of $C_{3-14}$cycloalkyl, aryl and heteroaryl is optionally substituted with one, two or three substituents each selected from $R_8$;

$R_7$ is azido, halogen, hydroxyl, oxo, cyano, $C_{1-8}$alkyl, halo-$C_{1-8}$alkyl, hydroxyl-$C_{1-8}$alkyl, $C_{1-8}$alkoxy-$C_{1-8}$alkyl, $C_{1-8}$alkoxy, carboxyl, $C_{1-8}$alkyl-carbonyl, $C_{1-8}$alkoxy-carbonyl, amino, $C_{1-8}$alkyl-amino, $(C_{1-8}alkyl)_2$-amino, amino-$C_{1-8}$alkyl, $C_{1-8}$alkyl-amino-$C_{1-8}$alkyl, $(C_{1-8}alkyl)_2$-amino-$C_{1-8}$alkyl, $[(C_{1-8}alkyl)_2$-amino-$C_{1-8}$alkyl, $C_{1-8}$alkyl]amino-$C_{1-8}$alkyl $(C_{1-8}alkyl)_2$-amino-carbonyl, $C_{1-8}$alkyl-carbonyl-amino, (carboxyl-$C_{1-8}$alkyl, $C_{1-8}$alkyl)amino-carbonyl-amino, $C_{3-14}$cycloalkyl, $C_{3-14}$cycloalkyl-amino, aryl, aryl-$C_{1-8}$alkyl, aryl-amino, (aryl,$C_{1-8}$alkyl)amino, aryl-$C_{1-8}$alkyl-amino, (aryl-$C_{1-8}$alkyl, $C_{1-8}$alkyl)amino, (aryl-$C_{1-8}$alkyl)$_2$-amino, aryl-$C_{1-8}$alkyl-amino-$C_{1-8}$alkyl, (aryl-$C_{1-8}$alkyl, $C_{1-8}$alkyl)amino-$C_{1-8}$alkyl, (aryl-$C_{1-8}$alkyl)$_2$-amino-$C_{1-8}$alkyl, aryl-amino-$C_{1-8}$alkyl, aryl-$C_{1-8}$alkoxy, aryl-$C_{1-8}$alkoxy-carbonyl-amino, heteroaryl, heteroaryl-$C_{1-8}$alkyl-amino-$C_{1-8}$alkyl, heterocyclyl, heterocyclyl-$C_{1-8}$alkyl, heterocyclyl-amino-$C_{1-8}$alkyl or heterocyclyl-oxy;

wherein each instance of $C_{3-14}$cycloalkyl is optionally substituted with one substituent selected from $R_9$;

wherein each instance of aryl is optionally substituted with one substituent selected from $R_{10}$; and, wherein each instance of heterocyclyl and heteroaryl is optionally substituted with one substituent selected from $R_{11}$;

$R_8$ is $C_{1-8}$alkyl;

$R_9$ is amino, $(C_{1-8}alkyl)_2$-amino or aryl-$C_{1-8}$alkyl-amino;

$R_{10}$ is halogen; and, $R_{11}$ is $C_{1-8}$alkyl.

4. The compound of claim 1, wherein $R_2$ is $C_{1-8}$alkyl selected from methyl, ethyl, propyl or isopropyl; hydroxyl-$C_{1-8}$alkyl selected from hydroxyl-methyl, hydroxyl-ethyl or hydroxyl-propyl; formyl-$C_{1-8}$alkyl selected from formylmethyl, formylethyl or formylpropyl; $C_{3-14}$cycloalkyl selected from cyclopropyl, cyclobutyl, cyclopentyl or cyclohexyl; or aryl-$C_{1-8}$alkyl selected from benzyl; and $R_3$ is $C_{1-8}$alkoxy selected from methoxy, ethoxy, propoxy or isopropoxy; or, $C_{1-8}$alkyl-$SO_2$-amino selected from methyl-$SO_2$-amino, ethyl-$SO_2$-amino, propyl-$SO_2$-amino or isopropyl-$SO_2$-amino.

5. The compound of claim 1, wherein $R_6$ is $C_{3-14}$cycloalkyl-amino-$C_{1-8}$alkyl, wherein $C_{3-14}$cycloalkyl is selected from cyclopropyl, cyclobutyl, cyclopentyl or cyclohexyl;

$(C_{3-14}$cycloalkyl, $C_{1-8}$alkyl)amino-$C_{1-8}$alkyl, wherein $C_{3-14}$cycloalkyl is selected from cyclopropyl, cyclobutyl or cyclopentyl;

$C_{3-14}$Cycloalkyl-$C_{1-8}$alkyl-amino-$C_{1-8}$alkyl, wherein $C_{3-14}$cycloalkyl is selected from cyclopropyl, cyclobutyl, cyclopentyl, cyclohexyl or cycloheptyl;

aryl, wherein aryl is selected from phenyl;

aryl-$C_{1-8}$alkoxy, wherein aryl is selected from phenyl;

aryl-amino, wherein aryl is selected from phenyl;

(aryl,$C_{1-8}$alkyl)amino, wherein aryl is selected from phenyl;

aryl-amino-$C_{1-8}$alkyl, wherein aryl is selected from phenyl;

aryl-$C_{1-8}$alkyl-amino-$C_{1-8}$alkyl, wherein aryl is selected from phenyl;

(aryl-$C_{1-8}$alkyl, $C_{1-8}$alkyl)amino-$C_{1-8}$alkyl, wherein aryl is selected from phenyl;
(aryl-$C_{1-8}$alkyl)$_2$-amino-$C_{1-8}$alkyl, wherein aryl is selected from phenyl;
heteroaryl, wherein heteroaryl is selected from pyrrolyl, thiazolyl, 1H-1,2,3-triazolyl, 1H-tetrazolyl, 2H-tetrazolyl, imidazolyl or pyridinyl;
heteroaryl-$C_{1-8}$alkyl-amino-$C_{1-8}$alkyl, wherein heteroaryl is selected from pyridin-2-yl, pyridin-3-yl or pyridin-4-yl;
(heteroaryl-$C_{1-8}$alkyl, $C_{1-8}$alkyl)amino-$C_{1-8}$alkyl, wherein heteroaryl is selected from pyridin-3-yl or pyridin-4-yl;
heterocyclyl, wherein heterocyclyl is selected from azetidinyl, pyrrolidinyl, tetrahydrofuranyl, piperidinyl, piperazinyl, morpholinyl, 1,4-diazepanyl, 1,3-dioxolanyl, 2,5-dihydro-1H-pyrrolyl, dihydro-1H-imidazolyl, 1,4,5,6-tetrahydropyrimidinyl, 1,2,3,6-tetrahydropyridinyl, tetrahydro-2H-pyranyl, 3,4-dihydroisoquinolin-(1H)-yl, 1,2,3,4-tetrahydroisoquinolinyl, hexahydropyrrolo[3,4-b][1,4]oxazin-(2H)-yl, (4aR,7aS)-hexahydropyrrolo[3,4-b][1,4]oxazin-(4aH)-yl, (cis)-octahydrocyclopenta[c]pyrrolyl, hexahydropyrrolo[3,4-b]pyrrol-(1H)-yl, (3aR,6aR)-hexahydropyrrolo[3,4-b]pyrrol-(1H)-yl, (3aR,6aS)-hexahydropyrrolo[3,4-c]pyrrol-(1H)-yl, 5H-pyrrolo[3,4-b]pyridin-(7H)-yl, 5,7-dihydro-6H-pyrrolo[3,4-b]pyridinyl, tetrahydro-1H-pyrrolo[3,4-b]pyridin-(2H,7H,7aH)-yl, hexahydro-1H-pyrrolo[3,4-b]pyridin-(2H)-yl, (4aR,7aR)-hexahydro-1H-pyrrolo[3,4-b]pyridin-(2H)-yl, octahydro-6H-pyrrolo[3,4-b]pyridinyl, (3aR,6aR)-hexahydrocyclopenta[c]pyrrol-(1H)-yl, (3aR,4R,6aS)-hexahydrocyclopenta[c]pyrrol-(1H)-yl, (3aR,4S,6aS)-hexahydrocyclopenta[c]pyrrol-(1H)-yl, (3aR,5r,6aS)-hexahydrocyclopenta[c]pyrrol-2(1H)-yl, 1,3-dihydro-2H-isoindolyl, octahydro-2H-isoindolyl, (3aS)-1,3,3a,4,5,6-hexahydro-2H-isoindolyl, (3aR,4R,7aS)-1H-isoindol-(3H,3aH,4H,5H,6H,7H,7aH)-yl, (3aR,7aS)-octahydro-2H-isoindolyl, (3aR,4R,7aS)-octahydro-2H-isoindolyl, (3aR,4S,7aS)-octahydro-2H-isoindolyl, 2,5-diazabicyclo[2.2.1]heptanyl, 2-azabicyclo[2.2.1]hept-5-enyl, 3-azabicyclo[3.1.0]hexanyl, (1R,5S,6s)-3-azabicyclo[3.1.0]hexanyl, (cis,cis)-3-azabicyclo[3.1.0]hexanyl, 3,6-diazabicyclo[3.1.0]hexanyl, (1S,5R,6R)-3-azabicyclo[3.2.0]heptanyl, (1S,5R,6S)-3-azabicyclo[3.2.0]heptanyl, 5-azaspiro[2.4]heptanyl, 2,6-diazaspiro[3.3]heptanyl, 2,5-diazaspiro[3.4]octanyl, 2,6-diazaspiro[3.4]octanyl, 2,7-diazaspiro[3.5]nonanyl, 2,7-diazaspiro[4.4]nonanyl, 2-azaspiro[4.5]decanyl or 2,8-diazaspiro[4.5]decanyl;
heterocyclyl-$C_{1-8}$alkyl, wherein heterocyclyl is selected from azetidinyl, pyrrolidinyl, tetrahydrofuranyl, piperidinyl, piperazinyl, morpholinyl, 1,4-diazepanyl, 1,3-dioxolanyl, 2,5-dihydro-1H-pyrrolyl, dihydro-1H-imidazolyl, 1,4,5,6-tetrahydropyrimidinyl, 1,2,3,6-tetrahydropyridinyl, tetrahydro-2H-pyranyl, 3,4-dihydroisoquinolin-(1H)-yl, 1,2,3,4-tetrahydroisoquinolinyl, hexahydropyrrolo[3,4-b][1,4]oxazin-(2H)-yl, (4aR,7aS)-hexahydropyrrolo[3,4-b][1,4]oxazin-(4aH)-yl, (cis)-octahydrocyclopenta[c]pyrrolyl, hexahydropyrrolo[3,4-b]pyrrol-(1H)-yl, (3aR,6aR)-hexahydropyrrolo[3,4-b]pyrrol-(1H)-yl, (3aR,6aS)-hexahydropyrrolo[3,4-c]pyrrol-(1H)-yl, 5H-pyrrolo[3,4-b]pyridin-(7H)-yl, 5,7-dihydro-6H-pyrrolo[3,4-b]pyridinyl, tetrahydro-1H-pyrrolo[3,4-b]pyridin-(2H,7H,7aH)-yl, hexahydro-1H-pyrrolo[3,4-b]pyridin-(2H)-yl, (4aR,7aR)-hexahydro-1H-pyrrolo[3,4-b]pyridin-(2H)-yl, octahydro-6H-pyrrolo[3,4-b]pyridinyl, (3aR,6aR)-hexahydrocyclopenta[c]pyrrol-(1H)-yl, (3aR,4R,6aS)-hexahydrocyclopenta[c]pyrrol-(1H)-yl, (3aR,4S,6aS)-hexahydrocyclopenta[c]pyrrol-(1H)-yl, (3aR,5r,6aS)-hexahydrocyclopenta[c]pyrrol-2(1H)-yl, 1,3-dihydro-2H-isoindolyl, octahydro-2H-isoindolyl, (3aS)-1,3,3a,4,5,6-hexahydro-2H-isoindolyl, (3aR,4R,7aS)-1H-isoindol-(3H,3aH,4H,5H,6H,7H,7aH)-yl, (3aR,7aS)-octahydro-2H-isoindolyl, (3aR,4R,7aS)-octahydro-2H-isoindolyl, (3aR,4S,7aS)-octahydro-2H-isoindolyl, 2,5-diazabicyclo[2.2.1]heptanyl, 2-azabicyclo[2.2.1]hept-5-enyl, 3-azabicyclo[3.1.0]hexanyl, (1R,5S,6s)-3-azabicyclo[3.1.0]hexanyl, (cis,cis)-3-azabicyclo[3.1.0]hexanyl, 3,6-diazabicyclo[3.1.0]hexanyl, (1S,5R,6R)-3-azabicyclo[3.2.0]heptanyl, (1S,5R,6S)-3-azabicyclo[3.2.0]heptanyl, 5-azaspiro[2.4]heptanyl, 2,6-diazaspiro[3.3]heptanyl, 2,5-diazaspiro[3.4]octanyl, 2,6-diazaspiro[3.4]octanyl, 2,7-diazaspiro[3.5]nonanyl, 2,7-diazaspiro[4.4]nonanyl, 2-azaspiro[4.5]decanyl or 2,8-diazaspiro[4.5]decanyl;
heterocyclyl-amino-$C_{1-8}$alkyl, wherein heterocyclyl is selected from azetidin-1-yl or piperidin-4-yl;
(heterocyclyl, $C_{1-8}$alkyl)amino-$C_{1-8}$alkyl, wherein heterocyclyl is selected from piperidin-3-yl or piperidin-4-yl;
(heterocyclyl, $C_{3-14}$cycloalkyl-$C_{1-8}$alkyl)amino-$C_{1-8}$alkyl, wherein heterocyclyl is selected from piperidin-3-yl or piperidin-4-yl;
heterocyclyl-$C_{1-8}$alkyl-amino-$C_{1-8}$alkyl, wherein heterocyclyl is selected from pyrrolidin-2-yl, piperidin-2-yl, piperidin-3-yl, piperidin-4-yl or tetrahydro-2H-pyran-4-yl; and
(heterocyclyl-oxy-$C_{1-8}$alkyl, $C_{1-8}$alkyl)amino selected from tetrahydro-2H-pyran-2-yl-oxy-$C_{1-8}$alkyl, $C_{1-8}$alkyl)amino.

6. The compound of claim 1, wherein $R_6$ is
heteroaryl, wherein heteroaryl is selected from pyridinyl; and,
heterocyclyl selected in each instance, when present, from azetidinyl, pyrrolidinyl, tetrahydrofuranyl, piperidinyl, piperazinyl, morpholinyl, 1,4-diazepanyl, 1,3-dioxolanyl, 2,5-dihydro-1H-pyrrolyl, dihydro-1H-imidazolyl, 1,4,5,6-tetrahydropyrimidinyl, 1,2,3,6-tetrahydropyridinyl, tetrahydro-2H-pyranyl, indolinyl, 2,3-dihydrobenzo[d]oxazolyl, 3,4-dihydro-2H-benzo[b][1,4]oxazinyl, 3,4-dihydroisoquinolin-(1H)-yl, 1,2,3,4-tetrahydroisoquinolinyl, 1,2,3,4-tetrahydroquinoxalinyl, hexahydropyrrolo[3,4-b][1,4]oxazin-(2H)-yl, (4aR,7aS)-hexahydropyrrolo[3,4-b][1,4]oxazin-(4aH)-yl, 3,4-dihydro-2H-pyrido[3,2-b][1,4]oxazinyl, (cis)-octahydrocyclopenta[c]pyrrolyl, hexahydropyrrolo[3,4-b]pyrrol-(1H)-yl, (3aR,6aR)-hexahydropyrrolo[3,4-b]pyrrol-(1H)-yl, (3aR,6aS)-hexahydropyrrolo[3,4-c]pyrrol-(1H)-yl, 5H-pyrrolo[3,4-b]pyridin-(7H)-yl, 5,7-dihydro-6H-pyrrolo[3,4-b]pyridinyl, tetrahydro-1H-pyrrolo[3,4-b]pyridin-(2H,7H,7aH)-yl, hexahydro-1H-pyrrolo[3,4-b]pyridin-(2H)-yl, (4aR,7aR)-hexahydro-1H-pyrrolo[3,4-b]pyridin-(2H)-yl, octahydro-6H-pyrrolo[3,4-b]pyridinyl, 2,3,4,9-tetrahydro-1H-carbazolyl, 1,2,3,4-tetrahydropyrazino[1,2-a]indolyl, 2,3-dihydro-1H-pyrrolo[1,2-a]indolyl, (3aR,6aR)-hexahydrocyclopenta[c]pyrrol-(1H)-yl, (3aR,4R,6aS)-hexahydrocyclopenta[c]pyrrol-(1H)-yl, (3aR,4S,6aS)-hexahydrocyclopenta[c]pyrrol-(1H)-yl, (3aR,5r,6aS)-hexahydrocyclopenta[c]pyrrol-(1H)-yl, 1,3-dihydro-2H-isoindolyl, octahydro-2H-isoindolyl, (3aS)-1,3,3a,4,5,6-hexahydro-2H-isoindolyl, (3aR,4R,7aS)-1H-isoindol-(3H,3aH,4H,5H,6H,7H,7aH)-yl, (3aR,7aS)-octahydro-2H- isoindolyl, (3aR,4R,7aS)-octahydro-2H-isoindolyl, (3aR,4S,7aS)-octahydro-2H-isoindolyl, 2,5-diazabicyclo[2.2.1]heptanyl, 2-azabicyclo[2.2.1]hept-5-enyl, 3-azabicyclo[3.1.0]hexanyl, (1R,5S,6s)-3-azabicyclo[3.1.0]hexanyl, (cis,cis)-3-azabicyclo[3.1.0]hexanyl, 3,6-diazabicyclo[3.1.0]hexanyl, (1S,5R,6R)-3-azabicyclo[3.2.0]heptanyl, (1S,5R,6S)-3-azabicyclo[3.2.0]heptanyl, 5-azaspiro[2.4]heptanyl, 2,6-diazaspiro[3.3]heptanyl, 2,5-diazaspiro[3.4]octanyl, 2,6-diazaspiro[3.4]octanyl, 2,7-diazaspiro[3.5]nonanyl, 2,7-diazaspiro[4.4]nonanyl, 2-azaspiro[4.5]decanyl or 2,8-diazaspiro[4.5]decanyl.

7. The compound of claim 1, wherein $R_6$ is
heteroaryl selected in each instance, when present, from pyridin-2-yl, pyridin-3-yl or pyridin-4-yl;
heterocyclyl selected in each instance, when present, from azetidin-1-yl, pyrrolidin-1-yl, pyrrolidin-2-yl, pyrrolidin-3-yl, tetrahydrofuran-2-yl, piperidin-1-yl, piperidin-2-yl, piperidin-3-yl, piperidin-4-yl, piperazin-1-yl, piperazin-2-yl, morpholin-4-yl, 1,4-diazepan-1-yl, 1,3-dioxolan-2-yl, dihydro-1H-imidazol-2-yl, 1,4,5,6-tetrahydropyrimidin-2-yl, 1,2,3,6-tetrahydropyridin-4-yl, tetrahydro-2H-pyran-2-yl, tetrahydro-2H-pyran-4-yl, 3,4-dihydroisoquinolin-2(1H)-yl, 1,2,3,4-tetrahydroisoquinolin-1-yl, 5H-pyrrolo[3,4-b]pyridin-6(7H)-yl, tetrahydro-1H-pyrrolo[3,4-b]pyridin-6(2H,7H,7aH)-yl, (3aR,4R,6aS)-hexahydrocyclopenta[c]pyrrol-2(1H)-yl, (3aR,4R,7aS)-1H-isoindol-2(3H,3aH,4H,5H,6H,7H,7aH)-yl, 2,5-diazabicyclo[2.2.1]heptan-2-yl, (1R,5S,6s)-3-azabicyclo[3.1.0]hexan-3-yl or (1R,5S,6s)-3-azabicyclo[3.1.0]hexan-6-yl.

8. The compound of claim 1, wherein $R_7$ is
$C_{3-14}$cycloalkyl, wherein $C_{3-14}$cycloalkyl is selected from cyclopropyl or cyclobutyl;
$C_{3-14}$cycloalkyl-amino, wherein $C_{3-14}$cycloalkyl is selected from cyclopropyl;
aryl, wherein aryl is selected from phenyl;
aryl-$C_{1-8}$alkyl, wherein aryl is selected from phenyl;
aryl-amino, wherein aryl is selected from phenyl;
(aryl,$C_{1-8}$alkyl)amino, wherein aryl is selected from phenyl;
aryl-$C_{1-8}$alkyl-amino, wherein aryl is selected from phenyl;
(aryl-$C_{1-8}$ alkyl, $C_{1-8}$ alkyl)amino, wherein aryl is selected from phenyl;
(aryl-$C_{1-8}$alkyl)$_2$-amino, wherein aryl is selected from phenyl;
aryl-$C_{1-8}$alkyl-amino-$C_{1-8}$alkyl, wherein aryl is selected from phenyl;
(aryl-$C_{1-8}$alkyl, $C_{1-8}$alkyl)amino-$C_{1-8}$alkyl, wherein aryl is selected from phenyl;
(aryl-$C_{1-8}$alkyl)$_2$-amino-$C_{1-8}$alkyl, wherein aryl is selected from phenyl;
aryl-amino-$C_{1-8}$alkyl, wherein aryl is selected from phenyl;
aryl-$C_{1-8}$alkoxy, wherein aryl is selected from phenyl;
aryl-$C_{1-8}$alkoxy-carbonyl-amino, wherein aryl is selected from phenyl;
heteroaryl, wherein heteroaryl is selected from pyridin-2-yl, pyridin-4-yl, thiazol-2-yl or 1H-1,2,3-triazol-1-yl;
heteroaryl-$C_{1-8}$alkyl-amino-$C_{1-8}$alkyl, wherein heteroaryl is selected from pyridin-2-yl, pyridin-3-yl or pyridin-4-yl;
heterocyclyl, wherein heterocyclyl is selected from pyrrolidin-1-yl, piperidin-1-yl or morpholin-4-yl;
heterocyclyl-$C_{1-8}$alkyl, wherein heterocyclyl is selected from pyrrolidin-1-yl;
heterocyclyl-amino-$C_{1-8}$alkyl, wherein heterocyclyl is selected from (1R,5S,6s)-3-azabicyclo[3.1.0]hexan-6-yl; and,
heterocyclyl-oxy, wherein heterocyclyl is selected from tetrahydro-2H-pyran-2-yl-oxy.

9. The compound of claim 1, wherein the compound or a form thereof is selected from:
5-ethyl-6-(1-methyl-1,2,3,4-tetrahydroquinolin-6-yl)-2-oxo-1,2-dihydropyridine-3-carboxylic acid
5-ethyl-4-hydroxy-6-(1-methyl-1,2,3,4-tetrahydroquinolin-6-yl)-2-oxo-1,2-dihydropyridine-3-carboxylic acid
5-ethyl-6-(4-methyl-3,4-dihydro-2H-benzo[b][1,4]oxazin-7-yl)-2-oxo-1,2-dihydropyridine-3-carboxylic acid
5-ethyl-4-hydroxy-6-(4-methyl-3,4-dihydro-2H-benzo[b][1,4]oxazin-7-yl)-2-oxo-1,2-dihydropyridine-3-carboxylic acid
5-ethyl-6-(1-methylindolin-5-yl)-2-oxo-1,2-dihydropyridine-3-carboxylic acid
5-ethyl-4-hydroxy-6-(1-methylindolin-5-yl)-2-oxo-1,2-dihydropyridine-3-carboxylic acid
5-ethyl-6-(1-methyl-1H-indol-6-yl)-2-oxo-1,2-dihydropyridine-3-carboxylic acid
5-ethyl-4-hydroxy-6-(1-methyl-1H-indol-6-yl)-2-oxo-1,2-dihydropyridine-3-carboxylic acid
5-ethyl-6-(1-ethyl-1H-indol-5-yl)-2-oxo-1,2-dihydropyridine-3-carboxylic acid
5-ethyl-6-(1-ethyl-1H-indol-5-yl)-4-hydroxy-2-oxo-1,2-dihydropyridine-3-carboxylic acid
5-ethyl-4-hydroxy-6-(3-methyl-2-oxo-2,3-dihydrobenzo[d]oxazol-6-yl)-2-oxo-1,2-dihydropyridine-3-carboxylic acid
5-ethyl-4-hydroxy-6-(2-methylbenzo[d]oxazol-6-yl)-2-oxo-1,2-dihydropyridine-3-carboxylic acid
5-ethyl-6-(1-methyl-1H-indol-3-yl)-2-oxo-1,2-dihydropyridine-3-carboxylic acid
5-ethyl-4-hydroxy-6-(1-methyl-1H-indol-3-yl)-2-oxo-1,2-dihydropyridine-3-carboxylic acid
5-ethyl-2-oxo-6-(2-phenylbenzo[d]oxazol-6-yl)-1,2-dihydropyridine-3-carboxylic acid
5-ethyl-4-hydroxy-2-oxo-6-(2-phenylbenzo[d]oxazol-6-yl)-1,2-dihydropyridine-3-carboxylic acid
6-(2-(dimethylamino)benzo[d]oxazol-6-yl)-5-ethyl-2-oxo-1,2-dihydropyridine-3-carboxylic acid
6-(2-(dimethylamino)benzo[d]oxazol-6-yl)-5-ethyl-4-hydroxy-2-oxo-1,2-dihydropyridine-3-carboxylic acid
5-ethyl-2-oxo-6-(quinolin-6-yl)-1,2-dihydropyridine-3-carboxylic acid
5-ethyl-4-hydroxy-2-oxo-6-(quinolin-6-yl)-1,2-dihydropyridine-3-carboxylic acid
5-ethyl-6-(1-methyl-1H-indol-5-yl)-2-oxo-1,2-dihydropyridine-3-carboxylic acid
5-ethyl-4-hydroxy-6-(1-methyl-1H-indol-5-yl)-2-oxo-1,2-dihydropyridine-3-carboxylic acid
5-ethyl-6-(1-(2-hydroxyethyl)-1H-indol-5-yl)-2-oxo-1,2-dihydropyridine-3-carboxylic acid
5-ethyl-4-hydroxy-6-(1-(2-hydroxyethyl)-1H-indol-5-yl)-2-oxo-1,2-dihydropyridine-3-carboxylic acid
6-(1-((1,3-dioxolan-2-yl)methyl)-1H-indol-5-yl)-5-ethyl-2-oxo-1,2-dihydropyridine-3-carboxylic acid
6-(1-((1,3-dioxolan-2-yl)methyl)-1H-indol-5-yl)-5-ethyl-4-hydroxy-2-oxo-1,2-dihydropyridine-3-carboxylic acid
5-ethyl-6-(9-methyl-2,3,4,9-tetrahydro-1H-carbazol-6-yl)-2-oxo-1,2-dihydropyridine-3-carboxylic acid 5-ethyl-4-hydroxy-6-(9-methyl-2,3,4,9-tetrahydro-1H-carbazol-6-yl)-2-oxo-1,2-dihydropyridine-3-carboxylic acid
5-ethyl-2-oxo-6-(1,2,3-trimethyl-1H-indol-5-yl)-1,2-dihydropyridine-3-carboxylic acid
5-ethyl-4-hydroxy-2-oxo-6-(1,2,3-trimethyl-1H-indol-5-yl)-1,2-dihydropyridine-3-carboxylic acid
5-ethyl-6-(1-methyl-1H-pyrrolo[2,3-b]pyridin-5-yl)-2-oxo-1,2-dihydropyridine-3-carboxylic acid
5-ethyl-4-hydroxy-6-(1-methyl-1H-pyrrolo[2,3-b]pyridin-5-yl)-2-oxo-1,2-dihydropyridine-3-carboxylic acid
5-isopropyl-6-(1-methyl-1H-indol-5-yl)-2-oxo-1,2-dihydropyridine-3-carboxylic acid
4-hydroxy-5-isopropyl-6-(1-methyl-1H-indol-5-yl)-2-oxo-1,2-dihydropyridine-3-carboxylic acid
5-cyclopropyl-6-(1-methyl-1H-indol-5-yl)-2-oxo-1,2-dihydropyridine-3-carboxylic acid
5-cyclopropyl-4-hydroxy-6-(1-methyl-1H-indol-5-yl)-2-oxo-1,2-dihydropyridine-3-carboxylic acid
6-(1,2-dimethyl-1H-indol-5-yl)-5-ethyl-2-oxo-1,2-dihydropyridine-3-carboxylic acid
6-(1,2-dimethyl-1H-indol-5-yl)-5-ethyl-4-hydroxy-2-oxo-1,2-dihydropyridine-3-carboxylic acid
5-ethyl-6-(2-(hydroxymethyl)-1-methyl-1H-indol-5-yl)-2-oxo-1,2-dihydropyridine-3-carboxylic acid
5-ethyl-4-hydroxy-6-(2-(hydroxymethyl)-1-methyl-1H-indol-5-yl)-2-oxo-1,2-dihydropyridine-3-carboxylic acid
5-ethyl-6-(1-methyl-1H-indazol-5-yl)-2-oxo-1,2-dihydropyridine-3-carboxylic acid
5-ethyl-4-hydroxy-6-(1-methyl-1H-indazol-5-yl)-2-oxo-1,2-dihydropyridine-3-carboxylic acid
5-ethyl-6-(3-methyl-3H-imidazo[4,5-b]pyridin-6-yl)-2-oxo-1,2-dihydropyridine-3-carboxylic acid
5-ethyl-6-(1-methyl-1H-benzo[d]imidazol-5-yl)-2-oxo-1,2-dihydropyridine-3-carboxylic acid
5-(5-carboxy-3-ethyl-6-oxo-1,6-dihydropyridin-2-yl)-1-methyl-1H-pyrrolo[2,3-c]pyridine-2-carboxylic acid
5-ethyl-2-oxo-6-(1H-pyrrolo[2,3-b]pyridin-5-yl)-1,2-dihydropyridine-3-carboxylic acid
6-(1,4-dimethyl-1,2,3,4-tetrahydroquinoxalin-6-yl)-5-ethyl-2-oxo-1,2-dihydropyridine-3-carboxylic acid
5-ethyl-2-oxo-6-(quinoxalin-6-yl)-1,2-dihydropyridine-3-carboxylic acid
5-ethyl-6-(4-methyl-3,4-dihydro-2H-pyrido[3,2-b][1,4]oxazin-7-yl)-2-oxo-1,2-dihydropyridine-3-carboxylic acid
6-(3-cyano-1-methyl-1H-pyrrolo[2,3-b]pyridin-5-yl)-5-ethyl-2-oxo-1,2-dihydropyridine-3-carboxylic acid
5-ethyl-2-oxo-6-(1,2,3,4-tetrahydropyrazino[1,2-a]indol-8-yl)-1,2-dihydropyridine-3-carboxylic acid
(R)-5-ethyl-6-(1-methyl-2-(1-methylpyrrolidin-2-yl)-1H-indol-5-yl)-2-oxo-1,2-dihydropyridine-3-carboxylic acid
6-(3-cyano-1-methyl-1H-indol-5-yl)-5-ethyl-2-oxo-1,2-dihydropyridine-3-carboxylic acid
6-(3-carbamoyl-1-methyl-1H-indol-5-yl)-5-ethyl-2-oxo-1,2-dihydropyridine-3-carboxylic acid
6-(3-(aminomethyl)-1-methyl-1H-indol-5-yl)-5-ethyl-2-oxo-1,2-dihydropyridine-3-carboxylic acid
6-(3-((dimethylamino)methyl)-1-methyl-1H-indol-5-yl)-5-ethyl-2-oxo-1,2-dihydropyridine-3-carboxylic acid
6-(3-((diethylamino)methyl)-1-methyl-1H-indol-5-yl)-5-ethyl-2-oxo-1,2-dihydropyridine-3-carboxylic acid
6-(3-((dibenzylamino)methyl)-1-methyl-1H-indol-5-yl)-5-ethyl-2-oxo-1,2-dihydropyridine-3-carboxylic acid
5-ethyl-6-(1-methyl-2-(pyrrolidin-1-ylmethyl)-1H-pyrrolo[3,2-b]pyridin-5-yl)-2-oxo-1,2-dihydropyridine-3-carboxylic acid
6-(2-(4,5-dihydro-1H-imidazol-2-yl)-1-methyl-1H-indol-5-yl)-5-ethyl-2-oxo-1,2-dihydropyridine-3-carboxylic acid
5-ethyl-6-(1-methyl-2-(1,4,5,6-tetrahydropyrimidin-2-yl)-1H-indol-5-yl)-2-oxo-1,2-dihydropyridine-3-carboxylic acid
6-(2-(2-(dimethylamino)propan-2-yl)-1-methyl-1H-indol-5-yl)-5-ethyl-2-oxo-1,2-dihydropyridine-3-carboxylic acid
5-ethyl-6-(1-methyl-2-(2-(pyrrolidin-1-yl)propan-2-yl)-1H-indol-5-yl)-2-oxo-1,2-dihydropyridine-3-carboxylic acid
6-(1,6-dimethyl-2-(pyrrolidin-1-ylmethyl)-1H-indol-5-yl)-5-ethyl-2-oxo-1,2-dihydropyridine-3-carboxylic acid
6-(1,6-dimethyl-2-(piperidin-1-ylmethyl)-1H-indol-5-yl)-5-ethyl-2-oxo-1,2-dihydropyridine-3-carboxylic acid
6-(6-chloro-1-methyl-2-(morpholinomethyl)-1H-indol-5-yl)-5-ethyl-2-oxo-1,2-dihydropyridine-3-carboxylic acid
6-(6-chloro-2-((diethylamino)methyl)-1-methyl-1H-indol-5-yl)-5-ethyl-2-oxo-1,2-dihydropyridine-3-carboxylic acid
6-(6-chloro-2-((dimethylamino)methyl)-1-methyl-1H-indol-5-yl)-5-ethyl-2-oxo-1,2-dihydropyridine-3-carboxylic acid
6-(1,6-dimethyl-2-(morpholinomethyl)-1H-indol-5-yl)-5-ethyl-2-oxo-1,2-dihydropyridine-3-carboxylic acid
6-(2-((diethylamino)methyl)-1,6-dimethyl-1H-indol-5-yl)-5-ethyl-2-oxo-1,2-dihydropyridine-3-carboxylic acid
6-(2-((dimethylamino)methyl)-1,6-dimethyl-1H-indol-5-yl)-5-ethyl-2-oxo-1,2-dihydropyridine-3-carboxylic acid
5-ethyl-6-(7-fluoro-1-methyl-2-(pyrrolidin-1-ylmethyl)-1H-indol-5-yl)-2-oxo-1,2-dihydropyridine-3-carboxylic acid
5-ethyl-6-(7-fluoro-1-methyl-2-(morpholinomethyl)-1H-indol-5-yl)-2-oxo-1,2-dihydropyridine-3-carboxylic acid
6-(1,7-dimethyl-2-(pyrrolidin-1-ylmethyl)-1H-indol-5-yl)-5-ethyl-2-oxo-1,2-dihydropyridine-3-carboxylic acid
6-(1,7-dimethyl-2-(piperidin-1-ylmethyl)-1H-indol-5-yl)-5-ethyl-2-oxo-1,2-dihydropyridine-3-carboxylic acid
6-(2-((diethylamino)methyl)-7-fluoro-1-methyl-1H-indol-5-yl)-5-ethyl-2-oxo-1,2-dihydropyridine-3-carboxylic acid
5-ethyl-6-(7-fluoro-1-methyl-2-(piperidin-1-ylmethyl)-1H-indol-5-yl)-2-oxo-1,2-dihydropyridine-3-carboxylic acid
6-(1,7-dimethyl-2-(morpholinomethyl)-1H-indol-5-yl)-5-ethyl-2-oxo-1,2-dihydropyridine-3-carboxylic acid
6-(2-((diethylamino)methyl)-1,7-dimethyl-1H-indol-5-yl)-5-ethyl-2-oxo-1,2-dihydropyridine-3-carboxylic acid
6-(2-((dimethylamino)methyl)-1,7-dimethyl-1H-indol-5-yl)-5-ethyl-2-oxo-1,2-dihydropyridine-3-carboxylic acid
6-(2-((dimethylamino)methyl)-7-fluoro-1-methyl-1H-indol-5-yl)-5-ethyl-2-oxo-1,2-dihydropyridine-3-carboxylic acid 5-ethyl-6-(6-methoxy-1-methyl-2-(pyrrolidin-1-ylmethyl)-1H-indol-5-yl)-2-oxo-1,2-dihydropyridine-3-carboxylic acid 5-ethyl-6-(6-methoxy-1-methyl-2-(morpholinomethyl)-1H-indol-5-yl)-2-oxo-1,2-dihydropyridine-3-carboxylic acid 6-(2-(azetidin-1-ylmethyl)-1-methyl-1H-indol-5-yl)-5-ethyl-2-oxo-1,2-dihydropyridine-3,4-dicarboxylic acid 5-ethyl-6-(1-methyl-2-(pyrrolidin-1-ylmethyl)-1H-indol-5-yl)-2-oxo-1,2-dihydropyridine-3,4-dicarboxylic acid 6-(2-((dimethylamino)methyl)-1-methyl-1H-indol-5-yl)-5-ethyl-2-oxo-1,2-dihydropyridine-3,4-dicarboxylic acid 5-ethyl-6-(1-methyl-2-((methylamino)methyl)-1H-indol-5-yl)-2-oxo-1,2-dihydropyridine-3-carboxylic acid 6-(2-((tert-butylamino)methyl)-1-methyl-1H-indol-5-yl)-5-ethyl-2-oxo-1,2-dihydropyridine-3-carboxylic acid 6-(2-((benzylamino)methyl)-1-methyl-1H-indol-5-yl)-5-ethyl-2-oxo-1,2-dihydropyridine-3-carboxylic acid 5-ethyl-6-(1-methyl-2-((2-phenylpropan-2-ylamino)methyl)-1H-indol-5-yl)-2-oxo-1,2-dihydropyridine-3-carboxylic acid (R)-5-ethyl-6-(1-methyl-2-((1-phenylethylamino)methyl)-1H-indol-5-yl)-2-oxo-1,2-dihydropyridine-3-carboxylic acid (S)-5-ethyl-6-(1-methyl-2-((1-phenylethylamino)methyl)-1H-indol-5-yl)-2-oxo-1,2-dihydropyridine-3-carboxylic acid (R)-5-ethyl-6-(1-methyl-2-((1-phenylpropylamino)methyl)-1H-indol-5-yl)-2-oxo-1,2-dihydropyridine-3-carboxylic acid (S)-5-ethyl-6-(1-methyl-2-((1-phenylpropylamino)methyl)-1H-indol-5-yl)-2-oxo-1,2-dihydropyridine-3-carboxylic acid 5-ethyl-6-(1-methyl-2-((pyridin-2-ylmethylamino)methyl)-1H-indol-5-yl)-2-oxo-1,2-dihydropyridine-3-carboxylic acid 6-(2-((benzyl(methyl)amino)methyl)-1-methyl-1H-indol-5-yl)-5-ethyl-2-oxo-1,2-dihydropyridine-3-carboxylic acid 6-(2-((dimethylamino)methyl)-1-methyl-1H-indol-5-yl)-5-ethyl-2-oxo-1,2-dihydropyridine-3-carboxylic acid 6-(2-((diethylamino)methyl)-1-methyl-1H-indol-5-yl)-5-ethyl-2-oxo-1,2-dihydropyridine-3-carboxylic acid 5-ethyl-6-(1-methyl-2-(pyrrolidin-1-ylmethyl)-1H-indol-5-yl)-2-oxo-1,2-dihydropyridine-3-carboxylic acid 5-ethyl-6-(2-((3-hydroxypyrrolidin-1-yl)methyl)-1-methyl-1H-indol-5-yl)-2-oxo-1,2-dihydropyridine-3-carboxylic acid (S)-6-(2-((3-aminopyrrolidin-1-yl)methyl)-1-methyl-1H-indol-5-yl)-5-ethyl-2-oxo-1,2-dihydropyridine-3-carboxylic acid 5-ethyl-6-(1-methyl-2-((3-(methylamino)pyrrolidin-1-yl)methyl)-1H-indol-5-yl)-2-oxo-1,2-dihydropyridine-3-carboxylic acid 6-(2-((3-(dimethylamino)pyrrolidin-1-yl)methyl)-1-methyl-1H-indol-5-yl)-5-ethyl-2-oxo-1,2-dihydropyridine-3-carboxylic acid (R)-5-ethyl-6-(2-((3-fluoropyrrolidin-1-yl)methyl)-1-methyl-1H-indol-5-yl)-2-oxo-1,2-dihydropyridine-3-carboxylic acid 5-ethyl-6-(1-methyl-2-((2-methylpyrrolidin-1-yl)methyl)-1H-indol-5-yl)-2-oxo-1,2-dihydropyridine-3-carboxylic acid 5-ethyl-6-(1-methyl-2-((2-phenylpyrrolidin-1-yl)methyl)-1H-indol-5-yl)-2-oxo-1,2-dihydropyridine-3-carboxylic acid (R)-5-ethyl-6-(2-((2-(hydroxymethyl)pyrrolidin-1-yl)methyl)-1-methyl-1H-indol-5-yl)-2-oxo-1,2-dihydropyridine-3-carboxylic acid 5-ethyl-6-(1-methyl-2-(piperidin-1-ylmethyl)-1H-indol-5-yl)-2-oxo-1,2-dihydropyridine-3-carboxylic acid 6-(2-((3,4-dihydroisoquinolin-2(1H)-yl)methyl)-1-methyl-1H-indol-5-yl)-5-ethyl-2-oxo-1,2-dihydropyridine-3-carboxylic acid 6-(2-((5H-pyrrolo[3,4-b]pyridin-6(7H)-yl)methyl)-1-methyl-1H-indol-5-yl)-5-ethyl-2-oxo-1,2-dihydropyridine-3-carboxylic acid 5-ethyl-6-(1-methyl-2-((tetrahydro-1H-pyrrolo[3,4-b]pyridin-6(2H,7H,7aH)-yl)methyl)-1H-indol-5-yl)-2-oxo-1,2-dihydropyridine-3-carboxylic acid 5-ethyl-6-(1-methyl-2-(morpholinomethyl)-1H-indol-5-yl)-2-oxo-1,2-dihydropyridine-3-carboxylic acid 6-(2-((cis-2,6-dimethylmorpholino)methyl)-1-methyl-1H-indol-5-yl)-5-ethyl-2-oxo-1,2-dihydropyridine-3-carboxylic acid 5-ethyl-6-(1-methyl-2-(piperazin-1-ylmethyl)-1H-indol-5-yl)-2-oxo-1,2-dihydropyridine-3-carboxylic acid 5-ethyl-6-(1-methyl-2-((4-methylpiperazin-1-yl)methyl)-1H-indol-5-yl)-2-oxo-1,2-dihydropyridine-3-carboxylic acid 5-ethyl-6-(2-((4-isopropylpiperazin-1-yl)methyl)-1-methyl-1H-indol-5-yl)-2-oxo-1,2-dihydropyridine-3-carboxylic acid 6-(2-(2,5-diazabicyclo[2.2.1]heptan-2-ylmethyl)-1-methyl-1H-indol-5-yl)-5-ethyl-2-oxo-1,2-dihydropyridine-3-carboxylic acid 6-(2-(((1R,5S,6s)-6-(dibenzylamino)-3-azabicyclo[3.1.0]hexan-3-yl)methyl)-1-methyl-1H-indol-5-yl)-5-ethyl-2-oxo-1,2-dihydropyridine-3-carboxylic acid 6-(2-((4-acetylpiperazin-1-yl)methyl)-1-methyl-1H-indol-5-yl)-5-ethyl-2-oxo-1,2-dihydropyridine-3-carboxylic acid 5-ethyl-6-(1-methyl-2-((N-methylacetamido)methyl)-1H-indol-5-yl)-2-oxo-1,2-dihydropyridine-3-carboxylic acid 6-(2-(((3aR,4R,7aS)-4-(benzyl(methyl)amino)-1H-isoindol-2(3H,3aH,4H,5H,6H,7H,7aH)-yl)methyl)-1-methyl-1H-indol-5-yl)-5-ethyl-2-oxo-1,2-dihydropyridine-3-carboxylic acid 6-(2-(((3aR,4R,6aS)-4-(dimethylamino)hexahydrocyclopenta[c]pyrrol-2(1H)-yl)methyl)-1-methyl-1H-indol-5-yl)-5-ethyl-2-oxo-1,2-dihydropyridine-3-carboxylic acid 5-ethyl-6-(1-methyl-2-(((3aR,4R,7aS)-4-(methylamino)-1H-isoindol-2(3H,3aH,4H,5H,6H,7H,7aH)-yl)methyl)-1H-indol-5-yl)-2-oxo-1,2-dihydropyridine-3-carboxylic acid 6-(2-(((3aR,4R,7aS)-4-(dimethylamino)-1H-isoindol-2(3H,3aH,4H,5H,6H,7H,7aH)-yl)methyl)-1-methyl-1H-indol-5-yl)-5-ethyl-2-oxo-1,2-dihydropyridine-3-carboxylic acid 6-(2-(aminomethyl)-1-methyl-1H-indol-5-yl)-5-ethyl-2-oxo-1,2-dihydropyridine-3-carboxylic acid 5-ethyl-2-oxo-6-(1-(pyrrolidin-1-yl)-2,3-dihydro-1H-pyrrolo[1,2-a]indol-7-yl)-1,2-dihydropyridine-3-carboxylic acid 6-(1-(dimethylamino)-2,3-dihydro-1H-pyrrolo[1,2-a]indol-7-yl)-5-ethyl-2-oxo-1,2-dihydropyridine-3-carboxylic acid 6-(1-(3-(dimethylamino)pyrrolidin-1-yl)-2,3-dihydro-1H-pyrrolo[1,2-a]indol-7-yl)-5-ethyl-2-oxo-1,2-dihydropyridine-3-carboxylic acid 5-ethyl-2-oxo-6-(1-(piperidin-1-yl)-2,3-dihydro-1H-pyrrolo[1,2-a]indol-7-yl)-1,2-dihydropyridine-3-carboxylic acid 5-ethyl-6-(1-morpholino-2,3-dihydro-1H-pyrrolo[1,2-a]indol-7-yl)-2-oxo-1,2-dihydropyridine-3-carboxylic acid 5-ethyl-6-(1-methyl-2-(1-(pyrrolidin-1-yl)ethyl)-1H-indol-5-yl)-2-oxo-1,2-dihydropyridine-3-carboxylic acid 5-ethyl-6-(4-fluoro-1-methyl-2-(pyrrolidin-1-ylmethyl)-1H-indol-5-yl)-2-oxo-1,2-dihydropyridine-3-carboxylic acid 5-ethyl-6-(1-methyl-2-(2-(pyrrolidin-1-yl)ethyl)-1H-indol-5-yl)-2-oxo-1,2-dihydropyridine-3-carboxylic acid 5-ethyl-6-(1-methyl-2-(2-(piperidin-1-yl)ethyl)-1H-indol-5-yl)-2-oxo-1,2-dihydropyridine-3-carboxylic acid 6-(2-(2-(dimethylamino)ethyl)-1-methyl-1H-indol-5-yl)-5-ethyl-2-oxo-1,2-dihydropyridine-3-carboxylic acid 5-ethyl-6-(1-methyl-2-(2-morpholinoethyl)-1H-indol-5-yl)-2-oxo-1,2-dihydropyridine-3-carboxylic acid 5-ethyl-4-hydroxy-6-(1-methyl-2-(pyrrolidin-1-ylmethyl)-1H-indol-5-yl)-2-oxo-1,2-dihydropyridine-3-carboxylic acid 5-ethyl-6-(2-((ethylamino)methyl)-1-methyl-1H-indol-5-yl)-4-hydroxy-2-oxo-1,2-dihydropyridine-3-carboxylic acid 6-(2-((dimethylamino)methyl)-1-methyl-1H-indol-5-yl)-5-ethyl-4-hydroxy-2-oxo-1,2-dihydropyridine-3-carboxylic acid 6-(2-((diethylamino)methyl)-1-methyl-1H-indol-5-yl)-5-ethyl-4-hydroxy-2-oxo-1,2-dihydropyridine-3-carboxylic acid 5-ethyl-4-hydroxy-6-(1-methyl-2-(morpholinomethyl)-1H-indol-5-yl)-2-oxo-1,2-dihydropyridine-3-carboxylic acid 5-ethyl-4-hydroxy-6-(1-methyl-2-((4-methylpiperazin-1-yl)methyl)-1H-indol-5-yl)-2-oxo-1,2-dihydropyridine-3-carboxylic acid 5-ethyl-4-hydroxy-6-(1-methyl-2-(((3S,5R)-3,4,5-trimethylpiperazine-1-yl)methyl)-1H-indol-5-yl)-2-oxo-1,2-dihydropyridine-3-carboxylic acid 5-ethyl-4-hydroxy-6-(1-methyl-2-(piperazin-1-ylmethyl)-1H-indol-5-yl)-2-oxo-1,2-dihydropyridine-3-carboxylic acid 6-(2-(((2S,6R)-2,6-dimethylmorpholino)methyl)-1-methyl-1H-indol-5-yl)-5-ethyl-4-hydroxy-2-oxo-1,2-dihydropyridine-3-carboxylic acid 5-ethyl-4-hydroxy-6-(1-methyl-2-((2-methylpyrrolidin-1-yl)methyl)-1H-indol-5-yl)-2-oxo-1,2-dihydropyridine-3-carboxylic acid 5-ethyl-4-hydroxy-6-(2-((4-isopropylpiperazin-1-yl)methyl)-1-methyl-1H-indol-5-yl)-2-oxo-1,2-dihydropyridine-3-carboxylic acid 6-(2-((4-acetylpiperazin-1-yl)methyl)-1-methyl-1H-indol-5-yl)-5-ethyl-4-hydroxy-2-oxo-1,2-dihydropyridine-3-carboxylic acid 6-(2-((3,3-difluoropyrrolidin-1-yl)methyl)-1-methyl-1H-indol-5-yl)-5-ethyl-4-hydroxy-2-oxo-1,2-dihydropyridine-3-carboxylic acid (R)-5-ethyl-6-(2-((3-fluoropyrrolidin-1-yl)methyl)-1-methyl-1H-indol-5-yl)-4-hydroxy-2-oxo-1,2-dihydropyridine-3-carboxylic acid 5-ethyl-4-hydroxy-6-(2-((3-hydroxypyrrolidin-1-yl)methyl)-1-methyl-1H-indol-5-yl)-2-oxo-1,2-dihydropyridine-3-carboxylic acid 5-ethyl-4-hydroxy-6-(2-((3-methoxypyrrolidin-1-yl)methyl)-1-methyl-1H-indol-5-yl)-2-oxo-1,2-dihydropyridine-3-carboxylic acid (S)-6-(2-((3-aminopyrrolidin-1-yl)methyl)-1-methyl-1H-indol-5-yl)-5-ethyl-4-hydroxy-2-oxo-1,2-dihydropyridine-3-carboxylic acid 5-ethyl-4-hydroxy-6-(1-methyl-2-((3-(methylamino)pyrrolidin-1-yl)methyl)-1H-indol-5-yl)-2-oxo-1,2-dihydropyridine-3-carboxylic acid 6-(2-(2,5-diazabicyclo[2.2.1]heptan-2-ylmethyl)-1-methyl-1H-indol-5-yl)-5-ethyl-4-hydroxy-2-oxo-1,2-dihydropyridine-3-carboxylic acid 6-(2-((3-acetamidopyrrolidin-1-yl)methyl)-1-methyl-1H-indol-5-yl)-5-ethyl-4-hydroxy-2-oxo-1,2-dihydropyridine-3-carboxylic acid 5-ethyl-4-hydroxy-6-(1-methyl-2-((tetrahydro-1H-pyrrolo[3,4-b]pyridin-6(2H,7H,7aH)-yl)methyl)-1H-indol-5-yl)-2-oxo-1,2-dihydropyridine-3-carboxylic acid 6-(2-((3-(2-aminopropan-2-yl)pyrrolidin-1-yl)methyl)-1-methyl-1H-indol-5-yl)-5-ethyl-4-hydroxy-2-oxo-1,2-dihydropyridine-3-carboxylic acid 6-(2-(azetidin-1-ylmethyl)-1-methyl-1H-indol-5-yl)-5-ethyl-4-hydroxy-2-oxo-1,2-dihydropyridine-3-carboxylic acid 5-ethyl-4-hydroxy-6-(2-((3-hydroxyazetidin-1-yl)methyl)-1-methyl-1H-indol-5-yl)-2-oxo-1,2-dihydropyridine-3-carboxylic acid 6-(2-((3-aminoazetidin-1-yl)methyl)-1-methyl-1H-indol-5-yl)-5-ethyl-4-hydroxy-2-oxo-1,2-dihydropyridine-3-carboxylic acid 6-(2-((3-(dimethylamino)azetidin-1-yl)methyl)-1-methyl-1H-indol-5-yl)-5-ethyl-4-hydroxy-2-oxo-1,2-dihydropyridine-3-carboxylic acid (S)-5-ethyl-4-hydroxy-6-(2-((2-(methoxycarbonyl)pyrrolidin-1-yl)methyl)-1-methyl-1H-indol-5-yl)-2-oxo-1,2-dihydropyridine-3-carboxylic acid 6-(2-((3-(dimethylcarbamoyl)pyrrolidin-1-yl)methyl)-1-methyl-1H-indol-5-yl)-5-ethyl-4-hydroxy-2-oxo-1,2-dihydropyridine-3-carboxylic acid 5-ethyl-4-hydroxy-6-(1-methyl-2-(piperidin-1-ylmethyl)-1H-indol-5-yl)-2-oxo-1,2-dihydropyridine-3-carboxylic acid 6-(2-((tert-butylamino)methyl)-1-methyl-1H-indol-5-yl)-5-ethyl-4-hydroxy-2-oxo-1,2-dihydropyridine-3-carboxylic acid 5-ethyl-6-(2-((3-fluoroazetidin-1-yl)methyl)-1-methyl-1H-indol-5-yl)-4-hydroxy-2-oxo-1,2-dihydropyridine-3-carboxylic acid 6-(2-((3,3-difluoroazetidin-1-yl)methyl)-1-methyl-1H-indol-5-yl)-5-ethyl-4-hydroxy-2-oxo-1,2-dihydropyridine-3-carboxylic acid 6-(2-(((1R,5S,6s)-6-(dibenzylamino)-3-azabicyclo[3.1.0]hexan-3-yl)methyl)-1-methyl-1H-indol-5-yl)-5-ethyl-4-hydroxy-2-oxo-1,2-dihydropyridine-3-carboxylic acid 6-(2-(((1R,5S,6s)-6-(dimethylamino)-3-azabicyclo[3.1.0]hexan-3-yl)methyl)-1-methyl-1H-indol-5-yl)-5-ethyl-4-hydroxy-2-oxo-1,2-dihydropyridine-3-carboxylic acid 6-(2-(((1R,5S,6s)-3-azabicyclo[3.1.0]hexan-6-ylamino)methyl)-1-methyl-1H-indol-5-yl)-5-ethyl-4-hydroxy-2-oxo-1,2-dihydropyridine-3-carboxylic acid 5-ethyl-4-hydroxy-6-(2-((isopropylamino)methyl)-1-methyl-1H-indol-5-yl)-2-oxo-1,2-dihydropyridine-3-carboxylic acid 6-(2-((3-(dimethylamino)pyrrolidin-1-yl)methyl)-1-methyl-1H-indol-5-yl)-5-ethyl-4-hydroxy-2-oxo-1,2-dihydropyridine-3-carboxylic acid 5-ethyl-6-(2-((2-fluoroethylamino)methyl)-1-methyl-1H-indol-5-yl)-4-hydroxy-2-oxo-1,2-dihydropyridine-3-carboxylic acid 6-(2-((2-((dimethylamino)methyl)pyrrolidin-1-yl)methyl)-1-methyl-1H-indol-5-yl)-5-ethyl-4-hydroxy-2-oxo-1,2-dihydropyridine-3-carboxylic acid 5-ethyl-4-hydroxy-6-(1-methyl-2-((methylamino)methyl)-1H-indol-5-yl)-2-oxo-1,2-dihydropyridine-3-carboxylic acid 5-ethyl-4-hydroxy-6-(1-methyl-2-((2-(methylamino)ethylamino)methyl)-1H-indol-5-yl)-2-oxo-1,2-dihydropyridine-3-carboxylic acid 6-(2-((2-aminoethylamino)methyl)-1-methyl-1H-indol-5-yl)-5-ethyl-4-hydroxy-2-oxo-1,2-dihydropyridine-3-carboxylic acid 6-(2-((3-(benzyl(methyl)amino)azetidin-1-yl)methyl)-1-methyl-1H-indol-5-yl)-5-ethyl-4-hydroxy-2-oxo-1,2-dihydropyridine-3-carboxylic acid 6-(2-((3-((2-(dimethylamino)ethyl)(methyl)amino)azetidin-1-yl)methyl)-1-methyl-1H-indol-5-yl)-5-ethyl-4-hydroxy-2-oxo-1,2-dihydropyridine-3-carboxylic acid 5-ethyl-4-hydroxy-6-(1-methyl-2-(((1R,5S,6s)-6-(methylamino)-3-azabicyclo[3.1.0]hexan-3-yl)methyl)-1H-indol-5-yl)-2-oxo-1,2-dihydropyridine-3-carboxylic acid 5-ethyl-4-hydroxy-6-(1-methyl-2-((phenylamino)methyl)-1H-indol-5-yl)-2-oxo-1,2-dihydropyridine-3-carboxylic acid 5-ethyl-4-hydroxy-6-(1-methyl-2-((4-methylpiperidin-1-yl)methyl)-1H-indol-5-yl)-2-oxo-1,2-dihydropyridine-3-carboxylic acid 6-(2-((4-(dimethylamino)piperidin-1-yl)methyl)-1-methyl-1H-indol-5-yl)-5-ethyl-4-hydroxy-2-oxo-1,2-dihydropyridine-3-carboxylic acid 6-(2-((4,4-difluoropiperidin-1-yl)methyl)-1-methyl-1H-indol-5-yl)-5-ethyl-4-hydroxy-2-oxo-1,2-dihydropyridine-3-carboxylic acid 6-(2-((3-(dimethylamino)piperidin-1-yl)methyl)-1-methyl-1H-indol-5-yl)-5-ethyl-4-hydroxy-2-oxo-1,2-dihydropyridine-3-carboxylic acid 6-(2-(1,4'-bipiperidin-1'-ylmethyl)-1-methyl-1H-indol-5-yl)-5-ethyl-4-hydroxy-2-oxo-1,2-dihydropyridine-3-carboxylic acid 6-(2-((4-aminopiperidin-1-yl)methyl)-1-methyl-1H-indol-5-yl)-5-ethyl-4-hydroxy-2-oxo-1,2-dihydropyridine-3-carboxylic acid (S)-6-(2-((3-aminopiperidin-1-yl)methyl)-1-methyl-1H-indol-5-yl)-5-ethyl-4-hydroxy-2-oxo-1,2-dihydropyridine-3-carboxylic acid 5-ethyl-4-hydroxy-6-(2-((4-hydroxypiperidin-1-yl)methyl)-1-methyl-1H-indol-5-yl)-2-oxo-1,2-dihydropyridine-3-carboxylic acid 5-ethyl-4-hydroxy-6-(2-((3-hydroxypiperidin-1-yl)methyl)-1-methyl-1H-indol-5-yl)-2-oxo-1,2-dihydropyridine-3-carboxylic acid 5-ethyl-4-hydroxy-6-(1-methyl-2-((4-(methylamino)piperidin-1-yl)methyl)-1H-indol-5-yl)-2-oxo-1,2-dihydropyridine-3-carboxylic acid (S)-5-ethyl-4-hydroxy-6-(1-methyl-2-((3-(methylamino)piperidin-1-yl)methyl)-1H-indol-5-yl)-2-oxo-1,2-dihydropyridine-3-carboxylic acid 5-ethyl-4-hydroxy-6-(1-methyl-2-((2-(trifluoromethyl)piperidin-1-yl)methyl)-1H-indol-5-yl)-2-oxo-1,2-dihydropyridine-3-carboxylic acid 5-ethyl-4-hydroxy-6-(2-((2-(2-methoxyethyl)piperidin-1-yl)methyl)-1-methyl-1H-indol-5-yl)-2-oxo-1,2-dihydropyridine-3-carboxylic acid 5-ethyl-4-hydroxy-6-(2-((2-(3-methoxypropyl)piperidin-1-yl)methyl)-1-methyl-1H-indol-5-yl)-2-oxo-1,2-dihydropyridine-3-carboxylic acid 5-ethyl-4-hydroxy-6-(1-methyl-2-((methyl(piperidin-4-yl)amino)methyl)-1H-indol-5-yl)-2-oxo-1,2-dihydropyridine-3-carboxylic acid 5-ethyl-4-hydroxy-6-(1-methyl-2-((methyl(piperidin-3-yl)amino)methyl)-1H-indol-5-yl)-2-oxo-1,2-dihydropyridine-3-carboxylic acid 5-ethyl-4-hydroxy-6-(1-methyl-2-((piperidin-4-ylamino)methyl)-1H-indol-5-yl)-2-oxo-1,2-dihydropyridine-3-carboxylic acid 6-(2-(((cyclopropylmethyl)(piperidin-4-yl)amino)methyl)-1-methyl-1H-indol-5-yl)-5-ethyl-4-hydroxy-2-oxo-1,2-dihydropyridine-3-carboxylic acid 6-(2-(((cyclopropylmethyl)(piperidin-3-yl)amino)methyl)-1-methyl-1H-indol-5-yl)-5-ethyl-4-hydroxy-2-oxo-1,2-dihydropyridine-3-carboxylic acid (S)-5-ethyl-4-hydroxy-6-(1-methyl-2-((2-((phenylamino)methyl)pyrrolidin-1-yl)methyl)-1H-indol-5-yl)-2-oxo-1,2-dihydropyridine-3-carboxylic acid 5-ethyl-4-hydroxy-6-(1-methyl-2-((3-(pyridin-2-yl)pyrrolidin-1-yl)methyl)-1H-indol-5-yl)-2-oxo-1,2-dihydropyridine-3-carboxylic acid 5-ethyl-4-hydroxy-6-(1-methyl-2-((3-(pyridin-4-yl)pyrrolidin-1-yl)methyl)-1H-indol-5-yl)-2-oxo-1,2-dihydropyridine-3-carboxylic acid 6-(2-((3-carboxyazetidin-1-yl)methyl)-1-methyl-1H-indol-5-yl)-5-ethyl-4-hydroxy-2-oxo-1,2-dihydropyridine-3-carboxylic acid 6-(2-((3-(dimethylcarbamoyl)azetidin-1-yl)methyl)-1-methyl-1H-indol-5-yl)-5-ethyl-4-hydroxy-2-oxo-1,2-dihydropyridine-3-carboxylic acid 5-ethyl-4-hydroxy-6-(2-((3-(hydroxymethyl)azetidin-1-yl)methyl)-1-methyl-1H-indol-5-yl)-2-oxo-1,2-dihydropyridine-3-carboxylic acid (R)-5-ethyl-4-hydroxy-6-(1-methyl-2-((1,1,1-trifluoropropan-2-ylamino)methyl)-1H-indol-5-yl)-2-oxo-1,2-dihydropyridine-3-carboxylic acid (S)-5-ethyl-4-hydroxy-6-(1-methyl-2-((1,1,1-trifluoropropan-2-ylamino)methyl)-1H-indol-5-yl)-2-oxo-1,2-dihydropyridine-3-carboxylic acid 6-(2-((1,3-difluoropropan-2-ylamino)methyl)-1-methyl-1H-indol-5-yl)-5-ethyl-4-hydroxy-2-oxo-1,2-dihydropyridine-3-carboxylic acid 5-ethyl-4-hydroxy-6-(1-methyl-2-((1-methylcyclopropylamino)methyl)-1H-indol-5-yl)-2-oxo-1,2-dihydropyridine-3-carboxylic acid 6-(2-(((3aR,4R,6aS)-4-aminohexahydrocyclopenta[c]pyrrol-2(1H)-yl)methyl)-1-methyl-1H-indol-5-yl)-5-ethyl-4-hydroxy-2-oxo-1,2-dihydropyridine-3-carboxylic acid 6-(2-(((3aR,4R,6aS)-4-(dimethylamino)hexahydrocyclopenta[c]pyrrol-2(1H)-yl)methyl)-1-methyl-1H-indol-5-yl)-5-ethyl-4-hydroxy-2-oxo-1,2-dihydropyridine-3-carboxylic acid 6-(2-(((3aR,4R,7aS)-4-(dimethylamino)-1H-isoindol-2(3H,3aH,4H,5H,6H,7H,7aH)-yl)methyl)-1-methyl-1H-indol-5-yl)-5-ethyl-4-hydroxy-2-oxo-1,2-dihydropyridine-3-carboxylic acid 6-(2-(((3aR,4R,7aS)-4-(benzyl(methyl)amino)-1H-isoindol-2(3H,3aH,4H,5H,6H,7H,7aH)-yl)methyl)-1-methyl-1H-indol-5-yl)-5-ethyl-4-hydroxy-2-oxo-1,2-dihydropyridine-3-carboxylic acid 6-(2-(((3aR,4R,6aS)-4-(dibenzylamino)hexahydrocyclopenta[c]pyrrol-2(1H)-yl)methyl)-1-methyl-1H-indol-5-yl)-5-ethyl-4-hydroxy-2-oxo-1,2-dihydropyridine-3-carboxylic acid 5-ethyl-4-hydroxy-6-(1-methyl-2-(((3aR,4R,7aS)-4-(methylamino)-1H-isoindol-2(3H,3aH,4H,5H,6H,7H,7aH)-yl)methyl)-1H-indol-5-yl)-2-oxo-1,2-dihydropyridine-3-carboxylic acid 6-(2-(((3aR,4R,7aS)-4-(dibenzylamino)-1H-isoindol-2(3H,3 aH,4H,5H,6H,7H,7aH)-yl)methyl)-1-methyl-1H-indol-5-yl)-5-ethyl-4-hydroxy-2-oxo-1,2-dihydropyridine-3-carboxylic acid 6-(2-(((3aR,4R,7aS)-4-amino-1H-isoindol-2(3H,3aH,4H,5H,6H,7H,7aH)-yl)methyl)-1-methyl-1H-indol-5-yl)-5-ethyl-4-hydroxy-2-oxo-1,2-dihydropyridine-3-carboxylic acid 6-(2-(((3aR,5r,6aS)-5-(dimethylamino)hexahydrocyclopenta[c]pyrrol-2(1H)-yl)methyl)-1-methyl-1H-indol-5-yl)-5-ethyl-4-hydroxy-2-oxo-1,2-dihydropyridine-3-carboxylic acid 6-(2-(((3aR,5r,6aS)-5-(dibenzylamino)hexahydrocyclopenta[c]pyrrol-2(1H)-yl)methyl)-1-methyl-1H-indol-5-yl)-5-ethyl-4-hydroxy-2-oxo-1,2-dihydropyridine-3-carboxylic acid 6-(2-(((3aR,5r,6aS)-5-aminohexahydrocyclopenta[c]pyrrol-2(1H)-yl)methyl)-1-methyl-1H-indol-5-yl)-5-ethyl-4-hydroxy-2-oxo-1,2-dihydropyridine-3-carboxylic acid 6-(2-(((3aR,5r,6aS)-5-(benzyl(methyl)amino)hexahydrocyclopenta[c]pyrrol-2(1H)-yl)methyl)-1-methyl-1H-indol-5-yl)-5-ethyl-4-hydroxy-2-oxo-1,2-dihydropyridine-3-carboxylic acid 5-ethyl-4-hydroxy-6-(1-methyl-2-(((3aR,5r,6aS)-5-(methylamino)hexahydrocyclopenta[c]pyrrol-2(1H)-yl)methyl)-1H-indol-5-yl)-2-oxo-1,2-dihydropyridine-3-carboxylic acid 6-(2-(aminomethyl)-1-methyl-1H-indol-5-yl)-5-ethyl-4-hydroxy-2-oxo-1,2-dihydropyridine-3-carboxylic acid 5-ethyl-4-hydroxy-6-(2-((4-methoxybenzylamino)methyl)-1-methyl-1H-indol-5-yl)-2-oxo-1,2-dihydropyridine-3-carboxylic acid 5-ethyl-6-(2-((4-fluorobenzylamino)methyl)-1-methyl-1H-indol-5-yl)-4-hydroxy-2-oxo-1,2-dihydropyridine-3-carboxylic acid 5-ethyl-4-hydroxy-6-(2-((2-methoxybenzylamino)methyl)-1-methyl-1H-indol-5-yl)-2-oxo-1,2-dihydropyridine-3-carboxylic acid 5-ethyl-4-hydroxy-6-(1-methyl-2-((3-methylbenzylamino)methyl)-1H-indol-5-yl)-2-oxo-1,2-dihydropyridine-3-carboxylic acid 5-ethyl-4-hydroxy-6-(1-methyl-2-((2-methylbenzylamino)methyl)-1H-indol-5-yl)-2-oxo-1,2-dihydropyridine-3-carboxylic acid 5-ethyl-4-hydroxy-6-(2-((3-methoxybenzylamino)methyl)-1-methyl-1H-indol-5-yl)-2-oxo-1,2-dihydropyridine-3-carboxylic acid 5-ethyl-4-hydroxy-6-(1-methyl-2-((4-methylbenzylamino)methyl)-1H-indol-5-yl)-2-oxo-1,2-dihydropyridine-3-carboxylic acid 5-ethyl-6-(2-((3-fluorobenzylamino)methyl)-1-methyl-1H-indol-5-yl)-4-hydroxy-2-oxo-1,2-dihydropyridine-3-carboxylic acid 5-ethyl-6-(2-((2-fluorobenzylamino)methyl)-1-methyl-1H-indol-5-yl)-4-hydroxy-2-oxo-1,2-dihydropyridine-3-carboxylic acid 5-ethyl-4-hydroxy-6-(2-(((2-methoxyethyl)(methyl)amino)methyl)-1-methyl-1H-indol-5-yl)-2-oxo-1,2-dihydropyridine-3-carboxylic acid 6-(2-((cycloheptylmethylamino)methyl)-1-methyl-1H-indol-5-yl)-5-ethyl-4-hydroxy-2-oxo-1,2-dihydropyridine-3-carboxylic acid 6-(2-((2-(dimethylamino)ethylamino)methyl)-1-methyl-1H-indol-5-yl)-5-ethyl-4-hydroxy-2-oxo-1,2-dihydropyridine-3-carboxylic acid 6-(2-(((2-(dimethylamino)ethyl)(methyl)amino)methyl)-1-methyl-1H-indol-5-yl)-5-ethyl-4-hydroxy-2-oxo-1,2-dihydropyridine-3-carboxylic acid 5-ethyl-4-hydroxy-2-oxo-6-(1-(pyrrolidin-1-yl)-2,3-dihydro-1H-pyrrolo[1,2-a]indol-7-yl)-1,2-dihydropyridine-3-carboxylic acid 5-ethyl-4-hydroxy-2-oxo-6-(1,2,3,4-tetrahydropyrazino[1,2-a]indol-8-yl)-1,2-dihydropyridine-3-carboxylic acid 5-ethyl-4-hydroxy-6-(1-methyl-2-(pyrrolidin-3-yl)-1H-indol-5-yl)-2-oxo-1,2-dihydropyridine-3-carboxylic acid 5-ethyl-4-hydroxy-6-(1-methyl-2-(2-(pyrrolidin-1-yl)propan-2-yl)-1H-indol-5-yl)-2-oxo-1,2-dihydropyridine-3-carboxylic acid 6-(2-(2-(dimethylamino)propan-2-yl)-1-methyl-1H-indol-5-yl)-5-ethyl-4-hydroxy-2-oxo-1,2-dihydropyridine-3-carboxylic acid 4-hydroxy-5-methyl-6-(1-methyl-2-(pyrrolidin-1-ylmethyl)-1H-indol-5-yl)-2-oxo-1,2-dihydropyridine-3-carboxylic acid 6-(2-((dimethylamino)methyl)-1-methyl-1H-indol-5-yl)-4-hydroxy-5-methyl-2-oxo-1,2-dihydropyridine-3-carboxylic acid 6-(2-((cyclopropylmethylamino)methyl)-1-methyl-1H-indol-5-yl)-4-hydroxy-5-methyl-2-oxo-1,2-dihydropyridine-3-carboxylic acid 6-(2-(azetidin-1-ylmethyl)-1-methyl-1H-indol-5-yl)-4-hydroxy-5-methyl-2-oxo-1,2-dihydropyridine-3-carboxylic acid 4-hydroxy-5-methyl-6-(1-methyl-2-((methylamino)methyl)-1H-indol-5-yl)-2-oxo-1,2-dihydropyridine-3-carboxylic acid 6-(2-((dimethylamino)methyl)-1-methyl-1H-indol-5-yl)-4-hydroxy-5-isopropyl-2-oxo-1,2-dihydropyridine-3-carboxylic acid 4-hydroxy-5-isopropyl-6-(1-methyl-2-(pyrrolidin-1-ylmethyl)-1H-indol-5-yl)-2-oxo-1,2-dihydropyridine-3-carboxylic acid 6-(2-(azetidin-1-ylmethyl)-1-methyl-1H-indol-5-yl)-4-hydroxy-5-isopropyl-2-oxo-1,2-dihydropyridine-3-carboxylic acid 6-(2-((cyclopropylmethylamino)methyl)-1-methyl-1H-indol-5-yl)-4-hydroxy-5-isopropyl-2-oxo-1,2-dihydropyridine-3-carboxylic acid 5-cyclopropyl-6-(2-((dimethylamino)methyl)-1-methyl-1H-indol-5-yl)-4-hydroxy-2-oxo-1,2-dihydropyridine-3-carboxylic acid 5-cyclopropyl-4-hydroxy-6-(1-methyl-2-(pyrrolidin-1-ylmethyl)-1H-indol-5-yl)-2-oxo-1,2-dihydropyridine-3-carboxylic acid 6-(2-(azetidin-1-ylmethyl)-1-methyl-1H-indol-5-yl)-5-cyclopropyl-4-hydroxy-2-oxo-1,2-dihydropyridine-3-carboxylic acid 5-cyclopropyl-6-(2-((cyclopropylmethylamino)methyl)-1-methyl-1H-indol-5-yl)-4-hydroxy-2-oxo-1,2-dihydropyridine-3-carboxylic acid 4-amino-5-ethyl-6-(1-methyl-2-(pyrrolidin-1-ylmethyl)-1H-indol-5-yl)-2-oxo-1,2-dihydropyridine-3-carboxylic acid
4-amino-6-(2-((dimethylamino)methyl)-1-methyl-1H-indol-5-yl)-5-ethyl-2-oxo-1,2-dihydropyridine-3-carboxylic acid
4-amino-5-ethyl-6-(1-methyl-2-(piperidin-1-ylmethyl)-1H-indol-5-yl)-2-oxo-1,2-dihydropyridine-3-carboxylic acid
4-amino-6-(2-((3-(dimethylamino)pyrrolidin-1-yl)methyl)-1-methyl-1H-indol-5-yl)-5-ethyl-2-oxo-1,2-dihydropyridine-3-carboxylic acid
6-(2-((butylamino)methyl)-1-methyl-1H-indol-5-yl)-5-ethyl-4-hydroxy-2-oxo-1,2-dihydropyridine-3-carboxylic acid
5-ethyl-4-hydroxy-6-(1-methyl-2-((pentylamino)methyl)-1H-indol-5-yl)-2-oxo-1,2-dihydropyridine-3-carboxylic acid
5-ethyl-6-(2-((hexylamino)methyl)-1-methyl-1H-indol-5-yl)-4-hydroxy-2-oxo-1,2-dihydropyridine-3-carboxylic acid
5-ethyl-6-(2-((heptylamino)methyl)-1-methyl-1H-indol-5-yl)-4-hydroxy-2-oxo-1,2-dihydropyridine-3-carboxylic acid
5-ethyl-4-hydroxy-6-(1-methyl-2-((octylamino)methyl)-1H-indol-5-yl)-2-oxo-1,2-dihydropyridine-3-carboxylic acid
5-ethyl-4-hydroxy-6-(1-methyl-2-((nonylamino)methyl)-1H-indol-5-yl)-2-oxo-1,2-dihydropyridine-3-carboxylic acid
5-allyl-6-(2-((dimethylamino)methyl)-1-methyl-1H-indol-5-yl)-4-hydroxy-2-oxo-1,2-dihydropyridine-3-carboxylic acid
6-(2-((dimethylamino)methyl)-1-methyl-1H-indol-5-yl)-4-hydroxy-2-oxo-5-propyl-1,2-dihydropyridine-3-carboxylic acid
4-hydroxy-6-(2-((2-methoxyethylamino)methyl)-1-methyl-1H-indol-5-yl)-5-methyl-2-oxo-1,2-dihydropyridine-3-carboxylic acid
6-(2-((ethylamino)methyl)-1-methyl-1H-indol-5-yl)-4-hydroxy-5-methyl-2-oxo-1,2-dihydropyridine-3-carboxylic acid
6-(2-((2-aminoethylamino)methyl)-1-methyl-1H-indol-5-yl)-4-hydroxy-5-methyl-2-oxo-1,2-dihydropyridine-3-carboxylic acid
4-hydroxy-5-methyl-6-(1-methyl-2-((2-(methylamino)ethylamino)methyl)-1H-indol-5-yl)-2-oxo-1,2-dihydropyridine-3-carboxylic acid
6-(2-((2-(dimethylamino)ethylamino)methyl)-1-methyl-1H-indol-5-yl)-4-hydroxy-5-methyl-2-oxo-1,2-dihydropyridine-3-carboxylic acid
4-hydroxy-6-(2-(((1-methoxypropan-2-ylamino)methyl)-1-methyl-1H-indol-5-yl)-5-methyl-2-oxo-1,2-dihydropyridine-3-carboxylic acid
6-(2-((sec-butylamino)methyl)-1-methyl-1H-indol-5-yl)-4-hydroxy-5-methyl-2-oxo-1,2-dihydropyridine-3-carboxylic acid
4-hydroxy-6-(2-((isopropylamino)methyl)-1-methyl-1H-indol-5-yl)-5-methyl-2-oxo-1,2-dihydropyridine-3-carboxylic acid
4-hydroxy-6-(2-(((1-hydroxypropan-2-ylamino)methyl)-1-methyl-1H-indol-5-yl)-5-methyl-2-oxo-1,2-dihydropyridine-3-carboxylic acid
4-hydroxy-6-(2-((2-hydroxyethylamino)methyl)-1-methyl-1H-indol-5-yl)-5-methyl-2-oxo-1,2-dihydropyridine-3-carboxylic acid
6-(2-((tert-butylamino)methyl)-1-methyl-1H-indol-5-yl)-4-hydroxy-5-methyl-2-oxo-1,2-dihydropyridine-3-carboxylic acid
4-hydroxy-5-methyl-6-(1-methyl-2-((propylamino)methyl)-1H-indol-5-yl)-2-oxo-1,2-dihydropyridine-3-carboxylic acid
4-hydroxy-6-(2-((isobutylamino)methyl)-1-methyl-1H-indol-5-yl)-5-methyl-2-oxo-1,2-dihydropyridine-3-carboxylic acid
6-(2-((cyclobutylamino)methyl)-1-methyl-1H-indol-5-yl)-4-hydroxy-5-methyl-2-oxo-1,2-dihydropyridine-3-carboxylic acid
6-(2-((cyclopropylamino)methyl)-1-methyl-1H-indol-5-yl)-4-hydroxy-5-methyl-2-oxo-1,2-dihydropyridine-3-carboxylic acid
4-hydroxy-5-methyl-6-(1-methyl-2-((1-methylcyclopropylamino)methyl)-1H-indol-5-yl)-2-oxo-1,2-dihydropyridine-3-carboxylic acid
6-(2-((diethylamino)methyl)-1-methyl-1H-indol-5-yl)-4-hydroxy-5-methyl-2-oxo-1,2-dihydropyridine-3-carboxylic acid
6-(2-(aminomethyl)-1-methyl-1H-indol-5-yl)-4-hydroxy-5-methyl-2-oxo-1,2-dihydropyridine-3-carboxylic acid
6-(3-cyano-1-methyl-1H-indol-5-yl)-5-ethyl-4-hydroxy-2-oxo-1,2-dihydropyridine-3-carboxylic acid
6-(3-cyano-1-methyl-2-(pyrrolidin-1-yl)-1H-indol-5-yl)-5-ethyl-4-hydroxy-2-oxo-1,2-dihydropyridine-3-carboxylic acid
6-(3-cyano-2-(dimethylamino)-1-methyl-1H-indol-5-yl)-5-ethyl-4-hydroxy-2-oxo-1,2-dihydropyridine-3-carboxylic acid
6-(3-cyano-2-methoxy-1-methyl-1H-indol-5-yl)-5-ethyl-4-hydroxy-2-oxo-1,2-dihydropyridine-3-carboxylic acid
6-(3-chloro-1-methyl-1H-indol-5-yl)-5-ethyl-4-hydroxy-2-oxo-1,2-dihydropyridine-3-carboxylic acid
6-(benzofuran-5-yl)-5-ethyl-2-oxo-1,2-dihydropyridine-3-carboxylic acid
6-(benzofuran-5-yl)-5-ethyl-4-hydroxy-2-oxo-1,2-dihydropyridine-3-carboxylic acid
6-(benzo[b]thiophen-5-yl)-5-ethyl-2-oxo-1,2-dihydropyridine-3-carboxylic acid
6-(benzo[b]thiophen-5-yl)-5-ethyl-4-hydroxy-2-oxo-1,2-dihydropyridine-3-carboxylic acid
5-ethyl-6-(3-fluoro-1-methyl-2-((methylamino)methyl)-1H-indol-5-yl)-4-hydroxy-2-oxo-1,2-dihydropyridine-3-carboxylic acid
5-ethyl-6-(2-((ethylamino)methyl)-3-fluoro-1-methyl-1H-indol-5-yl)-4-hydroxy-2-oxo-1,2-dihydropyridine-3-carboxylic acid
5-ethyl-6-(3-fluoro-2-((isopropylamino)methyl)-1-methyl-1H-indol-5-yl)-4-hydroxy-2-oxo-1,2-dihydropyridine-3-carboxylic acid
6-(2-((tert-butylamino)methyl)-3-fluoro-1-methyl-1H-indol-5-yl)-5-ethyl-4-hydroxy-2-oxo-1,2-dihydropyridine-3-carboxylic acid
6-(4-(benzyloxy)-1-methyl-1H-indol-5-yl)-5-ethyl-2-oxo-1,2-dihydropyridine-3-carboxylic acid
6-(4-(benzyloxy)-1-methyl-1H-indol-5-yl)-5-ethyl-4-hydroxy-2-oxo-1,2-dihydropyridine-3-carboxylic acid
5-ethyl-4-hydroxy-6-(4-hydroxy-1-methyl-1H-indol-5-yl)-2-oxo-1,2-dihydropyridine-3-carboxylic acid
4-hydroxy-6-(1-methyl-1H-indol-5-yl)-2-oxo-5-vinyl-1,2,5,6-tetrahydropyridine-3-carboxylic acid
5-chloro-4-hydroxy-6-(1-methyl-1H-indol-5-yl)-2-oxo-1,2-dihydropyridine-3-carboxylic acid 5-ethyl-4-hydroxy-6-(6-methoxy-1H-indol-2-yl)-2-oxo-1,2-dihydropyridine-3-carboxylic acid
5-ethyl-6-(5-fluoro-1H-indol-2-yl)-4-hydroxy-2-oxo-1,2-dihydropyridine-3-carboxylic acid
5-ethyl-6-(5-ethyl-1H-indol-2-yl)-4-hydroxy-2-oxo-1,2-dihydropyridine-3-carboxylic acid
5-ethyl-6-(6-ethyl-1H-indol-2-yl)-4-hydroxy-2-oxo-1,2-dihydropyridine-3-carboxylic acid
5-ethyl-4-hydroxy-2-oxo-6-(5-propyl-1H-indol-2-yl)-1,2-dihydropyridine-3-carboxylic acid
5-ethyl-4-hydroxy-2-oxo-6-(6-propyl-1H-indol-2-yl)-1,2-dihydropyridine-3-carboxylic acid
5-ethyl-6-(5-fluoro-6-methyl-1H-indol-2-yl)-4-hydroxy-2-oxo-1,2-dihydropyridine-3-carboxylic acid
6-(5-ethyl-1H-indol-2-yl)-4-hydroxy-5-methyl-2-oxo-1,2-dihydropyridine-3-carboxylic acid
6-(6-ethyl-1H-indol-2-yl)-4-hydroxy-5-methyl-2-oxo-1,2-dihydropyridine-3-carboxylic acid
6-(5-fluoro-6-methyl-1H-indol-2-yl)-4-hydroxy-5-methyl-2-oxo-1,2-dihydropyridine-3-carboxylic acid
5-ethyl-4-hydroxy-6-(2-methyl-2H-indazol-6-yl)-2-oxo-1,2-dihydropyridine-3-carboxylic acid
5-ethyl-4-hydroxy-6-(1-methyl-1H-indazol-6-yl)-2-oxo-1,2-dihydropyridine-3-carboxylic acid
5-ethyl-4-hydroxy-6-(1H-indazol-6-yl)-2-oxo-1,2-dihydropyridine-3-carboxylic acid
5-ethyl-4-hydroxy-6-(1H-indazol-5-yl)-2-oxo-1,2-dihydropyridine-3-carboxylic acid
5-ethyl-4-hydroxy-6-(2-methyl-2H-indazol-5-yl)-2-oxo-1,2-dihydropyridine-3-carboxylic acid
4-hydroxy-5-methyl-6-(1-methyl-1H-indazol-5-yl)-2-oxo-1,2-dihydropyridine-3-carboxylic acid
4-hydroxy-5-methyl-6-(2-methyl-2H-indazol-5-yl)-2-oxo-1,2-dihydropyridine-3-carboxylic acid
4-hydroxy-5-methyl-6-(1-methyl-1H-indazol-6-yl)-2-oxo-1,2-dihydropyridine-3-carboxylic acid
4-hydroxy-5-methyl-6-(2-methyl-2H-indazol-6-yl)-2-oxo-1,2-dihydropyridine-3-carboxylic acid
4-hydroxy-6-(1H-indazol-5-yl)-5-methyl-2-oxo-1,2-dihydropyridine-3-carboxylic acid
4-hydroxy-6-(1H-indazol-6-yl)-5-methyl-2-oxo-1,2-dihydropyridine-3-carboxylic acid
5-ethyl-4-hydroxy-6-(imidazo[1,2-a]pyridin-2-yl)-2-oxo-1,2-dihydropyridine-3-carboxylic acid
6-(4-(dimethylamino)-6-methylpyrazolo[1,5-a]pyrazin-2-yl)-5-ethyl-4-hydroxy-2-oxo-1,2-dihydropyridine-3-carboxylic acid
5-ethyl-4-hydroxy-6-(6-methyl-4-(pyrrolidin-1-yl)pyrazolo[1,5-a]pyrazin-2-yl)-2-oxo-1,2-dihydropyridine-3-carboxylic acid
5-ethyl-4-hydroxy-6-(1-methyl-1H-indol-4-yl)-2-oxo-1,2-dihydropyridine-3-carboxylic acid
4-hydroxy-5-methyl-6-(1-methyl-1H-indol-4-yl)-2-oxo-1,2-dihydropyridine-3-carboxylic acid
5-ethyl-4-hydroxy-6-(6-methoxy-1-methyl-1H-indol-2-yl)-2-oxo-1,2-dihydropyridine-3-carboxylic acid
5-ethyl-6-(5-fluoro-1-methyl-1H-indol-2-yl)-4-hydroxy-2-oxo-1,2-dihydropyridine-3-carboxylic acid
5-ethyl-6-(5-ethyl-1-methyl-1H-indol-2-yl)-4-hydroxy-2-oxo-1,2-dihydropyridine-3-carboxylic acid
5-ethyl-6-(6-ethyl-1-methyl-1H-indol-2-yl)-4-hydroxy-2-oxo-1,2-dihydropyridine-3-carboxylic acid
5-ethyl-4-hydroxy-6-(1-methyl-5-propyl-1H-indol-2-yl)-2-oxo-1,2-dihydropyridine-3-carboxylic acid
5-ethyl-4-hydroxy-6-(1-methyl-6-propyl-1H-indol-2-yl)-2-oxo-1,2-dihydropyridine-3-carboxylic acid
5-ethyl-6-(5-fluoro-1,6-dimethyl-1H-indol-2-yl)-4-hydroxy-2-oxo-1,2-dihydropyridine-3-carboxylic acid
5-ethyl-6-(2-(ethyl(methyl)amino)-2,3-dihydro-1H-pyrrolo[1,2-a]indol-7-yl)-4-hydroxy-2-oxo-1,2-dihydropyridine-3-carboxylic acid
5-ethyl-4-hydroxy-6-(2-(methyl(propyl)amino)-2,3-dihydro-1H-pyrrolo[1,2-a]indol-7-yl)-2-oxo-1,2-dihydropyridine-3-carboxylic acid
5-ethyl-4-hydroxy-6-(1H-indol-6-yl)-2-oxo-1,2-dihydropyridine-3-carboxylic acid
4-hydroxy-6-(1H-indol-6-yl)-5-methyl-2-oxo-1,2-dihydropyridine-3-carboxylic acid
5-ethyl-4-hydroxy-6-(1H-indol-5-yl)-2-oxo-1,2-dihydropyridine-3-carboxylic acid
4-hydroxy-6-(1H-indol-5-yl)-5-methyl-2-oxo-1,2-dihydropyridine-3-carboxylic acid
4-hydroxy-5-methyl-2-oxo-6-(2-oxoindolin-5-yl)-1,2-dihydropyridine-3-carboxylic acid
6-(6-(dimethylamino)naphthalen-2-yl)-5-ethyl-4-hydroxy-2-oxo-1,2-dihydropyridine-3-carboxylic acid
5-ethyl-4-hydroxy-6-(2-methylindolizin-6-yl)-2-oxo-1,2-dihydropyridine-3-carboxylic acid
5-ethyl-4-hydroxy-2-oxo-6-(1H-pyrrolo[3,2-b]pyridin-6-yl)-1,2-dihydropyridine-3-carboxylic acid
4-hydroxy-5-methyl-2-oxo-6-(1H-pyrrolo[3,2-b]pyridin-6-yl)-1,2-dihydropyridine-3-carboxylic acid
6-(9H-carbazol-2-yl)-5-ethyl-4-hydroxy-2-oxo-1,2-dihydropyridine-3-carboxylic acid
5-ethyl-4-hydroxy-2-oxo-6-(1H-pyrrolo[2,3-b]pyridin-6-yl)-1,2-dihydropyridine-3-carboxylic acid
4-hydroxy-5-methyl-2-oxo-6-(1H-pyrrolo[2,3-b]pyridin-6-yl)-1,2-dihydropyridine-3-carboxylic acid
5-ethyl-4-hydroxy-2-oxo-6-(1-phenyl-1H-indol-5-yl)-1,2-dihydropyridine-3-carboxylic acid
5-ethyl-4-hydroxy-2-oxo-6-(1-(pyridin-2-yl)-1H-indol-5-yl)-1,2-dihydropyridine-3-carboxylic acid
5-ethyl-4-hydroxy-2-oxo-6-(1-(4-(trifluoromethyl)phenyl)-1H-indol-5-yl)-1,2-dihydropyridine-3-carboxylic acid
5-ethyl-6-(1-(4-fluorophenyl)-1H-indol-5-yl)-4-hydroxy-2-oxo-1,2-dihydropyridine-3-carboxylic acid
5-ethyl-4-hydroxy-2-oxo-6-(1-(3-(pyrrolidin-1-yl)phenyl)-1H-indol-5-yl)-1,2-dihydropyridine-3-carboxylic acid
5-ethyl-4-hydroxy-2-oxo-6-(1-(4-(pyrrolidin-1-yl)phenyl)-1H-indol-5-yl)-1,2-dihydropyridine-3-carboxylic acid
5-ethyl-4-hydroxy-2-oxo-6-(2,3,4,9-tetrahydro-1H-pyrido[3,4-b]indol-7-yl)-1,2-dihydropyridine-3-carboxylic acid
5-ethyl-4-(hydroxy)-6-(2-methyl-2,3,4,9-tetrahydro-1H-pyrido[3,4-b]indol-7-yl)-2-oxo-1,2-dihydropyridine-3-carboxylic acid
5-ethyl-6-(2-ethyl-2,3,4,9-tetrahydro-1H-pyrido[3,4-b]indol-7-yl)-4-hydroxy-2-oxo-1,2-dihydropyridine-3-carboxylic acid
5-ethyl-4-hydroxy-2-oxo-6-(2-propyl-2,3,4,9-tetrahydro-1H-pyrido[3,4-b]indol-7-yl)-1,2-dihydropyridine-3-carboxylic acid
5-ethyl-4-hydroxy-6-(2-isopropyl-2,3,4,9-tetrahydro-1H-pyrido[3,4-b]indol-7-yl)-2-oxo-1,2-dihydropyridine-3-carboxylic acid
5-ethyl-4-hydroxy-2-oxo-6-(2,3,4,5-tetrahydro-1H-pyrido[4,3-b]indol-7-yl)-1,2-dihydropyridine-3-carboxylic acid 5-ethyl-4-hydroxy-6-(2-methyl-2,3,4,5-tetrahydro-1H-pyrido[4,3-b]indol-7-yl)-2-oxo-1,2-dihydropyridine-3-carboxylic acid 5-ethyl-6-(2-ethyl-2,3,4,5-tetrahydro-1H-pyrido[4,3-b]indol-7-yl)-4-hydroxy-2-oxo-1,2-dihydropyridine-3-carboxylic acid 6-(2-(4-cyanophenyl)-1H-indol-5-yl)-5-ethyl-4-hydroxy-2-oxo-1,2-dihydropyridine-3-carboxylic acid 5-ethyl-4-hydroxy-2-oxo-6-(2-phenyl-1H-indol-5-yl)-1,2-dihydropyridine-3-carboxylic acid, and 5-ethyl-4-hydroxy-2-oxo-6-(2-(4-(trifluoromethyl)phenyl)-1H-indol-5-yl)-1,2-dihydropyridine-3-carboxylic acid;

wherein the form of the compound is selected from a free acid, free base, salt, hydrate, solvate, clathrate, isotopologue, racemate, enantiomer, diastereomer, stereoisomer, polymorph or tautomer form thereof.

10. The compound of claim 1, wherein the compound or a form thereof is selected from:

6-([1,2,4]triazolo[1,5-a]pyridin-6-yl)-5-ethyl-2-oxo-1,2-dihydropyridine-3-carboxylic acid hydrochloride 6-([1,2,4]triazolo[4,3-a]pyridin-6-yl)-5-ethyl-2-oxo-1,2-dihydropyridine-3-carboxylic acid hydrochloride 5-ethyl-6-(imidazo[1,2-a]pyridin-6-yl)-2-oxo-1,2-dihydropyridine-3-carboxylic acid hydrochloride 6-(2-((dimethylamino)methyl)imidazo[1,2-a]pyridin-6-yl)-5-ethyl-2-oxo-1,2-dihydropyridine-3-carboxylic acid dihydrochloride 5-ethyl-2-oxo-6-(2-(pyrrolidin-1-ylmethyl)imidazo[1,2-a]pyridin-6-yl)-1,2-dihydropyridine-3-carboxylic acid dihydrochloride 5-ethyl-2-oxo-6-(2-(piperidin-1-ylmethyl)imidazo[1,2-a]pyridin-6-yl)-1,2-dihydropyridine-3-carboxylic acid dihydrochloride 6-(2-((diethylamino)methyl)imidazo[1,2-a]pyridin-6-yl)-5-ethyl-2-oxo-1,2-dihydropyridine-3-carboxylic acid dihydrochloride 5-ethyl-6-(6-methyl-5-(pyrrolidin-1-ylmethyl)-6H-thieno[2,3-b]pyrrol-2-yl)-2-oxo-1,2-dihydropyridine-3-carboxylic acid hydrochloride 6-(5-((dimethylamino)methyl)-6-methyl-6H-thieno[2,3-b]pyrrol-2-yl)-5-ethyl-2-oxo-1,2-dihydropyridine-3-carboxylic acid hydrochloride (R)-5-ethyl-6-(1-methyl-2-(pyrrolidin-2-yl)-1H-indol-5-yl)-2-oxo-1,2-dihydropyridine-3-carboxylic acid hydrochloride (S)-5-ethyl-6-(1-methyl-2-(pyrrolidin-2-yl)-1H-indol-5-yl)-2-oxo-1,2-dihydropyridine-3-carboxylic acid hydrochloride 5-ethyl-6-(1-methyl-2-(piperazin-2-yl)-1H-indol-5-yl)-2-oxo-1,2-dihydropyridine-3-carboxylic acid dihydrochloride 5-ethyl-6-(1-methyl-2-(1-methylpiperazin-2-yl)-1H-indol-5-yl)-2-oxo-1,2-dihydropyridine-3-carboxylic acid dihydrochloride 5-ethyl-6-(1-methyl-2-(pyrrolidin-3-yl)-1H-indol-5-yl)-2-oxo-1,2-dihydropyridine-3-carboxylic acid hydrochloride 6-(2-(2-aminoethyl)-1-methyl-1H-indol-5-yl)-5-ethyl-2-oxo-1,2-dihydropyridine-3-carboxylic acid hydrochloride 6-(2-((cyclobutyl(methyl)amino)methyl)-1-methyl-1H-indol-5-yl)-5-ethyl-4-hydroxy-2-oxo-1,2-dihydropyridine-3-carboxylic acid hydrochloride 6-(2-(((cyclopropylmethyl)(methyl)amino)methyl)-1-methyl-1H-indol-5-yl)-5-ethyl-4-hydroxy-2-oxo-1,2-dihydropyridine-3-carboxylic acid hydrochloride 6-(2-((cyclopentyl(methyl)amino)methyl)-1-methyl-1H-indol-5-yl)-5-ethyl-4-hydroxy-2-oxo-1,2-dihydropyridine-3-carboxylic acid hydrochloride 6-(2-((cyclopropyl(methyl)amino)methyl)-1-methyl-1H-indol-5-yl)-5-ethyl-4-hydroxy-2-oxo-1,2-dihydropyridine-3-carboxylic acid hydrochloride 6-(2-((benzylamino)methyl)-1-methyl-1H-indol-5-yl)-5-ethyl-4-hydroxy-2-oxo-1,2-dihydropyridine-3-carboxylic acid hydrochloride (R)-5-ethyl-4-hydroxy-6-(1-methyl-2-((1-phenylethylamino)methyl)-1H-indol-5-yl)-2-oxo-1,2-dihydropyridine-3-carboxylic acid hydrochloride (S)-5-ethyl-4-hydroxy-6-(1-methyl-2-((1-phenylethylamino)methyl)-1H-indol-5-yl)-2-oxo-1,2-dihydropyridine-3-carboxylic acid hydrochloride 5-ethyl-4-hydroxy-6-(1-methyl-2-((2-phenylpropan-2-ylamino)methyl)-1H-indol-5-yl)-2-oxo-1,2-dihydropyridine-3-carboxylic acid hydrochloride 6-(2-((benzyl(methyl)amino)methyl)-1-methyl-1H-indol-5-yl)-5-ethyl-4-hydroxy-2-oxo-1,2-dihydropyridine-3-carboxylic acid hydrochloride 5-ethyl-4-hydroxy-6-(1-methyl-2-((pyridin-2-ylmethylamino)methyl)-1H-indol-5-yl)-2-oxo-1,2-dihydropyridine-3-carboxylic acid hydrochloride 5-ethyl-4-hydroxy-6-(1-methyl-2-((pyridin-3-ylmethylamino)methyl)-1H-indol-5-yl)-2-oxo-1,2-dihydropyridine-3-carboxylic acid hydrochloride 5-ethyl-4-hydroxy-6-(1-methyl-2-((pyridin-4-ylmethylamino)methyl)-1H-indol-5-yl)-2-oxo-1,2-dihydropyridine-3-carboxylic acid hydrochloride 6-(2-((cyclohexylmethylamino)methyl)-1-methyl-1H-indol-5-yl)-5-ethyl-4-hydroxy-2-oxo-1,2-dihydropyridine-3-carboxylic acid hydrochloride 6-(2-((cyclopropylmethylamino)methyl)-1-methyl-1H-indol-5-yl)-5-ethyl-4-hydroxy-2-oxo-1,2-dihydropyridine-3-carboxylic acid hydrochloride 5-ethyl-4-hydroxy-6-(1-methyl-2-((methyl(pyridin-3-ylmethyl)amino)methyl)-1H-indol-5-yl)-2-oxo-1,2-dihydropyridine-3-carboxylic acid hydrochloride 5-ethyl-4-hydroxy-6-(1-methyl-2-((methyl(pyridin-4-ylmethyl)amino)methyl)-1H-indol-5-yl)-2-oxo-1,2-dihydropyridine-3-carboxylic acid hydrochloride 5-ethyl-4-hydroxy-6-(1-methyl-2-((1-(pyridin-4-yl)ethylamino)methyl)-1H-indol-5-yl)-2-oxo-1,2-dihydropyridine-3-carboxylic acid hydrochloride 5-ethyl-4-hydroxy-6-(1-methyl-2-(((tetrahydro-2H-pyran-4-yl)methylamino)methyl)-1H-indol-5-yl)-2-oxo-1,2-dihydropyridine-3-carboxylic acid hydrochloride 6-(2-((cyclopropylamino)methyl)-1-methyl-1H-indol-5-yl)-5-ethyl-4-hydroxy-2-oxo-1,2-dihydropyridine-3-carboxylic acid hydrochloride 6-(2-((cyclopentylamino)methyl)-1-methyl-1H-indol-5-yl)-5-ethyl-4-hydroxy-2-oxo-1,2-dihydropyridine-3-carboxylic acid hydrochloride 5-ethyl-6-(2-(((1-ethylpyrrolidin-2-yl)methylamino)methyl)-1-methyl-1H-indol-5-yl)-4-hydroxy-2-oxo-1,2-dihydropyridine-3-carboxylic acid dihydrochloride 5-ethyl-4-hydroxy-6-(1-methyl-2-(((1-methylpiperidin-3-yl)methylamino)methyl)-1H-indol-5-yl)-2-oxo-1,2-dihydropyridine-3-carboxylic acid dihydrochloride 6-(2-((cyclobutylamino)methyl)-1-methyl-1H-indol-5-yl)-5-ethyl-4-hydroxy-2-oxo-1,2-dihydropyridine-3-carboxylic acid hydrochloride 5-ethyl-4-hydroxy-6-(1-methyl-2-((((1-methylpiperidin-2-yl)methyl)amino)methyl)-1H-indol-5-yl)-2-oxo-1,2-dihydropyridine-3-carboxylic acid dihydrochloride 5-ethyl-4-hydroxy-6-(1-methyl-2-((((1-methylpiperidin-4-yl)methyl)amino)methyl)-1H-indol-5-yl)-2-oxo-1,2-dihydropyridine-3-carboxylic acid dihydrochloride 6-(2-((cyclobutylmethylamino)methyl)-1-methyl-1H-indol-5-yl)-5-ethyl-4-hydroxy-2-oxo-1,2-dihydropyridine-3-carboxylic acid hydrochloride 6-(2-((cyclopentylmethylamino)methyl)-1-methyl-1H-indol-5-yl)-5-ethyl-4-hydroxy-2-oxo-1,2-dihydropyridine-3-carboxylic acid hydrochloride 5-ethyl-4-hydroxy-6-(1-methyl-2-((neopentylamino)methyl)-1H-indol-5-yl)-2-oxo-1,2-dihydropyridine-3-carboxylic acid hydrochloride 5-ethyl-4-hydroxy-6-(1-methyl-2-((4-methyl-1,4-diazepan-1-yl)methyl)-1H-indol-5-yl)-2-oxo-1,2-dihydropyridine-3-carboxylic acid dihydrochloride 6-(2-((1,4-diazepan-1-yl)methyl)-1-methyl-1H-indol-5-yl)-5-ethyl-4-hydroxy-2-oxo-1,2-dihydropyridine-3-carboxylic acid dihydrochloride 5-ethyl-4-hydroxy-6-(1-methyl-2-((2-methylcyclopropyl)methyl)-1H-indol-5-yl)-2-oxo-1,2-dihydropyridine-3-carboxylic acid hydrochloride 6-(2-((cyclohexylamino)methyl)-1-methyl-1H-indol-5-yl)-5-ethyl-4-hydroxy-2-oxo-1,2-dihydropyridine-3-carboxylic acid hydrochloride 5-ethyl-4-hydroxy-6-(1-methyl-2-((1-(pyridin-3-yl)ethylamino)methyl)-1H-indol-5-yl)-2-oxo-1,2-dihydropyridine-3-carboxylic acid hydrochloride 6-(2-((allylamino)methyl)-1-methyl-1H-indol-5-yl)-5-ethyl-4-hydroxy-2-oxo-1,2-dihydropyridine-3-carboxylic acid hydrochloride 6-(2-((azetidin-3-ylamino)methyl)-1-methyl-1H-indol-5-yl)-5-ethyl-4-hydroxy-2-oxo-1,2-dihydropyridine-3-carboxylic acid dihydrochloride 5-ethyl-4-hydroxy-6-(1-methyl-2-((1-methylcyclobutylamino)methyl)-1H-indol-5-yl)-2-oxo-1,2-dihydropyridine-3-carboxylic acid hydrochloride 5-ethyl-4-hydroxy-6-(1-methyl-2-((1-methylazetidin-3-ylamino)methyl)-1H-indol-5-yl)-2-oxo-1,2-dihydropyridine-3-carboxylic acid dihydrochloride 5-ethyl-4-hydroxy-6-(1-methyl-2-((prop-2-ynylamino)methyl)-1H-indol-5-yl)-2-oxo-1,2-dihydropyridine-3-carboxylic acid hydrochloride 6-(2-amino-2,3-dihydro-1H-pyrrolo[1,2-a]indol-7-yl)-4-hydroxy-5-methyl-2-oxo-1,2-dihydropyridine-3-carboxylic acid hydrochloride 6-(2-amino-2,3-dihydro-1H-pyrrolo[1,2-a]indol-7-yl)-5-ethyl-4-hydroxy-2-oxo-1,2-dihydropyridine-3-carboxylic acid hydrochloride 5-ethyl-4-hydroxy-6-(7-(methylamino)-6,7,8,9-tetrahydropyrido[1,2-a]indol-2-yl)-2-oxo-1,2-dihydropyridine-3-carboxylic acid hydrochloride 4-hydroxy-5-methyl-6-(2-(methylamino)-2,3-dihydro-1H-pyrrolo[1,2-a]indol-7-yl)-2-oxo-1,2-dihydropyridine-3-carboxylic acid hydrochloride 5-ethyl-4-hydroxy-6-(2-(methylamino)-2,3-dihydro-1H-pyrrolo[1,2-a]indol-7-yl)-2-oxo-1,2-dihydropyridine-3-carboxylic acid hydrochloride 6-(2-(dimethylamino)-2,3-dihydro-1H-pyrrolo[1,2-a]indol-7-yl)-4-hydroxy-5-methyl-2-oxo-1,2-dihydropyridine-3-carboxylic acid hydrochloride 6-(2-(dimethylamino)-2,3-dihydro-1H-pyrrolo[1,2-a]indol-7-yl)-5-ethyl-4-hydroxy-2-oxo-1,2-dihydropyridine-3-carboxylic acid hydrochloride 6-(cis-2-(aminomethyl)-1-(methylamino)-2,3-dihydro-1H-pyrrolo[1,2-a]indol-7-yl)-5-ethyl-4-hydroxy-2-oxo-1,2-dihydropyridine-3-carboxylic acid bis-hydrochloride 6-(trans-7-amino-9-(methylamino)-6,7,8,9-tetrahydropyrido[1,2-a]indol-2-yl)-5-ethyl-4-hydroxy-2-oxo-1,2-dihydropyridine-3-carboxylic acid bis-hydrochloride 6-(2-((dimethylamino)methyl)-1H-indol-6-yl)-5-ethyl-4-hydroxy-2-oxo-1,2-dihydropyridine-3-carboxylic acid hydrochloride 5-ethyl-6-(2-((ethylamino)methyl)-1H-indol-6-yl)-4-hydroxy-2-oxo-1,2-dihydropyridine-3-carboxylic acid hydrochloride 6-(2-((sec-butylamino)methyl)-1H-indol-6-yl)-5-ethyl-4-hydroxy-2-oxo-1,2-dihydropyridine-3-carboxylic acid hydrochloride, and 6-(2-((ethylamino)methyl)-1H-indol-6-yl)-4-hydroxy-5-methyl-2-oxo-1,2-dihydropyridine-3-carboxylic acid hydrochloride;

wherein the form of the compound is selected from a free acid, free base, hydrate, solvate, clathrate, isotopologue, racemate, enantiomer, diastereomer, stereoisomer, polymorph or tautomer form thereof.

11. A method of treating or ameliorating a bacterial infection in a subject in need thereof comprising administering an effective amount of a compound of claim 1 to the subject.

12. The method of claim 11, wherein the bacterial infection results from a bacteria that is a Gram-negative or Gram-positive type.

13. The method of claim 11, wherein the bacterial infection results from a bacteria that is a multi-drug resistant Gram-negative or Gram-positive type.

14. The method of claim 11, wherein the bacterial infection results from a bacteria of the phyla selected from Acidobacteria; Actinobacteria; Aquificae; Bacteroidetes; Caldiserica; Chlamydiae; Chlorobi; Chloroflexi; Chrysiogenetes; Cyanobacteria; Deferribacteres; Deinococcus-Thermus; Dictyoglomi; Elusimicrobia; Fibrobacteres; Firmicutes; Fusobacteria; Gemmatimonadetes; Lentisphaerae; Nitrospira; Planctomycetes; Proteobacteria; Spirochaetes; Synergistetes; Tenericutes; Firmicutes; Thermodesulfobacteria; Thermomicrobia; Thermotogae; or Verrucomicrobia.

15. The method of claim 11, wherein the bacterial infection results from a bacteria of the phyla selected from Proteobacteria, Spirochaetes, Bacteriodetes, Chlamydiae, Firmicutes or Actinobacteria.

16. The method of claim 11, wherein the bacterial infection results from a bacterial species selected from *Acinetobacter baumannii, Bacillus anthracis, Bacillus subtilis, Enterobacter* spp., *Enterococcus faecalis, Enterococcus faecium, Escherichia coli, Francisella tularensis, Haemophilus influenzae, Klebsiella pneumoniae, Moraxella catarrhalis, Mycobacterium tuberculosis, Neisseria* spp., *Pseudomonas aeruginosa, Shigella* spp., *Staphylococcus aureus, Streptococcus pyogenes, Streptococcus pneumoniae* and *Yersinia pestis*.

17. The method of claim 11, wherein the effective amount of the compound or a form thereof is in a range of from about 0.001 mg/Kg/day to about 500 mg/Kg/day.

18. A pharmaceutical composition comprising an effective amount of a compound of claim 1 or a form thereof in admixture with a pharmaceutically acceptable excipient.

19. A combination therapy comprising an effective amount of a compound of claim 1 or a form thereof and an effective amount of an antibiotic or antibacterial agent.

20. The combination therapy of claim 19, wherein the agent is selected from one or more of Ciprofloxacin, Enoxacin, Gatifloxacin, Levofloxacin, Lomefloxacin, Moxifloxacin, Nalidixic acid, Norfloxacin or Ofloxacin.

21. The combination therapy of claim 19, wherein the agent is selected from one or more of Amikacin, Amoxicillin, Ampicillin, Arsphenamine, Azithromycin, Azlocillin, Aztreonam, Bacitracin, Capreomycin, Carbenicillin, Cefaclor, Cefadroxil, Cefalexin, Cefalotin, Cefamandole, Cefazolin, Cefdinir, Cefditoren, Cefixime, Cefoperazone, Cefotaxime, Cefoxitin, Cefpodoxime, Cefprozil, Ceftazidime, Ceftibuten, Ceftizoxime, Ceftriaxone, Cefuroxime, Chloramphenicol, Cilastatin, Clarithromycin, Clavulanate, Clindamycin, Clofazimine, Cloxacillin, Colistin, Cycloserine, Dalfopristin, Dapsone, Daptomycin, Dicloxacillin, Dirithromycin, Doripenem, Doxycycline, Erythromycin, Ethambutol, Ethionamide, Flucloxacillin, Fosfomycin, Furazolidone, Fusidic acid, Gentamicin, Imipenem, Isoniazid, Kanamycin, Lincomycin, Linezolid, Loracarbef, Mafenide, Meropenem, Methicillin, Metronidazole, Mezlocillin, Minocycline, Mupirocin, Nafcillin, Neomycin, Netilmicin, Nitrofurantoin, Oxacillin, Oxytetracycline, Paromomycin, Penicillin G, Penicillin V, Piperacillin, Platensimycin, Polymyxin B, Pyrazinamide, Quinupristin, Rapamycin, Rifabutin, Rifampicin, Rifampin, Rifapentine, Rifaximin, Roxithromycin, Silver sulfadiazine, Spectinomycin, Streptomycin, Sulbactam, Sulfacetamide, Sulfadiazine, Sulfamethizole, Sulfamethoxazole, Sulfanilimide, Sulfasalazine, Sulfisoxazole, Tazobactam, Teicoplanin, Telavancin, Telithromycin, Temocillin, Tetracycline, Thiamphenicol, Ticarcillin, Tigecycline, Tinidazole, Tobramycin, Trimethoprim, Troleandomycin or Vancomycin.

* * * * *